US010787647B2

(12) United States Patent
Abul-Husn et al.

(10) Patent No.: US 10,787,647 B2
(45) Date of Patent: Sep. 29, 2020

(54) HSD17B13 VARIANTS AND USES THEREOF

(71) Applicant: Regeneron Pharmaceuticals, Inc., Tarrytown, NY (US)

(72) Inventors: Noura S. Abul-Husn, New York, NY (US); Omri Gottesman, New York, NY (US); Alexander Li, White Plains, NY (US); Xiping Cheng, Millwood, NY (US); Yurong Xin, Stamford, CT (US); Evangelos Pefanis, Somers, NY (US); Suzanne Hartford, Putnam Valley, NY (US); Jesper Gromada, Scarsdale, NY (US); Frederick E. Dewey, Irvington, NY (US); Aris Baras, Bedford Corners, NY (US); Alan Shuldiner, Baltimore, MD (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/875,514

(22) Filed: Jan. 19, 2018

(65) Prior Publication Data
US 2018/0216104 A1 Aug. 2, 2018

Related U.S. Application Data

(60) Provisional application No. 62/449,335, filed on Jan. 23, 2017, provisional application No. 62/472,972, filed on Mar. 17, 2017, provisional application No. 62/581,918, filed on Nov. 6, 2017.

(51) Int. Cl.
| | |
|---|---|
| *C07H 21/04* | (2006.01) |
| *C12N 9/04* | (2006.01) |
| *C12N 15/113* | (2010.01) |
| *C12Q 1/6883* | (2018.01) |
| *C12Q 1/32* | (2006.01) |
| *C12Q 1/6827* | (2018.01) |
| *C12Q 1/6876* | (2018.01) |
| *A61K 47/61* | (2017.01) |
| *A61P 1/16* | (2006.01) |
| *A61K 38/44* | (2006.01) |
| *A61K 38/46* | (2006.01) |
| *C12N 9/22* | (2006.01) |
| *C12N 9/96* | (2006.01) |
| *C12N 15/11* | (2006.01) |
| *C12N 15/85* | (2006.01) |
| *C12N 15/90* | (2006.01) |
| *A61K 48/00* | (2006.01) |

(52) U.S. Cl.
CPC .......... *C12N 9/0006* (2013.01); *A61K 38/443* (2013.01); *A61K 38/465* (2013.01); *A61K 47/61* (2017.08); *A61P 1/16* (2018.01); *C12N 9/22* (2013.01); *C12N 9/96* (2013.01); *C12N 15/11* (2013.01); *C12N 15/1137* (2013.01); *C12N 15/85* (2013.01); *C12N 15/907* (2013.01); *C12Q 1/32* (2013.01); *C12Q 1/6827* (2013.01); *C12Q 1/6876* (2013.01); *C12Q 1/6883* (2013.01); *C12Y 101/01051* (2013.01); *C12Y 101/01062* (2013.01); *A61K 48/00* (2013.01); *C12N 2310/14* (2013.01); *C12N 2310/20* (2017.05); *C12N 2310/531* (2013.01); *C12N 2320/34* (2013.01); *C12N 2800/24* (2013.01); *C12N 2800/80* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 10,577,630 | B2 | 3/2020 | Zhang et al. |
| 2003/0004102 | A1 | 1/2003 | Ashkenazi et al. |
| 2007/0219169 | A1 | 9/2007 | Becourt et al. |
| 2010/0028879 | A1 | 2/2010 | Labrie et al. |
| 2010/0056384 | A1 | 3/2010 | Hobbs et al. |
| 2018/0179553 | A1 | 6/2018 | Watson et al. |

(Continued)

FOREIGN PATENT DOCUMENTS

| | | |
|---|---|---|
| CN | 103520724 A | 1/2014 |
| CN | 10469810 A | 6/2015 |

(Continued)

OTHER PUBLICATIONS

Tsai, Shengdar Q., and J. Keith Joung. "Defining and improving the genome-wide specificities of CRISPR—Cas9 nucleases." Nature Reviews Genetics 17.5 (2016): 300.*

(Continued)

*Primary Examiner* — Kimberly Chong
(74) *Attorney, Agent, or Firm* — Yongjin Choi; Alston & Bird, LLP

(57) ABSTRACT

Provided are compositions related to HSD17B13 variants, including isolated nucleic acids and proteins related to variants of HSD17B13, and cells comprising those nucleic acids and proteins. Also provided are methods related to HSD17B13 variants. Such methods include methods for modifying a cell through use of any combination of nuclease agents, exogenous donor sequences, transcriptional activators, transcriptional repressors, and expression vectors for expressing a recombinant HSD17B13 gene or a nucleic acid encoding an HSD17B13 protein. Also provided are therapeutic and prophylactic methods for treating a subject having or at risk of developing chronic liver disease.

52 Claims, 20 Drawing Sheets
Specification includes a Sequence Listing.

(56) References Cited

U.S. PATENT DOCUMENTS

| | | |
|---|---|---|
| 2018/0185516 A1 | 7/2018 | Ansell et al. |
| 2018/0216084 A1 | 8/2018 | Abul-Husn et al. |
| 2019/0002869 A1 | 1/2019 | Yin et al. |
| 2019/0316121 A1 | 10/2019 | Smith et al. |
| 2019/0365924 A1 | 12/2019 | Conway et al. |
| 2019/0390195 A1 | 12/2019 | Tondera et al. |

FOREIGN PATENT DOCUMENTS

| | | |
|---|---|---|
| EP | 3011032 B1 | 10/2019 |
| EP | 3620524 A1 | 3/2020 |
| WO | WO 1995/029255 A1 | 11/1995 |
| WO | WO 1997/020942 A1 | 6/1997 |
| WO | WO 2004/110459 A1 | 12/2004 |
| WO | WO 2005/108415 A2 | 11/2005 |
| WO | WO 2010/028110 A2 | 3/2010 |
| WO | WO 2013/177060 A2 | 11/2013 |
| WO | WO 2013/190075 A2 | 12/2013 |
| WO | WO 2017/048620 A1 | 3/2017 |
| WO | WO 2018/107026 A1 | 6/2018 |
| WO | WO 2018/107028 A1 | 6/2018 |
| WO | WO 2018/136702 A1 | 7/2018 |
| WO | WO 2018/136758 A1 | 7/2018 |
| WO | WO 2018/220211 A1 | 12/2018 |
| WO | WO 2019/183164 A1 | 9/2019 |
| WO | WO 2019/183329 A1 | 9/2019 |
| WO | WO 2019/237069 A1 | 12/2019 |
| WO | WO 2019/246203 A1 | 12/2019 |

OTHER PUBLICATIONS

Adam, et al., "Hydroxysteroid (17β) dehydrogenase 13 deficiency triggers hepatic steatosis and inflammation in mice,"The FASEB Journal, vol. 32:Epub ahead of print (Jan. 31, 2018).

Chambers, et al., "Genome-wide association study identifies loci influencing concentrations of liver enzymes in plasma," Nature Genetics, 43(11), 1131-1138 plus Online Methods and Supplementary Materials (Nov. 2011).

Gieger, et al., "New gene functions in megakaryopoiesis and platelet formation, " Nature, 480(7376): 201-208 plus Supplementary Information, (Apr. 24, 2012).

Kampf, et al., "The Human liver-specific proteome defined by transcriptomics and antibody-based profiling," The FASEB Journal, vol. 28:2901-2914, (Jul. 2014).

Liu, et al., "Molecular cloning and expression analysis of a new gene for short-chain dehydrogenase/reductase 9," Acta Biochim. Pol., 54(1):213-218, (2007).

Moeller, et al., "Integrated view on 17beta-hydroxysteriod dehydrogenases," Molecular and Cellular Endocrinology, 301:7-19, (2009).

Quadri, et al., "Mutations in SLC30A10 Cause Parkinsonism and Dystonia with Hypermanganesemia, Polycthermia, and Chronic Liver Disease," The American Journal of Human Genetics, 90:467-477 plus Supplemental Material, (Mar. 9, 2012).

Ratziu, et al., "Current efforts and trends in the treatment of NASH,"Journal of Hepatology, 62:S65-S75, (2015).

Santa Cruz Biotechnology, "17β-HSD13 Antibody (K-14):sc-161285" [Retrieved from the Internet Jun. 1, 2016: <www.scbt.com/datasheet-161285-17betahsd13-k-14-antibody.html>].

Santa Cruz Biotechnology, "17β-HSD13 siRNA (m), shRNA and Lentiviral Particle Gene Silencers" [Retrieved from the Internet Jun. 1, 2016: <www.scbt.com/datasheet-108263-17beta-hsd13-sima-m.html>].

Su, et al., "Comparative proteomic study reveals 17β-HSD13 as a pathogenic protein in nonalcoholic fatty liver disease," PNAS, 111(31):11437-11442, (Aug. 5, 2014).

Abul-Husn, et al., "A Protein-Truncating HSD17B13 Variant and Protection from Chronic Liver Disease," The New England Journal of Medicine, 378(12):1096-1106, (Mar. 22, 2018).

Edelman, et al., "Genetic analysis of nonalcohol fatty liver disease within a Caribbean-Hispanic population," Mol. Genetic. Genomic Med., 3(6):558-569, (2015).

Ford, et al., "A new Assay for Picomole Levels of Androsterone and Testosterone Using Co-immobilized Luciferase, Oxidoreductase, and Steroid Dehydrogenase,"Analytical Biocehemistry, 110(1), 43-48, (1981).

Ghanbari, et al., "Genetic Variations in MicroRNA-Binding Sites Affect MicroRNA-Mediated Regulation of Several Genes Associated With Cardio-metabolic Phenotypes,"Circl. Cardiovasc. Genet., 8(3):473-486, (2015).

Haapaniemi et al., "CRISPR-Cas9 genome editing induces a p53-mediated DNA damage response," Nat. Med. doi: 10.1038/s41591-018-0049-z, (Jun. 11, 2018, epub ahead of print).

Hotta, et al., "Association of the rs738409 polymorphism in PNPLA3 with liver damage and the development of nonalcoholic fatty liver disease," BMC Med. Genet., 11:172, (2010).

Ihry et al., "p53 inhibits CRISPR-Cas9 engineering in human pluripotent stem cells," Nat. Med. dio: 10.1038/s41591-018-0050-6 (Jun. 11, 2018, epub ahead of print).

Kahali, et al., "Insights from Genome-Wide Association Analyses of Nonalcoholic Fatty Liver Disease," Semin. Liver Dis., 35(4):375-391, (2015).

Kosicki et al., "Repair of double-strand breaks induced by CRISPR-Cas9 leads to large deletions and complex rearrangements," Nat. Biotechnol., 36(8): 765-771, (Jul. 16, 2018).

Krazeisen, et al., "Phytoestrogens inhibits human 17β-hydroxysteriod dehydrogenase type 5," Molecular and Cellular Endocrimology, 171(1-2):151-162, (2001).

Oniki, et al., "Influence of the PNPLA3 rs738409 Polymorphism on Non-Alcoholic Fatty Liver Disease and Renal Function among Normal Weight Subjects," PLoS One, 10(7):e0132640, (2015).

Shen, et al., "The rs738409 (I148M) variant of the PNPLA3 gene and cirrhosis: a meta-analysis," J. Lipid Res., 56(1):167-175, (2015).

WIPO Application No. PCT/US2018/014454 PCT International Search Report and Written Opinion of the International Searching Authority dated Jun. 6, 2018.

Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L—Mutant," MBio 6(4):e01122, Supplemental Material, (2015).

GenBank: : Accession No. DR004209, "TC104687 Human liver, large insert, pCMV expression library Homo sapiens cDNA clone TC104687 5' similar to Homo sapiens similar to hydroxysteroid (17-beta) dehydrogenase 11; hydroxysteroid 17-beta dehydrogenase 11 (LOC205983), mRNA sequence," submitted Jan. 2011. [Retrieved from the Internet Jun. 10, 2019:<URL: ncbi.nlm.nih.gov>].

Jiang et al., "Structural Biology. A Cas9-guide RNA complex preorganized for target DNA recognition," Science, 348(6242):1477-1481, (2015).

Jinek et al., "RNA-programmed genome editing in human cells," eLife, 2:e00471, (2013).

Komor et al., "CRISPR-Based Technologies for the Manipulation of Eukaryotic Genomes," Cell, 168(1-2):20-36, (2017).

Nishimasu et al., "Crystal Structure of Cas9 in Complex with Guide RNA and Target DNA," Cell, 156(5):935-949, (2014).

NP Cluster Report rs72613567, [Retrieved from the Internet Jun. 6, 2019 <URL: ncbi.nlm.nig.gov>].

PubMed NCBI Search Results for ((CRISPR[Title] or Cas9[Title]) and ("Jan. 1, 2012"[PDATE] : "Jan. 22, 2017")), <https://www.ncbi.nlm.nih.gov/pubmed>, retrieved on Sep. 22, 2019.

Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L—Mutant," MBio 6(4):e01122, (2015).

U.S. Appl. No. 62/449,335, filed Jan. 23, 2017.
U.S. Appl. No. 62/472,972, filed Mar. 17, 2017.
PCT/US2018/014454, filed Jan. 19, 2018.
U.S. Appl. No. 62/581,918, filed Nov. 6, 2017.
Altschul, et al., "Basic Local Alignment Search Tool," J. Mol. Biol., 215(3):403-410, (1990).

(56) References Cited

OTHER PUBLICATIONS

Altschul, et al., "Gapped Blast and PSI-Blast: a new generation of protein database search programs," Nucleic Acids Res., 25(17):3389-3402, (1997).

Brantly, et al. "Molecular basis of alpha-1-antitrypsin deficiency," Am. J. Med., 84(6A):13-31, (1988).

Brasaemle, et al., "Isolation of Lipid Droplets from Cells by Density Gradient Centrifugation," Curr. Protoc. Cell Biol., 3.15.1-3.15.12, (2005).

Browning, et al., "Prevalence of Hepatic Steatosis in an Urban Population in the United States: Impact of Ethnicity," Hepatology, 40(6):1387-1395, (2004).

Cohen, et al., "Human Fatty Liver Disease: Old Questions and New Insights," Science, 332(6037):1519-1523, (2011).

Denny, et al., "PheWAS: demonstrating the feasibility of a phenome-wide scan to discover gene—disease associations," Bioinformatics, 26(9):1205-1210, (2010).

Denny, et al., "Systematic comparison of phenome-wide association study of electronic medical record data and genome-wide association study data," Nat. Biotechnol., 31(12):1102-1110, (2013).

Dewey, et al. "Distribution and clinical impact of functional variants in 50,726 whole-exome sequences from the DiscovEHR Study," Science, 354(6319): aaf6814, (2016).

Ding, et al., "Isolating lipid droplets from multiple species," Nat. Protoc., 8(1):43-51, (2013).

Feitosa, et al., "The ERLIN1-CHUK-CWF19L1 gene cluster influences liver fat deposition and hepatic inflammation in the NHLBI Family Heart Study," Atherosclerosis, 218(1):175-180, (2013).

Huang, et al., "Expression and Characterization of a PNPLA3 Protein Isoform (I148M) Associated with Nonalcoholic Fatty Liver Disease," J. Biol. Chem., 286(43):37085-37093, (2011).

Kitamoto, et al., "Genome-wide scan revealed that polymorphisms in the PNPLA3, SAMM50, and PARVB genes are associated with development and progression of nonalcoholic fatty liver disease in Japan," Hum. Genet., 132(7):783-792, (2013).

Kleiner, et al., "Design and Validation of a Histological Scoring System for Nonalcoholic Fatty Liver Disease," Hepatology, 41(6):1313-1321, (2005).

Kochanek, et al., "Deaths: Final Data for 2014," Natl. Viral Stat. Rep., 65(4):1-122, (2016).

Kozlitna, et al., "Exome-wide association study identifies a TM6SF2 variant that confers susceptibility to nonalcoholic fatty liver disease," Nat. Genet., 46(4):352-356, (2014).

Lazo, et al., "Prevalence of Nonalcoholic Fatty Liver Disease in the United States: The Third National Health and Nutrition Examination Survey, 1988-1994," Am. J. Epidemiol., 178(1):38-45, (2013).

Leippe, et al., "Bioluminescent Nicotinamide Adenine Dinucleotide Detection Assays Part 1: Technology and Features," (2014), https://www.promega.com/resources/pubhub/bioluminescent-nicotinamide-adenine-dinucleotide-detection-assays/.

Li, et al. "LTB4 causes macrophage—mediated inflammation and directly induces insulin resistance in obesity," Nat. Med., 21(3):239-247, (2015).

Li, et al., "Fast and accurate short read alignment with Burrows—Wheeler transform," Bioinformatics, 25(14):1754-1760, (2009).

Liu, et al., "TM6SF2 rs58542926 influences hepatic fibrosis progression in patients with non-alcoholic fatty liver disease," Nat. Commun., 5:4309, pp. 1-6, (2014).

Mahdessian, et al., "TM6SF2 is a regulator of liver fat metabolism influecing triglyceride secretion and hepatic lipid droplet content," Proc. Natl. Acad. Sci. U.S.A., 111(24):8913-8918, (2014).

McKenna, et al., "The Genome Analysis Toolkit: A MapReduce framework for analyzing next-generation DNA sequencing data," Genome Res., 20(9):1297-1303, (2010).

Morgan, et al., "Eradication of Hepatitis C Virus Infection and the Development of Hepaocellular Carcinoma,"Ann. Intern. Med., 158(5 Pt 1):329-337 and W-158-W-160, (2013).

NCBI Reference Sequence: NM_001135230, "Homo sapiens hydroxysteroid 17-beta dehydrogenase 13 (HSD1B13), transcript variant B, mRNA," pp. 1-5, (2017).

NCBI Reference Sequence:NM_178135, "Homo spiens hydroxysteroid 17-beta dehydrogenase 13 (HSD17B13), transcript variant A, mRNA," pp. 1-5, (2017).

NCBI Reference Sequence: NP_001129702, "17-beta-hydroxysteroid dehydrogenase 13 isoform B (Homo sapiens)," pp. 1-4, (2017).

NCBI Reference Sequence: NP_835236, "17-beta-hydroxysteroid dehydrogenase 13 isoform A precursor (Homo sapiens)," pp. 1-4, (2017).

New England Biolabs Catalog (1998/1999), pp. 121 and 284, (1998).

Pirazzu, et al., "Patatin-like phospholipase domain-containing 3 (PNPLA3) I148M (rs738409) affects hepatic VLDL secretion in humans and in vitro," J. Hepatol., 57(6):1276-1282, (2012).

Promega, "Technical Manual: NAD(P)H-Glo Detection Systems," TM398, pp. 1-15, (2017).

Pruim, et al., "LocusZoom: regional Visualization of genome-wide association scan results," Bioinformatics, 26(18): 2336-2337, (2010).

Reid, et al., "Launching genomics into the cloud: development of Mercury, a next generation sequence analysis pipeline,"BMC Bioinformatics, 15:30, pp. 1-11, (2014).

Romeo, et al., "Genetic variation in PNPLA3 confers susceptibility to nonalcoholic fattey liver disease," Nat. Genet., 40(12):1461-1465, (2008).

Rotman, et al., "The Assiation of Genetic Variability in PNPLA3 with Histological Severity of Non-Alcoholic Fatty Liver Disease," Hepatology, 52(3):894-903, (2010).

Schiavinato, et al., "EMILIN-3, peculiar member of elastin mircofibril interface-located protein (EMILIN) family, has distinct expression patter, forms oligomeric assemblies and serves as transforming growth factor $\beta$ (TGF$\alpha$) antagonist," J. Biol. Chem Smagris, et al., "Inactivation of Tm5sf2 a Gene Defective in Fatty Liver Disearse, Impairs Lipidation but Not Secretion pf Very Low Density Lipoproteins," J. Biol. Chem., 291(20:10659-10676, (2016).

Smith, et al., "Comparison of Biosequences," Advances in Applied Mathematics, 2:482-489, (1981).

Sookoian, et al., "A nonsynonymous gene variant in the adiponutrin gene is associated with nonalcoholic fatty liver disease severity," J. Lipid Res., 50(10):2111-2116, (2009).

Sookoian, et al., "Genetic Variation in Transmembrane 6 Superfamily Member 2 and the Risk of Nonalcoholic Fatty Liver Disease and Histological Disease Severity,"Hepatology, 61 (2):515-252, (2015).

Speliotes, et al., "Genome-Wide Association Analysis Identifies Variants Associated with Nonalcoholic Fatty Liver Disease That Have Distinct Effects on Metabolic Traits," PLoS Genet., 7(3):e1001324, (2011).

Submitted SNP(ss) Report in Submission Format for NCBI Assay Id (ss#): ss557289122. Nov. 22, 2012, 1 printed page from www.ncbi.nlm.nih.gov/ (Year: 2012).

Trepo, et al., "PNPLA3 gene in liver diseases," J. Hepatol., 65(2):399-412, (2016).

UniProtKB-Q7Z5P4-1, "17-beta-hydroxysteroid dehydrogenase 13," p. 6, (2003).

Van Der Meer, et al., "Association Between Sustained Virological Response and All-Cause Mortality Among Patients With Chronic Hepatitis C and Advanced Hepatic Fibrosis," JAMA, 308(24):2584-2593, (2012).

Victor, et al., "The Dallas Heart Study: A Population-Based Probability Sample for the Multidisciplinary Study of Ethnic Differences in Cardiovascular Health," Am. J. Cardiol., 93(12):1473-1480, (2004).

Willer, et al., "Metal: fast and efficient meta-analysis of genomewide association scans," Bioinformatics, 26(17):2190-2191, (2010).

Williams, et al., "Prevalence of nonalcoholic fatty liver disease and nonalcoholic steatohepatitis among a largely middle-aged population utilizing ultrasound and liver biopsy: a prospective study," Gastroenterology, 140(1):124-131, (2011).

Wong, et al., "Nonalcoholic Steatohepatitis Is the Second Leading Etiology of Liver Disease Among Adults Awaiting Liver Transplantation in the United States," Gastroenterology, 148(3):547-555, (2015).

UniProtKB-Q7Z5P4-2, "17-beta-hydroxysteroid dehydrogenase 13," pp. 6-7, (2003).

(56) References Cited

OTHER PUBLICATIONS

Yang, et al., "GCTA: A Tool for Genome-wide Complex Trait Analysis," Am. J. Hum. Genet., 88(1):76-82, (2011).
Younossi, et al., "Changes in the Prevalence of the Most Common Causes of Chronic Liver Diseases in the United States From 1988 to 2008," Clin. Gastroenterol. Hepatol., 9(6):524-530, (2011).
Yuan, et al., "Population-Based Genome-wide Association Studies Reveal Six Loci Influencing Plasma Levels of Liver Enzymes," Am. J. Hum. Genet., 83(4):520-528, (2008).
Zhang, et al., "PowerBLAST: A New Network Blast Application for Interactive of Automated Sequence Analysis and Annotation," Genome Res., 7(6):649-656, (1997).
U.S. Appl. No. 15/913,366, Non-Final Office Action dated Feb. 4, 2020.
WIPO Application No. PCT/US2018/014357 PCT International Search Report and Written Opinion of the International Searching Authority dated Jun. 20, 2018.
WIPO Application No. PCT/US2019/023079 PCT International Search Report and Written Opinion of the International Searching Authority dated Jun. 26, 2019.
Tang, et al., "A mouse knockout library for secreted and transmembrane proteins," Nature Biotechnology, 28(7):749-755 plus Online Methods and Supplementary Information, (Jul. 2010).
Business Wire, "Arrowhead Pharmaceuticals Initiates Phase 1/2 Study of ARO-HSD in Normal Healthy Volunteers and Patients with NASH of Suspected NASH", Mar. 3, 2020, pp. 1-2. businesswire.com/news/home/20200303005396/en/Arrowhead-Pharmaceuticals-Initiates-Phase-12-Study-ARO-HSD.
Zhang et al., "Omic studies reveal the pathogenic lipid droplet proteins in non-alcoholic fatty liver disease", Protein Cell, 8(1):4-13, (2017).
U.S. Appl. No. 16/157,503, Non-Final Office Action dated Jun. 12, 2020.

\* cited by examiner

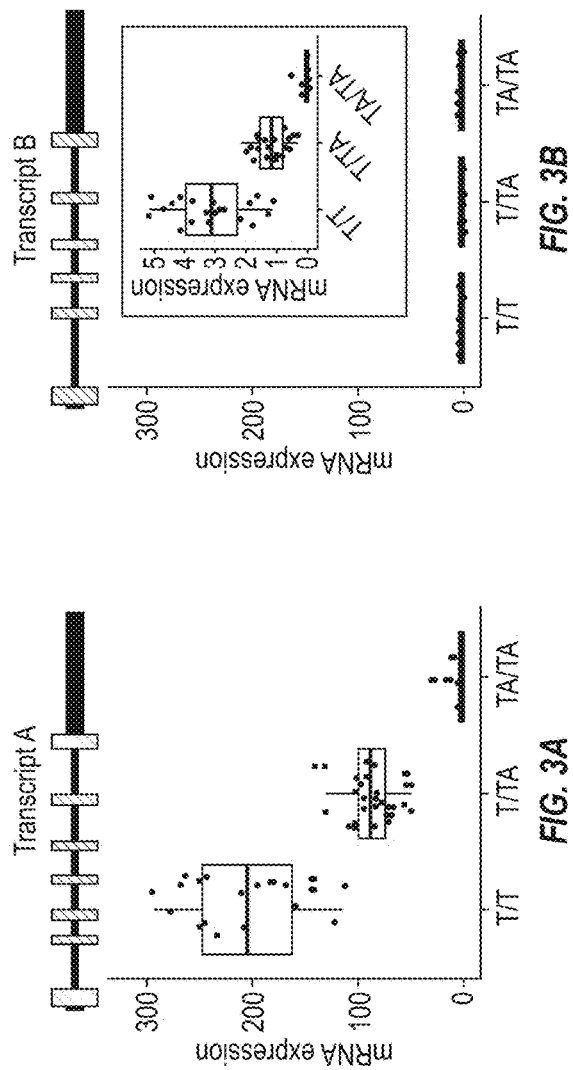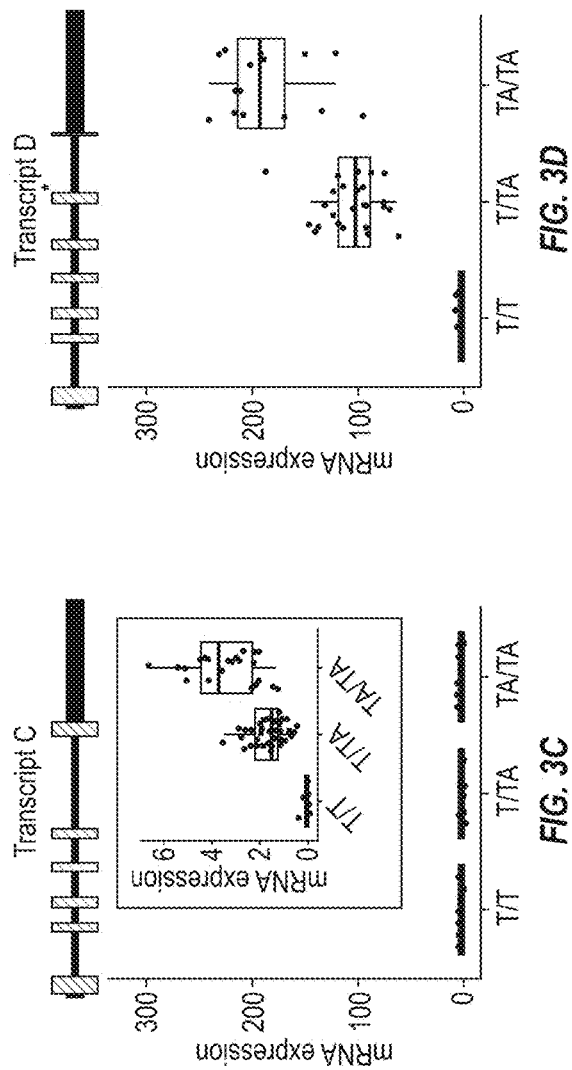
FIG. 3A  FIG. 3B  FIG. 3C  FIG. 3D

FIG. 7A

```
                              E5                                                    E6                                         E7
A_Form 205 ALGKTGIKTSCLCPVFVNTGFTKNPSTRLWPVLETDEVVRSLIDGILTNKKMIFVPSYINIFLRLQKFLPERASAI 280
B_Form 169 ALGKTGIKTSCLCPVFVNTGFTKNPSTRLWPVLETDEVVRSLIDGILTNKKMIFVPSYINIFLRLQKFLPERASAI 244
C_Form 205 ALGKTGIKTSCLCPVFVNTGFTKNPSTR..........................FLPERASAI 241
D_Form 205 ALGKTGIKTSCLCPVFVNTGFTKNPSTRLWPVLETDEVVRSLIDGILTNKKMIFVPSYINIFLRLQKVSS 274
E_Form 229 ALGKTGIKTSCLCPVFVNTGFTKNPSTRLWPVLETDEVVRSLIDGILTNKKMIFVPSYINIFLRLQKFLPERASAI 304
F_Form 205 ALGKTGIKTSCLCPVFVNTGFTKNPSTRLWPVLETDEVVRSLIDGILTNKKMIFVPSYINIFLRLQKFLPERASAI 280
G_Form 169 ALGKTGIKTSCLCPVFVNTGFTKNPSTRLWPVLETDEVVRSLIDGILTNKKMIFVPSYINIFLRLQKLSTAQNTQH 238
H_Form 229 ALGKTGIKTSCLCPVFVNTGFTKNPSTRLWPVLETDEVVRSLIDGILTNKKMIFVPSYINIFLRLQKVSS 298

E7
A_Form 281 LNRMQNIQFEAVVGHKIKMK 300 (SEQ ID NO: 12)
B_Form 245 LNRMQNIQFEAVVGHKIKMK 264 (SEQ ID NO: 13)
C_Form 242 LNRMQNIQFEAVVGHKIKMK 261 (SEQ ID NO: 14)
D_Form 274                          274 (SEQ ID NO: 15)
E_Form 305 LNRMQNIQFEAVVGHKIKMK 324 (SEQ ID NO: 16)
F_Form 281 LKHQ                 284 (SEQ ID NO: 17)
G_Form 238                          238 (SEQ ID NO: 18)
H_Form 298                          298 (SEQ ID NO: 19)
```

FIG. 7B

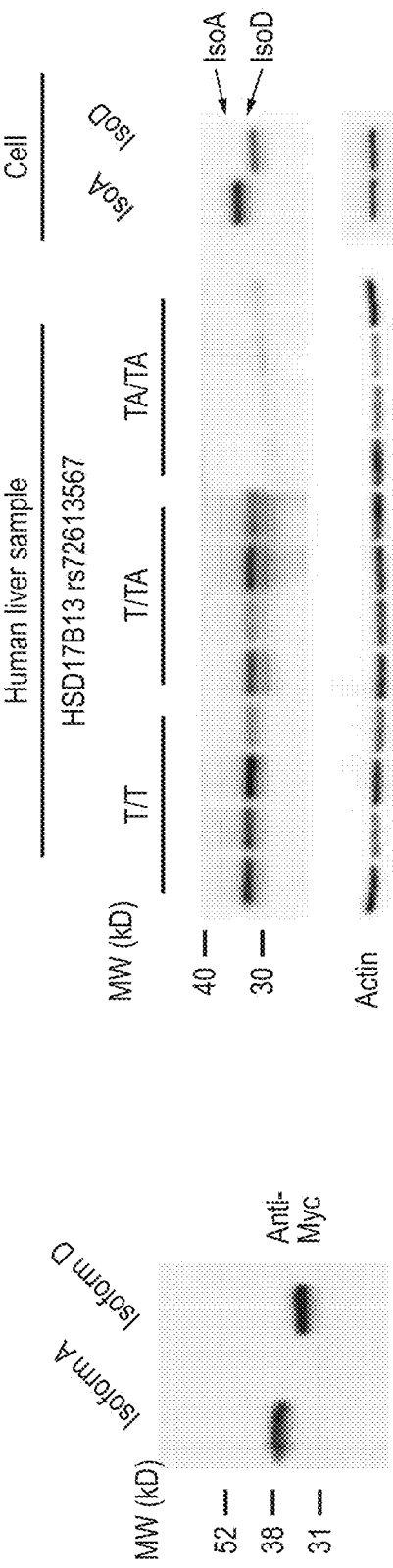
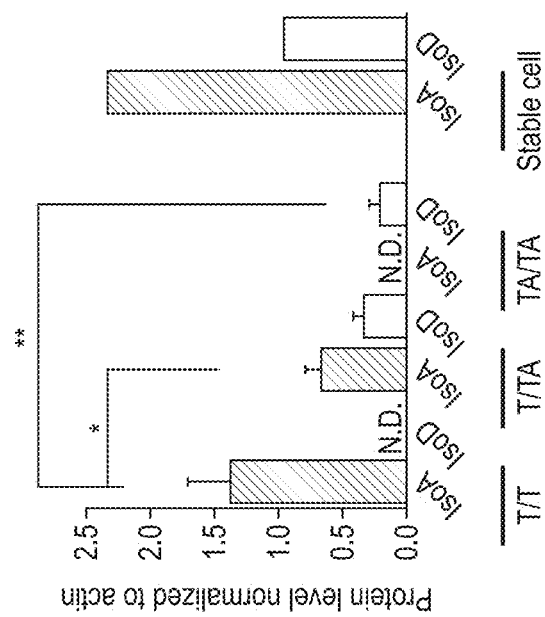
FIG. 10B
FIG. 10C
FIG. 10A

HSD17B13 VARIANTS AND USES THEREOF

CROSS-REFERENCE TO RELATED APPLICATIONS

This application claims the benefit of US Application No. 62/449,335, filed Jan. 23, 2017, US Application No. 62/472,972, filed Mar. 17, 2017, and US Application No.: 62/581,918, filed Nov. 6, 2017, each of which is herein incorporated by reference in its entirety for all purposes.

REFERENCE TO A SEQUENCE LISTING SUBMITTED AS A TEXT FILE VIA EFS WEB

The Sequence Listing written in file 507176SEQLIST.txt is 507 kilobytes, was created on Jan. 19, 2018, and is hereby incorporated by reference.

BACKGROUND

Chronic liver disease and cirrhosis are leading causes of morbidity and mortality in the United States, accounting for 38,170 deaths (1.5% of total deaths) in 2014 (Kochanek et al. (2016) *Natl Vital Stat Rep* 65:1-122, herein incorporated by reference in its entirety for all purposes). The most common etiologies of cirrhosis in the U.S. are alcoholic liver disease, chronic hepatitis C, and nonalcoholic fatty liver disease (NAFLD), together accounting for ~80% of patients awaiting liver transplant between 2004 and 2013 (Wong et al. (2015) *Gastroenterology* 148:547-555, herein incorporated by reference in its entirety for all purposes). The estimated prevalence of NAFLD in the U.S. is between 19 and 46 percent (Browning et al. (2004) *Hepatology* 40:1387-1395; Lazo et al. (2013) *Am J Epidemiol* 178:38-45; and Williams et al. (2011) *Gastroenterology* 140:124-131, each of which is herein incorporated by reference in its entirety for all purposes) and is rising over time (Younossi et al. (2011) *Clin Gastroenterol Hepatol* 9:524-530 e1; quiz e60 (2011), herein incorporated by reference in its entirety for all purposes), likely in conjunction with increased rates of obesity, its primary risk factor (Cohen et al. (2011) *Science* 332:1519-1523, herein incorporated by reference in its entirety for all purposes). While significant advances have been made in the treatment of hepatitis C (Morgan et al. (2013) *Ann Intern Med* 158:329-337 and van der Meer et al. (2012) *JAMA* 308:2584-2593, each of which is herein incorporated by reference in its entirety for all purposes), there are currently no evidence-based treatments for alcoholic or nonalcoholic liver disease and cirrhosis.

Previous genome wide association studies (GWAS) have identified a limited number of genes and variants associated with chronic liver disease. The most robustly validated genetic association to date is to a common missense variant in the patatin-like phospholipase domain containing 3 gene (PNPLA3 p.Ile148Met, rs738409), initially found to be associated with increased risk of nonalcoholic fatty liver disease (NAFLD) (Romeo et al. (2008) *Nat. Genet.* 40:1461-1465 and Speliotes et al. (2011) *PLoS Genet.* 7:e1001324, each of which is herein incorporated by reference in its entirety for all purposes), and subsequently found to be associated with disease severity (Rotman et al. (2010) *Hepatology* 52:894-903 and Sookoian et al. (2009) *J. Lipid Res.* 50:2111-2116, each of which is herein incorporated by reference in its entirety for all purposes) and progression (Trepo et al. (2016) *J. Hepatol.* doi:10.1016/j.j-hep.2016.03.011, herein incorporated by reference in its entirety for all purposes). Variation in the transmembrane 6 superfamily member 2 (TM6SF2) gene has also been shown to confer increased risk for NAFLD (Kozlitina et al. (2014) *Nat. Genet.* 46:352-356; Liu et al. (2014) *Nat. Commun.* 5:4309; and Sookoian et al. (2015) *Hepatology* 61:515-525, each of which is herein incorporated by reference in its entirety for all purposes). The normal functions of these two proteins are not well understood, though both have been proposed to be involved in hepatocyte lipid metabolism. How variants in PNPLA3 and TM6SF2 contribute to increased risk of liver disease has yet to be elucidated. GWAS have also identified several genetic factors to be associated with serum alanine aminotransferase (ALT) and aspartate aminotransferase (AST) (Chambers et al. (2011) *Nat. Genet.* 43:131-1138 and Yuan et al. (2008) *Am. J. Hum. Genet.* 83:520-528, each of which is herein incorporated by reference in its entirety for all purposes), quantitative markers of hepatocyte injury and liver fat accumulation that are frequently measured clinically. To date, there are no described protective genetic variants for chronic liver disease. The discovery of protective genetic variants in other settings, such as loss-of-function variants in PCSK9 that reduce the risk of cardiovascular disease, has been the catalyst for development of new classes of therapeutics.

Knowledge of genetic factors underlying the development and progression of chronic liver disease could improve risk stratification and provide the foundation for novel therapeutic strategies. A better understanding of underlying genetic factors is needed to improve risk stratification and generate novel therapies for liver disease.

SUMMARY

Methods and compositions are provided related to the HSD17B13 rs72613567 variant gene, variant HSD17B13 transcripts, and variant HSD17B13 protein isoforms.

In one aspect, provided are isolated nucleic acids comprising the mutant residue from the HSD17B13 rs72613567 variant gene. Such isolated nucleic acids can comprise at least 15 contiguous nucleotides of an HSD17B13 gene and have a thymine inserted between nucleotides corresponding to positions 12665 and 12666 of SEQ ID NO: 1 when optimally aligned with SEQ ID NO: 1. Optionally, the contiguous nucleotides are at least 90%, at least 95%, at least 96%, at least 97%, at least 98%, or at least 99% identical to a corresponding sequence in SEQ ID NO: 2 including position 12666 of SEQ ID NO: 2 when optimally aligned with SEQ ID NO: 2. Optionally, the HSD17B13 gene is a human HSD17B13 gene. Optionally, the isolated nucleic acid comprises at least 15, at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 11000, at least 12000, at least 13000, at least 14000, at least 15000, at least 16000, at least 17000, at least 18000, or at least 19000 contiguous nucleotides of SEQ ID NO: 2.

Some such isolated nucleic acids comprise an HSD17B13 minigene in which one or more nonessential segments of the gene have been deleted with respect to a corresponding wild type HSD17B13 gene. Optionally, the deleted segments comprise one or more intronic sequences. Optionally, the isolated nucleic acid further comprises an intron corresponding to intron 6 of SEQ ID NO: 2 when optimally aligned with SEQ ID NO: 2. Optionally, the intron is intron 6 of SEQ ID NO: 2.

In another aspect, provided are isolated nucleic acids corresponding with different HSD17B13 mRNA transcripts or cDNAs. Some such isolated nucleic acids comprise at least 15 contiguous nucleotides encoding all or part of an HSD17B13 protein, wherein the contiguous nucleic acids comprise a segment that is at least 90%, at least 95%, at least 96%, at least 97%, at least 98%, at least 99%, or 100% identical to a segment present in SEQ ID NO: 7 (HSD17B13 Transcript D), SEQ ID NO: 10 (HSD17B13 Transcript G), and SEQ ID NO: 11 (HSD17B13 Transcript H) that is not present in SEQ ID NO: 4 (HSD17B13 Transcript A). Optionally, the contiguous nucleotides further comprise a segment that is at least 90%, at least 95%, at least 96%, at least 97%, at least 98%, at least 99%, or 100% identical to a segment present in SEQ ID NO: 7 (HSD17B13 Transcript D) that is not present SEQ ID NO: 11 (HSD17B13 Transcript H), and wherein the contiguous nucleotides further comprise a segment that is at least 90%, at least 95%, at least 96%, at least 97%, at least 98%, at least 99%, or 100% identical to a segment present in SEQ ID NO: 7 (HSD17B13 Transcript D) that is not present in SEQ ID NO: 10 (HSD17B13 Transcript G). Optionally, the contiguous nucleotides further comprise a segment that is at least 90%, at least 95%, at least 96%, at least 97%, at least 98%, at least 99%, or 100% identical to a segment present in SEQ ID NO: 11 (HSD17B13 Transcript H) that is not present in SEQ ID NO: 7 (HSD17B13 Transcript D). Optionally, the contiguous nucleotides further comprise a segment that is at least 90%, at least 95%, at least 96%, at least 97%, at least 98%, at least 99%, or 100% identical to a segment present in SEQ ID NO: 10 (HSD17B13 Transcript G) that is not present in SEQ ID NO: 7 (HSD17B13 Transcript D).

Some such isolated nucleic acids comprise at least 15 contiguous nucleotides encoding all or part of an HSD17B13 protein, wherein the contiguous nucleotides comprise a segment that is at least 90%, at least 95%, at least 96%, at least 97%, at least 98%, at least 99%, or 100% identical to a segment present in SEQ ID NO: 8 (HSD17B13 Transcript E) that is not present in SEQ ID NO: 4 (HSD17B13 Transcript A). Optionally, the contiguous nucleotides further comprise a segment that is at least 90%, at least 95%, at least 96%, at least 97%, at least 98%, at least 99%, or 100% identical to a segment present in SEQ ID NO: 8 (HSD17B13 Transcript E) that is not present in SEQ ID NO: 11 (HSD17B13 Transcript H)

Some such isolated nucleic acids comprise at least 15 contiguous nucleotides encoding all or part of an HSD17B13 protein, wherein the contiguous nucleotides comprise a segment that is at least 90%, at least 95%, at least 96%, at least 97%, at least 98%, at least 99%, or 100% identical to a segment present in SEQ ID NO: 9 (HSD17B13 Transcript F) that is not present in SEQ ID NO: 4 (HSD17B13 Transcript A).

Some such isolated nucleic acids comprise at least 15 contiguous nucleotides encoding all or part of an HSD17B13 protein, wherein the contiguous nucleotides comprise a segment that is at least 90%, at least 95%, at least 96%, at least 97%, at least 98%, at least 99%, or 100% identical to a segment present in SEQ ID NO: 6 (HSD17B13 Transcript C) that is not present in SEQ ID NO: 4 (HSD17B13 Transcript A).

Optionally, the HSD17B13 protein is a human HSD17B13 protein. Optionally, the isolated nucleic acid comprises at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900, at least 1000, or at least 2000 contiguous nucleotides encoding all or part of an HSD17B13 protein.

Some such isolated nucleic acids comprise a sequence at least 90%, at least 95%, at least 96%, at least 97%, at least 98%, at least 99%, or 100% identical to the sequence set forth in SEQ ID NO: 6, 7, 8, 9, 10, or 11 (HSD17B13 Transcript C, D, E, F, G, or H) and encoding an HSD17B13 protein comprising the sequence set forth in SEQ ID NO: 14, 15, 16, 17, 18, or 19 (HSD17B13 Isoform C, D, E, F, G, or H), respectively.

In any of the above nucleic acids, the contiguous nucleotides can optionally comprise sequence from at least two different exons of an HSD17B13 gene without an intervening intron.

In another aspect, provided are proteins encoded by any of the above isolated nucleic acids.

In another aspect, provided are isolated nucleic acids that hybridize to or near the mutant residue from the HSD17B13 rs72613567 variant gene. Such isolated nucleic acids can comprise at least 15 contiguous nucleotides that hybridize to an HSD17B13 gene at a segment that includes or is within 1000, 500, 400, 300, 200, 100, 50, 45, 40, 35, 30, 25, 20, 15, 10, or 5 nucleotides of a position corresponding to position 12666 in SEQ ID NO: 2 when optimally aligned with SEQ ID NO: 2. Optionally, the segment is at least 90%, at least 95%, at least 96%, at least 97%, at least 98%, or at least 99% identical to a corresponding sequence in SEQ ID NO: 2 when optimally aligned with SEQ ID NO: 2. Optionally, the segment comprises at least 20, 25, 30, 35, 40, 45, 50, 60, 70, 80, 90, 100, 200, 300, 400, 500, 600, 700, 800, 900, 1000, or 2000 contiguous nucleotides of SEQ ID NO: 2. Optionally, the segment includes position 12666 in SEQ ID NO: 2 or a position corresponding to position 12666 in SEQ ID NO: 2 when optimally aligned with SEQ ID NO: 2. Optionally, the HSD17B13 gene is a human HSD17B13 gene. Optionally, the isolated nucleic acid is up to about 30, 40, 50, 100, 200, 300, 400, 500, 600, 700, 800, 900, or 1000 nucleotides in length. Optionally, the isolated nucleic acid is linked to a heterologous nucleic acid or comprises a heterologous label. Optionally, the heterologous label is a fluorescent label.

In another aspect, provided are isolated nucleic acids that hybridize to different HSD17B13 mRNA transcripts or cDNAs. Some such isolated nucleic acids hybridize to at least 15 contiguous nucleotides of a nucleic acid encoding an HSD17B13 protein, wherein the contiguous nucleotides comprise a segment that is at least 90%, at least 95%, at least 96%, at least 97%, at least 98%, at least 99%, or 100% identical to a segment present in SEQ ID NO: 7 (HSD17B13 Transcript D), SEQ ID NO: 10 (HSD17B13 Transcript G), and SEQ ID NO: 11 (HSD17B13 Transcript H) that is not present within SEQ ID NO: 4 (HSD17B13 Transcript A).

Some such isolated nucleic acids hybridize to at least 15 contiguous nucleotides of a nucleic acid encoding an HSD17B13 protein, wherein the contiguous nucleotides comprise a segment that is at least 90%, at least 95%, at least 96%, at least 97%, at least 98%, or at least 99% identical to a segment present in SEQ ID NO: 8 (HSD17B13 Transcript E) and SEQ ID NO: 11 (HSD17B13 Transcript H) that is not present in SEQ ID NO: 4 (HSD17B13 Transcript A).

Some such isolated nucleic acids hybridize to at least 15 contiguous nucleotides of a nucleic acid encoding an HSD17B13 protein, wherein the contiguous nucleotides comprise a segment that is at least 90%, at least 95%, at least 96%, at least 97%, at least 98%, or at least 99% identical to a segment in SEQ ID NO: 9 (HSD17B13 Transcript F) that is not present in SEQ ID NO: 4 (HSD17B13 Transcript A).

Some such isolated nucleic acids hybridize to at least 15 contiguous nucleotides of a nucleic acid encoding an HSD17B13 protein, wherein the contiguous nucleotides comprise a segment that is at least 90%, at least 95%, at least 96%, at least 97%, at least 98%, or at least 99% identical to a segment present in SEQ ID NO: 6 (HSD17B13 Transcript C) that is not present in SEQ ID NO: 4 (HSD17B13 Transcript A).

Optionally, the HSD17B13 protein is a human HSD17B13 protein. Optionally, the isolated nucleic acid is up to about 30, 40, 50, 100, 200, 300, 400, 500, 600, 700, 800, 900, or 1000 nucleotides in length. Optionally, the isolated nucleic acid is linked to a heterologous nucleic acid or comprises a heterologous label. Optionally, the heterologous label is a fluorescent label.

Optionally, any of the above isolated nucleic acids comprise DNA. Optionally, any of the above isolated nucleic acids comprise RNA. Optionally, any of the above isolated nucleic acids are an antisense RNA, a short hairpin RNA, or a small-interfering RNA. Optionally, any of the above isolated nucleic acids can include a non-natural nucleotide.

In another aspect, provided are vectors and exogenous donor sequences comprising any of the above isolated nucleic acids and a heterologous nucleic acid sequence.

In another aspect, provided is the use of any of the above isolated nucleic acids, vectors, or exogenous donor sequences in a method of detecting an HSD17B13 rs72613567 variant in a subject, a method of detecting the presence of HSD17B13 Transcript C, D, E, F, G, or H in a subject, a method of determining a subject's susceptibility to developing a chronic liver disease, method of diagnosing a subject with fatty liver disease, or a method of modifying an HSD17B13 gene in a cell, a method for altering expression of an HSD17B13 gene in a cell.

In another aspect, provided are guide RNAs that target the HSD17B13 gene. Such guide RNAs can be effective to direct a Cas enzyme to bind to or cleave an HSD17B13 gene, wherein the guide RNA comprises a DNA-targeting segment that hybridizes to a guide RNA recognition sequence within the HSD17B13 gene. That is, such guide RNAs can be effective to direct a Cas enzyme to bind to or cleave an HSD17B13 gene, wherein the guide RNA comprises a DNA-targeting segment that targets a guide RNA target sequence within the HSD17B13 gene. Such guide RNAs can be effective to direct a Cas enzyme to bind to or cleave an HSD17B13 gene, wherein the guide RNA comprises a DNA-targeting segment that targets a guide RNA target sequence within the HSD17B13 gene that includes or is proximate to a position corresponding to position 12666 of SEQ ID NO: 2 when the HSD17B13 gene is optimally aligned with SEQ ID NO: 2. Optionally, the guide RNA target sequence comprises, consists essentially of, or consists of any one of SEQ ID NOS: 226-239 and 264-268. Optionally, the DNA-targeting segment comprises, consists essentially of, or consists of any one of SEQ ID NOS: 1629-1642 and 1648-1652. Optionally, the guide RNA comprises, consists essentially of, or consists of any one of SEQ ID NOS: 706-719; 936-949; 1166-1179, 1396-1409, 725-729, 955-959, 1185-1189, and 1415-1419. Optionally, the guide RNA target sequence is selected from SEQ ID NOS: 226-239 or SEQ ID NOS: 230 and 231. Optionally, the guide RNA target sequence is selected from SEQ ID NOS: 226-230 and 264-268. Optionally, the guide RNA target sequence is within a region corresponding to exon 6 and/or intron 6 of SEQ ID NO: 2 when the HSD17B13 gene is optimally aligned with SEQ ID NO: 2. Optionally, the guide RNA target sequence is within a region corresponding to exon 6 and/or intron 6 and/or exon 7 of SEQ ID NO: 2 when the HSD17B13 gene is optimally aligned with SEQ ID NO: 2. Optionally, the guide RNA target sequence is within about 1000, 500, 400, 300, 200, 100, 50, 45, 40, 35, 30, 25, 20, 15, 10, or 5 nucleotides of the position corresponding to position 12666 of SEQ ID NO: 2 when the HSD17B13 gene is optimally aligned with SEQ ID NO: 2. Optionally, the guide RNA target sequence includes the position corresponding to position 12666 of SEQ ID NO: 2 when the HSD17B13 gene is optimally aligned with SEQ ID NO: 2.

Such guide RNAs can be effective to direct a Cas enzyme to bind to or cleave an HSD17B13 gene, wherein the guide RNA comprises a DNA-targeting segment that targets a guide RNA target sequence within the HSD17B13 gene that includes or is proximate to the start codon of the HSD17B13 gene. Optionally, the guide RNA target sequence comprises, consists essentially of, or consists of any one of SEQ ID NOS: 20-81 and 259-263. Optionally, the DNA-targeting segment comprises, consists essentially of, or consists of any one of SEQ ID NOS: 1423-1484 and 1643-1647. Optionally, the guide RNA comprises, consists essentially of, or consists of any one of SEQ ID NOS: 500-561, 730-791, 960-1021, 1190-1251, 720-724, 950-954, 1180-1184, and 1410-1414. Optionally, the guide RNA target sequence is selected from SEQ ID NOS: 20-81 and 259-263. Optionally, the guide RNA target sequence is selected from SEQ ID NOS: 21-23, 33, and 35. Optionally, the guide RNA target sequence is selected from SEQ ID NOS: 33 and 35. Optionally, the guide RNA target sequence is within a region corresponding to exon 1 of SEQ ID NO: 2 when the HSD17B13 gene is optimally aligned with SEQ ID NO: 2. Optionally, the guide RNA target sequence is within about 1000, 500, 400, 300, 200, 100, 50, 45, 40, 35, 30, 25, 20, 15, 10, or 5 nucleotides of the start codon.

Such guide RNAs can be effective to direct a Cas enzyme to bind to or cleave an HSD17B13 gene, wherein the guide RNA comprises a DNA-targeting segment that targets a guide RNA target sequence within the HSD17B13 gene that includes or is proximate to the stop codon of the HSD17B13 gene. Optionally, the guide RNA target sequence comprises, consists essentially of, or consists of any one of SEQ ID NOS: 82-225. Optionally, the DNA-targeting segment comprises, consists essentially of, or consists of any one of SEQ ID NOS: 1485-1628. Optionally, the guide RNA comprises, consists essentially of, or consists of any one of SEQ ID NOS: 562-705, 792-935, 1022-1165, and 1252-1395. Optionally, the guide RNA target sequence is selected from SEQ ID NOS: 82-225. Optionally, the guide RNA target sequence is within a region corresponding to exon 7 of SEQ ID NO: 2 when the HSD17B13 gene is optimally aligned with SEQ ID NO: 2. Optionally, the guide RNA target sequence is within about 1000, 500, 400, 300, 200, 100, 50, 45, 40, 35, 30, 25, 20, 15, 10, or 5 nucleotides of the stop codon.

Optionally, the HSD17B13 gene is a human HSD17B13 gene. Optionally, the HSD17B13 gene comprises SEQ ID NO: 2.

Some such guide RNAs comprise a Clustered Regularly Interspaced Short Palindromic Repeats (CRISPR) RNA (crRNA) comprising the DNA-targeting segment and a trans-activating CRISPR RNA (tracrRNA). Optionally, the guide RNA is a modular guide RNA in which the crRNA and the tracrRNA are separate molecules that hybridize to each other. Optionally, the crRNA comprises, consists essentially of, or consists of the sequence set forth in SEQ ID NO: 1421 and the tracrRNA comprises, consists essentially of, or consists of the sequence set forth in SEQ ID NO: 1422.

Optionally, the guide RNA is a single-guide RNA in which the crRNA is fused to the tracrRNA via a linker. Optionally, the single-guide RNA comprises, consists essentially of, or consists of the sequence set forth in any one of SEQ ID NOS: 1420 and 256-258.

In another aspect, provided are antisense RNAs, siRNAs, or shRNAs that hybridize to a sequence within an HSD17B13 transcript disclosed herein. Some such antisense RNAs, siRNAs, or shRNAs hybridize to a sequence within SEQ ID NO: 4 (HSD17B13 Transcript A). Optionally, the antisense RNA, siRNA, or shRNA can decrease expression of HSD17B13 Transcript A in a cell. Optionally, the antisense RNA, siRNA, or shRNA hybridizes to a sequence present in SEQ ID NO: 4 (HSD17B13 Transcript A) that is not present in SEQ ID NO: 7 (HSD17B13 Transcript D). Optionally, the antisense RNA, siRNA, or shRNA hybridizes to a sequence within exon 7 or a sequence spanning the exon 6-exon 7 boundary of SEQ ID NO: 4 (HSD17B13 Transcript A). Some such antisense RNAs, siRNAs, or shRNAs hybridize to a sequence within SEQ ID NO: 7 (HSD17B13 Transcript D). Optionally, the antisense RNA, siRNA, or shRNA can decrease expression of HSD17B13 Transcript D in a cell. Optionally, the antisense RNA, siRNA, or shRNA hybridizes to a sequence present in SEQ ID NO: 7 (HSD17B13 Transcript D) that is not present in SEQ ID NO: 4 (HSD17B13 Transcript A). Optionally, the antisense RNA, siRNA, or shRNA hybridizes to a sequence within exon 7 or a sequence spanning the exon 6-exon 7 boundary of SEQ ID NO: 7 (HSD17B13 Transcript D).

In another aspect, provided are DNAs encoding any of the above guide RNAs, antisense RNAs, siRNAs, or shRNAs. In another aspect, provided are vectors comprising a DNA encoding any of the above guide RNAs, antisense RNAs, siRNAs, or shRNAs and a heterologous nucleic acid. In another aspect, provided is the use of any of the above guide RNAs, antisense RNAs, siRNAs, or shRNAs DNAs encoding guide RNAs, antisense RNAs, siRNAs, or shRNAs or vectors comprising DNAs encoding guide RNAs, antisense RNAs, siRNAs, or shRNAs in a method of modifying an HSD17B13 gene in a cell or a method for altering expression of an HSD17B13 gene in a cell.

In another aspect, provided are compositions comprising any of the above isolated nucleic acids, any of the above guide RNAs, any of the above isolated polypeptides, any of the above antisense RNAs, siRNAs, or shRNAs, any of the above vectors, or any of the above exogenous donor sequences. Optionally, the composition comprises any of the above guide RNAs and a Cas protein, such as a Cas9 protein. Optionally, such compositions comprise a carrier increasing the stability of the isolated polypeptide, the guide RNA, the antisense RNA, the siRNA, the shRNA, the isolated nucleic acid, the vector, or the exogenous donor sequence. Optionally, the carrier comprises a poly(lactic acid) (PLA) microsphere, a poly(D,L-lactic-coglycolic-acid) (PLGA) microsphere, a liposome, a micelle, an inverse micelle, a lipid cochleate, or a lipid microtubule.

Also provided are cells comprising any of the above isolated nucleic acids, any of the above guide RNAs, any of the above antisense RNAs, siRNAs, or shRNAs, any of the above isolated polypeptides, or any of the above vectors. Optionally, the cell is a human cell, a rodent cell, a mouse cell, or a rat cell. Optionally, any of the above cells are liver cells or pluripotent cells.

Also provided are uses of any of the above guide RNAs in a method of modifying an HSD17B13 gene in a cell or a method for altering expression of an HSD17B13 gene in a cell. Also provided are uses of any of the above antisense RNAs, siRNAs, or shRNAs in a method for altering expression of an HSD17B13 gene in a cell.

Also provided are methods of modifying a cell, modifying an HSD17B13 gene, or altering expression of an HSD17B13 gene. Some such methods are for modifying an HSD17B13 gene in a cell, comprising contacting the genome of the cell with: (a) a Cas protein; and (b) a guide RNA that forms a complex with the Cas protein and targets a guide RNA target sequence within the HSD17B13 gene, wherein the guide RNA target sequence includes or is proximate to a position corresponding to position 12666 of SEQ ID NO: 2 when the HSD17B13 gene is optimally aligned with SEQ ID NO: 2, wherein the Cas protein cleaves the HSD17B13 gene. Optionally, the Cas protein is a Cas9 protein. Optionally, the guide RNA target sequence comprises, consists essentially of, or consists of any one of SEQ ID NOS: 226-239 and 264-268. Optionally, the DNA-targeting segment comprises, consists essentially of, or consists of any one of SEQ ID NOS: 1629-1642 and 1648-1652. Optionally, the guide RNA comprises, consists essentially of, or consists of any one of SEQ ID NOS: 706-719; 936-949; 1166-1179, 1396-1409, 725-729, 955-959, 1185-1189, and 1415-1419. Optionally, the guide RNA target sequence is selected from SEQ ID NOS: 226-239, or wherein the guide RNA target sequence is selected from SEQ ID NOS: 230 and 231. Optionally, the guide RNA target sequence is selected from SEQ ID NOS: 226-239 and 264-268 or is selected from SEQ ID NOS: 264-268. Optionally, the guide RNA target sequence is within a region corresponding to exon 6 and/or intron 6 of SEQ ID NO: 2 when the HSD17B13 gene is optimally aligned with SEQ ID NO: 2. Optionally, the guide RNA target sequence is within a region corresponding to exon 6 and/or intron 6 and/or exon 7 of SEQ ID NO: 2 when the HSD17B13 gene is optimally aligned with SEQ ID NO: 2. Optionally, the guide RNA target sequence is within about 1000, 500, 400, 300, 200, 100, 50, 45, 40, 35, 30, 25, 20, 15, 10, or 5 nucleotides of the position corresponding to position 12666 of SEQ ID NO: 2 when the HSD17B13 gene is optimally aligned with SEQ ID NO: 2. Optionally, the guide RNA target sequence includes the position corresponding to position 12666 of SEQ ID NO: 2 when the HSD17B13 gene is optimally aligned with SEQ ID NO: 2.

Some such methods further comprise contacting the genome with an exogenous donor sequence comprising a 5' homology arm that hybridizes to a target sequence 5' of the position corresponding to position 12666 of SEQ ID NO: 2 and a 3' homology arm that hybridizes to a target sequence 3' of the position corresponding to position 12666 of SEQ ID NO: 2, wherein the exogenous donor sequence recombines with the HSD17B13 gene. Optionally, the exogenous donor sequence further comprises a nucleic acid insert flanked by the 5' homology arm and the 3' homology arm. Optionally, the nucleic acid insert comprises a thymine, and wherein upon recombination of the exogenous donor sequence with the HSD17B13 gene, the thymine is inserted between nucleotides corresponding to positions 12665 and 12666 of SEQ ID NO: 1 when the HSD17B13 gene is optimally aligned with SEQ ID NO: 1. Optionally, the exogenous donor sequence is between about 50 nucleotides to about 1 kb in length or between about 80 nucleotides to about 200 nucleotides in length. Optionally, the exogenous donor sequence is a single-stranded oligodeoxynucleotide.

Some such methods are for modifying an HSD17B13 gene in a cell, comprising contacting the genome of the cell with: (a) a Cas protein; and (b) a first guide RNA that forms a complex with the Cas protein and targets a first guide RNA target sequence within the HSD17B13 gene, wherein the first guide RNA target sequence comprises the start codon for the HSD17B13 gene or is within about 10, 20, 30, 40, 50, 100, 200, 300, 400, 500, or 1,000 nucleotides of the start codon or is selected from SEQ ID NOS: 20-81 or is selected from SEQ ID NOS: 20-81 and 259-263, wherein the Cas protein cleaves or alters expression of the HSD17B13 gene. Optionally, the first guide RNA target sequence comprises, consists essentially of, or consists of any one of SEQ ID NOS: 20-81 and 259-263. Optionally, the first guide RNA target sequence comprises, consists essentially of, or consists of any one of SEQ ID NOS: 20-41, any one of SEQ ID NOS: 21-23, 33, and 35, or any one of SEQ ID NOS: 33 and 35. Optionally, the first guide RNA comprises, consists essentially of, or consists of a DNA-targeting segment that comprises any one of SEQ ID NOS: 1423-1484 and 1643-1647. Optionally, the first guide RNA comprises, consists essentially of, or consists of a DNA-targeting segment that comprises any one of SEQ ID NOS: 1447-1468, any one of SEQ ID NOS: 1448-1450, 1460, and 1462; or any one of SEQ ID NOS: 1460 and 1462. Optionally, the first guide RNA comprises, consists essentially of, or consists of any one of SEQ ID NOS: 500-561, 730-791, 960-1021, 1190-1251, 720-724, 950-954, 1180-1184, and 1410-1414. Optionally, the first guide RNA comprises, consists essentially of, or consists of any one of SEQ ID NOS: 524-545, 754-775, 984-1005, and 1214-1235, or any one of SEQ ID NOS: 295-297, 525-527, 755-757, 985-987, 1215-1217, 307, 309, 537, 539, 767, 769, 997, 999, 1227, and 1229, or any one of SEQ ID NOS: 307, 309, 537, 539, 767, 769, 997, 999, 1227, and 1229. Optionally, the first guide RNA target sequence is selected from SEQ ID NOS: 20-41, is selected from SEQ ID NOS: 21-23, 33, and 35, or is selected from SEQ ID NOS: 33 and 35. Optionally, the Cas protein is a Cas9 protein. Optionally, the Cas protein is a nuclease-active Cas protein. Optionally, the Cas protein is a nuclease-inactive Cas protein fused to a transcriptional activator domain or a nuclease-inactive Cas protein fused to a transcriptional repressor domain.

Some such methods further comprise contacting the genome of the cell with a second guide RNA that forms a complex with the Cas protein and targets a second guide RNA target sequence within the HSD17B13 gene, wherein the second guide RNA target sequence comprises the stop codon for the HSD17B13 gene or is within about 10, 20, 30, 40, 50, 100, 200, 300, 400, 500, or 1,000 nucleotides of the stop codon or is selected from SEQ ID NOS: 82-225, wherein the cell is modified to comprise a deletion between the first guide RNA target sequence and the second guide RNA target sequence. Optionally, the second guide RNA target sequence comprises, consists essentially of, or consists of any one of SEQ ID NOS: 82-225. Optionally, the second guide RNA comprises, consists essentially of, or consists of a DNA-targeting segment that comprises any one of SEQ ID NOS: 1485-1628. Optionally, the second guide RNA comprises, consists essentially of, or consists of any one of SEQ ID NOS: 562-705, 792-935, 1022-1165, and 1252-1395.

Some such methods are for decreasing expression of an HSD17B13 gene in a cell or decreasing expression of a particular HSD17B13 transcript (e.g., Transcript A or Transcript D) in a cell. Some such methods are for decreasing expression of an HSD17B13 gene in a cell, comprising: contacting the genome of the cell with an antisense RNA, an siRNA, or an shRNA that hybridizes to a sequence within exon 7 of SEQ ID NO: 4 (HSD17B13 Transcript A) and decreases expression of HSD17B13 Transcript A. Some such methods are for decreasing expression of an HSD17B13 gene in a cell, comprising: contacting the genome of the cell with an antisense RNAs, an siRNA, or an shRNA that hybridizes to a sequence within an HSD17B13 transcript disclosed herein. In some such methods, the antisense RNA, siRNA, or shRNA hybridizes to a sequence within SEQ ID NO: 4 (HSD17B13 Transcript A). Optionally, the antisense RNA, siRNA, or shRNA can decrease expression of HSD17B13 Transcript A in a cell. Optionally, the antisense RNA, siRNA, or shRNA hybridizes to a sequence present in SEQ ID NO: 4 (HSD17B13 Transcript A) that is not present in SEQ ID NO: 7 (HSD17B13 Transcript D). Optionally, the antisense RNA, siRNA, or shRNA hybridizes to a sequence within exon 7 or a sequence spanning the exon 6-exon 7 boundary of SEQ ID NO: 4 (HSD17B13 Transcript A). In some such methods, the antisense RNA, siRNA, or shRNA hybridizes to a sequence within SEQ ID NO: 7 (HSD17B13 Transcript D). Optionally, the antisense RNA, siRNA, or shRNA can decrease expression of HSD17B13 Transcript D in a cell. Optionally, the antisense RNA, siRNA, or shRNA hybridizes to a sequence present in SEQ ID NO: 7 (HSD17B13 Transcript D) that is not present in SEQ ID NO: 4 (HSD17B13 Transcript A). Optionally, the antisense RNA, siRNA, or shRNA hybridizes to a sequence within exon 7 or a sequence spanning the exon 6-exon 7 boundary of SEQ ID NO: 7 (HSD17B13 Transcript D).

In any of the above methods for of modifying an HSD17B13 gene or altering expression of an HSD17B13 gene, the method can further comprise introducing an expression vector into the cell, wherein the expression vector comprises a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. Optionally, the recombinant HSD17B13 gene is a human gene. Optionally, the recombinant HSD17B13 gene is an HSD17B13 minigene in which one or more nonessential segments of the gene have been deleted with respect to a corresponding wild type HSD17B13 gene. Optionally, the deleted segments comprise one or more intronic sequences. Optionally, the HSD17B13 minigene comprises an intron corresponding to intron 6 of SEQ ID NO: 2 when optimally aligned with SEQ ID NO: 2.

In any of the above methods for of modifying an HSD17B13 gene or altering expression of an HSD17B13 gene, the method can further comprise introducing an expression vector into the cell, wherein the expression vector comprises a nucleic acid encoding an HSD17B13 protein that is at least 90%, at least 95%, at least 96%, at least 97%, at least 98%, at least 99%, or 100% identical to SEQ ID NO: 15 (HSD17B13 Isoform D). Optionally, the nucleic acid encoding the HSD17B13 protein is at least 90%, at least 95%, at least 96%, at least 97%, at least 98%, at least 99%, or 100% identical to SEQ ID NO: 7 (HSD17B13 Transcript D) when optimally aligned with SEQ ID NO: 7.

In any of the above methods for of modifying an HSD17B13 gene or altering expression of an HSD17B13 gene, the method can further comprise introducing an HSD17B13 protein or fragment thereof into the cell. Optionally, the HSD17B13 protein or fragment thereof is at least 90%, at least 95%, at least 96%, at least 97%, at least 98%, at least 99%, or 100% identical to SEQ ID NO: 15 (HSD17B13 Isoform D).

Some such methods are for modifying a cell, comprising introducing an expression vector into the cell, wherein the expression vector comprises a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. Optionally, the recombinant HSD17B13 gene is a human gene. Optionally, the recombinant HSD17B13 gene is an HSD17B13 minigene in which one or more nonessential segments of the gene have been deleted with respect to a corresponding wild type HSD17B13 gene. Optionally, the deleted segments comprise one or more intronic sequences. Optionally, the HSD17B13 minigene comprises an intron corresponding to intron 6 of SEQ ID NO: 2 when optimally aligned with SEQ ID NO: 2.

Some such methods are for modifying a cell, comprising introducing an expression vector into the cell, wherein the expression vector comprises a nucleic acid encoding an HSD17B13 protein that is at least 90%, at least 95%, at least 96%, at least 97%, at least 98%, at least 99%, or 100% identical to SEQ ID NO: 15 (HSD17B13 Isoform D). Optionally, the nucleic acid encoding the HSD17B13 protein is at least 90%, at least 95%, at least 96%, at least 97%, at least 98%, at least 99%, or 100% identical to SEQ ID NO: 7 (HSD17B13 Transcript D) when optimally aligned with SEQ ID NO: 7.

Some such methods are for modifying a cell, comprising introducing an HSD17B13 protein or fragment thereof into the cell. Optionally, the HSD17B13 protein or fragment thereof is at least 90%, at least 95%, at least 96%, at least 97%, at least 98%, at least 99%, or 100% identical to SEQ ID NO: 15 (HSD17B13 Isoform D).

In any of the above methods of modifying a cell, modifying an HSD17B13 gene, or altering expression of an HSD17B13 gene, the cell can be a human cell, a rodent cell, a mouse cell, or a rat cell. Any of the cells can be pluripotent cells or differentiated cells. Any of the cells can be liver cells. In any of the above methods of modifying a cell, modifying an HSD17B13 gene, or altering expression of an HSD17B13 gene, the method or cell can be ex vivo or in vivo. The guide RNAs used in any of the above methods can be modular guide RNAs comprising separate crRNA and tracrRNA molecules that hybridize to each other or a single-guide RNA in which the crRNA portion is fused to the tracrRNA portion (e.g., by a linker).

In another aspect, provided are methods of treating a subject who has or is susceptible to developing a chronic liver disease. In another aspect, provided are methods of treating a subject who has or is susceptible to developing an alcoholic or nonalcoholic liver disease. Such subjects can be, for example, a subject who is not a carrier of the HSD17B13 rs72613567 variant or subject who is not a homozygous carrier of the HSD17B13 rs72613567 variant. Some such methods comprise a method of treating a subject who is not a carrier of the HSD17B13 rs72613567 variant and has or is susceptible to developing a chronic liver disease, comprising introducing into the subject: (a) a Cas protein or a nucleic acid encoding the Cas protein; (b) a guide RNA or a nucleic acid encoding the guide RNA, wherein the guide RNA forms a complex with the Cas protein and targets a guide RNA target sequence within an HSD17B13 gene, wherein the guide RNA target sequence includes or is proximate to a position corresponding to position 12666 of SEQ ID NO: 2 when the HSD17B13 gene is optimally aligned with SEQ ID NO: 2; and (c) an exogenous donor sequence comprising a 5' homology arm that hybridizes to a target sequence 5' of the position corresponding to position 12666 of SEQ ID NO: 2, a 3' homology arm that hybridizes to a target sequence 3' of the position corresponding to position 12666 of SEQ ID NO: 2, and a nucleic acid insert comprising a thymine flanked by the 5' homology arm and the 3' homology arm, wherein the Cas protein cleaves the HSD17B13 gene in a liver cell in the subject and the exogenous donor sequence recombines with the HSD17B13 gene in the liver cell, wherein upon recombination of the exogenous donor sequence with the HSD17B13 gene, the thymine is inserted between nucleotides corresponding to positions 12665 and 12666 of SEQ ID NO: 1 when the HSD17B13 gene is optimally aligned with SEQ ID NO: 1.

Optionally, the guide RNA target sequence is selected from SEQ ID NOS: 226-239, or wherein the guide RNA target sequence is selected from SEQ ID NOS: 230 and 231. Optionally, the guide RNA target sequence is selected from SEQ ID NOS: 226-239 and 264-268. Optionally, the guide RNA target sequence is within a region corresponding to exon 6 and/or intron 6 of SEQ ID NO: 2 when the HSD17B13 gene is optimally aligned with SEQ ID NO: 2. Optionally, the guide RNA target sequence is within a region corresponding to exon 6 and/or intron 6 and/or exon 7 of SEQ ID NO: 2 when the HSD17B13 gene is optimally aligned with SEQ ID NO: 2. Optionally, the guide RNA target sequence is within about 1000, 500, 400, 300, 200, 100, 50, 45, 40, 35, 30, 25, 20, 15, 10, or 5 nucleotides of the position corresponding to position 12666 of SEQ ID NO: 2 when the HSD17B13 gene is optimally aligned with SEQ ID NO: 2. Optionally, the guide RNA target sequence includes the position corresponding to position 12666 of SEQ ID NO: 2 when the HSD17B13 gene is optimally aligned with SEQ ID NO: 2.

Optionally, the exogenous donor sequence is between about 50 nucleotides to about 1 kb in length. Optionally, the exogenous donor sequence is between about 80 nucleotides to about 200 nucleotides in length. Optionally, the exogenous donor sequence is a single-stranded oligodeoxynucleotide.

Some such methods comprise a method of treating a subject who is not a carrier of the HSD17B13 rs72613567 variant and has or is susceptible to developing a chronic liver disease, comprising introducing into the subject: (a) a Cas protein or a nucleic acid encoding the Cas protein; (b) a first guide RNA or a nucleic acid encoding the first guide RNA, wherein the first guide RNA forms a complex with the Cas protein and targets a first guide RNA target sequence within an HSD17B13 gene, wherein the first guide RNA target sequence comprises the start codon for the HSD17B13 gene or is within about 10, 20, 30, 40, 50, 100, 200, 300, 400, 500, or 1,000 nucleotides of the start codon or is selected from SEQ ID NOS: 20-81 or is selected from SEQ ID NOS: 20-81 and 259-263; and (c) an expression vector comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1, wherein the Cas protein cleaves or alters expression of the HSD17B13 gene in a liver cell in the subject and the expression vector expresses the recombinant HSD17B13 gene in the liver cell in the subject. Some such methods comprise a method of treating a subject who is not a carrier of the HSD17B13 rs72613567 variant and has or is susceptible to developing a chronic liver disease, comprising introducing into the subject: (a) a Cas protein or a nucleic acid encoding the Cas protein; (b) a first guide RNA or a nucleic acid encoding the first guide RNA, wherein the first guide RNA forms a complex with the Cas protein and targets a first guide RNA target sequence within an HSD17B13 gene, wherein the first guide RNA target sequence comprises the start codon for the HSD17B13 gene or is within about 10, 20, 30, 40, 50, 100, 200, 300, 400, 500, or 1,000 nucleotides of the start codon or is selected from SEQ ID NOS: 20-81 or is selected from SEQ ID NOS: 20-81 and 259-263; and optionally (c) an expression vector comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1, wherein the Cas protein cleaves or alters expression of the HSD17B13 gene in a liver cell in the subject and the expression vector expresses the recombinant HSD17B13 gene in the liver cell in the subject.

Optionally, the first guide RNA target sequence is selected from SEQ ID NOS: 20-41, is selected from SEQ ID NOS: 21-23, 33, and 35, or is selected from SEQ ID NOS: 33 and 35. Optionally, the Cas protein is a nuclease-active Cas protein. Optionally, the Cas protein is a nuclease-inactive Cas protein fused to a transcriptional repressor domain.

Such methods can further comprise introducing into the subject a second guide RNA, wherein the second guide RNA forms a complex with the Cas protein and targets a second guide RNA target sequence within the HSD17B13 gene, wherein the second guide RNA target sequence comprises the stop codon for the HSD17B13 gene or is within about 10, 20, 30, 40, 50, 100, 200, 300, 400, 500, or 1,000 nucleotides of the stop codon or is selected from SEQ ID NOS: 82-225, wherein the Cas protein cleaves the HSD17B13 gene in the liver cell within both the first guide RNA target sequence and the second guide RNA target sequence, wherein the liver cell is modified to comprise a deletion between the first guide RNA target sequence and the second guide RNA target sequence.

Optionally, the recombinant HSD17B13 gene is an HSD17B13 minigene in which one or more nonessential segments of the gene have been deleted with respect to a corresponding wild type HSD17B13 gene. Optionally, the deleted segments comprise one or more intronic sequences. Optionally, the HSD17B13 minigene comprises an intron corresponding to intron 6 of SEQ ID NO: 2 when optimally aligned with SEQ ID NO: 2.

In any of the above therapeutic or prophylactic methods, the Cas protein can be a Cas9 proteins. In any of the above therapeutic or prophylactic methods, the subject can be a human. In any of the above therapeutic or prophylactic methods, the chronic liver disease can be a fatty liver disease, a nonalcoholic fatty liver disease (NAFLD), an alcoholic liver fatty liver disease, a cirrhosis, or a hepatocellular carcinoma. Likewise, in any of the above methods, the therapeutic or prophylactic method can be for a liver disease that is an alcoholic liver disease or a nonalcoholic liver disease.

Some such methods comprise a method of treating a subject who is not a carrier of the HSD17B13 rs72613567 variant and has or is susceptible to developing a chronic liver disease, comprising introducing into the subject: an antisense RNA, an siRNA, or an shRNA that hybridizes to a sequence within exon 7 or a sequence spanning the exon 6-exon 7 boundary of SEQ ID NO: 4 (HSD17B13 Transcript A) and decreases expression of HSD17B13 Transcript A in a liver cell in the subject. Some such methods comprise a method of treating a subject who is not a carrier of the HSD17B13 rs72613567 variant and has or is susceptible to developing a chronic liver disease, comprising introducing into the subject: an antisense RNAs, an siRNA, or an shRNA that hybridizes to a sequence within an HSD17B13 transcript disclosed herein. Optionally, the antisense RNA, siRNA, or shRNA hybridizes to a sequence within SEQ ID NO: 4 (HSD17B13 Transcript A). Optionally, the antisense RNA, siRNA, or shRNA can decrease expression of HSD17B13 Transcript A in a cell. Optionally, the antisense RNA, siRNA, or shRNA hybridizes to a sequence present in SEQ ID NO: 4 (HSD17B13 Transcript A) that is not present in SEQ ID NO: 7 (HSD17B13 Transcript D). Optionally, the antisense RNA, siRNA, or shRNA hybridizes to a sequence within exon 7 or a sequence spanning the exon 6-exon 7 boundary of SEQ ID NO: 4 (HSD17B13 Transcript A).

Optionally, such methods further comprise introducing an expression vector into the subject, wherein the expression vector comprises a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1, wherein the expression vector expresses the recombinant HSD17B13 gene in the liver cell in the subject.

Optionally, such methods further comprise introducing an expression vector into the subject, wherein the expression vector comprises a nucleic acid encoding an HSD17B13 protein that is at least 90%, at least 95%, at least 96%, at least 97%, at least 98%, at least 99%, or 100% identical to SEQ ID NO: 15 (HSD17B13 Isoform D), wherein the expression vector expresses the nucleic acid encoding the HSD17B13 protein in the liver cell in the subject. Optionally, the nucleic acid encoding the HSD17B13 protein is at least 90%, at least 95%, at least 96%, at least 97%, at least 98%, at least 99%, or 100% identical to SEQ ID NO: 7 (HSD17B13 Transcript D) when optimally aligned with SEQ ID NO: 7.

Optionally, such methods further comprise introducing a messenger RNA into the subject, wherein the messenger RNA encodes an HSD17B13 protein that is at least 90%, at least 95%, at least 96%, at least 97%, at least 98%, at least 99%, or 100% identical to SEQ ID NO: 15 (HSD17B13 Isoform D), wherein the mRNA expresses the HSD17B13 protein in the liver cell in the subject. Optionally, a complementary DNA reverse transcribed from the messenger RNA is at least 90%, at least 95%, at least 96%, at least 97%, at least 98%, at least 99%, or 100% identical to SEQ ID NO: 7 (HSD17B13 Transcript D) when optimally aligned with SEQ ID NO: 7.

Optionally, such methods further comprise introducing an HSD17B13 protein or fragment thereof into the subject. Optionally, the HSD17B13 protein or fragment thereof is at least 90%, at least 95%, at least 96%, at least 97%, at least 98%, at least 99%, or 100% identical to SEQ ID NO: 15 (HSD17B13 Isoform D).

Some such methods comprise a method of treating a subject who is not a carrier of the HSD17B13 rs72613567 variant and has or is susceptible to developing a chronic liver disease comprising introducing an expression vector into the subject, wherein the expression vector comprises a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1, wherein the expression vector expresses the recombinant HSD17B13 gene in a liver cell in the subject.

In any of the above methods, the recombinant HSD17B13 gene can be a human gene. In any of the above methods, the recombinant HSD17B13 gene can be at least 90%, at least 95%, at least 96%, at least 97%, at least 98%, or at least 99% identical to SEQ ID NO: 2 when optimally aligned with SEQ ID NO: 2. In any of the above methods, the recombinant HSD17B13 gene can be an HSD17B13 minigene in which one or more nonessential segments of the gene have been deleted with respect to a corresponding wild type HSD17B13 gene. Optionally, the deleted segments comprise one or more intronic sequences. Optionally, the HSD17B13 minigene comprises an intron corresponding to intron 6 of SEQ ID NO: 2 when optimally aligned with SEQ ID NO: 2.

Some such methods comprise a method of treating a subject who is not a carrier of the HSD17B13 rs72613567 variant and has or is susceptible to developing a chronic liver disease comprising introducing an expression vector into the subject, wherein the expression vector comprises a nucleic acid encoding an HSD17B13 protein that is at least 90%, at least 95%, at least 96%, at least 97%, at least 98%, at least 99%, or 100% identical to SEQ ID NO: 15 (HSD17B13 Isoform D), wherein the expression vector expresses the nucleic acid encoding the HSD17B13 protein in a liver cell in the subject. Optionally, the nucleic acid encoding the HSD17B13 protein is at least 90%, at least 95%, at least 96%, at least 97%, at least 98%, at least 99%, or 100% identical to SEQ ID NO: 7 (HSD17B13 Transcript D) when optimally aligned with SEQ ID NO: 7.

Some such methods comprise a method of treating a subject who is not a carrier of the HSD17B13 rs72613567 variant and has or is susceptible to developing a chronic liver disease comprising introducing a messenger RNA into the subject, wherein the messenger RNA encodes an HSD17B13 protein that is at least 90%, at least 95%, at least 96%, at least 97%, at least 98%, at least 99%, or 100% identical to SEQ ID NO: 15 (HSD17B13 Isoform D), wherein the mRNA expresses the HSD17B13 protein in the liver cell in the subject. Optionally, a complementary DNA reverse transcribed from the messenger RNA is at least 90%, at least 95%, at least 96%, at least 97%, at least 98%, at least 99%, or 100% identical to SEQ ID NO: 7 (HSD17B13 Transcript D) when optimally aligned with SEQ ID NO: 7.

Some such methods comprise a method of treating a subject who is not a carrier of the HSD17B13 rs72613567 variant and has or is susceptible to developing a chronic liver disease comprising introducing an HSD17B13 protein or fragment thereof into the liver of the subject. Optionally, the HSD17B13 protein or fragment thereof is at least 90%, at least 95%, at least 96%, at least 97%, at least 98%, at least 99%, or 100% identical to SEQ ID NO: 15 (HSD17B13 Isoform D).

In any of the above methods, the subject can be a human. In any of the above methods, the chronic liver disease can be nonalcoholic fatty liver disease (NAFLD), alcoholic liver fatty liver disease, cirrhosis, or hepatocellular carcinoma. Likewise, in any of the above methods, the therapeutic or prophylactic method can be for a liver disease that is an alcoholic liver disease or a nonalcoholic liver disease. In any of the above methods, the introducing into the subject can comprise hydrodynamic delivery, virus-mediated delivery, lipid-nanoparticle-mediated delivery, or intravenous infusion.

BRIEF DESCRIPTION OF THE FIGURES

FIG. 1A) and aspartate aminotransferase (AST; FIG. 1B) levels in the GHS discovery cohort. FIG. 1A shows that there were 31 variants in 16 genes significantly associated with ALT levels (N=41,414) at $P<1.0\times10^{-7}$. FIG. 1B shows that there were 12 variants in 10 genes significantly associated with AST levels (N=40,753) at $P<1.0\times10^{-7}$. All significant associations are shown in Table 2. There were thirteen variants in nine genes (indicated here by their gene name), including HSD17B13, that remained significantly associated with ALT or AST in a replication meta-analysis of three separate European-ancestry cohorts (Table 3). The association tests were well calibrated, as shown by exome-wide quantile-quantile plots and genomic control lambda values (FIG. 1A and FIG. 1B).

FIGS. 3A-3D show expression of four HSD17B13 Transcripts (A-D) in homozygous reference (T/T), heterozygous (T/TA), and homozygous alternate (TA/TA) carriers of the HSD17B13 rs72613567 splice variant. Each transcript is illustrated with a corresponding gene model. Coding regions in gene models are indicated in the striped boxes and untranslated regions in the black boxes. FIG. 3A shows a representation of Transcript A and expression data for Transcript A. FIG. 3B shows a representation of Transcript B and expression data for Transcript B. In Transcript B, exon 2 is skipped. FIG. 3C shows a representation of Transcript C and expression data for Transcript C. In Transcript C, exon 6 is skipped. FIG. 3D shows a representation of Transcript D and expression data for Transcript D. The asterisk in Transcript D illustrates insertion of G from rs72613567 at the 3' end of exon 6, which leads to premature truncation of the protein. Transcript D becomes the dominant transcript in homozygous carriers of the HSD17B13 splice variant. Gene expression is displayed in FPKM units (Fragments Per Kilobase of transcript per Million mapped reads). Insets in FIG. 3B and FIG. 3C show a zoomed-in view.

FIGS. 6A and 6D show that Transcripts E and H contain an additional exon between exons 3 and 4. FIG. 6B shows that Transcript F involves read-through from exon 6 to intron 6. FIG. 6C shows that in Transcript G, exon 2 is skipped. The asterisk in Transcripts G and H (FIGS. 6C and 6D, respectively) illustrates insertion of G from rs72613567 at the 3' end of exon 6, which leads to premature truncation of the protein. The transcripts are differentially expressed according to HSD17B13 genotype, as shown in the box plots. mRNA expression is displayed in FPKM units (Fragments Per Kilobase of transcript per Million mapped reads).

FIGS. 7A-7B show a protein sequence alignment of HSD17B13 protein isoforms A-H.

FIG. 8 shows in the Dallas Liver Study, HSD17B13 rs72613567 was associated with lower odds of any liver disease in an allele dosage-dependent manner. Similar allele dosage-dependent effects were observed across liver disease subtypes. Odds ratios were calculated using logistic regression, with adjustment for age, $age^2$, gender, BMI, and self-reported ethnicity.

FIGS. 10A-10E show expression, subcellular localization, and enzymatic activity of a novel HSD17B13 transcript. FIG. 10A shows a Western blot from HepG2 cells overexpressing HSD17B13 Transcripts A and D and shows that HSD17B13 Transcript D was translated to a truncated protein with lower molecular weight compared to HSD17B13 Transcript A. FIG. 10B shows HSD17B13 western blots from fresh frozen human liver and HEK293 cell samples. Human liver samples are from homozygous reference (T/T), heterozygous (T/TA), and homozygous alternate (TA/TA) carriers of the HSD17B13 rs72613567 splice variant. Cell samples are from HEK293 cells overexpressing non-tagged HSD17B13 Transcripts A and D. HSD17B13 Transcript D was translated to a truncated protein IsoD with lower molecular weight than HSD17B13 IsoA. FIG. 10C shows HSD17B13 IsoD protein levels were lower than IsoA protein levels from both human liver (left) and cell (right) samples. Protein level normalized to actin is shown in the bar columns; **P<0.001, *P<0.05. FIG. 10D shows enzymatic activity of HSD17B13 isoforms A and D to 17-beta estradiol (estradiol), leukotriene B4 (LTB4), and 13-Hydroxyoctadecadienoic acid (13(S)-HODE). HSD17B13 Isoform D shows <10% enzymatic activity of the corresponding values for Isoform A. FIG. 10E shows HSD17B13 Isoform D when overexpressed in HEK293 cells did not show much conversion of estradiol (substrate) to estrone (product) when measured in the culture media, while overexpressed HSD17B13 Isoform A showed robust conversion.

FIG. 11A shows RT-PCR of HSD17B13 from HEK 293 cells overexpressing HSD17B13 Transcripts A (IsoA) and D (IsoD), indicating that HSD17B13 IsoD RNA level was higher than IsoA RNA level. FIG. 11B shows a western blot from the same cell lines indicating that HSD17B13 Transcript D was translated to a truncated protein with lower molecular weight compared to HSD17B13 Transcript A. FIG. 11C shows that HSD17B13 IsoD protein levels were lower than IsoA protein levels although the RNA level was higher. HSD17B13 protein level was normalized to actin; *P<0.05.

FIG. 13A shows treatment with increasing concentrations of oleic acid increased triglyceride (TG) content to a similar extent in control (GFP overexpressing cells) and HSD17B13 Transcript A and D cell lines. FIG. 13B shows HSD17B13 Transcripts A and D RNA levels were similar in the cell lines. RNA levels are shown reads per kilobase of transcript per million mapped reads (RPKM). FIG. 13C shows a western blot from HepG2 cells overexpressing HSD17B13 Transcripts A and D. HSD17B13 Transcript D was translated to a truncated protein with lower molecular weight compared to HSD17B13 Transcript A. FIG. 13D shows HSD17B13 IsoD protein levels were lower than IsoA protein levels. Protein level normalized to actin; **P<0.01.

DEFINITIONS

Figure 1A:
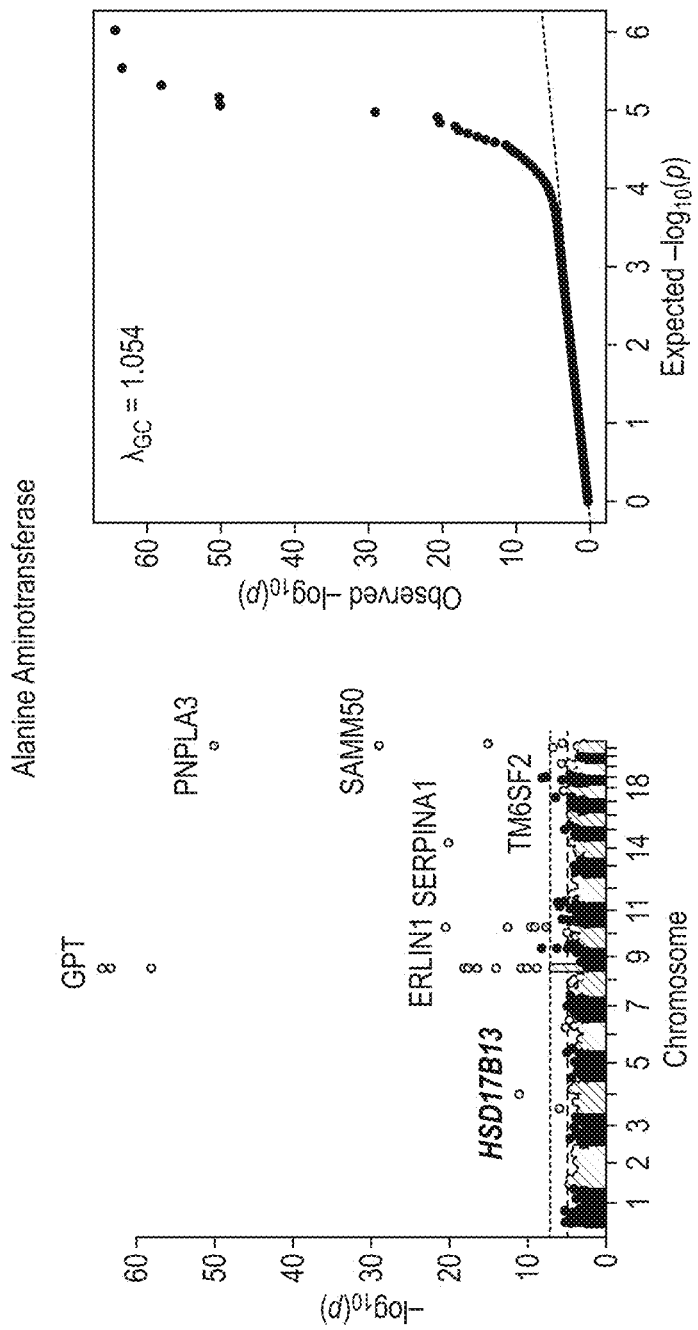
FIGS. 1A and 1B show Manhattan plots (left) and quantile-quantile plots (right) of single nucleotide variant associations with median alanine aminotransferase (ALT.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "wild type" includes entities having a structure and/or activity as found in a normal (as contrasted with mutant, diseased, altered, or so forth) state or context. Wild type genes and polypeptides often exist in multiple different forms (e.g., alleles).

The term "isolated" with respect to proteins and nucleic acid includes proteins and nucleic acids that are relatively purified with respect to other bacterial, viral, or cellular components that may normally be present in situ, up to and including a substantially pure preparation of the protein and the polynucleotide. The term "isolated" also includes proteins and nucleic acids that have no naturally occurring counterpart, have been chemically synthesized and are thus substantially uncontaminated by other proteins or nucleic acids, or has been separated or purified from most other cellular components with which they are naturally accompanied (e.g., other cellular proteins, polynucleotides, or cellular components).

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two portions that do not naturally occur together. Likewise, the term "heterologous" when used in the context of a promoter operably linked to a nucleic acid encoding a protein indicates that the promoter and the nucleic acid encoding the protein do not naturally occur together (i.e., are not naturally operably linked). For example, the term "heterologous," when used with reference to portions of a nucleic acid or portions of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

The term "label" refers to a chemical moiety or protein that is directly or indirectly detectable (e.g., due to its spectral properties, conformation, or activity) when attached to a target compound. The label can be directly detectable (fluorophore) or indirectly detectable (hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a calorimetric substrate (e.g., tetramethylbenzidine (TMB)) or a fluorogenic substrate to detect the presence of HRP. The term "label" can also refer to a tag that can be used, for example, to facilitate purification. Non-limiting examples of such tags include myc, HA, FLAG or 3×FLAG, 6× His or polyhistidine, glutathione-S-transferase (GST), maltose binding protein, an epitope tag, or the Fc portion of immunoglobulin. Numerous labels are known and include, for example, particles, fluorophores, haptens, enzymes and their calorimetric, fluorogenic and chemiluminescent substrates and other labels.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "HSD17B13 locus" may refer to the specific location of an HSD17B13 gene, HSD17B13 DNA sequence, HSD17B13-encoding sequence, or HSD17B13 position on a chromosome of the genome of an organism that has been identified as to where such a sequence resides. An "HSD17B13 locus" may comprise a regulatory element of an HSD17B13 gene, including, for example, an enhancer, a promoter, 5' and/or 3' UTR, or a combination thereof.

The term "gene" refers to a DNA sequence in a chromosome that codes for a product (e.g., an RNA product and/or a polypeptide product) and includes the coding region interrupted with one or more non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene. The term "gene" also encompasses "minigenes."

The term "minigene" refers to a gene in which one or more nonessential segments of the gene have been deleted with respect to a corresponding naturally occurring germline gene but in which at least one intron remains. Deleted segments can be intronic sequences. For example, deleted segments can be intronic sequences of at least about 500 base pairs to several kilobases. Typically, intronic sequences that do not encompass essential regulatory elements may be deleted. The gene segments comprising a minigene will typically be arranged in the same linear order as is present in the germline gene, but this will not always be the case. Some desired regulatory elements (e.g., enhancers, silencers) may be relatively position-insensitive so that the regulatory element will function correctly even if positioned differently in a minigene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a minigene. Similarly, some genes may have exons which are alternatively spliced at the RNA level. Thus, a minigene may have fewer exons and/or exons in a different linear order than the corresponding germline gene and still encode a functional gene product. A cDNA encoding a gene product may also be used to construct a minigene (e.g., a hybrid cDNA-genomic fusion).

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

The term "variant" or "genetic variant" refers to a nucleotide sequence differing from the sequence most prevalent in a population (e.g., by one nucleotide). For example, some variations or substitutions in a nucleotide sequence alter a codon so that a different amino acid is encoded resulting in a genetic variant polypeptide. The term "variant" can also refer to a gene differing in sequence from the sequence most prevalent in a population at a position that does not change the amino acid sequence of the encoded polypeptide (i.e., a conserved change). Genetic variants can be associated with risk, associated with protection, or can be neutral.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "primer" refers to an oligonucleotide capable of acting as a point of initiation of polynucleotide synthesis along a complementary strand when placed under conditions in which synthesis of a primer extension product complementary to a polynucleotide is catalyzed. Such conditions include the presence of four different nucleotide triphosphates or nucleoside analogs and one or more agents for polymerization, such as DNA polymerase and/or reverse transcriptase, in an appropriate buffer (including substituents which are cofactors, or which affect pH, ionic strength, and so forth), and at a suitable temperature. Extension of the primer in a sequence specific manner can include, for example, methods of PCR, DNA sequencing, DNA extension, DNA polymerization, RNA transcription, or reverse transcription. A primer must be sufficiently long to prime the synthesis of extension products in the presence of an agent for polymerase. A typical primer is at least about 5 nucleotides in length of a sequence substantially complementary to the target sequence, but longer primers are preferred. Typically, primers are about 15-30 nucleotides in length, but longer primers may also be employed. A primer sequence need not be exactly complementary to a template or target sequence but must be sufficiently complementary to hybridize with a template or target sequence. The term "primer pair" means a set of primers including a 5' upstream primer, which hybridizes to the 5' end of the DNA sequence to be amplified and a 3' downstream primer, which hybridizes to the complement of the 3' end of the sequence to be amplified. Primer pairs can be used for amplification of a target polynucleotide (e.g., by polymerase chain reaction (PCR) or other conventional nucleic-acid amplification methods). "PCR" or "polymerase chain reaction" is a technique used for the amplification of specific DNA segments (see U.S. Pat. Nos. 4,683,195 and 4,800,159, each of which is herein incorporated by reference in its entirety for all purposes).

The term "probe" refers to a molecule which can detectably distinguish between target molecules differing in structure. Detection can be accomplished in a variety of different ways depending on the type of probe used and the type of target molecule. Thus, for example, detection may be based on discrimination of activity levels of the target molecule, but preferably is based on detection of specific binding. Examples of such specific binding include antibody binding and nucleic acid probe hybridization. Thus, probes can include, for example, enzyme substrates, antibodies and antibody fragments, and nucleic acid hybridization probes. For example, a probe can be an isolated polynucleotide attached to a conventional detectable label or reporter molecule, such as a radioactive isotope, ligand, chemiluminescent agent, enzyme, or the like. Such a probe is complementary to a strand of a target polynucleotide, such as a polynucleotide comprising the HSD17B13 rs72613567 variant or specific HSD17B13 mRNA transcripts. Deoxyribonucleic acid probes may include those generated by PCR using HSD17B13-mRNA/cDNA-specific primers or HSD17B13-rs72613567-specific primers, oligonucleotide probes synthesized in vitro, or DNA obtained from bacterial artificial chromosome, fosmid, or cosmid libraries. Probes include not only deoxyribonucleic or ribonucleic acids but also polyamides and other probe materials that can specifically detect the presence of a target DNA sequence. For nucleic acid probes, detection reagents can include, for example, radiolabeled probes, enzymatic labeled probes (e.g., horse radish peroxidase and alkaline phosphatase), affinity labeled probes (e.g., biotin, avidin, and streptavidin), and fluorescent labeled probes (e.g., 6-FAM, VIC, TAMRA, MGB, fluorescein, rhodamine, and texas red). The nucleic acid probes described herein can readily be incorporated into one of the established kit formats which are well known.

The term "antisense RNA" refers to a single-stranded RNA that is complementary to a messenger RNA strand transcribed in a cell.

The term "small interfering RNA (siRNA)" refers to a typically double-stranded RNA molecule that induces the RNA interference (RNAi) pathway. These molecules can vary in length (generally between 18-30 base pairs) and contain varying degrees of complementarity to their target mRNA in the antisense strand. Some, but not all, siRNAs have unpaired overhanging bases on the 5' or 3' end of the sense strand and/or the antisense strand. The term "siRNA" includes duplexes of two separate strands, as well as single strands that can form hairpin structures comprising a duplex region. The double-stranded structure can be, for example, less than 20, 25, 30, 35, 40, 45, or 50 nucleotides in length. For example, the double-stranded structure can be from about 21-23 nucleotides in length, from about 19-25 nucleotides in length, or from about 19-23 nucleotides in length.

The term "short hairpin RNA (shRNA)" refers to a single strand of RNA bases that self-hybridizes in a hairpin structure and can induce the RNA interference (RNAi) pathway upon processing. These molecules can vary in length (generally about 50-90 nucleotides in length, or in some cases up to greater than 250 nucleotides in length, e.g., for micro-RNA-adapted shRNA). shRNA molecules are processed within the cell to form siRNAs, which in turn can knock down gene expression. shRNAs can be incorporated into vectors. The term "shRNA" also refers to a DNA molecule from which a short, hairpin RNA molecule may be transcribed.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. Some components throughout the description can have active variants and fragments. Such components include, for example, Cas9 proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A subject nucleic acid such as a primer or a guide RNA hybridizes to or targets a position or includes a position proximate to a specified nucleotide position in a reference nucleic acid when it is within about 1000, 500, 400, 300, 200, 100, 50, 45, 40, 35, 30, 25, 20, 15, 10, or 5 nucleotides of the position.

The term "biological sample" refers to a sample of biological material, within or obtainable from a subject, from which a nucleic acid or protein is recoverable. The term biological sample can also encompass any material derived by processing the sample, such as cells or their progeny. Processing of the biological sample may involve one or more of filtration, distillation, extraction, concentration, fixation, inactivation of interfering components, and the like. In some embodiments, a biological sample comprises a nucleic acid, such as genomic DNA, cDNA, or mRNA. In some embodiments, a biological sample comprises a protein. A subject can be any organism, including, for example, a human, a non-human mammal, a rodent, a mouse, or a rat. The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample.

The term "control sample" refers to a sample obtained from a subject who does not have the HSD17B13 rs72613567 variant, and preferably is homozygous for the wild type allele of the HSD17B13 gene. Such samples can be obtained at the same time as a biological sample or on a different occasion. A biological sample and a control sample can both be obtained from the same tissue or bodily fluid.

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body, such as a cell within an organism or body) and to processes or reactions that occur within a natural environment. The term "ex vivo" includes cells that have been removed from the body of an individual and to processes or reactions that occur within such cells.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a Cas9 protein" or "at least one Cas9 protein" can include a plurality of Cas9 proteins, including mixtures thereof.

Statistically significant means $p<0.05$.

DETAILED DESCRIPTION

I. Overview

Provided herein is an HSD17B13 variant discovered to be associated with reduced alanine and aspartate transaminase levels; a reduced risk of chronic liver diseases including nonalcoholic and alcoholic liver fatty liver disease, cirrhosis, and hepatocellular carcinoma; and reduced progression from simple steatosis to more clinically advanced stages of chronic liver disease. Also provided herein are previously unidentified transcripts of the HSD17B13 gene associated with the variant.

Isolated nucleic acids and proteins related to variants of HSD17B13, and cells comprising those nucleic acids and proteins are provided herein. Also provided are methods for modifying a cell through use of any combination of nuclease agents, exogenous donor sequences, transcriptional activators, transcriptional repressors, and expression vectors for expressing a recombinant HSD17B13 gene or a nucleic acid encoding an HSD17B13 protein. Also provided are therapeutic and prophylactic methods for treating a subject having or at risk of developing chronic liver disease.

II. HSD17B13 Variants

Provided herein are isolated nucleic acids and proteins related to variants of HSD17B13 (also known as hydroxysteroid 17-beta dehydrogenase 13, 17-beta-hydroxysteroid dehydrogenase 13, 17β-hydroxysteroid dehydrogenase-13, 17β-HSD13, short-chain dehydrogenase/reductase 9, SCDR9, HMFN0376, NIIL497, and SDR16C3). The human HSD17B13 gene is approximately 19 kb in length and includes seven exons and six introns located at 4q22.1 in the genome. Exemplary human HSD17B13 protein sequences are assigned UniProt Accession No. Q7Z5P4 (SEQ ID NOS: 240 and 241; Q7Z5P4-1 and Q7Z5P4-2, respectively) and NCBI Reference Sequence Nos. NP_835236 and NP_001129702 (SEQ ID NOS: 242 and 243, respectively). Exemplary human HSD17B13 mRNAs are assigned NCBI Reference Sequence Nos. NM_178135 and NM_001136230 (SEQ ID NOS: 244 and 245, respectively).

In particular, provided herein is a splice variant of HSD17B13 (rs72613567) having an insertion of an adenine adjacent to the donor splice site in intron 6. The adenine is an insertion on the forward (plus) strand of the chromosome, which corresponds to an inserted thymine on the reverse (minus) strand of the chromosome. Because the human HSD17B13 gene is transcribed in the reverse direction, this nucleotide insertion is reflected as an inserted thymine in the exemplary HSD17B13 rs72613567 variant sequence provided in SEQ ID NO: 2 relative to the exemplary wild type HSD17B13 gene sequence provided in SEQ ID NO: 1. The insertion will therefore be referred to herein as a thymine inserted between positions 12665 and 12666 in SEQ ID NO: 1 or at position 12666 in SEQ ID NO: 2.

Figure 4:
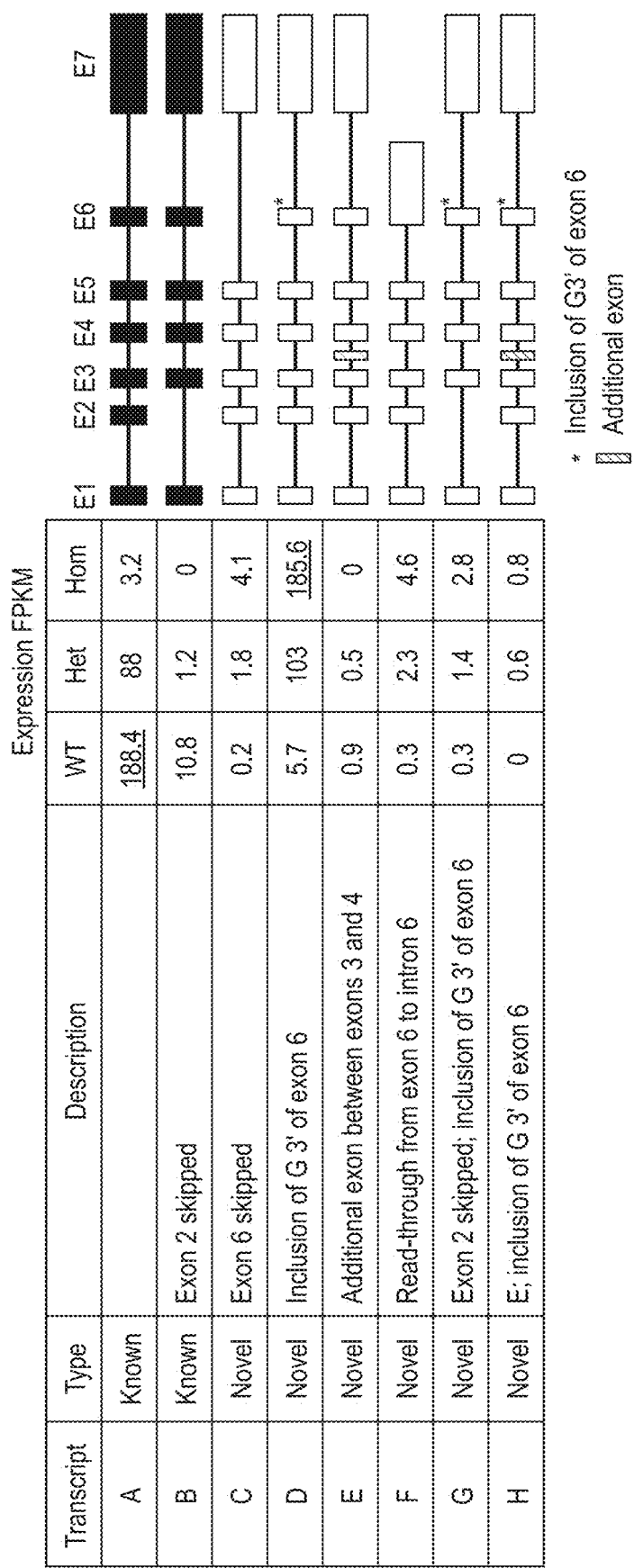
FIG. 4 shows that RNA-Seq studies of human liver reveal eight HSD17B13 transcripts, including six novel HSD17B13 transcripts (Transcripts C-H). Expression of the transcripts is displayed in FPKM units (fragments per kilobase of transcript per million mapped reads). Structures of the transcripts are provided on the right side of the figure.

Two mRNA transcripts (A and B; SEQ ID NOS: 4 and 5, respectively) were previously identified to be expressed in subjects with the wild type HSD17B13 gene. Transcript A includes all seven exons of the HSD17B13 gene, whereas exon 2 is skipped in Transcript B. Transcript A is the dominant transcript in wild type subjects. Provided herein, however, are six additional, previously unidentified, HSD17B13 transcripts that are expressed (C-H, SEQ ID NOS: 6 to 11, respectively). These transcripts are shown in FIG. 4. In Transcript C, exon 6 is skipped compared to Transcript A. In Transcript D, there is an insertion of a guanine 3' of exon 6, resulting in a frameshift in and premature truncation of exon 7 compared to Transcript A. In Transcript E, there is an additional exon between exons 3 and 4 compared to Transcript A. In Transcript F, which is expressed only in HSD17B13 rs72613567 variant carriers, there is read-through from exon 6 into intron 6 compared to Transcript A. In Transcript G, exon 2 is skipped, and there is an insertion of a guanine 3' of exon 6, resulting in a frameshift in and premature truncation of exon 7 compared to Transcript A. In Transcript H, there is an additional exon between exons 3 and 4, and there is an insertion of a guanine 3' of exon 6, resulting in a frameshift in and premature truncation of exon 7 compared to Transcript A. Transcripts C, D, F, G, and H are dominant in HSD17B13 rs72613567 variant carriers, with Transcript D being the most abundant transcript in carriers of the HSD17B13 rs72613567 variant. Also provided herein is one additional, previously unidentified, HSD17B13 transcript that is expressed at low levels (F', SEQ ID NO: 246). Like Transcript F, Transcript F' also includes a read-through from exon 6 into intron 6 compared to Transcript A, but, in contrast to Transcript F, the read-through does not include the inserted thymine present in the HSD17B13 rs72613567 variant gene. The nucleotide positions of the exons within the HSD17B13 genes for each Transcript are provided below.

| Nucleotide Positions in SEQ ID NO: 1 for Exons of HSD17B13 Transcripts More Prevalent in Subjects Homozygous for Wild Type HSD17B13 Gene. | | | | |
|---|---|---|---|---|
| | Transcript A | Transcript B | Transcript E | Transcript F' |
| Exon 1 | 1-275 | 1-275 | 1-275 | 1-275 |
| Exon 2 | 4471-4578 | skipped | 4471-4578 | 4471-4578 |
| Exon 3 | 5684-5815 | 5684-5815 | 5684-5815 | 5684-5815 |
| Exon 3' | not present | not present | 6210-6281 | not present |
| Exon 4 | 7308-7414 | 7308-7414 | 7308-7414 | 7308-7414 |
| Exon 5 | 8947-9084 | 8947-9084 | 8947-9084 | 8947-9084 |
| Exon 6 | 12548-12664 | 12548-12664 | 12548-12664 | 12548-13501* |
| Exon 7 | 17599-19118 | 17599-19118 | 17599-19118 | skipped |

*Includes read-through from exon 6 into intron 6; read-through = positions 12665-13501

| Nucleotide Positions in SEQ ID NO: 2 for Exons of HSD17B13 Transcripts More Prevalent in Subjects Homozygous for rs72613567 HSD17B13 Variant Gene (Insertion of T at Position 12666). | | | | | |
|---|---|---|---|---|---|
| | Transcript C | Transcript D | Transcript F | Transcript G | Transcript H |
| Exon 1 | 1-275 | 1-275 | 1-275 | 1-275 | 1-275 |
| Exon 2 | 4471-4578 | 4471-4578 | 4471-4578 | skipped | 4471-4578 |
| Exon 3 | 5684-5815 | 5684-5815 | 5684-5815 | 5684-5815 | 5684-5815 |
| Exon 3' | not present | not present | not present | not present | 6210-6281 |
| Exon 4 | 7308-7414 | 7308-7414 | 7308-7414 | 7308-7414 | 7308-7414 |
| Exon 5 | 8947-9084 | 8947-9084 | 8947-9084 | 8947-9084 | 8947-9084 |
| Exon 6 | skipped | 12548-12665^ | 12548-13502* | 12548-12665^ | 12548-12665^ |
| Exon 7 | 17600-19119 | 17600-19119 | skipped | 17600-19119 | 17600-19119 |

^Includes additional residue 12665 at 3' end compared to Transcript A
*Includes read-through from exon 6 into intron 6; read-through = positions 12665-13502

As explained in more detail elsewhere herein, the HSD17B13 rs72613567 variant is associated with reduced alanine and aspartate transaminase levels and a reduced risk of chronic liver diseases including nonalcoholic and alcoholic liver fatty liver disease, cirrhosis, and hepatocellular carcinoma. The HSD17B13 rs72613567 variant is also associated with reduced progression from simple steatosis to more clinically advanced stages of chronic liver disease.

A. Nucleic Acids

Disclosed herein are isolated nucleic related to HSD17B13 variants and variant HSD17B13 transcripts. Also disclosed are isolated nucleic acids that hybridize under stringent or moderate conditions with any of the nucleic acids disclosed herein. Such nucleic acids can be useful, for example, to express HSD17B13 variant proteins or as primers, probes, exogenous donor sequences, guide RNAs, antisense RNAs, shRNAs, and siRNAs, each of which is described in more detail elsewhere herein.

Also disclosed are functional nucleic acids that can interact with the disclosed polynucleotides. Functional nucleic acids are nucleic acid molecules that have a specific function, such as binding a target molecule or catalyzing a specific reaction. Examples of functional nucleic acids include antisense molecules, aptamers, ribozymes, triplex forming molecules, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternatively, the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. Antisense molecules generally bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; and 6,057,437, each of which is herein incorporated by reference in its entirety for all purposes. Examples of antisense molecules include antisense RNAs, small interfering RNAs (siRNAs), and short hairpin RNAs (shRNAs), which are described in greater detail elsewhere herein.

The isolated nucleic acids disclosed herein can comprise RNA, DNA, or both RNA and DNA. The isolated nucleic acids can also be linked or fused to a heterologous nucleic acid sequence, such as in a vector, or a heterologous label. For example, the isolated nucleic acids disclosed herein can be in a vector or exogenous donor sequences comprising the isolated nucleic acid and a heterologous nucleic acid sequence. The isolated nucleic acids can also be linked or fused to a heterologous label, such as a fluorescent label. Other examples of labels are disclosed elsewhere herein.

The disclosed nucleic acids molecules can be made up of, for example, nucleotides or non-natural or modified nucleotides, such as nucleotide analogs or nucleotide substitutes. Such nucleotides include a nucleotide that contains a modified base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The nucleic acids molecules disclosed herein can comprise one or more nucleotide analogs or substitutions. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as pseudouridine, uracil-5-yl, hypoxanthin-9-yl (I), and 2-aminoadenin-9-yl. Modified bases include, for example, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found, for example, in U.S. Pat. No. 3,687,808; Englisch et al. (1991) *Angewandte Chemie, International Edition* 30:613; and Sanghvi, Y. S., Chapter 15, Antisense Research and Applications, pages 289-302, Crooke, S. T. and Lebleu, B. ed., CRC Press, 1993, each of which is herein incorporated by reference in its entirety for all purposes. Certain nucleotide analogs, such as 5-substituted pyrimidines, 6-azapyrimidines and N-2, N-6 and O-6 substituted purines, including 2-aminopropyladenine, 5-propynyluracil, 5-propynylcytosine, and 5-methylcytosine can increase the stability of duplex formation. Often base modifications can be combined with, for example, a sugar modification, such as 2'-O-methoxyethyl, to achieve unique properties such as increased duplex stability. There are numerous US patents, such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these is herein incorporated by reference in its entirety for all purposes.

Nucleotide analogs can also include modifications of the sugar moiety. Modifications to the sugar moiety can include, for example, natural modifications of the ribose and deoxy ribose as well as synthetic modifications. Sugar modifications include, for example, the following modifications at the 2' position: OH; F; O—, S—, or N-alkyl; O—, S—, or N-alkenyl; O—, S— or N-alkynyl; or O-alkyl-O-alkyl, wherein the alkyl, alkenyl, and alkynyl may be substituted or unsubstituted C1 to C10, alkyl or C2 to C10 alkenyl and alkynyl. Exemplary 2' sugar modifications also include, for example, —O[(CH2)$_n$ O]m CH3, —O(CH2)$_n$OCH3, —O(CH2)$_n$ NH2, —O(CH2)$_n$ CH3, —O(CH2)$_n$ —ONH2, and —O(CH2)$_n$ON[(CH2)$_n$CH3)]2, where n and m are from 1 to about 10.

Other modifications at the 2' position include, for example, $C_1$ to $C_{10}$ lower alkyl, substituted lower alkyl, alkaryl, aralkyl, O-alkaryl or O-aralkyl, SH, SCH3, OCN, Cl, Br, CN, CF3, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S.

Nucleotide sugar analogs may also have sugar mimetics such as cyclobutyl moieties in place of the pentofuranosyl sugar. There are numerous US patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety for all purposes.

Nucleotide analogs can also be modified at the phosphate moiety. Modified phosphate moieties include, for example, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous US patents teach how to make and use nucleotides containing modified phosphates and include, for example, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety for all purposes.

Nucleotide substitutes include molecules having similar functional properties to nucleotides, but which do not contain a phosphate moiety, such as peptide nucleic acid (PNA). Nucleotide substitutes include molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes also include nucleotides or nucleotide analogs that have had the phosphate moiety or sugar moieties replaced. Nucleotide substitutes may not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous US patents disclose how to make and use these types of phosphate replacements and include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety for all purposes.

It is also understood in a nucleotide substitute that both the sugar and the phosphate moieties of the nucleotide can be replaced, by, for example, an amide type linkage (aminoethylglycine) (PNA). U.S. Pat. Nos. 5,539,082; 5,714,331; and 5,719,262 teach how to make and use PNA molecules, each of which is herein incorporated by reference in its entirety for all purposes. See also Nielsen et al. (1991) *Science* 254:1497-1500, herein incorporated by reference in its entirety for all purposes.

It is also possible to link other types of molecules (conjugates) to nucleotides or nucleotide analogs to enhance, for example, cellular uptake. Conjugates can be chemically linked to the nucleotide or nucleotide analogs. Such conjugates include, for example, lipid moieties such as a cholesterol moiety (Letsinger et al. (1989) *Proc. Natl. Acad. Sci. USA* 86:6553-6556, herein incorporated by reference in its entirety for all purposes), cholic acid (Manoharan et al. (1994) *Bioorg. Med. Chem. Let.* 4:1053-1060, herein incorporated by reference in its entirety for all purposes), a thioether such as hexyl-S-tritylthiol (Manoharan et al. (1992) *Ann. N.Y. Acad. Sci.* 660:306-309; Manoharan et al. (1993) *Bioorg. Med. Chem. Let.* 3:2765-2770, herein incorporated by reference in its entirety for all purposes), a thiocholesterol (Oberhauser et al. (1992) *Nucl. Acids Res.* 20:533-538, herein incorporated by reference in its entirety for all purposes), an aliphatic chain such as dodecandiol or undecyl residues (Saison-Behmoaras et al. (1991) *EMBO J.* 10:1111-1118; Kabanov et al. (1990) *FEBS Lett.* 259:327-330; Svinarchuk et al. (1993) *Biochimie* 75:49-54, each of which is herein incorporated by reference in its entirety for all purposes), a phospholipid such as di-hexadecyl-rac-glycerol or triethylammonium 1,2-di-O-hexadecyl-rac-glycero-3-H-phosphonate (Manoharan et al. (1995) *Tetrahedron Lett.* 36:3651-3654; Shea et al. (1990) *Nucl. Acids Res.* 18:3777-3783, each of which is herein incorporated by reference in its entirety for all purposes), a polyamine or a polyethylene glycol chain (Manoharan et al. (1995) *Nucleosides & Nucleotides* 14:969-973, herein incorporated by reference in its entirety for all purposes), or adamantane acetic acid (Manoharan et al. (1995) *Tetrahedron Lett.* 36:3651-3654, herein incorporated by reference in its entirety for all purposes), a palmityl moiety (Mishra et al. (1995) *Biochim. Biophys. Acta* 1264:229-237), or an octadecylamine or hexylamino-carbonyl-oxycholesterol moiety (Crooke et al. (1996) *J. Pharmacol. Exp. Ther.* 277:923-937, herein incorporated by reference in its entirety for all purposes). Numerous US patents teach the preparation of such conjugates and include, for example, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety for all purposes.

The isolated nucleic acids disclosed herein can comprise a nucleotide sequence of a naturally occurring HSD17B13 gene or mRNA transcript, or can comprise a non-naturally occurring sequence. In one example, the non-naturally occurring sequence can differ from the non-naturally occurring sequence due to synonymous mutations or mutations that do not affect the encoded HSD17B13 protein. For example, the sequence can be identical with the exception of synonymous mutations or mutations that do not affect the encoded HSD17B13 protein. A synonymous mutation or substitution is the substitution of one nucleotide for another in an exon of a gene coding for a protein such that the produced amino acid sequence is not modified. This is possible because of the degeneracy of the genetic code, with some amino acids being coded for by more than one three-base pair codon. Synonymous substitutions are used, for example, in the process of codon optimization.

Also disclosed herein are proteins encoded by the nucleic acids disclosed herein and compositions comprising an isolated nucleic acid or protein disclosed herein and a carrier increasing the stability of the isolated nucleic acid or protein (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

(1) Nucleic Acids Including Mutant Residue of HSD17B13 rs72613567 Variant

Disclosed herein are isolated nucleic acids comprising at least 15 contiguous nucleotides of an HSD17B13 gene and having a thymine at a position corresponding to position 12666 (or thymines at positions corresponding to positions 12666 and 12667) of the HSD17B13 rs72613567 variant (SEQ ID NO: 2) when optimally aligned with the HSD17B13 rs72613567 variant. That is, disclosed herein are isolated nucleic acids comprising at least 15 contiguous nucleotides of an HSD17B13 gene and having a thymine inserted between nucleotides corresponding to positions 12665 and 12666 of the wild type HSD17B13 gene (SEQ ID NO: 1) when optimally aligned with the wild type HSD17B13 gene. Such isolated nucleic acids can be useful, for example, to express HSD17B13 variant transcripts and proteins or as exogenous donor sequences. Such isolated nucleic acids can also be useful, for example, as guide RNAs, primers, and probes.

The HSD17B13 gene can be an HSD17B13 gene from any organism. For example, the HSD17B13 gene can be a human HSD17B13 gene or an ortholog from another organism, such as a non-human mammal, a rodent, a mouse, or a rat.

It is understood that gene sequences within a population can vary due to polymorphisms such as single-nucleotide polymorphisms. The examples provided herein are only exemplary sequences. Other sequences are also possible. As one example, the at least 15 contiguous nucleotides can be at least 90%, at least 95%, at least 96%, at least 97%, at least 98%, or at least 99% identical to a corresponding sequence in the HSD17B13 rs72613567 variant (SEQ ID NO: 2) including position 12666 or positions 12666 and 12667 of SEQ ID NO: 2 when optimally aligned with SEQ ID NO: 2. Optionally, the isolated nucleic acid comprises at least 15 contiguous nucleotides of SEQ ID NO: 2 including position 12666 or positions 12666 and 12667 of SEQ ID NO: 2. As another example, the at least 15 contiguous nucleotides can be at least 90%, at least 95%, at least 96%, at least 97%, at least 98%, or at least 99% identical to a corresponding sequence in the wild type HSD17B13 gene (SEQ ID NO: 1) including positions 12665 and 12666 of SEQ ID NO: 1 when optimally aligned with SEQ ID NO: 1, wherein a thymine is present between the positions corresponding to positions 12665 and 12666 of SEQ ID NO: 1. Optionally, the isolated nucleic acid comprises at least 15 contiguous nucleotides of SEQ ID NO: 1 including positions 12665 and 12666 of SEQ ID NO: 1, wherein a thymine is present between the positions corresponding to positions 12665 and 12666 of SEQ ID NO: 1.

The isolated nucleic acid can comprise, for example, at least 20, 25, 30, 35, 40, 45, 50, 60, 70, 80, 90, 100, 200, 300, 400, 500, 600, 700, 800, 900, or 1000 contiguous nucleotides of an HSD17B13 gene. Alternatively, the isolated nucleic acid can comprise, for example, at least 1000, 2000, 3000, 4000, 5000, 6000, 7000, 8000, 9000, 10000, 11000, 12000, 13000, 14000, 15000, 16000, 17000, 18000, or 19000 contiguous nucleotides of an HSD17B13 gene.

In some cases, the isolated nucleic acid can comprise an HSD17B13 minigene in which one or more nonessential segments of the gene have been deleted with respect to a corresponding wild type HSD17B13 gene. As one example, the deleted segments comprise one or more intronic sequences. Such HSD17B13 minigenes can comprise, for example, exons corresponding to exons 1-7 from HSD17B13 Transcript D and an intron corresponding to intron 6 in SEQ ID NO: 2 when optimally aligned with SEQ ID NO: 2. As one example, an HSD17B13 minigene may comprise exons 1-7 and intron 6 from SEQ ID NO: 2. Minigenes are described in more detail elsewhere herein.

(2) Nucleic Acids Hybridizing to Sequence Adjacent to or Including Mutant Residue of HSD17B13 rs72613567 Variant Also disclosed herein are isolated nucleic acids comprising at least 15 contiguous nucleotides that hybridize to an HSD17B13 gene (e.g., an HSD17B13 minigene) at a segment that includes or is within 1000, 500, 400, 300, 200, 100, 50, 45, 40, 35, 30, 25, 20, 15, 10, or 5 nucleotides of a position corresponding to position 12666 or positions 12666 and 12667 of the HSD17B13 rs72613567 variant (SEQ ID NO: 2) when optimally aligned with the HSD17B13 rs72613567 variant. Such isolated nucleic acids can be useful, for example, as guide RNAs, primers, probes, or exogenous donor sequences.

The HSD17B13 gene can be an HSD17B13 gene from any organism. For example, the HSD17B13 gene can be a human HSD17B13 gene or an ortholog from another organism, such as a non-human mammal, a mouse, or a rat.

As one example, the at least 15 contiguous nucleotides can hybridize to a segment of the HSD17B13 gene or HSD17B13 minigene that is at least 90%, at least 95%, at least 96%, at least 97%, at least 98%, or at least 99% identical to a corresponding sequence in the HSD17B13 rs72613567 variant (SEQ ID NO: 2) when optimally aligned with SEQ ID NO: 2. Optionally, the isolated nucleic acid can hybridize to at least 15 contiguous nucleotides of SEQ ID NO: 2. Optionally, the isolated nucleic acid hybridizes to a segment including position 12666 or positions 12666 and 12667 in SEQ ID NO: 2 or a position corresponding to position 12666 or positions 12666 and 12667 in SEQ ID NO: 2 when optimally aligned with SEQ ID NO: 2.

The segment to which the isolated nucleic acid can hybridize can comprise, for example, at least 20, 25, 30, 35, 40, 45, 50, 55, 60, 65, 70, 75, 80, 75, 90, 95, 100, 200, 300, 400, 500, 600, 700, 800, 900, or 1000 contiguous nucleotides of an HSD17B13 gene. Alternatively, the isolated nucleic acid can comprise, for example, at least 1000, 2000, 3000, 4000, 5000, 6000, 7000, 8000, 9000, 10000, 11000, 12000, 13000, 14000, 15000, 16000, 17000, 18000, or 19000 contiguous nucleotides of an HSD17B13 gene. Alternatively, the segment to which the isolated nucleic acid can hybridize can be, for example, up to 20, 25, 30, 35, 40, 45, 50, 55, 60, 65, 70, 75, 80, 75, 90, 95, 100, 200, 300, 400, 500, 600, 700, 800, 900, or 1000 contiguous nucleotides of an HSD17B13 gene. For example, the segment can be about 15 to 100 nucleotides in length, or about 15-35 nucleotides in length.

(3) cDNAs and Variant Transcripts Produced by HSD17B13 rs72613567 Variant

Also provided are nucleic acids corresponding to all or part of an mRNA transcript or a cDNA corresponding to any one of Transcripts A-H (SEQ ID NOS: 4-11, respectively), and particularly Transcripts C-H, when optimally aligned with the any one of Transcripts A-H. It is understood that gene sequences and within a population and mRNA sequences transcribed from such genes can vary due to polymorphisms such as single-nucleotide polymorphisms. The sequences provided herein for each Transcript are only exemplary sequences. Other sequences are also possible. Specific, non-limiting examples are provided below. Such isolated nucleic acids can be useful, for example, to express HSD17B13 variant transcripts and proteins.

The isolated nucleic acid can be of any length. For example, the isolated nucleic acid can comprise at least 10, 15, 20, 25, 30, 35, 40, 45, 50, 60, 70, 80, 90, 100, 200, 300, 400, 500, 600, 700, 800, 900, 1000, or 2000 contiguous nucleotides encoding all or part of an HSD17B13 protein. In some cases, the isolated nucleic acids comprises contiguous nucleotides encoding all or part of an HSD17B13 protein, wherein the contiguous nucleotides comprise sequence from at least two different exons of an HSD17B13 gene (e.g., spanning at least one exon-exon boundary of an HSD17B13 gene without an intervening intron).

HSD17B13 Transcript D (SEQ ID NO: 7), Transcript G (SEQ ID NO: 10), and Transcript H (SEQ ID NO: 11) include an insertion of a guanine at the 3' end of exon 6, resulting in a frameshift in exon 7 and premature truncation of the region of the HSD17B13 protein encoded by exon 7 compared to Transcript A. Accordingly, provided herein are isolated nucleic acids comprising a segment (e.g., at least 15 contiguous nucleotides) present in Transcripts D, G, and H (or fragments or homologs thereof) that is not present in Transcript A (or a fragment or homolog thereof). Such regions can be readily identified by comparing the sequences of the Transcripts. For example, provided herein are isolated nucleic acids comprising at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region spanning the exon 6-exon 7 boundary in SEQ ID NO: 7 (HSD17B13 Transcript D), SEQ ID NO: 10 (HSD17B13 Transcript G), or SEQ ID NO: 11 (HSD17B13 Transcript H) when optimally aligned with SEQ ID NO: 7, 10, or 11, respectively, and the segment includes a guanine at a residue corresponding to residue 878 at the 3' end of exon 6 in SEQ ID NO: 7 (i.e., an insertion of a guanine at the 3' end of exon 6 relative to Transcript A in addition to the guanine at the start of exon 7), a residue corresponding to residue 770 at the 3' end of exon 6 in SEQ ID NO: 10 (i.e., an insertion of a guanine at the 3' end of exon 6 relative to Transcript B in addition to the guanine at the start of exon 7), or a residue corresponding to residue 950 at the 3' end of exon 6 in SEQ ID NO: 11 (i.e., an insertion of a guanine at the 3' end of exon 6 relative to Transcript E in addition to the guanine at the start of exon 7). It is understood that such a nucleic acid would include a sufficient number of nucleotides in each of exons 6 and 7 to distinguish the inserted guanine from other features in the HSD17B13 Transcripts (e.g., from the guanine at the start of exon 7, from the read-through into intron 6 in Transcript F, or from the deleted exon 6 in Transcript C).

As one example, the isolated nucleic acid can comprise at least 15 contiguous nucleotides (e.g., at least 20 contiguous nucleotides or at least 30 contiguous nucleotides) of SEQ ID NO: 7 spanning the exon 6-exon 7 boundary, optionally comprising exons 6 and 7 of SEQ ID NO: 7, and optionally comprising the entire sequence of SEQ ID NO: 7. Optionally, the isolated nucleic acid further comprises a segment present in Transcript D (or a fragment or homolog thereof) that is not present in Transcript G (or a fragment or homolog thereof), and the isolated nucleic acid further comprises a segment present in Transcript D (or a fragment or homolog thereof) that is not present in Transcript H (or a fragment or homolog thereof). Such regions can be readily identified by comparing the sequences of the Transcripts. For example, such isolated nucleic acids can comprise a segment of the contiguous nucleotides (e.g., at least 5 contiguous nucleotides, at least 10 contiguous nucleotides or at least 15 contiguous nucleotides) that is at least 90%, at least 95%, at least 96%, at least 97%, at least 98%, or at least 99% identical to a region spanning the boundary of exons 3 and 4 of SEQ ID NO: 7 (HSD17B13 Transcript D) when optimally aligned with SEQ ID NO: 7 to distinguish from Transcript H. Likewise, such isolated nucleic acids can comprise a segment of the contiguous nucleotides (e.g., at least 5 contiguous nucleotides, at least 10 contiguous nucleotides or at least 15 contiguous nucleotides) that is at least 90%, at least 95%, at least 96%, at least 97%, at least 98%, or at least 99% identical to a region within exon 2 of SEQ ID NO: 7 (HSD17B13 Transcript D), a region spanning the exon 1-exon 2 boundary of SEQ ID NO: 7, or a region spanning the exon 2-exon 3 boundary of SEQ ID NO: 7 when optimally aligned with SEQ ID NO: 7 to distinguish from Transcript G. Optionally, the isolated nucleic acid comprises a sequence at least 90%, at least 95%, at least 96%, at least 97%, at least 98%, or at least 99% identical to the sequence set forth in SEQ ID NO: 7 (HSD17B13 Transcript D) and encodes an HSD17B13 protein comprising the sequence set forth in SEQ ID NO: 15 (HSD17B13 Isoform D). Like Transcript D, Transcript H (SEQ ID NO: 11) includes an insertion of a guanine 3' of exon 6 compared to Transcript A. Transcript H further includes an additional exon (exon 3') between exons 3 and 4 compared to Transcript A and Transcript D. Accordingly, provided herein are isolated nucleic acids as described for above comprising a segment present in Transcripts D, G, and H (or fragments or homologs thereof) that is not present in Transcript A (or a fragment or homolog thereof) but further comprising a segment (e.g., at least 15 contiguous nucleotides) of Transcript H (or a fragment or homolog thereof) that is not present in Transcript D (or a fragment or homolog thereof). Such regions can be readily identified by comparing the sequences of the Transcripts. For example, provided herein are isolated nucleic acids as described for Transcript D, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region within exon 3' of SEQ ID NO: 11 (HSD17B13 Transcript H), a region spanning the exon 3-exon 3' boundary of SEQ ID NO: 11, or a region spanning the exon 3'-exon 4 boundary of SEQ ID NO: 11 when optimally aligned with SEQ ID NO: 11. It is understood that such a nucleic acid would include a sufficient number of nucleotides in each of exons 3 and 3' or each of exons 3' and 4 to distinguish from other features in the HSD17B13 transcripts (e.g., from the boundary of exons 3 and 4). For example, the region of exon 3' can comprise the entire exon 3'. Optionally, the isolated nucleic acid comprises a sequence at least 90%, at least 95%, at least 96%, at least 97%, at least 98%, or at least 99% identical to the sequence set forth in SEQ ID NO: 11 (HSD17B13 Transcript H) and encodes an HSD17B13 protein comprising the sequence set forth in SEQ ID NO: 19 (HSD17B13 Isoform H).

As one example, the isolated nucleic acid can comprise at least 15 contiguous nucleotides (e.g., at least 20 contiguous nucleotides or at least 30 contiguous nucleotides) of SEQ ID NO: 11 including a region within exon 3', a region spanning the exon 3-exon 3' boundary, or a region spanning the exon 3'-exon 4 boundary, optionally comprising the entire exon 3' of SEQ ID NO: 11, and optionally comprising the entire sequence of SEQ ID NO: 11.

Like Transcript D, Transcript G (SEQ ID NO: 10) includes an insertion of a guanine 3' of exon 6 compared to Transcript A. In addition, however, Transcript G is missing exon 2 compared to Transcript A and Transcript D (i.e., Transcript G includes an exon 1-exon 3 boundary not present in Transcripts A and D). Accordingly, provided herein are isolated nucleic acids as described above comprising a segment present in Transcripts D, G, and H (or fragments or homologs thereof) that is not present in Transcript A (or a fragment or homolog thereof) but further comprising a segment (e.g., at least 15 contiguous nucleotides) from Transcript G (or a fragment or homolog thereof) that is not present in Transcript D (or a fragment or homolog thereof). Such regions can be readily identified by comparing the sequences of the Transcripts. For example, provided herein are isolated nucleic acids as described for Transcript D, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region spanning the exon 1-exon 3 boundary in SEQ ID NO: 10 (HSD17B13 Transcript G) when optimally aligned with SEQ ID NO: 10. It is understood that such a nucleic acid would include a sufficient number of nucleotides in each of exons 1 and 3 to distinguish from other features in the HSD17B13 Transcripts (e.g., the boundary of exons 1 and 2 or the boundary of exons 2 and 3). For example, the region can comprise the entirety of exons 1 and 3 in SEQ ID NO: 10. Optionally, the isolated nucleic acid comprises a sequence at least 90%, at least 95%, at least 96%, at least 97%, at least 98%, or at least 99% identical to the sequence set forth in SEQ ID NO: 10 (HSD17B13 Transcript G) and encodes an HSD17B13 protein comprising the sequence set forth in SEQ ID NO: 18 (HSD17B13 Isoform G).

As one example, the isolated nucleic acid can comprise at least 15 contiguous nucleotides (e.g., at least 20 contiguous nucleotides or at least 30 contiguous nucleotides) of SEQ ID NO: 10 including a region spanning the exon 1-exon 3 boundary, optionally comprising the exons 1 and 3 of SEQ ID NO: 10, and optionally comprising the entire sequence of SEQ ID NO: 10.

Also provided herein are isolated nucleic acids comprising a segment (e.g., at least 15 contiguous nucleotides) present in Transcript E (or a fragment or homolog thereof) that is not present in Transcript A (or a fragment or homolog thereof). Such regions can be readily identified by comparing the sequences of the Transcripts. Transcript E (SEQ ID NO: 8) includes an additional exon between exons 3 and 4 compared to Transcript A. Accordingly, provided herein are isolated nucleic acids comprising at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region within exon 3' of SEQ ID NO: 8 (HSD17B13 Transcript E), a region spanning the exon 3-exon 3' boundary of SEQ ID NO: 8, or a region spanning the exon 3'-exon 4 boundary of SEQ ID NO: 8 when optimally aligned with SEQ ID NO: 8. It is understood that such a nucleic acid would include a sufficient number of nucleotides in each of exons 3 and 3' or each of exons 3' and 4 to distinguish from other features in the HSD17B13 transcripts (e.g., from the boundary of exons 3 and 4). For example, the region of exon 3' can comprise the entire exon 3'. Optionally, the isolated nucleic acid further comprises a segment (e.g., at least 15 contiguous nucleotides) from Transcript E (or a fragment or homolog thereof) that is not present in Transcript H (or a fragment or homolog thereof). Such regions can be readily identified by comparing the sequences of the Transcripts. For example, provided herein are isolated nucleic acids as described above, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region spanning the exon 6-exon 7 boundary in SEQ ID NO: 8 (HSD17B13 Transcript E) when optimally aligned with SEQ ID NO: 8. It is understood that such a nucleic acid would include a sufficient number of nucleotides in each of exons 6 and 7 to distinguish from other features in the HSD17B13 Transcripts (particularly the additional guanine at the 3' end of exon 6 in Transcript H)). For example, the region can comprise the entirety of exons 6 and 7 in SEQ ID NO: 8. Optionally, the isolated nucleic acid comprises a sequence at least 90%, at least 95%, at least 96%, at least 97%, at least 98%, or at least 99% identical to the sequence set forth in SEQ ID NO: 8 (HSD17B13 Transcript E) and encodes an HSD17B13 protein comprising the sequence set forth in SEQ ID NO: 16 (HSD17B13 Isoform E).

As one example, the isolated nucleic acid can comprise at least 15 contiguous nucleotides (e.g., at least 20 contiguous nucleotides or at least 30 contiguous nucleotides) of SEQ ID NO: 8 including a region within exon 3', a region spanning the exon 3-exon 3' boundary, or a region spanning the exon 3'-exon 4 boundary, optionally comprising the entire exon 3' of SEQ ID NO: 8, and optionally comprising the entire sequence of SEQ ID NO: 8.

Also provided herein are isolated nucleic acids comprising a segment (e.g., at least 15 contiguous nucleotides) present in Transcript F (or a fragment or homolog thereof) that is not present in Transcript A (or a fragment or homolog thereof). Such regions can be readily identified by comparing the sequences of the Transcripts. Transcript F (SEQ ID NO: 9) includes a read-through from exon 6 into intron 6 compared to Transcript A, and the read-through includes the inserted thymine present in the HSD17B13 rs72613567 variant gene. Accordingly, provided herein are isolated nucleic acids comprising at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region within the read-through into intron 6 in SEQ ID NO: 9 (HSD17B13 Transcript F) or a region spanning the boundary between the read-through into intron 6 and the rest of exon 6 in SEQ ID NO: 9 when optimally aligned with SEQ ID NO: 9. It is understood that such a nucleic acid would a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F (i.e., the inserted thymine) that is not present in Transcript F' (SEQ ID NO: 246). Transcript F' also includes a read-through from exon 6 into intron 6 compared to Transcript A, but the read-through does not include the inserted thymine present in the HSD17B13 rs72613567 variant gene. For example, the region can be the entire read-through into intron 6 in SEQ ID NO: 9. Optionally, the isolated nucleic acid comprises a sequence at least 90%, at least 95%, at least 96%, at least 97%, at least 98%, or at least 99% identical to the sequence set forth in SEQ ID NO: 9 (HSD17B13 Transcript F) and encodes an HSD17B13 protein comprising the sequence set forth in SEQ ID NO: 17 (HSD17B13 Isoform F).

As one example, the isolated nucleic acid can comprise at least 15 contiguous nucleotides (e.g., at least 20 contiguous nucleotides or at least 30 contiguous nucleotides) of SEQ ID NO: 9 including a region within the read-through into intron 6 or a region spanning the boundary between the read-through into intron 6 and the rest of exon 6, optionally comprising the entire read-through into intron 6, and optionally comprising the entire sequence of SEQ ID NO: 9.

Also provided herein are isolated nucleic acids comprising a segment (e.g., at least 15 contiguous nucleotides) present in Transcript F' (or a fragment or homolog thereof) that is not present in Transcript A (or a fragment or homolog thereof). Such regions can be readily identified by comparing the sequences of the Transcripts. Transcript F' (SEQ ID NO: 246) includes a read-through from exon 6 into intron 6 compared to Transcript A, and the read-through does not include the inserted thymine present in the HSD17B13 rs72613567 variant gene. Accordingly, provided herein are isolated nucleic acids comprising at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region within the read-through into intron 6 in SEQ ID NO: 246 (HSD17B13 Transcript F') or a region spanning the boundary between the read-through into intron 6 and the rest of exon 6 in SEQ ID NO: 246 when optimally aligned with SEQ ID NO: 246. It is understood that such a nucleic acid would a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F' that is not present in Transcript F (SEQ ID NO: 9). The read-through in Transcript F includes the inserted thymine present in the HSD17B13 rs72613567 variant gene, whereas the read-through in Transcript F' does not. For example, the region can be the entire read-through into intron 6 in SEQ ID NO: 246. Optionally, the isolated nucleic acid comprises a sequence at least 90%, at least 95%, at least 96%, at least 97%, at least 98%, or at least 99% identical to the sequence set forth in SEQ ID NO: 246 (HSD17B13 Transcript F') and encodes an HSD17B13 protein comprising, consisting essentially of, or consisting of the sequence set forth in SEQ ID NO: 247 (HSD17B13 Isoform F').

As one example, the isolated nucleic acid can comprise at least 15 contiguous nucleotides (e.g., at least 20 contiguous nucleotides or at least 30 contiguous nucleotides) of SEQ ID NO: 246 including a region within the read-through into intron 6 or a region spanning the boundary between the read-through into intron 6 and the rest of exon 6, optionally comprising the entire read-through into intron 6, and optionally comprising the entire sequence of SEQ ID NO: 246.

Also provided herein are isolated nucleic acids comprising a segment (e.g., at least 15 contiguous nucleotides) present in Transcript C (or a fragment or homolog thereof) that is not present in Transcript A (or a fragment or homolog thereof). Such regions can be readily identified by comparing the sequences of the Transcripts. Transcript C (SEQ ID NO: 6) is missing exon 6 compared to Transcript A (i.e., Transcript C includes an exon 5-exon 7 boundary not present in Transcript A). Accordingly, provided herein are isolated nucleic acids comprising at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least 90%, at least 95%, at least 96%, at least 97%, at least 98%, or at least 99% identical to a region spanning the exon 5-exon 7 boundary in SEQ ID NO: 6 (HSD17B13 Transcript C) when optimally aligned with SEQ ID NO: 6. It is understood that such a nucleic acid would a sufficient number of nucleotides in each of exons 5 and 7 to distinguish from other features in the HSD17B13 Transcripts (e.g., from boundary of exons 5 and 6 or of exons 6 and 7 in other HSD17B13 Transcripts). For example, the region can comprise the entirety of exons 5 and 7 in SEQ ID NO: 6. Optionally, the isolated nucleic acid comprises a sequence at least 90%, at least 95%, at least 96%, at least 97%, at least 98%, or at least 99% identical to the sequence set forth in SEQ ID NO: 6 (HSD17B13 Transcript C) and encodes an HSD17B13 protein comprising the sequence set forth in SEQ ID NO: 14 (HSD17B13 Isoform C).

As one example, the isolated nucleic acid can comprise at least 15 contiguous nucleotides (e.g., at least 20 contiguous nucleotides or at least 30 contiguous nucleotides) of SEQ ID NO: 6 including a region spanning the exon 5-exon 7 boundary, optionally comprising the entirety of exons 5 and 7 in SEQ ID NO: 6, and optionally comprising the entire sequence of SEQ ID NO: 6.

(4) Nucleic Acids Hybridizing to cDNAs and Variant HSD17B13 Transcripts

Also provided are nucleic acids hybridizing to segments of an mRNA transcript or a cDNA corresponding to any one of Transcripts A-H (SEQ ID NOS: 4-11, respectively), and particularly Transcripts C-H, when optimally aligned with the any one of Transcripts A-H. Specific, non-limiting examples are provided below. Such isolated nucleic acids can be useful, for example, primers, probes, antisense RNAs, siRNAs, or shRNAs.

The segment to which the isolated nucleic acid can hybridize can comprise, for example, at least 5, at least 10, or at least 15 contiguous nucleotides of a nucleic acid encoding an HSD17B13 protein. The segment to which the isolated nucleic acid can hybridize can comprise, for example, at least 20, 25, 30, 35, 40, 45, 50, 55, 60, 65, 70, 75, 80, 75, 90, 95, 100, 200, 300, 400, 500, 600, 700, 800, 900, 1000, or 2000 contiguous nucleotides of a nucleic acid encoding an HSD17B13 protein. Alternatively, the segment to which the isolated nucleic acid can hybridize can be, for example, up to 20, 25, 30, 35, 40, 45, 50, 55, 60, 65, 70, 75, 80, 75, 90, 95, 100, 200, 300, 400, 500, 600, 700, 800, 900, or 1000 contiguous nucleotides of a nucleic acid encoding an HSD17B13 protein. For example, the segment can be about 15 to 100 nucleotides in length, or about 15-35 nucleotides in length.

HSD17B13 Transcript D (SEQ ID NO: 7), Transcript G (SEQ ID NO: 10), and Transcript H (SEQ ID NO: 11) include an insertion of a guanine at the 3' end of exon 6, resulting in a frameshift in and premature truncation of exon 7 compared to Transcript A. Accordingly, provided herein are isolated nucleic acids comprising a region (e.g., at least 15 contiguous nucleotides) that hybridizes to a segment present in Transcripts D, G, and H (or fragments or homologs thereof) that is not present in Transcript A (or a fragment or homolog thereof). Such regions can be readily identified by comparing the sequences of the Transcripts. For example, provided herein are isolated nucleic acids that hybridize to at least 15 contiguous nucleotides of a nucleic acid encoding an HSD17B13 protein, wherein contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region spanning the exon 6-exon 7 boundary in SEQ ID NO: 7 (HSD17B13 Transcript D) when optimally aligned with SEQ ID NO: 7, and the segment includes a guanine at a residue corresponding to residue 878 at the 3' end of exon 6 in SEQ ID NO: 7 (i.e., an insertion of a guanine at the 3' end of exon 6 relative to Transcript A in addition to the guanine at the start of exon 7). Alternatively, provided herein are isolated nucleic acids that hybridize to at least 15 contiguous nucleotides of a segment of a nucleic acid encoding an HSD17B13 protein, wherein the contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region spanning the exon 6-exon 7 boundary in SEQ ID NO: 10 (HSD17B13 Transcript G) when optimally aligned with SEQ ID NO: 10, and the segment includes a guanine at a residue corresponding to residue 770 at the 3' end of exon 6 in SEQ ID NO: 10 (i.e., an insertion of a guanine at the 3' end of exon 6 relative to Transcript B in addition to the guanine at the start of exon 7). Alternatively, provided herein are isolated nucleic acids comprising that hybridize to at least 15 contiguous nucleotides of a nucleic acid encoding an HSD17B13 protein, wherein the contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region spanning the exon 6-exon 7 boundary in SEQ ID NO: 11 (HSD17B13 Transcript H) when optimally aligned with SEQ ID NO: 11, and the segment includes a guanine at a residue corresponding to residue 950 at the 3' end of exon 6 in SEQ ID NO: 11 (i.e., an insertion of a guanine at the 3' end of exon 6 relative to Transcript E in addition to the guanine at the start of exon 7). It is understood that such nucleic acids would be designed to hybridize to a sufficient number of nucleotides in each of exons 6 and 7 to distinguish the inserted guanine from other features in the HSD17B13 Transcripts (e.g., from the read-through into intron 6 in Transcript F or from the deleted exon 6 in Transcript C).

As one example, the segment can comprise a region of SEQ ID NO: 7 spanning the exon 6-exon 7 boundary (i.e., including the guanine at residue 878 of SEQ ID NO: 7). As another example, the segment can comprise a region of SEQ ID NO: 10 spanning the exon 6-exon 7 boundary (i.e., including the guanine at residue 770 of SEQ ID NO: 10). As another example, the segment can comprise a region of SEQ ID NO: 11 spanning the exon 6-exon 7 boundary (i.e., including the guanine at residue 950 of SEQ ID NO: 11).

Optionally, the isolated nucleic acid further comprises a region (e.g., 15 contiguous nucleotides) that hybridizes to a segment present in Transcript D (or a fragment or homolog thereof) that is not present in Transcript G (or a fragment or homolog thereof), and the isolated nucleic acid further comprises a region that hybridizes to a segment present in Transcript D (or a fragment or homolog thereof) that is not present in Transcript H (or a fragment or homolog thereof). Such segments can be readily identified by comparing the sequences of the Transcripts. For example, the segment (e.g., at least 5 contiguous nucleotides, at least 10 contiguous nucleotides or at least 15 contiguous nucleotides) present in Transcript D (or a fragment or homolog thereof) that is not present in Transcript H (or a fragment or homolog thereof) can be at least 90%, at least 95%, at least 96%, at least 97%, at least 98%, or at least 99% identical to a region spanning the boundary of exons 3 and 4 of SEQ ID NO: 7 (HSD17B13 Transcript D) when optimally aligned with SEQ ID NO: 7 to distinguish from Transcript H. Likewise, the segment (e.g., at least 5 contiguous nucleotides, at least 10 contiguous nucleotides or at least 15 contiguous nucleotides) present in Transcript D (or a fragment or homolog thereof) that is not present in Transcript G (or a fragment or homolog thereof) can be at least 90%, at least 95%, at least 96%, at least 97%, at least 98%, or at least 99% identical to a region within exon 2 of SEQ ID NO: 7 (HSD17B13 Transcript D), a region spanning the exon 1-exon 2 boundary of SEQ ID NO: 7, or a region spanning the exon 2-exon 3 boundary of SEQ ID NO: 7 when optimally aligned with SEQ ID NO: 7 to distinguish from Transcript G.

Like Transcript D, Transcript H (SEQ ID NO: 11) includes an insertion of a guanine at the 3' end of exon 6 compared to Transcript A. Transcript H further includes an additional exon between exons 3 and 4 compared to Transcript A and Transcript D. Accordingly, provided herein are isolated nucleic acids as described above comprising a region that hybridizes to a segment present in Transcripts D, G, and H (or fragments or homologs thereof) that is not present in Transcript A (or a fragment or homolog thereof) but further comprising a region (e.g., at least 15 contiguous nucleotides) that hybridizes to a segment that is present in Transcript H (or a fragment or homolog thereof) but not in Transcript D (or a fragment or homolog thereof). Such regions can be readily identified by comparing the sequences of the Transcripts. For example, the segment can be at least 90%, at least 95%, at least 96%, at least 97%, at least 98%, at least 99%, or 100% identical to a region (e.g., at least 5 contiguous nucleotides, at least 10 contiguous nucleotides or at least 15 contiguous nucleotides) within exon 3' of SEQ ID NO: 11 (HSD17B13 Transcript H), a region spanning the exon 3-exon 3' boundary of SEQ ID NO: 11, or a region spanning the exon 3'-exon 4 boundary of SEQ ID NO: 11 when optimally aligned with SEQ ID NO: 11. It is understood that such a nucleic acid would be designed to hybridize to a sufficient number of nucleotides in each of exons 3 and 3' or each of exons 3' and 4 to distinguish from other features in the HSD17B13 transcripts (e.g., from the boundary of exons 3 and 4).

As one example, the segment can comprise a region of SEQ ID NO: 11 within exon 3', spanning the exon 3-exon 3' boundary, or spanning the exon 3'-exon 4 boundary.

Like Transcript D, Transcript G (SEQ ID NO: 10) includes an insertion of a guanine at the 3' end of exon 6 compared to Transcript A. In addition, however, Transcript G is missing exon 2 compared to Transcript A and Transcript D (i.e., Transcript G includes an exon 1-exon 3 boundary not present in Transcripts A and D). Accordingly, provided herein are isolated nucleic acids as described above comprising a region that hybridizes to a segment present in Transcripts D, G, and H (or fragments or homologs thereof) that is not present in Transcript A (or a fragment or homolog thereof) but further comprising a region (e.g., at least 15 contiguous nucleotides) that hybridizes to a segment present in Transcript G (or a fragment or homolog thereof) but not in Transcript D (or a fragment or homolog thereof). Such regions can be readily identified by comparing the sequences of the Transcripts. For example, the segment can be at least 90%, at least 95%, at least 96%, at least 97%, at least 98%, at least 99%, or 100% identical to a region (e.g., at least 5 contiguous nucleotides, at least 10 contiguous nucleotides or at least 15 contiguous nucleotides) spanning the exon 1-exon 3 boundary in SEQ ID NO: 10 (HSD17B13 Transcript G) when optimally aligned with SEQ ID NO: 10. It is understood that such a nucleic acid would be designed to hybridize to a sufficient number of nucleotides in each of exons 1 and 3 to distinguish from other features in the HSD17B13 Transcripts (e.g., the boundary of exons 1 and 2 or the boundary of exons 2 and 3).

As one example, the segment can comprise a region of SEQ ID NO: 10 spanning the exon 1-exon 3 boundary.

Also provided are isolated nucleic acids comprising a region (e.g., at least 15 contiguous nucleotides) that hybridizes to a segment of a nucleic acid encoding an HSD17B13 protein that is present in Transcript E (or a fragment or homolog thereof) but not in Transcript A (or a fragment or homolog thereof). Such regions can be readily identified by comparing the sequences of the Transcripts. Transcript E (SEQ ID NO: 8) includes an additional exon between exons 3 and 4 compared to Transcript A. Accordingly, provided herein are isolated nucleic acids that hybridize to at least 15 contiguous nucleotides of a nucleic acid encoding an HSD17B13 protein, wherein the contiguous nucleotides comprise a segment that is at least 90%, at least 95%, at least 96%, at least 97%, at least 98%, at least 99%, or 100% identical to a region (e.g., at least 5 contiguous nucleotides, at least 10 contiguous nucleotides or at least 15 contiguous nucleotides) within exon 3' of SEQ ID NO: 8 (HSD17B13 Transcript E), a region spanning the exon 3-exon 3' boundary of SEQ ID NO: 8, or a region spanning the exon 3'-exon 4 boundary of SEQ ID NO: 8 when optimally aligned with SEQ ID NO: 8. It is understood that such a nucleic acid would be designed to hybridize to a sufficient number of nucleotides in each of exons 3 and 3' or each of exons 3' and 4 to distinguish from other features in the HSD17B13 transcripts (e.g., from the boundary of exons 3 and 4).

As one example, the segment can comprise a region of SEQ ID NO: 8 within exon 3', spanning the exon 3-exon 3' boundary of SEQ ID NO: 8, or spanning the exon 3'-exon 4 boundary.

Optionally, the isolated nucleic acid further comprises a region (e.g., 15 contiguous nucleotides) that hybridizes to a segment present in Transcript E (or a fragment or homolog thereof) that is not present in Transcript H (or a fragment or homolog thereof). Such segments can be readily identified by comparing the sequences of the Transcripts. For example, the segment (e.g., at least 5 contiguous nucleotides, at least 10 contiguous nucleotides or at least 15 contiguous nucleotides) present in Transcript E (or a fragment or homolog thereof) that is not present in Transcript H (or a fragment or homolog thereof) can be at least 90%, at least 95%, at least 96%, at least 97%, at least 98%, or at least 99% identical to a region spanning the boundary of exons 6 and 7 of SEQ ID NO: 8 (HSD17B13 Transcript E) when optimally aligned with SEQ ID NO: 8 to distinguish from Transcript G. It is understood that such a nucleic acid would be designed to hybridize to a sufficient number of nucleotides in each of exons 6 and 7 to distinguish from other features in the HSD17B13 Transcripts (particularly the additional guanine at the 3' end of exon 6 in Transcript H)).

Also provided are isolated nucleic acids comprising a region (e.g., at least 15 contiguous nucleotides) that hybridizes to a segment of a nucleic acid encoding an HSD17B13 protein that is present in Transcript F (or a fragment or homolog thereof) but not in Transcript A (or a fragment or homolog thereof). Such regions can be readily identified by comparing the sequences of the Transcripts. Transcript F (SEQ ID NO: 9) includes a read-through from exon 6 to intron 6 compared to Transcript A. Accordingly, provided herein are isolated nucleic acids that hybridize to at least 15 contiguous nucleotides of a nucleic acid encoding an HSD17B13 protein, wherein the contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region within the read-through into intron 6 in SEQ ID NO: 9 (HSD17B13 Transcript F) or a region spanning the boundary between the read-through into intron 6 and the rest of exon 6 in SEQ ID NO: 9 when optimally aligned with SEQ ID NO: 9. It is understood that such a nucleic acid would be designed to hybridize to a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F (i.e., the inserted thymine) that is not present in Transcript F' (SEQ ID NO: 246). Transcript F' also includes a read-through from exon 6 into intron 6 compared to Transcript A, but the read-through does not include the inserted thymine present in the HSD17B13 rs72613567 variant gene.

As one example, the segment can comprise a region of SEQ ID NO: 9 within the read-through into intron 6 or spanning the boundary between the read-through into intron 6 and the rest of exon 6.

Also provided are isolated nucleic acids comprising a region (e.g., at least 15 contiguous nucleotides) that hybridizes to a segment of a nucleic acid encoding an HSD17B13 protein that is present in Transcript F' (or a fragment or homolog thereof) but not in Transcript A (or a fragment or homolog thereof). Such regions can be readily identified by comparing the sequences of the Transcripts. Transcript F' (SEQ ID NO: 246) includes a read-through from exon 6 to intron 6 compared to Transcript A. Accordingly, provided herein are isolated nucleic acids that hybridize to at least 15 contiguous nucleotides of a nucleic acid encoding an HSD17B13 protein, wherein the contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region within the read-through into intron 6 in SEQ ID NO: 246 (HSD17B13 Transcript F') or a region spanning the boundary between the read-through into intron 6 and the rest of exon 6 in SEQ ID NO: 246 when optimally aligned with SEQ ID NO: 246. It is understood that such a nucleic acid would be designed to hybridize to a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F' that is not present in Transcript F (SEQ ID NO: 9). The read-through in Transcript F includes the inserted thymine present in the HSD17B13 rs72613567 variant gene, whereas the read-through in Transcript F' does not.

As one example, the segment can comprise a region of SEQ ID NO: 246 within the read-through into intron 6 or spanning the boundary between the read-through into intron 6 and the rest of exon 6.

Also provided are isolated nucleic acids comprising a region (e.g., at least 15 contiguous nucleotides) that hybridizes to a segment of a nucleic acid encoding an HSD17B13 protein that is present in Transcript C (or a fragment or homolog thereof) but not in Transcript A (or a fragment or homolog thereof). Such regions can be readily identified by comparing the sequences of the Transcripts. Transcript C (SEQ ID NO: 6) is missing exon 6 compared to Transcript A (i.e., Transcript C includes an exon 5-exon 7 boundary not present in Transcript A). Accordingly, provided herein are isolated nucleic acids that hybridize to at least 15 contiguous nucleotides of a nucleic acid encoding an HSD17B13 protein, wherein the contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region spanning the exon 5-exon 7 boundary in SEQ ID NO: 6 (HSD17B13 Transcript C) when optimally aligned with SEQ ID NO: 6. It is understood that such a nucleic acid would be designed to hybridize to a sufficient number of nucleotides in exons 5 and 7 to distinguish from other features in the HSD17B13 Transcripts (e.g., from boundary of exons 5 and 6 or of exons 6 and 7 in other HSD17B13 Transcripts).

As one example, the segment can comprise a region from SEQ ID NO: 6 spanning the exon 5-exon 7 boundary.

Also provided herein are isolated nucleic acids (e.g., antisense RNAs, siRNAs, or shRNAs) that hybridize to at least 15 contiguous nucleotides of a nucleic acid encoding an HSD17B13 protein, wherein contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region of HSD17B13 Transcript D (SEQ ID NO: 7). The isolated nucleic acids can comprise a region (e.g., at least 15 contiguous nucleotides) that hybridizes to a segment present in Transcript D (or fragments or homologs thereof) that is not present in Transcript A (or a fragment or homolog thereof). Such regions can be readily identified by comparing the sequences of the Transcripts. HSD17B13 Transcript D (SEQ ID NO: 7) includes an insertion of a guanine at the 3' end of exon 6, resulting in a frameshift in and premature truncation of exon 7 compared to Transcript A (SEQ ID NO: 4). For example, provided herein are isolated nucleic acids that hybridize to at least 15 contiguous nucleotides of a nucleic acid encoding an HSD17B13 protein, wherein contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region spanning the exon 6-exon 7 boundary in SEQ ID NO: 7 (HSD17B13 Transcript D) when optimally aligned with SEQ ID NO: 7. The segment can include a guanine at a residue corresponding to residue 878 at the 3' end of exon 6 in SEQ ID NO: 7 (i.e., an insertion of a guanine at the 3' end of exon 6 relative to Transcript A in addition to the guanine at the start of exon 7). It is understood that such nucleic acids would be designed to hybridize to a sufficient number of nucleotides in each of exons 6 and 7 to distinguish the inserted guanine from other features in the HSD17B13 Transcripts (e.g., from the read-through into intron 6 in Transcript F or from the deleted exon 6 in Transcript C).

Also provided herein are isolated nucleic acids (e.g., antisense RNAs, siRNAs, or shRNAs) that hybridize to at least 15 contiguous nucleotides of a nucleic acid encoding an HSD17B13 protein, wherein contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region of HSD17B13 Transcript A (SEQ ID NO: 4). The isolated nucleic acids can comprise a region (e.g., at least 15 contiguous nucleotides) that hybridizes to a segment present in Transcript A (or fragments or homologs thereof) that is not present in Transcript D (or a fragment or homolog thereof). Such regions can be readily identified by comparing the sequences of the Transcripts. HSD17B13 Transcript D (SEQ ID NO: 7) includes an insertion of a guanine at the 3' end of exon 6, resulting in a frameshift in and premature truncation of exon 7 compared to Transcript A (SEQ ID NO: 4). For example, provided herein are isolated nucleic acids that hybridize to at least 15 contiguous nucleotides of a nucleic acid encoding an HSD17B13 protein, wherein contiguous nucleotides comprise a segment (e.g., at least 5 contiguous nucleotides, at least 10 contiguous nucleotides or at least 15 contiguous nucleotides) that is at least 90%, at least 95%, at least 96%, at least 97%, at least 98%, at least 99%, or 100% identical to a region spanning the exon 6-exon 7 boundary in SEQ ID NO: 4 (HSD17B13 Transcript A) when optimally aligned with SEQ ID NO: 4.

(5) Vectors

Also provided are vectors comprising any of the nucleic acids disclosed herein and a heterologous nucleic acid. The vectors can be viral or nonviral vectors capable of transporting a nucleic acid. In some cases, a vector can be a plasmid (e.g., a circular double-stranded DNA into which additional DNA segments can be ligated). In some cases, a vector can be a viral vector, wherein additional DNA segments can be ligated into the viral genome. In some cases, a vector can autonomously replicate in a host cell into which it is introduced (e.g., bacterial vectors having a bacterial origin of replication and episomal mammalian vectors). In other cases, vectors (e.g., non-episomal mammalian vectors) can be integrated into the genome of a host cell upon introduction into the host cell and thereby are replicated along with the host genome. Moreover, certain vectors can direct the expression of genes to which they are operatively linked. Such vectors can be referred to as "recombinant expression vectors" or "expression vectors." Such vectors can also be targeting vectors (i.e., exogenous donor sequences) as disclosed elsewhere herein.

In some cases, the proteins encoded by the disclosed genetic variants are expressed by inserting nucleic acids encoding the disclosed genetic variants into expression vectors such that the genes are operatively linked to necessary expression control sequences such as transcriptional and translational control sequences. Expression vectors can include, for example, plasmids, retroviruses, adenoviruses, adeno-associated viruses (AAV), plant viruses such as cauliflower mosaic virus, tobacco mosaic virus, cosmids, YACs, EBV derived episomes, and the like. In some instances, nucleic acids comprising the disclosed genetic variants can be ligated into a vector such that transcriptional and translational control sequences within the vector serve their intended function of regulating the transcription and translation of the genetic variant. The expression vector and expression control sequences are chosen to be compatible with the expression host cell used. Nucleic acid sequences comprising the disclosed genetic variants can be inserted into separate vectors or into the same expression vector. A nucleic acid sequence comprising the disclosed genetic variants can be inserted into the expression vector by standard methods (e.g., ligation of complementary restriction sites on the nucleic acid comprising the disclosed genetic variants and vector, or blunt end ligation if no restriction sites are present).

In addition to a nucleic acid sequence comprising the disclosed genetic variants, the recombinant expression vectors can carry regulatory sequences that control the expression of the genetic variant in a host cell. The design of the expression vector, including the selection of regulatory sequences can depend on such factors as the choice of the host cell to be transformed, the level of expression of protein desired, and so forth. Preferred regulatory sequences for mammalian host cell expression can include, for example, viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. Further description of viral regulatory elements, and sequences thereof is provided in U.S. Pat. Nos. 5,168,062; 4,510,245; and 4,968,615, each of which is herein incorporated by reference in its entirety for all purposes. Methods of expressing polypeptides in bacterial cells or fungal cells (e.g., yeast cells) are also well known.

In addition to a nucleic acid sequence comprising the disclosed genetic variants and regulatory sequences, the recombinant expression vectors can carry additional sequences, such as sequences that regulate replication of the vector in host cells (e.g., origins of replication) and selectable marker genes. A selectable marker gene can facilitate selection of host cells into which the vector has been introduced (see e.g., U.S. Pat. Nos. 4,399,216; 4,634,665; and 5,179,017, each of which is herein incorporated by reference in its entirety for all purposes). For example, a selectable marker gene can confer resistance to drugs, such as G418, hygromycin, or methotrexate, on a host cell into which the vector has been introduced. Exemplary selectable marker genes include the dihydrofolate reductase (DHFR) gene (for use in dhfr-host cells with methotrexate selection/amplification), the neo gene (for G418 selection), and the glutamate synthetase (GS) gene.

B. Proteins

Disclosed herein are isolated HSD17B13 proteins and fragments thereof, and particularly HSD17B13 proteins and fragments thereof produced by the HSD17B13 rs72613567 variant.

The isolated proteins disclosed herein can comprise an amino acid sequence of a naturally occurring HSD17B13 protein, or can comprise a non-naturally occurring sequence. In one example, the non-naturally occurring sequence can differ from the non-naturally occurring sequence due to conservative amino acid substitutions. For example, the sequence can be identical with the exception of conservative amino acid substitutions.

The isolated proteins disclosed herein can be linked or fused to heterologous polypeptides or heterologous molecules or labels, numerous examples of which are disclosed elsewhere herein. For example, the proteins can be fused to a heterologous polypeptide providing increased or decreased stability. The fused domain or heterologous polypeptide can be located at the N-terminus, the C-terminus, or internally within the protein. A fusion partner may, for example, assist in providing T helper epitopes (an immunological fusion partner), or may assist in expressing the protein (an expression enhancer) at higher yields than the native recombinant protein. Certain fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

A fusion protein may be directly fused to the heterologous molecule or may be linked to the heterologous molecule via a linker, such as a peptide linker. Suitable peptide linker sequences may be chosen, for example, based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in Maratea et al. (1985) *Gene* 40:39-46; Murphy et al. (1986) *Proc. Natl. Acad. Sci. USA* 83:8258-8262; U.S. Pat. Nos. 4,935,233; and 4,751,180, each of which is herein incorporated by reference in its entirety. A linker sequence may generally be, for example, from 1 to about 50 amino acids in length. Linker sequences are generally not required when the first and second polypeptides have non-essential N-terminal amino acid regions that can be used to separate the functional domains and prevent steric interference.

The proteins can also be operably linked to a cell-penetrating domain. For example, the cell-penetrating domain can be derived from the HIV-1 TAT protein, the TLM cell-penetrating motif from human hepatitis B virus, MPG, Pep-1, VP22, a cell-penetrating peptide from Herpes simplex virus, or a polyarginine peptide sequence. See, e.g., WO 2014/089290, herein incorporated by reference in its entirety for all purposes. The cell-penetrating domain can be located at the N-terminus, the C-terminus, or anywhere within the protein.

The proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

The isolated proteins herein can also comprise non-natural or modified amino acids or peptide analogs. For example, there are numerous D-amino acids or amino acids which have a different functional substituent than the naturally occurring amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site-specific way (Thorson et al. (1991) *Methods Molec. Biol.* 77:43-73; Zoller (1992) *Current Opinion in Biotechnology* 3:348-354; Ibba, (1995) *Biotechnology & Genetic Engineering Reviews* 13:197-216; Cahill et al. (1989) *TIBS* 14(10):400-403; Benner (1993) TIB Tech 12:158-163; and Ibba and Hennecke (1994) *Biotechnology* 12:678-682, each of which are herein incorporated by reference in its entirety for all purposes).

Molecules can be produced that resemble peptides, but that are not connected via a natural peptide linkage. For example, linkages for amino acids or amino acid analogs can include CH2NH—, —CH2S—, —CH2-, —CH=CH— (cis and trans), —COCH2-, —CH(OH)CH2-, and —CHH2SO— (see, e.g., Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley (1994) *Trends Pharm Sci* 15(12):463-468; Hudson et al. (1979) *Int J Pept Prot Res* 14:177-185; Spatola et al. (1986) *Life Sci* 38:1243-1249; Hann (1982) *Chem. Soc Perkin Trans.* I 307-314; Almquist et al. (1980) *J. Med. Chem.* 23:1392-1398; Jennings-White et al. (1982) *Tetrahedron Lett* 23:2533); Szelke et al. European Appin, EP 45665 CA (1982): 97:39405 (1982); Holladay et al. (1983) *Tetrahedron. Lett* 24:4401-4404; and Hruby (1982) *Life Sci* 31:189-199; each of which is incorporated herein by reference in its entirety for all purposes. Peptide analogs can have more than one atom between the bond atoms, such as b-alanine, gaminobutyric acid, and the like.

Amino acid analogs and peptide analogs often have enhanced or desirable properties, such as, more economical production, greater chemical stability, enhanced pharmacological properties (half-life, absorption, potency, efficacy, and so forth), altered specificity (e.g., a broad-spectrum of biological activities), reduced antigenicity, and others desirable properties.

D-amino acids can be used to generate more stable peptides because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations (see, e.g., Rizo and Gierasch (1992) *Ann. Rev. Biochem.* 61:387, herein by reference in its entirety for all purposes).

Also disclosed herein are nucleic acids encoding any of the proteins disclosed herein. This includes all degenerate sequences related to a specific polypeptide sequence (i.e., all nucleic acids having a sequence that encodes one particular polypeptide sequence as well as all nucleic acids, including degenerate nucleic acids, encoding the disclosed variants and derivatives of the protein sequences). Thus, while each particular nucleic acid sequence may not be written out herein, each and every sequence is in fact disclosed and described herein through the disclosed polypeptide sequences.

Also disclosed herein are compositions comprising an isolated polypeptide or protein disclosed herein and a carrier increasing the stability of the isolated polypeptide. Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

(1) HSD17B13 Proteins and Fragments

Disclosed herein are isolated HSD17B13 proteins and fragments thereof, particularly HSD17B13 proteins and fragments thereof produced by the HSD17B13 rs72613567 variant, or particularly HSD17B13 Isoforms C, D, E, F, F', G, and H. Such proteins can include, for example an isolated polypeptide comprising at least 5, 6, 8, 10, 12, 14, 15, 16, 18, 20, 22, 24, 25, 30, 35, 40, 45, 50, 60, 70, 80, 90, 100, 150, 200, 250, or 300 contiguous amino acids of HSD17B13 Isoform C, D, E, F, F', G, or H or a fragment thereof. It is understood that gene sequences within a population and proteins encoded by such genes can vary due to polymorphisms such as single-nucleotide polymorphisms. The sequences provided herein for each HSD17B13 isoform are only exemplary sequences. Other sequences are also possible. For example, the isolated polypeptide comprises an amino acid sequence (e.g., a sequence of contiguous amino acids) at least 90%, at least 95%, at least 96%, at least 97%, at least 98%, at least 99%, or 100% identical to HSD17B13 Isoform C, D, E, F, F', G, or H when optimally aligned with Isoform C, D, E, F, F', G, or H, respectively. Optionally, the isolated polypeptide comprises a sequence identical to HSD17B13 Isoform C, D, E, F, F', G, or H.

As one example, the isolated polypeptide can comprise a segment (e.g., at least 8 contiguous amino acids) that is present in Isoforms D, G, and H (or fragments or homologs thereof) that is not present in Isoform A (or a fragment or homolog thereof). Such regions can be readily identified by comparing the sequences of the Isoforms. The region encoded by exon 7 in Isoforms D, G, and H is frameshifted and truncated compared to the region encoded by exon 7 in Isoform A. Thus, such an isolated polypeptide can comprise at least 5, 6, 8, 10, 12, 14, 15, 16, 18, 20, 22, 24, 25, 30, 35, 40, 45, 50, 60, 70, 80, 90, 100, 150, or 200 contiguous amino acids of an HSD17B13 protein (e.g., at least 8 contiguous amino acids, at least 10 contiguous amino acids, or at least 15 contiguous amino acids of an HSD17B13 protein), wherein a segment of the contiguous amino acids (e.g., at least 3 contiguous amino acids, at least 5 contiguous amino acids, at least 8 contiguous amino acids, at least 10 contiguous amino acids, or at least 15 contiguous amino acids) is at least 90%, at least 95%, at least 96%, at least 97%, at least 98%, at least 99%, or 100% identical to a segment including at least a portion of the region encoded by exon 7 in SEQ ID NO: 15 (HSD17B13 Isoform D), SEQ ID NO: 18 (HSD17B13 Isoform G), or SEQ ID NO: 19 (HSD17B13 Isoform H) when the isolated polypeptide is optimally aligned with SEQ ID NO: 15, 18, or 19, respectively.

Such isolated polypeptides can further comprise a segment present in Isoform D (or a fragment or homolog thereof) that is not present in Isoform G (or a fragment or homolog thereof), and can further comprise a segment present in Isoform D (or a fragment or homolog thereof) that is not present in Isoform H (or a fragment or homolog thereof). Such regions can be readily identified by comparing the sequences of the Isoforms. For example, such isolated polypeptides can comprise a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least 90%, at least 95%, at least 96%, at least 97%, at least 98%, or at least 99% identical to a segment spanning the boundary of the regions encoded by exons 3 and 4 of SEQ ID NO: 15 (HSD17B13 Isoform D) when optimally aligned with SEQ ID NO: 15 to distinguish from Isoform H. Likewise, such isolated polypeptides can comprise a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least 90%, at least 95%, at least 96%, at least 97%, at least 98%, or at least 99% identical to a segment within the region encoded by exon 2 in SEQ ID NO: 15 (HSD17B13 Isoform D), a segment spanning the boundary of the regions encoded by exons 1 and 2 in SEQ ID NO: 15, or a segment spanning the boundary of the regions encoded by exons 2 and 3 in SEQ ID NO: 15 when optimally aligned with SEQ ID NO: 15 to distinguish from Isoform G.

Like Isoform D, the region encoded by exon 7 in Isoform H (SEQ ID NO: 19) is frameshifted and truncated compared to Isoform A. In addition, however, Isoform H includes a region encoded by an additional exon (exon 3') between exons 3 and 4 compared to Isoforms A and D. Accordingly, such an isolated polypeptide can be as described above comprising a segment that is present in Isoforms D, G, and H (or fragments or homologs thereof) that is not present in Isoform A (or a fragment or homolog thereof) but further comprising a segment (e.g., at least 8 contiguous amino acids) from Isoform H (or a fragment or homolog thereof) that is not present in Isoform D (or a fragment or homolog thereof). Such regions can be readily identified by comparing the sequences of the Isoforms. For example, such an isolated polypeptide can further comprise a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least 90%, at least 95%, at least 96%, at least 97%, at least 98%, at least 99%, or 100% identical to a segment including at least a portion of the region encoded by exon 3' in SEQ ID NO: 19 (HSD17B13 Isoform H) when the isolated polypeptide is optimally aligned with SEQ ID NO: 19.

Like Isoform D, the region encoded by exon 7 in Isoform G (SEQ ID NO: 18) is frameshifted and truncated compared to Isoform A. In addition, however, Isoform G is missing the region encoded by exon 2 compared to Isoforms A and D and thus includes an exon 1-exon 3 boundary not present in Isoforms A and D. Accordingly, such an isolated polypeptide can be as described above comprising a segment that is present in Isoforms D, G, and H (or fragments or homologs thereof) that is not present in Isoform A (or a fragment or homolog thereof) but further comprising a segment (e.g., at least 8 contiguous amino acids) from Isoform G (or a fragment or homolog thereof) that is not present in Isoform D (or a fragment or homolog thereof). Such regions can be readily identified by comparing the sequences of the Isoforms. For example, such an isolated polypeptide can further comprise a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least 90%, at least 95%, at least 96%, at least 97%, at least 98%, at least 99%, or 100% identical to a segment spanning the boundary of the regions encoded by exons 1 and 3 in SEQ ID NO: 18 (HSD17B13 Isoform G) when the isolated polypeptide is optimally aligned with SEQ ID NO: 18.

Also provided herein are isolated polypeptides comprising a segment (e.g., at least 8 contiguous amino acids) that is present in Isoform E (or a fragment or homolog thereof) that is not present in Isoform A (or a fragment or homolog thereof). Isoform E includes a region encoded by an additional exon (exon 3') between exons 3 and 4 that is not present in Isoform A. Such regions can be readily identified by comparing the sequences of the Isoforms. Accordingly, the isolated polypeptide can comprise at least 5, 6, 8, 10, 12, 14, 15, 16, 18, 20, 22, 24, 25, 30, 35, 40, 45, 50, 60, 70, 80, 90, 100, 150, or 200 contiguous amino acids of an HSD17B13 protein (e.g., at least 8 contiguous amino acids, at least 10 contiguous amino acids, or at least 15 contiguous amino acids of an HSD17B13 protein), wherein a segment of the contiguous amino acids (e.g., at least 3 contiguous amino acids, at least 5 contiguous amino acids, at least 8 contiguous amino acids, at least 10 contiguous amino acids, or at least 15 contiguous amino acids) is at least 90%, at least 95%, at least 96%, at least 97%, at least 98%, at least 99%, or 100% identical to a segment including at least a portion of the region encoded by exon 3' in SEQ ID NO: 16 (HSD17B13 Isoform E) or SEQ ID NO: 19 (HSD17B13 Isoform H) when the isolated polypeptide is optimally aligned with SEQ ID NO: 16 or 19, respectively. Optionally, such an isolated polypeptide can further comprise a segment (e.g., at least 8 contiguous amino acids) from Isoform E (or a fragment or homolog thereof) that is not present in Isoform H (or a fragment or homolog thereof). Such regions can be readily identified by comparing the sequences of the Isoforms. For example, such an isolated polypeptide can further comprise a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least 90%, at least 95%, at least 96%, at least 97%, at least 98%, at least 99%, or 100% identical a segment spanning the boundary of the regions encoded by exons 6 and 7 in SEQ ID NO: 16 (HSD17B13 Isoform E) when the isolated polypeptide is optimally aligned with SEQ ID NO: 16.

Also provided is an isolated polypeptide comprising a segment (e.g., at least 8 contiguous amino acids) present in Isoform F (or a fragment or homolog thereof) that is not present in Isoform A (or a fragment or homolog thereof). Isoform F includes a region encoded by read-through from exon 6 into intron 6 that is not present in Isoform A. Such regions can be readily identified by comparing the sequences of the Isoforms. Accordingly, the isolated polypeptide can comprise at least 5, 6, 8, 10, 12, 14, 15, 16, 18, 20, 22, 24, 25, 30, 35, 40, 45, 50, 60, 70, 80, 90, 100, 150, or 200 contiguous amino acids of an HSD17B13 protein (e.g., at least 8 contiguous amino acids, at least 10 contiguous amino acids, or at least 15 contiguous amino acids of an HSD17B13 protein), wherein a segment of the contiguous amino acids (e.g., at least 3 contiguous amino acids, at least 5 contiguous amino acids, at least 8 contiguous amino acids, at least 10 contiguous amino acids, or at least 15 contiguous amino acids) is at least 90%, at least 95%, at least 96%, at least 97%, at least 98%, at least 99%, or 100% identical to a segment including at least a portion of the region encoded by the read-through into intron 6 in SEQ ID NO: 17 (HSD17B13 Isoform F) when the isolated polypeptide is optimally aligned with SEQ ID NO: 17.

Also provided is an isolated polypeptide comprising a segment (e.g., at least 8 contiguous amino acids) present in Isoform C (or a fragment or homolog thereof) that is not present in Isoform A (or a fragment or homolog thereof). Isoform C is missing the region encoded by exon 6 compared to Isoform A and includes an exon 5-exon 7 boundary not present in Isoform A. Such regions can be readily identified by comparing the sequences of the Isoforms. Accordingly, the isolated polypeptide can comprise at least 5, 6, 8, 10, 12, 14, 15, 16, 18, 20, 22, 24, 25, 30, 35, 40, 45, 50, 60, 70, 80, 90, 100, 150, or 200 contiguous amino acids of an HSD17B13 protein (e.g., at least 8 contiguous amino acids, at least 10 contiguous amino acids, or at least 15 contiguous amino acids of an HSD17B13 protein), wherein a segment of the contiguous amino acids (e.g., at least 3 contiguous amino acids, at least 5 contiguous amino acids, at least 8 contiguous amino acids, at least 10 contiguous amino acids, or at least 15 contiguous amino acids) is at least 90%, at least 95%, at least 96%, at least 97%, at least 98%, at least 99%, or 100% identical to a segment spanning the boundary of the regions encoded by exons 5 and 7 in SEQ ID NO: 14 (HSD17B13 Isoform C) when the isolated polypeptide is optimally aligned with SEQ ID NO: 14.

Any of the isolated polypeptides disclosed herein can be linked to a heterologous molecule or heterologous label. Examples of such heterologous molecules or labels are disclosed elsewhere herein. For example, the heterologous molecule can be an immunoglobulin Fc domain, a peptide tag as disclosed elsewhere herein, poly(ethylene glycol), polysialic acid, or glycolic acid.

(2) Methods of Producing HSD17B13 Proteins or Fragments

Also disclosed are methods of producing any of the HSD17B13 proteins or fragments thereof disclosed herein. Such HSD17B13 proteins or fragments thereof can be produced by any suitable method. For example, HSD17B13 proteins or fragments thereof can be produced from host cells comprising nucleic acids (e.g., recombinant expression vectors) encoding such HSD17B13 proteins or fragments thereof. Such methods can comprise culturing a host cell comprising a nucleic acid (e.g., recombinant expression vector) encoding an HSD17B13 protein or fragment thereof, thereby producing the HSD17B13 protein or fragment thereof. The nucleic acid can be operably linked to a promoter active in the host cell, and the culturing can be under conditions whereby the nucleic acid is expressed. Such methods can further comprise recovering the expressed HSD17B13 protein or fragment thereof. The recovering can further comprise purifying the HSD17B13 protein or fragment thereof.

Examples of suitable systems for protein expression include bacterial cell expression systems (e.g., *Escherichia coli, Lactococcus lactis*), yeast cell expression systems (e.g., *Saccharomyces cerevisiae, Pichia pastoris*), insect cell expression systems (e.g., baculovirus-mediated protein expression), and mammalian cell expression systems.

Examples of nucleic acids encoding HSD17B13 proteins or fragments thereof are disclosed in more detail elsewhere herein. Optionally, such nucleic acids are codon optimized for expression in the host cell. Optionally, such nucleic acids are operably linked to a promoter active in the host cell. The promoter can be a heterologous promoter (i.e., a promoter than is not a naturally occurring HSD17B13 promoter). Examples of promoters suitable for *Escherichia coli* include arabinose, lac, tac, and T7 promoters. Examples of promoters suitable for *Lactococcus lactis* include P170 and nisin promoters. Examples of promoters suitable for *Saccharomyces cerevisiae* include constitutive promoters such as alcohol dehydrogenase (ADHI) or enolase (ENO) promoters or inducible promoters such as PHO, CUP1, GAL1, and G10. Examples of promoters suitable for Pichia pastoris include the alcohol oxidase I (AOX I) promoter, the glyceraldehyde 3 phosphate dehydrogenase (GAP) promoter, and the glutathione dependent formaldehyde dehydrogenase (FLDI) promoter. An example of a promoter suitable for a baculovirus-mediated system is the late viral strong polyhedrin promoter.

Optionally, the nucleic acid further encodes a tag in frame with the HSD17B13 protein or fragment thereof to facilitate protein purification. Examples of tags are disclosed elsewhere herein. Such tags can, for example, bind to a partner ligand (e.g., immobilized on a resin) such that the tagged protein can be isolated from all other proteins (e.g., host cell proteins). Affinity chromatography, high performance liquid chromatography (HPLC), and size exclusion chromatography (SEC) are examples of methods that can be used to improve the purity of the expressed protein.

Other methods can also be used to produce HSD17B13 proteins or fragments thereof. For example, two or more peptides or polypeptides can be linked together by protein chemistry techniques. For example, peptides or polypeptides can be chemically synthesized using either Fmoc (9-fluorenylmethyloxycarbonyl) or Boc (tert-butyloxycarbonoyl) chemistry. Such peptides or polypeptides can be synthesized by standard chemical reactions. For example, a peptide or polypeptide can be synthesized and not cleaved from its synthesis resin, whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively. (Grant G A (1992) Synthetic Peptides: A User Guide. W. H. Freeman and Co., N.Y. (1992); and Bodansky M and Trost B., Ed. (1993) Principles of Peptide Synthesis. Springer-Verlag Inc., NY, each of which is herein incorporated by reference in its entirety for all purposes). Alternatively, the peptide or polypeptide can be independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides, or whole protein domains (Abrahmsen L et al. (1991) *Biochemistry* 30:4151, herein incorporated by reference in its entirety for all purposes). Alternatively, native chemical ligation of synthetic peptides can be utilized to synthetically construct large peptides or polypeptides from shorter peptide fragments. This method can consist of a two-step chemical reaction (Dawson et al. (1994) *Science* 266:776-779, herein incorporated by reference in its entirety for all purposes). The first step can be the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate can undergo spontaneous, rapid intramolecular reaction to form a native peptide bond at the ligation site (Baggiolini et al. (1992) *FEBS Lett* 307:97-101; Clark-Lewis et al. (1994) *J Biol Chem* 269:16075; Clark-Lewis et al. (1991) *Biochemistry* 30:3128; and Rajarathnam et al. (1994) *Biochemistry* 33:6623-6630, each of which is herein incorporated by reference in its entirety for all purposes).

Alternatively, unprotected peptide segments can be chemically linked where the bond formed between the peptide segments as a result of the chemical ligation is an unnatural (non-peptide) bond (Schnolzer et al. (1992) *Science* 256:221, herein incorporated by reference in its entirety for all purposes). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992), herein incorporated by reference in its entirety for all purposes).

C. Cells

Also provided herein are cells (e.g., recombinant host cells) comprising any of the nucleic acids and proteins disclosed herein. The cells can be in vitro, ex vivo, or in vivo. Nucleic acids can be linked to a promoter and other regulatory sequences so they are expressed to produce an encoded protein. Any type of cell is provided.

The cell can be, for example, a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cell can also be a primary somatic cell, or a cell that is not a primary somatic cell. Somatic cells can include any cell that is not a gamete, germ cell, gametocyte, or undifferentiated stem cell. The cell can also be a primary cell. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Such cells also include would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK 293 cells), and mouse embryonic fibroblast cells (e.g., 3T3 cells). Numerous types of immortalized cells are well known. Immortalized or primary cells include cells that are typically used for culturing or for expressing recombinant genes or proteins.

The cell can also be a differentiated cell, such as a liver cell (e.g., a human liver cell).

The cell can be from any source. For example, the cell can be a eukaryotic cell, an animal cell, a plant cell, or a fungal (e.g., yeast) cell. Such cells can be fish cells or bird cells, or such cells can be mammalian cells, such as human cells, non-human mammalian cells, rodent cells, mouse cells or rat cells. Mammals include, for example, humans, non-human primates, monkeys, apes, cats dogs, horses, bulls, deer, bison, sheep, rodents (e.g., mice, rats, hamsters, guinea pigs), livestock (e.g., bovine species such as cows, steer, etc.; ovine species such as sheep, goats, etc.; and porcine species such as pigs and boars). Birds include, for example, chickens, turkeys, ostrich, geese, ducks, etc. Domesticated animals and agricultural animals are also included. The term "non-human animal" excludes humans.

For mouse cells, the mouse can be any strain, including, for example, from a 129 strain, a C57BL/6 strain, a BALB/c strain, a Swiss Webster strain, a mix of 129 and C57BL/6, strains, a mix of BALB/c and C57BL/6 strains, a mix of 129 and BALB/c strains, and a mix of BALB/c, C57BL/6, and 129 strains. For example, a mouse can be at least partially from a BALB/c strain (e.g., at least about 25%, at least about 50%, at least about 75% derived from a BALB/c strain, or about 25%, about 50%, about 75%, or about 100% derived from a BALB/c strain). In one example, the mouse is a strain comprising 50% BALB/c, 25% C57BL/6, and 25% 129. Alternatively, the mouse comprises a strain or strain combination that excludes BALB/c.

Examples of 129 strains include 129P1, 129P2, 129P3, 129X1, 129S1 (e.g., 129I/SV, 129I/Sv1m), 129S2, 129S4, 129S5, 129S9/SvEvH, 129S6 (129/SvEvTac), 129S7, 129S8, 129T1, and 129T2. See, e.g., Festing et al. (1999) *Mammalian Genome* 10(8):836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Mouse cells also be from a mix of an aforementioned 129 strain and an aforementioned C57BL/6 strain (e.g., 50% 129 and 50% C57BL/6). Likewise, mouse cells can be from a mix of aforementioned 129 strains or a mix of aforementioned BL/6 strains (e.g., the 129S6 (129/SvEvTac) strain).

For rat cells, the rat can be any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be from a strain derived from a mix of two or more strains recited above. For example, the rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. In some cases, the rats are from an inbred rat strain. See, e.g., US 2014/0235933 A1, herein incorporated by reference in its entirety for all purposes.

III. Methods of Modifying or Altering Expression of HSD17B13

Various methods are provided for modifying a cell through use of any combination of nuclease agents, exogenous donor sequences, transcriptional activators, transcriptional repressors, antisense molecules such as antisense RNA, siRNA, and shRNA, HSD17B13 proteins or fragments thereof, and expression vectors for expressing a recombinant HSD17B13 gene or a nucleic acid encoding an HSD17B13 protein. The methods can occur in vitro, ex vivo, or in vivo. The nuclease agents, exogenous donor sequences, transcriptional activators, transcriptional repressors, antisense molecules such as antisense RNA, siRNA, and shRNA, HSD17B13 proteins or fragments thereof, and expression vectors can be introduced into the cell in any form and by any means as described elsewhere herein, and all or some can be introduced simultaneously or sequentially in any combination. Some methods involve only altering an endogenous HSD17B13 gene in a cell. Some methods involve only altering expression of an endogenous HSD17B13 gene through use of transcriptional activators or repressors or through use of antisense molecules such as antisense RNA, siRNA, and shRNA. Some methods involve only introducing a recombinant HSD17B13 gene or nucleic acid encoding an HSD17B13 protein or fragment thereof into a cell. Some methods involve only introducing an HSD17B13 protein or fragment thereof into a cell (e.g., any one of or any combination of the HSD17B13 proteins or fragments thereof disclosed herein or any one of or any combination of HSD17B13 Isoforms A-H or fragments thereof disclosed herein). For example, such methods can involve introducing one or more of HSD17B13 Isoforms C, D, F, G, and H (or fragments thereof) into a cell or introducing HSD17B13 Isoform D (or a fragment thereof) into a cell. Alternatively, such methods can involve introducing one or more of HSD17B13 Isoforms A, B, and E or Isoforms A, B, E, and F' (or fragments thereof) into a cell or introducing HSD17B13 Isoform A (or a fragment thereof) into a cell. Other methods can involve both altering an endogenous HSD17B13 gene in a cell and introducing an HSD17B13 protein or fragment thereof or recombinant HSD17B13 gene or nucleic acid encoding an HSD17B13 protein or fragment thereof into the cell. Yet other methods can involve both altering expression of an endogenous HSD17B13 gene in a cell and introducing an HSD17B13 protein or fragment thereof or recombinant HSD17B13 gene or nucleic acid encoding an HSD17B13 protein or fragment thereof into the cell.

A. Methods of Modifying HSD17B13 Nucleic Acids

Various methods are provided for modifying an HSD17B13 gene in a genome within a cell (e.g., a pluripotent cell or a differentiated cell such as a liver cell) through use of nuclease agents and/or exogenous donor sequences. The methods can occur in vitro, ex vivo, or in vivo. The nuclease agent can be used alone or in combination with an exogenous donor sequence. Alternatively, the exogenous donor sequence can be used alone or in combination with a nuclease agent.

Repair in response to double-strand breaks (DSBs) occurs principally through two conserved DNA repair pathways: non-homologous end joining (NHEJ) and homologous recombination (HR). See Kasparek & Humphrey (2011) *Seminars in Cell & Dev. Biol.* 22:886-897, herein incorporated by reference in its entirety for all purposes. NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break.

Repair of a target nucleic acid (e.g., an HSD17B13 gene) mediated by an exogenous donor sequence can include any process of exchange of genetic information between the two polynucleotides. For example, NHEJ can also result in the targeted integration of an exogenous donor sequence through direct ligation of the break ends with the ends of the exogenous donor sequence (i.e., NHEJ-based capture). Such NHEJ-mediated targeted integration can be preferred for insertion of an exogenous donor sequence when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site (beyond the overhangs created by Cas-mediated cleavage) is not needed, which can be beneficial when attempting targeted insertion into organisms that have genomes for which there is limited knowledge of the genomic sequence. The integration can proceed via ligation of blunt ends between the exogenous donor sequence and the cleaved genomic sequence, or via ligation of sticky ends (i.e., having 5' or 3' overhangs) using an exogenous donor sequence that is flanked by overhangs that are compatible with those generated by the Cas protein in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Repair can also occur via homology directed repair (HDR) or homologous recombination (BR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Targeted genetic modifications to an HSD17B13 gene in a genome can be generated by contacting a cell with an exogenous donor sequence comprising a 5' homology arm that hybridizes to a 5' target sequence at a target genomic locus within the HSD17B13 gene and a 3' homology arm that hybridizes to a 3' target sequence at the target genomic locus within the HSD17B13 gene. The exogenous donor sequence can recombine with the target genomic locus to generate the targeted genetic modification to the HSD17B13 gene. As one example, the 5' homology arm can hybridize to a target sequence 5' of the position corresponding to position 12666 of SEQ ID NO: 2, and the 3' homology arm can hybridize to a target sequence 3' of the position corresponding to position 12666 of SEQ ID NO: 2 when the HSD17B13 gene is optimally aligned with SEQ ID NO: 2. Such methods can result, for example, in an HSD17B13 gene in which a thymine is inserted between nucleotides corresponding to positions 12665 and 12666 of SEQ ID NO: 1 when the HSD17B13 gene is optimally aligned with SEQ ID NO: 1 (or an adenine is inserted at the corresponding position on the opposite strand). As another example, the 5' and 3' homology arms can hybridize to 5' and 3' target sequences, respectively, at positions corresponding to those flanking exon 6 in SEQ ID NO: 1 when the HSD17B13 gene is optimally aligned with SEQ ID NO: 1. Such methods can result, for example, in an HSD17B13 gene in which a sequence corresponding to exon 6 of SEQ ID NO: 1 when the HSD17B13 gene is optimally aligned with SEQ ID NO: 1 has been deleted. As another example, the 5' and 3' homology arms can hybridize to 5' and 3' target sequences, respectively, at positions corresponding to those flanking exon 2 in SEQ ID NO: 1 when the HSD17B13 gene is optimally aligned with SEQ ID NO: 1. Such methods can result, for example, in an HSD17B13 gene in which a sequence corresponding to exon 2 of SEQ ID NO: 1 when the HSD17B13 gene is optimally aligned with SEQ ID NO: 1 has been deleted. As another example, the 5' and 3' homology arms can hybridize to 5' and 3' target sequences, respectively, at positions corresponding to the exon 6/intron 6 boundary in SEQ ID NO: 1 when the HSD17B13 gene is optimally aligned with SEQ ID NO: 1. As another example, the 5' and 3' homology arms can hybridize to 5' and 3' target sequences, respectively, at positions corresponding to exon 6 and exon 7 in SEQ ID NO: 1 when the HSD17B13 gene is optimally aligned with SEQ ID NO: 1. Such methods can result, for example, in an HSD17B13 gene in which a thymine is inserted between nucleotides corresponding to positions 12665 and 12666 of SEQ ID NO: 1 when the HSD17B13 gene is optimally aligned with SEQ ID NO: 1 (or an adenine is inserted at the corresponding position on the opposite strand). As another example, the 5' and 3' homology arms can hybridize to 5' and 3' target sequences, respectively, at positions corresponding to those flanking or within the region corresponding to the donor splice site in intron 6 of SEQ ID NO: 1 (i.e., the region at the 5' end of intron 6 in SEQ ID NO: 1). Such methods can result, for example, in an HSD17B13 gene in which the donor splice site in intron 6 is disrupted. Examples of exogenous donor sequences are disclosed elsewhere herein.

Targeted genetic modifications to an HSD17B13 gene in a genome can also be generated by contacting a cell with a nuclease agent that induces one or more nicks or double-strand breaks at a target sequence at a target genomic locus within the HSD17B13 gene. Such methods can result, for example, in an HSD17B13 gene in which the region corresponding to the donor splice site in intron 6 of SEQ ID NO: 1 is disrupted (i.e., the region at the 5' end of intron 6 in SEQ ID NO: 1). Examples and variations of nuclease agents that can be used in the methods are described elsewhere herein.

For example, targeted genetic modifications to an HSD17B13 gene in a genome can be generated by contacting a cell or the genome of a cell with a Cas protein and one or more guide RNAs that hybridize to one or more guide RNA recognition sequences within a target genomic locus in the HSD17B13 gene. That is, targeted genetic modifications to an HSD17B13 gene in a genome can be generated by contacting a cell or the genome of a cell with a Cas protein and one or more guide RNAs that target one or more guide RNA target sequences within a target genomic locus in the HSD17B13 gene. For example, such methods can comprise contacting a cell with a Cas protein and a guide RNA that target a guide RNA target sequence within the HSD17B13 gene. As one example, the guide RNA target sequence is within a region corresponding to exon 6 and/or intron 6 of SEQ ID NO: 2 when the HSD17B13 gene is optimally aligned with SEQ ID NO: 2. As one example, the guide RNA target sequence is within a region corresponding to exon 6 and/or intron 6 and/or exon 7 (e.g., exon 6 and/or intron 6, or exon 6 and/or exon 7), of SEQ ID NO: 2 when the HSD17B13 gene is optimally aligned with SEQ ID NO: 2. As another example, the guide RNA target sequence can includes or is proximate to a position corresponding to position 12666 of SEQ ID NO: 2 when the HSD17B13 gene is optimally aligned with SEQ ID NO: 2. For example, the guide RNA target sequence can be within about 1000, 500, 400, 300, 200, 100, 50, 45, 40, 35, 30, 25, 20, 15, 10, or 5 nucleotides of the position corresponding to position 12666 of SEQ ID NO: 2 when the HSD17B13 gene is optimally aligned with SEQ ID NO: 2. As yet another example, the guide RNA target sequence can include or be proximate to the start codon of an HSD17B13 gene or the stop codon of an HSD17B13 gene. For example, the guide RNA target sequence can be within about 10, 20, 30, 40, 50, 100, 200, 300, 400, 500, or 1,000 nucleotides of the start codon or the stop codon. The Cas protein and the guide RNA form a complex, and the Cas protein cleaves the guide RNA target sequence. Cleavage by the Cas protein can create a double-strand break or a single-strand break (e.g., if the Cas protein is a nickase). Such methods can result, for example, in an HSD17B13 gene in which the region corresponding to the donor splice site in intron 6 of SEQ ID NO: 1 is disrupted (i.e., the region at the 5' end of intron 6 in SEQ ID NO: 1), the start codon is disrupted, the stop codon is disrupted, or the coding sequence is deleted. Examples and variations of Cas (e.g., Cas9) proteins and guide RNAs that can be used in the methods are described elsewhere herein.

In some methods, two or more nuclease agents can be used. For example, two nuclease agents can be used, each targeting a nuclease target sequence within a region corresponding to exon 6 and/or intron 6, or exon 6 and/or exon 7, of SEQ ID NO: 2 when the HSD17B13 gene is optimally aligned with SEQ ID NO: 2, or including or proximate to a position corresponding to position 12666 of SEQ ID NO: 2 when the HSD17B13 gene is optimally aligned with SEQ ID NO: 2 (e.g., within about 1000, 500, 400, 300, 200, 100, 50, 45, 40, 35, 30, 25, 20, 15, 10, or 5 nucleotides of the position corresponding to position 12666 of SEQ ID NO: 2 when the HSD17B13 gene is optimally aligned with SEQ ID NO: 2). For example, two nuclease agents can be used, each targeting a nuclease target sequence within a region corresponding to exon 6 and/or intron 6 and/or exon 7, of SEQ ID NO: 2 when the HSD17B13 gene is optimally aligned with SEQ ID NO: 2. As another example, two or more nuclease agents can be used, each targeting a nuclease target sequence including or proximate to the start codon. As another example, two nuclease agents can be used, one targeting a nuclease target sequence including or proximate to the start codon, and one targeting a nuclease target sequence including or proximate to the stop codon, wherein cleavage by the nuclease agents can result in deletion of the coding region between the two nuclease target sequences. As yet another example, three or more nuclease agents can be used, with one or more (e.g., two) targeting nuclease target sequences including or proximate to the start codon, and one or more (e.g., two) targeting nuclease target sequences including or proximate to the stop codon, wherein cleavage by the nuclease agents can result in deletion of the coding region between the nuclease target sequences including or proximate to the start codon and the nuclease target sequence including or proximate to the stop codon.

Optionally, the cell can be further contacted with one or more additional guide RNAs that target additional guide RNA target sequences within the target genomic locus in the HSD17B13 gene. By contacting the cell with one or more additional guide RNAs (e.g., a second guide RNA that target a second guide RNA target sequence), cleavage by the Cas protein can create two or more double-strand breaks or two or more single-strand breaks (e.g., if the Cas protein is a nickase).

Optionally, the cell can additionally be contacted with one or more exogenous donor sequences which recombine with the target genomic locus in the HSD17B13 gene to generate a targeted genetic modification. Examples and variations of exogenous donor sequences that can be used in the methods are disclosed elsewhere herein.

The Cas protein, guide RNA(s), and exogenous donor sequence(s) can be introduced into the cell in any form and by any means as described elsewhere herein, and all or some of the Cas protein, guide RNA(s), and exogenous donor sequence(s) can be introduced simultaneously or sequentially in any combination.

In some such methods, the repair of the target nucleic acid (e.g., the HSD17B13 gene) by the exogenous donor sequence occurs via homology-directed repair (HDR). Homology-directed repair can occur when the Cas protein cleaves both strands of DNA in the HSD17B13 gene to create a double-strand break, when the Cas protein is a nickase that cleaves one strand of DNA in the target nucleic acid to create a single-strand break, or when Cas nickases are used to create a double-strand break formed by two offset nicks. In such methods, the exogenous donor sequence comprises 5' and 3' homology arms corresponding to 5' and 3' target sequences. The guide RNA target sequence(s) or cleavage site(s) can be adjacent to the 5' target sequence, adjacent to the 3' target sequence, adjacent to both the 5' target sequence and the 3' target sequence, or adjacent to neither the 5' target sequence nor the 3' target sequence. Optionally, the exogenous donor sequence can further comprise a nucleic acid insert flanked by the 5' and 3' homology arms, and the nucleic acid insert is inserted between the 5' and 3' target sequences. If no nucleic acid insert is present, the exogenous donor sequence can function to delete the genomic sequence between the 5' and 3' target sequences. Examples of exogenous donor sequences are disclosed elsewhere herein.

Alternatively, the repair of the HSD17B13 gene mediated by the exogenous donor sequence can occur via non-homologous end joining (NHEJ)-mediated ligation. In such methods, at least one end of the exogenous donor sequence comprises a short single-stranded region that is complementary to at least one overhang created by Cas-mediated cleavage in the HSD17B13 gene. The complementary end in the exogenous donor sequence can flank a nucleic acid insert. For example, each end of the exogenous donor sequence can comprise a short single-stranded region that is complementary to an overhang created by Cas-mediated cleavage in the HSD17B13 gene, and these complementary regions in the exogenous donor sequence can flank a nucleic acid insert.

Overhangs (i.e., staggered ends) can be created by resection of the blunt ends of a double-strand break created by Cas-mediated cleavage. Such resection can generate the regions of microhomology needed for fragment joining, but this can create unwanted or uncontrollable alterations in the HSD17B13 gene. Alternatively, such overhangs can be created by using paired Cas nickases. For example, the cell can be contacted with first and second nickases that cleave opposite strands of DNA, whereby the genome is modified through double nicking. This can be accomplished by contacting a cell with a first Cas protein nickase, a first guide RNA that target a first guide RNA target sequence within the target genomic locus in the HSD17B13 gene, a second Cas protein nickase, and a second guide RNA that targets a second guide RNA target sequence within target genomic locus in the HSD17B13 gene. The first Cas protein and the first guide RNA form a first complex, and the second Cas protein and the second guide RNA form a second complex. The first Cas protein nickase cleaves a first strand of genomic DNA within the first guide RNA target sequence, the second Cas protein nickase cleaves a second strand of genomic DNA within the second guide RNA target sequence, and optionally the exogenous donor sequence recombines with the target genomic locus in the HSD17B13 gene to generate the targeted genetic modification.

The first nickase can cleave a first strand of genomic DNA (i.e., the complementary strand), and the second nickase can cleave a second strand of genomic DNA (i.e., the non-complementary strand). The first and second nickases can be created, for example, by mutating a catalytic residue in the RuvC domain (e.g., the D10A mutation described elsewhere herein) of Cas9 or mutating a catalytic residue in the HNH domain (e.g., the H840A mutation described elsewhere herein) of Cas9. In such methods, the double nicking can be employed to create a double-strand break having staggered ends (i.e., overhangs). The first and second guide RNA target sequences can be positioned to create a cleavage site such that the nicks created by the first and second nickases on the first and second strands of DNA create a double-strand break. Overhangs are created when the nicks within the first and second CRISPR RNA target sequences are offset. The offset window can be, for example, at least about 5 bp, 10 bp, 20 bp, 30 bp, 40 bp, 50 bp, 60 bp, 70 bp, 80 bp, 90 bp, 100 bp or more. See, e.g., Ran et al. (2013) Cell 154:1380-1389; Mali et al. (2013) Nat. Biotech.31:833-838; and Shen et al. (2014) Nat. Methods 11:399-404, each of which is herein incorporated by reference in its entirety for all purposes.

(1) Types of Targeted Genetic Modifications

Various types of targeted genetic modifications can be introduced using the methods described herein. Such targeted modifications can include, for example, additions of one or more nucleotides, deletions of one or more nucleotides, substitutions of one or more nucleotides, a point mutation, or a combination thereof. For example, at least 1, 2, 3, 4, 5, 7, 8, 9, 10 or more nucleotides can be changed (e.g., deleted, inserted, or substituted) to form the targeted genomic modification. The deletions, insertions, or substitutions can be of any size, as disclosed elsewhere herein. See, e.g., Wang et al. (2013) Cell 153:910-918; Mandalos et al. (2012) PLOS ONE 7:e45768:1-9; and Wang et al. (2013) Nat Biotechnol. 31:530-532, each of which is herein incorporated by reference in its entirety for all purposes.

Such targeted genetic modifications can result in disruption of a target genomic locus. Disruption can include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation), and it can result in inactivation (i.e., loss of function) or loss of an allele. For example, a targeted modification can comprise disruption of the start codon of an HSD17B13 gene such that the start codon is no longer functional.

In a specific example, a targeted modification can comprise a deletion between first and second guide RNA target sequences or Cas cleavage sites. If an exogenous donor sequence (e.g., repair template or targeting vector) is used, the modification can comprise a deletion between first and second guide RNA target sequences or Cas cleavage sites as well as an insertion of a nucleic acid insert between the 5' and 3' target sequences.

Alternatively, if an exogenous donor sequence is used, alone or in combination with a nuclease agent, the modification can comprise a deletion between the 5' and 3' target sequences as well as an insertion of a nucleic acid insert between the 5' and 3' target sequences in the pair of first and second homologous chromosomes, thereby resulting in a homozygous modified genome. Alternatively, if the exogenous donor sequence comprises 5' and 3' homology arms with no nucleic acid insert, the modification can comprise a deletion between the 5' and 3' target sequences.

The deletion between the first and second guide RNA target sequences or the deletion between the 5' and 3' target sequences can be a precise deletion wherein the deleted nucleic acid consists of only the nucleic acid sequence between the first and second nuclease cleavage sites or only the nucleic acid sequence between the 5' and 3' target sequences such that there are no additional deletions or insertions at the modified genomic target locus. The deletion between the first and second guide RNA target sequences can also be an imprecise deletion extending beyond the first and second nuclease cleavage sites, consistent with imprecise repair by non-homologous end joining (NHEJ), resulting in additional deletions and/or insertions at the modified genomic locus. For example, the deletion can extend about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more beyond the first and second Cas protein cleavage sites. Likewise, the modified genomic locus can comprise additional insertions consistent with imprecise repair by NHEJ, such as insertions of about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more.

The targeted genetic modification can be, for example, a biallelic modification or a monoallelic modification. Biallelic modifications include events in which the same modification is made to the same locus on corresponding homologous chromosomes (e.g., in a diploid cell), or in which different modifications are made to the same locus on corresponding homologous chromosomes. In some methods, the targeted genetic modification is a monoallelic modification. A monoallelic modification includes events in which a modification is made to only one allele (i.e., a modification to the HSD17B13 gene in only one of the two homologous chromosomes). Homologous chromosomes include chromosomes that have the same genes at the same loci but possibly different alleles (e.g., chromosomes that are paired during meiosis). The term allele includes any of one or more alternative forms of a genetic sequence. In a diploid cell or organism, the two alleles of a given sequence typically occupy corresponding loci on a pair of homologous chromosomes.

A monoallelic mutation can result in a cell that is heterozygous for the targeted HSD17B13 modification. Heterozygosity includes situation in which only one allele of the HSD17B13 gene (i.e., corresponding alleles on both homologous chromosomes) have the targeted modification.

A biallelic modification can result in homozygosity for a targeted modification. Homozygosity includes situations in which both alleles of the HSD17B13 gene (i.e., corresponding alleles on both homologous chromosomes) have the targeted modification. Alternatively, a biallelic modification can result in compound heterozygosity (e.g., hemizygosity) for the targeted modification. Compound heterozygosity includes situations in which both alleles of the target locus (i.e., the alleles on both homologous chromosomes) have been modified, but they have been modified in different ways (e.g., a targeted modification in one allele and inactivation or disruption of the other allele). For example, in the allele without the targeted modification, a double-strand break created by the Cas protein may have been repaired by non-homologous end joining (NHEJ)-mediated DNA repair, which generates a mutant allele comprising an insertion or a deletion of a nucleic acid sequence and thereby causes disruption of that genomic locus. For example, a biallelic modification can result in compound heterozygosity if the cell has one allele with the targeted modification and another allele that is not capable of being expressed. Compound heterozygosity includes hemizygosity. Hemizygosity includes situations in which only one allele (i.e., an allele on one of two homologous chromosomes) of the target locus is present. For example, a biallelic modification can result in hemizygosity for a targeted modification if the targeted modification occurs in one allele with a corresponding loss or deletion of the other allele.

(2) Identifying Cells with Targeted Genetic Modifications

The methods disclosed herein can further comprise identifying a cell having a modified HSD17B13 gene. Various methods can be used to identify cells having a targeted genetic modification, such as a deletion or an insertion. Such methods can comprise identifying one cell having the targeted genetic modification in the HSD17B13 gene. Screening can be done to identify such cells with modified genomic loci.

The screening step can comprise a quantitative assay for assessing modification of allele (MOA) (e.g., loss-of-allele (LOA) and/or gain-of-allele (GOA) assays) of a parental chromosome. For example, the quantitative assay can be carried out via a quantitative PCR, such as a real-time PCR (qPCR). The real-time PCR can utilize a first primer set that recognizes the target genomic locus and a second primer set that recognizes a non-targeted reference locus. The primer set can comprise a fluorescent probe that recognizes the amplified sequence. The loss-of-allele (LOA) assay inverts the conventional screening logic and quantifies the number of copies of the native locus to which the mutation was directed. In a correctly targeted cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector. For example, the combined use of GOA and LOA assays will reveal a correctly targeted heterozygous clone as having lost one copy of the native target gene and gained one copy of the drug resistance gene or other inserted marker.

As an example, quantitative polymerase chain reaction (qPCR) can be used as the method of allele quantification, but any method that can reliably distinguish the difference between zero, one, and two copies of the target gene or between zero, one, and two copies of the nucleic acid insert can be used to develop a MOA assay. For example, TAQMAN® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus(loci) which is replaced by successful targeting (i.e., a LOA assay). The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus(loci) has been replaced by homologous recombination will result in an increase of one Ct for the target TAQMAN® reaction without an increase in the Ct for the reference gene when compared to DNA from non-targeted cells. For a GOA assay, another TAQMAN® probe can be used to determine the Ct of the nucleic acid insert that is replacing the targeted gene(s) or locus(loci) by successful targeting.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes). Conventional assays for screening for targeted modifications, such as long-range PCR, Southern blotting, or Sanger sequencing, can also be used. Such assays typically are used to obtain evidence for a linkage between the inserted targeting vector and the targeted genomic locus. For example, for a long-range PCR assay, one primer can recognize a sequence within the inserted DNA while the other recognizes a target genomic locus sequence beyond the ends of the targeting vector's homology arms.

Next generation sequencing (NGS) can also be used for screening. Next-generation sequencing can also be referred to as "NGS" or "massively parallel sequencing" or "high throughput sequencing." In the methods disclosed herein, it is not necessary to screen for targeted cells using selection markers. For example, the MOA and NGS assays described herein can be relied on without using selection cassettes.

B. Methods of Altering Expression of HSD17B13 Nucleic Acids

Various methods are provided for altering expression of nucleic acids encoding HSD17B13 proteins. In some methods, expression is altered through cleavage with a nuclease agent to cause disruption of the nucleic acid encoding the HSD17B13 protein, as described in further detail elsewhere herein. In some methods, expression is altered through use of a DNA-binding protein fused or linked to a transcription activation domain or a transcription repression domain. In some methods, expression is altered through use of RNA interference compositions, such as antisense RNA, shRNA, or siRNA.

In one example, expression of an HSD17B13 gene or a nucleic acid encoding an HSD17B13 protein can be modified by contacting a cell or the genome within a cell with a nuclease agent that induces one or more nicks or double-strand breaks at a target sequence at a target genomic locus within the HSD17B13 gene or nucleic acid encoding an HSD17B13 protein. Such cleavage can result in disruption of expression of the HSD17B13 gene or nucleic acid encoding an HSD17B13 protein. For example, the nuclease target sequence can include or be proximate to the start codon of an HSD17B13 gene. For example, the target sequence can be within about 10, 20, 30, 40, 50, 100, 200, 300, 400, 500, or 1,000 nucleotides of the start codon, and cleavage by the nuclease agent can disrupt the start codon. As another example, two or more nuclease agents can be used, each targeting a nuclease target sequence including or proximate to the start codon. As another example, two nuclease agents can be used, one targeting a nuclease target sequence including or proximate to the start codon, and one targeting a nuclease target sequence including or proximate to the stop codon, wherein cleavage by the nuclease agents can result in deletion of the coding region between the two nuclease target sequences. As yet another example, three or more nuclease agents can be used, with one or more (e.g., two) targeting nuclease target sequences including or proximate to the start codon, and one or more (e.g., two) targeting nuclease target sequences including or proximate to the stop codon, wherein cleavage by the nuclease agents can result in deletion of the coding region between the nuclease target sequences including or proximate to the start codon and the nuclease target sequence including or proximate to the stop codon. Other examples of modifying an HSD17B13 gene or a nucleic acid encoding an HSD17B13 protein are disclosed elsewhere herein.

In another example, expression of an HSD17B13 gene or a nucleic acid encoding an HSD17B13 protein can be modified by contacting a cell or the genome within a cell with a DNA-binding protein that binds to a target genomic locus within the HSD17B13 gene. The DNA-binding protein can be, for example, a nuclease-inactive Cas protein fused to a transcriptional activator domain or a transcriptional repressor domain. Other examples of DNA-binding proteins include zinc finger proteins fused to a transcriptional activator domain or a transcriptional repressor domain, or Transcription Activator-Like Effector (TALE) proteins fused to a transcriptional activator domain or a transcriptional repressor domain. Examples of such proteins are disclosed elsewhere herein. For example, in some methods, a transcriptional repressor can be used to decrease expression of a wild type HSD17B13 gene or an HSD17B13 gene that is not the rs72613567 variant (e.g., to decrease expression of HSD17B13 Transcript or Isoform A). Likewise, in some methods, a transcriptional activator can be used to increase expression of an HSD17B13 gene rs72613567 variant gene (e.g., to increase expression of HSD17B13 Transcript or Isoform D).

The target sequence (e.g., guide RNA target sequence) for the DNA-binding protein can be anywhere within the HSD17B13 gene or a nucleic acid encoding an HSD17B13 protein suitable for altering expression. As one example, the target sequence can be within a regulatory element, such as an enhancer or promoter, or can be in proximity to a regulatory element. For example, the target sequence can include or be proximate to the start codon of an HSD17B13 gene. For example, the target sequence can be within about 10, 20, 30, 40, 50, 100, 200, 300, 400, 500, or 1,000 nucleotides of the start codon.

In another example, antisense molecules can be used to alter expression of an HSD17B13 gene or a nucleic acid encoding an HSD17B13 protein. Examples of antisense molecules include antisense RNAs, small interfering RNAs (siRNAs), and short hairpin RNAs (shRNAs). Such antisense RNAs, siRNAs, or shRNAs can be designed to target any region of an mRNA. For example, the antisense RNAs, siRNAs, or shRNAs can be designed to target a region unique to one or more of the HSD17B13 transcripts disclosed herein, or a region common to one or more of the HSD17B13 transcripts disclosed herein. Examples of nucleic acids hybridizing to cDNAs and variant HSD17B13 transcripts are disclosed in more detail elsewhere herein. For example, the antisense RNA, siRNA, or shRNA can hybridize to a sequence within SEQ ID NO: 4 (HSD17B13 Transcript A). Optionally, the antisense RNA, siRNA, or shRNA can decrease expression of HSD17B13 Transcript A in a cell. Optionally, the antisense RNA, siRNA, or shRNA hybridizes to a sequence present in SEQ ID NO: 4 (HSD17B13 Transcript A) that is not present in SEQ ID NO: 7 (HSD17B13 Transcript D). Optionally, the antisense RNA, siRNA, or shRNA hybridizes to a sequence within exon 7 or a sequence spanning the exon 6-exon 7 boundary of SEQ ID NO: 4 (HSD17B13 Transcript A).

As another example, the antisense RNA, siRNA, or shRNA can hybridize to a sequence within SEQ ID NO: 7 (HSD17B13 Transcript D). Optionally, the antisense RNA, siRNA, or shRNA can decrease expression of HSD17B13 Transcript D in a cell. Optionally, the antisense RNA, siRNA, or shRNA hybridizes to a sequence present in SEQ ID NO: 7 (HSD17B13 Transcript D) that is not present in SEQ ID NO: 4 (HSD17B13 Transcript A). Optionally, the antisense RNA, siRNA, or shRNA hybridizes to a sequence within exon 7 or a sequence spanning the exon 6-exon 7 boundary of SEQ ID NO: 7 (HSD17B13 Transcript D).

C. Introducing Nucleic Acids and Proteins into Cells

The nucleic acids and proteins disclosed herein can be introduced into a cell by any means. "Introducing" includes presenting to the cell the nucleic acid or protein in such a manner that the sequence gains access to the interior of the cell. The introducing can be accomplished by any means, and one or more of the components (e.g., two of the components, or all of the components) can be introduced into the cell simultaneously or sequentially in any combination. For example, an exogenous donor sequence can be introduced prior to the introduction of a nuclease agent, or it can be introduced following introduction of nuclease agent (e.g., the exogenous donor sequence can be administered about 1, 2, 3, 4, 8, 12, 24, 36, 48, or 72 hours before or after introduction of the nuclease agent). See, e.g., US 2015/0240263 and US 2015/0110762, each of which is herein incorporated by reference in its entirety for all purposes. Contacting the genome of a cell with a nuclease agent or exogenous donor sequence can comprise introducing one or more nuclease agents or nucleic acids encoding nuclease agents (e.g., one or more Cas proteins or nucleic acids encoding one or more Cas proteins, and one or more guide RNAs or nucleic acids encoding one or more guide RNAs (i.e., one or more CRISPR RNAs and one or more tracrRNAs)) and/or one or more exogenous donor sequences into the cell. Contacting the genome of cell (i.e., contacting a cell) can comprise introducing only one of the above components, one or more of the components, or all of the components into the cell.

A nuclease agent can be introduced into the cell in the form of a protein or in the form of a nucleic acid encoding the nuclease agent, such as an RNA (e.g., messenger RNA (mRNA)) or DNA. When introduced in the form of a DNA, the DNA can be operably linked to a promoter active in the cell. Such DNAs can be in one or more expression constructs.

For example, a Cas protein can be introduced into the cell in the form of a protein, such as a Cas protein complexed with a gRNA, or in the form of a nucleic acid encoding the Cas protein, such as an RNA (e.g., messenger RNA (mRNA)) or DNA. A guide RNA can be introduced into the cell in the form of an RNA or in the form of a DNA encoding the guide RNA. When introduced in the form of a DNA, the DNA encoding the Cas protein and/or the guide RNA can be operably linked to a promoter active in the cell. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs, DNAs encoding one or more tracrRNAs, and DNA encoding a Cas protein can be components of separate nucleic acid molecules).

In some methods, DNA encoding a nuclease agent (e.g., a Cas protein and a guide RNA) and/or DNA encoding an exogenous donor sequence can be introduced into a cell via DNA minicircles. See, e.g., WO 2014/182700, herein incorporated by reference in its entirety for all purposes. DNA minicircles are supercoiled DNA molecules that can be used for non-viral gene transfer that have neither an origin of replication nor an antibiotic selection marker. Thus, DNA minicircles are typically smaller in size than plasmid vector. These DNAs are devoid of bacterial DNA, and thus lack the unmethylated CpG motifs found in bacterial DNA.

The methods provided herein do not depend on a particular method for introducing a nucleic acid or protein into the cell, only that the nucleic acid or protein gains access to the interior of a least one cell. Methods for introducing nucleic acids and proteins into various cell types are known and include, for example, stable transfection methods, transient transfection methods, and virus-mediated methods.

Transfection protocols as well as protocols for introducing nucleic acids or proteins into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell can also be accomplished by microinjection. Microinjection of an mRNA is preferably into the cytoplasm (e.g., to deliver mRNA directly to the translation machinery), while microinjection of a protein or a DNA encoding a DNA encoding a Cas protein is preferably into the nucleus. Alternatively, microinjection can be carried out by injection into both the nucleus and the cytoplasm: a needle can first be introduced into the nucleus and a first amount can be injected, and while removing the needle from the cell a second amount can be injected into the cytoplasm. If a nuclease agent protein is injected into the cytoplasm, the protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); Meyer et al. (2010) *Proc. Natl. Acad. Sci. USA* 107:15022-15026 and Meyer et al. (2012) *Proc. Nati. Acad. Sci. USA* 109:9354-9359.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein.

Introduction of nucleic acids and proteins into cells can also be accomplished by hydrodynamic delivery (HDD). Hydrodynamic delivery has emerged as a near-perfect method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule.

The introduction of nucleic acids or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In some cases, the cells employed in the methods and compositions have a DNA construct stably incorporated into their genome. In such cases, the contacting can comprise providing a cell with the construct already stably incorporated into its genome. For example, a cell employed in the methods disclosed herein may have a preexisting Cas-encoding gene stably incorporated into its genome (i.e., a Cas-ready cell). "Stably incorporated" or "stably introduced" or "stably integrated" includes the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

D. Nuclease Agents and DNA-Binding Proteins

Any nuclease agent that induces a nick or double-strand break into a desired target sequence or any DNA-binding protein that binds to a desired target sequence can be used in the methods and compositions disclosed herein. A naturally occurring or native nuclease agent can be employed so long as the nuclease agent induces a nick or double-strand break in a desired target sequence. Likewise, a naturally occurring or native DNA-binding protein can be employed so long as the DNA-binding protein binds to the desired target sequence. Alternatively, a modified or engineered nuclease agent or DNA-binding protein can be employed. An "engineered nuclease agent or DNA-binding protein" includes a nuclease agent or DNA-binding protein that is engineered (modified or derived) from its native form to specifically recognize a desired target sequence. Thus, an engineered nuclease agent or DNA-binding protein can be derived from a native, naturally occurring nuclease agent or DNA-binding protein or it can be artificially created or synthesized. The engineered nuclease agent or DNA-binding protein can recognize a target sequence, for example, wherein the target sequence is not a sequence that would have been recognized by a native (non-engineered or non-modified) nuclease agent or DNA-binding protein. The modification of the nuclease agent or DNA-binding protein can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of nuclease agents or DNA-binding proteins (i.e., an engineered nuclease agent or DNA-binding protein) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent or DNA-binding protein, wherein the active variants retain the ability to cut at a desired target sequence and hence retain nick or double-strand-break-inducing activity or retain the ability to bind a desired target sequence. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence.

The term "target sequence for a nuclease agent" includes a DNA sequence at which a nick or double-strand break is induced by a nuclease agent. Likewise, the term "target sequence for a DNA-binding protein" includes a DNA sequence to which a DNA-binding protein will bind. The target sequence can be endogenous (or native) to the cell or the target sequence can be exogenous to the cell. A target sequence that is exogenous to the cell is not naturally occurring in the genome of the cell. The target sequence can also exogenous to the polynucleotides of interest that one desires to be positioned at the target locus. In some cases, the target sequence is present only once in the genome of the host cell.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are known (e.g., TAQMAN® qPCR assay, Frendewey et al. (2010) *Methods in Enzymology* 476:295-307, herein incorporated by reference in its entirety for all purposes).

The length of the target sequence can vary, and includes, for example, target sequences that are about 30-36 bp for a zinc finger protein or zinc finger nuclease (ZFN) pair (i.e., about 15-18 bp for each ZFN), about 36 bp for a Transcription Activator-Like Effector (TALE) protein or Transcription Activator-Like Effector Nuclease (TALEN), or about 20 bp for a CRISPR/Cas9 guide RNA.

The target sequence of the DNA-binding protein or nuclease agent can be positioned anywhere in or near the target genomic locus. The target sequence can be located within a coding region of a gene (e.g., the HSD17B13 gene), or within regulatory regions that influence the expression of the gene. A target sequence of the DNA-binding protein or nuclease agent can be located in an intron, an exon, a promoter, an enhancer, a regulatory region, or any non-protein coding region.

One type of DNA-binding protein that can be employed in the various methods and compositions disclosed herein is a Transcription Activator-Like Effector (TALE). A TALE can be fused or linked to, for example, an epigenetic modification domain, a transcriptional activation domain, or a transcriptional repressor domain. Examples of such domains are described with respect to Cas proteins, below, and can also be found, for example, in WO 2011/145121, herein incorporated by reference in its entirety for all purposes. Correspondingly, one type of nuclease agent that can be employed in the various methods and compositions disclosed herein is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease such as FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *Proc. Natl. Acad. Sci. U.S.A.* 107(50:21617-21622; Scholze & Boch (2010) *Virulence* 1:428-432; Christian et al. (2010) *Genetics* 186:757-761; Li et al. (2011) *Nucleic Acids Res.* 39(1):359-372; and Miller et al. (2011) *Nature Biotechnology* 29:143-148, each of which is herein incorporated by reference in its entirety for all purposes.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety for all purposes. In various embodiments, TAL effector nucleases are engineered that cut in or near a target nucleic acid sequence in, for example, a genomic locus of interest, wherein the target nucleic acid sequence is at or near a sequence to be modified by a an exogenous donor sequence. The TAL nucleases suitable for use with the various methods and compositions provided herein include those that are specifically designed to bind at or near target nucleic acid sequences to be modified by exogenous donor sequences as described elsewhere herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

Another example of a DNA-binding protein is a zinc finger protein. Such zinc finger proteins can be linked or fused to, for example, an epigenetic modification domain, a transcriptional activation domain, or a transcriptional repressor domain. Examples of such domains are described with respect to Cas proteins, below, and can also be found, for example, in WO 2011/145121, herein incorporated by reference in its entirety for all purposes. Correspondingly, another example of a nuclease agent that can be employed in the various methods and compositions disclosed herein is a zinc-finger nuclease (ZFN). In some ZFNs, each monomer of the ZFN comprises three or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US 2006/0246567; US 2008/0182332; US 2002/0081614; US 2003/0021776; WO 2002/057308 A2; US 2013/0123484; US 2010/0291048; WO 2011/017293 A2; and Gaj et al. (2013) *Trends in Biotechnology* 31(7):397-405, each of which is herein incorporated by reference in its entirety for all purposes.

Other suitable DNA-binding proteins and nuclease agents for use in the methods and compositions described herein include CRISPR-Cas systems, which are described elsewhere herein.

The DNA-binding protein or nuclease agent may be introduced into the cell by any known means. A polypeptide encoding the DNA-binding protein or nuclease agent may be directly introduced into the cell. Alternatively, a polynucleotide encoding the DNA-binding protein or nuclease agent can be introduced into the cell. When a polynucleotide encoding the DNA-binding protein or nuclease agent is introduced into the cell, the DNA-binding protein or nuclease agent can be transiently, conditionally, or constitutively expressed within the cell. For example, the polynucleotide encoding the DNA-binding protein or nuclease agent can be contained in an expression cassette and be operably linked to a conditional promoter, an inducible promoter, a constitutive promoter, or a tissue-specific promoter. Such promoters are discussed in further detail elsewhere herein. Alternatively, the DNA-binding protein or nuclease agent can be introduced into the cell as an mRNA encoding a DNA-binding protein or a nuclease agent.

A polynucleotide encoding a DNA-binding protein or nuclease agent can be stably integrated in the genome of the cell and operably linked to a promoter active in the cell. Alternatively, a polynucleotide encoding a DNA-binding protein or nuclease agent can be in a targeting vector or in a vector or a plasmid that is separate from the targeting vector comprising the insert polynucleotide.

When the DNA-binding protein or nuclease agent is provided to the cell through the introduction of a polynucleotide encoding the DNA-binding protein or nuclease agent, such a polynucleotide encoding a DNA-binding protein or nuclease agent can be modified to substitute codons having a higher frequency of usage in the cell of interest, as compared to the naturally occurring polynucleotide sequence encoding the DNA-binding protein or nuclease agent. For example, the polynucleotide encoding the DNA-binding protein or nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

E. CRISPR-Cas Systems

The methods disclosed herein can utilize Clustered Regularly Interspersed Short Palindromic Repeats (CRISPR)/CRISPR-associated (Cas) systems or components of such systems to modify a genome within a cell. CRISPR-Cas systems include transcripts and other elements involved in the expression of, or directing the activity of, Cas genes. A CRISPR-Cas system can be a type I, a type II, or a type III system. Alternatively a CRISPR/Cas system can be, for example, a type V system (e.g., subtype V-A or subtype V-B). The methods and compositions disclosed herein can employ CRISPR-Cas systems by utilizing CRISPR complexes (comprising a guide RNA (gRNA) complexed with a Cas protein) for site-directed cleavage of nucleic acids.

The CRISPR-Cas systems used in the methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, non-naturally occurring CRISPR/Cas systems can employ CRISPR complexes comprising a gRNA and a Cas protein that do not naturally occur together, a Cas protein that does not occur naturally, or a gRNA that does not occur naturally.

(1) Cas Proteins and Polynucleotides Encoding Cas Proteins

Cas proteins generally comprise at least one RNA recognition or binding domain that can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break in the HSD17B13 gene (e.g., a double-strand break with blunt ends), or it can be a nickase that creates a single-strand break in the HSD17B13 gene.

Examples of Cas proteins include Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, and Cu1966, and homologs or modified versions thereof.

An exemplary Cas protein is a Cas9 protein or a protein derived from a Cas9 protein from a type II CRISPR/Cas system. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) Cell 163(3):759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens,* and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break at a guide RNA target sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes.

Cas proteins (e.g., nuclease-active Cas proteins or nuclease-inactive Cas proteins) can also be operably linked to heterologous polypeptides as fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. Examples of transcriptional activation domains include a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. Other examples include activation domains from Oct1, Oct-2A, SP1, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, TRAB1PC4, and HSF1. See, e.g., US 2016/0237456, EP3045537, and WO 2011/145121, each of which is incorporated by reference in its entirety for all purposes. In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) *Nature* 517(7536):583-588, herein incorporated by reference in its entirety for all purposes. Examples of transcriptional repressor domains include inducible cAMP early repressor (ICER) domains, Kruppel-associated box A (KRAB-A) repressor domains, YY1 glycine rich repressor domains, Sp 1-like repressors, E(spl) repressors, IκB repressor, and MeCP2. Other examples include transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., EP3045537 and WO 2011/145121, each of which is incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to a heterologous polypeptide that provides for subcellular localization. Such heterologous polypeptides can include, for example, one or more nuclear localization signals (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be operably linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290, herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to exogenous donor sequences or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian* 1 *Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor sequence or labeled nucleic acid can be tethered to the C-terminus, the N-terminus, or to an internal region within the Cas protein. Preferably, the exogenous donor sequence or labeled nucleic acid is tethered to the C-terminus or the N-terminus of the Cas protein. Likewise, the Cas protein can be tethered to the 5' end, the 3' end, or to an internal region within the exogenous donor sequence or labeled nucleic acid. That is, the exogenous donor sequence or labeled nucleic acid can be tethered in any orientation and polarity. Preferably, the Cas protein is tethered to the 5' end or the 3' end of the exogenous donor sequence or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

(2) Guide RNAs

A "guide RNA" or "gRNA" is an RNA molecule that binds to a Cas protein (e.g., Cas9 protein) and targets the Cas protein to a specific location within a target DNA (e.g., the HSD17B13 gene). In particular, disclosed herein are guide RNAs effective to direct a Cas enzyme to bind to or cleave an HSD17B13 locus or HSD17B13 gene. One exemplary guide RNA is a guide RNA effective to direct a Cas enzyme to bind to or cleave an HSD17B13 gene, wherein the guide RNA comprises a DNA-targeting segment that hybridizes to a guide RNA recognition sequence (i.e., targets a guide RNA target sequence) within the HSD17B13 gene that includes or is proximate to a position corresponding to position 12666 of SEQ ID NO: 2 when the HSD17B13 gene is optimally aligned with SEQ ID NO: 2. By target a guide RNA target sequence is meant hybridize to the complementary strand sequence that is the reverse complement of the guide RNA target sequence on the non-complementary strand. For example, the guide RNA target sequence can be within about 5, 10, 15, 20, 25, 30, 35, 40, 45, 50, 100, 200, 300, 400, 500, or 1,000 nucleotides of a position corresponding to position 12666 of SEQ ID NO: 2 when the HSD17B13 gene is optimally aligned with SEQ ID NO: 2. Other exemplary guide RNAs comprise a DNA-targeting segment that targets a guide RNA target sequence within the HSD17B13 gene that is within a region corresponding to exon 6 and/or intron 6 of SEQ ID NO: 2 when the HSD17B13 gene is optimally aligned with SEQ ID NO: 2. Other exemplary guide RNAs comprise a DNA-targeting segment that targets a guide RNA target sequence within the HSD17B13 gene that is within a region corresponding to exon 6 and/or intron 6 and/or exon 7 of SEQ ID NO: 2 when the HSD17B13 gene is optimally aligned with SEQ ID NO: 2. Other exemplary guide RNAs comprise a DNA-targeting segment that hybridizes to a guide RNA recognition sequence (i.e., targets a guide RNA target sequence) within the HSD17B13 gene that includes or is proximate to the start codon of the HSD17B13 gene or includes or is proximate to the stop codon of the HSD17B13 gene. For example, the guide RNA target sequence can be within about 5, 10, 15, 20, 25, 30, 35, 40, 45, 50, 100, 200, 300, 400, 500, or 1,000 nucleotides of the start codon or within about 5, 10, 15, 20, 25, 30, 35, 40, 45, 50, 100, 200, 300, 400, 500, or 1,000 nucleotides of the stop codon. For example, the guide RNA target sequence can be within a region corresponding to exon 1 of SEQ ID NO: 1 or 2 when the HSD17B13 gene is optimally aligned with SEQ ID NO: 1 or 2. Likewise, the guide RNA target sequence can be within a region corresponding to exon 7 of SEQ ID NO: 1 or 2 when the HSD17B13 gene is optimally aligned with SEQ ID NO: 1 or 2. The HSD17B13 gene can be an HSD17B13 gene from any organism. For example, the HSD17B13 gene can be a human HSD17B13 gene or an ortholog from another organism, such as a non-human mammal, a rodent, a mouse, or a rat.

Examples of guide RNA target sequences at the 5' end of the human HSD17B13 gene comprise, consist essentially of, or consist of the sequences set forth in SEQ ID NOS: 20-81 and are set forth in the table below. Examples of guide RNA DNA-targeting segments corresponding to SEQ ID NOS: 20-81 are set forth in in the table below and are identical to SEQ ID NOS: 20-81 except with uracils instead of thymines. A guide RNA DNA-targeting segment can comprise, consist essentially of, or consist of any the DNA-targeting segment sequences set forth in the table below. Examples of guide RNA target sequences adjacent to the transcription start site (TSS) of the human HSD17B13 gene comprise, consist essentially of, or consist of the sequences set forth in SEQ ID NOS: 20-41 and are set forth in the table below. Exemplary guide RNA target sequences adjacent to the TSS include SEQ ID NOS: 21-23, 33, and 35. SEQ ID NOS: 33 and 35 are closest to the TSS. Exemplary crRNAs and sgRNAs (comprising scaffold version 1, 2, 3, or 4) corresponding to the guide RNA target sequences at the 5' end of the human HSD17B13 gene comprise, consist essentially of, or consist of any of the sequences set forth in the table below.

| Guide RNA Target Sequences at 5' End of the Human HSD17B13 Gene | | | | | | | | | |
|---|---|---|---|---|---|---|---|---|---|
| | | | | SEQ ID NO | | | | | |
| | | | gRNA Target | DNA-Targeting | | sgRNA | | | |
| Strand | PAM | Guide RNA Target Sequence | Seq | Segment | crRNA | v1 | v2 | v3 | v4 |
| - | GGG | TGTCAGGTTAGTTAGATGAA | 42 | 1423 | 270 | 500 | 730 | 960 | 1190 |
| - | AGG | GTGTCAGGTTAGTTAGATGA | 43 | 1424 | 271 | 501 | 731 | 961 | 1191 |
| + | AGG | CCTGACACATATACAGACTA | 44 | 1425 | 272 | 502 | 732 | 962 | 1192 |
| + | GGG | CTGACACATATACAGACTAA | 45 | 1426 | 273 | 503 | 733 | 963 | 1193 |
| - | AGG | CCTTAGTCTGTATATGTGTC | 46 | 1427 | 274 | 504 | 734 | 964 | 1194 |
| + | AGG | CATATACAGACTAAGGGACC | 47 | 1428 | 275 | 505 | 735 | 965 | 1195 |
| + | GGG | ATATACAGACTAAGGGACCA | 48 | 1429 | 276 | 506 | 736 | 966 | 1196 |
| - | TGG | TCAAAGTTTGATAAATTCCC | 49 | 1430 | 277 | 507 | 737 | 967 | 1197 |
| + | TGG | AAAATACAAAGATAAGTAGA | 50 | 1431 | 278 | 508 | 738 | 968 | 1198 |
| + | TGG | ACTCTGTGACTTTAAAAAGT | 51 | 1432 | 279 | 509 | 739 | 969 | 1199 |
| - | AGG | GGTTCTGTGGGATATTAATA | 52 | 1433 | 280 | 510 | 740 | 970 | 1200 |
| - | GGG | ACAGAGCATATTGGTTCTGT | 53 | 1434 | 281 | 511 | 741 | 971 | 1201 |
| - | TGG | GACAGAGCATATTGGTTCTG | 54 | 1435 | 282 | 512 | 742 | 972 | 1202 |

-continued

Guide RNA Target Sequences at 5' End of the Human HSD17B13 Gene

| | | | gRNA Target | DNA-Targeting | SEQ ID NO | | | | |
|---|---|---|---|---|---|---|---|---|---|
| | | | | | | sgRNA | | | |
| Strand | PAM | Guide RNA Target Sequence | Seq | Segment | crRNA | v1 | v2 | v3 | v4 |
| − | TGG | TGCAAAACGACAGAGCATAT | 55 | 1436 | 283 | 513 | 743 | 973 | 1203 |
| − | AGG | GAGCTGGGCATGGAATAGGC | 56 | 1437 | 284 | 514 | 744 | 974 | 1204 |
| − | AGG | ACTGGAGCTGGGCATGGAAT | 57 | 1438 | 285 | 515 | 745 | 975 | 1205 |
| − | TGG | CTCATTACTGGAGCTGGGCA | 58 | 1439 | 286 | 516 | 746 | 976 | 1206 |
| − | GGG | TTGTTCTCATTACTGGAGCT | 59 | 1440 | 287 | 517 | 747 | 977 | 1207 |
| − | TGG | ATTGTTCTCATTACTGGAGC | 60 | 1441 | 288 | 518 | 748 | 978 | 1208 |
| − | TGG | GGGGAGATTGTTCTCATTAC | 61 | 1442 | 289 | 519 | 749 | 979 | 1209 |
| − | GGG | GAGGAGAAAATCTGTGGCTG | 62 | 1443 | 290 | 520 | 750 | 980 | 1210 |
| − | GGG | AGAGGAGAAAATCTGTGGCT | 63 | 1444 | 291 | 521 | 751 | 981 | 1211 |
| − | TGG | CAGAGGAGAAAATCTGTGGC | 64 | 1445 | 292 | 522 | 752 | 982 | 1212 |
| − | TGG | TCCTCAGAGGAGAAAATCTG | 65 | 1446 | 293 | 523 | 753 | 983 | 1213 |
| − | AGG | TGAAGTTTTTCATTCCTCAG | 20 | 1447 | 294 | 524 | 754 | 984 | 1214 |
| + | AGG | CTTCACCAACGACTCCAAGT | 21 | 1448 | 295 | 525 | 755 | 985 | 1215 |
| − | TGG | CTACTCCTACTTGGAGTCGT | 22 | 1449 | 296 | 526 | 756 | 986 | 1216 |
| + | TGG | CTCCAAGTAGGAGTAGATGA | 23 | 1450 | 297 | 527 | 757 | 987 | 1217 |
| − | TGG | CACCATCATCTACTCCTACT | 24 | 1451 | 298 | 528 | 758 | 988 | 1218 |
| + | AGG | TGATGGTGATCAGAAGCAGA | 25 | 1452 | 299 | 529 | 759 | 989 | 1219 |
| + | AGG | TCAGAAGCAGAAGGATTTCT | 26 | 1453 | 300 | 530 | 760 | 990 | 1220 |
| + | TGG | GATTTCTAGGATGATGTTCA | 27 | 1454 | 301 | 531 | 761 | 991 | 1221 |
| + | TGG | TTGCTCTGTCCTCTTCCTTC | 28 | 1455 | 302 | 532 | 762 | 992 | 1222 |
| − | AGG | AGGACTGAACCAGAAGGAAG | 29 | 1456 | 303 | 533 | 763 | 993 | 1223 |
| − | AGG | TACACAAGGACTGAACCAGA | 30 | 1457 | 304 | 534 | 764 | 994 | 1224 |
| + | AGG | TTCAGTCCTTGTGTAGTCCT | 31 | 1458 | 305 | 535 | 765 | 995 | 1225 |
| + | GGG | TCAGTCCTTGTGTAGTCCTA | 32 | 1459 | 306 | 536 | 766 | 996 | 1226 |
| + | AGG | GTCCTTGTGTAGTCCTAGGG | 33 | 1460 | 307 | 537 | 767 | 997 | 1227 |
| + | AGG | CTTGTGTAGTCCTAGGGAGG | 34 | 1461 | 308 | 538 | 768 | 998 | 1228 |
| − | AGG | CTCCTCCCTAGGACTACACA | 35 | 1462 | 309 | 539 | 769 | 999 | 1229 |
| − | AGG | GTAGACAGTACCTCCTCCCT | 36 | 1463 | 310 | 540 | 770 | 1000 | 1230 |
| + | AGG | TACTGTCTACACAGAGCTCT | 37 | 1464 | 311 | 541 | 771 | 1001 | 1231 |
| + | GGG | ACTGTCTACACAGAGCTCTA | 38 | 1465 | 312 | 542 | 772 | 1002 | 1232 |
| + | AGG | TCTACACAGAGCTCTAGGGA | 39 | 1466 | 313 | 543 | 773 | 1003 | 1233 |
| + | GGG | CTACACAGAGCTCTAGGGAA | 40 | 1467 | 314 | 544 | 774 | 1004 | 1234 |
| + | GGG | TACACAGAGCTCTAGGGAAG | 41 | 1468 | 315 | 545 | 775 | 1005 | 1235 |
| + | TGG | GGGGTGTGCCCAGTTGTTAA | 66 | 1469 | 316 | 546 | 776 | 1006 | 1236 |
| + | GGG | GGGTGTGCCCAGTTGTTAAT | 67 | 1470 | 317 | 547 | 777 | 1007 | 1237 |

Guide RNA Target Sequences at 5' End of the Human HSD17B13 Gene

| | | | | SEQ ID NO | | | | | |
|---|---|---|---|---|---|---|---|---|---|
| | | | gRNA Target | DNA-Targeting | | sgRNA | | | |
| Strand | PAM | Guide RNA Target Sequence | Seq | Segment | crRNA | v1 | v2 | v3 | v4 |
| − | GGG | TGGTAGTCCCATTAACAACT | 68 | 1471 | 318 | 548 | 778 | 1008 | 1238 |
| − | TGG | CTGGTAGTCCCATTAACAAC | 69 | 1472 | 319 | 549 | 779 | 1009 | 1239 |
| + | TGG | TTGTTAATGGGACTACCAGA | 70 | 1473 | 320 | 550 | 780 | 1010 | 1240 |
| + | TGG | TACCAGATGGAAGCCAGCTT | 71 | 1474 | 321 | 551 | 781 | 1011 | 1241 |
| − | TGG | TTCCAAAGCTGGCTTCCATC | 72 | 1475 | 322 | 552 | 782 | 1012 | 1242 |
| + | AGG | TGGAAGCCAGCTTTGGAAGC | 73 | 1476 | 323 | 553 | 783 | 1013 | 1243 |
| − | TGG | ACAAGGCCTGCTTCCAAAGC | 74 | 1477 | 324 | 554 | 784 | 1014 | 1244 |
| + | TGG | GCCTTGTTCACGTGTTCTAA | 75 | 1478 | 325 | 555 | 785 | 1015 | 1245 |
| + | GGG | CCTTGTTCACGTGTTCTAAT | 76 | 1479 | 326 | 556 | 786 | 1016 | 1246 |
| − | AGG | CCCATTAGAACACGTGAACA | 77 | 1480 | 327 | 557 | 787 | 1017 | 1247 |
| − | AGG | TTGGCATCACTTCATATTTG | 78 | 1481 | 328 | 558 | 788 | 1018 | 1248 |
| − | TGG | CTTGTGCTCTTGGCATCACT | 79 | 1482 | 329 | 559 | 789 | 1019 | 1249 |
| − | TGG | AGCACACTCTCTTGTGCTCT | 80 | 1483 | 330 | 560 | 790 | 1020 | 1250 |
| + | TGG | GCACAAGAGAGTGTGCTCTC | 81 | 1484 | 331 | 561 | 791 | 1021 | 1251 |

Examples of guide RNA target sequences at the 3' end of the human HSD17B13 gene comprise, consist essentially of, or consist of the sequences set forth in SEQ ID NOS: 82-225 and are set forth in the table below. Examples of guide RNA DNA-targeting segments corresponding to SEQ ID NOS: 82-225 are set forth in SEQ ID NOS: 1485-1628, respectively, which are identical to SEQ ID NOS: 82-225 except with uracils instead of thymines. A guide RNA DNA-targeting segment can comprise, consist essentially of, or consist of any the sequences set forth in SEQ ID NOS: 1485-1628. Exemplary crRNAs and sgRNAs (comprising scaffold version 1, 2, 3, or 4) corresponding to the guide RNA target sequences at the 3' end of the human HSD17B13 gene comprise, consist essentially of, or consist of any of the sequences set forth in the table below.

Guide RNA Target Sequences at 3' End of the Human HSD17B13 Gene

| | | | | SEQ ID NO | | | | | |
|---|---|---|---|---|---|---|---|---|---|
| | | | gRNA | | | sgRNA | | | |
| Strand | PAM | Guide RNA Target Sequence | Target Seq | | crRNA | v1 | v2 | v3 | v4 |
| + | AGG | GCTTAATCTCACACATAGAA | 82 | | 332 | 562 | 792 | 1022 | 1252 |
| + | GGG | CTTAATCTCACACATAGAAA | 83 | | 333 | 563 | 793 | 1023 | 1253 |
| + | GGG | TTAATCTCACACATAGAAAG | 84 | | 334 | 564 | 794 | 1024 | 1254 |
| − | TGG | AGGAGTGCTGGTTTATCAAC | 85 | | 335 | 565 | 795 | 1025 | 1255 |
| − | TGG | TTCTTTGACAGCAGGAGTGC | 86 | | 336 | 566 | 796 | 1026 | 1256 |
| − | AGG | ACTCTGGTTTCTTTGACAGC | 87 | | 337 | 567 | 797 | 1027 | 1257 |
| + | TGG | ACCAGAGTTGAGAAAACCCC | 88 | | 338 | 568 | 798 | 1028 | 1258 |
| − | TGG | TCCAGGGGTTTTCTCAACTC | 89 | | 339 | 569 | 799 | 1029 | 1259 |
| − | GGG | CAGTTATTAAATGAATCCAG | 90 | | 340 | 570 | 800 | 1030 | 1260 |
| − | GGG | GCAGTTATTAAATGAATCCA | 91 | | 341 | 571 | 801 | 1031 | 1261 |

Guide RNA Target Sequences at 3' End of the Human HSD17B13 Gene

| Strand | PAM | Guide RNA Target Sequence | Target Seq | crRNA | v1 | v2 | v3 | v4 |
|---|---|---|---|---|---|---|---|---|
| − | AGG | GGCAGTTATTAAATGAATCC | 92 | 342 | 572 | 802 | 1032 | 1262 |
| − | TGG | TGGATGGTAACAGCTACATC | 93 | 343 | 573 | 803 | 1033 | 1263 |
| + | TGG | GCTGTTACCATCCACATCCT | 94 | 344 | 574 | 804 | 1034 | 1264 |
| − | TGG | TCAAGAACCAAGGATGTGGA | 95 | 345 | 575 | 805 | 1035 | 1265 |
| − | TGG | TCCTTCAAGAACCAAGGATG | 96 | 346 | 576 | 806 | 1036 | 1266 |
| − | AGG | TGAGTGTCCTTCAAGAACCA | 97 | 347 | 577 | 807 | 1037 | 1267 |
| + | AGG | TTTTATTTTATAACTACAAG | 98 | 348 | 578 | 808 | 1038 | 1268 |
| + | AGG | TTGTTTTAATAAAAACAAG | 99 | 349 | 579 | 809 | 1039 | 1269 |
| − | TGG | TATTATAGAATGCTTTTGCA | 100 | 350 | 580 | 810 | 1040 | 1270 |
| + | TGG | CAAGATTAGTCTTGATGTAG | 101 | 351 | 581 | 811 | 1041 | 1271 |
| + | GGG | AAGATTAGTCTTGATGTAGT | 102 | 352 | 582 | 812 | 1042 | 1272 |
| + | CGG | AGTCTTGATGTAGTGGGAGT | 103 | 353 | 583 | 813 | 1043 | 1273 |
| + | AGG | TTTTTCTATTAAAAAAAAAA | 104 | 354 | 584 | 814 | 1044 | 1274 |
| + | TGG | TCTATTAAAAAAAAAAAGGC | 105 | 355 | 585 | 815 | 1045 | 1275 |
| + | GGG | CTATTAAAAAAAAAAAGGCT | 106 | 356 | 586 | 816 | 1046 | 1276 |
| + | CGG | AAAAAAAAAAAGGCTGGGCA | 107 | 357 | 587 | 817 | 1047 | 1277 |
| + | TGG | AAAAAAAAGGCTGGGCACGG | 108 | 358 | 588 | 818 | 1048 | 1278 |
| + | TGG | CACCCGTAATCCCAGCACTT | 109 | 359 | 589 | 819 | 1049 | 1279 |
| + | GGG | ACCCGTAATCCCAGCACTTT | 110 | 360 | 590 | 820 | 1050 | 1280 |
| + | AGG | CGTAATCCCAGCACTTTGGG | 111 | 361 | 591 | 821 | 1051 | 1281 |
| − | GGG | TCCCAAAGTGCTGGGATTAC | 112 | 362 | 592 | 822 | 1052 | 1282 |
| − | CGG | CTCCCAAAGTGCTGGGATTA | 113 | 363 | 593 | 823 | 1053 | 1283 |
| + | AGG | CCCAGCACTTTGGGAGGCCG | 114 | 364 | 594 | 824 | 1054 | 1284 |
| − | GGG | CCTCGGCCTCCCAAAGTGCT | 115 | 365 | 595 | 825 | 1055 | 1285 |
| + | AGG | GCACTTTGGGAGGCCGAGGC | 116 | 366 | 596 | 826 | 1056 | 1286 |
| + | TGG | CTTTGGGAGGCCGAGGCAGG | 117 | 367 | 597 | 827 | 1057 | 1287 |
| + | AGG | GCCGAGGCAGGTGGATCACG | 118 | 368 | 598 | 828 | 1058 | 1288 |
| − | CGG | ACCTCGTGATCCACCTGCCT | 119 | 369 | 599 | 829 | 1059 | 1289 |
| + | AGG | GGCAGGTGGATCACGAGGTC | 120 | 370 | 600 | 830 | 1060 | 1290 |
| + | TGG | GGCAGGTGGATCACGAGGTC | 121 | 371 | 601 | 831 | 1061 | 1291 |
| + | TGG | TCAGGAGATCGAGACCATCT | 122 | 372 | 602 | 832 | 1062 | 1292 |
| − | TGG | CGAGACCATCTTGGCTAACA | 123 | 373 | 603 | 833 | 1063 | 1293 |
| − | GGG | TTTCACCATGTTAGCCAAGA | 124 | 374 | 604 | 834 | 1064 | 1294 |
| − | GGG | TTGTATTTTTGTAGAGACG | 125 | 375 | 605 | 835 | 1065 | 1295 |
| − | CGG | TTTGTATTTTTTGTAGAGAC | 126 | 376 | 606 | 836 | 1066 | 1296 |
| + | CGG | TTTTGTATTTTTTGTAGAGA | 127 | 377 | 607 | 837 | 1067 | 1297 |

Guide RNA Target Sequences at 3' End of the Human HSD17B13 Gene

| | | | | SEQ ID NO | | | | |
|---|---|---|---|---|---|---|---|---|
| | | | gRNA | | | sgRNA | | |
| Strand | PAM | Guide RNA Target Sequence | Target Seq | crRNA | v1 | v2 | v3 | v4 |
| + | GGG | AAAAATACAAAAAATTAGCC | 128 | 378 | 608 | 838 | 1068 | 1298 |
| + | TGG | TACAAAAAATTAGCCGGGTG | 129 | 379 | 609 | 839 | 1069 | 1299 |
| + | TGG | AAAAAATTAGCCGGGTGTGG | 130 | 380 | 610 | 840 | 1070 | 1300 |
| + | CGG | AAATTAGCCGGGTGTGGTGG | 131 | 381 | 611 | 841 | 1071 | 1301 |
| + | GGG | AATTAGCCGGGTGTGGTGGC | 132 | 382 | 612 | 842 | 1072 | 1302 |
| - | CGG | CAGGCGCCCGCCACCACACC | 133 | 383 | 613 | 843 | 1073 | 1303 |
| + | AGG | GCCTGTAGTCCCAGCTACTC | 134 | 384 | 614 | 844 | 1074 | 1304 |
| + | AGG | TGTAGTCCCAGCTACTCAGG | 135 | 385 | 615 | 845 | 1075 | 1305 |
| - | AGG | TCCTGAGTAGCTGGGACTAC | 136 | 386 | 616 | 846 | 1076 | 1306 |
| + | AGG | CCCAGCTACTCAGGAGGCTG | 137 | 387 | 617 | 847 | 1077 | 1307 |
| - | GGG | CCTCAGCCTCCTGAGTAGCT | 138 | 388 | 618 | 848 | 1078 | 1308 |
| - | TGG | GCCTCAGCCTCCTGAGTAGC | 139 | 389 | 619 | 849 | 1079 | 1309 |
| + | TGG | AGGAGGCTGAGGCAGGAGAA | 140 | 390 | 620 | 850 | 1080 | 1310 |
| + | CGG | GCAGGAGAATGGCGTGAACC | 141 | 391 | 621 | 851 | 1081 | 1311 |
| + | GGG | CAGGAGAATGGCGTGAACCC | 142 | 392 | 622 | 852 | 1082 | 1312 |
| + | AGG | GAGAATGGCGTGAACCCGGG | 143 | 393 | 623 | 853 | 1083 | 1313 |
| + | TGG | AATGGCGTGAACCCGGGAGG | 144 | 394 | 624 | 854 | 1084 | 1314 |
| - | GGG | CACTGCAAGCTCCACCTCCC | 145 | 395 | 625 | 855 | 1085 | 1315 |
| - | CGG | TCACTGCAAGCTCCACCTCC | 146 | 396 | 626 | 856 | 1086 | 1316 |
| + | TGG | CATACCACTGCACTCCAGCC | 147 | 397 | 627 | 857 | 1087 | 1317 |
| + | GGG | ATACCACTGCACTCCAGCCT | 148 | 398 | 628 | 858 | 1088 | 1318 |
| - | TGG | TCGCCCAGGCTGGAGTGCAG | 149 | 399 | 629 | 859 | 1089 | 1319 |
| - | TGG | TCTCACTCTTTCGCCCAGGC | 150 | 400 | 630 | 860 | 1090 | 1320 |
| - | AGG | GGAGTCTCACTCTTTCGCCC | 151 | 401 | 631 | 861 | 1091 | 1321 |
| - | TGG | TGTTTTTTGTTTTTTTGAGA | 152 | 402 | 632 | 862 | 1092 | 1322 |
| - | TGG | AGGAAGAAAGAAAGGTTTTT | 153 | 403 | 633 | 863 | 1093 | 1323 |
| - | AGG | AGAAGAAAAGGAAGAAAGAA | 154 | 404 | 634 | 864 | 1094 | 1324 |
| + | TGG | CTTTCTTCCTTTTCTTCTCT | 155 | 405 | 635 | 865 | 1095 | 1325 |
| + | GGG | TTTCTTCCTTTTCTTCTCTT | 156 | 406 | 636 | 866 | 1096 | 1326 |
| - | AGG | AATGGACCCAAGAGAAGAAA | 157 | 407 | 637 | 867 | 1097 | 1327 |
| - | TGG | GGCTATTACATAAGAAACAA | 158 | 408 | 638 | 868 | 1098 | 1328 |
| - | TGG | CACAGGAAAAGGAACTGTAC | 159 | 409 | 639 | 869 | 1099 | 1329 |
| - | AGG | ATTAAAGCTAACACAGGAAA | 160 | 410 | 640 | 870 | 1100 | 1330 |
| - | AGG | TCAAAATTAAAGCTAACAC | 161 | 411 | 641 | 871 | 1101 | 1331 |
| + | TGG | TAAAATTGTCTAAACATCTC | 162 | 412 | 642 | 872 | 1102 | 1332 |

Guide RNA Target Sequences at 3' End of the Human HSD17B13 Gene

| Strand | PAM | Guide RNA Target Sequence | gRNA Target Seq | crRNA | sgRNA v1 | v2 | v3 | v4 |
|---|---|---|---|---|---|---|---|---|
| − | AGG | AGAGATGTTTAGACAATTTT | 163 | 413 | 643 | 873 | 1103 | 1333 |
| + | AGG | TCTAAACATCTCTGGGACCA | 164 | 414 | 644 | 874 | 1104 | 1334 |
| − | TGG | TTTATGCTTTCATATATCCT | 165 | 415 | 645 | 875 | 1105 | 1335 |
| + | AGG | AGCATAAATTACAAAGAAAA | 166 | 416 | 646 | 876 | 1106 | 1336 |
| + | TGG | TACAAAGAAAAAGGTTATCA | 167 | 417 | 647 | 877 | 1107 | 1337 |
| + | GGG | ACAAAGAAAAAGGTTATCAT | 168 | 418 | 648 | 878 | 1108 | 1338 |
| + | GGG | CAAAGAAAAAGGTTATCATG | 169 | 419 | 649 | 879 | 1109 | 1339 |
| + | CGG | TCTGAGATTTAAAATAGAGT | 170 | 420 | 650 | 880 | 1110 | 1340 |
| − | AGG | CTTATAAGATACATTATGAA | 171 | 421 | 651 | 881 | 1111 | 1341 |
| + | AGG | TATCTTATAAGACTATAAAA | 172 | 422 | 652 | 882 | 1112 | 1342 |
| + | GGG | ATCTTATAAGACTATAAAAA | 173 | 423 | 653 | 883 | 1113 | 1343 |
| + | AGG | TTATAAGACTATAAAAAGGG | 174 | 424 | 654 | 884 | 1114 | 1344 |
| + | AGG | TAAAAGGGAGGAAATATAG | 175 | 425 | 655 | 885 | 1115 | 1345 |
| + | GGG | AAAAAGGGAGGAAATATAGA | 176 | 426 | 656 | 886 | 1116 | 1346 |
| + | TGG | AAATATAGAGGGTCCACTTT | 177 | 427 | 657 | 887 | 1117 | 1347 |
| + | TGG | TATAGAGGGTCCACTTTTGG | 178 | 428 | 658 | 888 | 1118 | 1348 |
| − | TGG | ACTCTGAAGTCCACCAAAAG | 179 | 429 | 659 | 889 | 1119 | 1349 |
| + | TGG | AGAATAGAGTTGCACCGTTT | 180 | 430 | 660 | 890 | 1120 | 1350 |
| − | TGG | AAAACGGTGCAACTCTATTC | 181 | 431 | 661 | 891 | 1121 | 1351 |
| + | AGG | CCGTTTTGGGCTAATGAAAA | 182 | 432 | 662 | 892 | 1122 | 1352 |
| − | CGG | CCTTTTTCATTAGCCCAAAA | 183 | 433 | 663 | 893 | 1123 | 1353 |
| + | AGG | TGGGCTAATGAAAAAGGAAG | 184 | 434 | 664 | 894 | 1124 | 1354 |
| + | AGG | TAATGAAAAAGGAAGAGGCT | 185 | 435 | 665 | 895 | 1125 | 1355 |
| + | GGG | AATGAAAAAGGAAGAGGCTA | 186 | 436 | 666 | 896 | 1126 | 1356 |
| + | AGG | CTGAATCTTAAAATATGTCC | 187 | 437 | 667 | 897 | 1127 | 1357 |
| − | TGG | CAGGCAGCTTTATCTCAACC | 188 | 438 | 668 | 898 | 1128 | 1358 |
| − | AGG | CTAAGAGATCAAGTTTCAGC | 189 | 439 | 669 | 899 | 1129 | 1359 |
| + | TGG | GTGTTCTTGTTGATATTCTG | 190 | 440 | 670 | 900 | 1130 | 1360 |
| + | TGG | CTTGTTGATATTCTGTGGCA | 191 | 441 | 671 | 901 | 1131 | 1361 |
| + | TGG | TCTGTGGCATGGCTACAGAT | 192 | 442 | 672 | 902 | 1132 | 1362 |
| − | AGG | AGAACTTATTTACACAGGGA | 193 | 443 | 673 | 903 | 1133 | 1363 |
| − | GGG | AAAGAGAACTTATTTACACA | 194 | 444 | 674 | 904 | 1134 | 1364 |
| − | AGG | CAAAGAGAACTTATTTACAC | 195 | 445 | 675 | 905 | 1135 | 1365 |
| + | AGG | TTCTCTTTGTATTTACTTTT | 196 | 446 | 676 | 906 | 1136 | 1366 |
| + | GGG | TCTCTTTGTATTTACTTTTA | 197 | 447 | 677 | 907 | 1137 | 1367 |
| + | AGG | CTTTGTATTTACTTTTAGGG | 198 | 448 | 678 | 908 | 1138 | 1368 |

Guide RNA Target Sequences at 3' End of the Human HSD17B13 Gene

| | | | | SEQ ID NO | | | | | |
|---|---|---|---|---|---|---|---|---|---|
| | | | | gRNA | | sgRNA | | | |
| Strand | PAM | Guide RNA Target Sequence | Target Seq | crRNA | v1 | v2 | v3 | v4 |
|---|---|---|---|---|---|---|---|---|
| + | TGG | AGCTTTTGTCCACCTTTAAA | 199 | 449 | 679 | 909 | 1139 | 1369 |
| − | TGG | TTTATTTTTCCATTTAAAGG | 200 | 450 | 680 | 910 | 1140 | 1370 |
| − | AGG | TATTTTATTTTTCCATTTAA | 201 | 451 | 681 | 911 | 1141 | 1371 |
| − | AGG | CTTACATAAACATACTTAAA | 202 | 452 | 682 | 912 | 1142 | 1372 |
| + | AGG | TAAGCACAGAAGTTTTTAAG | 203 | 453 | 683 | 913 | 1143 | 1373 |
| + | AGG | AAGTTTTTAAGAGGCATGAA | 204 | 454 | 684 | 914 | 1144 | 1374 |
| − | AGG | ATATTTACGTAGTTTTTCAT | 205 | 455 | 685 | 915 | 1145 | 1375 |
| + | AGG | CGTAAATATTCTTGAGAAAC | 206 | 456 | 686 | 916 | 1146 | 1376 |
| + | AGG | TTCTTGAGAAACAGGAAGAC | 207 | 457 | 687 | 917 | 1147 | 1377 |
| − | TGG | TAATATTAAAAACATTGGTT | 208 | 458 | 688 | 918 | 1148 | 1378 |
| + | AGG | CCAATGTTTTTAATATTATC | 209 | 459 | 689 | 919 | 1149 | 1379 |
| − | TGG | CCTGATAATATTAAAAACAT | 210 | 460 | 690 | 920 | 1150 | 1380 |
| + | TGG | CATTATCATGCATACATCTC | 211 | 461 | 691 | 921 | 1151 | 1381 |
| + | TGG | ATCATGCATACATCTCTGGC | 212 | 462 | 692 | 922 | 1152 | 1382 |
| + | TGG | TTCATTTCATTTTGATTTTG | 213 | 463 | 693 | 923 | 1153 | 1383 |
| − | TGG | ATTCAATTTGAAGCAGTGGT | 214 | 464 | 694 | 924 | 1154 | 1384 |
| − | TGG | GAATATTCAATTTGAAGCAG | 215 | 465 | 695 | 925 | 1155 | 1385 |
| + | AGG | CATACGATTTAAAATCGCT | 216 | 466 | 696 | 926 | 1156 | 1386 |
| + | AGG | AAAATCGCTGAGGCGCGTTC | 217 | 467 | 697 | 927 | 1157 | 1387 |
| − | AGG | TTTTTTTTTCTTTTTTGTAC | 218 | 468 | 698 | 928 | 1158 | 1388 |
| − | TGG | CTGTTGTCAAAGATTTTAAA | 219 | 469 | 699 | 929 | 1159 | 1389 |
| + | TGG | TGACAACAGAGTTCTGTTTT | 220 | 470 | 700 | 930 | 1160 | 1390 |
| + | TGG | AGAATACGCTGAGAGTTATC | 221 | 471 | 701 | 931 | 1161 | 1391 |
| − | AGG | GCAAGAGAAGAAAAGAACGG | 222 | 472 | 702 | 932 | 1162 | 1392 |
| − | CGG | GTTGCAAGAGAAGAAAAGAA | 223 | 473 | 703 | 933 | 1163 | 1393 |
| − | TGG | ATGCACACGTAAAAGAGAGG | 224 | 474 | 704 | 934 | 1164 | 1394 |
| − | AGG | AAGATGCACACGTAAAAGAG | 225 | 475 | 705 | 935 | 1165 | 1395 |

Examples of guide RNA target sequences proximate to a position corresponding to position 12666 of SEQ ID NO: 2 comprise, consist essentially of, or consist of the sequences set forth in SEQ ID NOS: 226-239 and are set forth in the table below. Examples of guide RNA DNA-targeting segments corresponding to SEQ ID NOS: 226-239 are set forth in SEQ ID NOS: 1629-1642, respectively, which are identical to SEQ ID NOS: 226-239 except with uracils instead of thymines. A guide RNA DNA-targeting segment can comprise, consist essentially of, or consist of any the sequences set forth in SEQ ID NOS: 1629-1642. Exemplary guide RNA target sequences proximate to a position corresponding to position 12666 of SEQ ID NO: 2 include SEQ ID NOS: 230 and 231. Exemplary crRNAs and sgRNAs (comprising scaffold version 1, 2, 3, or 4) corresponding to the guide RNA target sequences proximate to a position corresponding to position 12666 of SEQ ID NO: 2 comprise, consist essentially of, or consist of any of the sequences set forth in the table below.

Guide RNA Target Sequences Near rs72613567 Variation

| Strand | PAM | Guide RNA Target Sequence | Distance to Variation (bp) | gRNA Target Seq | SEQ ID NO crRNA | sgRNA v1 | v2 | v3 | v4 |
|---|---|---|---|---|---|---|---|---|---|
| + | TGG | ATCATGCATACATCTCTGGC | 107 | 226 | 476 | 706 | 936 | 1166 | 1396 |
| + | TGG | TTCATTTCATTTTGATTTTG | 74 | 227 | 477 | 707 | 937 | 1167 | 1397 |
| − | TGG | ATTCAATTTGAAGCAGTGGT | 62 | 228 | 478 | 708 | 938 | 1168 | 1398 |
| − | TGG | GAATATTCAATTTGAAGCAG | 58 | 229 | 479 | 709 | 939 | 1169 | 1399 |
| + | AGG | CATACGATTTAAAATCGCTG | 22 | 230 | 480 | 710 | 940 | 1170 | 1400 |
| + | AGG | AAAATCGCTGAGGCGCGTTC | 12 | 231 | 481 | 711 | 941 | 1171 | 1401 |
| − | AGG | TTTTTTTTTCTTTTTTGTAC | 22 | 232 | 482 | 712 | 942 | 1172 | 1402 |
| − | TGG | CTGTTGTCAAAGATTTTAAA | 40 | 233 | 483 | 713 | 943 | 1173 | 1403 |
| + | TGG | TGACAACAGAGTTCTGTTTT | 65 | 234 | 484 | 714 | 944 | 1174 | 1404 |
| + | TGG | AGAATACGCTGAGAGTTATC | 94 | 235 | 485 | 715 | 945 | 1175 | 1405 |
| − | AGG | GCAAGAGAAGAAAAGAACGG | 121 | 236 | 486 | 716 | 946 | 1176 | 1406 |
| − | CGG | GTTGCAAGAGAAGAAAAGAA | 124 | 237 | 487 | 717 | 947 | 1177 | 1407 |
| − | TGG | ATGCACACGTAAAAGAGAGG | 146 | 238 | 488 | 718 | 948 | 1178 | 1408 |
| − | AGG | AAGATGCACACGTAAAAGAG | 149 | 239 | 489 | 719 | 949 | 1179 | 1409 |

Examples of guide RNA target sequences in the mouse Hsd17b13 gene proximate to a position corresponding to position 12666 of SEQ ID NO: 2 when the mouse Hsd17b13 gene is optimally aligned with SEQ ID NO: 2 comprise, consist essentially of, or consist of the sequences set forth in Table 12 in Example 4. Examples of guide RNA target sequences at the 5' end of the mouse Hsd17b13 gene comprise, consist essentially of, or consist of the sequences set forth Table 12 in Example 4. Examples of guide RNA DNA-targeting segments corresponding to those guide RNA target sequences are also set forth in Table 12 in Example 4. A guide RNA DNA-targeting segment can comprise, consist essentially of, or consist of any those sequences. Exemplary crRNAs and sgRNAs (comprising scaffold version 1, 2, 3, or 4) corresponding to the guide RNA target sequences in Table 12 in Example 4 can comprise, consist essentially of, or consist of any of the crRNA or sgRNA sequences set forth in Table 12 in Example 4.

Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 1421). Any of the DNA-targeting segments disclosed herein can be joined to the 5' end of SEQ ID NO: 1421 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGUC-CGUUAUCAACUUGAAAAAGUGGCACC GAGUCG-GUGCUUU (SEQ ID NO: 1422).

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that targets a guide RNA target sequence by hybridizing to the opposite strand (i.e., the complementary strand). If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence (i.e., the complementary strand of the guide RNA recognition sequence on the strand opposite of the guide RNA target sequence) in a target DNA. The DNA-targeting segment of a gRNA interacts with a target DNA (e.g., the HSD17B13 gene) in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting sequence and the complementary strand of the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the complementary strand of the guide RNA recognition sequence within the target DNA can be at least 60% over about 20 contiguous nucleotides. As an example, the percent complementarity between the DNA-targeting sequence and the complementary strand of the guide RNA recognition sequence within the target DNA is 100% over the 14 contiguous nucleotides at the 5' end of the complementary strand of the guide RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the complementary strand of the guide RNA recognition sequence within the target DNA is 100% over the seven contiguous nucleotides at the 5' end of the complementary strand of the guide RNA recognition sequence within the complementary strand of the target DNA and as low as 0% over the remainder. In such a case, the DNA-targeting sequence can be considered to be 7 nucleotides in length. In some guide RNAs, at least 17 nucleotides within the DNA-targeting sequence are complementary to the target DNA. For example, the DNA-targeting sequence can be 20 nucleotides in length and can comprise 1, 2, or 3 mismatches with the complementary strand of the guide RNA recognition sequence. Preferably, the mismatches are not adjacent to a protospacer adjacent motif (PAM) sequence (e.g., the mismatches are in the 5' end of the DNA-targeting sequence, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs have the DNA-targeting segment and a scaffold sequence (i.e., the protein-binding or Cas-binding sequence of the guide RNA). For example, such guide RNAs have a 5' DNA-targeting segment and a 3' scaffold sequence. Exemplary scaffold sequences comprise, consist essentially of, or consist of:

```
                                              (version 1; SEQ ID NO: 1420)
GUUUUAGAGCUAGAAAUAGCAAGUUAAAAUAAGGCUAGUCCGUUAUCAAC

UUGAAAAAGUGGCACCGAGUCGGUGCU;

(version 2; SEQ ID NO: 256)
GUUGGAACCAUUCAAAACAGCAUAGCAAGUUAAAAUAAGGCUAGUCCGUU

AUCAACUUGAAAAAGUGGCACCGAGUCGGUGC;

(version 3; SEQ ID NO: 257)
GUUUUAGAGCUAGAAAUAGCAAGUUAAAAUAAGGCUAGUCCGUUAUCAAC

UUGAAAAAGUGGCACCGAGUCGGUGC;
and (version 4; SEQ ID NO: 258)
GUUUAAGAGCUAUGCUGGAAACAGCAUAGCAAGUUUAAAUAAGGCUAGUC

CGUUAUCAACUUGAAAAAGUGGCACCGAGUCGGUGC.
```

Guide RNAs targeting any of the guide RNA target sequences disclosed herein (e.g., SEQ ID NOS: 20-239 and 259-268) can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of SEQ ID NOS: 1420, 256, 257, or 258 to form a single guide RNA (chimeric guide RNA). Guide RNA versions 1, 2, 3, and 4 as disclosed elsewhere herein refer to DNA-targeting segments joined with scaffold versions 1, 2, 3, and 4, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) Nature 517(7536):583-588, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be prepared by chemical synthesis.

The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid. The vector can further comprise an exogenous donor sequence and/or the vector can further comprise a nucleic acid encoding a Cas protein. Alternatively, the DNA encoding the gRNA can be in a vector or a plasmid that is separate from the vector comprising an exogenous donor sequence and/or the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Also disclosed herein are compositions comprising one or more guide RNAs (e.g., 1, 2, 3, 4, or more guide RNAs) disclosed herein and a carrier increasing the stability of the isolated nucleic acid or protein (e.g., prolonging the period under given conditions of storage (e.g., −, 20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein. Such compositions can further comprise one or more (e.g., 1, 2, 3, 4, or more) exogenous donor sequences and/or one or more (e.g., 1, 2, 3, 4, or more) targeting vectors and/or one or more (e.g., 1, 2, 3, 4, or more) expression vectors as disclosed elsewhere herein.

(3) Guide RNA Recognition Sequences and Guide RNA Target Sequences

The term "guide RNA recognition sequence" includes nucleic acid sequences present in a target DNA (e.g., the HSD17B13 gene) to which a DNA-targeting segment of a gRNA will bind, provided sufficient conditions for binding exist. The term guide RNA recognition sequence as used herein encompasses both strands of the target double-stranded DNA (i.e., the sequence on the complementary strand to which the guide RNA hybridizes and the corresponding sequence on the non-complementary strand adjacent to the protospacer adjacent motif (PAM)). The term "guide RNA target sequence" as used herein refers specifically to the sequence on the non-complementary strand adjacent to the PAM (i.e., upstream or 5' of the PAM). That is, the guide RNA target sequence refers to the sequence on the non-complementary strand corresponding to the sequence to which the guide RNA hybridizes on the complementary strand. A guide RNA target sequence is equivalent to the DNA-targeting segment of a guide RNA, but with thymines instead of uracils. As one example, a guide RNA target sequence for a Cas9 enzyme would refer to the sequence on the non-complementary strand adjacent to the 5'-NGG-3' PAM. Guide RNA recognition sequences include sequences to which a guide RNA is designed to have complementarity, where hybridization between the complementary strand of a guide RNA recognition sequence and a DNA targeting sequence of a guide RNA promotes the formation of a CRISPR complex. Full complementarity is not necessarily required, provided that there is sufficient complementarity to cause hybridization and promote formation of a CRISPR complex. Guide RNA recognition sequences or guide RNA target sequences also include cleavage sites for Cas proteins, described in more detail below. A guide RNA recognition sequence or guide RNA target sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "non-complementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to the complementary strand of a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence" or guide RNA target sequence. The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence or guide RNA target sequence of the nickase on the first strand is separated from the guide RNA recognition sequence or guide RNA target sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific binding and/or cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA target sequence on the non-complementary strand opposite of the strand to which the guide RNA hybridizes. Optionally, the guide RNA target sequence can be flanked on the 3' end by the PAM. Alternatively, the guide RNA target sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-N$_1$GG-3', where N is any DNA nucleotide and is immediately 3' of the guide RNA recognition sequence of the non-complementary strand of the target DNA (i.e., immediately 3' of the guide RNA target sequence). As such, the PAM sequence of the complementary strand would be 5'-CCN$_2$-3', where N$_2$ is any DNA nucleotide and is immediately 5' of the guide RNA recognition sequence of the complementary strand of the target DNA. In some such cases, N$_1$ and N$_2$ can be complementary and the N$_1$-N$_2$ base pair can be any base pair (e.g., N$_1$=C and N$_2$=G; N$_1$=G and N$_2$=C; N$_1$=A and N$_2$=T; or N$_1$=T, and N$_2$=A). In the case of Cas9 from *S. aureus*, the PAM can be NNGRRT or NNGRR, where N can be A, G, C, or T, and R can be G or A. In some cases (e.g., for FnCpf1), the PAM sequence can be upstream of the 5' end and have the sequence 5'-TTN-3'.

Examples of guide RNA target sequences or guide RNA target sequences in addition to a PAM sequence are provided below. For example, the guide RNA target sequence can be a 20-nucleotide DNA sequence immediately preceding an NGG motif recognized by a Cas9 protein. Examples of such guide RNA target sequence plus a PAM sequence are GN$_{19}$NGG (SEQ ID NO: 248) or N$_{20}$NGG (SEQ ID NO: 249). See, e.g., WO 2014/165825, herein incorporated by reference in its entirety for all purposes. The guanine at the 5' end can facilitate transcription by RNA polymerase in cells. Other examples of guide RNA target sequences plus a PAM sequence can include two guanine nucleotides at the 5' end (e.g., GGN$_{20}$NGG; SEQ ID NO: 250) to facilitate efficient transcription by T7 polymerase in vitro. See, e.g., WO 2014/065596, herein incorporated by reference in its entirety for all purposes. Other guide RNA target sequences plus a PAM sequence can have between 4-22 nucleotides in length of SEQ ID NOS: 248-250, including the 5' G or GG and the 3' GG or NGG. Yet other guide RNA target sequences can have between 14 and 20 nucleotides in length of SEQ ID NOS: 248-250.

The guide RNA recognition sequence or guide RNA target sequence can be any nucleic acid sequence endogenous or exogenous to a cell. The guide RNA recognition sequence or guide RNA target sequence can be a sequence coding a gene product (e.g., a protein) or a non-coding sequence (e.g., a regulatory sequence) or can include both.

As one example, the guide RNA recognition sequence or guide RNA target sequence can be within a region corresponding to exon 6 and/or intron 6, exon 6 and/or exon 7, or exon 6 and/or intron 6 and/or exon 7 of SEQ ID NO: 2 when the HSD17B13 gene is optimally aligned with SEQ ID NO: 2. As another example, the guide RNA recognition sequence or guide RNA target sequence can include or is proximate to a position corresponding to position 12666 of SEQ ID NO: 2 when the HSD17B13 gene is optimally aligned with SEQ ID NO: 2. For example, the guide RNA recognition sequence or guide RNA target sequence can be within about 1000, 500, 400, 300, 200, 100, 50, 45, 40, 35, 30, 25, 20, 15, 10, or 5 nucleotides of the position corresponding to position 12666 of SEQ ID NO: 2 when the HSD17B13 gene is optimally aligned with SEQ ID NO: 2. As yet another example, the guide RNA recognition sequence or guide RNA target sequence can include or be proximate to the start codon of an HSD17B13 gene or the stop codon of an HSD17B13 gene. For example, the guide RNA recognition sequence or guide RNA target sequence can be within about 10, 20, 30, 40, 50, 100, 200, 300, 400, 500, or 1,000 nucleotides of the start codon or the stop codon. Examples of such guide RNA target sequences and of guide RNAs targeting such guide RNA target sequences are disclosed elsewhere herein.

F. Exogenous Donor Sequences or Targeting Vectors

The methods and compositions disclosed herein can utilize exogenous donor sequences (e.g., targeting vectors or repair templates) to modify an HSD17B13 gene, either without cleavage of the HSD17B13 gene or following cleavage of the HSD17B13 gene with a nuclease agent. An exogenous donor sequence refers to any nucleic acid or vector that includes the elements that are required to enable site-specific recombination with a target sequence. Using exogenous donor sequences in combination with nuclease agents may result in more precise modifications within the HSD17B13 gene by promoting homology-directed repair.

In such methods, the nuclease agent cleaves the HSD17B13 gene to create a single-strand break (nick) or double-strand break, and the exogenous donor sequence recombines the HSD17B13 gene via non-homologous end joining (NHEJ)-mediated ligation or through a homology-directed repair event. Optionally, repair with the exogenous donor sequence removes or disrupts the nuclease cleavage site so that alleles that have been targeted cannot be re-targeted by the nuclease agent.

Exogenous donor sequences can comprise deoxyribonucleic acid (DNA) or ribonucleic acid (RNA), they can be single-stranded or double-stranded, and they can be in linear or circular form. For example, an exogenous donor sequence can be a single-stranded oligodeoxynucleotide (ssODN). See, e.g., Yoshimi et al. (2016) *Nat. Commun.* 7:10431, herein incorporated by reference in its entirety for all purposes. An exemplary exogenous donor sequence is between about 50 nucleotides to about 5 kb in length, is between about 50 nucleotides to about 3 kb in length, or is between about 50 to about 1,000 nucleotides in length. Other exemplary exogenous donor sequences are between about 40 to about 200 nucleotides in length. For example, an exogenous donor sequence can be between about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Alternatively, an exogenous donor sequence can be between about 50 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Alternatively, an exogenous donor sequence can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. Alternatively, an exogenous donor sequence can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length.

In one example, an exogenous donor sequence is an ssODN that is between about 80 nucleotides and about 200 nucleotides in length (e.g., about 120 nucleotides in length). In another example, an exogenous donor sequences is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor sequences can include modifications or sequences that provide for additional desirable features (e.g., modified or regulated stability; tracking or detecting with a fluorescent label; a binding site for a protein or protein complex; and so forth). Exogenous donor sequences can comprise one or more fluorescent labels, purification tags, epitope tags, or a combination thereof. For example, an exogenous donor sequence can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and -6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor sequence that has been directly integrated into a cleaved HSD17B13 gene having protruding ends compatible with the ends of the exogenous donor sequence. The label or tag can be at the 5' end, the 3' end, or internally within the exogenous donor sequence. For example, an exogenous donor sequence can be conjugated at 5' end with the IR700 fluorophore from Integrated DNA Technologies (5'IRDYE®700).

Exogenous donor sequences can also comprise nucleic acid inserts including segments of DNA to be integrated in the HSD17B13 gene. Integration of a nucleic acid insert in the HSD17B13 gene can result in addition of a nucleic acid sequence of interest in the HSD17B13 gene, deletion of a nucleic acid sequence of interest in the HSD17B13 gene, or replacement of a nucleic acid sequence of interest in the HSD17B13 gene (i.e., deletion and insertion). Some exogenous donor sequences are designed for insertion of a nucleic acid insert in the HSD17B13 gene without any corresponding deletion in the HSD17B13 gene. Other exogenous donor sequences are designed to delete a nucleic acid sequence of interest in the HSD17B13 gene without any corresponding insertion of a nucleic acid insert. Yet other exogenous donor sequences are designed to delete a nucleic acid sequence of interest in the HSD17B13 gene and replace it with a nucleic acid insert.

The nucleic acid insert or the corresponding nucleic acid in the HSD17B13 gene being deleted and/or replaced can be various lengths. An exemplary nucleic acid insert or corresponding nucleic acid in the HSD17B13 gene being deleted and/or replaced is between about 1 nucleotide to about 5 kb in length or is between about 1 nucleotide to about 1,000 nucleotides in length. For example, a nucleic acid insert or a corresponding nucleic acid in the HSD17B13 gene being deleted and/or replaced can be between about 1 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Likewise, a nucleic acid insert or a corresponding nucleic acid in the HSD17B13 gene being deleted and/or replaced can be between about 1 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Likewise, a nucleic acid insert or a corresponding nucleic acid in the HSD17B13 gene being deleted and/or replaced can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length.

The nucleic acid insert can comprise genomic DNA or any other type of DNA. For example, the nucleic acid insert can comprise cDNA.

The nucleic acid insert can comprise a sequence that is homologous to all or part of the HSD17B13 gene (e.g., a portion of the gene encoding a particular motif or region of a HSD17B13 protein). For example, the nucleic acid insert can comprise a sequence that comprises one or more point mutations (e.g., 1, 2, 3, 4, 5, or more) or one or more nucleotide insertions or deletions compared with a sequence targeted for replacement in the HSD17B13 gene.

The nucleic acid insert or the corresponding nucleic acid in the HSD17B13 gene being deleted and/or replaced can be a coding region such as an exon; a non-coding region such as an intron, an untranslated region, or a regulatory region (e.g., a promoter, an enhancer, or a transcriptional repressor-binding element); or any combination thereof.

The nucleic acid insert can also comprise a conditional allele. The conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

Nucleic acid inserts can also comprise a polynucleotide encoding a selection marker. Alternatively, the nucleic acid inserts can lack a polynucleotide encoding a selection marker. The selection marker can be contained in a selection cassette. Optionally, the selection cassette can be a self-deleting cassette. See, e.g., U.S. Pat. No. 8,697,851 and US 2013/0312129, each of which is herein incorporated by reference in its entirety for all purposes. As an example, the self-deleting cassette can comprise a CreI gene (comprises two exons encoding a Cre recombinase, which are separated by an intron) operably linked to a mouse Prm1 promoter and a neomycin resistance gene operably linked to a human ubiquitin promoter. Exemplary selection markers include neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

The nucleic acid insert can also comprise a reporter gene. Exemplary reporter genes include those encoding luciferase, f3-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. Such reporter genes can be operably linked to a promoter active in a cell being targeted. Examples of promoters are described elsewhere herein.

The nucleic acid insert can also comprise one or more expression cassettes or deletion cassettes. A given cassette can comprise one or more of a nucleotide sequence of interest, a polynucleotide encoding a selection marker, and a reporter gene, along with various regulatory components that influence expression. Examples of selectable markers and reporter genes that can be included are discussed in detail elsewhere herein.

The nucleic acid insert can comprise a nucleic acid flanked with site-specific recombination target sequences. Alternatively, the nucleic acid insert can comprise one or more site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, or a combination thereof. In one example, the site-specific recombination sites flank a polynucleotide encoding a selection marker and/or a reporter gene contained within the nucleic acid insert. Following integration of the nucleic acid insert in the HSD17B13 gene, the sequences between the site-specific recombination sites can be removed. Optionally, two exogenous donor sequences can be used, each with a nucleic acid insert comprising a site-specific recombination site. The exogenous donor sequences can be targeted to 5' and 3' regions flanking a nucleic acid of interest. Following integration of the two nucleic acid inserts into the target genomic locus, the nucleic acid of interest between the two inserted site-specific recombination sites can be removed.

Nucleic acid inserts can also comprise one or more restriction sites for restriction endonucleases (i.e., restriction enzymes), which include Type I, Type II, Type III, and Type IV endonucleases. Type I and Type III restriction endonucleases recognize specific recognition sequences, but typically cleave at a variable position from the nuclease binding site, which can be hundreds of base pairs away from the cleavage site (recognition sequence). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1-20 nucleotides from the recognition sequence. Type IV restriction enzymes target methylated DNA. Restriction enzymes are further described and classified, for example in the REBASE database (webpage at rebase.neb.com; Roberts et al., (2003) *Nucleic Acids Res.* 31:418-420; Roberts et al., (2003) *Nucleic Acids Res.* 31:1805-1812; and Belfort et al. (2002) in Mobile DNA II, pp. 761-783, Eds. Craigie et al., (ASM Press, Washington, D.C.)).

(1) Donor Sequences for Non-Homologous-End-Joining-Mediated Insertion

Some exogenous donor sequences have short single-stranded regions at the 5' end and/or the 3' end that are complementary to one or more overhangs created by nuclease-mediated or Cas-protein-mediated cleavage at the target genomic locus (e.g., in the HSD17B13 gene). These overhangs can also be referred to as 5' and 3' homology arms. For example, some exogenous donor sequences have short single-stranded regions at the 5' end and/or the 3' end that are complementary to one or more overhangs created by Cas-protein-mediated cleavage at 5' and/or 3' target sequences at the target genomic locus. Some such exogenous donor sequences have a complementary region only at the 5' end or only at the 3' end. For example, some such exogenous donor sequences have a complementary region only at the 5' end complementary to an overhang created at a 5' target sequence at the target genomic locus or only at the 3' end complementary to an overhang created at a 3' target sequence at the target genomic locus. Other such exogenous donor sequences have complementary regions at both the 5' and 3' ends. For example, other such exogenous donor sequences have complementary regions at both the 5' and 3' ends e.g., complementary to first and second overhangs, respectively, generated by Cas-mediated cleavage at the target genomic locus. For example, if the exogenous donor sequence is double-stranded, the single-stranded complementary regions can extend from the 5' end of the top strand of the donor sequence and the 5' end of the bottom strand of the donor sequence, creating 5' overhangs on each end. Alternatively, the single-stranded complementary region can extend from the 3' end of the top strand of the donor sequence and from the 3' end of the bottom strand of the template, creating 3' overhangs.

The complementary regions can be of any length sufficient to promote ligation between the exogenous donor sequence and the HSD17B13 gene. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Preferably, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.*31:833-838; and Shen et al. (2014) *Nat. Methods* 11:399-404, each of which is herein incorporated by reference in its entirety for all purposes. In such cases, a double-stranded exogenous donor sequence can be designed with single-stranded complementary regions that are complementary to the overhangs created by the nicks within the first and second guide RNA target sequences and by the nicks within the third and fourth guide RNA target sequences. Such an exogenous donor sequence can then be inserted by non-homologous-end-joining-mediated ligation.

(2) Donor Sequences for Insertion by Homology-Directed Repair

Some exogenous donor sequences (i.e., targeting vectors) comprise homology arms. If the exogenous donor sequence also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor sequence. The 5' and 3' homology arms correspond to regions within the HSD17B13 gene, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor sequence can be any degree of sequence identity that allows for homologous recombination to occur. For example, the amount of sequence identity shared by the homology arm of the exogenous donor sequence (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25 to about 30, about 30 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length, such that the homology arms have sufficient homology to undergo homologous recombination with the corresponding target sequences within the HSD17B13 gene. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

The homology arms can correspond to a locus that is native to a cell (e.g., the targeted locus). Alternatively, for example, they can correspond to a region of a heterologous or exogenous segment of DNA that was integrated into the genome of the cell, including, for example, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library, or can be derived from synthetic DNA.

When a nuclease agent is used in combination with an exogenous donor sequence, the 5' and 3' target sequences are preferably located in sufficient proximity to the nuclease cleavage site so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the HSD17B13 gene that correspond to the 5' and 3' homology arms of the exogenous donor sequence are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor sequence can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous donor sequence and the nuclease cleavage site can vary. For example, target sequences can be located 5' to the nuclease cleavage site, target sequences can be located 3' to the nuclease cleavage site, or the target sequences can flank the nuclease cleavage site.

IV. Therapeutic and Prophylactic Applications

Also provided are therapeutic methods and methods of treatment or prophylaxis of a chronic liver disease in a subject having or at risk for the disease using the methods disclosed herein for modifying or altering expression of an endogenous HSD17B13 gene. Also provided are therapeutic methods and methods of treatment or prophylaxis of a liver disease such as an alcoholic liver disease or a nonalcoholic liver disease in a subject having or at risk for the disease using the methods disclosed herein for modifying or altering expression of an endogenous HSD17B13 gene. Also provided are therapeutic methods and methods of treatment or prophylaxis of a chronic liver disease in a subject having or at risk for the disease using methods for decreasing expression of HSD17B13 mRNA transcripts or using methods for providing recombinant nucleic acids encoding HSD17B13 proteins, providing mRNAs encoding HSD17B13 proteins, or providing HSD17B13 proteins to the subject. Also provided are therapeutic methods and methods of treatment or prophylaxis of a liver disease such as an alcoholic liver disease or a nonalcoholic liver disease in a subject having or at risk for the disease using methods for decreasing expression of HSD17B13 mRNA transcripts or using methods for providing recombinant nucleic acids encoding HSD17B13 proteins, providing mRNAs encoding HSD17B13 proteins, or providing HSD17B13 proteins to the subject. The methods can comprise introducing one or more nucleic acids or proteins into the subject, into the liver of the subject, or into a cell (e.g., liver cell) of the subject (e.g., in vivo or ex vivo).

Chronic liver diseases include diseases of the liver which last over a period of six months and can include, for example, diseases of the liver involving progressive destruction and regeneration of the liver parenchyma that can lead to fibrosis and cirrhosis. Chronic liver diseases can be alcoholic liver diseases or nonalcoholic liver diseases. Liver pathologies encompassed by chronic liver diseases can include, for example, inflammation (e.g., chronic hepatitis), liver cirrhosis, and hepatocellular carcinoma. Types of chronic liver disease are disclosed elsewhere herein and include, for example, fatty liver disease, nonalcoholic fatty liver disease, alcoholic fatty liver disease, cirrhosis, and hepatocellular carcinoma. Symptoms and signs of chronic liver diseases are known and can include, for example, enlarged liver, fatigue, pain in the upper right abdomen, abdominal swelling (ascites), enlarged blood vessels just beneath the skin's surface, enlarged breasts in men, enlarged spleen, red palms, and yellowing of the skin and eyes (jaundice). Testing for chronic liver diseases can involve blood tests, imaging of the liver, and biopsy of the liver. An individual is at increased risk of a chronic liver disease if the subject has at least one known risk-factor (e.g., genetic factor such as a disease-causing mutation) placing individuals with that risk factor at a statistically significant greater risk of developing the disease than individuals without the risk factor. Risk factors for chronic liver diseases are also well known and can include, for example, excessive alcohol use, obesity, high cholesterol, high levels of triglycerides in the blood, polycystic ovary syndrome, sleep apnea, type 2 diabetes, underactive thyroid (hypothyroidism), underactive pituitary gland (hypopituitarism), and metabolic syndromes including raised blood lipids.

The term "subject" includes human and other mammalian subjects (e.g., feline, canine, rodent, mouse, or rat) or non-mammalian subjects (e.g., poultry) that receive either prophylactic or therapeutic treatment. Such subjects can be, for example, a subject (e.g., a human) who is not a carrier of the HSD17B13 rs72613567 variant (or is only a heterozygous carrier of the HSD17B13 rs72613567 variant) and has or is susceptible to developing a chronic liver disease. Various methods are possible for detecting the presence of the HSD17B13 rs72613567 variant in a biological sample comprising genomic DNA, for detecting the presence or levels of any one of or a combination of HSD17B13 Transcripts C, D, E, F, F', G, and H, and particularly D, in a biological sample comprising mRNA or cDNA, or for detecting the presence or levels of any one of or a combination of HSD17B13 protein Isoforms C, D, E, F, F', G, or H, and particularly D, in a biological sample comprising protein. Methods for detecting the presence of a sequence in genomic DNA and for detecting the presence of a particular mRNA transcript or protein isoform are well-known. It is understood that gene sequences within a population and mRNAs and proteins encoded by such genes can vary due to polymorphisms such as single-nucleotide polymorphisms. The sequences provided herein for the HSD17B13 gene and for each HSD17B13 Transcript and HSD17B13 Isoform are only exemplary sequences for the HSD17B13 gene and for each HSD17B13 Transcript and HSD17B13 isoform. Other sequences for the HSD17B13 gene and for each HSD17B13 Transcript and HSD17B13 Isoform are also possible.

For example, a method for detecting an HSD17B13 rs72613567 variant in a cell or in a subject such as a human subject can comprise, for example, obtaining a biological sample from the subject comprising an HSD17B13 gene, and performing an assay on the biological sample that determines that a position of the HSD17B13 gene corresponding to position 12666 of SEQ ID NO: 2 when the HSD17B13 gene and SEQ ID NO: 2 are optimally aligned is occupied by a thymine or that a thymine is inserted between positions corresponding to positions 12665 and 12666 when the HSD17B13 gene and SEQ ID NO: 1 are optimally aligned. It is understood that determining that a position of the HSD17B13 gene corresponding to position 12666 of SEQ ID NO: 2 when the HSD17B13 gene and SEQ ID NO: 2 are optimally aligned is occupied by a thymine means that the identity of a sufficient number of nucleotides is determined in the positions flanking the positions corresponding to positions 12665 and 12666 of SEQ ID NO: 1 that it can be determined that a thymine is inserted between the positions corresponding to positions 12665 and 12666 of SEQ ID NO: 1. Such assays can comprise, for example determining the identity of positions of the HSD17B13 gene corresponding to position 12666 of SEQ ID NO: 2 (or positions 12665 and 12666 of SEQ ID NO: 1) and one or more surrounding positions (e.g., at least 1, 2, 3, 4, 5, 6, 7, 8, 9, or 10 positions flanking one side or each side of position 12666 of SEQ ID NO: 2 or positions 12665 and 12666 of SEQ ID NO: 1) when the HSD17B13 gene and SEQ ID NO: 2 (or SEQ ID NO: 1) are optimally aligned. The assay in such a method can comprise, for example, sequencing a portion of the HSD17B13 gene including a position corresponding to position 12666 or positions 12666 and 12667 of SEQ ID NO: 2 when the HSD17B13 gene and SEQ ID NO: 2 are optimally aligned. Likewise, the assay can comprise sequencing a portion of the HSD17B13 gene including positions corresponding to positions 12665 and 12666 of SEQ ID NO: 1 when the HSD17B13 gene and SEQ ID NO: 1 are optimally aligned. Alternatively, the assay in such a method can comprise contacting the biological sample with a primer or probe that specifically hybridizes to the HSD17B13 rs72613567 variant and not the corresponding wild type HSD17B13 sequence (e.g., under stringent conditions), and determining whether hybridization has occurred.

Such methods can comprise genome editing or gene therapy. For example, an endogenous HSD17B13 gene that is not the HSD17B13 rs72613567 variant can be modified to comprise the variation associated with the HSD17B13 rs72613567 variant (i.e., an insertion of a thymine between nucleotides corresponding to positions 12665 and 12666 of SEQ ID NO: 1 when the HSD17B13 gene is optimally aligned with SEQ ID NO: 1, or an insertion of an adenine at the corresponding position on the opposite strand). As another example, an endogenous HSD17B13 gene that is not the HSD17B13 rs72613567 variant can be knocked out or inactivated. Likewise, an endogenous HSD17B13 gene that is not the HSD17B13 rs72613567 variant can be knocked out or inactivated, and an HSD17B13 gene comprising the modification associated with the HSD17B13 rs72613567 variant (e.g., the full HSD17B13 rs72613567 variant or a minigene comprising the modification) can be introduced and expressed. Similarly, an endogenous HSD17B13 gene that is not the HSD17B13 rs72613567 variant can be knocked out or inactivated, and a recombinant DNA encoding any one of or any combination of HSD17B13 Isoforms C, D, F, G, and H (or fragments thereof) can be introduced and expressed, an mRNA encoding any one of or any combination of HSD17B13 Isoforms C, D, F, G, and H (or fragments thereof) can be introduced and expressed (e.g., intracellular protein replacement therapy), or any one of or any combination of HSD17B13 Isoforms C, D, F, G, and H (or fragments thereof) can be introduced (e.g., protein replacement therapy). In particular embodiments, the combination of HSD17B13 Isoforms (or DNA or mRNA encoding) is a combination comprising HSD17B13 Isoform D (e.g., D, DC, DF, DG, DH, DCF, DCG, DCH, DFG, DFH, DGH, DCFG, DCFH, DCGH, DFGH, or DCFGH).

Other such methods can comprise introducing and expressing a recombinant HSD17B13 gene comprising the modification associated with the HSD17B13 rs72613567 variant (e.g., the full HSD17B13 rs72613567 variant or a minigene comprising the modification), introducing and expressing recombinant nucleic acids (e.g., DNA) encoding any one of or any combination of HSD17B13 Isoforms C, D, F, G, and H or fragments thereof, introducing and expressing one or more mRNAs encoding any one of or any combination of HSD17B13 Isoforms C, D, F, G, and H or fragments thereof (e.g., intracellular protein replacement therapy), or introducing any one of or any combination of HSD17B13 Isoforms C, D, F, G, and H or fragments thereof (e.g., protein replacement therapy) without knocking out or inactivating an endogenous HSD17B13 gene that is not the HSD17B13 rs72613567 variant. In particular embodiments, the combination of HSD17B13 isoforms (or DNA or mRNA encoding) is a combination comprising HSD17B13 Isoform D (e.g., D, DC, DF, DG, DH, DCF, DCG, DCH, DFG, DFH, DGH, DCFG, DCFH, DCGH, DFGH, or DCFGH). Optionally, such methods can also be done in combination with methods in which an HSD17B13 transcript whose expression decreases in carriers of the HSD17B13 rs72613567 variant (e.g., Transcripts A, B, E, and F') is targeted for reduced expression, such as through use of antisense RNA, siRNA, or shRNA. In particular embodiments, the HSD17B13 transcripts targeted for reduced expression are a combination comprising Transcript A (e.g., A, AB, AE, AF', ABE, ABF', AEF', or ABEF').

An HSD17B13 gene or minigene or a DNA encoding any one of or any combination of HSD17B13 Isoforms C, D, F, G, and H or fragments thereof can be introduced and expressed in the form of an expression vector that does not modify the genome, it can be introduced in the form of a targeting vector such that it genomically integrates into an HSD17B13 locus, or it can be introduced such that it genomically integrates into a locus other than the HSD17B13 locus, such as a safe harbor locus. The genomically integrated HSD17B13 gene can be operably linked to an HSD17B13 promoter or to another promoter, such as an endogenous promoter at the site of integration. Safe harbor loci are chromosomal sites where transgenes can be stably and reliably expressed in all tissues of interest without adversely affecting gene structure or expression. Safe harbor loci can have, for example, one or more or all of the following characteristics: (1) distance of greater than 50 kb from the 5' end of any gene; distance of greater than 300 kb from any cancer-related gene; distance of greater than 300 kb from any microRNA; outside a gene transcription unit, and outside of ultra-conserved regions. Examples of suitable safe harbor loci include adeno-associated virus site 1 (AAVS1), the chemokine (CC motif) receptor 5 (CCR5) gene locus, and the human orthologue of mouse ROSA26 locus.

Combinations of HSD17B13 protein isoforms or nucleic acids encoding HSD17B13 protein isoforms that can be introduced and expressed include, for example, C, D, F, G, H, CD, CF, CG, CH, DF, DG, DH, FG, FH, GH, CDF, CDG, CDH, CFG, CFH, CGH, DFG, DFH, DGH, FGH, CDFG, CDFH, CFGH, DFGH, and CDFGH. In particular methods, HSD17B13 Isoform D or a nucleic acid encoding Isoform D (alone or in combination with other isoforms) is introduced or expressed. Exemplary sequences for each of these isoforms and transcripts are provided elsewhere herein. It is understood, however, that gene sequences and within a population, mRNA sequences transcribed from such genes, and proteins translated from such mRNAs can vary due to polymorphisms such as single-nucleotide polymorphisms. The sequences provided herein for each transcript and isoform are only exemplary sequences. Other sequences are also possible.

Combinations of HSD17B13 Transcripts whose expression can be targeted for reduction through antisense RNA, shRNA, or siRNA include, for example, A, B, E, F', AB, AE, AF', BE, BF', ABE, ABF', AEF', BEF', and ABEF'. In particular methods, HSD17B13 Transcript A (alone or in combination with other transcripts) is targeted. For example, the antisense RNA, siRNA, or shRNA can hybridize to a sequence within SEQ ID NO: 4 (HSD17B13 Transcript A). Optionally, the antisense RNA, siRNA, or shRNA hybridizes to a sequence present in SEQ ID NO: 4 (HSD17B13 Transcript A) that is not present in SEQ ID NO: 7 (HSD17B13 Transcript D). Optionally, the antisense RNA, siRNA, or shRNA hybridizes to a sequence within exon 7 or a sequence spanning the exon 6-exon 7 boundary of SEQ ID NO: 4 (HSD17B13 Transcript A).

For example, some such methods comprise a method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject: (a) a nuclease agent (or nucleic acid encoding) that binds to a nuclease target sequence within an HSD17B13 gene, wherein the nuclease target sequence includes or is proximate to a position corresponding to position 12666 of SEQ ID NO: 2 when the HSD17B13 gene is optimally aligned with SEQ ID NO: 2; and (b) an exogenous donor sequence comprising a 5' homology arm that hybridizes to a target sequence 5' of the position corresponding to position 12666 of SEQ ID NO: 2, a 3' homology arm that hybridizes to a target sequence 3' of the position corresponding to position 12666 of SEQ ID NO: 2, and a nucleic acid insert comprising a thymine flanked by the 5' homology arm and the 3' homology arm. The nuclease agent can cleave the HSD17B13 gene in a liver cell in the subject, and the exogenous donor sequence can recombine with the HSD17B13 gene in the liver cell, wherein upon recombination of the exogenous donor sequence with the HSD17B13 gene, the thymine is inserted between nucleotides corresponding to positions 12665 and 12666 of SEQ ID NO: 1 when the HSD17B13 gene is optimally aligned with SEQ ID NO: 1. Examples of nuclease agents (e.g., a Cas9 protein and a guide RNA) that can be used in such methods are disclosed elsewhere herein. Examples of suitable guide RNAs and guide RNA target sequences are disclosed elsewhere herein. Examples of exogenous donor sequences that can be used in such methods are disclosed elsewhere herein.

As another example, some such methods comprise a method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject an exogenous donor sequence comprising a 5' homology arm that hybridizes to a target sequence 5' of the position corresponding to position 12666 of SEQ ID NO: 2, a 3' homology arm that hybridizes to a target sequence 3' of the position corresponding to position 12666 of SEQ ID NO: 2, and a nucleic acid insert comprising a thymine flanked by the 5' homology arm and the 3' homology arm. The exogenous donor sequence can recombine with the HSD17B13 gene in the liver cell, wherein upon recombination of the exogenous donor sequence with the HSD17B13 gene, the thymine is inserted between nucleotides corresponding to positions 12665 and 12666 of SEQ ID NO: 1 when the HSD17B13 gene is optimally aligned with SEQ ID NO: 1. Examples of exogenous donor sequences that can be used in such methods are disclosed elsewhere herein.

Some such methods comprise a method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject: (a) a nuclease agent (or nucleic acid encoding) that binds to a nuclease target sequence within an HSD17B13 gene, wherein the nuclease target sequence comprises the start codon for the HSD17B13 gene or is within about 10, 20, 30, 40, 50, 100, 200, 300, 400, 500, or 1,000 nucleotides of the start codon or is selected from SEQ ID NOS: 20-81. The nuclease agent can cleave and disrupt expression of the HSD17B13 gene in a liver cell in the subject. Some such methods comprise a method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject: (a) a nuclease agent (or nucleic acid encoding) that binds to a nuclease target sequence within an HSD17B13 gene, wherein the nuclease target sequence comprises the start codon for the HSD17B13 gene or is within about 10, 20, 30, 40, 50, 100, 200, 300, 400, 500, or 1,000 nucleotides of the start codon or is selected from SEQ ID NOS: 20-81; and (b) an expression vector comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. The expression vector can be one that does not genomically integrate. Alternatively, a targeting vector (i.e., exogenous donor sequence) can be introduced comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. The nuclease agent can cleave and disrupt expression of the HSD17B13 gene in a liver cell in the subject, and the expression vector can express the recombinant HSD17B13 gene in the liver cell in the subject. Alternatively, the genomically integrated, recombinant HSD17B13 gene can express in the liver cell in the subject. Examples of nuclease agents (e.g., a nuclease-active Cas9 protein and guide RNA) that can be used in such methods are disclosed elsewhere herein. Examples of suitable guide RNAs and guide RNA target sequences are disclosed elsewhere herein. Step (b) can alternatively comprise introducing an expression vector or targeting vector comprising a nucleic acid (e.g., DNA) encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or comprising a sequence that is at least 90%, at least 95%, at least 96%, at least 97%, at least 98%, at least 99%, or 100% identical to HSD17B13 Transcript C, D, F, G, or H or a fragment thereof. Likewise, step (b) can alternatively comprise introducing an mRNA encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or having a complementary DNA (or a portion thereof) that is at least 90%, at least 95%, at least 96%, at least 97%, at least 98%, at least 99%, or 100% identical to HSD17B13 Transcript C, D, F, G, or H or a fragment thereof. Likewise, step (b) can alternatively comprise introducing a protein comprising a sequence that is at least 90%, at least 95%, at least 96%, at least 97%, at least 98%, at least 99%, or 100% identical to HSD17B13 Isoform C, D, F, G, or H or a fragment thereof. In specific methods, the transcript can be HSD17B13 Transcript D (e.g., SEQ ID NO: 7), or the isoform can be HSD17B13 Isoform D (e.g., SEQ ID NO: 15). In other specific methods, a combination of HSD17B13 Isoforms, or expression vectors or targeting vectors encoding a combination of HSD17B13 Isoforms, or mRNAs encoding a combination of HSD17B13 Isoforms can be introduced (e.g., D, DC, DF, DG, DH, DCF, DCG, DCH, DFG, DFH, DGH, DCFG, DCFH, DCGH, DFGH, or DCFGH).

In some such methods, a second nuclease agent is also introduced into the subject or into the liver cell in the subject, wherein the second nuclease agent binds to a second nuclease target sequence within the HSD17B13 gene, wherein the second nuclease target sequence comprises the stop codon for the HSD17B13 gene or is within about 10, 20, 30, 40, 50, 100, 200, 300, 400, 500, or 1,000 nucleotides of the stop codon or is selected from SEQ ID NOS: 82-225, wherein the nuclease agent cleaves the HSD17B13 gene in the liver cell within both the first nuclease target sequence and the second nuclease target sequence, wherein the liver cell is modified to comprise a deletion between the first nuclease target sequence and the second nuclease target sequence. For example, the second nuclease agent can be a Cas9 protein and a guide RNA. Suitable guide RNAs and guide RNA target sequences in proximity to the stop codon are disclosed elsewhere herein.

Such methods can also comprise a method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject: (a) a DNA-binding protein (or nucleic acid encoding) that binds to a DNA-binding protein target sequence within an HSD17B13 gene, wherein the DNA-binding protein target sequence comprises the start codon for the HSD17B13 gene or is within about 10, 20, 30, 40, 50, 100, 200, 300, 400, 500, or 1,000 nucleotides of the start codon or is selected from SEQ ID NOS: 20-81. The DNA-binding protein can alter (e.g., reduce) expression of the HSD17B13 gene in a liver cell in the subject. Such methods can also comprise a method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject: (a) a DNA-binding protein (or nucleic acid encoding) that binds to a DNA-binding protein target sequence within an HSD17B13 gene, wherein the DNA-binding protein target sequence comprises the start codon for the HSD17B13 gene or is within about 10, 20, 30, 40, 50, 100, 200, 300, 400, 500, or 1,000 nucleotides of the start codon or is selected from SEQ ID NOS: 20-81; and (b) an expression vector comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. The expression vector can be one that does not genomically integrate. Alternatively, a targeting vector (i.e., exogenous donor sequence) can be introduced comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. The DNA-binding protein can alter (e.g., reduce) expression of the HSD17B13 gene in a liver cell in the subject, and the expression vector can express the recombinant HSD17B13 gene in the liver cell in the subject. Alternatively, the genomically integrated, recombinant HSD17B13 gene can express in the liver cell in the subject. Examples of DNA-binding proteins suitable for use in such methods are disclosed elsewhere herein. Such DNA-binding proteins (e.g., Cas9 protein and guide RNA) can be fused or operably linked to a transcriptional repressor domain. For example, the DNA-binding protein can be a catalytically inactive Cas9 protein fused to a transcriptional repressor domain. Such a DNA-binding protein fused to a transcriptional repressor domain can be used, for example, to decrease expression of a wild type HSD17B13 gene or an HSD17B13 gene that is not the rs72613567 variant (e.g., to decrease expression of HSD17B13 Transcript or Isoform A). Examples of suitable guide RNAs and guide RNA target sequences are disclosed elsewhere herein. Step (b) can alternatively comprise introducing an expression vector or targeting vector comprising a nucleic acid (e.g., DNA) encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or comprising a sequence that is at least 90%, at least 95%, at least 96%, at least 97%, at least 98%, at least 99%, or 100% identical to HSD17B13 Transcript C, D, F, G, or H or a fragment thereof. Likewise, step (b) can alternatively comprise introducing an mRNA encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or having a complementary DNA (or a portion thereof) that is at least 90%, at least 95%, at least 96%, at least 97%, at least 98%, at least 99%, or 100% identical to HSD17B13 Transcript C, D, F, G, or H or a fragment thereof. Likewise, step (b) can alternatively comprise introducing a protein comprising a sequence that is at least 90%, at least 95%, at least 96%, at least 97%, at least 98%, at least 99%, or 100% identical to HSD17B13 Isoform C, D, F, G, or H or a fragment thereof. In specific methods, the transcript can be HSD17B13 Transcript D (e.g., SEQ ID NO: 7), or the isoform can be HSD17B13 Isoform D (e.g., SEQ ID NO: 15). In other specific methods, a combination of HSD17B13 Isoforms, or expression vectors or targeting vectors encoding a combination of HSD17B13 Isoforms, or mRNAs encoding a combination of HSD17B13 Isoforms can be introduced (e.g., D, DC, DF, DG, DH, DCF, DCG, DCH, DFG, DFH, DGH, DCFG, DCFH, DCGH, DFGH, or DCFGH).

Such methods can also comprise a method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject: an antisense RNA, an siRNA, or an shRNA that hybridizes to a sequence within a region of one or more of HSD17B13 Transcripts A, B, E, and F' (and particularly A) that optionally is not present in one or more HSD17B13 Transcripts C, D, F, G, and H (and particularly D). Optionally, the antisense RNA, siRNA, or shRNA hybridizes to a sequence within SEQ ID NO: 4 (HSD17B13 Transcript A), and the antisense RNA, siRNA, or shRNA can decrease expression of HSD17B13 Transcript A in a cell. Optionally, the antisense RNA, siRNA, or shRNA hybridizes to a sequence present in SEQ ID NO: 4 (HSD17B13 Transcript A) that is not present in SEQ ID NO: 7 (HSD17B13 Transcript D). Optionally, the antisense RNA, siRNA, or shRNA hybridizes to a sequence within exon 7 or a sequence spanning the exon 6-exon 7 boundary of SEQ ID NO: 4 (HSD17B13 Transcript A). For example, the antisense RNA, siRNA, or shRNA can hybridize to sequence within a region in exon 7 or a region spanning the exon 6-exon 7 boundary of SEQ ID NO: 4 (HSD17B13 Transcript A) and decrease expression of HSD17B13 Transcript A in a liver cell in the subject. Optionally, such methods can further comprise introducing into the subject an expression vector comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. The expression vector can be one that does not genomically integrate. Alternatively, a targeting vector (i.e., exogenous donor sequence) can be introduced comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. In methods in which an expression vector is used, the expression vector can express the recombinant HSD17B13 gene in the liver cell in the subject. Alternatively, in methods in which a recombinant HSD17B13 gene is genomically integrated, the recombinant HSD17B13 gene can express in the liver cell in the subject. Such methods can alternatively comprise introducing an expression vector or targeting vector comprising a nucleic acid (e.g., DNA) encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or comprising a sequence that is at least 90%, at least 95%, at least 96%, at least 97%, at least 98%, at least 99%, or 100% identical to HSD17B13 Transcript C, D, F, G, or H or a fragment thereof. Likewise, such methods can alternatively comprise introducing an mRNA encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or having a complementary DNA (or a portion thereof) that is at least 90%, at least 95%, at least 96%, at least 97%, at least 98%, at least 99%, or 100% identical to HSD17B13 Transcript C, D, F, G, or H or a fragment thereof. Likewise, such methods can alternatively comprise introducing a protein comprising a sequence that is at least 90%, at least 95%, at least 96%, at least 97%, at least 98%, at least 99%, or 100% identical to HSD17B13 Isoform C, D, F, G, or H or a fragment thereof. In specific methods, the transcript can be HSD17B13 Transcript D (e.g., SEQ ID NO: 7), or the isoform can be HSD17B13 Isoform D (e.g., SEQ ID NO: 15). In other specific methods, a combination of HSD17B13 Isoforms, or expression vectors or targeting vectors encoding a combination of HSD17B13 Isoforms, or mRNAs encoding a combination of HSD17B13 Isoforms can be introduced (e.g., D, DC, DF, DG, DH, DCF, DCG, DCH, DFG, DFH, DGH, DCFG, DCFH, DCGH, DFGH, or DCFGH).

Other such methods can comprise method of treating a subject who is not a carrier of the HSD17B13 rs72613567 variant (or is only a heterozygous carrier of the HSD17B13 rs72613567 variant) and has or is susceptible to developing a chronic liver disease, comprising introducing into the subject or introducing into a liver cell in the subject an expression vector, wherein the expression vector comprises a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1, wherein the expression vector expresses the recombinant HSD17B13 gene in a liver cell in the subject. The expression vector can be one that does not genomically integrate. Alternatively, a targeting vector (i.e., exogenous donor sequence) can be introduced comprising a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1. In methods in which an expression vector is used, the expression vector can express the recombinant HSD17B13 gene in the liver cell in the subject. Alternatively, in methods in which a recombinant HSD17B13 gene is genomically integrated, the recombinant HSD17B13 gene can express in the liver cell in the subject. Such methods can alternatively comprise introducing an expression vector or targeting vector comprising a nucleic acid (e.g., DNA) encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or comprising a sequence that is at least 90%, at least 95%, at least 96%, at least 97%, at least 98%, at least 99%, or 100% identical to HSD17B13 Transcript C, D, F, G, or H or a fragment thereof. Likewise, such methods can alternatively comprise introducing an mRNA encoding an HSD17B13 protein that is at least 90%, at least 95%, at least 96%, at least 97%, at least 98%, at least 99%, or 100% identical to HSD17B13 Isoform C, D, F, G, or H or a fragment thereof and/or having a complementary DNA (or a portion thereof) that is at least 90%, at least 95%, at least 96%, at least 97%, at least 98%, at least 99%, or 100% identical to HSD17B13 Transcript C, D, F, G, or H or a fragment thereof. Likewise, such methods can alternatively comprise introducing a protein comprising a sequence that is at least 90%, at least 95%, at least 96%, at least 97%, at least 98%, at least 99%, or 100% identical to HSD17B13 Isoform C, D, F, G, or H or a fragment thereof. In specific methods, the transcript can be HSD17B13 Transcript D (e.g., SEQ ID NO: 7), or the isoform can be HSD17B13 Isoform D (e.g., SEQ ID NO: 15). In other specific methods, a combination of HSD17B13 Isoforms, or expression vectors or targeting vectors encoding a combination of HSD17B13 Isoforms, or mRNAs encoding a combination of HSD17B13 Isoforms can be introduced (e.g., D, DC, DF, DG, DH, DCF, DCG, DCH, DFG, DFH, DGH, DCFG, DCFH, DCGH, DFGH, or DCFGH).

Suitable expression vectors and recombinant HSD17B13 genes for use in any of the above methods are disclosed elsewhere herein. For example, the recombinant HSD17B13 gene can be the full rs72613567 variant gene or can be an HSD17B13 minigene in which one or more nonessential segments of the gene have been deleted with respect to a corresponding wild type HSD17B13 gene. As an example, the deleted segments can comprise one or more intronic sequences, and the minigene can comprise an intron corresponding to intron 6 of SEQ ID NO: 2 when optimally aligned with SEQ ID NO: 2. An example of a full rs72613567 variant gene is one that is at least 90%, at least 95%, at least 96%, at least 97%, at least 98%, or at least 99% identical to SEQ ID NO: 2 when optimally aligned with SEQ ID NO: 2.

Some such methods comprise a method of modifying a cell (e.g., a liver cell) in a subject having or susceptible to developing a chronic liver disease. In such methods, the nuclease agents and/or exogenous donor sequences and/or recombinant expression vectors can be introduced into the cell via administration in an effective regime meaning a dosage, route of administration and frequency of administration that delays the onset, reduces the severity, inhibits further deterioration, and/or ameliorates at least one sign or symptom of a chronic liver disease being treated. The term "symptom" refers to a subjective evidence of a disease as perceived by the subject, and a "sign" refers to objective evidence of a disease as observed by a physician. If a subject is already suffering from a disease, the regime can be referred to as a therapeutically effective regime. If the subject is at elevated risk of the disease relative to the general population but is not yet experiencing symptoms, the regime can be referred to as a prophylactically effective regime. In some instances, therapeutic or prophylactic efficacy can be observed in an individual patient relative to historical controls or past experience in the same subject. In other instances, therapeutic or prophylactic efficacy can be demonstrated in a preclinical or clinical trial in a population of treated subjects relative to a control population of untreated subjects.

Delivery can be any suitable method, as disclosed elsewhere herein. For example, the nuclease agents or exogenous donor sequences or recombinant expression vectors can be delivered by vector delivery, viral delivery, particle-mediated delivery, nanoparticle-mediated delivery, liposome-mediated delivery, exosome-mediated delivery, lipid-mediated delivery, lipid-nanoparticle-mediated delivery, cell-penetrating-peptide-mediated delivery, or implantable-device-mediated delivery. Some specific examples include hydrodynamic delivery, virus-mediated delivery, and lipid-nanoparticle-mediated delivery.

Administration can be by any suitable route including, for example, parenteral, intravenous, oral, subcutaneous, intra-arterial, intracranial, intrathecal, intraperitoneal, topical, intranasal, or intramuscular. A specific example which is often used, for example, for protein replacement therapies is intravenous infusion. The frequency of administration and the number of dosages can be depend on the half-life of the nuclease agents or exogenous donor sequences or recombinant expression vectors, the condition of the subject, and the route of administration among other factors. Pharmaceutical compositions for administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

Other such methods comprise an ex vivo method in a cell from a subject having or susceptible to developing a chronic liver disease. The cell with the targeted genetic modification can then be transplanted back into the subject.

Any of the therapeutic or prophylactic methods disclosed herein can further comprise administering a therapeutic tailored to prevent or alleviate one or more symptoms associated with progression to more clinically advanced stages of chronic liver disease (e.g., progression from simple steatosis to more clinically advanced stages of chronic liver disease, or progression from simple steatosis to one or more of steatohepatitis, fibrosis, cirrhosis, and hepatocellular carcinoma). For examples, such treatments could be focused on preventing or reducing inflammation or preventing or reducing fibrosis. Examples of such therapeutics in development are provided below.

| Drug (Company) | Stage | Type | Gene Target | Notes |
|---|---|---|---|---|
| OCA—Obeticholic acid (Intercept) | Phase III | Agonist | NR1H4 (FXR) | Improved NAS, reversed fibrosis in Phase IIb |
| GS-9674 (Gilead) | Phase I | | | |
| Simtuzumab (Gilead) | Phase II | Inhibitor | LOXL2 | Potential to reverse fibrosis (NASH/PSC) |
| GS-4997 (Gilead) | Phase II | Inhibitor | MAP3K5 | Reduces oxidative stress |
| NDI-010976 (Gilead) | Phase I | Inhibitor | ACACA ACACB | Prevent lipogenesis |
| GFT505/Elafibranor (Genfit) | Phase III | Agonist | PPARA PPARD | Break down fatty acids, block fat & glucose production, dec inflammation |
| Aramchol (Galmed) | Phase II | Inhibitor | SCD (ABCA1) | Fatty acid-bile acid conjugate; boosts liver fat metabolism |
| Cenicriviroc (Tobira) | Phase IIb | Inhibitor | CCR2 CCR5 | Chemokine receptors are involved in inflammation and fibrosis |
| GR-MD-02 (Galectin Therapeutics) | Phase II | Inhibitor | LGALS3 | Galectin-3 is upregulated in fibrosis |
| TD139 (Galecto Biotech) | Phase I | | | |
| SHP626 (Shire) | Phase I | Inhibitor | SLC10A2 | Interferes with bile acid recycling |
| PXS4728A - (Boehringer Ingelheim) | Phase I | Inhibitor | AOC3 | Anti-inflammatory |
| RP103 - Cysteamine bitartrate (Raptor) | Phase II | Depleting agent | CTNS | Cysteine-depleting; potential anti-oxidant |

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

| SEQ ID NO | Type | Description |
|---|---|---|
| 1 | DNA | HSD17B13 Wild Type Genomic Sequence (Human Genome Assembly GRCh38) Transcripts More Prevalent in Subjects with Wild Type HSD17B13 Gene: Transcript A Exon 1 = 1-275 |

| SEQ ID NO | Type | Description |
|---|---|---|
| | | Exon 2 = 4471-4578<br>Exon 3 = 5684-5815<br>Exon 4 = 7308-7414<br>Exon 5 = 8947-9084<br>Exon 6v1 = 12548-12664<br>Exon 7 = 17599-19118<br>Transcript B<br>Exon 1 = 1-275<br>Exon 2 = skipped<br>Exon 3 = 5684-5815<br>Exon 4 = 7308-7414<br>Exon 5 = 8947-9084<br>Exon 6v1 = 12548-12664<br>Exon 7 = 17599-19118<br>Transcript E<br>Exon 1 = 1-275<br>Exon 2 = 4471-4578<br>Exon 3 = 5684-5815<br>Exon 3' = 6210-6281<br>Exon 4 = 7308-7414<br>Exon 5 = 8947-9084<br>Exon 6v1 = 12548-12664<br>Exon 7 = 17599-19118<br>Transcript F'<br>Exon 1 = 1-275<br>Exon 2 = 4471-4578<br>Exon 3 = 5684-5815<br>Exon 4 = 7308-7414<br>Exon 5 = 8947-9084<br>Exon 6v3 = 12548-13501 (Read-through from exon 6 into intron 6 = 12665-13501)<br>Exon 7 = skipped |
| 2 | DNA | HSD17B13 Genomic Sequence Variant (Human Genome Assembly GRCh38; rs72613567-insertion of T at chr4: 87310241-87310240): Insertion of T at position 12666<br>Transcripts More Prevalent in Subjects with rs72613567 HSD17B13 Gene Variant:<br>Transcript C<br>Exon 1 = 1-275<br>Exon 2 = 4471-4578<br>Exon 3 = 5684-5815<br>Exon 4 = 7308-7414<br>Exon 5 = 8947-9084<br>Exon 6 = skipped<br>Exon 7 = 17600-19119<br>Transcript D<br>Exon 1 = 1-275<br>Exon 2 = 4471-4578<br>Exon 3 = 5684-5815<br>Exon 4 = 7308-7414<br>Exon 5 = 8947-9084<br>Exon 6v2 = 12548-12665 (Includes additional residue 12665 at 3' end)<br>Exon 7 = 17600-19119<br>Transcript F<br>Exon 1 = 1-275<br>Exon 2 = 4471-4578<br>Exon 3 = 5684-5815<br>Exon 4 = 7308-7414<br>Exon 5 = 8947-9084<br>Exon 6v3 = 12548-13502 (Read-through from exon 6 into intron 6 = 12665-13502)<br>Exon 7 = skipped<br>Transcript G<br>Exon 1 = 1-275<br>Exon 2 = skipped<br>Exon 3 = 5684-5815<br>Exon 4 = 7308-7414<br>Exon 5 = 8947-9084<br>Exon 6v2 = 12548-12665 (Includes additional residue 12665 at 3' end)<br>Exon 7 = 17600-19119<br>Transcript H<br>Exon 1 = 1-275<br>Exon 2 = 4471-4578<br>Exon 3 = 5684-5815<br>Exon 3' = 6210-6281<br>Exon 4 = 7308-7414<br>Exon 5 = 8947-9084 |

-continued

| SEQ ID NO | Type | Description |
|---|---|---|
| | | Exon 6v2 = 12548-12665 (Includes additional residue 12665 at 3' end) |
| | | Exon 7 = 17600-19119 |
| 3 | DNA | Endogenous HSD17B13 Promoter (−499 to 100 relative to transcription start site (TSS)) |
| 4 | DNA | HSD17B13 Transcript A cDNA |
| 5 | DNA | HSD17B13 Transcript B cDNA |
| 6 | DNA | HSD17B13 Transcript C cDNA |
| 7 | DNA | HSD17B13 Transcript D cDNA |
| 8 | DNA | HSD17B13 Transcript E cDNA |
| 9 | DNA | HSD17B13 Transcript F cDNA |
| 10 | DNA | HSD17B13 Transcript G cDNA |
| 11 | DNA | HSD17B13 Transcript H cDNA |
| 12 | Protein | HSD17B13 Protein Isoform A |
| 13 | Protein | HSD17B13 Protein Isoform B |
| 14 | Protein | HSD17B13 Protein Isoform C |
| 15 | Protein | HSD17B13 Protein Isoform D |
| 16 | Protein | HSD17B13 Protein Isoform E |
| 17 | Protein | HSD17B13 Protein Isoform F |
| 18 | Protein | HSD17B13 Protein Isoform G |
| 19 | Protein | HSD17B13 Protein Isoform H |
| 20-41 | DNA | Human HSD17B13 TSS Guide RNA Target Sequences |
| 42-81 | DNA | Other Human HSD17B13 5' Guide RNA Target Sequences |
| 82-225 | DNA | Human HSD17B13 3' Guide RNA Target Sequences |
| 226-239 | DNA | Human HSD17B13 Guide RNA Target Sequences Near rs72613567 Variation |
| 240 | Protein | Human HSD17B13 Protein Q7Z5P4-1 |
| 241 | Protein | Human HSD17B13 Protein Q7Z5P4-2 |
| 242 | Protein | Human HSD17B13 Protein NP_835236.2 |
| 243 | Protein | Human HSD17B13 Protein NP_001129702.1 |
| 244 | DNA | Human HSD17B13 cDNA NM_178135.4 |
| 245 | DNA | Human HSD17B13 cDNA NM_001136230.2 |
| 246 | DNA | HSD17B13 Transcript F' |
| 247 | Protein | HSD17B13 Protein Isoform F' |
| 248-250 | DNA | Guide RNA Target Sequences Plus PAM |
| 251 | DNA | PST516 Primer |
| 252 | DNA | PST517 Primer |
| 253 | DNA | DE002 Primer |
| 254 | DNA | HSD17B13 Primer 1 |
| 255 | DNA | HSD17B13 Primer 2 |
| 256-258 | RNA | Guide RNA Scaffolds v2-v4 |
| 259-263 | DNA | Mouse 5' Guide RNA Target Sequences |
| 264-268 | DNA | Mouse Exon 6/7 Guide RNA Target Sequences |
| 269 | DNA | Mouse Hsd17b13 Locus |
| 270-489 | RNA | Human HSD17B13 crRNAs |
| 490-499 | RNA | Mouse Hsd17b13 crRNAs |
| 500-719 | RNA | Human HSD17B13 sgRNAs v1 |
| 720-729 | RNA | Mouse Hsd17b13 sgRNAs v1 |
| 730-949 | RNA | Human HSD17B13 sgRNAs v2 |
| 950-959 | RNA | Mouse Hsd17b13 sgRNAs v2 |
| 960-1179 | RNA | Human HSD17B13 sgRNAs v3 |
| 1180-1189 | RNA | Mouse Hsd17b13 sgRNAs v3 |
| 1190-1409 | RNA | Human HSD17B13 sgRNAs v4 |
| 1410-1419 | RNA | Mouse Hsd17b13 sgRNAs v4 |
| 1420 | RNA | Guide RNA Scaffold v1 |
| 1421 | RNA | crRNA tail |
| 1422 | RNA | tracrRNA |
| 1423-1642 | RNA | Human HSD17B13 Guide RNA DNA-Targeting Segments |
| 1643-1652 | RNA | Mouse Hsd17b13 Guide RNA DNA-Targeting Segments |

EXAMPLES

Example 1. Variant 17beta-hydroxysteroid dehydrogenase 13 Protects Against Chronic Liver Disease Chronic liver disease and cirrhosis are leading causes of morbidity and mortality in the U.S. (Kochanek et al. (2016) *Natl Vital Stat Rep* 65:1-122, herein incorporated by reference in its entirety for all purposes). The most common etiologies of cirrhosis are alcoholic liver disease, chronic hepatitis C, and nonalcoholic fatty liver disease (NAFLD), together accounting for ~80% of patients awaiting liver transplant (Wong et al. (2015) *Gastroenterology* 148:547-555, herein incorporated by reference in its entirety for all purposes). Notably, the estimated prevalence of NAFLD in the U.S. is between 19 and 46 percent (Browning et al. (2004) *Hepatology* 40:1387-1395; Lazo et al. (2013) *Am J Epidemiol* 178:38-45; and Williams et al. (2011) *Gastroenterology* 140:124-131, each of which is herein incorporated by reference in its entirety for all purposes) and is rising over time (Younossi et al. (2011) *Clin Gastroenterol Hepatol* 9:524-530 e1; quiz e60 (2011), herein incorporated by reference in its entirety for all purposes), likely in conjunction with increased rates of obesity. To date, there remains much uncertainty about the inter-individual variation in NAFLD progression and outcomes; knowledge of underlying genetic factors could improve risk stratification and provide the foundation for novel therapeutic strategies. Here, we show that carriers of a splice variant in HSD17B13

(encoding hydroxysteroid-17-beta dehydrogenase 13) have reduced risk of alcoholic and nonalcoholic liver disease, and reduced risk of NAFLD progression. Association studies of whole exome sequence data linked to electronic health records from 46,544 European ancestry participants in the DiscovEHR study led to the identification of a splice variant in HSD17B13 (rs72613567) associated with reduced alanine transaminase and aspartate transaminase levels; these findings were replicated in three separate cohorts comprising 12,528 individuals. In the discovery cohort, variant HSD17B13 was associated with reduced risk of alcoholic and nonalcoholic liver disease, cirrhosis, and hepatocellular carcinoma. In a bariatric surgery cohort, the variant was associated with reduced risk of histopathological steatohepatitis in individuals with steatosis. RNA sequencing of human liver samples from the bariatric surgery cohort revealed that homozygous carriers of the splice variant predominantly express a novel transcript coding for a truncated HSD17B13 isoform. These findings shed new light on the role of HSD17B13 in promoting liver disease progression, and its potential as a therapeutic target for steatohepatitis and cirrhosis.

Previous genome wide association studies (GWAS) have identified a limited number of genes and variants associated with chronic liver disease. The most robustly validated genetic association to date is to a common missense variant in the patatin-like phospholipase domain containing 3 gene (PNPLA3 p.Ile148Met, rs738409), initially found to be associated with increased risk of nonalcoholic fatty liver disease (NAFLD) (Romeo et al. (2008) Nat Genet 40:1461-1465 and Speliotes et al. (2011) PLoS Genet 7:e1001324, each of which is herein incorporated by reference in its entirety for all purposes), and subsequently found to be associated with disease severity (Rotman et al. (2010) Hepatology 52:894-903 and Sookoian et al. (2009) J Lipid Res 50:2111-2116, each of which is herein incorporated by reference in its entirety for all purposes) and progression (Trepo et al. (2016) J Hepatol doi:10.1016/j.jhep.2016.03.011, herein incorporated by reference in its entirety for all purposes). Variation in the transmembrane 6 superfamily member 2 (TM6SF2) gene has also been shown to confer increased risk for NAFLD (Kozlitina et al. (2014) Nat Genet 46:352-356, Liu et al. (2014) Nat Commun 5:4309, and Sookoian et al. (2015) Hepatology 61:515-525, each of which is herein incorporated by reference in its entirety for all purposes). The normal functions of these two proteins are not well understood, though both have been proposed to be involved in hepatocyte lipid metabolism. How variants in PNPLA3 and TM6SF2 contribute to increased risk of liver disease has yet to be elucidated. GWAS have also identified several genetic factors to be associated with serum alanine aminotransferase (ALT) and aspartate aminotransferase (AST) (Chambers et al. (2011) Nat Genet 43:1131-1138 and Yuan et al. (2008) Am J Hum Genet 83:520-528, each of which is herein incorporated by reference in its entirety for all purposes), quantitative markers of hepatocyte injury and liver fat accumulation that are frequently measured clinically. To date, there are no described protective genetic variants for chronic liver disease. The discovery of protective genetic variants in other settings, such as loss-of-function variants in PCSK9 that reduce the risk of cardiovascular disease, has been the catalyst for development of new classes of therapeutics.

The DiscovEHR collaboration between the Regeneron Genetics Center and the Geisinger Health System (GHS) couples exome sequencing to de-identified electronic health record (EHR) data to enable genetic discoveries and precision medicine (Dewey et al. (2016) Science 354(6319) doi:10.1126/science.aaf6814, herein incorporated by reference in its entirety for all purposes). The DiscovEHR cohort is comprised of patients recruited from primary and specialty medical care cohorts across the GHS integrated healthcare system, including bariatric surgery patients with liver biopsy specimens (Gorden et al. (2013) Hum Hered 75:34-43, herein incorporated by reference in its entirety for all purposes). In this study, we undertook a comprehensive functional genomics approach to assess the contribution of exome sequence variation to quantitative traits, disease diagnoses, and histopathologic phenotypes relevant to chronic liver disease and cirrhosis in 49,188 individuals of European descent from the DiscovEHR cohort, with follow-up studies using whole exome sequencing of 9,883 individuals of European ancestry.

Using whole exome sequence data linked to EHR-derived phenotypes, we first carried out an association study of serum ALT and AST measures in 46,544 individuals of European descent from the DiscovEHR cohort ("GHS discovery cohort"). Clinical characteristics of the cohort are described in Table 1A. There were 41,908 individuals with EHR-documented transaminase measures (including 40,561 individuals with both ALT and AST measures). We used a linear mixed model (Yang et al. (2011) Am J Hum Genet 88:76-82, herein incorporated by reference in its entirety for all purposes) to detect associations between $\log_{10}$-transformed median ALT and AST levels (adjusted for sex, age, age$^2$, body mass index (BMI) and the first four principle components of ancestry) and 502,219 biallelic single variants with minor allele frequency greater than 0.1%. Using an exome-wide significance threshold of $P<1.0\times10^{-7}$, we identified 35 variants in 19 genes significantly associated with ALT or AST, including eight variants in seven genes that were associated with both ALT and AST (FIG. 1 and Table 2).

TABLE 1A

Demographics and clinical characteristics of sequenced European-ancestry individuals from the discovery and replication cohorts.

| Characteristic | Discovery Cohort (N = 46,544) | Bariatric Surgery Cohort (N = 2,644) | Dallas Heart Study (N = 1,357) | Penn Medicine Biobank (N = 8,526) |
|---|---|---|---|---|
| Age (years) - median (IQR) | 62.9 (49.6-73.8) | 52.9 (44.1-61.2) | 46.0 (38.0-54.0) | 68.0 (60.0-76.0) |
| Female sex - number (%) | 26,875 (57.7) | 2,119 (80.1) | 724 (53.4) | 3,242 (38.0) |
| Body mass index - median (IQR) | 29.9 (35.4-44.8) | 47.4 (42.0-53.7) | 28 (25-32) | 30 (25-32) |

TABLE 1A-continued

Demographics and clinical characteristics of sequenced European-ancestry individuals from the discovery and replication cohorts.

| Characteristic | Discovery Cohort (N = 46,544) | Bariatric Surgery Cohort (N = 2,644) | Dallas Heart Study (N = 1,357) | Penn Medicine Biobank (N = 8,526) |
|---|---|---|---|---|
| Transaminase level (U/L) - median (IQR) | | | | |
| Alanine aminotransferase (ALT) | 22.0 (17.0-29.0) | 23.0 (17.5-29.5) | 20.0 (15.0-27.0) | 22.0 (17.0-30.0) |
| Aspartate aminotransferase (AST) | 23.0 (20.0-27.5) | 23.0 (20.0-27.0) | 21.0 (18.0-25.0) | 24.0 (20.0-30.5) |
| Presence of liver disease (by ICD-9 code) - N (%) | | | | |
| Alcoholic liver disease | 197 (0.4) | 7 (0.3) | — | — |
| Alcoholic cirrhosis | 130 (0.3) | 3 (0.1) | — | — |
| Nonalcoholic, non-viral liver disease | 1,938 (4.2) | 1,543 (58.4) | — | — |
| Nonalcoholic cirrhosis | 382 (0.8) | 24 (0.9) | — | — |
| Hepatocellular carcinoma | 76 (0.2) | 1 (0.04) | — | — |
| No liver disease | 30,628 (65.8) | 1 (0.04) | — | — |

Table 1B. Demographics and clinical characteristics of genotyped multi-ethnic cases and controls from the Dallas Liver and Pediatric Liver Studies.

TABLE 1B

Demographics and clinical characteristics of genotyped multi-ethnic cases and controls from the Dallas Liver and Pediatric Liver Studies.

| Characteristic | Dallas Liver Study Cases (N = 517) | Dallas Liver Study Controls (N = 4,279) | Dallas Pediatric Liver Study Cases (N = 203) | Dallas Pediatric Liver Study Controls (N = 244) |
|---|---|---|---|---|
| Age (years) - median (IQR) | 55 (48-60) | 44 (36-53) | 12 (10-15) | 12 (11-14) |
| Female sex - number (%) | 277 (54) | 2,494 (58) | 65 (32) | 126 (52) |
| Body mass index - median (IQR) | 30 (27-35) | 30 (26-35) | 30 (27-34) | 31 (28-35) |
| Self-reported ethnicity | | | | |
| African American | 33 (6) | 2,291 (54) | — | — |
| European American | 158 (31) | 1,266 (30) | — | — |
| Hispanic American | 326 (63) | 722 (17) | 203 (100) | 244 (100) |
| Presence of liver disease (by ICD-9 code) - N (%) | | | | |
| Alcoholic liver disease | 223 (43) | — | — | — |
| Alcoholic cirrhosis | 215 (42) | — | — | — |
| Nonalcoholic, non-viral liver disease | 212 (20) | — | — | — |
| Nonalcoholic cirrhosis | 100 (19) | — | — | — |
| Hepatocellular carcinoma | 44 (9) | — | — | — |
| No liver disease | — | 4,279 (100) | — | −244 (100) |

TABLE 2

Single nucleotide variants associated with serum transaminase levels at $P < 1.0 \times 10^{-7}$ in the discovery cohort.

| Trait | CHR | BP | REF | ALT | rsID | Gene | Annotation | AA Substitution | Beta (SE) | P | AAF | N | REF/REF | REF/ALT | ALT/ALT | REF/REF | REF/ALT | ALT/ALT |
|---|---|---|---|---|---|---|---|---|---|---|---|---|---|---|---|---|---|---|
| | | | | | | | | | | | | | | N | | | Mean AST or ALT level (U/L) | |
| ALT | 1 | 220970028 | A | G | rs2644438 | MARC1 | missense | p.Thr165Ala | 0.008 (0.001) | 4.67E-08 | 0.7067 | 41,414 | 3,515 | 17,262 | 20,637 | 23.88 | 24.52 | 24.92 |
| | 4 | 88231392 | T | TA | *rs72613567 | HSD17B13 | splice donor | | -0.009 (0.001) | 4.16E-12 | 0.2634 | 41,414 | 22,441 | 16,130 | 2,843 | 25.02 | 24.26 | 24.1 |
| | 8 | 144997604 | C | T | rs371119003 | PLEC | missense | p.Ala2302Thr | -0.160 (0.026) | 1.30E-09 | 0.0005 | 41,413 | 41,373 | 40 | 0 | 24.67 | 18.1 | NA |
| | 8 | 145008502 | G | A | | PLEC | missense | p.Arg522Cys | -0.268 (0.032) | 3.26E-17 | 0.0003 | 41,414 | 41,387 | 27 | 0 | 24.67 | 13.8 | NA |
| | 8 | 145692918 | G | A | rs35968570 | KIFC2 | missense | p.Glu174Lys | -0.033 (0.005) | 1.40E-11 | 0.0139 | 41,414 | 40,271 | 1,133 | 10 | 24.67 | 12.07 | NA |
| | 8 | 145730072 | G | A | rs143408057 | GPT | missense | p.Arg83His | -0.314 (0.036) | 3.28E-18 | 0.0003 | 41,414 | 41,393 | 21 | 0 | 24.67 | 12.07 | NA |
| | 8 | 145730161 | C | T | rs201815297 | GPT | missense | p.Ala87Val | -0.224 (0.014) | 6.28E-59 | 0.0018 | 41,414 | 41,270 | 144 | 0 | 24.7 | 14.68 | NA |
| | 8 | 145730221 | G | A | rs112574791 | GPT | missense | p.Arg107Lys | -0.033 (0.005) | 4.25E-11 | 0.0136 | 41,414 | 40,293 | 1,111 | 10 | 24.71 | 23.09 | 18.35 |
| | 8 | 145731636 | T | G | rs145155876 | GPT | stop gained | p.Tyr326* | -0.235 (0.031) | 1.76E-14 | 0.0004 | 41,394 | 41,364 | 30 | 0 | 24.67 | 14.07 | NA |
| | 8 | 145732114 | G | C | rs141505249 | GPT | missense | p.Glu430Gln | -0.224 (0.013) | 8.84E-64 | 0.0019 | 41,375 | 41,223 | 150 | 2 | 24.7 | 14.48 | 13.75 |
| | 8 | 145732151 | G | A | rs143462595 | GPT | missense | p.Arg442His | -0.077 (0.013) | 1.18E-09 | 0.0021 | 41,406 | 41,232 | 174 | 0 | 24.68 | 20.87 | NA |
| | 8 | 145732180 | G | C | rs147998249 | GPT | missense | p.Val452Leu | -0.225 (0.013) | 8.19E-65 | 0.0019 | 41,413 | 41,254 | 159 | 0 | 24.7 | 14.74 | NA |
| | 8 | 145732305 | G | GC | | GPT | frameshift | p.Glu475fs | -0.271 (0.031) | 1.00E-18 | 0.0004 | 41,414 | 41,385 | 29 | 0 | 24.67 | 14.24 | NA |
| | 8 | 145748532 | A | G | rs567402720 | LRRC24 | missense | p.Leu290Ser | -0.185 (0.028) | 3.42E-11 | 0.0004 | 41,393 | 41,358 | 35 | 0 | 24.67 | 17.71 | NA |
| | 9 | 117122202 | C | T | rs3748177 | AKNA | synonymous | p.Glu755Glu | -0.007 (0.001) | 9.51E-09 | 0.5232 | 41,414 | 9,414 | 20,645 | 11,355 | 25.12 | 24.72 | 24.18 |
| | 9 | 117124731 | G | A | rs3748176 | AKNA | missense | p.Pro624Leu | -0.007 (0.001) | 4.31E-09 | 0.5230 | 41,412 | 9,427 | 20,634 | 11,351 | 25.12 | 24.73 | 24.17 |
| | 10 | 101595996 | T | A | rs17222723 | ABCC2 | missense | p.Val1188Glu | -0.015 (0.003) | 2.97E-08 | 0.0608 | 41,414 | 36,543 | 4,704 | 167 | 24.77 | 23.97 | 22.12 |
| | 10 | 101606861 | G | T | rs1137968 | ABCC2 | synonymous | p.Val1430Val | -0.015 (0.003) | 2.71E-08 | 0.0608 | 41,414 | 36,543 | 4,704 | 167 | 24.77 | 23.97 | 22.04 |
| | 10 | 101610533 | C | T | rs8187707 | ABCC2 | synonymous | p.His1496His | -0.015 (0.003) | 2.77E-08 | 0.0608 | 41,414 | 36,542 | 4,706 | 166 | 24.77 | 23.97 | 22.03 |
| | 10 | 101611294 | G | A | rs8187710 | ABCC2 | missense | p.Cys1515Tyr | -0.015 (0.003) | 2.15E-08 | 0.0611 | 41,414 | 36,519 | 4,726 | 169 | 24.77 | 23.97 | 21.99 |
| | 10 | 101912064 | T | C | *rs2862954 | ERLIN1 | missense | p.Ile291Val | -0.012 (0.001) | 2.43E-21 | 0.4755 | 41,414 | 11,318 | 20,819 | 9,277 | 25.32 | 24.71 | 23.77 |
| | 10 | 101977883 | C | T | rs2230804 | CHUK | missense | p.Val268Ile | -0.009 | 1.93E-13 | 0.5072 | 41,414 | 10,048 | 20,733 | 10,633 | 25.18 | 24.75 | 24.01 |

TABLE 2-continued

Single nucleotide variants associated with serum transaminase levels at $P < 1.0 \times 10^{-7}$ in the discovery cohort.

| Trait | CHR | BP | REF | ALT | rsID | Gene | Annotation | AA Substitution | Beta (SE) | P | AAF | N | N REF/REF | N REF/ALT | N ALT/ALT | Mean AST or ALT level (U/L) REF/REF | REF/ALT | ALT/ALT |
|---|---|---|---|---|---|---|---|---|---|---|---|---|---|---|---|---|---|---|
| | 10 | 113917085 | T | A | rs2254537 | GPAM | synonymous | p.Pro681Pro | -0.008 (0.001) | 4.61E-10 | 0.7073 | 41,414 | 3,627 | 16,984 | 20,803 | 25 | 24.97 | 24.36 |
| | 10 | 113940329 | T | C | rs2792751 | GPAM | missense | p.Ile43Val | -0.008 (0.001) | 2.54E-10 | 0.7097 | 41,412 | 3,567 | 16,910 | 20,935 | 25 | 24.98 | 24.35 |
| | 14 | 94844947 | C | T | *rs28929474 | SERPINA1 | missense | p.Glu366Lys | 0.042 (0.005) | 9.28E-21 | 0.0171 | 41,414 | 40,006 | 1,399 | 9 | 24.58 | 26.91 | 43.89 |
| | 19 | 19379549 | C | T | *rs58542926 | TM6SF2 | missense | p.Glu167Lys | 0.014 (0.002) | 4.76E-09 | 0.0759 | 41,413 | 35,388 | 5,780 | 245 | 24.52 | 25.46 | 26.84 |
| | 22 | 44324727 | C | G | *rs738409 | PNPLA3 | missense | p.Ile148Met | 0.023 (0.002) | 1.34E-50 | 0.2351 | 41,414 | 24,257 | 14,837 | 2,320 | 24.06 | 24.99 | 28.91 |
| | 22 | 44324730 | C | T | rs738408 | PNPLA3 | synonymous | p.Pro149Pro | 0.023 (0.002) | 1.11E-50 | 0.2349 | 41,414 | 24,273 | 14,824 | 2,317 | 24.06 | 24.98 | 28.92 |
| | 22 | 44342116 | A | G | rs2294918 | PNPLA3 | missense | p.Lys434Glu | 0.007 (0.001) | 8.26E-08 | 0.5986 | 41,412 | 6,691 | 19,833 | 14,888 | 24.15 | 24.47 | 25.15 |
| | 22 | 44368122 | A | G | *rs3761472 | SAMM50 | missense | p.Asp110Gly | 0.019 (0.002) | 8.85E-30 | 0.1682 | 41,413 | 28,626 | 11,618 | 1,169 | 24.23 | 25.36 | 28.45 |
| | 22 | 44395451 | T | C | *rs1007863 | PARVB | missense | p.Trp37Arg | 0.011 (0.001) | 7.98E-16 | 0.3963 | 41,414 | 15,036 | 19,920 | 6,458 | 24.15 | 24.6 | 26.09 |
| AST | 4 | 88231392 | T | TA | *rs72613567 | HSD17B13 | splice donor | | -0.005 (0.001) | 6.24E-10 | 0.2638 | 40,753 | 22,068 | 15,870 | 2,815 | 24.47 | 24.1 | 23.96 |
| | 10 | 18242311 | A | G | rs10764176 | SLC39A12 | missense | p.Ser36Gly | -0.006 | 1.09E-10 | 0.2881 | 40,753 | 20,645 | 16,738 | 3,370 | 24.47 | 24.15 | 23.85 |

TABLE 2-continued

Single nucleotide variants associated with serum transaminase levels at $P < 1.0 \times 10^{-7}$ in the discovery cohort.

| Trait | CHR | BP | REF | ALT | rsID | Gene | Annotation | AA Substitution | Beta (SE) | P | AAF | N | N REF/REF | N REF/ALT | N ALT/ALT | Mean AST or ALT level (U/L) REF/REF | Mean AST or ALT level (U/L) REF/ALT | Mean AST or ALT level (U/L) ALT/ALT |
|---|---|---|---|---|---|---|---|---|---|---|---|---|---|---|---|---|---|---|
| | 10 | 101157378 | CGTT | C | | GOT1 | inframe indel | p.Asn389del | −0.221 (0.024) | 1.96E−20 | 0.0002 | 40,753 | 40,733 | 20 | 0 | 24.29 | 14.7 | NA |
| | 10 | 101165533 | G | C | rs374966349 | GOT1 | missense | p.Gln208Glu | 0.271 (0.027) | 2.43E−24 | 0.0002 | 40,753 | 40,736 | 17 | 0 | 24.28 | 44.5 | NA |
| | 10 | 101912064 | T | C | *rs2862954 | ERLIN1 | missense | p.Ile291Val | −0.005 (0.001) | 4.82E−09 | 0.4754 | 40,753 | 11,138 | 20,486 | 9,129 | 24.59 | 24.26 | 23.99 |
| | 11 | 22271870 | A | T | rs7481951 | ANO5 | missense | p.Leu322Phe | 0.004 (0.001) | 9.61E−08 | 0.5833 | 40,722 | 7,123 | 19,686 | 13,913 | 24.03 | 24.22 | 24.53 |
| | 14 | 94844947 | C | T | *rs28929474 | SERPINA1 | missense | p.Glu366Lys | 0.027 (0.003) | 2.44E−20 | 0.0172 | 40,753 | 39,361 | 1,384 | 8 | 24.24 | 25.76 | 34.5 |
| | 19 | 19379549 | C | T | *rs58542926 | TM6SF2 | missense | p.Glu167Lys | 0.008 (0.002) | 6.54E−08 | 0.0760 | 40,752 | 34,811 | 5,698 | 243 | 24.21 | 24.74 | 25.43 |
| | 22 | 44324727 | C | G | *rs738409 | PNPLA3 | missense | p.Ile148Met | 0.014 (0.001) | 8.31E−46 | 0.2343 | 40,753 | 23,889 | 14,622 | 2,242 | 23.96 | 24.48 | 26.62 |
| | 22 | 44324730 | C | T | *rs738408 | PNPLA3 | synonymous | p.Pro149Pro | 0.014 (0.001) | 8.93E−46 | 0.2341 | 40,753 | 23,905 | 14,609 | 2,239 | 23.96 | 24.47 | 26.63 |
| | 22 | 44368122 | A | G | *rs3761472 | SAMM50 | missense | p.Asp110Gly | 0.011 (0.001) | 1.22E−22 | 0.1680 | 40,752 | 28,170 | 11,450 | 1,132 | 24.07 | 24.64 | 26.24 |
| | 22 | 44395451 | T | C | *rs1007863 | PARVB | missense | p.Trp37Arg | 0.006 (0.001) | 1.31E−13 | 0.3961 | 40,753 | 14,761 | 19,678 | 6,314 | 24.02 | 24.23 | 25.1 |

*Indicates variants having exome-wide significant associations with both ALT and AST.

Abbreviations: AAF, alternate allele frequency; Alt, alternate allele; ALT, alanine aminotransferase; AST, aspartate aminotransferase; Ref, reference allele; SE, standard error.

To replicate these associations, we analyzed the 35 AST- or ALT-associated variants ascertained via whole exome sequencing in three separate European-ancestry cohorts: 2,644 bariatric surgery patients from DiscovEHR ("GHS bariatric surgery cohort"), 1,357 individuals from the Dallas Heart Study, and 8,526 individuals from the Penn Medicine Biobank (Table 1A). In meta-analysis of the replication cohorts, thirteen variants in nine genes were significantly associated (Bonferroni significance threshold of P<1.43×10$^{-3}$) with ALT or AST (Table 3). These included previously reported liver disease-associated genes and variants, such as PNPLA3 p.Ile148Met (Romeo et al. (2008) *Nat Genet* 40:1461-1465, herein incorporated by reference in its entirety for all purposes), TM6SF2 p.Glu167Lys (Kozlitina et al. (2014) *Nat Genet* 46:352-356, herein incorporated by reference in its entirety for all purposes), and SERPINA1 p.Glu366Lys (Z allele associated with alpha-1-anti-trypsin deficiency) (Brantly et al. (1988) *Am J Med* 84:13-31, herein incorporated by reference in its entirety for all purposes), SAMM50, and ERLIN1. SERPINA1 encodes alpha-1-anti-trypsin, whose functional deficiency is known to cause hereditary liver disease; the association with SAMM50 may be mediated via linkage disequilibrium with variation in PNPLA3, and ERLIN1 has been implicated in liver fat deposition. Several variants in GPT and GOT1, the genes encoding ALT and AST, respectively, were significantly associated with either ALT or AST levels but have not been previously reported to be associated with liver disease. SLC39A12 has not previously been linked to transaminases or liver disease. Meta-analysis also replicated novel associations in our discovery cohort between decreased levels of ALT (beta (SE) −0.009 (0.001); P=4.16×10$^{-12}$) and AST (beta (SE) −0.005 (0.001); P=6.24×10$^{-10}$) and a splice variant in HSD17B13, the gene encoding hydroxysteroid 17-beta dehydrogenase 13, an uncharacterized member of the 17-beta hydroxysteroid dehydrogenase family. This variant, rs72613567, corresponds to the insertion of an A nucleotide adjacent to the donor splice site (TA allele). Replication meta-analysis P-values for these associations were 3.85×10$^{-5}$ and 9.38×10$^{-5}$, and joint meta-analysis P-values were 1.17×10$^{-15}$ and 6.82×10$^{-13}$ for ALT and AST, respectively (Table 3). A prior GWAS identified a nearby locus at 4q22 (rs6834314) as being associated with ALT levels (Chambers et al. (2011) *Nat Genet* 43:1131-1138, herein incorporated by reference in its entirety for all purposes); to our knowledge, there are no previous studies describing any association with rs72613567.

TABLE 3

Replication and joint meta-analysis of 35 exome-wide significant single nucleotide variants from the discovery cohort in three separate European-ancestry cohorts.

| | | | | | | | | | GHS Discovery Cohort | | | Replication Cohorts GHS Bariatric Surgery Cohort | |
|---|---|---|---|---|---|---|---|---|---|---|---|---|---|
| Trait | Chr | BP | Ref | Alt | RSID | Gene | Ann | AA Substitution | Beta (SE) | P | N | Beta (SE) | P |
| ALT | 1 | 220970028 | A | G | rs2642438 | MARC1 | mis | p.Thr165Ala | 0.008 (0.001) | 4.67E−08 | 41,414 | 0.005 (0.005) | 3.10E−01 |
| | 4 | 88231392 | T | TA | rs72613567 | HSD17B13 | spl | | −0.009 (0.001) | 4.16E−12 | 41,414 | −0.010 (0.005) | 5.57E−02 |
| | 8 | 144997604 | C | T | rs371119003 | PLEC | mis | p.Ala2302Thr | −0.160 (0.026) | 1.30E−09 | 41,413 | −0.492 (0.165) | 2.84E−03 |
| | 8 | 145008502 | G | A | | PLEC | mis | p.Arg522Cys | −0.268 (0.032) | 3.26E−17 | 41,414 | −0.161 (0.165) | 3.29E−01 |
| | 8 | 145692918 | G | A | rs35968570 | KIFC2 | mis | p.Glu174Lys | −0.033 (0.005) | 1.40E−11 | 41,414 | −0.009 (0.020) | 6.48E−01 |
| | 8 | 145730072 | G | A | rs143408057 | GPT | mis | p.Arg83His | −0.314 (0.036) | 3.28E−18 | 41,414 | −0.189 (0.165) | 2.50E−01 |
| | 8 | 145730161 | C | T | rs201815297 | GPT | mis | p.Ala87Val | −0.224 (0.014) | 6.28E−59 | 41,414 | −0.341 (0.074) | 3.64E−06 |
| | 8 | 145730221 | G | A | rs112574791 | GPT | mis | p.Arg107Lys | −0.033 (0.005) | 4.25E−11 | 41,414 | −0.009 (0.020) | 6.45E−01 |
| | 8 | 145731636 | T | G | rs145155876 | GPT | stop | p.Tyr326* | −0.235 (0.031) | 1.76E−14 | 41,394 | −0.314 (0.165) | 5.71E−02 |
| | 8 | 145732114 | G | C | rs141505249 | GPT | mis | p.Glu430Gln | −0.224 (0.013) | 8.84E−64 | 41,375 | −0.273 (0.048) | 9.83E−09 |
| | 8 | 145732151 | G | A | rs143462595 | GPT | mis | p.Arg442His | −0.077 (0.013) | 1.18E−09 | 41,406 | −0.115 (0.058) | 4.82E−02 |
| | 8 | 145732180 | G | C | rs147998249 | GPT | mis | p.Val452Leu | −0.225 (0.013) | 8.19E−65 | 41,413 | −0.273 (0.050) | 4.26E−08 |
| | 8 | 145732305 | G | GC | | GPT | fs | p.Glu475fs | −0.271 (0.031) | 1.00E−18 | 41,414 | −0.161 (0.165) | 3.29E−01 |
| | 8 | 145748532 | A | G | rs567402720 | LRRC24 | mis | p.Leu290Ser | −0.185 (0.028) | 3.42E−11 | 41,393 | −0.161 (0.165) | 3.29E−01 |
| | 9 | 117122202 | C | T | rs3748177 | AKNA | syn | p.Glu755Glu | −0.007 (0.001) | 9.51E−09 | 41,414 | −0.004 (0.005) | 4.09E−01 |
| | 9 | 117124731 | G | A | rs3748176 | AKNA | mis | p.Pro624Leu | −0.007 (0.001) | 4.31E−09 | 41,412 | −0.004 (0.005) | 3.90E−01 |
| | 10 | 101595996 | T | A | rs17222723 | ABCC2 | mis | p.Val1188Glu | −0.015 (0.003) | 2.97E−08 | 41,414 | −0.002 (0.010) | 8.01E−01 |
| | 10 | 101606861 | G | T | rs1137968 | ABCC2 | syn | p.Val1430Val | −0.015 (0.003) | 2.71E−08 | 41,414 | −0.003 (0.010) | 7.74E−01 |
| | 10 | 101610533 | C | T | rs8187707 | ABCC2 | syn | p.His1496His | −0.015 (0.003) | 2.77E−08 | 41,414 | −0.003 (0.010) | 7.93E−01 |

TABLE 3-continued

Replication and joint meta-analysis of 35 exome-wide significant single nucleotide variants from the discovery cohort in three separate European-ancestry cohorts.

| Trait | Chr | BP | Ref | Alt | rsID | Gene | Type | Protein | Beta (SE) | P | N | Beta (SE) | P |
|---|---|---|---|---|---|---|---|---|---|---|---|---|---|
| | 10 | 101611294 | G | A | rs8187710 | ABCC2 | mis | p.Cys1515Tyr | −0.015 (0.003) | 2.15E−08 | 41,414 | −0.001 (0.010) | 9.11E−01 |
| | 10 | 101912064 | T | C | rs2862954 | ERLIN1 | mis | p.Ile291Val | −0.012 (0.001) | 2.43E−21 | 40,834 | −0.010 (0.005) | 2.91E−02 |
| | 10 | 101977883 | C | T | rs2230804 | CHUK | mis | p.Val268Ile | −0.009 (0.001) | 1.93E−13 | 41,414 | −0.006 (0.005) | 2.05E−01 |
| | 10 | 113917085 | T | A | rs2254537 | GPAM | syn | p.Pro681Pro | −0.008 (0.001) | 4.61E−10 | 41,414 | −0.003 (0.005) | 5.80E−01 |
| | 10 | 113940329 | T | C | rs2792751 | GPAM | mis | p.Ile43Val | −0.008 (0.001) | 2.54E−10 | 41,412 | −0.003 (0.005) | 5.61E−01 |
| | 14 | 94844947 | C | T | rs28929474 | SERPINA1 | mis | p.Glu366Lys | 0.042 (0.005) | 9.28E−21 | 41,414 | 0.035 (0.020) | 7.97E−02 |
| | 19 | 19379549 | C | T | rs58542926 | TM6SF2 | mis | p.Glu167Lys | 0.014 (0.002) | 4.76E−09 | 41,413 | 0.040 (0.010) | 2.40E−05 |
| | 22 | 44324727 | C | G | rs738409 | PNPLA3 | mis | p.Ile148Met | 0.023 (0.002) | 1.34E−50 | 41,414 | 0.019 (0.006) | 5.54E−04 |
| | 22 | 44324730 | C | T | rs738408 | PNPLA3 | syn | p.Pro149Pro | 0.023 (0.002) | 1.11E−50 | 41,414 | 0.019 (0.006) | 5.51E−04 |
| | 22 | 44342116 | A | G | rs2294918 | PNPLA3 | mis | p.Lys434Glu | 0.007 (0.001) | 8.26E−08 | 41,412 | 0.001 (0.005) | 7.77E−01 |
| | 22 | 44368122 | A | G | rs3761472 | SAMM50 | mis | p.Asp110Gly | 0.019 (0.002) | 8.85E−30 | 41,413 | 0.009 (0.006) | 1.66E−01 |
| | 22 | 44395451 | T | C | rs1007863 | PARVB | mis | p.Trp37Arg | 0.011 (0.001) | 7.98E−16 | 41,414 | 0.003 (0.005) | 5.22E−01 |
| AST | 4 | 88231392 | T | TA | rs72613567 | HSD17B13 | spl | | −0.005 (0.001) | 6.24E−10 | 40,753 | −0.010 (0.003) | 3.12E−03 |
| | 10 | 18242311 | A | G | rs10764176 | SLC39A12 | mis | p.Ser36Gly | −0.006 (0.001) | 1.09E−10 | 40,753 | −0.010 (0.003) | 2.91E−03 |
| | 10 | 101157378 | CGTT | C | | GOT1 | inf | p.Asn389del | −0.221 (0.024) | 1.96E−20 | 40,753 | −0.205 (0.062) | 8.57E−04 |
| | 10 | 101165533 | G | C | rs374966349 | GOT1 | mis | p.Gln208Glu | 0.271 (0.027) | 2.43E−24 | 40,753 | NA (NA) | NA |
| | 10 | 101912064 | T | C | rs2862954 | ERLIN1 | mis | p.Ile291Val | −0.005 (0.001) | 4.82E−09 | 40,753 | −0.004 (0.003) | 1.54E−01 |
| | 11 | 22271870 | A | T | rs7481951 | ANO5 | mis | p.Leu322Phe | 0.004 (0.001) | 9.61E−08 | 40,722 | −0.001 (0.003) | 7.85E−01 |
| | 14 | 94844947 | C | T | rs28929474 | SERPINA1 | mis | p.Glu366Lys | 0.027 (0.003) | 2.44E−20 | 40,753 | 0.023 (0.013) | 7.79E−02 |
| | 19 | 19379549 | C | T | rs58542926 | TM6SF2 | mis | p.Glu167Lys | 0.008 (0.002) | 6.54E−08 | 40,192 | 0.023 (0.006) | 1.99E−04 |
| | 22 | 44324727 | C | G | rs738409 | PNPLA3 | mis | p.Ile148Met | 0.014 (0.001) | 8.31E−46 | 40,753 | 0.014 (0.004) | 1.27E−04 |
| | 22 | 44324730 | C | T | rs738408 | PNPLA3 | syn | p.Pro149Pro | 0.014 (0.001) | 8.93E−46 | 40,753 | 0.014 (0.004) | 1.32E−04 |
| | 22 | 44368122 | A | G | rs3761472 | SAMM50 | mis | p.Asp110Gly | 0.011 (0.001) | 1.22E−22 | 40,752 | 0.008 (0.004) | 6.03E−02 |
| | 22 | 44395451 | T | C | rs1007863 | PARVB | mis | p.Trp37Arg | 0.006 (0.001) | 1.31E−13 | 40,753 | 0.003 (0.003) | 4.12E−01 |

| | | | Replication Cohorts | | | | | | **Replication Meta-Analysis (N = 3) | | ***Joint Meta-Analysis (N = 4) | |
|---|---|---|---|---|---|---|---|---|---|---|---|---|
| | | | GHS Bariatric Surgery Cohort | | | Dallas Heart Study | | | U. Penn | | | | |
| Trait | Chr | BP | N | Beta (SE) | P | N | Beta (SE) | P | N | Beta (SE) | P | Beta (SE) | P |
| ALT | 1 | 220970028 | 2475 | 0.011 (0.008) | 1.76E−01 | 1357 | 0.007 (0.004) | 1.02E−01 | 6158 | 0.007 (0.003) | 2.31E−02 | 0.008 (0.001) | 3.38E−09 |
| | 4 | 88231392 | 2475 | −0.016 (0.008) | 6.60E−02 | 1357 | −0.013 (0.004) | 1.33E−03 | 6158 | −0.013 (0.003) | *3.85E−05 | −0.010 (0.001) | 1.17E−15 |
| | 8 | 144997604 | 2475 | NA (NA) | NA | | −0.051 (0.072) | 4.79E−01 | 6158 | −0.121 (0.066) | 6.56E−02 | −0.155 (0.025) | 2.68E−10 |
| | 8 | 145008502 | 2475 | NA (NA) | NA | | −0.247 (0.143) | 8.48E−02 | 6158 | −0.210 (0.108) | 5.23E−02 | −0.264 (0.031) | 5.54E−18 |
| | 8 | 145692918 | 2475 | 0.032 (0.036) | 3.76E−01 | 1356 | −0.053 (0.018) | 3.72E−03 | 6158 | −0.025 (0.013) | 4.69E−02 | −0.032 (0.005) | 2.25E−12 |
| | 8 | 145730072 | 2475 | NA (NA) | NA | | −0.298 (0.101) | 3.26E−03 | 6158 | −0.268 (0.086) | 1.88E−03 | −0.308 (0.033) | 2.79E−20 |
| | 8 | 145730161 | 2475 | NA (NA) | NA | | −0.143 (0.054) | 8.50E−03 | 6158 | −0.213 (0.044) | *1.14E−06 | −0.223 (0.013) | 4.49E−64 |
| | 8 | 145730221 | 2475 | 0.028 (0.036) | 4.37E−01 | 1357 | −0.060 (0.018) | 5.60E−04 | 6158 | −0.031 (0.013) | 1.36E−02 | −0.033 (0.005) | 1.92E−12 |
| | 8 | 145731636 | 2475 | −0.317 (0.140) | 2.35E−02 | 1356 | −0.148 (0.143) | 3.04E−01 | 6157 | −0.256 (0.086) | 2.79E−03 | −0.237 (0.029) | 1.94E−16 |

TABLE 3-continued

Replication and joint meta-analysis of 35 exome-wide significant single nucleotide variants from the discovery cohort in three separate European-ancestry cohorts.

| | | | | | | | | | | | | |
|---|---|---|---|---|---|---|---|---|---|---|---|---|
| | 8 | 145732114 | 2474 | −0.240 (0.075) | 1.36E−03 | 1357 | −0.197 (0.041) | 1.31E−06 | 6157 | −0.231 (0.029) | *7.24E−16 | −0.225 (0.012) | 6.06E−78 |
| | 8 | 145732151 | 2475 | −0.106 (0.099) | 2.86E−01 | 1356 | −0.049 (0.041) | 2.27E−01 | 6157 | −0.074 (0.032) | 1.88E−02 | −0.076 (0.012) | 7.03E−11 |
| | 8 | 145732180 | 2475 | −0.191 (0.070) | 6.58E−03 | 1357 | −0.197 (0.041) | 1.31E−06 | 6158 | −0.221 (0.029) | *1.41E−14 | −0.224 (0.012) | 1.04E−77 |
| | 8 | 145732305 | 2475 | NA (NA) | NA | NA | −0.509 (0.203) | 1.21E−02 | 6158 | −0.299 (0.128) | 1.93E−02 | −0.273 (0.030) | 6.44E−20 |
| | 8 | 145748532 | 2475 | NA (NA) | NA | NA | −0.307 (0.143) | 3.21E−02 | 6158 | −0.244 (0.108) | 2.40E−02 | −0.189 (0.027) | 2.93E−12 |
| | 9 | 117122202 | 2475 | 0.004 (0.008) | 6.18E−01 | 1357 | −0.007 (0.004) | 5.29E−02 | 6158 | −0.005 (0.003) | 8.42E−02 | −0.007 (0.001) | 3.08E−09 |
| | 9 | 117124731 | 2475 | 0.003 (0.008) | 7.33E−01 | 1356 | −0.007 (0.004) | 4.24E−02 | 6158 | −0.005 (0.003) | 6.15E−02 | −0.007 (0.001) | 1.00E−09 |
| | 10 | 101595996 | 2475 | −0.007 (0.017) | 6.88E−01 | 1357 | −0.017 (0.007) | 1.55E−02 | 6158 | −0.012 (0.005) | 3.43E−02 | −0.014 (0.002) | 3.44E−09 |
| | 10 | 101606861 | 2475 | −0.008 (0.017) | 6.28E−01 | 1357 | −0.017 (0.007) | 1.70E−02 | 6158 | −0.012 (0.005) | 3.25E−02 | −0.014 (0.002) | 2.99E−09 |
| | 10 | 101610533 | 2475 | −0.008 (0.017) | 6.28E−01 | 1357 | −0.017 (0.007) | 1.76E−02 | 6158 | −0.012 (0.005) | 3.43E−02 | −0.014 (0.002) | 3.23E−09 |
| | 10 | 101611294 | 2475 | −0.010 (0.017) | 5.40E−01 | 1357 | −0.016 (0.007) | 2.77E−02 | 6158 | −0.011 (0.005) | 5.21E−02 | −0.014 (0.002) | 4.09E−09 |
| | 10 | 101912064 | 2475 | −0.006 (0.007) | 4.02E−01 | 1356 | −0.009 (0.004) | 2.06E−02 | 6158 | −0.009 (0.003) | *1.14E−03 | −0.011 (0.001) | 1.76E−23 |
| | 10 | 101977883 | 2475 | 0.0001 (0.008) | 9.94E−01 | 1357 | −0.011 (0.004) | 3.91E−03 | 6158 | −0.008 (0.003) | 4.33E−03 | −0.009 (0.001) | 3.59E−15 |
| | 10 | 113917085 | 2475 | −0.013 (0.008) | 1.15E−01 | 1357 | −0.008 (0.004) | 5.12E−02 | 6158 | −0.007 (0.003) | 2.07E−02 | −0.008 (0.001) | 3.28E−11 |
| | 10 | 113940329 | 2475 | −0.013 (0.008) | 1.33E−01 | 1357 | −0.008 (0.004) | 4.77E−02 | 6158 | −0.007 (0.003) | 2.00E−02 | −0.008 (0.001) | 1.77E−11 |
| | 14 | 94844947 | 2475 | 0.034 (0.032) | 2.92E−01 | 1357 | 0.054 (0.013) | 1.63E−05 | 6158 | 0.047 (0.010) | *2.82E−06 | 0.043 (0.004) | 1.59E−25 |
| | 19 | 19379549 | 2475 | 0.024 (0.014) | 9.50E−02 | 1357 | 0.013 (0.008) | 7.51E−02 | 6158 | 0.024 (0.006) | *1.37E−05 | 0.016 (0.002) | 1.15E−12 |
| | 22 | 44324727 | 2475 | 0.006 (0.009) | 5.43E−01 | 1357 | 0.016 (0.004) | 2.05E−04 | 6158 | 0.016 (0.003) | *7.45E−07 | 0.021 (0.001) | 3.55E−55 |
| | 22 | 44324730 | 2475 | 0.006 (0.009) | 5.43E−01 | 1357 | 0.016 (0.004) | 2.14E−04 | 6158 | 0.016 (0.003) | *7.73E−07 | 0.021 (0.001) | 3.10E−55 |
| | 22 | 44342116 | 2475 | 0.005 (0.008) | 5.18E−01 | 1357 | 0.005 (0.004) | 2.16E−01 | 6158 | 0.004 (0.003) | 1.91E−01 | 0.006 (0.001) | 6.24E−08 |
| | 22 | 44368122 | 2475 | −0.001 (0.01) | 9.37E−01 | 1357 | 0.018 (0.005) | 4.02E−04 | 6158 | 0.012 (0.004) | *7.69E−04 | 0.018 (0.002) | 1.08E−31 |
| | 22 | 44395451 | 2475 | 0.008 (0.008) | 3.13E−01 | 1357 | 0.009 (0.004) | 2.50E−02 | 6158 | 0.007 (0.003) | 1.78E−02 | 0.010 (0.001) | 1.16E−16 |
| AST | 4 | 88231392 | 2469 | −0.012 (0.006) | 5.32E−02 | 1357 | −0.007 (0.004) | 5.56E−02 | 6166 | −0.009 (0.002) | *8.38E−05 | −0.006 (0.001) | 6.82E−13 |
| | 10 | 18242311 | 2469 | −0.003 (0.006) | 5.80E−01 | 1357 | −0.009 (0.004) | 1.03E−02 | 6166 | −0.009 (0.002) | *1.16E−04 | −0.006 (0.001) | 1.10E−13 |
| | 10 | 101157378 | 2469 | NA (NA) | NA | NA | −0.243 (0.088) | 5.97E−03 | 6165 | −0.218 (0.051) | *1.66E−05 | −0.220 (0.022) | 1.68E−24 |
| | 10 | 101165533 | NA | NA (NA) | NA | NA | 0.339 (0.079) | 1.85E−05 | 6166 | 0.339 (0.079) | *1.85E−05 | 0.278 (0.025) | 3.25E−28 |
| | 10 | 101912064 | 2469 | −0.007 (0.006) | 2.21E−01 | 1357 | −0.004 (0.003) | 1.94E−01 | 6166 | −0.005 (0.002) | 2.51E−02 | −0.005 (0.001) | 3.68E−10 |
| | 11 | 22271870 | 2466 | 0.006 (0.006) | 2.85E−01 | 1357 | −0.002 (0.003) | 5.46E−01 | 6165 | 0.000 (0.002) | 8.43E−01 | 0.004 (0.001) | 1.13E−06 |
| | 14 | 94844947 | 2469 | 0.044 (0.024) | 6.98E−02 | 1357 | 0.055 (0.011) | 4.01E−07 | 6166 | 0.042 (0.008) | *9.54E−08 | 0.029 (0.003) | 6.71E−26 |
| | 19 | 19379549 | 2469 | 0.010 (0.011) | 3.42E−01 | 1356 | 0.004 (0.007) | 5.94E−01 | 6166 | 0.014 (0.004) | *1.20E−03 | 0.009 (0.002) | 5.92E−10 |
| | 22 | 44324727 | 2469 | 0.004 (0.007) | 5.44E−01 | 1357 | 0.015 (0.004) | 4.87E−05 | 6166 | 0.013 (0.002) | *5.51E−08 | 0.014 (0.001) | 3.14E−52 |
| | 22 | 44324730 | 2469 | 0.004 (0.007) | 5.44E−01 | 1357 | 0.015 (0.004) | 4.96E−05 | 6166 | 0.013 (0.002) | *5.81E−08 | 0.014 (0.001) | 3.55E−52 |
| | 22 | 44368122 | 2469 | −0.001 (0.008) | 9.45E−01 | 1357 | 0.016 (0.004) | 2.64E−04 | 6166 | 0.010 (0.003) | *3.40E−04 | 0.011 (0.001) | 1.91E−25 |
| | 22 | 44395451 | 2469 | 0.006 (0.006) | 2.95E−01 | 1357 | 0.009 (0.003) | 6.17E−03 | 6166 | 0.006 (0.002) | 7.34E−03 | 0.006 (0.001) | 3.62E−15 |

*Indicates P-values meeting the Bonferroni significance threshold of $P < 1.43 \times 10^{-3}$.
**Replication meta-analysis includes the three replication cohorts: GHS Bariatric Surgery Cohort, Dallas Heart Study, and Penn Medicine Biobank.
***Joint meta-analysis includes the discovery cohort and the three replication cohorts: GHS Discovery Cohort, GHS Bariatric Surgery Cohort, Dallas Heart Study, and Penn Medicine Biobank.
Abbreviations: AAF, alternate allele frequency; Alt, alternate allele; ALT, alanine aminotransferase; AST, aspartate aminotransferase; Ref, reference allele; SE, standard error; ann, annotation; mis, missense; syn, synonymous; spl, splice donor; stop, stop gained; fs, frameshift; inf, inframe indel.

Figure 5A:
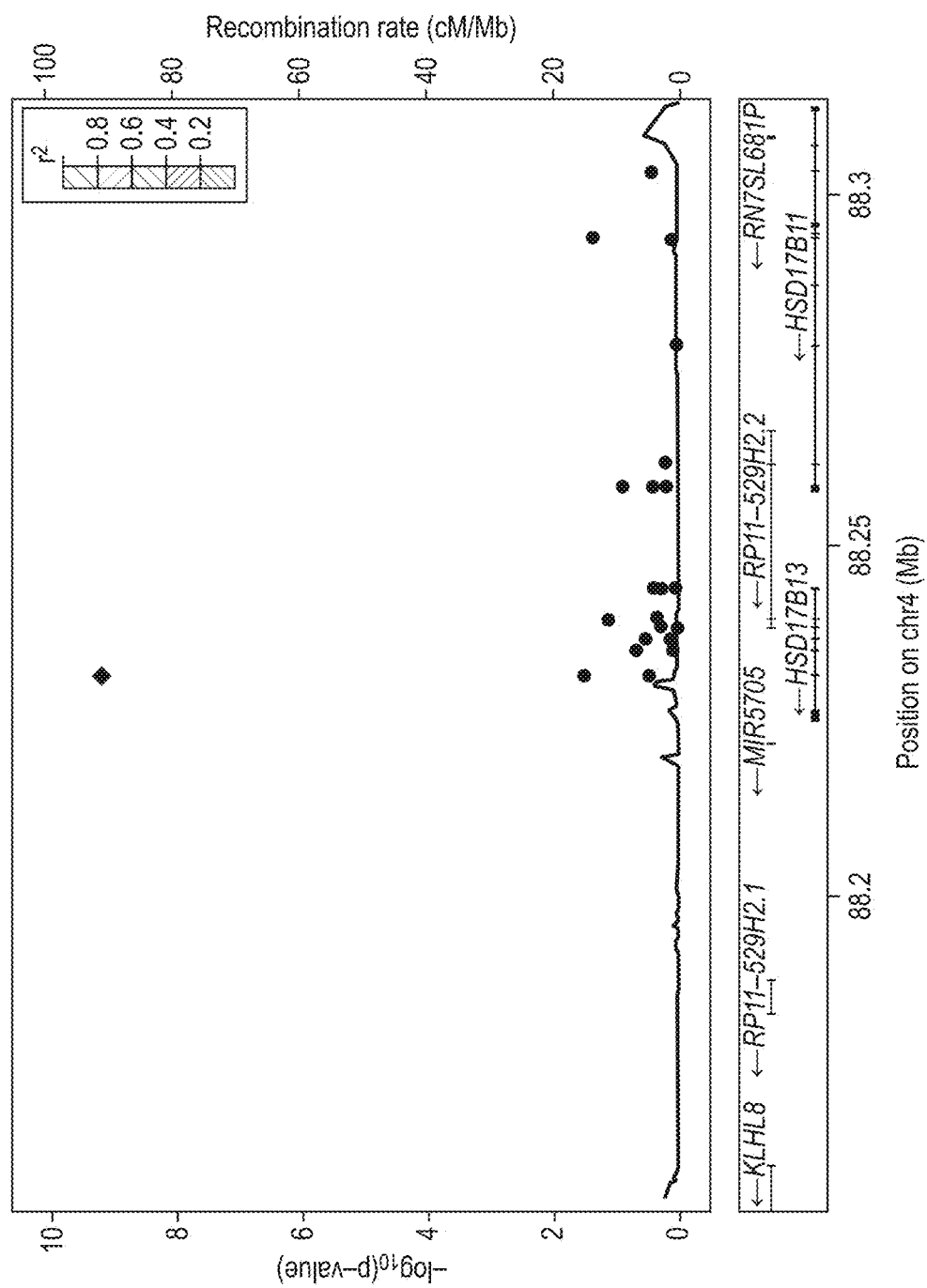
FIGS. 5A and 5B show locus-zoom plots of HSD17B13 (regional association plots in the region around HSD17B13) in the GHS discovery cohort for ALT and AST, respectively. No significant recombination across the region was observed. Diamonds indicate the splice variant rs72613567. Each circle indicates a single nucleotide variant with the color of the circle indicating the linkage disequilibrium ($r^2$ calculated in the DiscovEHR cohort) between that variant and rs72613567. Lines indicate estimated recombination rates in HapMap. The bottom panels show the relative position and the transcribed strand of each gene in the locus. There were no significant associations between ALT or AST and coding or splice region variants in the neighboring gene HSD17B11 (most significant P-values $1.4 \times 10^{-1}$ and $4.3 \times 10^{-2}$ for ALT and AST, respectively).
Figure 5B:
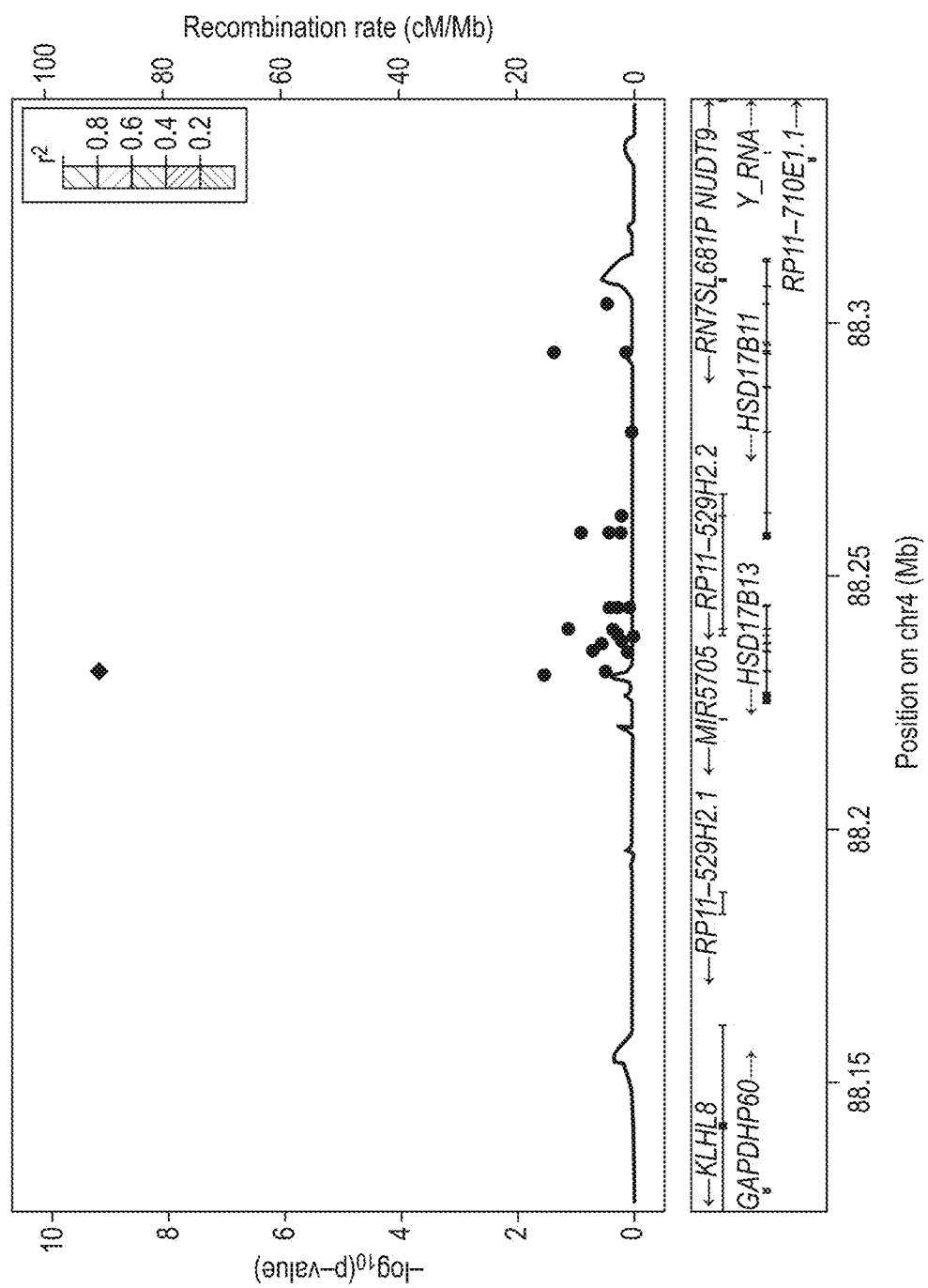
Figure 6A:
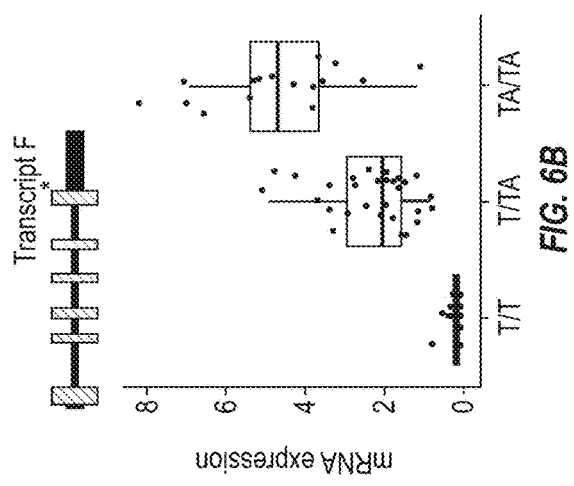
FIGS. 6A-6D show mRNA expression of four additional novel HSD17B13 transcripts (E-H) in homozygous reference (T/T), heterozygous (T/TA), and homozygous alternate (TA/TA) carriers of the HSD17B13 splice variant. Each transcript is illustrated with a corresponding gene model. Coding regions in gene models are indicated in striped boxes and untranslated regions in black boxes.
Figure 6B:
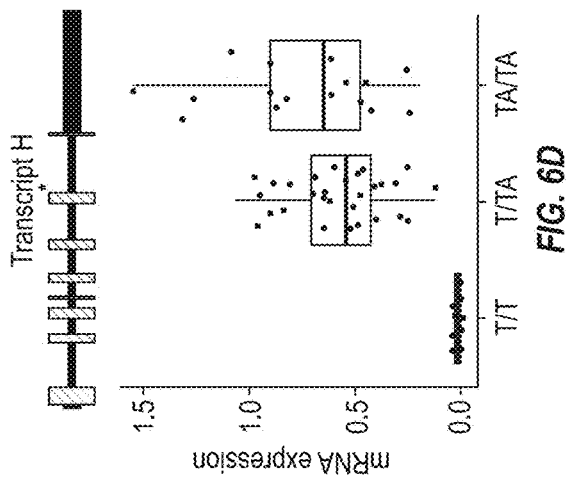
Figure 6C:
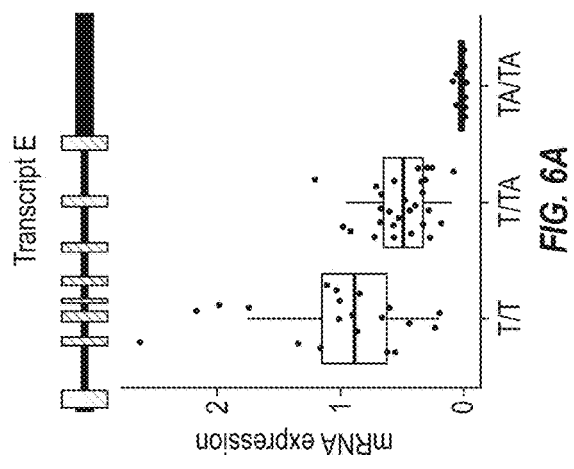
Figure 6D:
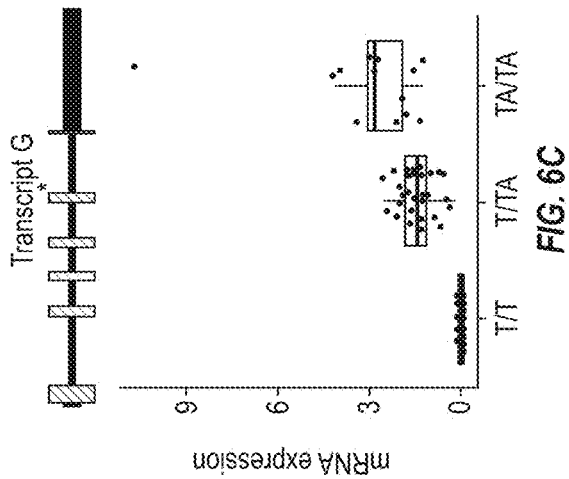

HSD17B13 is 30 kb upstream of HSD17B11, a member of the same gene family, and both genes lie within a single large haplotype block in Europeans. We did not observe any association between coding or splice variants in HSD17B11 and transaminase levels in the discovery cohort (FIGS. 5A and 5B; most significant discovery P-values $1.36 \times 10^{-1}$ for ALT and $4.32 \times 10^{-2}$ for AST) or in the joint meta-analysis of the discovery cohort and three replication cohorts (most significant P-values $6.25 \times 10^{-3}$ and $1.17 \times 10^{-5}$ for ALT and AST, respectively). Furthermore, linkage disequilibrium of rs72613567 with variants in HSD17B11 was modest across all ancestry groups, including in European Americans that largely comprise our discovery group, and also in Hispanic and African Americans represented in the Dallas Heart Study ($r^2<0.4$ with all ascertained variants in HSD17B11 in all ancestry groups; data not shown). Collectively, these findings suggest HSD17B13 as the gene in the genomic region that is most likely to be functionally related to transaminase levels.

Next, we sought to establish whether variants associated with ALT or AST levels were also associated with chronic liver disease. In the discovery cohort, we used EHR diagnosis codes to broadly define cases of alcoholic and nonalcoholic (non-viral) liver disease, as well as the following disease sequelae: alcoholic cirrhosis, nonalcoholic cirrhosis, and hepatocellular carcinoma (HCC). A common control group ("no liver disease") was defined as individuals with no diagnosis codes for any type of liver disease (Table 1). We tested the twelve transaminase-associated variants from the discovery and replication cohorts for association with chronic liver disease, using a Bonferroni significance threshold of P<0.05/24 ($P<2.08 \times 10^{-3}$) to account for the thirteen variants and two broad chronic liver disease categories (alcoholic and nonalcoholic) tested (Table 4). Overall, we found significant associations between six variants in five genes (HSD17B13, SERPINA1, TM6SF2, PNPLA3, and SAMM50) and chronic liver disease phenotypes. The SERPINA1, TM6SF2, PNPLA3, and SAMM50 associations confirm previously reported associations. Variants in GPT, GOT1, ERLIN1, and SLC39A12 were not significantly associated with any liver disease phenotype. The HSD17B13 association with liver disease reported here is novel and the first potentially protective genetic variant described.

TABLE 4

Association of twelve exome-wide significant and replicating single nucleotide variants with liver disease phenotypes in the discovery cohort.

| CHR:BP:Ref:Alt | Gene | rsID | Alcoholic liver disease OR (95% CI) | P-value | Alcoholic cirrhosis OR (95% CI) | P-value |
|---|---|---|---|---|---|---|
| 4:88231392:T:TA | HSD17B13 | rs72613567 | 0.62 (0.48-0.81) | *1.82E−04 | 0.56 (0.41-0.78) | *3.35E−04 |
| 8:145730161:C:T | GPT | rs201815297 | 3.83 (1.05-13.94) | 8.88E−02 | 6.33 (1.71-23.43) | 2.88E−02 |
| 8:145732114:G:C | GPT | rs141505249 | 0.77 (0.06-10.73) | 8.43E−01 | 1.13 (0.08-15.39) | 9.30E−01 |
| 8:145732180:G:C | GPT | rs147998249 | 0.73 (0.05-11.76) | 8.17E−01 | 1.07 (0.07-17.16) | 9.60E−01 |
| 10:18242311:A:G | SLC39A12 | rs10764176 | 0.85 (0.68-1.07) | 1.64E−01 | 0.92 (0.70-1.22) | 5.80E−01 |
| 10:101157378:CGTT:C | GOT1 | | 4.60 (0.25-86.41) | 3.93E−01 | 7.11 (0.38-133.19) | 3.00E−01 |
| 10:101165533:G:C | GOT1 | rs374966349 | 2.20 (0.13-37.68) | 6.24E−01 | 3.47 (0.20-59.04) | 4.70E−01 |
| 14:94844947:C:T | SERPINA1 | rs28929474 | 2.49 (1.49-4.17) | 2.30E−03 | 3.35 (1.93-5.83) | *3.01E−04 |
| 19:19379549:C:T | TM6SF2 | rs58542926 | 1.47 (1.06-2.04) | 2.76E−02 | 1.35 (0.89-2.04) | 1.80E−01 |
| 22:44324727:C:G | PNPLA3 | rs738409 | 1.76 (1.43-2.18) | *4.98E−07 | 2.07 (1.60-2.67) | *1.08E−07 |
| 22:44324730:C:T | PNPLA3 | rs738408 | 1.77 (1.43-2.18) | *4.70E−07 | 2.07 (1.61-2.67) | *1.03E−07 |
| 22:44368122:A:G | SAMM50 | rs3761472 | 1.90 (1.52-2.38) | *1.36E−07 | 2.28 (1.75-2.98) | *1.83E−08 |

| CHR:BP:Ref:Alt | Nonalcoholic liver disease OR (95% CI) | P-value | Nonalcoholic cirrhosis OR (95% CI) | P-value | Hepatocellular carcinoma OR (95% CI) | P-value |
|---|---|---|---|---|---|---|
| 4:88231392:T:TA | 0.84 (0.78-0.91) | *1.31E−05 | 0.74 (0.62-0.88) | *4.48E−04 | 0.67 (0.45-1.00) | 4.66E−02 |
| 8:145730161:C:T | 0.23 (0.04-1.14) | 1.86E−02 | 1.25 (0.24-6.38) | 7.98E−01 | 3.66 (0.70-19.01) | 2.01E−01 |
| 8:145732114:G:C | 1.02 (0.49-2.11) | 9.70E−01 | 0.36 (0.02-5.37) | 3.82E−01 | 1.84 (0.15-23.25) | 6.88E−01 |
| 8:145732180:G:C | 1.03 (0.49-2.17) | 9.30E−01 | 0.34 (0.02-5.59) | 3.67E−01 | 1.74 (0.11-27.05) | 7.21E−01 |
| 10:18242311:A:G | 0.92 (0.86 (0.99) | 3.43E−02 | 1.03 (0.88-1.21) | 7.15E−01 | 1.29 (0.93-1.79) | 1.37E−01 |
| 10:101157378:CGTT:C | 2.37 (0.61-9.27) | 2.50E−01 | 8.27 (1.44-47.49) | 5.92E−02 | 9.81 (0.52-183.54) | 2.43E−01 |

TABLE 4-continued

Association of twelve exome-wide significant and replicating single nucleotide variants with liver disease phenotypes in the discovery cohort.

| | | | | | | |
|---|---|---|---|---|---|---|
| 10:101165533:G:C | 1.63 (0.53-4.96) | 4.20E−01 | 1.17 (0.07-20.09) | 9.13E−01 | 5.37 (0.32-91.12) | 3.55E−01 |
| 14:94844947:C:T | 1.50 (1.21-1.87) | *5.29E−04 | 2.99 (2.11-4.24) | *9.08E−08 | 1.86 (0.74-4.67) | 2.40E−01 |
| 19:19379549:C:T | 1.36 (1.21-1.52) | *2.42E−07 | 1.64 (1.31-2.05) | *6.04E−05 | 1.93 (1.22-3.04) | 1.08E−02 |
| 22:44324727:C:G | 1.65 (1.54-1.78) | *1.31E−41 | 2.05 (1.76-2.38) | *1.70E−19 | 2.20 (1.60-3.02) | *5.59E−06 |
| 22:44324730:C:T | 1.65 (1.54-1.78) | *1.42E−41 | 2.05 (1.77-2.38) | *1.45E−19 | 2.20 (1.60-3.03) | *5.41E−06 |
| 22:44368122:A:G | 1.52 (1.41-1.65) | *7.33E−24 | 1.86 (1.58-2.19) | *1.81E−12 | 1.66 (1.16-2.39) | 1.05E−02 |

*Indicates P-values meeting the Bonferroni significance threshold of $P < 2.08 \times 10^{-3}$.

Figure 2A:
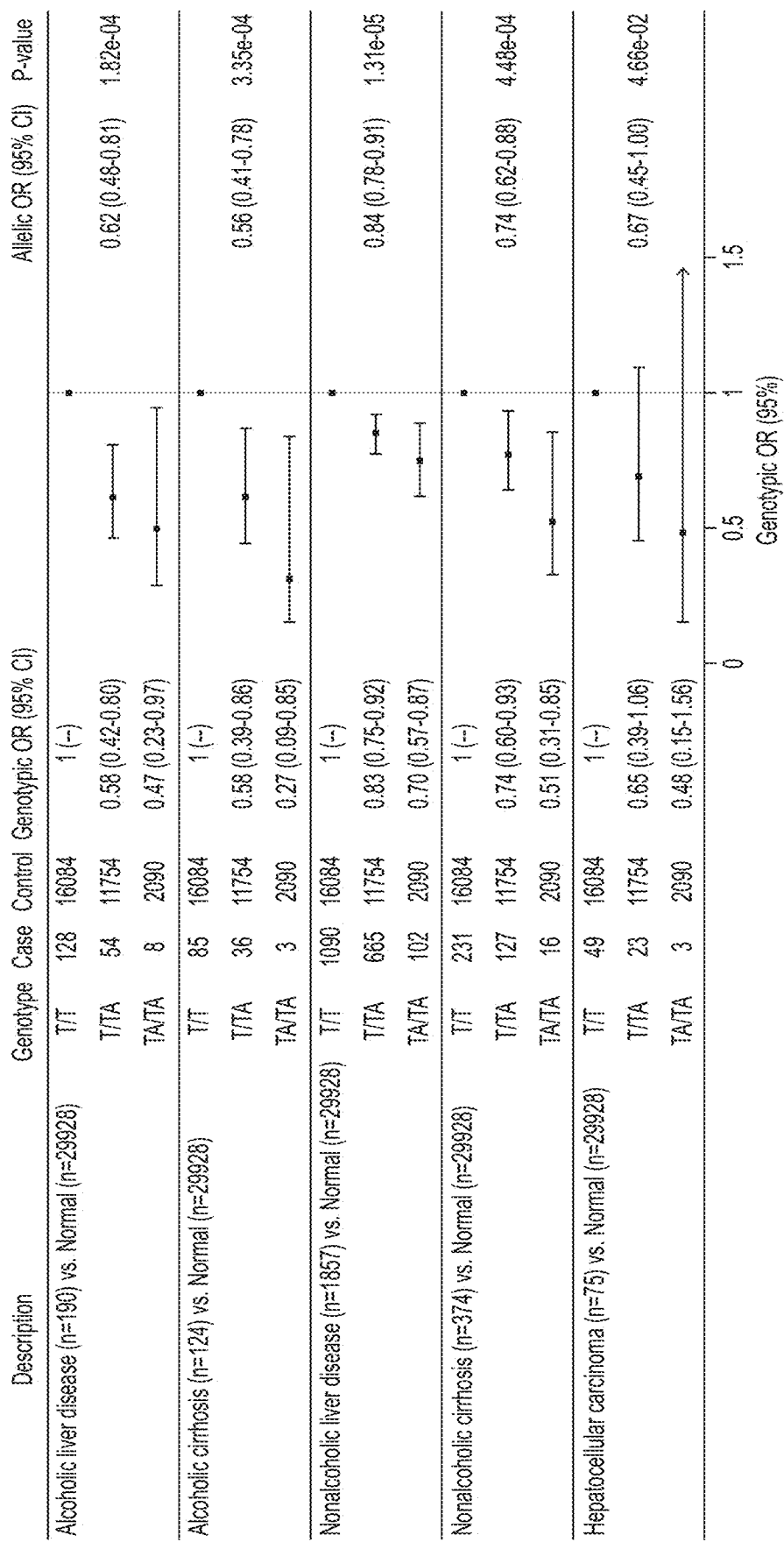
FIGS. 2A and 2B show that HSD17B13 rs72613567:TA is associated with reduced risk of alcoholic and nonalcoholic liver disease phenotypes in the discovery cohort (FIG. 2A), and with reduced risk of progression from simple steatosis to steatohepatitis and fibrosis in the bariatric surgery cohort (FIG. 2B). Odds ratios were calculated using logistic regression, with adjustment for age, $age^2$, sex, BMI, and principal components of ancestry. Genotypic odds ratios for heterozygous (Het OR) and homozygous (Hom OR) carriers are also shown. In the GHS discovery cohort in FIG. 2A, variant HSD17B13 was associated with significantly reduced risk of nonalcoholic and alcoholic liver disease, cirrhosis, and hepatocellular carcinoma in an allele dosage-dependent manner. In the GHS bariatric surgery cohort in FIG. 2B, HSD17B13 rs72613567 was associated with 13% and 52% lower odds of nonalcoholic steatohepatitis (NASH), and 13% and 61% lower odds of fibrosis, in heterozygous and homozygous TA carriers, respectively.

The alternate (TA) allele of HSD17B13 rs72613567 was observed at higher frequency in controls compared to participants with any of the chronic liver disease phenotypes evaluated (FIG. 2A and Table 5). After adjustment for age, age$^2$, sex, BMI, and ancestry, we observed 38% lower odds of alcoholic liver disease (odds ratio [OR] 0.62; 95% confidence interval [CI] 0.48-0.81, P=1.8×10$^{-4}$) and 16% lower odds of nonalcoholic (non-viral) liver disease (OR 0.84, 95% CI 0.78-0.91, P=1.3×10$^{-5}$) per TA allele. When restricting to cases with cirrhosis, the TA allele was associated with 44% lower odds of alcoholic (OR 0.56, 95% CI 0.41-0.78, P=3.4×10$^{-4}$) and 26% lower odds of nonalcoholic (OR 0.74, 95% CI 0.62-0.88, P=4.5×10$^{-4}$) cirrhosis. The TA allele was nominally associated with 33% lower odds of HCC per allele (OR 0.67, 95% CI 0.45-1.00, P=4.7×10$^{-2}$). Unadjusted genotypic ORs suggested a co-dominant effect; for example, for alcoholic cirrhosis, the OR was 0.59 (95% CI 0.40-0.86) for heterozygous T/TA carriers and 0.26 (95% CI 0.08-0.82) for homozygous TA/TA carriers, and for nonalcoholic cirrhosis, the OR was 0.75 (95% CI 0.61-0.93) for heterozygous and 0.55 (95% CI 0.34-0.91) for homozygous carriers.

Thus, in the discovery cohort, the alternate (TA) allele of HSD17B13 rs72613567 was associated with lower odds of all EHR-derived chronic liver disease phenotypes evaluated, in a consistent allele dosage-dependent manner (FIG. 2A): all categories of alcoholic liver disease, heterozygous odds ratio (OR$_{het}$) [95% confidence interval] 0.58 [0.42-0.79], homozygous OR (OR$_{hom}$) 0.46 [0.23-0.94], allelic OR (OR$_{allelic}$) 0.62 [0.48-0.81], P=1.82×10$^4$; all categories of nonalcoholic liver disease, OR$_{het}$ 0.84 [0.76-0.92], OR$_{hom}$ 0.73 [0.59-0.89], OR$_{allelic}$ 0.84 [0.78-0.91], P=1.31×10$^{-5}$. The TA allele was also associated with lower odds of the most advanced forms of these chronic liver diseases (as defined by EHR-derived diagnostic codes), namely alcoholic and nonalcoholic cirrhosis and HCC. The TA allele was associated with 42% and 73% lower odds of alcoholic cirrhosis for heterozygotes and homozygotes, respectively (OR$_{het}$ 0.59 [0.40-0.86], OR$_{hom}$ 0.26 [0.08-0.82], OR$_{allelic}$ 0.56 [0.41-0.78], P=3.35×10$^{-4}$), 26% and 49% lower odds of nonalcoholic cirrhosis for heterozygotes and homozygotes, respectively (OR$_{het}$ 0.75 [0.61-0.93], OR$_{hom}$ 0.55 [0.34-0.91], OR$_{allelic}$ 0.74 [0.62-0.88], P=4.48×10$^{-4}$). The TA allele was also nominally associated with lower odds of HCC.

Figure 8:
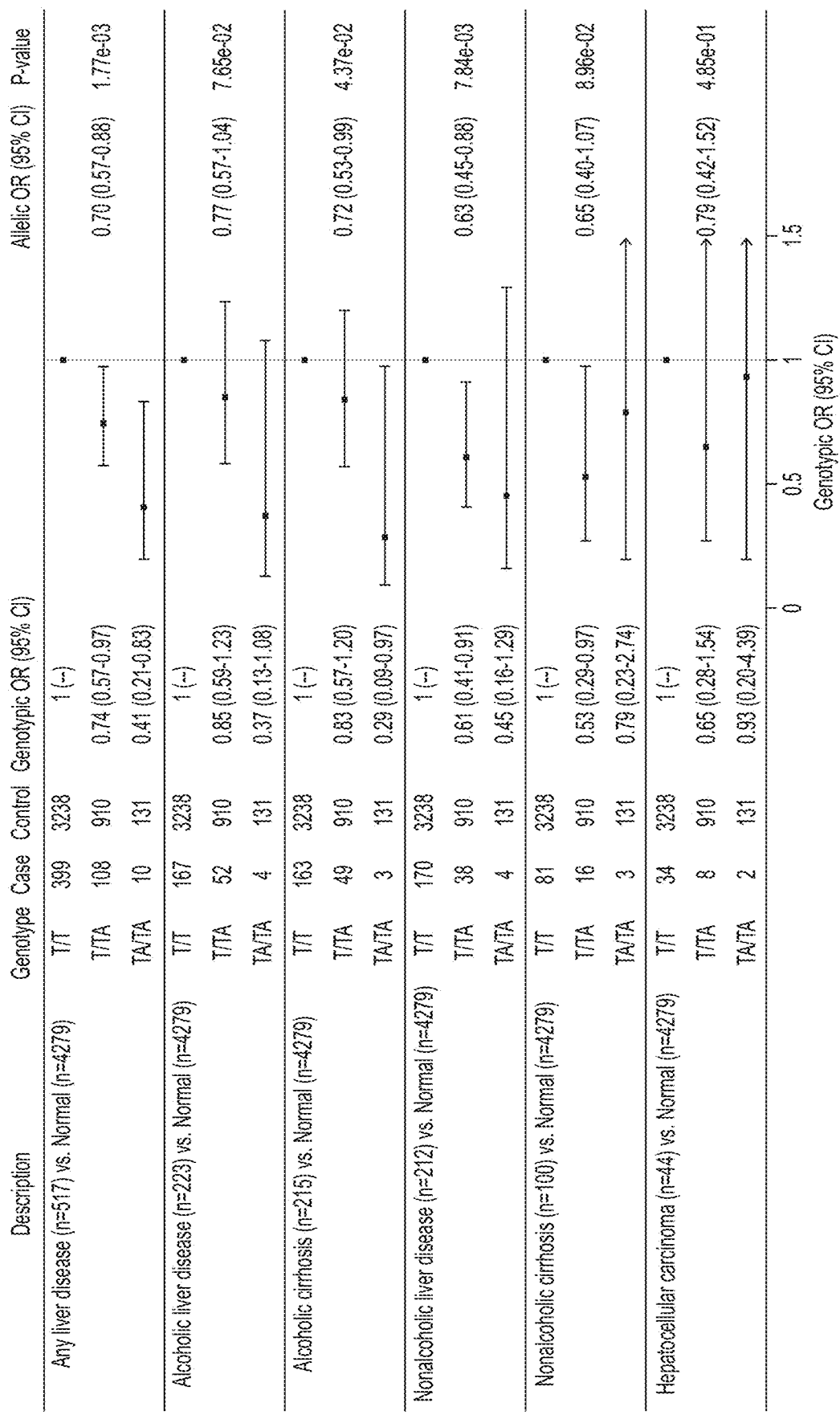
FIG. 8 shows that HSD17B13 rs72613567:TA is associated with reduced risk of alcoholic and nonalcoholic liver disease phenotypes. Specifically.

Next, we sought to confirm and extend these findings in the multi-ethnic Dallas Liver Study (DLS) and the Dallas Pediatric Liver Study (DPLS), including African American, European American, and Hispanic American adults and children (Table 1B). In the DLS, the TA allele was associated with lower odds of any liver disease in an allele-dosage dependent manner (OR$_{het}$ 0.74 [0.57-0.97], OR$_{hom}$ 0.41 [0.21M.83], OR$_{allelic}$ 0.70 [0.5-0.88], P=1.77×10$^{-3}$, FIG. 8). Similar allele dosage-dependent effects were observed across EHR-derived liver disease subtypes, including protective associations with advanced, cirrhotic forms of alcoholic (OR$_{allelic}$ 0.72 [0.53-0.99], P=4.37×10$^{-2}$) and nonalcoholic (OR$_{allelic}$ 0.65 [0.40-1.07], P=8.96×10$^{-2}$) liver disease. In subset analyses of individuals grouped by self-reported ethnicity, the association with liver disease remained significant in Hispanic Americans, in particular, because of the high rate of liver disease in this subpopulation (n=326 cases and 722 controls, OR$_{allelic}$ 0.51 [0.35-0.74], P=3.98×10$^{-4}$); similar numerical trends, which did not achieve statistical significance, were also noted in the African American (n=33 cases and 2,291 controls, OR$_{allelic}$ 0.74 [0.25-2.47], P=0.67) and European American (n=158 cases and 1,266 controls, OR$_{allelic}$ 0.87 [0.65-1.15], P=0.32) subsets of the DLS. In the DPLS, a separate study of Hispanic American pediatric liver disease patients and obese controls (Table 1B), the TA allele was also associated with lower odds of liver disease (OR$_{allelic}$ 0.59 [0.36-0.97], P=3.6×10$^{-2}$). Thus, the HSD17B13 rs72613567:TA allele was associated with reduced odds of multiple forms of chronic liver disease, including cirrhosis, in adults and children in three independent populations.

Figure 2B:
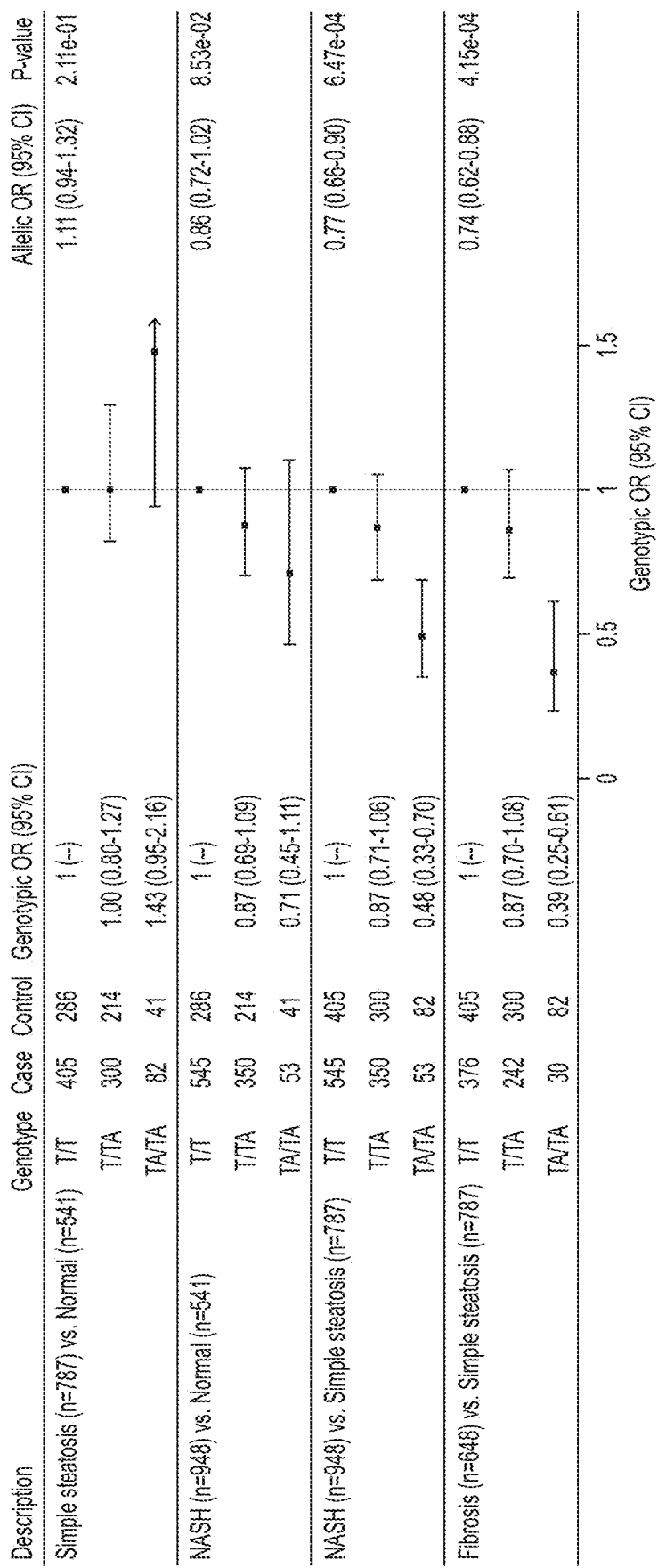
Figure 9:
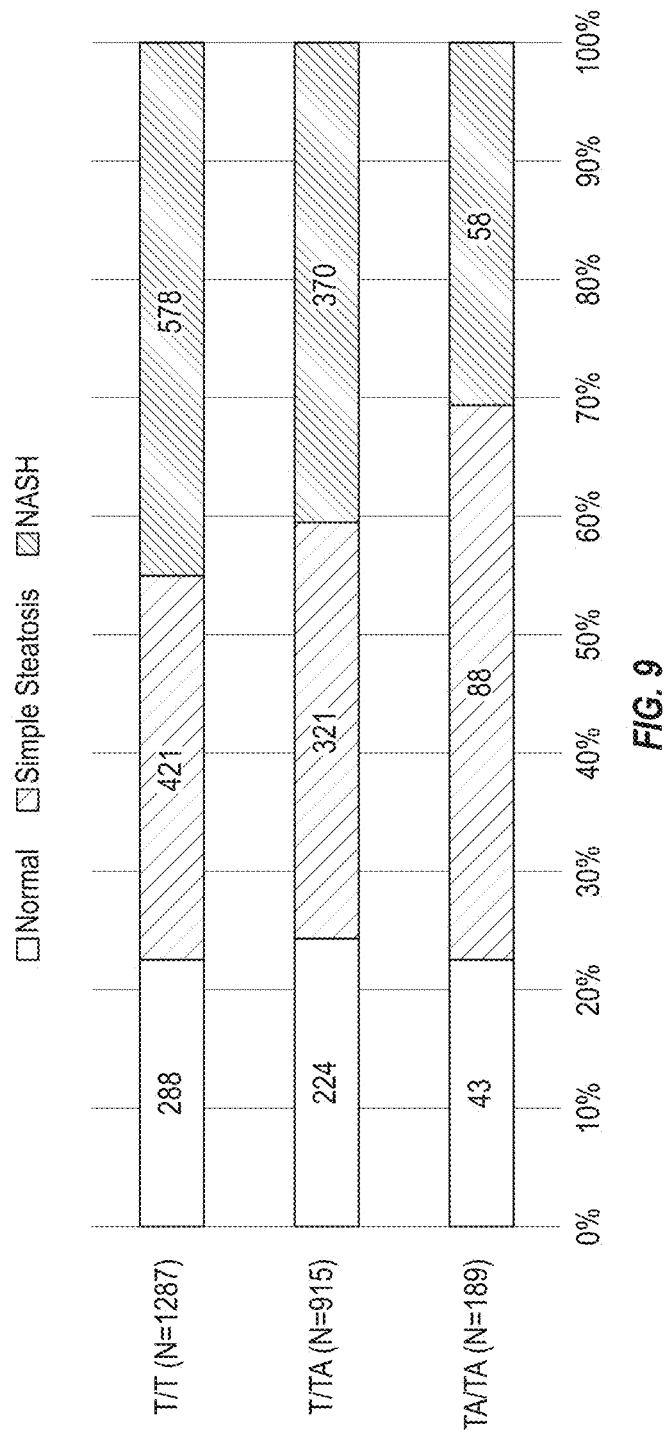
FIG. 9 shows HSD17B13 rs72613567 is associated with reduced risk of progression from simple steatosis to steatohepatitis and fibrosis. Specifically, it shows that prevalence of histopathologically-characterized liver disease according to HSD17B13 rs72613567 genotype in 2,391 individuals with liver biopsies from the GHS bariatric surgery cohort. The prevalence of normal liver did not appear to differ by genotype (P=0.5 by Chi-squared test for trend in proportions), but the prevalence of NASH decreased ($P=1.6 \times 10^{-4}$) and that of simple steatosis increased ($P=1.1 \times 10^{-3}$) with each TA allele.

NAFLD describes a spectrum of disease ranging from fatty liver without evidence of significant inflammation (designated as "simple steatosis" upon histopathological examination) to more clinically impactful manifestations (designated as "nonalcoholic steatohepatitis" (NASH), with histopathological evidence of lobular inflammation, hepatocyte ballooning, and/or fibrosis). To understand the relationship between the HSD17B13 TA allele and histologically defined NAFLD and NASH, we performed tests of association of rs72613567 in 2,391 whole exome sequenced individuals with liver biopsy samples from the GHS bariatric surgery cohort. Among these individuals, there were 555 (23%) with no evidence of steatosis, steatohepatitis, or fibrosis ("normal"), 830 (35%) with simple steatosis, and 1006 (42%) with NASH (i.e. evidence of lobular inflammation, hepatocyte ballooning, or fibrosis). The HSD17B13 TA allele was not significantly associated with simple steatosis (OR 1.11, 95% CI 0.94-1.32, P=0.21) or NASH (OR 0.86, 95% CI 0.72-1.02, P=0.09) compared to normal liver (FIG. 2B and Table 5). When comparing prevalence of normal liver, simple steatosis, and NASH by genotype, it was observed that the prevalence of normal liver did not appear to differ by genotype (23%, 24%, and 23% for T/T, T/TA, and TA/TA carriers, respectively, P=0.5 by Chi-squared test for trend in proportions), but that the prevalence of NASH decreased (45%, 40%, and 31% for T/T, T/TA, and TA/TA carriers, respectively, P=1.6×10$^{-4}$) and that of simple steatosis increased (33%, 35%, and 47% for T/T, T/TA, and TA/TA carriers, respectively, P=1.1×10$^{-3}$) with each TA allele (FIG. 9). Among individuals with steatosis, the TA allele was associated with statistically significantly lower odds of NASH, as compared to simple steatosis, in an allele dosage-dependent manner. On the background of simple steatosis, the TA allele was associated with 23% lower odds of NASH (OR 0.77, 95% CI 0.66-0.90, P=6.5×10$^{-4}$), suggesting a role for HSD17B13 in mediating the progression of NAFLD to more advanced stages of NASH and fibrosis. Genotypic association results were consistent with a co-dominant effect; in the NASH vs. simple steatosis comparison, the OR was 0.84 (95% CI 0.69-1.02) for heterozygous T/TA carriers, and 0.48 (95% CI 0.34-0.68) for homozygous TA/TA carriers.

G nucleotide at the 3' end of exon 6, leading to premature protein truncation. Novel transcripts were validated by RT-PCR, and the D transcript was additionally validated by long read cDNA sequencing. The expression levels of these transcripts varied according to HSD17B13 rs72613567 genotype; levels of transcripts A and B decreased, while those of transcripts C and D increased in an allele-dose-dependent manner in T/TA heterozygotes and TA/TA homozygotes (FIG. 3). Transcript A, encoding a 300 amino acid protein, was the predominant transcript in T/T in T/T homozygotes (FIG. 3A), while transcript D, encoding the prematurely truncated protein, was the predominant transcript in TA/TA homozygotes (FIG. 3D). These expression patterns suggest a functional role for HSD17B13 rs72613567 in determining HSD17B13 isoform expression. Four additional transcripts (E-H) with very low levels of

TABLE 5

HSD17B13 rs72613567 is associated with reduced risk of alcoholic and nonalcoholic liver disease phenotypes in the discovery cohort, and with reduced risk of progression from nonalcoholic fatty liver disease to nonalcoholic steatohepatitis and fibrosis in the bariatric surgery cohort.

| | | Cases | | | | Controls | | | |
| --- | --- | --- | --- | --- | --- | --- | --- | --- | --- |
| Cohort | Definitions | N | REF/REF | REF/ALT | ALT/ALT | Definitions | N | REF/REF | REF/ALT |
| Discovery cohort | Alcoholic liver disease | 197 | 133 | 56 | 8 | No liver disease | 30,522 | 16413 | 11969 |
| | Alcoholic cirrhosis | 130 | 89 | 38 | 3 | | | | |
| | Nonalcoholic liver disease | 1930 | 1131 | 692 | 107 | | | | |
| | Nonalcoholic cirrhosis | 381 | 235 | 129 | 17 | | | | |
| | Hepatocellular carcinoma | 76 | 49 | 24 | 3 | | | | |
| Bariatric surgery cohort | Simple steatosis | 830 | 421 | 321 | 88 | Normal | 555 | 288 | 224 |
| | NASH | 1006 | 578 | 370 | 58 | | | | |
| | NASH | 1006 | 578 | 370 | 58 | Simple steatosis | 830 | 421 | 321 |

| Cohort | Definitions | Controls ALT/ALT | AAF | Het OR (95% CI) | Hom OR (95% CI) | Per-allele OR (95% CI) | P-value |
| --- | --- | --- | --- | --- | --- | --- | --- |
| Discovery cohort | Alcoholic liver disease | 2140 | 0.266 | 0.58 (0.42-0.79) | 0.46 (0.23-0.94) | 0.62 (0.48-0.81) | 1.82E−04 |
| | Alcoholic cirrhosis | | 0.266 | 0.59 (0.40-0.86) | 0.26 (0.08-0.82) | 0.56 (0.41-0.78) | 3.35E−04 |
| | Nonalcoholic liver disease | | 0.264 | 0.84 (0.76-0.92) | 0.73 (0.59-0.89) | 0.84 (0.78-0.91) | 1.31E−05 |
| | Nonalcoholic cirrhosis | | 0.266 | 0.75 (0.61-0.93) | 0.55 (0.34-0.91) | 0.74 (0.62-0.88) | 4.48E−04 |
| | Hepatocellular carcinoma | | 0.266 | 0.67 (0.41-1.10) | 0.47 (0.15-1.51) | 0.67 (0.45-1.00) | 4.66E−02 |
| Bariatric surgery cohort | Simple steatosis | 43 | 0.291 | 0.98 (0.78-1.23) | 1.39 (0.94-2.08) | 1.11 (0.94-1.32) | 2.11E−01 |
| | NASH | | 0.255 | 0.82 (0.66-1.02) | 0.67 (0.44-1.02) | 0.86 (0.72-1.02) | 8.53E−02 |
| | NASH | 88 | 0.268 | 0.84 (0.69-1.02) | 0.48 (0.34-0.68) | 0.77 (0.66-0.90) | 6.47E−04 |

Figure 7A:
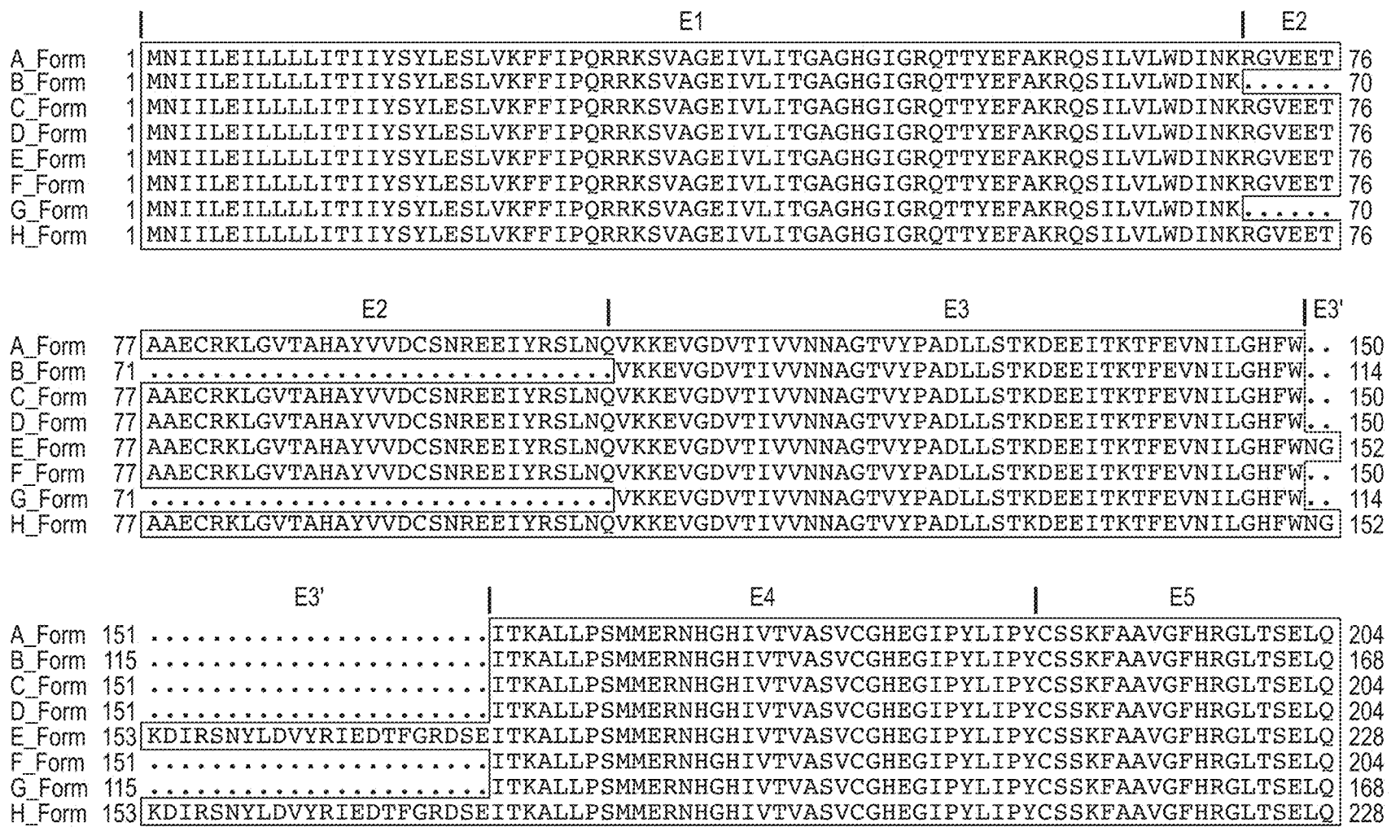

We next sought to understand how the HSD17B13 TA allele affects expression of known and novel transcripts of the gene. We used RNA sequencing to assess HSD17B13 mRNA expression in histologically normal liver samples from 22 homozygous reference (T/T), 30 heterozygous (T/TA), and 17 homozygous alternate (TA/TA) carriers of the HSD17B13 rs72613567 splice variant (FIG. 3). In addition to the two known HSD17B13 transcripts, A and B, two novel transcripts were identified: transcript C lacking exon 6, and transcript D characterized by the insertion of a expression were also identified (FIG. 6A-6D). Protein sequence alignment of all identified HSD17B13 isoforms is shown in FIG. 7A-7B.

HSD17B13 has been previously described as a lipid-droplet associated protein in human hepatocytes (Su et al. (2014) Proc Natl Acad Sci USA 111:11437-11442, herein incorporated by reference in its entirety for all purposes). We evaluated protein isoform expression and localization in a perpetual human liver cell line (HepG2 hepatoma cells) stably transduced with lentivirus expressing known and novel isoforms A-D of HSD17B13. HSD17B13 isoform A localized to lipid droplets in untreated and oleic acid-treated cells. Isoform A was mainly detected on membranes surrounding BODIPY-labeled lipid droplets, and co-localized with the lipid droplet coat protein perilipin (PLIN). Similar subcellular localization was observed for HSD17B13 isoform D at the lipid droplet surface; however, lipid droplets appeared larger following oleic acid treatment. In contrast, isoforms B and C co-localized with the endoplasmic reticulum marker calnexin.

In summary, using exome sequence data linked to EHR and liver biopsy data from 49,188 individuals from the DiscovEHR study population, and in follow-up studies of exome sequence data from 9,883 additional individuals with ALT and AST measurements, we discovered a novel association between a splice variant in HSD17B13, transaminase levels, and chronic liver disease phenotypes. In our study, variant HSD17B13 reduced the risk of nonalcoholic and alcoholic liver disease, and cirrhosis. This, to our knowledge, is the first report of an exonic variant with a protective association with chronic liver disease phenotypes. The HSD17B13 TA allele was not associated with simple steatosis, but reduced the risk of histopathologic steatohepatitis in individuals with steatosis, suggesting a role for HSD17B13 in progression to more clinically advanced stages of chronic liver disease. The consistency of protective associations in four independent cohorts (GHS discovery, GHS bariatric, DLS, and DPLS) across several different liver disease categories, characterized using EHR diagnosis codes as well as histopathological definitions of liver disease, together with the striking allele dosage-dependence of the associations, support the notion that the reported HSD17B13 variant protects from progression to more clinically advanced stages of chronic liver disease. The observed allele dosage-dependence also argues that more profound regulation of HSD17B13 function may result in more profound effects on disease risk and progression.

Other 17beta-hydroxysteroid dehydrogenase family members are known to be involved in sex steroid and fatty acid metabolism (Moeller and Adamski (2009) *Mol Cell Endocrinol* 301:7-19, herein incorporated by reference in its entirety for all purposes), but little is known about the function of HSD17B13. HSD17B13 is expressed primarily in the liver (Liu et al. (2007) *Acta Biochim Pol* 54:213-218, herein incorporated by reference in its entirety for all purposes), where it localizes to lipid droplets (Su et al. (2014) *Proc Natl Acad Sci USA* 111:11437-11442, herein incorporated by reference in its entirety for all purposes), consistent with a role for HSD17B13 in the pathogenesis of fatty liver disease. Our data are consistent with recent findings that HSD17B13 overexpression increased lipogenesis in mouse liver, and increased the number and size of lipid droplets in cultured hepatocytes (Su et al. (2014) *Proc Natl Acad Sci USA* 111:11437-11442, herein incorporated by reference in its entirety for all purposes). Two previous studies have also shown that hepatic expression of HSD17B13 protein is increased in patients with fatty liver (Su et al. (2014) *Proc Natl Acad Sci USA* 111:11437-11442 and Kampf et al. (2014) *FASEB J* 28:2901-2914, each of which is herein incorporated by reference in its entirety for all purposes). Two genes with variants that have been reported to be associated with increased risk of liver disease—PNPLA3 and TM6SF2-also have physiological roles in hepatocyte lipid metabolism. The variant in HSD17B13 that we describe here is the first protective variant for liver disease, and may provide an avenue to new therapeutic strategies targeting chronic liver disease, similar to genetic variants that have guided the way to new therapeutics in other domains.

Overall, our data support HSD17B13 as a novel therapeutic target to reduce the risk of chronic liver disease in humans. Importantly, our data indicate that targeting of HSD17B13 could reduce progression from NAFLD to later stages of NASH, fibrosis, and cirrhosis, which are associated with significant morbidity and mortality, and for which there are currently no effective treatments.

Methods

Study Participants. Human genetics studies were conducted as part of the DiscovEHR collaboration of the Regeneron Genetics Center and the Geisinger Health System (GHS). The study was approved by the GHS Institutional Review Board. The two DiscovEHR study populations (discovery cohort and bariatric surgery cohort) originated from the first 50,726 consented participants≥18 years of age from the MYCODE® Community Health Initiative of GHS (Dewey et al. (2016) *Science* 354(6319) doi:10.1126/science.aaf6814, herein incorporated by reference in its entirety for all purposes). The GHS discovery cohort consisted of 46,544 European individuals recruited from outpatient primary care and specialty clinics between 2007 and 2016, excluding all those recruited to the bariatric surgery cohort. The GHS bariatric surgery cohort consisted of 2,644 European individuals who had been referred for bariatric surgery.

Replication studies included 1,357 European individuals from the Dallas Heart Study and 8,527 European individuals from the Penn Medicine Biobank. The Dallas Heart Study is a probability-based population cohort study of Dallas County residents aged 30 to 65 years (Victor et al. (2004) *Am J Cardiol* 93:1473-1480, herein incorporated by reference in its entirety for all purposes. The Penn Medicine Biobank includes participants recruited from the University of Pennsylvania Health System and consented for biospecimen storage, access to EHR data, and permission to recontact.

Replication studies of the associations with chronic liver disease included 517 individuals from the Dallas Liver Study (DLS) and 447 individuals from the Dallas Pediatric Liver Study (DPLS). The DLS is a biobank of patients with liver disease of non-viral etiology. Recruitment began in January 2015 and is ongoing. Participants were recruited from liver clinics at UT Southwestern and Parkland Health and Hospital System, Dallas. The biobank was approved by the UT Southwestern Institutional Review Board. Participants provided written informed consent. Participants completed a questionnaire on ethnic/racial background, medical history, lifestyle factors, and family history of liver disease and other diseases. Additional clinical information was extracted from medical records by a trained technician. We included all African American, European American, and Hispanic American patients with DNA available at the time of the present study (n=517). The DPLS is a biobank of children recruited from pediatric liver clinics at UT Southwestern and Parkland Health and Hospital System, Dallas, and from an obesity clinic at Children's Medical Center, Dallas. The biobank was approved by the UT Southwestern Institutional Review Board. The legal guardians of the participants provided written informed consent. Clinical information was extracted from medical records by a trained technician. As more than 95% of the patients were Hispanic Americans, we only included Hispanic American patients and controls in the present study (n=203 patients and 244 controls).

Sample Preparation and Sequencing. Sample preparation and whole exome sequencing were performed at the Regeneron Genetics Center as previously described (Dewey et al. (2016) *Science* 354(6319) doi:10.1126/science.aaf6814, herein incorporated by reference in its entirety for all purposes). In brief, exome capture was performed using NimbleGen probes according to the manufacturer's recommended protocol (Roche NimbleGen). The captured DNA was PCR amplified and quantified by qRT-PCR (Kapa Biosystems). The multiplexed samples were sequenced using 75 bp paired-end sequencing on an Illumina v4 HiSeq 2500 to a coverage depth sufficient to provide greater than 20× haploid read depth of over 85% of targeted bases in 96% of samples (approximately 80× mean haploid read depth of targeted bases). Raw sequence data from each Illumina Hiseq 2500 run were uploaded to the DNAnexus platform (Reid et al. (2014) *BMC Bioinformatics* 15, 30 doi:10.1186/1471-2105-15-30) for sequence read alignment and variant identification. In brief, raw sequence data were converted from BCL files to sample-specific FASTQ-files, which were aligned to the human reference build GRCh37.p13 with BWA-mem (Li and Durbin (2009) *Bioinformatics* 25:1754-1760, herein incorporated by reference in its entirety for all purposes). Single nucleotide variants (SNV) and insertion/deletion (indel) sequence variants were identified using the Genome Analysis Toolkit (McKenna et al. (2010) *Genome Res* 20:1297-1303, herein incorporated by reference in its entirety for all purposes).

Targeted Genotyping of rs72613567 in the Dallas Liver and Pediatric Liver Studies. HSD17B13 rs72613567 was genotyped by TAQMAN® assay in the Dallas Liver Study and Dallas Pediatric Liver Study, and by exome sequencing in the Dallas Heart Study. TAQMAN® calls were verified by Sanger sequencing of 5 individuals with each genotype.

Clinical Measurements and Chronic Liver Disease Definitions in the Discovery Cohort. Clinical laboratory measurements for ALT and AST were extracted from EHRs of participants from the GHS discovery cohort and bariatric surgery cohort. Median ALT and AST values were calculated for all participants with two or more measurements, and were $log_{10}$ transformed to normalize the distribution prior to association analyses.

*International Classification of Diseases, Ninth Revision* (ICD-9) disease codes were extracted from EHRs and collapsed into clinical disease categories for non-viral, nonalcoholic (ICD-9 571.40, 571.41, 571.49, 571.5, 571.8, 571.9) or alcoholic (ICD-9 571.0, 571.1, 571.2, 571.3) liver disease case definitions. Additional case definitions based on single diagnosis codes included: alcoholic cirrhosis (ICD-9 571.2), nonalcoholic cirrhosis (ICD-9 571.5), and HCC (ICD-9 155.0). For these case definitions, a common control group without liver disease was defined as participants with no case criteria or single-encounter or problem-list diagnosis code indicating any type of liver disease.

Liver Histopathologic Phenotype Definitions in the Bariatric Surgery Cohort. The GHS bariatric surgery cohort consisted of 2,644 individuals of European descent, with intra-operative liver biopsy specimens available from 2,391 of these individuals. Liver biopsy specimens were formalin-fixed and stained with hematoxylin and eosin for routine histology, and Masson's trichrome stain for assessment of fibrosis, as previously described (Gerhard et al. (2011) *Patient Saf Surg* 5,1, doi:10.1186/1754-9493-5-1, herein incorporated by reference in its entirety for all purposes). Histologic diagnoses were determined by hepatopathologists using previously established criteria (Brunt et al. (1999) *Am J Gastroenterol* 94:2467-2474, herein incorporated by reference in its entirety for all purposes). Histologic diagnoses were used to defined the following phenotypes: 1) Normal: no evidence of steatosis, NASH, or fibrosis; 2) Simple steatosis: Steatosis (regardless of grade) with no evidence of NASH or fibrosis; 3) NASH/fibrosis: Any presence of lobular inflammation or hepatocyte ballooning (regardless of grade), or any presence of fibrosis (regardless of stage); 4) Fibrosis: Any presence of fibrosis (regardless of stage).

Exome-Wide Association Analysis of Liver Enzymes. In the GHS discovery cohort, we tested 502,219 biallelic variants with missing data rate<1%, Hardy-Weinberg equilibrium p-value>1.0×10$^{-6}$, and minor allele frequency>0.1% for association with transaminase levels. $Log_{10}$-transformed median ALT and AST were adjusted for age, age$^2$, sex, BMI, and the first four principal components of ancestry. To account for relatedness among study participants, we also fit a genetic relatedness matrix as a random-effects covariate. Both principal components and the genetic relatedness matrix were constructed from 39,858 non-MHC markers in approximate linkage equilibrium and with minor allele frequency>0.1%. We used linear mixed models as implemented in the GCTA package (Yang et al. (2011) *Am J Hum Genet* 88:76-82, herein incorporated by references in its entirety for all purposes) to test for association between trait residuals and single nucleotide variants. The tests were well-calibrated, as shown by exome-wide quantile-quantile plots and genomic control lambda values (FIG. 1).

Replication Meta-Analysis of Liver Enzyme Associations. We attempted to replicate associations in the GHS discovery cohort in three separate European-ancestry cohorts: the GHS bariatric surgery cohort, the Dallas Heart Study, and the Penn Medicine Biobank (described above). ALT and AST measures in the GHS bariatric surgery cohort and from Penn Medicine Biobank were login-transformed and adjusted for age, age$^2$, sex, BMI, and the first four principal components of ancestry. ALT and AST measures from the Penn Medicine Biobank samples were $log_{10}$-transformed and adjusted for age, age$^2$, sex, BMI, and the first four principal components of ancestry. Genetic relatedness matrices were included as random-effects covariates, and analysis was performed using linear mixed models in GCTA. In the Dallas Heart study, $log_{10}$-transformed ALT and AST measures were adjusted for age, age$^2$, sex, and the first ten principal components of ancestry, and analysis was performed using linear regression implemented in PLINK. Summary statistics for the three replication cohorts were meta-analyzed using METAL (replication meta-analysis) (Willer et al. (2010) Bioinformatics 26:2190-2191, herein incorporated by reference in its entirety for all purposes). Summary statistics for the discovery cohort and the three replication cohorts were meta-analyzed similarly (joint meta-analysis).

Association Analysis with Chronic Liver Disease Phenotypes. We analyzed nine significant and replicated single nucleotide variants from the liver enzyme ExWAS for associations with binary liver disease phenotypes defined from the GHS discovery cohort, as described above. We used a Bonferroni significance threshold of P<0.05/26 (P<1.92×10$^{-3}$) to account for the thirteen variants and two broad chronic liver disease categories (alcoholic and nonalcoholic) tested. Variant HSD17B13 was further tested for association with histopathologically defined liver phenotypes from the GHS bariatric surgery cohort, as described above. Odds ratios were estimated with the use of Firth's penalized likelihood method of logistic regression after adjustment for age, age$^2$, sex, BMI, and the first four principal components of ancestry. Unadjusted genotypic odds ratios were also estimated for HSD17B13 rs72613567.

Odds ratios for liver disease in the DLS were estimated by logistic regression, adjusted for age, age$^2$, gender, BMI, and self-reported ethnicity. Participants from the Dallas Heart Study with available rs72613567 genotypes were used as normal controls (n=4,279). Odds ratios in the DPLS were estimated by logistic regression.

Software. Genetic association analyses were performed using GCTA software, version 1.25.0 (Yang et al. (2011) *Am J Hum Genet* 88:76-82, herein incorporated by reference in its entirety for all purposes), and PLINK, version 1.9.0. Quantile-quantile and Manhattan plots were generated using R software, version 3.2.1 (R Project for Statistical Computing). Regional association plots were generated using LocusZoom (Pruim et al. (2010) *Bioinformatics* 26:2336-2337, herein incorporated by reference in its entirety for all purposes).

RNA Sequencing Studies. RNA quality and concentration was evaluated by running total RNA on an Agilent RNA Nano Bioanalyzer chip; all samples had an RNA integrity number (RIN) greater than 8. Polyadenlylated RNA transcripts were isolated using two rounds of enrichment with oligo(dT)25 beads (Thermo Fisher Scientific). Samples were purified and concentrated with RNAclean XP beads (Beckman Coulter) and heat-fragmented to approximately 140 base pairs. First-strand synthesis was completed with SuperScript III reverse transcriptase (Thermo Fisher Scientific) using random hexamers; dTTP was replaced with dUTP during second-strand synthesis. Samples were processed according to our standard DNA library preparation method referenced above for exomes with the addition of a uracil DNA-glycosylase step to generate strand-specific sequencing libraries. Samples were pooled and sequenced using 75 bp paired-end sequencing on an Illumina v4 HiSeq 2500.

Identification of Novel HSD17B13 Transcripts. Reads were mapped to the Human.B38 using ARRAYSTUDIO® software (OMICSOFT®, Cary, N.C.) allowing two mismatches. Two approaches were employed to identify novel HSD17B13 transcripts. Novel exon junctions were discovered based on Gencode v24. De novo transcript assembly was run using Trinity (v2.2.0) in default setting. Custom gene models were built to incorporate novel transcripts of HSD17B13, and transcript quantification was estimated by read alignment to the custom gene model. Protein sequence alignment of all identified HSD17B13 isoforms is shown in FIGS. 7A and 7B.

RT-PCR Validation of Novel Transcripts. RT-PCR on total RNA from human liver samples was performed using the SUPERSCRIPT™ One-Step RT-PCR System with Platinum™ Taq DNA Polymerase (Thermofisher). Each 50 uL RT-PCR reaction contained 1× Reaction Mix, 500 nM each forward and reverse primers (PST516: ATGAACATCATC-CTAGAAATCCTTC (SEQ ID NO: 251) and PST517: ATCATGCATACATCTCTGGCTGGAG (SEQ ID NO: 252)), 1 µL of RT/Platinum Taq, and 75 ng RNA. Cycling conditions were: one cycle of 45° C. for 30 min; one cycle of 94° C. for 2 min; 40 cycles of 94° C. for 20 s, 53° C. for 30 s, and 72° C. for 90 s; one cycle of 72° C. for 5 min; then a 10° C. hold. Products were purified using the QIAquick PCR Purification Kit (Qiagen) and submitted for direct Sanger sequencing using the primer DE002 (ATCAGAACT-TCAGGCCTTGG (SEQ ID NO: 253)). To identify the B and C transcripts, the RT-PCR products were run out on a 2% agarose gel stained with SYBR GOLDSYBR® Gold Nucleic Acid Gel Stain (Thermofisher), and bands of the expected molecular weight were excised and purified using the QIAquick Gel Extraction Kit (Qiagen), then subjected to cloning with the TOPO® TA Cloning Kit (Thermofisher). Sequencing of the TOPO clones was performed using, M13F and M13R sequencing primers. Sequence analysis was performed using the Sequencher DNA analysis software (Gene Codes Corporation).

PacBio Validation of Novel Transcripts. Full-length HSD17B13 transcripts were amplified directly from 50 ng of total RNA with the SuperScript III One-step RT-PCR System with Platinum Taq High Fidelity (Thermo Fisher Scientific) using gene-specific primers in the first (GCAAAGC-CATGAACATCATCC (SEQ ID NO: 254) and last exons (TCTTGATGTAGTGGGAGTCGGATT (SEQ ID NO: 255)) to generate an amplicon of ~2.2 kb (maximum predicted size transcript). Amplicons were verified on an Agilent Bioanalyzer. PacBio-compatible barcoded adapters were ligated to the amplicons and cleaned with PacBio PB beads (Pacific Biosciences). Libraries were pooled in equal amounts and sequenced on one SMRT cell for 180 min on the PacBio RSII platform. The data were demultiplexed using PacBio software smrtanalysis v2.3 tool labelzmw and then analyzed with ConsensusTools AmpliconAnalysis. Resulting amplicons were compared to HSD17B13 RefSeq genes to determine isoform and genotype status.

Subcellular Localization of HSD17B13 Isoforms. HepG2 cells were cultured in Eagle's Minimum Essential Medium supplemented with 10% fetal bovine serum. HSD17B13 Transcripts A, B, C, and D were sub-cloned into Myc-DDK backbone lentivirus constructs, and lentivirus were generated. HepG2 cells were infected with lentivirus carrying the various HSD17B13 transcripts. Stable cell lines expressing each HSD17B13 transcript were selected with 1-3 mg/ml Geneticin G-418 sulfate in complete culture medium for two weeks. Selected HepG2 cells were treated with or without 200 µM oleic acid overnight then fixed. HSD17B13 isoforms were labeled with mouse anti-Myc antibody. Lipid droplets were labeled with BODIPY FL dye (Sigma). Lipid coat protein and endoplasmic reticulum were labeled with rabbit anti-PLIN antibody (Sigma) and rabbit anti-calnexin antibody (Cell Signaling Technology), respectively. Secondary antibodies for immunofluorescence were Alexa Fluor 488 donkey anti-rabbit IgG and Alexa Fluor 594 donkey anti-mouse IgG (Jackson ImmunoResearch).

Example 2. Effect of rs72613567:TA on HSD17B13 mRNA and HSD17B13 Protein Expression The effect of the HSD17B13 rs72613567:TA allele on expression of known and novel transcripts of the gene was examined. RNA sequencing was used to assess HSD17B13 mRNA expression in histologically normal liver samples from 22 T/T homozygous, 30 T/TA heterozygous, and 17 TA/TA homozygous carriers of the HSD17B13 rs72613567 splice variant. In addition to the two known HSD17B13 transcripts, A and B, two novel transcripts were identified: Transcript C, which lacked exon 6, and Transcript D which contained an insertion of a guanine nucleotide at the 3' end of exon 6, which would be predicted to result in premature truncation of the protein. The transcripts were validated by RT-PCR and Sanger sequencing (data not shown). The D transcript was also validated using long read cDNA sequencing. The expression levels of these transcripts varied according to HSD17B13 rs72613567 genotype; levels of transcript A decreased, while the level of transcripts D increased in an allele dosage-dependent manner with each TA allele (see FIGS. 3A, 3D, and 10B). Transcript A, which encodes the full-length 300 amino acid protein, was the predominant transcript in T/T homozygotes, while transcript D, which encodes the prematurely truncated protein, was the predominant transcript in TA/TA homozygotes. In human liver biopsy tissue, the truncated isoform D protein was minimally present in heterozygotes and TA/TA homozygotes, and isoform A protein abundance was reduced in an allele dosage-dependent manner (see FIGS. 10B and 10C). These data are consistent with HSD17B13 rs72613567 altering mRNA splicing, resulting in the synthesis of a truncated form of the protein with substantially reduced expression in human liver.

Referring to FIGS. 10A-10E, expression, subcellular localization, and enzymatic activity of a novel HSD17B13 transcript is shown. Expression of HSD17B13 transcripts A and D in homozygous reference (T/T), heterozygous (T/TA), and homozygous alternate (TA/TA) carriers of the HSD17B13 rs72613567 splice variant is shown in FIGS. 3A and 3D. Coding regions in gene models are indicated in the striped boxes and untranslated regions in the black boxes. The asterisk in transcript D indicates the insertion of G from rs72613567 at the 3' end of exon 6, which leads to premature truncation of the protein. mRNA expression is displayed in FPKM units (Fragments Per Kilobase of transcript per Million mapped reads). A Western blot from HepG2 cells overexpressing HSD17B13 transcripts A and D shows that HSD17B13 transcript D was translated to a truncated protein with lower molecular weight compared to HSD17B13 transcript A (see FIG. 10A). Similar results were observed with an HSD17B13 western blot from fresh frozen human liver and HEK293 cell samples (see FIG. 10B). Human liver samples were from homozygous reference (T/T), heterozygous (T/TA), and homozygous alternate (TA/TA) carriers of the HSD17B13 rs72613567 splice variant. Cell samples were from HEK293 cells overexpressing non-tagged HSD17B13 transcripts A and D. HSD17B13 Transcript D was translated to a truncated protein IsoD with lower molecular weight than HSD17B13 IsoA. HSD17B13 IsoD protein levels were lower than IsoA protein levels from both human liver (left) and cell (right) samples (see FIG. 10C). Protein level normalized to actin is shown in the bar columns in FIG. 10C; **P<0.001, *P<0.05. Both HSD17B13 Isoforms A and D were localized on lipid droplet membrane in HepG2 stably overexpressing HSD17B13 transcripts A or D were labelled with BODIPY to show lipid droplets and anti-Myc to show HSD17B13 localization (data not shown). Enzymatic activity of HSD17B13 isoforms A and D to 17-beta estradiol (estradiol), leukotriene B4 (LTB4), and 13-Hydroxyoctadecadienoic acid (13(S)-HODE) was also assessed (see FIG. 10D). HSD17B13 Isoform D showed <10% enzymatic activity of the corresponding values for Isoform A. HSD17B13 Isoform D when overexpressed in HEK293 cells did not show much conversion of estradiol (substrate) to estrone (product) when measured in the culture media, while overexpressed HSD17B13 Isoform A showed robust conversion (see FIG. 10E).

HSD17B13 is expressed primarily in the liver (Liu et al., *Acta Biochim. Pol.,* 2007, 54, 213-8, herein incorporated by reference in its entirety for all purposes), where it localizes to lipid droplets (Su et al., *Proc. Natl. Acad. Sci. USA,* 2014, 111, 11437-42, herein incorporated by reference in its entirety for all purposes), consistent with a role in the pathogenesis of fatty liver disease. The expression of HSD171B3 and its localization was evaluated in an immortalized human liver cell line stably transduced with lentivirus expressing HSD17B13 Transcripts A and D. HSD17B13 Isoform A was mainly detected on membranes surrounding BODIPY-labeled lipid droplets (data not shown). Similar subcellular localization was observed for HSD17B13 Isoform D at the lipid droplet surface (see FIG. 10D).

To understand the functional consequences of premature truncation of HSD17B13 protein due to rs72613567:TA, the enzymatic activity of Isoforms A and D was evaluated in vitro using recombinant protein. Greater than 300 putative substrates were examined, of which estradiol, leukotriene B4, and 13-Hydroxyoctadecadienoic acid were enzymatically converted by HSD17B13, resulting in oxidation of a hydroxyl to a ketone group. HSD17B13 Isoform D showed greatly reduced activity towards the three substrates (see FIG. 10D).

Figure 10E:
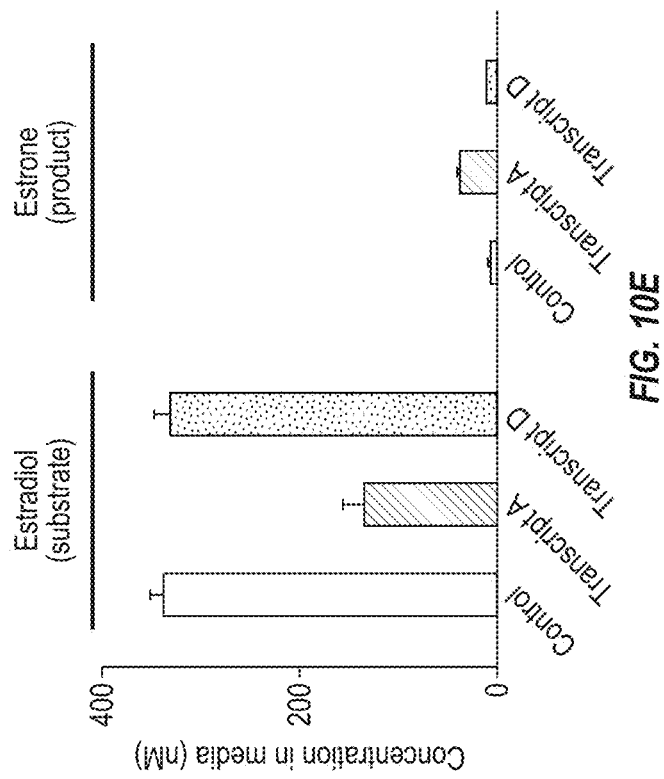
Figure 10D:
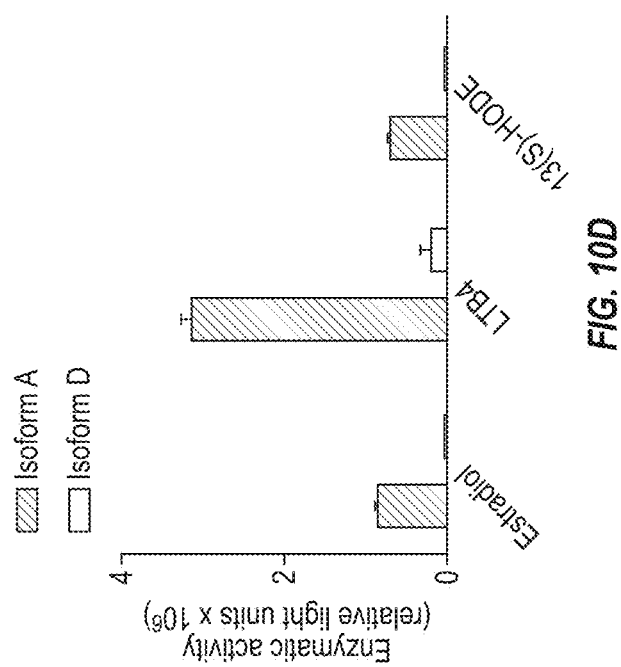

Compared to GFP control, HSD17B13-Transcript-A-overexpressing cells had lower concentration of estradiol as well as higher concentration of estrone in the cell culture medium, suggesting enzyme activity against estradiol (see FIG. 10E). HSD17B13-Transcript-D-overexpressing cells had similar ratio of estrone/estradiol to GFP control cells, suggesting that HSD17B13 Transcript D has significant loss of function. The mass spectrometry analysis revealed rapid conversion of estrone into hydroxyestrone and other products accounting for the low accumulation of estrone compared to consumed estradiol.

Through large-scale exome sequencing, a novel association was identified between a splice variant in HSD17B13 and decreased serum transaminase levels, as well as reduced risk of nonalcoholic and alcoholic forms of liver disease, including advanced cirrhotic forms of liver disease and HCC. To our knowledge, this is the first report of a protein-altering variant that has a protective association with liver disease. The HSD17B13 rs72613567:TA allele was not associated with simple steatosis, but reduced the risk of progression to NASH. The consistency of the dosage-dependent protective associations in four independent cohorts (DiscovEHR, an independent bariatric surgery cohort in DiscovEHR, DLS, and DPLS) across several different liver disease categories and ethnicities support the notion that the reported HSD17B13 variant protects from progression to more clinically advanced stages of chronic liver disease. The observed allele dosage-dependence also argues that more profound regulation of HSD17B13 function may result in more profound effects on disease risk and progression.

The association findings described herein were primarily based on observations in European and Hispanic Americans who have elevated BMI. HSD17B13 is in close proximity with HSD17B11, a member of the same gene family with high sequence similarity to HSD17B13 but broader tissue distribution. Overall, the data presented herein support the position that HSD17B13 is a potential therapeutic target for prevention and treatment of fatty liver disease in humans. The data presented herein indicate that targeting of HSD17B13 could reduce progression of liver disease from steatosis to later stages of NASH, fibrosis, and cirrhosis, which are associated with significant morbidity and mortality, and for which there are currently no effective treatments.

Example 3. Variant 17Beta-Hydroxysteroid Dehydrogenase 13 Protects Against Chronic Liver Disease To identify genetic factors contributing to chronic liver disease, we utilized exome sequence data and electronic health records from 46,544 participants in the DiscovEHR human genetics study. We identified genetic variants associated with established biomarkers of hepatic injury (serum alanine aminotransferase (ALT) and aspartate aminotransferase (AST)) to nominate candidates that might be associated with chronic liver disease. Candidate variants replicating in three additional cohorts (12,527 individuals) were subsequently evaluated for association with clinical diagnoses of chronic liver disease in DiscovEHR and two independent cohorts (total of 37,892 individuals). We also examined the association with histopathological severity of liver disease in an independent bariatric surgery cohort (n=2,391 human liver samples).

A splice variant (rs72613567:TA) in HSD17B13, encoding the hepatic lipid droplet protein 17-beta hydroxysteroid dehydrogenase 13, was reproducibly associated with reduced ALT (P=$4.2\times10^{-12}$) and AST (P=$6.2\times10^{-10}$) levels. In DiscovEHR, this variant was associated with reduced risk of alcoholic and nonalcoholic liver disease (by 38%, 95% confidence interval (CI) 19%-52%; and by 16%, 95% CI 9%-22%, respectively, for each rs72613567:TA allele) and cirrhosis (by 44%, 95% CI 22-59%; and by 26%, 95% CI 12%-38% for alcoholic and nonalcoholic cirrhosis, respectively, for each rs72613567:TA allele) in an allele dosage-dependent manner; associations were confirmed in two independent cohorts. rs72613567:TA was associated with decreased severity of histological features of nonalcoholic steatohepatitis (NASH) (23% reduction, 95% CI 10%-34% for each rs72613567:TA allele among individuals with fatty liver disease). rs72613567:TA results in an unstable and truncated protein with reduced enzymatic activity against steroid substrates.

A loss-of-function variant in HSD17B13 was associated with reduced risk of alcoholic and nonalcoholic liver disease, and progression from steatosis to NASH.

Study Design and Participants

Human genetics studies were conducted as part of the DiscovEHR collaboration of the Regeneron Genetics Center and Geisinger Health System (GHS). The two DiscovEHR study populations (discovery cohort and bariatric surgery cohort) originated from the first 50,726 consented participants>18 years of age from the MyCode® Community Health Initiative of GHS. The GHS discovery cohort consisted of 46,544 European individuals recruited from outpatient primary care and specialty clinics between 2007 and 2016, excluding all those recruited to the bariatric surgery cohort. The GHS bariatric surgery cohort consisted of 2,644 European individuals who had been referred for bariatric surgery.

Replication studies of associations with liver transaminases included 1,357 European individuals from the Dallas Heart Study and 8,527 European individuals from the Penn Medicine Biobank. The Dallas Heart Study is a probability-based population cohort study of Dallas County residents aged 30 to 65 years (Victor et al., Am. J. Cardiol., 2004; 93, 1473-80, herein incorporated by reference in its entirety for all purposes). The Penn Medicine Biobank includes participants recruited from the University of Pennsylvania Health System and consented for biospecimen storage, access to EHR data, and permission to recontact.

Replication studies of the associations with chronic liver disease included 517 individuals from the Dallas Liver Study (DLS) and 447 individuals from the Dallas Pediatric Liver Study (DPLS). The DLS is a biobank of patients with liver disease of non-viral etiology. Recruitment began in January 2015 and is ongoing. Participants were recruited from liver clinics at UT Southwestern and Parkland Health and Hospital System, Dallas. Participants completed a questionnaire on ethnic/racial background, medical history, lifestyle factors, and family history of liver disease and other diseases. Additional clinical information was extracted from medical records by a trained technician. We included all African American, European American, and Hispanic American patients with DNA available at the time of the present study (n=517) with controls from the Dallas Heart Study. The DPLS is a biobank of Hispanic children recruited from pediatric liver clinics at UT Southwestern and Parkland Health and Hospital System, Dallas, and from an obesity clinic at Children's Medical Center, Dallas. Clinical information was extracted from medical records by a trained technician. As more than 95% of the patients were Hispanic Americans, we only included Hispanic American patients and controls in the present study (n=205 patients and 234 controls).

Clinical Measurements and Chronic Liver Disease Definitions in the Discovery Cohort Clinical laboratory measurements for ALT and AST were extracted from EHRs of participants from the GHS discovery cohort and bariatric surgery cohort. Median ALT and AST values were calculated for all participants with two or more measurements, and were $\log_{10}$-transformed to normalize the distribution prior to association analyses.

International Classification of Diseases, Ninth Revision (ICD-9) disease diagnosis codes were extracted from EHRs and collapsed into clinical disease categories for non-viral, nonalcoholic (ICD-9 571.40, 571.41, 571.49, 571.5, 571.8, 571.9) or alcoholic (ICD-9 571.0, 571.1, 571.2, 571.3) liver disease case definitions. Additional case definitions based on single diagnosis codes included: alcoholic cirrhosis (ICD-9 571.2), nonalcoholic cirrhosis (ICD-9 571.5), and HCC (ICD-9 155.0). For these case definitions, a common control group without liver disease ("no liver disease") was defined as participants with no case criteria or single-encounter or problem-list diagnosis code indicating any type of liver disease.

Liver Histopathologic Phenotype Definitions in the Bariatric Surgery Cohort

The GHS bariatric surgery cohort consisted of 2,644 individuals of European descent. Wedge biopsies of the liver were obtained intraoperatively during bariatric surgery from 2,391 of these individuals. The biopsies were consistently obtained 10 cm to the left of falciform ligament prior to any liver retraction or surgery on the stomach. The biopsy was divided into sections, with the primary section delivered to the clinical pathologists for liver histology (fixed in 10% neutral buffered formalin and stained with hematoxylin and eosin for routine histology and Masson's trichrome for assessment of fibrosis) and remaining sections stored within a research biobank (frozen in RNAlater and/or liquid nitrogen). Liver histology was conducted by an experienced pathologist and subsequently re-reviewed by a second experienced pathologist using the NASH Clinical Research Network scoring system (Kleiner et al., Hepatology, 2005, 41, 1313-21, herein incorporated by reference in its entirety for all purposes) as follows: steatosis grade 0 (<5% parenchymal involvement), 1 (5 to <33%), 2 (34 to <66%), and 3 (>67%); lobular inflammation grade 0 (no foci), grade 1 (mild, <2 foci per 200× field), grade 2 (moderate, 2-4 foci per 200× field), grade 3 (severe,>4 foci per 200× field); fibrosis Stage 0 (none), Stage 1 (perisinusoidal or periportal fibrosis), Stage 2 (perisinusoidal and periportal fibrosis), Stage 3 (bridging fibrosis), and Stage 4 (cirrhosis). These histologic diagnoses were used to defined the following phenotypes: 1) Normal: no evidence of steatosis, NASH, or fibrosis; 2) Simple steatosis: Steatosis (regardless of grade) with no evidence of NASH or fibrosis; 3) NASH: Any presence of lobular inflammation or hepatocyte ballooning (regardless of grade), or any presence of fibrosis (regardless of stage); 4) Fibrosis: Any presence of fibrosis (regardless of stage).

Sample Preparation, Sequencing, and Genotyping

DNA sample preparation and whole exome sequencing for the participants in the DiscovEHR study, the Dallas Heart Study, and the Penn Medicine Biobank were performed at the Regeneron Genetics (Dewey et al., *Science* In Press, 2016, herein incorporated by reference in its entirety for all purposes). HSD17B13 rs72613567 was genotyped by Taqman assay (and verified by Sanger sequencing in 5 individuals of each genotype) in the Dallas Liver Study and Dallas Pediatric Liver Study.

In particular, exome capture was performed using NimbleGen probes according to the manufacturer's recommended protocol (Roche NimbleGen). The captured DNA was PCR amplified and quantified by qRT-PCR (Kapa Biosystems). The multiplexed samples were sequenced using 75 bp paired-end sequencing on an Illumina v4 HiSeq 2500 to a coverage depth sufficient to provide greater than 20× haploid read depth of over 85% of targeted bases in 96% of samples (approximately 80× mean haploid read depth of targeted bases). Raw sequence data from each Illumina Hiseq 2500 run were uploaded to the DNAnexus platform (Reid et al., *BMC Bioinformatics*, 2014, 15, 30, herein incorporated by reference in its entirety for all purposes) for sequence read alignment and variant identification. In brief, raw sequence data were converted from BCL files to sample-specific FASTQ-files, which were aligned to the human reference build GRCh37.p13 with BWA-mem (Li et al., *Bioinformatics*, 2009, 25, 1754-60, herein incorporated by reference in its entirety for all purposes). Single nucleotide variants (SNV) and insertion/deletion (indel) sequence variants were identified using the Genome Analysis Toolkit (McKenna et al., *Genome Res.*, 2010, 20, 1297-303, herein incorporated by reference in its entirety for all purposes).

Exome-Wide Association Analysis of Liver Enzymes and Chronic Liver Disease Phenotypes We used linear mixed models to test 502,219 biallelic variants that had missing data rate of <1%, Hardy-Weinberg equilibrium P-value>$1.0\times10^{-6}$, and minor allele frequency>0.1% for association with transaminase levels. For variants with exome wide significant associations with transaminases (p<$1\times10^{-7}$) in the GHS discovery cohort, we performed association analyses and meta-analysis, in the European-ancestry replication studies described above. We used a Bonferroni significance threshold determined by the number of variants tested to define replicated associations. Meta-analysis of discovery and replication studies was also performed. All P-values reported in the text correspond to the allelic model.

We subsequently tested transaminase-associated single nucleotide variants for associations with chronic liver disease phenotypes. We used a Bonferroni significance threshold determined by the number of variants and broad chronic liver disease categories tested to determine significance of associations. We further tested replicated novel variants for association with histopathologically defined liver phenotypes from the GHS bariatric surgery cohort. We also performed a phenome-wide study of associations of replicated novel variants with 405 quantitative clinical measurements and 3,168 clinical diagnoses.

In particular, we tested 502,219 biallelic variants with missing data rate<1%, Hardy-Weinberg equilibrium P-value>$1.0\times10^{-6}$, and minor allele frequency>0.1% for association with transaminase levels. $Log_{10}$-transformed median ALT and AST were adjusted for age, age$^2$, sex, BMI, and the first four principal components of ancestry. To account for relatedness among study participants, we also fit a genetic relatedness matrix as a random-effects covariate. Both principal components and the genetic relatedness matrix were constructed from 39,858 non-MHC markers in approximate linkage equilibrium and with minor allele frequency>0.1%. We used linear mixed models as implemented in the GCTA package (Yang et al., *Am. J. Hum. Genet.*, 2011, 88, 76-82, herein incorporated by reference in its entirety for all purposes) to test for association between trait residuals and single nucleotide variants. All P-values reported in the text correspond to the allelic model.

We attempted to replicate associations in the GHS discovery cohort in three separate European-ancestry cohorts: the GHS bariatric surgery cohort, the Dallas Heart Study, and the Penn Medicine Biobank (described above). ALT and AST measures from the GHS bariatric surgery cohort and from Penn Medicine Biobank were login-transformed and adjusted for age, age$^2$, sex, BMI, and the first four principal components of ancestry. Genetic relatedness matrices were included as random-effects covariates, and analysis was performed using linear mixed models in GCTA. In the Dallas Heart study, $log_{10}$-transformed ALT and AST measures were adjusted for age, age$^2$, sex, BMI, and the first ten principal components of ancestry, and analysis was performed using linear regression implemented in PLINK. Summary statistics for the three replication cohorts were meta-analyzed using METAL (Willer et al., *Bioinformatics*, 2010, 26, 2190-1, herein incorporated by reference in its entirety for all purposes) (replication meta-analysis). Summary statistics for the discovery cohort and the three replication cohorts were meta-analyzed similarly (joint meta-analysis).

Association Analysis with Chronic Liver Disease Phenotypes

We analyzed thirteen significant and replicated single nucleotide variants from the liver enzyme ExWAS for associations with chronic liver disease phenotypes defined from the GHS discovery cohort, as described above. We used a Bonferroni significance threshold of P<0.05/26 (P<$1.92\times10^{-3}$) to account for the thirteen variants and two broad chronic liver disease categories (alcoholic and non-alcoholic) tested. The HSD17B13 rs72613567 variant was further tested for association with histopathologically defined liver phenotypes from the GHS bariatric surgery cohort, as described above. Odds ratios were estimated with the use of Firth's penalized likelihood method of logistic regression after adjustment for age, age$^2$, sex, BMI, and the first four principal components of ancestry. Genotypic odds ratios were estimated for HSD17B13 rs72613567 using the same covariates.

Odds ratios for liver disease in the DLS were estimated by logistic regression, adjusted for age, age$^2$, sex, body mass index, and self-reported ethnicity. Participants from the Dallas Heart Study with available rs72613567 genotypes were used as normal controls (n=4,279). Odds ratios in the DPLS were estimated by logistic regression.

Phenome-Wide Association Study of HSD17B13 rs72613567

We performed a phenome-wide study of associations of HSD17B13 rs72613567 with 405 quantitative EHR-derived anthropometric, vital sign, laboratory, electrocardiographic, echocardiographic, and bone densitometry measurements, and also with 3,168 EHR-derived clinical diagnoses. Median laboratory values for individuals with serial outpatient measures were calculated following removal of likely spurious values that were >3 standard deviations from the intraindividual median value; maximum and minimum values were also calculated. We then calculated trait residuals for all laboratory traits after adjustment for age, age$^2$, sex, and the first ten principal components of ancestry, and applied appropriate transformations prior to association analysis. ICD-9 based diagnosis codes were collapsed to hierarchical clinical disease groups and corresponding controls using a modified version of the groupings proposed by Denny et al (Denny et al., *Nature Biotechnology*, 2013, 31, 1102-10 and Denny et al., *Bioinformatics*, 2010, 26, 1205-10, each of which is herein incorporated by reference in its entirety for all purposes). ICD-9 based diagnoses required one or more of the following: a problem list entry of the diagnosis code or an encounter diagnosis code entered for two separate clinical encounters on separate calendar days.

Analyses of association with transformed quantitative clinical measurement residuals were performed using linear regression, and analyses of association with clinical diagnoses were performed using logistic regression adjusted for age, age$^2$, sex, and the first four principal components. Alleles were coded using both additive (0 for reference allele homozygotes, 1 for heterozygotes, and 2 for alternative allele homozygotes) and recessive (0 for reference allele homozygotes and heterozygotes, 1 for alternative allele homozygotes) models.

Software

Genetic association analyses were performed using GCTA software, version 1.25.07 and PLINK, version 1.9.0. Quantile-quantile and Manhattan plots were generated using R software, version 3.2.1 (R Project for Statistical Computing). Regional association plots were generated using LocusZoom (Pruim et al., *Bioinformatics*, 2010, 26, 2336-7, herein incorporated by reference in its entirety for all purposes).

RNA Sequencing Studies

RNA quality and concentration was evaluated by running total RNA on an Agilent RNA Nano Bioanalyzer chip; all samples had an RNA integrity number (RIN) greater than 8. Polyadenlylated RNA transcripts were isolated using two rounds of enrichment with oligo(dT)25 beads (Thermo Fisher Scientific). Samples were purified and concentrated with RNAclean XP beads (Beckman Coulter) and heat-fragmented to approximately 140 base pairs. First-strand synthesis was completed with SuperScript III reverse transcriptase (Thermo Fisher Scientific) using random hexamers; dTTP was replaced with dUTP during second-strand synthesis. Samples were processed according to our standard DNA library preparation method referenced above for exomes with the addition of a uracil DNA-glycosylase step to generate strand-specific sequencing libraries.

Identification and Validation of Novel HSD17B13 Transcripts

Reads were mapped to the Human.B38 using ArrayStudio® software (OmicSoft®, Cary, N.C.) allowing two mismatches. Two approaches were employed to identify novel HSD17B13 transcripts. Novel exon junctions were discovered based on Gencode v24 using ArrayStudio. De novo transcript assembly was carried out using Trinity (v2.2.0) in default setting. Custom gene models were built to incorporate novel transcripts of HSD17B13, and transcript quantification was estimated by read alignment to the custom gene model. Protein sequence alignment of all identified HSD17B13 isoforms is shown in FIGS. 7A and 7B. RT-PCR was performed on total RNA from human liver samples was performed using the SuperScript™ One-Step RT-PCR System with Platinum™ Taq DNA Polymerase (Thermo Fisher). Each 50 µL RT-PCR reaction contained 1× Reaction Mix, 500 nM each forward and reverse primers (PST516: ATGAACATCATCCTAGAAATCCTTC (SEQ ID NO: 251) and PST517: ATCATGCATACATCTCTGGCTGGAG (SEQ ID NO: 252)), 1 µL of RT/Platinum Taq, and 75 ng RNA. Cycling conditions were: one cycle of 45° C. for 30 minutes; one cycle of 94° C. for 2 minutes; 40 cycles of 94° C. for 20 seconds, 53° C. for 30 seconds, and 72° C. for 90 seconds; one cycle of 72° C. for 5 minutes; then a 10° C. hold. Products were purified using the QIAquick PCR Purification Kit (Qiagen) and submitted for direct Sanger sequencing using the primer DE002 (ATCAGAACTTCA-GGCCTTGG (SEQ ID NO: 253)). To identify the B and C transcripts, the RT-PCR products were run out on a 2% agarose gel stained with SYBR GoldSYBR® Gold Nucleic Acid Gel Stain (ThermoFisher), and bands of the expected molecular weight were excised and purified using the QIA-quick Gel Extraction Kit (Qiagen), then subjected to cloning with the TOPO® TA Cloning Kit (ThermoFisher). Sequencing of the TOPO clones was performed using M13F and M13R sequencing primers. Sequence analysis was performed using the Sequencher DNA analysis software (Gene Codes Corporation). Full-length HSD17B13 transcripts were amplified directly from 50 ng of total RNA with the SuperScript III One-step RT-PCR System with Platinum Taq High Fidelity (ThermoFisher Scientific) using gene-specific primers in the first (GCAAAGCCATGAACATCATCC (SEQ ID NO: 254)) and last exons (TCTTGATG-TAGTGGGAGTCGGATT (SEQ ID NO: 255)) to generate an amplicon of about 2.2 kb (maximum predicted size transcript). Amplicons were verified on an Agilent Bioanalyzer. PacBio-compatible barcoded adapters were ligated to the amplicons and cleaned with PacBio PB beads (Pacific Biosciences). Libraries were pooled in equal amounts and sequenced on one SMRT cell for 180 minutes on the PacBio RSII platform. The data was demultiplexed using PacBio software smrtanalysis v2.3 tool labelzmw and then analyzed with ConsensusTools AmpliconAnalysis. Resulting amplicons were compared to HSD17B13 RefSeq genes to determine isoform and genotype status.

Subcellular Localization of HSD17B13 Isoforms

HepG2 cells were cultured in Eagle's Minimum Essential Medium supplemented with 10% fetal bovine serum. HSD17B13 transcripts A and D were sub-cloned into Myc-DDK backbone lentivirus constructs, and lentivirus were generated. HepG2 cells were infected with lentivirus carrying the HSD17B13 transcripts. Stable cell lines expressing each HSD17B13 transcript were selected with 1-3 mg/ml Geneticin G-418 sulfate in complete culture medium for two weeks. Following fixation, HSD17B13 isoforms were detected with mouse anti-Myc antibody. Lipid droplets were labeled with BODIPY FL dye (Sigma). Secondary antibodies for immunofluorescence were Alexa Fluor 488 donkey anti-rabbit IgG and Alexa Fluor 594 donkey anti-mouse IgG (Jackson ImmunoResearch).

Quantification of HSD171B3 Protein Expression in Human Liver Biopsy Tissue and Stable Cell Lines Human liver and cell pellet samples were homogenized in ice-cold 1×RIPA lysis buffer (EMD Millipore) in the presence of protease and phosphatase inhibitor mixtures (ThermoFisher). Supernatant was collected and used for protein concentration using BCA protein assay (ThermoFisher). Human tissue and cell lysates were loaded and separated on SDS/PAGE gels (Bio-Rad) and transferred to PVDF membranes (Bio-Rad). The membranes were blocked for 1 hour with 5% (wt/vol) milk in 1×TBS supplemented with 0.1% Tween20 (Bio-Rad). Membranes were incubated with antibody at 4° C. overnight against HSD17B13 (1:200, Thermo- Fisher) and B-Actin (1:500, Cell Signaling Technology). Bound antibody was detected using HRP-conjugated anti-rabbit antibody (1:10,000, Jackson ImmunoResearch) and enhanced using chemi-luminescence reagent (Thermo-Fisher). Band intensities were quantified using Image J software.

Real-Time Semi-Quantitative PCR

RNA was extracted from cell using TRIzol® (Invitrogen, Carlsbad, Calif.). First-strand cDNA was synthesized using Superscript III RT (Invitrogen) and utilized for Semi-Quantitative PCR based on intron-spanning primers. A QuantStudio 6 Flex Real-Time PCR System was used to measure the expression level of transcripts. Primers of HSD17B13 and TBP were ordered from IDT (Integrated DNA Technologies). Relative gene expression was analyzed with the $\Delta\Delta$Ct method, providing a fold-change of expression normalized to the house-keeping gene TBP ($\Delta$Ct).

Lipid Droplet Isolation and Characterization by Western Blotting

Lipid droplets were prepared from HepG2 cells stably expressing HSD17B13 transcript A (IsoA) or transcript D (IsoD) as previously reported (Brasaemle D L, Wolins N E. Isolation of lipid droplets from cells by density gradient centrifugation, Current protocols in cell biology 2006; Chapter 3:Unit 3 15 and Ding et al., Nature Protocols, 2013, 8, 43-51, each of which is herein incorporated by reference in its entirety for all purposes). In brief, HepG2 cells stably expressing HSD17B13 IsoA, IsoD, or the parental line were incubated overnight with 1 mM oleic acid. The following lipid loading, cells were scraped and resuspended in hypotonic lysis buffer (20 mM Tris, pH 7.5, 1 mM EDTA) supplemented with 1× Halt™ protease/phosphatase inhibitors (Thermo) and lysed by cavitation at 50 bar for 8 minutes. Lysates were centrifuged at 1000 g/4° C. for 10 minutes, and the post-nuclear supernatant (PNS) was mixed with sucrose to a final volume of 2 mL and concentration of 20% in ultracentrifuge tubes. Then 1.5 mL of 5% sucrose and another 1.5 mL of hypotonic lysis buffer was layered on top of the lysate. Tubes were centrifuged at 182,000 g/4° C. for 40 minutes, and the lipid droplet (LD) layers were transferred to new tubes. The remaining volume in the tube was aspirated, and the pelleted (total membrane, TM) was resuspended in 0.5 mL hypotonic lysis buffer. The PNS, LD, and TM fractions were mixed with 1× radioimmunoprecipitation (RIPA) buffer (EMD)+NuPAGE™ LDS Sample Buffer (Thermo) and β-mercaptoethanol and sonicated for 3 hours at 37° C. The TM lysate was diluted 2.5-fold to normalize to the PNS. Lysates were run on 4-20% SDS-PAGE gels (Biorad), transferred using the Trans-Blot (Biorad) onto low fluorescence PVDF membranes, and blocked for 1 hour in Odyssey TBS Blocking Buffer. Membranes were incubated overnight with the following antibodies: a-HSD17B13 (Abgent, cat # AP5729a 1:500); LD marker: α-ADRP (Proteintech, 152-94-1-AP, 1:2500); LD marker: a-TIP47 (Proteintech, 10694 1:2000); lysosome marker: α-LAMP1 (Novus, NBP2-25183, 1:1000); cytosolic marker: α-GAPDH (Proteintech, 60004-1-Ig, 1:2000); endoplasmic reticulum marker: α-calreticulin (Abcam, ab92516, 1:1000); mitochondrial marker: α-COX IV (Abcam, ab33985, 1:500); cytoskeleton marker: α-actin (Sigma, A5441, 1:4000). The next day membranes were washed 4 times with Tris-buffered saline+0.1% Tween, then incubated for 1 hour at room temperature with blocking buffer containing IRDye® α-rabbit (800CW) and α-mouse (680RD) secondary antibodies (Li-Cor) at 1:5,000 and 1:10,000 dilutions, respectively. Gels were washed again with TBST and imaged using the Odyssey.

Quantification of Intracellular Triglyceride Content

The triglyceride (TG) content from the stable cells was determined using a TG quantification kit (Abcam). In the assay, TG are converted to free fatty acids and glycerol. The glycerol is then oxidized to generate a product which is quantified (spectrophotometry at $\lambda$=570 nm).

Substrate Screening of Steroid and Bioactive Lipid Libraries Against Purified Recombinant HSD17B13

Reactions were performed in a final volume of 40 µL of assay buffer (0.2 M Tris-HCl, pH 7.5) which contained 500 µM $NAD^{\pm}$, 5 µM bioactive lipid or 50 µM steroid (all in a final concentration of 5% DMSO), and 100 ng recombinant human HSD17B13. Reactions were incubated for 3 hours, at 23° C., after which an equal volume NADH-Glo Detection Reagent (Promega) was added. Following a 1 hour incubation at 23° C., the relative light units (RLUs) were measured on an Envision Plate Reader (Perkin Elmer). Raw RLU values were normalized as percent of control (50 µM estradiol) following subtraction of negative control (5% DMSO) using the following formula: Percent of control (POC)= 100×(Sample (RLU)−Negative CTRLaverage)/(Positive CTRLaverage−Negative CTRLaverage).

In Vitro and Cellular Characterization of HSD17B13 Enzymatic Activity

Recombinant human HSD17B13 protein was purified from E. coli (Genscript) transformed with plasmid DNA harboring HSD17B13 transcript A or transcript D. The HSD17B13 variants contained a 10× His tag at the C terminus and were purified from soluble fraction using a $Ni2^+$ affinity purification. Enzymatic activity was determined through measurement of NADH production using the NAD(P)H-Glo Detection System (Promega). Reactions were performed for 3 hours at 25° C. in 0.2 M Tris-HCl, pH 7.5, 0.5 mM $NAD^+$, 75 µM of substrate (Sigma) and 500 ng purified enzyme in a final volume of 100 µL. After incubation, 20 µL of the reaction was combined with 20 µL luciferase reagent (Promega), incubated at room temperature for 1 hour and read on an Envision Plate Reader (Perkin Elmer).

HEK293 cells overexpressing HSD17B13 transcript A, transcript D or green fluorescent protein (GFP, control) were used to investigate the activity of HSD17B13 against estradiol in a cell-based assay. Estradiol (1 µM) was fed to each cell type. After 48 hours, the media was collected and the concentration of estradiol and its converted product estrone were identified and quantified by LC-MS.

Association of Exonic Variants with Aspartate and Alanine Aminotransferases

Figure 1B:
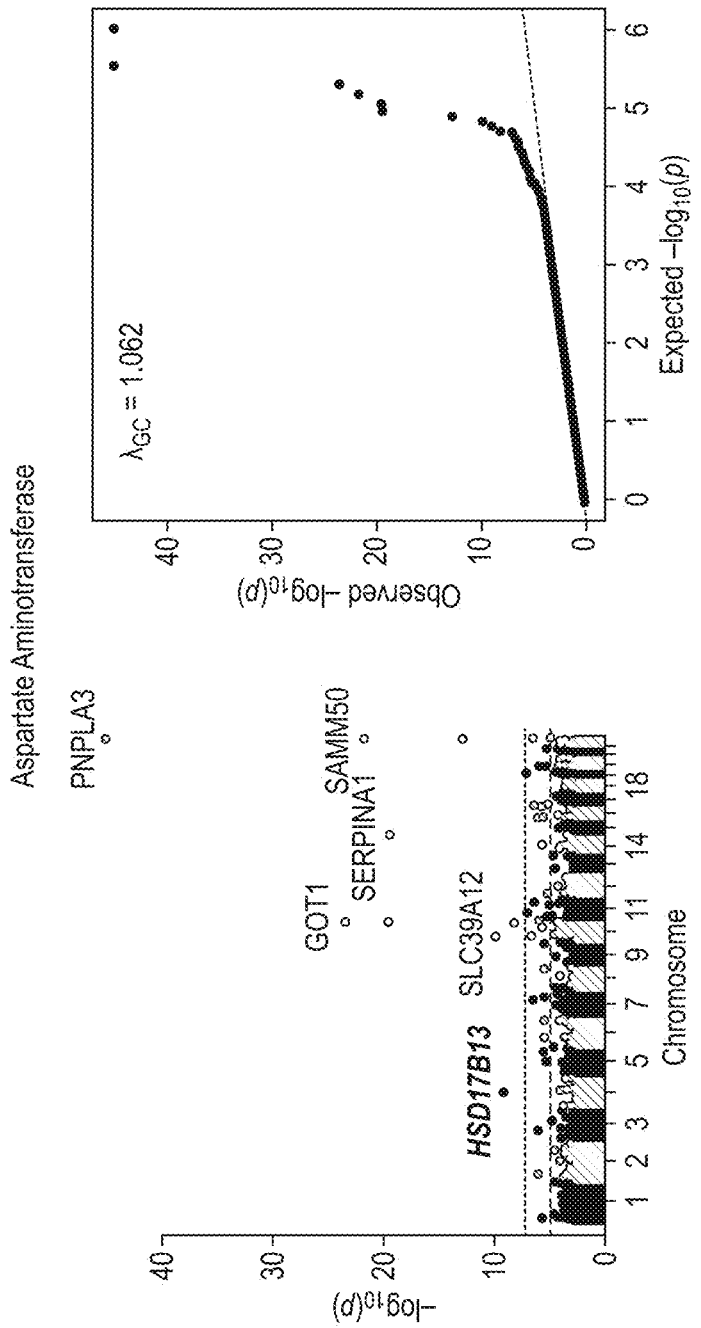

We tested 502,219 biallelic single genetic variants for association with serum ALT or AST levels in 46,544 individuals of European descent from the DiscovEHR study ("GHS discovery cohort"; basic demographics in Table 6). A total of 35 variants in 19 genes were found to be associated with ALT or AST at $P<1.0\times10^{-7}$ (FIGS. 1A and 1B, and Table 7). We performed replication studies in three cohorts of European-ancestry individuals: 1) bariatric surgery patients (n=2,644) from DiscovEHR ("GHS bariatric surgery cohort"); 2) 1,357 individuals from the Dallas Heart Study; and 3) 8,526 individuals from the Penn Medicine Biobank. In meta-analysis of the replication cohorts, thirteen variants in nine genes were significantly associated with serum levels of ALT or AST (Bonferroni significance threshold of $P<1.43\times10^{-3}$ for 35 variants tested, Table 8). These included variants that were previously reported to be associated with elevated transaminase levels, such as PNPLA37, TM6SF211, SERPINA122, SAMM5023, and ERLIN124. SERPINA1 encodes alpha-1-antitrypsin, whose functional deficiency causes liver disease; the association with SAMM50 is mediated via linkage disequilibrium with variation in PNPLA3, and ERLIN1 has been implicated in liver fat deposition. We also identified variants that were not previously reported to be associated with liver disease. These included several variants in GPT and GOT1, the genes encoding ALT and AST, respectively, and SLC39A12, which encodes solute carrier family 39 member 12.

We also identified a reproducible association between a variant in HSD17B13, the gene encoding hydroxysteroid 17-beta dehydrogenase 13, an uncharacterized member of the 17-beta hydroxysteroid dehydrogenase family, and decreased levels of ALT (discovery P=$4.2 \times 10^{-12}$, replication P=$1.7 \times 10^{-4}$) and AST (discovery P=$6.2 \times 10^{-10}$, replication P=$1.7 \times 10^{-4}$, Table 8). The associated variant, rs72613567, is an insertion of an adenine adjacent to the donor splice site of exon six (TA allele), and had an allele frequency of 26.0% in the GHS discovery cohort. Previously, Chambers et al. identified a nearby locus at 4q22 (rs6834314) associated with ALT levels (Chambers et al., *Nat. Genet.*, 2011, 43, 1131-1138, doi:10.1038/ng.970, herein incorporated by reference in its entirety for all purposes); rs72613567 has not heretofore been reported to be associated with transaminase levels. HSD17B13 is 30 kb upstream of HSD17B11, another member of the same gene family. We did not observe exome-wide significant associations between coding or splice variants in HSD17B11 and transaminase levels in the discovery cohort (FIGS. 5A and 5B) or in the joint meta-analysis of the discovery cohort and three replication cohorts. Furthermore, linkage disequilibrium of rs72613567 with variants in HSD17B11 was modest across all ancestry groups ($r^2 < 0.4$ with all ascertained variants in HSD17B11 in all ancestry groups). Collectively, these findings suggest HSD17B13 as the gene in the genomic region that is most likely to be functionally related to transaminase levels.

TABLE 6

Demographics and clinical characteristics of sequenced European-ancestry individuals from the discovery and replication cohorts.

| Characteristic | Discovery Cohort (N = 46,544) | Bariatric Surgery Cohort (N = 2,644) | Dallas Heart Study (N = 1,357) | Penn Medicine Biobank (N = 8,526) |
|---|---|---|---|---|
| Age (years) - median (IQR) | 62.9 (49.6-73.8) | 52.9 (44.1-61.2) | 46.0 (38.0-54.0) | 68.0 (60.0-76.0) |
| Female sex - number (%) | 26,875 (57.7) | 2,119 (80.1) | 724 (53.4) | 3,242 (38.0) |
| Body mass index - median (IQR) | 29.9 (35.4-44.8) | 47.4 (42.0-53.7) | 28 (25-32) | 30 (25-32) |
| Transaminase level (U/L) - median (IQR) | | | | |
| Alanine aminotransferase (ALT) | 22.0 (17.0-29.0) | 23.0 (17.5-29.5) | 20.0 (15.0-27.0) | 22.0 (17.0-30.0) |
| Aspartate aminotransferase (AST) | 23.0 (20.0-27.5) | 23.0 (20.0-27.0) | 21.0 (18.0-25.0) | 24.0 (20.0-30.5) |
| Presence of liver disease (by ICD-9 code) - N (%) | | | | |
| Alcoholic liver disease | 197 (0.4) | 7 (0.3) | — | — |
| Alcoholic cirrhosis | 130 (0.3) | 3 (0.1) | — | — |
| Nonalcoholic, non-viral liver disease | 1,938 (4.2) | 1,543 (58.4) | — | — |
| Nonalcoholic cirrhosis | 382 (0.8) | 24 (0.9) | — | — |
| Hepatocellular carcinoma | 76 (0.2) | 1 (0.04) | — | — |
| No liver disease | 30,628 (65.8) | 1 (0.04) | — | — |

TABLE 7

Single nucleotide variants associated with serum transaminase levels at P < $1.0 \times 10^{-7}$ in the discovery cohort.

| Trait | CHR | BP | REF | ALT | rsID | Gene | Annotation | AA Substitution | Beta (SE) |
|---|---|---|---|---|---|---|---|---|---|
| ALT | 1 | 220970028 | A | G | rs2642438 | MARC1 | missense | p.Thr165Ala | 0.008 (0.001) |
| | 4 | 88231392 | T | TA | *rs72613567 | HSD17B13 | splice donor | | −0.009 (0.001) |
| | 8 | 144997604 | C | T | rs371119003 | PLEC | missense | p.Ala2302Thr | −0.160 (0.026) |
| | 8 | 145008502 | G | A | | PLEC | missense | p.Arg522Cys | −0.268 (0.032) |
| | 8 | 145692918 | G | A | rs35968570 | KIFC2 | missense | p.Glu174Lys | −0.033 (0.005) |
| | 8 | 145730072 | G | A | rs143408057 | GPT | missense | p.Arg83His | −0.314 (0.036) |
| | 8 | 145730161 | C | T | rs201815297 | GPT | missense | p.Ala87Val | −0.224 (0.014) |
| | 8 | 145730221 | G | A | rs112574791 | GPT | missense | p.Arg107Lys | −0.033 (0.005) |
| | 8 | 145731636 | T | G | rs145155876 | GPT | stop gained | p.Tyr326* | −0.235 (0.031) |
| | 8 | 145732114 | G | C | rs141505249 | GPT | missense | p.Glu430Gln | −0.224 (0.013) |

TABLE 7-continued

Single nucleotide variants associated with serum transaminase levels at $P < 1.0 \times 10^{-7}$ in the discovery cohort.

| Trait | CHR | BP | REF | ALT | rsID | Gene | Effect | Protein | Beta (SE) |
|---|---|---|---|---|---|---|---|---|---|
| | 8 | 145732151 | G | A | rs143462595 | GPT | missense | p.Arg442His | −0.077 (0.013) |
| | 8 | 145732180 | G | C | rs147998249 | GPT | missense | p.Val452Leu | −0.225 (0.013) |
| | 8 | 145732305 | G | GC | | GPT | frameshift | p.Glu475fs | −0.271 (0.031) |
| | 8 | 145748532 | A | G | rs567402720 | LRRC24 | missense | p.Leu290Ser | −0.185 (0.028) |
| | 9 | 117122202 | C | T | rs3748177 | AKNA | synonymous | p.Glu755Glu | −0.007 (0.001) |
| | 9 | 117124731 | G | A | rs3748176 | AKNA | missense | p.Pro624Leu | −0.007 (0.001) |
| | 10 | 101595996 | T | A | rs17222723 | ABCC2 | missense | p.Val1188Glu | −0.015 (0.003) |
| | 10 | 101606861 | G | T | rs1137968 | ABCC2 | synonymous | p.Val1430Val | −0.015 (0.003) |
| | 10 | 101610533 | C | T | rs8187707 | ABCC2 | synonymous | p.His1496His | −0.015 (0.003) |
| | 10 | 101611294 | G | A | rs8187710 | ABCC2 | missense | p.Cys1515Tyr | −0.015 (0.003) |
| | 10 | 101912064 | T | C | *rs2862954 | ERLIN1 | missense | p.Ile291Val | −0.012 (0.001) |
| | 10 | 101977883 | C | T | rs2230804 | CHUK | missense | p.Val268Ile | −0.009 (0.001) |
| | 10 | 113917085 | T | A | rs2254537 | GPAM | synonymous | p.Pro681Pro | −0.008 (0.001) |
| | 10 | 113940329 | T | C | rs2792751 | GPAM | missense | p.Ile43Val | −0.008 (0.001) |
| | 14 | 94844947 | C | T | *rs28929474 | SERPINA1 | missense | p.Glu366Lys | 0.042 (0.005) |
| | 19 | 19379549 | C | T | *rs58542926 | TM6SF2 | missense | p.Glu167Lys | 0.014 (0.002) |
| | 22 | 44324727 | C | G | *rs738409 | PNPLA3 | missense | p.Ile148Met | 0.023 (0.002) |
| | 22 | 44324730 | C | T | *rs738408 | PNPLA3 | synonymous | p.Pro149Pro | 0.023 (0.002) |
| | 22 | 44342116 | A | G | rs2294918 | PNPLA3 | missense | p.Lys434Glu | 0.007 (0.001) |
| | 22 | 44368122 | A | G | *rs3761472 | SAMM50 | missense | p.Asp110Gly | 0.019 (0.002) |
| | 22 | 44395451 | T | C | *rs1007863 | PARVB | missense | p.Trp37Arg | 0.011 (0.001) |
| AST | 4 | 88231392 | T | TA | *rs72613567 | HSD17B13 | splice donor | | −0.005 (0.001) |
| | 10 | 18242311 | A | G | rs10764176 | SLC39A12 | missense | p.Ser36Gly | −0.006 (0.001) |
| | 10 | 101157378 | CGTT | C | | GOT1 | inframe indel | p.Asn389del | −0.221 (0.024) |
| | 10 | 101165533 | G | C | rs374966349 | GOT1 | missense | p.Gln208Glu | 0.271 (0.027) |
| | 10 | 101912064 | T | C | *rs2862954 | ERLIN1 | missense | p.Ile291Val | −0.005 (0.001) |
| | 11 | 22271870 | A | T | rs7481951 | ANO5 | missense | p.Leu322Phe | 0.004 (0.001) |
| | 14 | 94844947 | C | T | *rs28929474 | SERPINA1 | missense | p.Glu366Lys | 0.027 (0.003) |
| | 19 | 19379549 | C | T | *rs58542926 | TM6SF2 | missense | p.Glu167Lys | 0.008 (0.002) |
| | 22 | 44324727 | C | G | *rs738409 | PNPLA3 | missense | p.Ile148Met | 0.014 (0.001) |
| | 22 | 44324730 | C | T | *rs738408 | PNPLA3 | synonymous | p.Pro149Pro | 0.014 (0.001) |
| | 22 | 44368122 | A | G | *rs3761472 | SAMM50 | missense | p.Asp110Gly | 0.011 (0.001) |
| | 22 | 44395451 | T | C | *rs1007863 | PARVB | missense | p.Trp37Arg | 0.006 (0.001) |

| Trait | CHR | BP | REF | ALT | P | AAF | N | N REF/REF | N REF/ALT | N ALT/ALT | Mean AST or ALT level (U/L) REF/REF | Mean REF/ALT | Mean ALT/ALT |
|---|---|---|---|---|---|---|---|---|---|---|---|---|---|
| ALT | 1 | 220970028 | A | G | 4.67E−08 | 0.7067 | 41,414 | 3,515 | 17,262 | 20,637 | 23.88 | 24.52 | 24.92 |
| | 4 | 88231392 | T | TA | 4.16E−12 | 0.2634 | 41,414 | 22,441 | 16,130 | 2,843 | 25.02 | 24.26 | 24.1 |
| | 8 | 144997604 | C | T | 1.30E−09 | 0.0005 | 41,413 | 41,373 | 40 | 0 | 24.67 | 18.1 | NA |
| | 8 | 145008502 | G | A | 3.26E−17 | 0.0003 | 41,414 | 41,387 | 27 | 0 | 24.67 | 13.8 | NA |
| | 8 | 145692918 | G | A | 1.40E−11 | 0.0139 | 41,414 | 40,271 | 1,133 | 10 | 24.67 | 12.07 | NA |

TABLE 7-continued

Single nucleotide variants associated with serum transaminase levels at $P < 1.0 \times 10^{-7}$ in the discovery cohort.

|     | 8  | 145730072 | G    | A  | 3.28E-18 | 0.0003 | 41,414 | 41,393 | 21     | 0      | 24.67 | 12.07 | NA    |
|-----|----|-----------|------|----|----------|--------|--------|--------|--------|--------|-------|-------|-------|
|     | 8  | 145730161 | C    | T  | 6.28E-59 | 0.0018 | 41,414 | 41,270 | 144    | 0      | 24.7  | 14.68 | NA    |
|     | 8  | 145730221 | G    | A  | 4.25E-11 | 0.0136 | 41,414 | 40,293 | 1,111  | 10     | 24.71 | 23.09 | 18.35 |
|     | 8  | 145731636 | T    | G  | 1.76E-14 | 0.0004 | 41,394 | 41,364 | 30     | 0      | 24.67 | 14.07 | NA    |
|     | 8  | 145732114 | G    | C  | 8.84E-64 | 0.0019 | 41,375 | 41,223 | 150    | 2      | 24.7  | 14.48 | 13.75 |
|     | 8  | 145732151 | G    | A  | 1.18E-09 | 0.0021 | 41,406 | 41,232 | 174    | 0      | 24.68 | 20.87 | NA    |
|     | 8  | 145732180 | G    | C  | 8.19E-65 | 0.0019 | 41,413 | 41,254 | 159    | 0      | 24.7  | 14.74 | NA    |
|     | 8  | 145732305 | G    | GC | 1.00E-18 | 0.0004 | 41,414 | 41,385 | 29     | 0      | 24.67 | 14.24 | NA    |
|     | 8  | 145748532 | A    | G  | 3.42E-11 | 0.0004 | 41,393 | 41,358 | 35     | 0      | 24.67 | 17.71 | NA    |
|     | 9  | 117122202 | C    | T  | 9.51E-09 | 0.5232 | 41,414 | 9,414  | 20,645 | 11,355 | 25.12 | 24.72 | 24.18 |
|     | 9  | 117124731 | G    | A  | 4.31E-09 | 0.5230 | 41,412 | 9,427  | 20,634 | 11,351 | 25.12 | 24.73 | 24.17 |
|     | 10 | 101595996 | T    | A  | 2.97E-08 | 0.0608 | 41,414 | 36,543 | 4,704  | 167    | 24.77 | 23.97 | 22.12 |
|     | 10 | 101606861 | G    | T  | 2.71E-08 | 0.0608 | 41,414 | 36,543 | 4,704  | 167    | 24.77 | 23.97 | 22.04 |
|     | 10 | 101610533 | C    | T  | 2.77E-08 | 0.0608 | 41,414 | 36,542 | 4,706  | 166    | 24.77 | 23.97 | 22.03 |
|     | 10 | 101611294 | G    | A  | 2.15E-08 | 0.0611 | 41,414 | 36,519 | 4,726  | 169    | 24.77 | 23.97 | 21.99 |
|     | 10 | 101912064 | T    | C  | 2.43E-21 | 0.4755 | 41,414 | 11,318 | 20,819 | 9,277  | 25.32 | 24.71 | 23.77 |
|     | 10 | 101977883 | C    | T  | 1.93E-13 | 0.5072 | 41,414 | 10,048 | 20,733 | 10,633 | 25.18 | 24.75 | 24.01 |
|     | 10 | 113917085 | T    | A  | 4.61E-10 | 0.7073 | 41,414 | 3,627  | 16,984 | 20,803 | 25    | 24.97 | 24.36 |
|     | 10 | 113940329 | T    | C  | 2.54E-10 | 0.7097 | 41,412 | 3,567  | 16,910 | 20,935 | 25    | 24.98 | 24.35 |
|     | 14 | 94844947  | C    | T  | 9.28E-21 | 0.0171 | 41,414 | 40,006 | 1,399  | 9      | 24.58 | 26.91 | 43.89 |
|     | 19 | 19379549  | C    | T  | 4.76E-09 | 0.0759 | 41,413 | 35,388 | 5,780  | 245    | 24.52 | 25.46 | 26.84 |
|     | 22 | 44324727  | C    | G  | 1.34E-50 | 0.2351 | 41,414 | 24,257 | 14,837 | 2,320  | 24.06 | 24.99 | 28.91 |
|     | 22 | 44324730  | C    | T  | 1.11E-50 | 0.2349 | 41,414 | 24,273 | 14,824 | 2,317  | 24.06 | 24.98 | 28.92 |
|     | 22 | 44342116  | A    | G  | 8.26E-08 | 0.5986 | 41,412 | 6,691  | 19,833 | 14,888 | 24.15 | 24.47 | 25.15 |
|     | 22 | 44368122  | A    | G  | 8.85E-30 | 0.1682 | 41,413 | 28,626 | 11,618 | 1,169  | 24.23 | 25.36 | 28.45 |
|     | 22 | 44395451  | T    | C  | 7.98E-16 | 0.3963 | 41,414 | 15,036 | 19,920 | 6,458  | 24.15 | 24.6  | 26.09 |
| AST | 4  | 88231392  | T    | TA | 6.24E-10 | 0.2638 | 40,753 | 22,068 | 15,870 | 2,815  | 24.47 | 24.1  | 23.96 |
|     | 10 | 18242311  | A    | G  | 1.09E-10 | 0.2881 | 40,753 | 20,645 | 16,738 | 3,370  | 24.47 | 24.15 | 23.85 |
|     | 10 | 101157378 | CGTT | C  | 1.96E-20 | 0.0002 | 40,753 | 40,733 | 20     | 0      | 24.29 | 14.7  | NA    |
|     | 10 | 101165533 | G    | C  | 2.43E-24 | 0.0002 | 40,753 | 40,736 | 17     | 0      | 24.28 | 44.5  | NA    |
|     | 10 | 101912064 | T    | C  | 4.82E-16 | 0.4754 | 40,753 | 11,138 | 20,486 | 9,129  | 24.59 | 24.26 | 23.99 |
|     | 11 | 22271870  | A    | T  | 9.61E-08 | 0.5833 | 40,722 | 7,123  | 19,686 | 13,913 | 24.03 | 24.22 | 24.53 |
|     | 14 | 94844947  | C    | T  | 2.44E-20 | 0.0172 | 40,753 | 39,361 | 1,384  | 8      | 24.24 | 25.76 | 34.5  |
|     | 19 | 19379549  | C    | T  | 6.54E-08 | 0.0760 | 40,752 | 34,811 | 5,698  | 243    | 24.21 | 24.74 | 25.43 |
|     | 22 | 44324727  | C    | G  | 8.31E-46 | 0.2343 | 40,753 | 23,889 | 14,622 | 2,242  | 23.96 | 24.48 | 26.62 |
|     | 22 | 44324730  | C    | T  | 8.93E-46 | 0.2341 | 40,753 | 23,905 | 14,609 | 2,239  | 23.96 | 24.47 | 26.63 |
|     | 22 | 44368122  | A    | G  | 1.22E-22 | 0.1680 | 40,752 | 28,170 | 11,450 | 1,132  | 24.07 | 24.64 | 26.24 |
|     | 22 | 44395451  | T    | C  | 1.31E-13 | 0.3961 | 40,753 | 14,761 | 19,678 | 6,314  | 24.02 | 24.23 | 25.1  |

*Indicates variants having exome-wide significant associations with both ALT and AST.
Abbreviations: AAF, alternate allele frequency; Alt, alternate allele; ALT, alanine aminotransferase; AST, aspartate aminotransferase; Ref, reference allele; SE, standard error.

TABLE 8

Replication and joint meta-analysis of 35 exome-wide significant single nucleotide variants from the discovery cohort in three separate European-ancestry cohorts.

| | | | | | | | | | GHS Discovery Cohort | | |
|---|---|---|---|---|---|---|---|---|---|---|---|
| Trait | Chr | BP | Ref | Alt | RSID | Gene | Ann | AA Substitution | Beta (SE) | P | N |
| ALT | 1 | 220970028 | A | G | rs2642438 | MARC1 | mis | p.Thr165Ala | 0.008 (0.001) | 4.67E-08 | 41,414 |
|  | 4 | 88231392 | T | TA | rs72613567 | HSD17B13 | spl |  | -0.009 (0.001) | 4.16E-12 | 41,414 |
|  | 8 | 144997604 | C | T | rs371119003 | PLEC | mis | p.Ala2302Thr | -0.160 (0.026) | 1.30E-09 | 41,413 |
|  | 8 | 145008502 | G | A |  | PLEC | mis | p.Arg522Cys | -0.268 (0.032) | 3.26E-17 | 41,414 |
|  | 8 | 145692918 | G | A | rs35968570 | KIFC2 | mis | p.Glu174Lys | -0.033 (0.005) | 1.40E-11 | 41,414 |
|  | 8 | 145730072 | G | A | rs143408057 | GPT | mis | p.Arg83His | -0.314 (0.036) | 3.28E-18 | 41,414 |
|  | 8 | 145730161 | C | T | rs201815297 | GPT | mis | p.Ala87Val | -0.224 (0.014) | 6.28E-59 | 41,414 |
|  | 8 | 145730221 | G | A | rs112574791 | GPT | mis | p.Arg107Lys | -0.033 (0.005) | 4.25E-11 | 41,414 |
|  | 8 | 145731636 | T | G | rs145155876 | GPT | stop | p.Tyr326* | -0.235 (0.031) | 1.76E-14 | 41,394 |
|  | 8 | 145732114 | G | C | rs141505249 | GPT | mis | p.Glu430Gln | -0.224 (0.013) | 8.84E-64 | 41,375 |
|  | 8 | 145732151 | G | A | rs143462595 | GPT | mis | p.Arg442His | -0.077 (0.013) | 1.18E-09 | 41,406 |
|  | 8 | 145732180 | G | C | rs147998249 | GPT | mis | p.Val452Leu | -0.225 (0.013) | 8.19E-65 | 41,413 |

TABLE 8-continued

Replication and joint meta-analysis of 35 exome-wide significant single nucleotide variants from the discovery cohort in three separate European-ancestry cohorts.

| Trait | Chr | BP | Ref | Alt | rsID | Gene | Type | Protein | Beta (SE) | P | N |
|---|---|---|---|---|---|---|---|---|---|---|---|
| | 8 | 145732305 | G | GC | | GPT | fs | p.Glu475fs | -0.271 (0.031) | 1.00E-18 | 41,414 |
| | 8 | 145748532 | A | G | rs567402720 | LRRC24 | mis | p.Leu290Ser | -0.185 (0.028) | 3.42E-11 | 41,393 |
| | 9 | 117122202 | C | T | rs3748177 | AKNA | syn | p.Glu755Glu | -0.007 (0.001) | 9.51E-09 | 41,414 |
| | 9 | 117124731 | G | A | rs3748176 | AKNA | mis | p.Pro624Leu | -0.007 (0.001) | 4.31E-09 | 41,412 |
| | 10 | 101595996 | T | A | rs17222723 | ABCC2 | mis | p.Val1188Glu | -0.015 (0.003) | 2.97E-08 | 41,414 |
| | 10 | 101606861 | G | T | rs1137968 | ABCC2 | syn | p.Val1430Val | -0.015 (0.003) | 2.71E-08 | 41,414 |
| | 10 | 101610533 | C | T | rs8187707 | ABCC2 | syn | p.His1496His | -0.015 (0.003) | 2.77E-08 | 41,414 |
| | 10 | 101611294 | G | A | rs8187710 | ABCC2 | mis | p.Cys1515Tyr | -0.015 (0.003) | 2.15E-08 | 41,414 |
| | 10 | 101912064 | T | C | rs2862954 | ERLIN1 | mis | p.Ile291Val | -0.012 (0.001) | 2.43E-21 | 40,834 |
| | 10 | 101977883 | C | T | rs2230804 | CHUK | mis | p.Val268Ile | -0.009 (0.001) | 1.93E-13 | 41,414 |
| | 10 | 113917085 | T | A | rs2254537 | GPAM | syn | p.Pro681Pro | -0.008 (0.001) | 4.61E-10 | 41,414 |
| | 10 | 113940329 | T | C | rs2792751 | GPAM | mis | p.Ile43Val | -0.008 (0.001) | 2.54E-10 | 41,412 |
| | 14 | 94844947 | C | T | rs28929474 | SERPINA1 | mis | p.Glu366Lys | 0.042 (0.005) | 9.28E-21 | 41,414 |
| | 19 | 19379549 | C | T | rs58542926 | TM6SF2 | mis | p.Glu167Lys | 0.014 (0.002) | 4.76E-09 | 41,413 |
| | 22 | 44324727 | C | G | rs738409 | PNPLA3 | mis | p.Ile148Met | 0.023 (0.002) | 1.34E-50 | 41,414 |
| | 22 | 44324730 | C | T | rs738408 | PNPLA3 | syn | p.Pro149Pro | 0.023 (0.002) | 1.11E-50 | 41,414 |
| | 22 | 44342116 | A | G | rs2294918 | PNPLA3 | mis | p.Lys434Glu | 0.007 (0.001) | 8.26E-08 | 41,412 |
| | 22 | 44368122 | A | G | rs3761472 | SAMM50 | mis | p.Asp110Gly | 0.019 (0.002) | 8.85E-30 | 41,413 |
| | 22 | 44395451 | T | C | rs1007863 | PARVB | mis | p.Trp37Arg | 0.011 (0.001) | 7.98E-16 | 41,414 |
| AST | 4 | 88231392 | T | TA | rs72613567 | HSD17B13 | spl | | -0.005 (0.001) | 6.24E-10 | 40,753 |
| | 10 | 18242311 | A | G | rs10764176 | SLC39A12 | mis | p.Ser36Gly | -0.006 (0.001) | 1.09E-10 | 40,753 |
| | 10 | 101157378 | CGTT | C | | GOT1 | inf | p.Asn389del | -0.221 (0.024) | 1.96E-20 | 40,753 |
| | 10 | 101165533 | G | C | rs374966349 | GOT1 | mis | p.Gln208Glu | 0.271 (0.027) | 2.43E-24 | 40,753 |
| | 10 | 101912064 | T | C | rs2862954 | ERLIN1 | mis | p.Ile291Val | -0.005 (0.001) | 4.82E-09 | 40,753 |
| | 11 | 22271870 | A | T | rs7481951 | ANO5 | mis | p.Leu322Phe | 0.004 (0.001) | 9.61E-08 | 40,722 |
| | 14 | 94844947 | C | T | rs28929474 | SERPINA1 | mis | p.Glu366Lys | 0.027 (0.003) | 2.44E-20 | 40,753 |
| | 19 | 19379549 | C | T | rs58542926 | TM6SF2 | mis | p.Glu167Lys | 0.008 (0.002) | 6.54E-08 | 40,192 |
| | 22 | 44324727 | C | G | rs738409 | PNPLA3 | mis | p.Ile148Met | 0.014 (0.001) | 8.31E-46 | 40,753 |
| | 22 | 44324730 | C | T | rs738408 | PNPLA3 | syn | p.Pro149Pro | 0.014 (0.001) | 8.93E-46 | 40,753 |
| | 22 | 44368122 | A | G | rs3761472 | SAMM50 | mis | p.Asp110Gly | 0.011 (0.001) | 1.22E-22 | 40,752 |
| | 22 | 44395451 | T | C | rs1007863 | PARVB | Mis | p.Trp37Arg | 0.006 (0.001) | 1.31E-13 | 40,753 |

| | | | GHS Bariatric Surgery Cohort | | | Dallas Heart Study | | | U. Penn | | |
|---|---|---|---|---|---|---|---|---|---|---|---|
| Trait | Chr | BP | Beta (SE) | P | N | Beta (SE) | P | N | Beta (SE) | P | N |
| ALT | 1 | 220970028 | 0.005 (0.005) | 3.10E-01 | 2475 | 0.011 (0.008) | 1.76E-01 | 1357 | 0.007 (0.004) | 1.02E-01 | 6158 |
| | 4 | 88231392 | -0.010 (0.005) | 5.57E-02 | 2475 | -0.016 (0.008) | 6.60E-02 | 1357 | -0.013 (0.004) | 1.33E-03 | 6158 |
| | 8 | 144997604 | -0.492 (0.165) | 2.84E-03 | 2475 | NA (NA) | NA | NA | -0.051 (0.072) | 4.79E-01 | 6158 |
| | 8 | 145008502 | -0.161 (0.165) | 3.29E-01 | 2475 | NA (NA) | NA | NA | -0.247 (0.143) | 8.48E-02 | 6158 |

TABLE 8-continued

Replication and joint meta-analysis of 35 exome-wide significant single nucleotide variants from the discovery cohort in three separate European-ancestry cohorts.

|  | Chr | Position | Beta (SE) | P | N | Beta (SE) | P | N | Beta (SE) | P | N |
|---|---|---|---|---|---|---|---|---|---|---|---|
|  | 8 | 145692918 | −0.009 (0.020) | 6.48E−01 | 2475 | 0.032 (0.036) | 3.76E−01 | 1356 | −0.053 (0.018) | 3.72E−03 | 6158 |
|  | 8 | 145730072 | −0.189 (0.165) | 2.50E−01 | 2475 | NA (NA) | NA | NA | −0.298 (0.101) | 3.26E−03 | 6158 |
|  | 8 | 145730161 | −0.341 (0.074) | 3.64E−06 | 2475 | NA (NA) | NA | NA | −0.143 (0.054) | 8.50E−03 | 6158 |
|  | 8 | 145730221 | −0.009 (0.020) | 6.45E−01 | 2475 | 0.028 (0.036) | 4.37E−01 | 1357 | −0.060 (0.018) | 5.60E−04 | 6158 |
|  | 8 | 145731636 | −0.314 (0.165) | 5.71E−02 | 2475 | −0.317 (0.140) | 2.35E−02 | 1356 | −0.148 (0.143) | 3.04E−01 | 6157 |
|  | 8 | 145732114 | −0.273 (0.048) | 9.83E−09 | 2474 | −0.240 (0.075) | 1.36E−03 | 1357 | −0.197 (0.041) | 1.31E−06 | 6157 |
|  | 8 | 145732151 | −0.115 (0.058) | 4.82E−02 | 2475 | −0.106 (0.099) | 2.86E−01 | 1356 | −0.049 (0.041) | 2.27E−01 | 6157 |
|  | 8 | 145732180 | −0.273 (0.050) | 4.26E−08 | 2475 | −0.191 (0.070) | 6.58E−03 | 1357 | −0.197 (0.041) | 1.31E−06 | 6158 |
|  | 8 | 145732305 | −0.161 (0.165) | 3.29E−01 | 2475 | NA (NA) | NA | NA | −0.509 (0.203) | 1.21E−02 | 6158 |
|  | 8 | 145748532 | −0.161 (0.165) | 3.29E−01 | 2475 | NA (NA) | NA | NA | −0.307 (0.143) | 3.21E−02 | 6158 |
|  | 9 | 117122202 | −0.004 (0.005) | 4.09E−01 | 2475 | 0.004 (0.008) | 6.18E−01 | 1357 | −0.007 (0.004) | 5.29E−02 | 6158 |
|  | 9 | 117124731 | −0.004 (0.005) | 3.90E−01 | 2475 | 0.003 (0.008) | 7.33E−01 | 1356 | −0.007 (0.004) | 4.24E−02 | 6158 |
|  | 10 | 101595996 | −0.002 (0.010) | 8.01E−01 | 2475 | −0.007 (0.017) | 6.88E−01 | 1357 | −0.017 (0.007) | 1.55E−02 | 6158 |
|  | 10 | 101606861 | −0.003 (0.010) | 7.74E−01 | 2475 | −0.008 (0.017) | 6.28E−01 | 1357 | −0.017 (0.007) | 1.70E−02 | 6158 |
|  | 10 | 101610533 | −0.003 (0.010) | 7.93E−01 | 2475 | −0.008 (0.017) | 6.28E−01 | 1357 | −0.017 (0.007) | 1.76E−02 | 6158 |
|  | 10 | 101611294 | −0.001 (0.010) | 9.11E−01 | 2475 | −0.010 (0.017) | 5.40E−01 | 1357 | −0.016 (0.007) | 2.77E−02 | 6158 |
|  | 10 | 101912064 | −0.010 (0.005) | 2.91E−02 | 2475 | −0.006 (0.007) | 4.02E−01 | 1356 | −0.009 (0.004) | 2.06E−02 | 6158 |
|  | 10 | 101977883 | −0.006 (0.005) | 2.05E−01 | 2475 | 0.0001 (0.008) | 9.94E−01 | 1357 | −0.011 (0.004) | 3.91E−03 | 6158 |
|  | 10 | 113917085 | −0.003 (0.005) | 5.80E−01 | 2475 | −0.013 (0.008) | 1.15E−01 | 1357 | −0.008 (0.004) | 5.12E−02 | 6158 |
|  | 10 | 113940329 | −0.003 (0.005) | 5.61E−01 | 2475 | −0.013 (0.008) | 1.33E−01 | 1357 | −0.008 (0.004) | 4.77E−02 | 6158 |
|  | 14 | 94844947 | 0.035 (0.020) | 7.97E−02 | 2475 | 0.034 (0.032) | 2.92E−01 | 1357 | 0.054 (0.013) | 1.63E−05 | 6158 |
|  | 19 | 19379549 | 0.040 (0.010) | 2.40E−05 | 2475 | 0.024 (0.014) | 9.50E−02 | 1357 | 0.013 (0.008) | 7.51E−02 | 6158 |
|  | 22 | 44324727 | 0.019 (0.006) | 5.54E−04 | 2475 | 0.006 (0.009) | 5.43E−01 | 1357 | 0.016 (0.004) | 2.05E−04 | 6158 |
|  | 22 | 44324730 | 0.019 (0.006) | 5.51E−04 | 2475 | 0.006 (0.009) | 5.43E−01 | 1357 | 0.016 (0.004) | 2.14E−04 | 6158 |
|  | 22 | 44342116 | 0.001 (0.005) | 7.77E−01 | 2475 | 0.005 (0.008) | 5.18E−01 | 1357 | 0.005 (0.004) | 2.16E−01 | 6158 |
|  | 22 | 44368122 | 0.009 (0.006) | 1.66E−01 | 2475 | −0.001 (0.01) | 9.37E−01 | 1357 | 0.018 (0.005) | 4.02E−04 | 6158 |
|  | 22 | 44395451 | 0.003 (0.005) | 5.22E−01 | 2475 | 0.008 (0.008) | 3.13E−01 | 1357 | 0.009 (0.004) | 2.50E−02 | 6158 |
| AST | 4 | 88231392 | −0.010 (0.003) | 3.12E−03 | 2469 | −0.012 (0.006) | 5.32E−02 | 1357 | −0.007 (0.004) | 5.56E−02 | 6166 |
|  | 10 | 18242311 | −0.010 (0.003) | 2.91E−03 | 2469 | −0.003 (0.006) | 5.80E−01 | 1357 | −0.009 (0.004) | 1.03E−02 | 6166 |
|  | 10 | 101157378 | −0.205 (0.062) | 8.57E−04 | 2469 | NA (NA) | NA | NA | −0.243 (0.088) | 5.97E−03 | 6165 |
|  | 10 | 101165533 | NA (NA) | NA | NA | NA (NA) | NA | NA | 0.339 (0.079) | 1.85E−05 | 6166 |
|  | 10 | 101912064 | −0.004 (0.003) | 1.54E−01 | 2469 | −0.007 (0.006) | 2.21E−01 | 1357 | −0.004 (0.003) | 1.94E−01 | 6166 |
|  | 11 | 22271870 | −0.001 (0.003) | 7.85E−01 | 2466 | 0.006 (0.006) | 2.85E−01 | 1357 | −0.002 (0.003) | 5.46E−01 | 6165 |
|  | 14 | 94844947 | 0.023 (0.013) | 7.79E−02 | 2469 | 0.044 (0.024) | 6.98E−02 | 1357 | 0.055 (0.011) | 4.01E−07 | 6166 |
|  | 19 | 19379549 | 0.023 (0.006) | 1.99E−04 | 2469 | 0.010 (0.011) | 3.42E−01 | 1356 | 0.004 (0.007) | 5.94E−01 | 6166 |
|  | 22 | 44324727 | 0.014 (0.004) | 1.27E−04 | 2469 | 0.004 (0.007) | 5.44E−01 | 1357 | 0.015 (0.004) | 4.87E−05 | 6166 |
|  | 22 | 44324730 | 0.014 (0.004) | 1.32E−04 | 2469 | 0.004 (0.007) | 5.44E−01 | 1357 | 0.015 (0.004) | 4.96E−05 | 6166 |
|  | 22 | 44368122 | 0.008 (0.004) | 6.03E−02 | 2469 | −0.001 (0.008) | 9.45E−01 | 1357 | 0.016 (0.004) | 2.64E−04 | 6166 |
|  | 22 | 44395451 | 0.003 (0.004) | 4.12E−01 | 2469 | 0.006 (0.007) | 2.95E−01 | 1357 | 0.009 (0.004) | 6.17E−03 | 6166 |

TABLE 8-continued

Replication and joint meta-analysis of 35 exome-wide significant single nucleotide variants from the discovery cohort in three separate European-ancestry cohorts.

| | | | (0.003) | (0.006) | (0.003) | |
|---|---|---|---|---|---|---|
| | | | colspan=2: **Replication Meta-Analysis (N = 3) | colspan=2: ***Joint Meta-Analysis (N = 4) | |
| Trait | Chr | BP | Beta (SE) | P | Beta (SE) | P |
| ALT | 1 | 220970028 | 0.007 (0.003) | 2.31E−02 | 0.008 (0.001) | 3.38E−09 |
| | 4 | 88231392 | −0.013 (0.003) | *3.85E−05 | −0.010 (0.001) | 1.17E−15 |
| | 8 | 144997604 | −0.121 (0.066) | 6.56E−02 | −0.155 (0.025) | 2.68E−10 |
| | 8 | 145008502 | −0.210 (0.108) | 5.23E−02 | −0.264 (0.031) | 5.54E−18 |
| | 8 | 145692918 | −0.025 (0.013) | 4.69E−02 | −0.032 (0.005) | 2.25E−12 |
| | 8 | 145730072 | −0.268 (0.086) | 1.88E−03 | −0.308 (0.033) | 2.79E−20 |
| | 8 | 145730161 | −0.213 (0.044) | *1.14E−06 | −0.223 (0.013) | 4.49E−64 |
| | 8 | 145730221 | −0.031 (0.013) | 1.36E−02 | −0.033 (0.005) | 1.92E−12 |
| | 8 | 145731636 | −0.256 (0.086) | 2.79E−03 | −0.237 (0.029) | 1.94E−16 |
| | 8 | 145732114 | −0.231 (0.029) | *7.24E−16 | −0.225 (0.012) | 6.06E−78 |
| | 8 | 145732151 | −0.074 (0.032) | 1.88E−02 | −0.076 (0.012) | 7.03E−11 |
| | 8 | 145732180 | −0.221 (0.029) | *1.41E−14 | −0.224 (0.012) | 1.04E−77 |
| | 8 | 145732305 | −0.299 (0.128) | 1.93E−02 | −0.273 (0.030) | 6.44E−20 |
| | 8 | 145748532 | −0.244 (0.108) | 2.40E−02 | −0.189 (0.027) | 2.93E−12 |
| | 9 | 117122202 | −0.005 (0.003) | 8.42E−02 | −0.007 (0.001) | 3.08E−09 |
| | 9 | 117124731 | −0.005 (0.003) | 6.15E−02 | −0.007 (0.001) | 1.00E−09 |
| | 10 | 101595996 | −0.012 (0.005) | 3.43E−02 | −0.014 (0.002) | 3.44E−09 |
| | 10 | 101606861 | −0.012 (0.005) | 3.25E−02 | −0.014 (0.002) | 2.99E−09 |
| | 10 | 101610533 | −0.012 (0.005) | 3.43E−02 | −0.014 (0.002) | 3.23E−09 |
| | 10 | 101611294 | −0.011 (0.005) | 5.21E−02 | −0.014 (0.002) | 4.09E−09 |
| | 10 | 101912064 | −0.009 (0.003) | *1.14E−03 | −0.011 (0.001) | 1.76E−23 |
| | 10 | 101977883 | −0.008 (0.003) | 4.33E−03 | −0.009 (0.001) | 3.59E−15 |
| | 10 | 113917085 | −0.007 (0.003) | 2.07E−02 | −0.008 (0.001) | 3.28E−11 |
| | 10 | 113940329 | −0.007 (0.003) | 2.00E−02 | −0.008 (0.001) | 1.77E−11 |
| | 14 | 94844947 | 0.047 (0.010) | *2.82E−06 | 0.043 (0.004) | 1.59E−25 |
| | 19 | 19379549 | 0.024 (0.006) | *1.37E−05 | 0.016 (0.002) | 1.15E−12 |
| | 22 | 44324727 | 0.016 (0.003) | *7.45E−07 | 0.021 (0.001) | 3.55E−55 |
| | 22 | 44324730 | 0.016 (0.003) | *7.73E−07 | 0.021 (0.001) | 3.10E−55 |
| | 22 | 44342116 | 0.004 (0.003) | 1.91E−01 | 0.006 (0.001) | 6.24E−08 |
| | 22 | 44368122 | 0.012 (0.004) | *7.69E−04 | 0.018 (0.002) | 1.08E−31 |
| | 22 | 44395451 | 0.007 (0.003) | 1.78E−02 | 0.010 (0.001) | 1.16E−16 |
| AST | 4 | 88231392 | −0.009 (0.002) | *8.38E−05 | −0.006 (0.001) | 6.82E−13 |
| | 10 | 18242311 | −0.009 (0.002) | *1.16E−04 | −0.006 (0.001) | 1.10E−13 |
| | 10 | 101157378 | −0.218 (0.051) | *1.66E−05 | −0.220 (0.022) | 1.68E−24 |

TABLE 8-continued

Replication and joint meta-analysis of 35 exome-wide significant single nucleotide variants from the discovery cohort in three separate European-ancestry cohorts.

| | | | | | |
|---|---|---|---|---|---|
| 10 | 101165533 | 0.339 (0.079) | *1.85E−05 | 0.278 (0.025) | 3.25E−28 |
| 10 | 101912064 | −0.005 (0.002) | 2.51E−02 | −0.005 (0.001) | 3.68E−10 |
| 11 | 22271870 | 0.000 (0.002) | 8.43E−01 | 0.004 (0.001) | 1.13E−06 |
| 14 | 94844947 | 0.042 (0.008) | *9.54E−08 | 0.029 (0.003) | 6.71E−26 |
| 19 | 19379549 | 0.014 (0.004) | *1.20E−03 | 0.009 (0.002) | 5.92E−10 |
| 22 | 44324727 | 0.013 (0.002) | *5.51E−08 | 0.014 (0.001) | 3.14E−52 |
| 22 | 44324730 | 0.013 (0.002) | *5.81E−08 | 0.014 (0.001) | 3.55E−52 |
| 22 | 44368122 | 0.010 (0.003) | *3.40E−04 | 0.011 (0.001) | 1.91E−25 |
| 22 | 44395451 | 0.006 (0.002) | 7.34E−03 | 0.006 (0.001) | 3.62E−15 |

*Indicates P-values meeting the Bonferroni significance threshold of $P < 1.43 \times 10^{-3}$.
**Replication meta-analysis includes the three replication cohorts: GHS Bariatric Surgery Cohort, Dallas Heart Study, and Penn Medicine Biobank.
***Joint meta-analysis includes the discovery cohort and the three replication cohorts: GHS Discovery Cohort, GHS Bariatric Surgery Cohort, Dallas Heart Study, and Penn Medicine Biobank.
Abbreviations: AAF, alternate allele frequency; Alt, alternate allele; ALT, alanine aminotransferase; AST, aspartate aminotransferase; Ref, reference allele; SE, standard error; ann, annotation; mis, missense; syn, synonymous; spl, splice donor; stop, stop gained; fs, frameshift; inf, inframe indel.

Association of Exonic Variants with Clinical Diagnoses of Chronic Liver Disease

Next, we analyzed the relationship between the thirteen transaminase-associated variants in the nine genes found in the discovery and replication cohorts and chronic liver disease, including alcoholic and nonalcoholic (non-viral) liver disease, as well as the most advanced forms of chronic liver disease: alcoholic cirrhosis, nonalcoholic cirrhosis, and hepatocellular carcinoma (HCC). Using a Bonferroni significance threshold of $P<1.92\times10^{-3}$ for the thirteen variants tested, we found significant associations between six variants in five genes (HSD17B13, SERPINA1, TM6SF2, PNPLA3, and SAMM50) and chronic liver disease phenotypes (Table 9). The SERPINA1, TM6SF2, PNPLA3, and SAMM50 associations confirm previously reported associations. In the discovery cohort, HSD17B13 rs72613567:TA was associated with lower odds of all EHR-derived categories of both alcoholic and nonalcoholic liver disease in an allele dosage-dependent manner (FIG. 2A): all categories of alcoholic liver disease, heterozygous odds ratio ($OR_{het}$) (95% confidence interval) 0.58 (0.42-0.80), homozygous OR ($OR_{hom}$) 0.47 (0.23-0.97), allelic OR ($OR_{allelic}$) 0.62 (0.48-0.81), $P=1.8\times10^{-4}$; all categories of nonalcoholic liver disease, $OR_{het}$ 0.83 (0.75-0.92), $OR_{hom}$ 0.70 (0.57-0.87), $OR_{allelic}$ 0.84 (0.78-0.91), $P=1.3\times10^{-5}$. HSD17B13 rs72613567:TA was also associated with lower odds of alcoholic and nonalcoholic cirrhosis, with 42% and 73% lower odds of alcoholic cirrhosis for heterozygotes and homozygotes, respectively, ($OR_{het}$ 0.58 (0.39-0.86), $OR_{hom}$ 0.27 (0.09-0.85), $OR_{allelic}$ 0.56 (0.41-0.78), $P=3.4\times10^{-4}$) and 26% and 49% lower odds of nonalcoholic cirrhosis for heterozygotes and homozygotes, respectively ($OR_{het}$ 0.74 (0.60-0.93), $OR_{hom}$ 0.51 (0.31-0.85), $OR_{allelic}$ 0.74 (0.62-0.88), $P=4.5\times10^{-4}$). HSD17B13 rs72613567:TA was also nominally associated with lower odds of HCC.

We sought to confirm and extend these findings in the multi-ethnic Dallas Liver Study (DLS) and the Dallas Pediatric Liver Study (DPLS, Table 10). In the DLS, the TA allele was associated with lower odds of any liver disease in an allele-dosage dependent manner ($OR_{het}$ 0.74 (0.57-0.97), $OR_{hom}$ 0.41 (0.21-0.83), $OR_{allelic}$ 0.70 (0.5-0.88), $P=1.8\times10^{-3}$, FIG. 8). Similar effects were observed across EHR-derived liver disease subtypes, including protective associations with advanced, cirrhotic forms of alcoholic ($OR_{allelic}$ 0.72 (0.53-0.99), $P=4.4\times10^{-2}$) and nonalcoholic ($OR_{allelic}$ 0.65 (0.40-1.07), $P=9.0\times10^{-2}$) liver disease. In subset analyses of individuals grouped by self-reported ethnicity, the association with liver disease was significant in Hispanic Americans (n=326 cases and 722 controls, $OR_{allelic}$ 0.51 (0.35-0.74), $P=4.0\times10^{-4}$); similar numerical trends, which did not achieve statistical significance, were also noted in the African American (n=33 cases and 2,291 controls, $OR_{allelic}$ 0.74 (0.25-2.47), $P=0.67$) and European American (n=158 cases and 1,266 controls, $OR_{allelic}$ 0.87 (0.65-1.15), $P=0.32$) subsets of the DLS. In the DPLS, a separate study of Hispanic American pediatric liver disease patients and obese controls, the TA allele was also associated with lower odds of liver disease ($OR_{allelic}$ 0.61 (0.37-0.99), $P=4.6\times10^{-2}$). Thus, HSD17B13 rs72613567: TA was associated with reduced odds of multiple forms of chronic liver disease, including cirrhosis, in adults and children in three independent populations.

TABLE 9

Association of twelve exome-wide significant and replicating single nucleotide variants with liver disease phenotypes in the discovery cohort.

| | | | Alcoholic liver disease | | Alcoholic cirrhosis | |
|---|---|---|---|---|---|---|
| CHR:BP:Ref:Alt | Gene | rsID | OR (95% CI) | P-value | OR (95% CI) | P-value |
| 4:88231392:T:TA | HSD17B13 | rs72613567 | 0.62 (0.48-0.81) | *1.82E−04 | 0.56 (0.41-0.78) | *3.35E−04 |
| 8:145730161:C:T | GPT | rs201815297 | 3.83 (1.05-13.94) | 8.88E−02 | 6.33 (1.71-23.43) | 2.88E−02 |

TABLE 9-continued

Association of twelve exome-wide significant and replicating single nucleotide variants with liver disease phenotypes in the discovery cohort.

| CHR:BP:Ref:Alt | Gene | rsID | OR | P-value | OR | P-value |
|---|---|---|---|---|---|---|
| 8:145732114:G:C | GPT | rs141505249 | 0.77 (0.06-10.73) | 8.43E-01 | 1.13 (0.08-15.39) | 9.30E-01 |
| 8:145732180:G:C | GPT | rs147998249 | 0.73 (0.05-11.76) | 8.17E-01 | 1.07 (0.07-17.16) | 9.60E-01 |
| 10:18242311:A:G | SLC39A12 | rs10764176 | 0.85 (0.68-1.07) | 1.64E-01 | 0.92 (0.70-1.22) | 5.80E-01 |
| 10:101157378:CGTT:C | GOT1 | | 4.60 (0.25-86.41) | 3.93E-01 | 7.11 (0.38-133.19) | 3.00E-01 |
| 10:101165533:G:C | GOT1 | rs374966349 | 2.20 (0.13-37.68) | 6.24E-01 | 3.47 (0.20-59.04) | 4.70E-01 |
| 14:94844947:C:T | SERPINA1 | rs28929474 | 2.49 (1.49-4.17) | 2.30E-03 | 3.35 (1.93-5.83) | *3.01E-04 |
| 19:19379549:C:T | TM6SF2 | rs58542926 | 1.47 (1.06-2.04) | 2.76E-02 | 1.35 (0.89-2.04) | 1.80E-01 |
| 22:44324727:C:G | PNPLA3 | rs738409 | 1.76 (1.43-2.18) | *4.98E-07 | 2.07 (1.60-2.67) | *1.08E-07 |
| 22:44324730:C:T | PNPLA3 | rs738408 | 1.77 (1.43-2.18) | *4.70E-07 | 2.07 (1.61-2.67) | *1.03E-07 |
| 22:44368122:A:G | SAMM50 | rs3761472 | 1.90 (1.52-2.38) | *1.36E-07 | 2.28 (1.75-2.98) | *1.83E-08 |

| | | | Nonalcoholic liver disease | | Nonalcoholic cirrhosis | | Hepatocellular carcinoma | |
|---|---|---|---|---|---|---|---|---|
| CHR:BP:Ref:Alt | Gene | rsID | OR (95% CI) | P-value | OR (95% CI) | P-value | OR (95% CI) | P-value |
| 4:88231392:T:TA | HSD17B13 | rs72613567 | 0.84 (0.78-0.91) | *1.31E-05 | 0.74 (0.62-0.88) | *4.48E-04 | 0.67 (0.45-1.00) | 4.66E-02 |
| 8:145730161:C:T | GPT | rs201815297 | 0.23 (0.04-1.14) | 1.86E-02 | 1.25 (0.24-6.38) | 7.98E-01 | 3.66 (0.70-19.01) | 2.01E-01 |
| 8:145732114:G:C | GPT | rs141505249 | 1.02 (0.49-2.11) | 9.70E-01 | 0.36 (0.02-5.37) | 3.82E-01 | 1.84 (0.15-23.25) | 6.88E-01 |
| 8:145732180:G:C | GPT | rs147998249 | 1.03 (0.49-2.17) | 9.30E-01 | 0.34 (0.02-5.59) | 3.67E-01 | 1.74 (0.11-27.05) | 7.21E-01 |
| 10:18242311:A:G | SLC39A12 | rs10764176 | 0.92 (0.86 0.99) | 3.43E-02 | 1.03 (0.88-1.21) | 7.15E-01 | 1.29 (0.93-1.79) | 1.37E-01 |
| 10:101157378:CGTT:C | GOT1 | | 2.37 (0.61-9.27) | 2.50E-01 | 8.27 (1.44-47.49) | 5.92E-02 | 9.81 (0.52-183.54) | 2.43E-01 |
| 10:101165533:G:C | GOT1 | rs374966349 | 1.63 (0.53-4.96) | 4.20E-01 | 1.17 (0.07-20.09) | 9.13E-01 | 5.37 (0.32-91.12) | 3.55E-01 |
| 14:94844947:C:T | SERPINA1 | rs28929474 | 1.50 (1.21-1.87) | *5.29E-04 | 2.99 (2.11-4.24) | *9.08E-08 | 1.86 (0.74-4.67) | 2.40E-01 |
| 19:19379549:C:T | TM6SF2 | rs58542926 | 1.36 (1.21-1.52) | *2.42E-07 | 1.64 (1.31-2.05) | *6.04E-05 | 1.93 (1.22-3.04) | 1.08E-02 |
| 22:44324727:C:G | PNPLA3 | rs738409 | 1.65 (1.54-1.78) | *1.31E-41 | 2.05 (1.76-2.38) | *1.70E-19 | 2.20 (1.60-3.02) | *5.59E-06 |
| 22:44324730:C:T | PNPLA3 | rs738408 | 1.65 (1.54-1.78) | *1.42E-41 | 2.05 (1.77-2.38) | *1.45E-19 | 2.20 (1.60-3.03) | *5.41E-06 |
| 22:44368122:A:G | SAMM50 | rs3761472 | 1.52 (1.41-1.65) | *7.33E-24 | 1.86 (1.58-2.19) | *1.81E-12 | 1.66 (1.16-2.39) | 1.05E-02 |

*Indicates P-values meeting the Bonferroni significance threshold of $P < 2.08 \times 10^{-3}$.

TABLE 10

Demographics and clinical characteristics of genotyped multi-ethnic cases and controls from the Dallas Liver and Pediatric Liver Studies.

| Characteristic | Dallas Liver Study Cases (N = 517) | Dallas Liver Study Controls (N = 4,279) | Dallas Pediatric Liver Study Cases (N = 203) | Dallas Pediatric Liver Study Controls (N = 244) |
|---|---|---|---|---|
| Age (years) - median (IQR) | 55 (48-60) | 44 (36-53) | 12 (10-15) | 12 (11-14) |
| Female sex - number (%) | 277 (54) | 2,494 (58) | 65 (32) | 126 (52) |
| Body mass index - median (IQR) | 30 (27-35) | 30 (26-35) | 30 (27-34) | 31 (28-35) |
| Self-reported ethnicity | | | | |
| African American | 33 (6) | 2,291 (54) | — | — |
| European American | 158 (31) | 1,266 (30) | — | — |
| Hispanic American | 326 (63) | 722 (17) | 203 (100) | 244 (100) |

TABLE 10-continued

Demographics and clinical characteristics of genotyped multi-ethnic cases and controls from the Dallas Liver and Pediatric Liver Studies.

| Characteristic | Dallas Liver Study Cases (N = 517) | Dallas Liver Study Controls (N = 4,279) | Dallas Pediatric Liver Study Cases (N = 203) | Dallas Pediatric Liver Study Controls (N = 244) |
|---|---|---|---|---|
| Presence of liver disease (by ICD-9 code) - N (%) | | | | |
| Alcoholic liver disease | 223 (43) | — | — | — |
| Alcoholic cirrhosis | 215 (42) | — | — | — |
| Nonalcoholic, non-viral liver disease | 212 (20) | — | — | — |
| Nonalcoholic cirrhosis | 100 (19) | — | — | — |
| Hepatocellular carcinoma | 44 (9) | — | — | — |
| No liver disease | — | 4,279 (100) | — | –244 (100) |

Association of HSD17B13 rs72613567:TA with Liver Pathology

NAFLD describes a disease spectrum ranging from liver fat accumulation without evidence of significant inflammation (simple steatosis), to more clinically impactful NASH. To confirm the association between the HSD17B13 rs72613567:TA and EHR-derived liver disease diagnoses codes, and to further understand its association with histopathological progression of steatosis to NASH, we performed tests of association in the GHS bariatric surgery cohort. In this cohort of 2,391 of the whole exome sequenced individuals assessed by liver biopsy at the time of bariatric surgery, a total of 555 (23%) individuals had no evidence of steatosis, steatohepatitis, or fibrosis ("normal"), 830 (35%) had simple steatosis, and 1006 (42%) had NASH. When comparing prevalence of normal liver, simple steatosis, and NASH by genotype, it was observed that the prevalence of normal liver did not appear to differ by genotype (23%, 24%, and 23% for T/T, T/TA, and TA/TA carriers, respectively, P=0.5 by Chi-squared test for trend in proportions), but that the prevalence of NASH decreased (45%, 40%, and 31% for T/T, T/TA, and TA/TA carriers, respectively, P=1.6×10$^{-4}$) and that of simple steatosis increased (33%, 35%, and 47% for T/T, T/TA, and TA/TA carriers, respectively, P=1.1×10$^{-3}$) with each TA allele (FIG. 9). Among individuals with steatosis, the TA allele was associated with statistically significantly lower odds of both NASH and fibrosis, as compared to simple steatosis (OR$_{allelic}$ 0.77 (0.66-0.90), P=6.5×10$^{-4}$ for NASH; OR$_{allelic}$ 0.74 (0.62-0.88), P=4.15×10$^{-4}$ for fibrosis; FIG. 2B), in an allele dosage-dependent manner. Altogether, these data suggest a role for HSD17B13 in mediating NAFLD progression from simple steatosis to more advanced stages of NASH and fibrosis.

Association of HSD17B13 rs72613567:TA with Clinical Quantitative Traits and Diagnoses To more comprehensively examine the clinical consequences of the HSD17B13 splice variant, we performed a phenome-wide study of associations of HSD17B13 rs72613567:TA with 405 quantitative EHR-derived anthropometric, vital sign, laboratory, electrocardiographic, echocardiographic, and bone densitometry measurements, and also with 3,168 EHR-derived clinical diagnoses. Using Bonferroni significance thresholds of 1.23×10$^{-4}$ and 1.58×10$^{-5}$ for associations with quantitative clinical measurements and clinical diagnoses, respectively, we identified statistically significant associations of the HSD17B13 rs72613567:TA allele with higher platelet counts, in addition to the associations with hepatic transaminases (Table 11). There were no statistically significant associations with clinical diagnoses other than chronic liver disease (OR (95% CI)=0.88 (0.84-0.93); P=9.14×10$^{-6}$; AAF=0.263; N Cases total=4031, T/T=2331, T/TA=1449, TA/TA=251; N Controls Total=35701, T/T=19238, T/TA=13984, TA/TA=2479).

TABLE 11

Phenome-Wide Study of Associations of HSD17B13 rs72613567:TA with Quantitative Clinical Measurements.

| Phenotype | Effect | SE | P | AAF | N Total | T/T | T/TA | TA/TA |
|---|---|---|---|---|---|---|---|---|
| Alanine Aminotransferase median:Adjusted(Residual Log) | −0.009 | 0.001 | *1.74E-12* | 0.264 | 44038 | 23868 | 17115 | 3055 |
| Aspartate Aminotransferase median:Adjusted(Residual Log) | −0.006 | 0.001 | *2.75E-11* | 0.264 | 43370 | 23493 | 16851 | 3026 |
| Alanine Aminotransferase max:Adjusted(Residual Log) | −0.013 | 0.002 | *1.39E-09* | 0.264 | 43905 | 23797 | 17065 | 3043 |
| Aspartate Aminotransferase max:Adjusted(Residual Log) | −0.010 | 0.002 | *8.73E-09* | 0.264 | 42733 | 23145 | 16609 | 2979 |
| Platelets median:Adjusted(Residual Log) | 0.004 | 0.001 | *1.44E-08* | 0.264 | 46182 | 25020 | 17944 | 3218 |
| Alanine Aminotransferase min:Adjusted(Residual Log) | −0.008 | 0.002 | *2.47E-07* | 0.264 | 44029 | 23864 | 17111 | 3054 |
| Platelets min:Adjusted(Residual) | 1.919 | 0.443 | *1.47E-05* | 0.264 | 46181 | 25020 | 17943 | 3218 |
| Platelets max:Adjusted(Residual Log) | 0.004 | 0.001 | *3.03E-05* | 0.264 | 46165 | 25014 | 17936 | 3215 |
| Aspartate Aminotransferase min:Adjusted(Residual Log) | −0.004 | 0.001 | *5.00E-05* | 0.264 | 43327 | 23471 | 16831 | 3025 |

Bolding and italicization indicates P-values meeting the Bonferroni significance threshold of P < 1.23 × 10$^{-4}$.

Abbreviations: AAF, alternate allele frequency; SE, standard error.

Figure 11C:
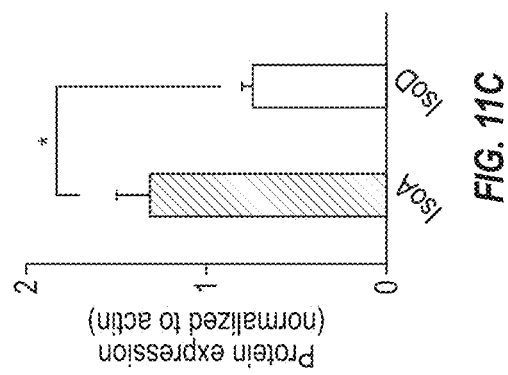
FIGS. 11A-11C show that HSD17B13 Isoform D protein has lower molecular weight and is unstable when overexpressed in HEK 293 cells.
Figure 11B:
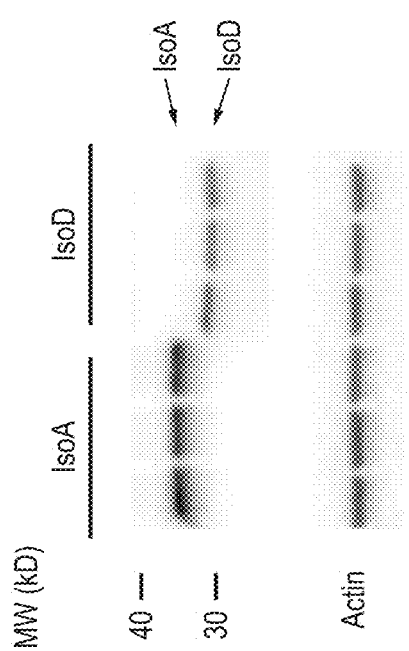
Figure 11A:
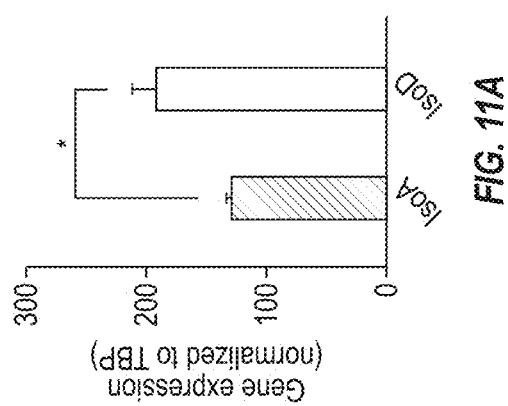

Effect of HSD17B13 rs72613567:TA on HSD17B13 mRNA and HSD17B13 Protein Expression We next examined the effect of the HSD17B13 rs72613567:TA allele on expression of known and novel transcripts of the gene. We used RNA sequencing to assess HSD17B13 mRNA expression in histologically normal liver samples from 22 T/T homozygous, 30 T/TA heterozygous, and 17 TA/TA homozygous carriers of the HSD17B13 rs72613567 splice variant. In addition to the two known HSD17B13 transcripts, A and B, two novel transcripts were identified: transcript C, which lacked exon 6, and transcript D which contained an insertion of a guanine nucleotide at the 3' end of exon 6, which would be predicted to result in premature truncation of the protein. Four additional transcripts (E-H) were expressed at very low levels (FIGS. 3A-3D and 6A-6D). The transcripts were validated by RT-PCR and Sanger sequencing. The D transcript was also validated using long read cDNA sequencing. Protein sequence alignment of all identified HSD17B13 isoforms (A-H) is shown in FIGS. 7A and 7B. The expression levels of these transcripts varied according to HSD17B13 rs72613567 genotype; levels of transcripts A and B decreased, while those of transcripts C and D increased in an allele dosage-dependent manner with each TA allele (FIGS. 3A-3D). Transcript A, which encodes the full-length 300 amino acid protein, was the predominant transcript in T/T homozygotes, while transcript D, which encodes the prematurely truncated protein, was the predominant transcript in TA/TA homozygotes. In human liver biopsy tissue, the truncated isoform D protein was minimally present in heterozygotes and TA/TA homozygotes, and isoform A protein abundance was reduced in an allele dosage-dependent manner (FIGS. 10B and 10C). Heterologous expression of isoforms A and D in HEK 293 cells indicated reduced abundance of isoform D relative to mRNA expression, suggesting instability of the D isoform when compared to isoform A (FIGS. 11A-11C). These data are consistent with HSD17B13 rs72613567 altering mRNA splicing, resulting in the synthesis of a truncated form of the protein with substantially reduced expression in human liver.

Expression of HSD17B13 in Human Liver Cells

Figure 12:
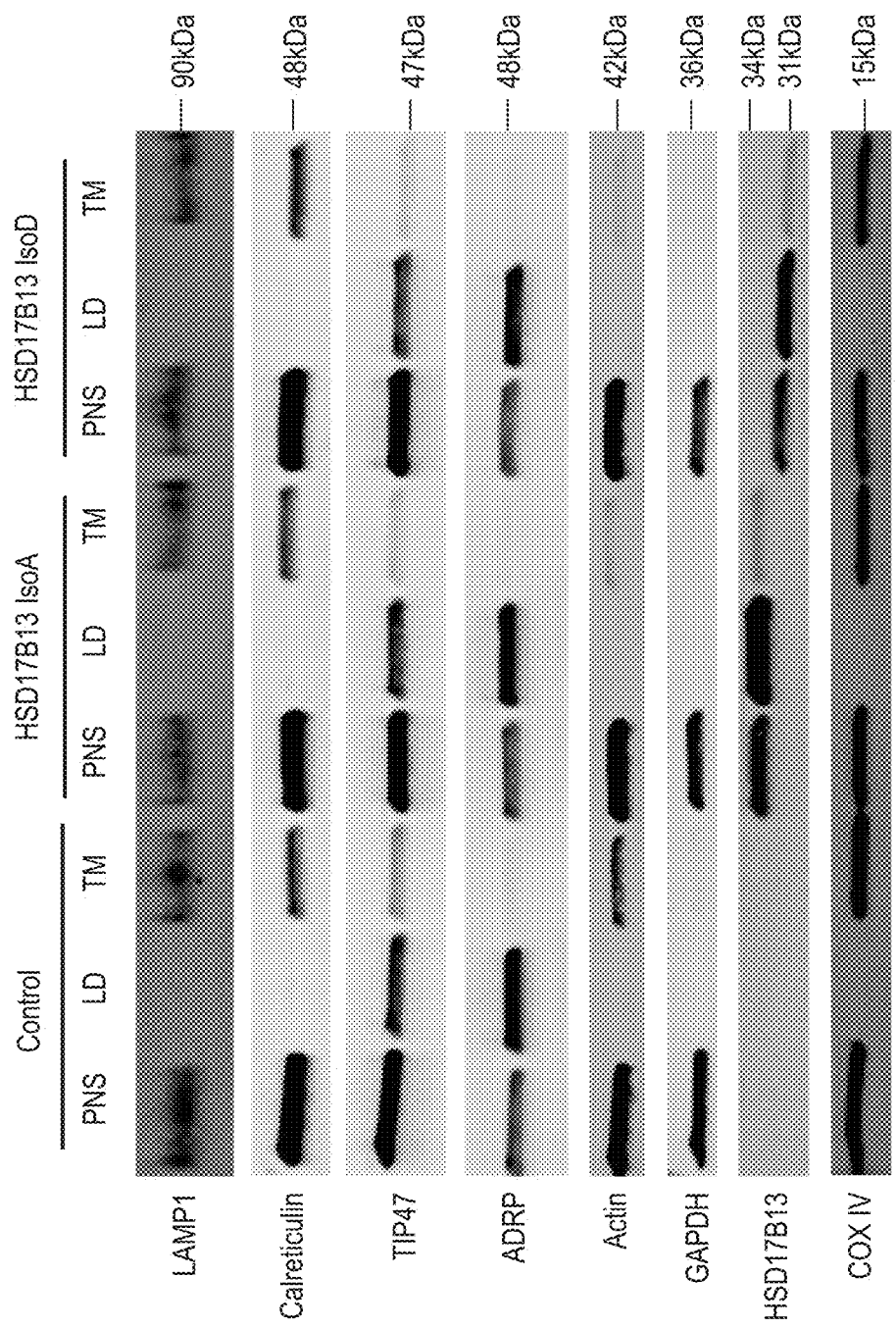
FIG. 12 shows similar localization patterns of HSD17B13 isoform A and isoform D to isolated lipid droplets (LD) derived from HepG2 stable cell lines. ADRP and TIP47 were used as lipid droplet markers. LAMP1, calreticulin, and COX IV were used as markers for the lysosomal, endoplasmic reticulum, and mitochondrial compartments, respectively. GAPDH was included as a cytosolic marker, and actin was used as a cytoskeletal marker. This experiment was repeated twice in HepG2 cells, with the above being representative of both runs. PNS=Post-nuclear fraction; TM=total membrane.
Figure 13B:
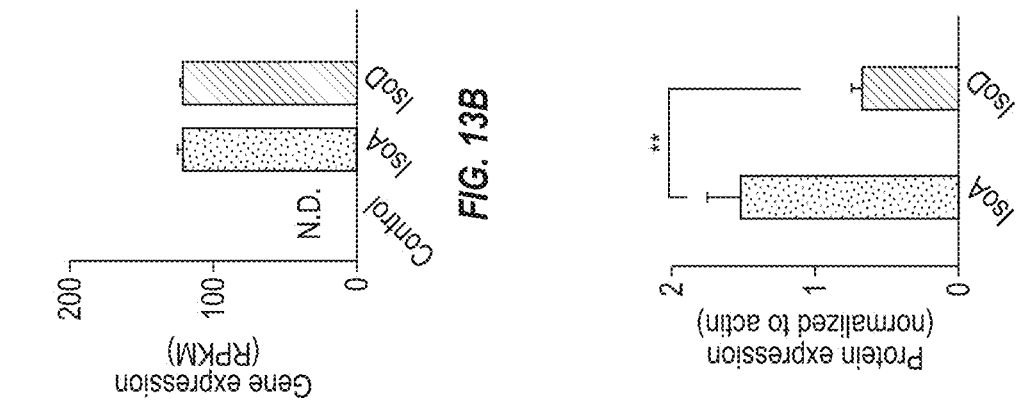
FIGS. 13A-13D show oleic acid increased triglyceride content in HepG2 cells overexpressing HSD17B13 Transcript A or D.
Figure 13D:
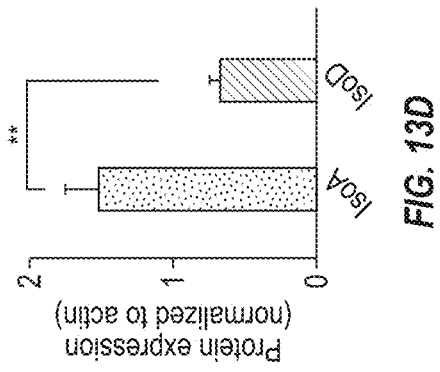
Figure 13A:
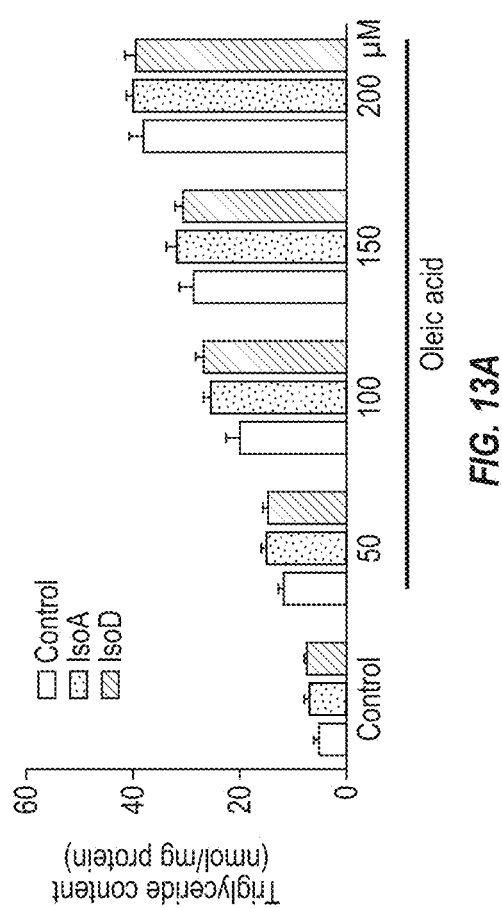
Figure 13C:
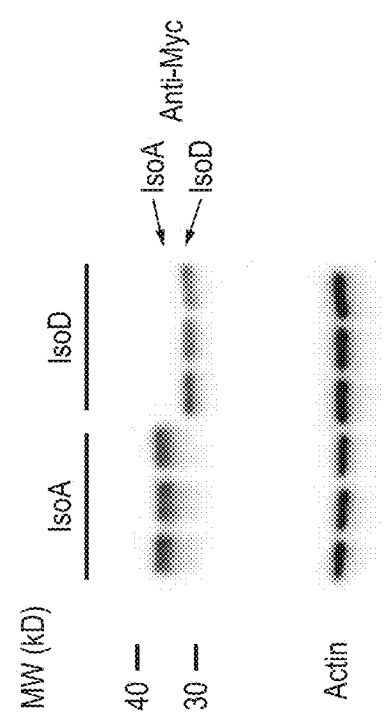

HSD17B13 is expressed primarily in the liver (Liu et al., *Acta Biochim. Pol.* 2007, 54, 213-218, herein incorporated by reference in its entirety for all purposes), where it localizes to lipid droplets (Su et al., *Proc. Natl. Acad. Sci. USA*, 2014, 111, 11437-11442, doi:10.1073/pnas.1410741111, herein incorporated by reference in its entirety for all purposes), consistent with a role in the pathogenesis of fatty liver disease. We evaluated the expression of HSD17B13 and its localization in an immortalized human liver cell line stably transduced with lentivirus expressing HSD17B13 transcript A or D. HSD17B13 isoform A was mainly detected on membranes surrounding BODIPY-labeled lipid droplets (data not shown). Similar subcellular localization was observed for HSD17B13 isoform D at the lipid droplet surface (data not shown and FIG. 12). No differences in intracellular triglyceride content were observed with oleic acid treatment of cell lines overexpressing GFP control or HSD17B13 isoforms A or D (FIGS. 13A-13D).

Effect of rs72613567:TA on HSD17B13 Activity in vitro and in Cellular Models

Figure 14:
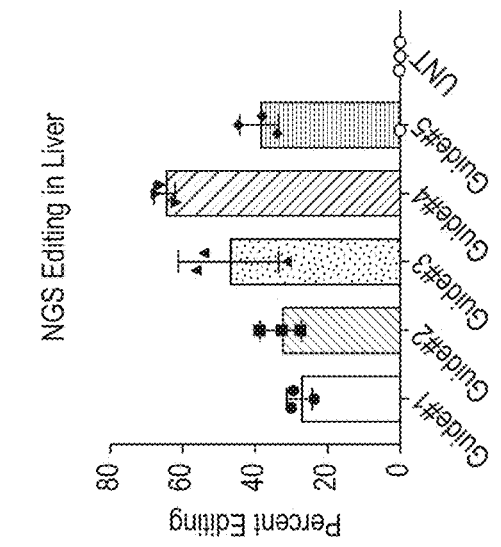
FIG. 14 shows $K_m$ and $V_{max}$ values for estradiol using purified recombinant HSD17B13 protein. For $K_m$ and $V_{max}$ determinations, assays were performed with a dose range of 17β-estradiol between 0.2 μM to 200 μM and time points from 5 minutes to 180 minutes, with 500 μM $NAD^+$ and 228 nM HSD17B13. $V_{max}$ and $K_m$ were then determined using the Michaelis-Menten model and Prism software (GraphPad Software, USA).

To understand the functional consequences of premature truncation of the HSD17B13 protein due to rs72613567:TA, we evaluated the enzymatic activity of isoforms A and D in vitro using recombinant protein and nicotinamide adenine dinucleotide as cofactor. We tested 265 unique putative substrates, and identified steroid substrates and bioactive lipids (e.g. leukotriene B4) as enzymatic substrates of HS17B13. We focused subsequent characterization of HSD17B13 enzymatic activity on enzymatic conversion of estradiol ($V_{max}$ and $K_m$ values in FIG. 14), which resulted in oxidation of a hydroxyl to a ketone group. HSD17B13 isoform D showed greatly reduced activity towards estradiol in vitro (FIG. 10D) and in cell-based enzymatic conversion assays (FIG. 10E) when compared to HSD17B13 isoform A.

By linking large-scale exome sequencing to EHR-derived clinical phenotypes, we identified a novel association between a splice variant in HSD17B13 and decreased serum transaminase levels, as well as reduced risk of nonalcoholic and alcoholic forms of liver disease. These associations were observed consistently in four independent cohorts, and across several different liver disease categories, including advanced cirrhotic forms of liver disease and HCC. The HSD17B13 rs72613567:TA allele was not associated with simple steatosis, but was associated with reduced risk of NASH and fibrosis, suggesting that this variant allele protects from progression to more clinically advanced stages of chronic liver disease. In a phenome-wide association study, HSD17B13 rs72613567:TA was not significantly associated with clinical diagnoses or measurements other than chronic liver disease and associated clinical measurements (hepatic transaminases and platelet counts), suggesting that the clinical effects of the variant allele may be specific to chronic liver disease.

Other hydroxysteroid 17-beta dehydrogenase family members are involved in sex steroid and fatty acid metabolism (Moeller, *Mol. Cell. Endocrinol.*, 2009, 301, 7-19, doi:10.1016/j.mce.2008.10.040, herein incorporated by reference in its entirety for all purposes), but little is known about the function of HSD17B13. HSD17B13 overexpression was shown previously to increase lipogenesis in mouse liver, and to increase the number and size of lipid droplets in cultured hepatocytes (Su et al., *Proc. Natl. Acad. Sci. USA*, 2014, 111, 11437-11442, doi:10.1073/pnas.1410741111, herein incorporated by reference in its entirety for all purposes). Two previous studies also showed that hepatic expression of HSD17B13 protein is increased in patients with fatty liver (Su et al., *Proc. Natl. Acad. Sci. USA*, 2014, 111, 11437-11442, doi:10.1073/pnas.1410741111 and Kampf et al., *FASEB J.*, 2014, 28, 2901-2914, doi:10.109643.14-250555, each of which is herein incorporated by reference in its entirety for all purposes). Our data suggest that both HSD17B13 isoforms are expressed on the lipid droplet membrane, but do not appear to modulate intracellular neutral fat content, a finding that mirrors the lack of an association between the HSD17B13 rs72613567:TA and simple steatosis in humans. Although the physiological substrates of HSD17B13 are not known, enzymatic studies demonstrate that the HSD17B13 isoform encoded by the HSD17B13 rs72613567:TA allele is catalytically defective against estradiol. While at this time it is not clear if any of the substrates tested are critical for liver disease, it is intriguing that HSD17B13 has enzymatic activity against several bioactive lipid species (e.g. leukotriene B4) that have previously been implicated in lipid-mediated inflammation (Li et al., *Nature Medicine*, 2015, 21, 239-247, doi:10.1038/nm.3800, herein incorporated by reference in its entirety for all purposes).

This HSD17B13 variant may provide an avenue to new therapeutic strategies targeting chronic liver disease, similar to genetic variants that have guided the way to new therapeutics in other domains. Our data indicate that HSD17B13 modulates progression of liver disease from steatosis to later stages of NASH, fibrosis, and cirrhosis, which are associated with significant morbidity and mortality, and for which there are currently no effective treatments.

Example 4. Modification of Mouse Hsd17b13 Locus Using CRISPR/Cas9 Ex Vivo and In Vivo As a proof of concept for targeting Hsd17b13 using the CRISPR/Cas9 system, mouse Hsd17b13 guide RNAs targeting either the exon 1 region or the exon 6/7 region of the mouse Hsd17b13 locus were tested. The guide RNA target sequences are provided in Table 12. The guide RNA DNA-targeting segments corresponding to SEQ ID NOS: 259-268 are set forth in SEQ ID NOS: 1643-1652, respectively, which are identical to SEQ ID NOS: 259-268 except with uracils instead of thymines. The NCBI Gene ID for mouse Hsd17b13 (hydroxysteroid (17-beta) dehydrogenase 13 is 243168 (SEQ ID NO: 269). The mouse genomic locus is on chromosome 5, NC_000071.6 (103955442 . . . 103977388, complement).

TABLE 12

Guide RNA Target Sequences for Mouse

| Region of Hsd17b13 | # | Guide RNA Target Sequence | gRNA Target Seq | crRNA | sgRNA v1 | sgRNA v2 | sgRNA v3 | sgRNA v4 |
|---|---|---|---|---|---|---|---|---|
| Exon 1 | 1 | GGCAGACCGTTCTCATCACG | 259 | 490 | 720 | 950 | 1180 | 1410 |
|  | 2 | CTTTACCAGTGACTCCAGGT | 260 | 491 | 721 | 951 | 1181 | 1411 |
|  | 3 | GTCACAGATTTCCTTCTCCG | 261 | 492 | 722 | 952 | 1182 | 1412 |
|  | 4 | AGATGATGACGCCCACCAGA | 262 | 493 | 723 | 953 | 1183 | 1413 |
|  | 5 | GGAGAAGGAAATCTGTGACC | 263 | 494 | 724 | 954 | 1184 | 1414 |
| Exons 6/7 | 1 | TGCGAGGAACTTACTTTTCC | 264 | 495 | 725 | 955 | 1185 | 1415 |
|  | 2 | AGAGAAATATTGATATAGGA | 265 | 496 | 726 | 956 | 1186 | 1416 |
|  | 3 | TATCAATATTTCTCTGATCC | 266 | 497 | 727 | 957 | 1187 | 1417 |
|  | 4 | ATCGCTTTTAAGGCACGCTC | 267 | 498 | 728 | 958 | 1188 | 1418 |
|  | 5 | TATACGACTGATCGCTTTTA | 268 | 499 | 729 | 959 | 1189 | 1419 |

The guide RNAs were first tested ex vivo in primary mouse hepatocytes isolated from hybrid wild type mice (75% C57BL/6NTac 25% 12956/SvEvTac). Livers from mice were perfused with 50 mL liver perfusion medium containing 1× PenStrep, followed by 50 mL liver digestion medium (HBSS, 100 mM CaC12, 500 mM HEPES, collagenase). Once livers appeared digested, they were placed into wash medium containing 1× PenStrep and L-glutamine. The livers were torn to release the hepatocytes from the liver through gentle shaking. Once cells were released, they were put through a 70 μm mesh filter and spun at 50 g for 4 minutes at 4° C. The pellets were washed 2× with wash buffer. The pellets were then re-suspended in 20 mL of 38-40% Percoll and spun at 200g×10 min at 4° C. The pellet was washed 2× and re-suspended in plating medium (Williams E Media, 1× Penstrep, 1× L-glutamine, 5% FBS). Cells were plated at 300,000 cells per well in 24-well collagen-coated tissue culture plates. After the cells were allowed to attach for 6-18 hrs, the plating medium was replaced with medium without FBS. Reagents used are shown in Table 13.

TABLE 13

Reagents for Isolation of Primary Hepatocytes.

| Material | Catalog Number |
|---|---|
| Liver Perfusion Media | Gibco [17701-038] |
| HBSS (1x) | Gibco [14175-079] |

TABLE 13-continued

Reagents for Isolation of Primary Hepatocytes.

| Material | Catalog Number |
|---|---|
| Hepatocyte Wash Media | Gibco [17704-024] |
| Williams E media | Gibco [A12176-01] |
| Penstrep (100x) | Gibco [15140163] |
| L-glutamine (200 mM) | Gibco [25030081] |
| FBS supplement | Gibco [A13450] |
| HEPES | Gibco [15630080] |
| Collagen | Gibco [A1048301] |
| Acetic acid | Sigma [A6283] |
| Liberase TM | Roche [TM05401119001] |
| Primary Hepatocyte Thawing and Plating Supplements | Gibco [CM3000] |
| Primary Hepatocyte Maintenance Supplements | Gibco [CM4000] |
| Percoll | GE [17-0891-01] |

Ribonucleoprotein complexes (RNPs) containing Cas9 and a mouse Hsd17b13 gRNA were added to the freshly isolated primary mouse hepatocytes. For ex vivo experiments in primary mouse hepatocytes, modular guide RNAs having a separate crRNA and tracrRNA were used. The crRNA SEQ ID NOs are set forth in Table 12, and the tracrRNA sequence is set forth in SEQ ID NO: 1422. Each Cas9/gRNA RNP complex was transfected at a final concentration of 2 nM using CRISPRMAX™. After 48 hrs, DNA lysates were prepared from the cells, and next-generation sequencing was performed for each guide RNA tested to determine insertion/deletion (indel) frequency over the predicted cut sites.

Figure 15:
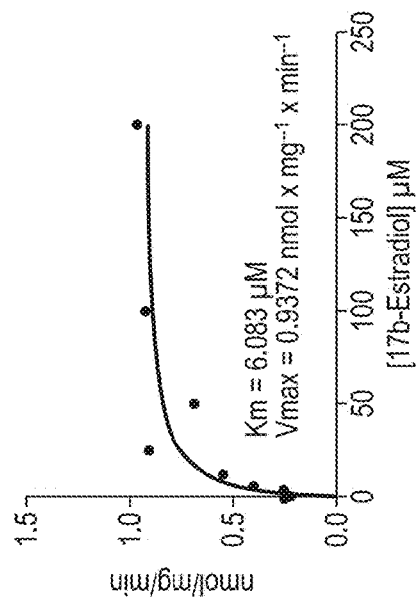
FIG. 15 shows percent genome editing (total number of insertions or deletions observed within a window 20 base pairs on either side of the Cas9-induced DNA break over the total number of sequences read in the PCR reaction from a pool of lysed cells) at the mouse Hsd17b13 locus as determined by next-generation sequencing (NGS) in primary hepatocytes isolated from hybrid wild type mice (75% C57BL/6NTac 25% 12956/SvEvTac). The samples tested included hepatocytes treated with ribonucleoprotein complexes containing Cas9 and guide RNAs designed to target the mouse Hsd17b13 locus.

FIG. 15 shows editing levels (% reads with indels) in the mouse Hsd17b13 gene with each of the guide RNAs in primary mouse hepatocytes, including each of the five guide RNAs targeting the exon 1 region and each of the five guide RNAs targeting the exon 6/7 region. Editing efficiency refers to the total number of insertions or deletions observed over the total number of sequences read in the PCR reaction from a pool of lysed cells as determined by next generation sequencing. Nearly all of the guide RNAs showed an editing efficiency of at least 20%.

Next, the five mouse Hsd17b13 guide RNAs were tested in vivo in mice with a genomically integrated Cas9 gene (Cas9-ready mice). For in vivo experiments in mice, chimeric single guide RNAs were used. The DNA-targeting sequence for each guide RNA is equivalent to the guide RNA target sequence set forth in Table 12, with uracils replacing the thymines. Each single guide RNA included the DNA-target sequence upstream (5') of the gRNA scaffold set forth in SEQ ID NO: 1420. The sgRNA SEQ ID NOs are set forth in Table 12 (column for sgRNA v1). Other sgRNA variations using different guide RNA scaffold are included in Table 12 but were not tested. For each guide RNA, three Cas9-ready male mice were dosed per group. Guide RNAs were introduced via adeno-associated virus (AAV8) carrying an sgRNA expression cassette by tail vein injection (1E11 per mouse in 100 μL PBS). Wild type mice that do not express any Cas9 were dosed with all five guide RNAs as a negative control. Three weeks post-injection, the animals were euthanized, and blood serum was harvested along with liver and other tissues. The tissues were processed into DNA lysates that were then analyzed by NGS sequencing.

Figure 16:
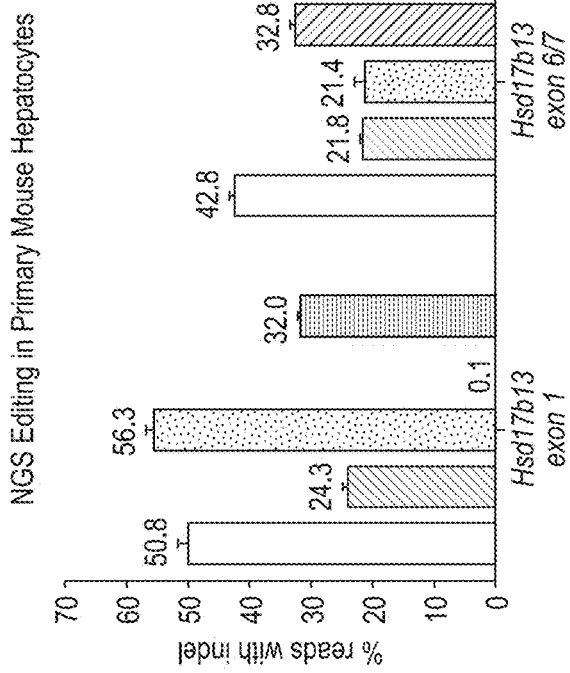
FIG. 16 shows percent genome editing (total number of insertions or deletions observed over the total number of sequences read in the PCR reaction from a pool of lysed cells) at the mouse Hsd17b13 locus as determined by next-generation sequencing (NGS) in samples isolated from mouse livers three weeks post-injection of AAV8 containing sgRNA expression cassettes designed to target mouse Hsd17b13 into Cas9-ready mice. Wild type mice not expressing any Cas9 were injected with AAV8 containing all of the sgRNA expression cassettes were used as a negative control.

As shown in FIG. 16, NGS sequencing showed significant editing in liver for all five guide RNAs (percent editing of at least 20% for each). Editing efficiency refers to the total number of insertions or deletions observed over the total number of sequences read in the PCR reaction from a pool of lysed cells. Minimal or no statistically significant levels of gene editing were observed in other tissues (data not shown).

Serum chemistry analysis for the liver enzymes ALT, AST, triglycerides, total cholesterol, HDL, LDL, non-esterified fatty acids (NEFA), and albumin showed little difference between various treatment groups (data not shown).

Figure 17A:
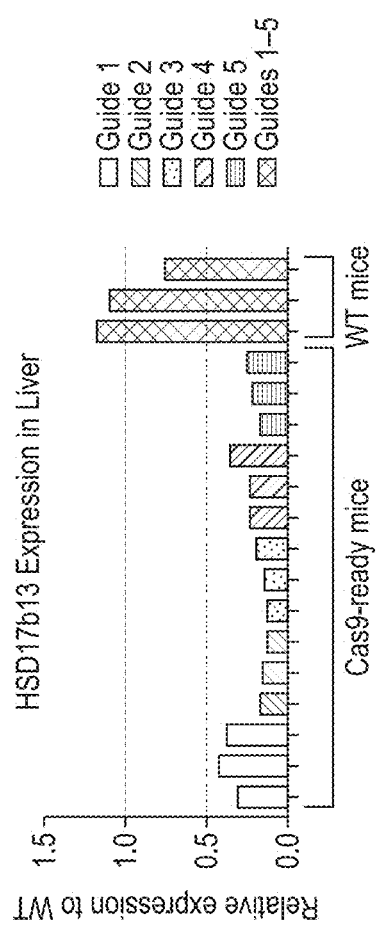
FIGS. 17A and 17B show relative mRNA expression for mouse Hsd17b13 and a non-target HSD family member, respectively, as determined by RT-qPCR in liver samples from Cas9-ready mice treated with AAV8 carrying guide RNA expression cassettes designed to target mouse Hsd17b13. Wild type mice not expressing any Cas9 were injected with AAV8 carrying guide RNA expression cassettes for all of the guide RNAs were used as a negative control.
Figure 17B:
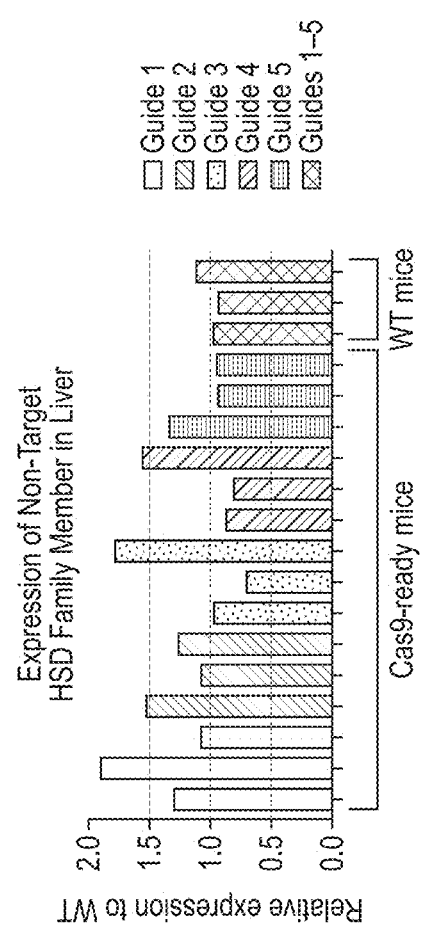

Hsd17b13 expression was evaluated by assessing equal mass amounts of RNA from liver by RT-qPCR. The genomic DNA was degraded so that it would not count towards the qPCR reaction. The RNA was reverse transcribed and then an assay specific to Cas9 was used to detect Cas9 transcripts. Each individual Hsd17b13 guide RNA showed at least 50% ablation of Hsd17b13 mRNA expression. See FIG. 17A. In contrast, no significant decreases were observed in expression of a non-target HSD family member. See FIG. 17B.

We claim:

1. A method of modifying or altering expression of an HSD17B13 gene in a cell, comprising introducing into the cell:
   (a) a Cas9 protein or a nucleic acid encoding the Cas9 protein; and
   (b) a first guide RNA or a DNA encoding the first guide RNA, wherein the first guide RNA comprises a first CRISPR RNA (crRNA) portion and a first trans-activating CRISPR RNA (tracrRNA) portion, wherein the first guide RNA forms a complex with the Cas9 protein and targets a first guide RNA target sequence within the HSD17B13 gene, wherein the first guide RNA target sequence includes or is proximate to the start codon for the HSD17B13 gene, and
   wherein the Cas9 protein cleaves the first guide RNA target sequence to generate a targeted genetic modification in the HSD17B13 gene or the Cas9 protein binds the first guide RNA target sequence and alters expression of the HSD17B13 gene.

2. The method of claim 1, wherein:
   (a) the first guide RNA target sequence comprises any one of SEQ ID NOS: 20-81 and 259-263; and/or
   (b) the first guide RNA comprises a DNA-targeting segment that comprises any one of SEQ ID NOS: 1423-1484 and 1643-1647; and/or
   (c) the first guide RNA comprises any one of SEQ ID NOS: 500-561, 730-791, 960-1021, 1190-1251, 720-724, 950-954, 1180-1184, and 1410-1414.

3. The method of claim 2, wherein:
   (a) the first guide RNA target sequence comprises any one of SEQ ID NOS: 20-41, any one of SEQ ID NOS: 21-23, 33, and 35, or any one of SEQ ID NOS: 33 and 35; and/or
   (b) the first guide RNA comprises a DNA-targeting segment that comprises any one of SEQ ID NOS: 1447-1468, any one of SEQ ID NOS: 1448-1450, 1460, and 1462; or any one of SEQ ID NOS: 1460 and 1462; and/or
   (c) the first guide RNA comprises any one of SEQ ID NOS: 524-545, 754-775, 984-1005, and 1214-1235, or any one of SEQ ID NOS: 295-297, 525-527, 755-757, 985-987, 1215-1217, 307, 309, 537, 539, 767, 769, 997, 999, 1227, and 1229, or any one of SEQ ID NOS: 307, 309, 537, 539, 767, 769, 997, 999, 1227, and 1229.

4. The method of claim 1, wherein the Cas9 protein is a nuclease-active Cas9 protein.

5. The method of claim 1, wherein the Cas9 protein is a nuclease-inactive Cas9 protein fused to a transcriptional repressor domain.

6. The method of claim 1, wherein the Cas9 protein is a nuclease-inactive Cas9 protein fused to a transcriptional activator domain, and wherein the HSD17B13 gene comprises a thymine inserted between nucleotides corresponding to positions 12665 and 12666 of SEQ ID NO: 1 when the HSD17B13 gene is optimally aligned with SEQ ID NO: 1.

7. The method of claim 1, further comprising introducing into the cell a second guide RNA or a DNA encoding the second guide RNA, wherein the second guide RNA comprises a second CRISPR RNA (crRNA) portion and a second trans-activating CRISPR RNA (tracrRNA) portion, wherein the second guide RNA forms a complex with the Cas9 protein and targets a second guide RNA target sequence within the HSD17B13 gene, wherein the second guide RNA target sequence includes or is proximate to the stop codon for the HSD17B13 gene, wherein the cell is modified to comprise a deletion between the first guide RNA target sequence and the second guide RNA target sequence.

8. The method of claim 7, wherein:
   (a) the second guide RNA target sequence comprises any one of SEQ ID NOS: 82-225; and/or
   (b) the second guide RNA comprises a DNA-targeting segment that comprises any one of SEQ ID NOS: 1485-1628; and/or
   (c) the second guide RNA comprises any one of SEQ ID NOS: 562-705, 792-935, 1022-1165, and 1252-1395.

9. The method of claim 1, further comprising introducing an expression vector into the cell, wherein the expression vector comprises a recombinant HSD17B13 gene comprising a thymine inserted between nucleotides corresponding to positions 12665 and 12666 of SEQ ID NO: 1 when the recombinant HSD17B13 gene is optimally aligned with SEQ ID NO: 1.

10. The method of claim 9, wherein the recombinant HSD17B13 gene is a human gene.

11. The method of claim 9, wherein the recombinant HSD17B13 gene is an HSD17B13 minigene in which one or more nonessential segments of the gene have been deleted with respect to a corresponding wild type HSD17B13 gene.

12. The method of claim 11, wherein the deleted segments comprise one or more intronic sequences.

13. The method of claim 11, wherein the HSD17B13 minigene comprises an intron corresponding to intron 6 of SEQ ID NO: 2 when optimally aligned with SEQ ID NO: 2.

14. The method of claim 1, further comprising introducing an expression vector into the cell, wherein the expression vector comprises a nucleic acid encoding an HSD17B13 protein that is at least 90%, at least 95%, at least 96%, at least 97%, at least 98%, at least 99%, or 100% identical to SEQ ID NO: 15 (HSD17B13 Isoform D).

15. The method of claim 14, wherein the nucleic acid encoding the HSD17B13 protein is at least 90%, at least 95%, at least 96%, at least 97%, at least 98%, at least 99%, or 100% identical to SEQ ID NO: 7 (HSD17B13 Transcript D) when optimally aligned with SEQ ID NO: 7.

16. The method of claim 1, further comprising introducing an HSD17B13 protein or fragment thereof into the cell, wherein the HSD17B13 protein or fragment thereof is at least 90%, at least 95%, at least 96%, at least 97%, at least 98%, at least 99%, or 100% identical to SEQ ID NO: 15 (HSD17B13 Isoform D).

17. The method of claim 1, wherein the cell is a mouse cell, a rat cell, or a human cell.

18. The method of claim 1, wherein the cell is a human liver cell, a mouse liver cell, a rat liver cell, a mouse pluripotent cell, or a rat pluripotent cell.

19. The method of claim 1, wherein the cell is ex vivo or in vivo.

20. The method of claim 18, wherein the cell is the human liver cell.

21. The method of claim 20, wherein the cell is in vivo.

22. The method of claim 1, wherein the method results in loss of function of the HSD17B13 gene.

23. The method of claim 1, wherein the method results in disruption of the start codon of the HSD17B13 gene.

24. The method of claim 1, wherein the first guide RNA target sequence is within a region corresponding to exon 1 of SEQ ID NO: 1 or 2 when the HSD17B13 gene is optimally aligned with SEQ ID NO: 1 or 2.

25. The method of claim 1, wherein the method further comprises introducing into the cell a second guide RNA or a DNA encoding the second guide RNA, wherein the second guide RNA forms a complex with the Cas9 protein and targets a second guide RNA target sequence within the HSD17B13 gene, wherein the second guide RNA target sequence includes or is proximate to the start codon for the HSD17B13 gene.

26. The method of claim 7, wherein the coding sequence of the HSD17B13 gene is deleted.

27. The method of claim 7, wherein the second guide RNA target sequence is within a region corresponding to exon 7 of SEQ ID NO: 1 or 2 when the HSD17B13 gene is optimally aligned with SEQ ID NO: 1 or 2.

28. The method of claim 1, wherein the method comprises introducing into the cell the nucleic acid encoding the Cas9 protein.

29. The method of claim 28, wherein the method comprises introducing into the cell the nucleic acid encoding the Cas9 protein, wherein the nucleic acid encoding the Cas9 protein comprises DNA.

30. The method of claim 28, wherein the method comprises introducing into the cell the nucleic acid encoding the Cas9 protein, wherein the nucleic acid encoding the Cas9 protein comprises RNA.

31. The method of claim 1, wherein the method comprises introducing into the cell the first guide RNA in the form of RNA.

32. The method of claim 1, wherein the method comprises introducing into the cell the DNA encoding the first guide RNA.

33. The method of claim 1, wherein the Cas9 protein or the nucleic acid encoding the Cas9 protein and/or the first guide RNA or the DNA encoding the first guide RNA are introduced into the cell via lipid-nanoparticle-mediated delivery.

34. The method of claim 1, wherein the Cas9 protein or the nucleic acid encoding the Cas9 protein and/or the first guide RNA or the DNA encoding the first guide RNA are introduced into the cell via adeno-associated virus.

35. The method of claim 2, wherein the cell is a human cell, and wherein:
(a) the first guide RNA target sequence comprises any one of SEQ ID NOS: 20-81; and/or
(b) the first guide RNA comprises a DNA-targeting segment that comprises any one of SEQ ID NOS: 1423-1484; and/or
(c) the first guide RNA comprises any one of SEQ ID NOS: 500-561, 730-791, 960-1021, and 1190-1251.

36. The method of claim 35, wherein:
(a) the first guide RNA target sequence comprises any one of SEQ ID NOS: 20-41, any one of SEQ ID NOS: 21-23, 33, and 35, or any one of SEQ ID NOS: 33 and 35; and/or
(b) the first guide RNA comprises a DNA-targeting segment that comprises any one of SEQ ID NOS: 1447-1468, any one of SEQ ID NOS: 1448-1450, 1460, and 1462; or any one of SEQ ID NOS: 1460 and 1462; and/or
(c) the first guide RNA comprises any one of SEQ ID NOS: 524-545, 754-775, 984-1005, and 1214-1235, or any one of SEQ ID NOS: 295-297, 525-527, 755-757, 985-987, 1215-1217, 307, 309, 537, 539, 767, 769, 997, 999, 1227, and 1229, or any one of SEQ ID NOS: 307, 309, 537, 539, 767, 769, 997, 999, 1227, and 1229.

37. The method of claim 2, wherein the cell is a mouse cell, and wherein:
(a) the first guide RNA target sequence comprises any one of SEQ ID NOS: 259-263; and/or
(b) the first guide RNA comprises a DNA-targeting segment that comprises any one of SEQ ID NOS: 1643-1647; and/or
(c) the first guide RNA comprises any one of SEQ ID NOS: 720-724, 950-954, 1180-1184, and 1410-1414.

38. The method of claim 7, wherein the cell is a human cell, and wherein:
(a) the first guide RNA target sequence comprises any one of SEQ ID NOS: 20-81; and/or
(b) the first guide RNA comprises a DNA-targeting segment that comprises any one of SEQ ID NOS: 1423-1484; and/or
(c) the first guide RNA comprises any one of SEQ ID NOS: 500-561, 730-791, 960-1021, and 1190-1251; and/or
(d) the second guide RNA target sequence comprises any one of SEQ ID NOS: 82-225; and/or
(e) the second guide RNA comprises a DNA-targeting segment that comprises any one of SEQ ID NOS: 1485-1628; and/or
(f) the second guide RNA comprises any one of SEQ ID NOS: 562-705, 792-935, 1022-1165, and 1252-1395.

39. The method of claim 1, wherein the first guide RNA is a single-molecule guide RNA in which the first crRNA portion is linked to the first tracrRNA portion.

40. The method of claim 39, wherein the first guide RNA comprises the sequence set forth in SEQ ID NO: 1420, 256, 257, or 258.

41. The method of claim 1, wherein the first crRNA portion and the first tracrRNA portion are separate RNA molecules.

42. The method of claim 41, wherein the first crRNA portion comprises the sequence set forth in SEQ ID NO: 1421 and/or the first tracrRNA portion comprises the sequence set forth in SEQ ID NO: 1422.

43. The method of claim 1, wherein the first guide RNA comprises a modification providing for modified or regulated stability.

44. The method of claim 1, wherein the first guide RNA target sequence is within about 10, 20, 30, 40, 50, 100, 200, 300, 400, 500, or 1,000 nucleotides of the start codon for the HSD17B13 gene.

45. The method of claim 44, wherein the first guide RNA target sequence comprises the start codon for the HSD17B13 gene.

46. The method of claim 7, wherein the method results in deletion of an HSD17B13 coding region between the first guide RNA target sequence and the second guide RNA target sequence.

47. The method of claim 7, wherein the second guide RNA target sequence is within about 10, 20, 30, 40, 50, 100, 200, 300, 400, 500, or 1,000 nucleotides of the stop codon for the HSD17B13 gene.

48. The method of claim 47, wherein the second guide RNA target sequence comprises the stop codon for the HSD17B13 gene.

49. The method of claim 25, wherein the second guide RNA target sequence is within about 10, 20, 30, 40, 50, 100, 200, 300, 400, 500, or 1,000 nucleotides of the start codon for the HSD17B13 gene.

50. The method of claim 49, wherein the second guide RNA target sequence comprises the start codon for the HSD17B13 gene.

51. The method of claim 1, wherein the targeted genetic modification is generated by repair of the cleaved first guide RNA target sequence by non-homologous end-joining.

52. The method of claim 1, wherein the targeted genetic modification is generated by repair of the cleaved first guide RNA target sequence by homologous recombination.

\* \* \* \* \*

SEQUENCE LISTING

<160> NUMBER OF SEQ ID NOS: 1652

<210> SEQ ID NO 1
<211> LENGTH: 19118
<212> TYPE: DNA
<213> ORGANISM: Homo sapiens

<400> SEQUENCE: 1

```
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataaggtaat gtatacatct tccaactttt     300
taaagtcaca gagtaagata tgtattttaa gaattatttg acttaccatc tacttatctt     360 tgtattttttg ttttcaaag tttgataaat tccctggtcc cttagtctgt atatgtgtca     420
ggttagttag atgaagggaa tgtaattaag aactaagcag cgatttttat gacatggtgt     480
gcaggttgat agaaagactc aggagccagt ctccttccaa gctgctaaat gaggcaagtc     540
acatattatc tctcagcctg ttttcttggc tctgaagtgg ggataataac ttaggggatg     600
ggcaagaacg ggatctgaaa attacagcta caaacaaaag tcaaacgaag aacttgcaac     660 agaaacctt agtgcctccc ctcatgcaca agcaacacag ttctaaaata tttactgtct     720 gacccttac agaaaatgtt tgccagtccg tagtcaaaag gattaaataa gtaatatttt     780
cagcacttag catatgataa acgatacgtg gcacatgata aacaataact gtgttaaata     840
aaatatgtgc gcagtgagtc aggcttttcc ttggacatta gtattttttcc tgtgttctta     900 cttgtaaaca ctacattaac aaccccaaat aaaactgaag gaactgaaat cttgtatcat     960
tttctctaaa cttgtaaatt ctggtaaggc catgaaaata tatgcagaga agtgtttaca    1020
ggattttagg attggaaaaa ttgtgaagta ctccttgaga atcacatttt ctgcaaatta    1080
cagtggtttt aattaccatt atattattac tttctcatgt tctttgctgt catgtttagt    1140
tgaaacctaa aatgtctctt acacttagag aactaattct tttctgtttt ttttctgaat    1200
agtgaagaat actatacaaa aaagctacta catttttatt taacagatat gagcatttat    1260
ataatagagg agttgatgta tataaaaatg atttgccatc ttttttggtct ttgaagaaat    1320 tcgaatgaac tttctggaag atagcaagaa tttacaaata gagaaaattg ttgcctgctg    1380
```

```
ttctcaggca tttgtccaaa aatataaata agtataaatc tatgaaaagg gcttgatgaa    1440
atctaaccct caaatctctt tccagatgtg tattttttggg gaaagggcta tatttattaa    1500
gtttttttta aattttaaaa tttccagaga caagagaaaa gtaaattaga aggaagtcgt    1560
attaaaaatg acttaagggc gggtgcagtg gctcacacct gtaatcccag cactttggga    1620
gacggaggtg ggcagattgc tggagcccag gagttcaaga ccagcctggg cagcacagca    1680 aaaccccccaa ctctacaaaa aatacaaaaa ttagctgggt gcgggggtgc acacccgtag    1740
tcccagctac tcgggaggct gaggtgggag gatcgtttca gttcaggaag ccaaggctgc    1800
aatgagctat gatggcatca ttgcactcca agctgggcaa tagagccagg ctctgtctca    1860
aaaaaaataa aaaagactt aagaaaaata ggtaacccaa cctcaaaaat tctctttgaa    1920
tcattaaatt tcatggttaa acatttaagc tactgaatga ttcactctaa ggctgtaatg    1980
taactcagat ctcctttagg cgaggaagat gctggctgag ttttcatcat aactggctcc    2040
ttttgccctg tgagatgaga gacacagtag cagtttggct cttatgcaat ctaaactgtt    2100
gcgttgggaa tacggttcaa aaaacacatt ggagtttaag ctaaagcaag tgttttgcta    2160
acaaaaagac aaggcatcac attttgcaat tgtctagctc agttataaaa cagaagaata    2220
ggccggacgc ggtggctcac gcctgtaatc ccagcacttt gggaggccga gacgggcgga    2280
tcacgaggtc aggagatcga gaccatcctg gataacacag tgaaacccccg tctctactaa    2340 aaatacaaaa aaattagcca ggcgtagtgg cgggcgcctg tagtcccagc tactcgggag    2400
gctgaggcag gagaatggtg tgaacccggg aggcggagct tgcagtgagc cgagatgacg    2460
ccactgcact ccagcctggg cgacagagcg agactccgtc tcaaaaaaaa aaaaaaaaa    2520 aaaactgaag aataattaat tcttcaatca aacatctga tgaatgctct ggtaacttat    2580
gctctctact gacctagaaa caaatgagag agtatggtgt ggtttgtgca atctggcagt    2640
gagcaagcta ccaactaaat cagtgaaaga ctctccctatt ctttttttac tcttctgcaa    2700
tcccacaaaa ggctatttga ggggatactg actttgagac tgggtcctaa catccatgtt    2760 tgggagttc aggctgctgc tccagggttt agcctacagt agcgaaatac aaaggaccca    2820
gagaccactc attcaaggtt tgccctaaat agcagcaaca ccactgtcat ctcaatacac    2880
gaagaatagg gcttttcagg tatccttgcc tctttgtcac agagaagagt ttacagattg    2940
tgagacggaa aagtataatt tttaaaacct tataatattt tctataaaag tcacctgagg    3000
tgaaaacttg aaaagaatta taattttcca gaatgtgagt caagaaacat tagagcaatt    3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtagcag catggtctcc    3240
ctatgaaagt ccttcttctt taaggagact tctttccctt ccctcctagg aggatgagtc    3300
agaatcatca agaaaatat gatgggcaga ggcatacagt ttaccattac cactagttta    3360
gaattactac ttagcacttt actgcctatt acatagttgg tgctcaacaa atgtatgata    3420
aattaatggt tgagtttttc tttcttctcc atattcatct tccatgacac cacgaagagc    3480 aatgttttc aagaatgttc ttcaaggttt gaaagtagcc tgcttagag aaactgccta    3540 ctgtacagcc tccaaccaag aggaaaagct gaaaaaagca tgaagggatt tgttttgtt    3600 ttgtttgttt tggttttaat atgagcattc cctggcagaa aagccagggg taatctcatt    3660
gcaactaggc aatcactctc aagaaatttt ctaacaaata aggaggccaa ttttttattt    3720
```

```
attttgagac gaagtcccac tctgtcaccc aggttggagt gcaatggaat gatttcagct    3780
cactgcaacc tccgcctccc gggttcaagt gattctcctg tctaaacttc ccgagtagct    3840
gggattacag gctcccacca ccacgcccag ctaatttttt gtattttag tagagatggg     3900 gtttcaccat tttggccaga ctggtctcaa actcctgacc tcaagtgatc caccctcctc    3960
ggcctcctaa agtgctggga ttacaggcgt gagccaccac acctgaccca ggaggccaat    4020
ttttaaaagg ttaactaatc ttcatgtcca aatgaatgt taattgttca ttttggacat     4080
gaatgttaat tttttttttt tttttttttg agacagagtc tcactctgtt gcccaggctg    4140
gagtccagtg gcactatctc cactcactgc aacttcctcc tcccaggttc aagcaattat    4200
cctgcctcag cctcccaagt agctgggatt acaggcccac accatcaggc ctggctaatt    4260
tttgtatttt tagtagagac ggggtttcac catgttggcc aggctggtct tgaactcctg    4320
acctcgtgat ccgccctcct cggccaacca agtgctggg attacaggcg tgagccaccg     4380
cgcctagccg aatgttaatt gtctaaaaat ttttcttctc caatgtcttc tcctccactt    4440
ttttcggaat ttgtttcttc ctaattacag cgcggtgtgg aggaaactgc agctgagtgc    4500
cgaaaactag gcgtcactgc gcatgcgtat gtggtagact gcagcaacag agaagagatc    4560
tatcgctctc taaatcaggt gagactgcag gttcacaaat ttcttcagat tattttgttt    4620
cctaggacgc tgacgtggaa aatgagaaag gtctttatga ctgcctgatt taaattggat    4680
tttagctgct aactgaagta gttatgtcac caaggaagga tatatacttt ttttcttgta    4740
tgtaatccac tcagctctgc ccattattat tgttcatatt attaatcaat ttcattctga    4800
tcagaagtgt gagcagtggc acagagtgac tgacaaaaga tttatcatca gggaatatgg    4860
atcacttcct agttttgttt tagtcctatt aactttgcag taattccagc ttctctttaa    4920
ttatttccct tgtgagattt tattttggtg ttaatgtagt cttctgtaga aaatgtaata    4980
ttaataatta ttatcacaat tattttaaaa gagtaaatac caaataatca caatgaacta    5040
agcactctaa caaactttac atttttaat tcaatcccta caataactct gtaaacttca     5100
ttttacagat aagcaaatta tgactcagag aggttaagcc agacccaggt catgtagtta    5160
ttaggttatg aaaccaggat ttctcaacca gcactttaga ccaggtgcgg tggttcacac    5220
atgtaatccc agcactttgt gaggccaagg tggaaggatc acatgagacc aagagttcaa    5280
gaccagccca ggcaacatag tgagacccta tctctaaaaa aaaaaaaaa aaaaaaaaa     5340 aaagtttaaa gaaaaacaca ttttaaaaa atgaacactt taaaaatatt tggtcagaat     5400
ttatatagga atttatcaac ataaatgtta atttcacttt actgataaac ttgcaaaaca    5460
tgatgtgctg ggtactgaaa tttagatgtt aaaagaacag tttatcccac ctttatgaca    5520
gtgttccctt ggcctccacg atttgagctc aacagtctgt cttgcctgaa ctctgagaga    5580
cctcatacaa tagaagaaag actctcatct ttggattata ttggtcccaa aactttgagt    5640
ttgaataata cacccagtga agtgttctt tcaatttcaa aaggtgaaga aagaagtggg     5700
tgatgtaaca atcgtggtga ataatgctgg gacagtatat ccagccgatc ttctcagcac    5760
caaggatgaa gagattacca agacatttga ggtcaacatc ctaggacatt tttgggtgag    5820
tgtgagtcag aaacatttct gatttgtgca ccttctctta agatacatga aacttataac    5880
ggagttcaca tacttctgga caggaaactg gccagatctt tgccttaatc aagaatcatt    5940
aaatttgttt gagtagaaga gccacagagt ctctgacaca aggacacaga attcaagtgg    6000
acacaacaca ccagaatgta agctacttgg tctgtcttgt ccaccagtat ctgacacaaa    6060
gcttggcatg taccaggagc tcaacaaatg tttgtggagg tttgttaagg gttgtcagtg    6120
```

```
tacatctttt caatgctgtc acttgtgact tcattttttt ccctccacac catgattttg    6180
taatgtgtcc tcattttgtg gaattttaga atggaaagga catcagaagt aattacttgg    6240
atgtatatag gatcgaggac acttttggac gagactctga ggcaagtgtt ctagatccat    6300
ggggtgctgg aactgagaaa tgcagctata cagacctcat ataattggtt agttttgtgg    6360
gagatggaaa tatcaacttc aactgccttt gtatagaaat ttttatgatt aatcttccag    6420
tgcctcaata ttagtgtaga atctagggca gatctggatt ctagaagaaa gaagaaaaaa    6480
aagagatgtg tccccttac ctttaccagc tcttcacata tgtgaattgg ctcccatgcc     6540
caccaaacta cacggagacc tcatacatta gctacctata gctgcataac aaattataca    6600
aaacttagtg gtttaaagca acaatgtatg ttcactatcc tctcacagtt tctatgggtt    6660
gggaatttgg aggtagcttg ggtttgggagt tctagttcta tgaatttgca taggattttat  6720 taaattctta taaaatttta ttgatgtttc tcacaaaaga ggttttggaa aaaaaagaaa    6780
gacttgtttt ctgtaacatc aacatataat atacaatatt acaaataggg agatagtgaa    6840
ttcaatcatg attcattagt gtggtgtaga actctcagct tacactactc aactgtctta    6900
atacagttac acaagatttc actcttttaa ttagaatgat aaagcccaa accaaaaaat     6960 tatatgacac caaattatca taaggaataa ttttagttct gaaaactctg aattttccc     7020 ttaatattgt ttagatgaca tatccaaaaa aggatctatt tgattccttc tgaagggaag    7080
gagggggagt actgagatta gtgttggcat ggggcttacc ataccaataa atttgtatct    7140
ttatttctat catttgtaaa gaattaatca tggaatgctt ggaagtattt tatttcattg    7200
tataagttct ctcaaatgcc tttctgtctt aacaaaaata aaactacctg atttggaaac    7260
ctaacgtcta tgtcattgtc tttcttcttt ctgcaatgat ccttaagatc acaaaagcac    7320
ttcttccatc gatgatggag agaaatcatg gccacatcgt cacagtggct tcagtgtgcg    7380
gccacgaagg gattccttac ctcatcccat attggtaagt atcacatgcc agccatgtta    7440
tatattttta tactttgaag ggagcattac acttcaaatt gttaccactg gagagtcctg    7500
gttcttggca tcttgaacaa agaattggac aaaactcacc aacaaagcca ggaaagaatg    7560
aagcaacaaa agcagagatt tattgaaaat gaaagtacgc tttacagggt gggagtgggc    7620
ccaagcacag gggctcaaga gccaattaca gaattttctg gggtttaaat accccctaga    7680
ggtttccact ggttacttgg tgtacgccct atgtaaatga agaggatgaa ttaaagttac    7740
agagtcgttt actcagtgta caccatatgt aaatggagag gatatttcct gtcatagctg    7800
gagtgtttcc atttgattta gttctaggaa gtcagcatga atcggcctta tgttccctgc    7860
ctccagaccc tgttctcctg cctcaagatt acaatgctga gagcagagtg atttggattt    7920 acagaatta aatttatagt agtttagaat gattttttaa atgactttt ctaaaacaat      7980 gaaaccaggt tgtaattata tttaagatat ttttagattt ctgcaaactc ctctgtagaa    8040
caatgagaga aaacagtaat gccaagcatg tttccattgt ttcctggaat aagaaacaga    8100
aaccccacag actgagaagc aaaacctaca gaagctaaaa tgaacacatg tctatgtcat    8160
ggccttggtg cccaagataa gacaatcaga gtggtccctg gatcaaaaca ttttacagtg    8220
tgcttgtgcc atgaaagtgt gtgtgtgtgt gtgtgtgtgt gtgtgagaga gagagagaga    8280
gagaaaacga ctctacctga ctaaaagttg cagataccac actccatgca ccaccaaaga    8340
cataaaggga aggaggtgag aggcgttaag gatgtactgc tgtatttgcc aaatatcctt    8400
tcctgtaaac tcttctccag atcctcataa taaaattaag aggccaaagt ggcaaccatt    8460
```

```
gtcaagagaa aaactatcaa ccattgtcaa gagaataact cagttattga gagagagagg   8520
agaaatgagc agagtcctac agaagtctgt caacacagat accagttttg tagaatttct   8580
aaatgtattt ttcctgattc atattttca aaataaaagc agcaataaaa actgattaga    8640
aaacagtttg aagattcaat ggaaaaacct tacatgtagg atggaaaact gaacattaag   8700
ccaatcaata gagttatttt tgttcttttg ttatcattgt tgtttaagaa atgagatacg   8760
ttcacaattc tgcttaatca tgtaagaaaa tgaaatgaa ttgccattta tactctcaga    8820
aaaatcacaa gtggctgatt tttggcttcc acttgttctt aagccaaatg ataccgcctt   8880
ctcacagaaa gctgaggatt ggtttcactc tcccttagct aacaatgctt aataattctc   8940
ttacagttcc agcaaatttg ccgctgttgg ctttcacaga ggtctgacat cagaacttca   9000
ggccttggga aaaactggta tcaaaacctc atgtctctgc ccagttttg tgaatactgg     9060 gttcaccaaa atccaagca caaggtaagg tcaaaatcaa gttagaatgg gtatgtggta    9120
tgataaattg atatgaaaac taatgagaaa tgtttaggca ggccaactaa tagaagaaaa   9180
tgaagaagga aaaataattt ttcttattat tattattatc ttgaaattaa aggaataaag   9240
ggggaaaaca cattagggac tagcaggaat gatcagccac cgatgaactg ggatattat    9300 ttgtgtccgg gagaaagcac atacatttga tcaccgttac caccctgtct ttaaaatgca   9360
aatgttccaa ggaccagcaa ataaattgag tatctagctc cttagtcaag gtgaatttct   9420
gcaagaactc ttgtctctgg tgagacagga tttgagacca caagagaaga aaattagtc    9480 ctgaaaggag aagaaaaaag caggaaggtg tggataagaa cccgaaaatt aagccatctg   9540
cttaacaaat ttttctaatc ctagtatata ttctgctgca ggttaacaaa atatactaag   9600
cttaatgatt cgaaaccaat ttttactgg aagggaatta atcctaaata tattcattca     9660
aaagaactaa acaattctct gttgagtgcc gcctcatttg aggatactga ctcttacagc   9720
ctgagttagc tatgtggtct ctgcagctgg aatcactccc tgccactgga gtccttcatg   9780
gtgttagacc ataggtactg ttgactaaag aaaaaaaaaa gttttgttt ttattttgt      9840 ttttttgag acagagtctc actctgtcac ccaggctgga gtacagtggc gcgatctcag    9900
ctcaccgcaa cctccgcctt tctgggttca agcaattctc cttcctcagc ctcctgagta   9960
tttggattac aggcgcccac caccacgcct ggctaatttt tgtatttta gtagagacgg   10020 ggtttcacca tgttggccag gctggtctca aactcctgac ctcaggtgtc ctacctgcct   10080
tggcctccta aaatgctggg attacaggag tgagccacca tgcccggcca aaaaaataag  10140
tttttaaaga attaaaggtc atcctggcta acacagtgaa accccgtctc tactaaaaaa  10200
cacaaaaaaa ttagccgggc gtggtggcgg gcgcctgtag tcccagctgc gcgggaggct  10260
gaggcaggag aatggcgtga acccgggagg cggagcttgc agtgagccga gatcgcgcca  10320
ctgcactcca gcctgggcga cagagcgaga ctccgtctca aaaaaaaaa aaaaaaaaa    10380 aaaaaaaaga attaaaggtg ttaattttat ttagaagcct tactgaagac tacagtcgga  10440
ggcctatagc ctgagagcag ccctttagag aggttcagtt gaactgttct gatagtgggg  10500
gccatgtgct ctatcctgta ttgtcttcaa agcatctttc cagagagctg cacattgtca  10560
cagagtcagg gactttgtga aattatgctg acaaccagaa gtgagtaaac gtggcttctt  10620
acatttgcta cgttgtctca cagtacttaa taagtatgca atatgtaagt aaatactata  10680
gtactattgc aactcctgat tgttttctta gacaaggaat tgggcccaat aaaaaccctc  10740
ttggtaggca ttcaggcttc gtgtaccatg agctttccta agggtatcct gccactcttg  10800
gggaaggcat gatagatgag gggagtaagg ataatggaac tctgggtaca gggttcctgg  10860
```

```
gggctaactt agaggtagac acaggcaatg ctaaatattt gggattgatt ttatagaggt    10920
tgctagattg tgaatttcct tagtaagggc taaggcattg atatgtaatg tcacacttgg    10980
ctccgaggct gggttgttgg atccatgtag atgaaatcag ggagagaaag ggcagaacgg    11040
agtaatttag aaatgtattg atttgtatta ctctctgttg gcttgctatt caaggcagtg    11100
gagaactcaa tcacataata atctgcagca aaccacagat catcccaggg aatgaagttt    11160
taacattcgc tggctcccta actcctcacc cagcctttac attcactggc tgttcagtcc    11220
atgcctggac atcttaattt gaatacaaca ttttaaatcc attttctgt catcatcttg      11280
cactaacaga caattctaca ctaagcctat gtttatgaat atttctcaag agtacatgta    11340
cacagccttc agtataagga aaactggaag tatgacatac ctccagttgt catactcctt    11400
gggcccctct taaattctca ttaaactgca ggataggcaa gtcagaggtg aatctcaaat    11460
acgaaattct taccggaaag gggttccaat ccagacccca agagagggtt cttagatttc    11520
tcgcaagaaa taattcgggg caaggccaca gtgcaaagca aaagcaagtt tattaggaaa    11580
gtaaaggagt agagaacagc tactccatgg agaagaatgg cttgagctgc tccaccaagg    11640
gtatttagag ttacttcttg attatatgct aaacaagggg tggattattc atgagttttc    11700
cgggaaaagg gtgagcaatt cccagaactg agatttcctc cccttttag gccatatagg     11760
gtaacttcct gccattgcca tggtatttgt aaactgtcat agtgctggtg gaagtgtctc    11820
ttagcttgct aatgtattat agttagctta taatgagcag tgaggacaac cagaggtcac    11880
tttcatcacc atcttggttt tggtgggttt tggccggctt ctttactgca ccctatttta    11940
tcaacaaggt ctttatgacc tgaatcttgt gccaacctcc tatctcatcc tgtgacaaag    12000
aatgccttaa cttcctggga atgcagccca gtaggtgtca gccttatttt acccagaccc    12060
tattcaagat ggagttgctc tgatttaaac gcctctgaca aaatgacgac ctcaaaacaa    12120
tccagcttta tggaatacct ccacaagaaa gaaagtatac ttagctatag aattttctcc    12180
ttgcatccaa caggctttga gatgtcagat gttttcttcc tgtcccatga ttaatcctag    12240
ccattcctct ttcttgtctg gctccactac tccttaccat ctaatgcctc gccaccattt    12300
tgatattttg actaagtgag ctatgaaaca cacctactgg atatgaaagt ataagtttct    12360
gataacaaaa catcaacatg ggatgtggag gaagtgggta gggtggcatt aatgcagcaa    12420
atcctggaat attttaaatc ttcattctaa atttagtaaa aatataggat aattttcctg    12480
ccatcattta cttataaaat taaaatttta gaaaataaaa ataatatttt cctcttttta    12540
atcacagatt atggcctgta ttggagacag atgaagtcgt aagaagtctg atagatggaa    12600
tacttaccaa taagaaaatg attttttgttc catcgtatat caatatcttt ctgagactac    12660
agaagtaagt acagcacaga acacccaaat actaaaacac caatagagct ttttttttg      12720
ctttttttt ttttagacag agtctcactc tgtcaccctg gctggattgc ggtggttgca     12780
gtggcatgat cttggctcac tgcaacctcc gcctcctggg ttcaagcaat tctcatgcct    12840
cagaccccca agtaactggg attataggtg tgtgctgcca cactacaccc agctaatttt    12900
tgtatttttt gatagagaca ggtttcccca tgttggccag gctggactcg aactcctgac    12960
ctcaagttat cctcctgtct cggcctccca agtgctggg attacagtca tgagccacca    13020
tgcctggccc aatagagcta ttattatgga gcatctttca gttgtgaaaa ttggcatgga    13080
aactctccat ccctggggag aacagttatt tcctctgtta ttttcctacc cagtctataa    13140
aaagagagtg attcattttc tctaccaaat ctactgtctc tgcccaaact ttgctgaaga    13200
```

```
ctattctaac taaaggaaac acagtttaaa aagaatgcaa tatagtgaag tagttaataa    13260
taaagactcc attttttaaaa gtctgctgga agtttggttg ggattgcact gaatctatag    13320
agcaattggg gagtattgac atatcaacaa tattgagttt tctaatccaa gaacataata    13380
tctatttttta aaatcttctt caaaatcttt aaatctttaa attgtatttt gtagtttttg    13440
gtgtttaagt cttgcacata ttttgtcaga tttattccaa agtatttcac gggttctttt    13500
tttttttttt tttttttttt ttgagacaga gtttcaccct tgttgcccag gctggagtgc    13560
agtggcgtga tcttggctca ctgcagcttc tgcctcctgg cttcaagtga ttctcctgcc    13620
tcagcctccc aagtagctgg gattacaggc acctgccccc tcgcccaact aactttttgt    13680
gtttgtagta gagacagggt ttcaccatgt tggccaggct ggtctcgaac tcctgacctc    13740
atgtgatcca cctgcctcag cctcccaaag tgctgggatt acaggcatga gccatcatgc    13800
ccagccctat ttgacggttt ttgacgctaa tgcaagtggc attttaaaaa attttatatt    13860
tcccattgtt tgttgtcagt atatattgga ttttttgtaat ttgatctcat attttgcagt    13920
cttgctaaat tgctaaacct cttttttgcta aactcgataa gctttttttt ttttggtaga    13980
ttcctgggcc tctaattttc tttatgggaa agttttttaat tacaaattta atttctttaa    14040
tagctacatg gctattcaat ttacttatta attcttggta atgtgtgtct ttcaaggaat    14100
ttgtccatt catctaagtt gtagaatttc tttggcataa atttgtacat aacattccct    14160
tattatcctt ttaatgtctt tagaatgtct tatttattta tttatttatt tttattatat    14220
tttttttgaga cagagtctcg ctctgttgcc caggctggag tgcagtggca caatcttggc    14280
tcactgcaag ctccgccttc tgggttcatg ccattctcct gcctcagcct ccctagttgc    14340
tgggactaca ggcgcctgca accatgccca gcttattttt tttttttttt tttttttttt    14400
tttttttttt tttttttttt tagtagagac ggggtttcac cctgttagcc aggatggtct    14460
cgatctcctg acctggtgat ccgcccgcct cagcctccca aagtgctggg attacaggcg    14520
tgagccacca gcccagcct atttatttat ttagtagaga cagtctcact ttgctgccca    14580
ggcaacaaag gttttgaatg cctggcctca agcagtcctc ctgccttggc ctcccaaagt    14640
gctgggatta caggcatgag ccactgcacc tggccaaatg aatatgctga taatatcttc    14700
tttataagga tgacataaga ataaaataat gtaatacaaa caaagcccct gtcactgaaa    14760
atgtatagac ttcaaatgtt aaagtcttag agaacagaat ttatatgaaa tagcaacagc    14820
aacaatttcc cagaggaaat actctctcag cttctcttctg aggagcagtt tctaaattga    14880
aattgtatca gtgagaagat aactatacta acttcataag ccttgggcct ttttgaaaca    14940
aatccatata aactatgaac aaacttgaaa tagaacaatt tgagaacagg gtacaaactg    15000
cattggtgta tcaatttcag tatttggttt tagcttaaat agactgactt gagataacat    15060
aaggagaacc ttgacccca agcaacatca tctcgcgagt tgactaggcc gggtgtggtg    15120
tctcacgcct gtaattccag cactttggga ggccacagca ggcagatcac ttgaggtcag    15180
gcattcgaga ccagcctggc caacatggtg aaacctcagc tctactaaag atacgaaaat    15240
tagcaggcat agtggcctgc acctgtaata ccaggcactc gcaggagaat cccttgaacc    15300
cggaaggcgg agattgcagt aaaccatgat tgtgccactg cactccagcc tgggcaacag    15360
gagactctgt ctcggaaaaa taaatttttt aaaaaaatga aaaaaaataa agttgacta    15420
aattagtgtc ttggtactaa gcactgtagg aagtgagttt catggaaccc caactctctt    15480
ggggcccaaa gcaagtcata ttaatattga aaattacatg catatacatg catatgacca    15540
aggtgataaa aacaattatt ctgcctgagt tggagaatag tatcccagta aaataaacaa    15600
```

```
gagtctcaaa gtcttttgta tcctttgaag ctgtcatggt ggtttgtaac taggcaacag    15660
gtatatattg ttaatcttct ttgcatttaa ttccttttat agagagacac aatttttacga    15720 gcagatgcaa ttactagcat gaaggtttct ttgtgagggt agttaaaagg cccacatgag    15780
ctctcttctt atccttgtcc ttctttcagc cagatcttcc ctgccccttt gctcattcca    15840
tctttcaccc acctaccccc aaaacaagga agtaaatctt gcattagtca acaataccaa    15900
agtgattttc aatatgactt tctctgcaga atgttattat ttctgcctct ttacattcac    15960
atactgtctt cctttttttt ttttttttt tttttttttt tagattgggt ctcactctgt    16020
tgcccaggct ggagtgcagt ggcttgatct cagctcactg taacctccac ctcctgagtt    16080
caagcaattc tcctgcctca gcctcctgag tagctgggat tacaggcatg tgccaccaca    16140
cctggctagt ttttttgtat ttttagtaga cacagggttt caccatgttg gtcaagctgg    16200
tctcgaactc ctgacctcat gatctgacca cctgtgcctc tcaaagtgct gggattacag    16260
gcgtgagcca ccgggccagc cactctcttc ctttcagttg cctactcatc tcttatgcat    16320
tcctggacat cagttgtcct tttgaagctt tcctccacta tcccagccca tgtgaatcct    16380
ccttccagtt atagcccctta attctagatg gctgatattt ttcaataatt gttttaagat    16440
gaccatttta gcctatcagc taaacaatat caaagacaat agctatttt caagtacttt    16500 agtttacctt attatagagt gcataataga tattcagtaa atagtaaagg agaggtgaag    16560
gcttgcatag aatggattct ggtggtgtct cttggtgagc ttttagcatc aagattaatc    16620
agcagtttca gcaatgagct cagaccttca gttttagatc tttactcata tcagataaga    16680
gagtgagaag agtggtatgt atcagtgctt tatttatatt tgcatccaat ttgaactatg    16740
aatattacaa aggtgcacac ataggttcag acagattgat ttaaaatgac caaagatgac    16800
ctgtcgtaag caacctgggt atcttaagat gcactccttg gagagggaat gttcctaaaa    16860
acattttcag agggacgaac tgtatgaaat tcagtaaaac ataaatcatg aggaaaactg    16920
attactctct ttttgacatg aaatgagagt tttaatgcat ggttacgatt attaacgtac    16980
tccgctgcaa gacgttaata aagttactgt tttgcaggct agaatgtctt gatgctgtaa    17040
tcagaacaca ctttttcccc tttcttccag cttcaaatgc agattcataa ttgggctgac    17100
ttctaataac tgcaatgttt tctgccttgg gcttgcagca gaagcctgac aaaatagtgt    17160
ttgtttaggc aataatttat ttatttattt attgagatgg agtttcattc ttgtcgccca    17220
ggctggagtg caatggcgtg atctcggctc actgcaacct ctgtgttcag caataatttt    17280
agactttacc ttacttgtga ttactatagc aattactata gccacaaggc ataatttta c   17340 tgtctcattt caattttatg aatttgaatg ttttacact tttcctaatg aagtccacta    17400
tgaagttatg tcaaaaaaaa aaagaaaaa gaaagatgca cacgtaaaag agaggtggtt    17460
gcaagagaag aaaagaacgg aggaaagtta aacgcaaacc agataactct cagcgtattc    17520
taaatgacca aaaacagaac tctgttgtca aagattttaa atggaaaatt tttcaatttt    17580 ttttttctttt ttgtacaggt ttcttcctga acgcgcctca gcgatttaa atcgtatgca    17640 gaatattcaa tttgaagcag tggttggcca caaaatcaaa atgaaatgaa taaataagct    17700
ccagccagag atgtatgcat gataatgata tgaatagttt cgaatcaatg ctgcaaagct    17760
ttatttcaca tttttcagt cctgataata ttaaaaacat tggtttggca ctagcagcag    17820
tcaaacgaac aagattaatt acctgtcttc ctgtttctca agaatattta cgtagttttt    17880
cataggtctg tttttccttt catgcctctt aaaaacttct gtgcttacat aaacatactt    17940
```

```
aaaaggttttt ctttaagata ttttatttttt ccatttaaag gtggacaaaa gctacctccc   18000
taaaagtaaa tacaaagaga acttatttac acagggaagg tttaagactg ttcaagtagc   18060
attccaatct gtagccatgc cacagaatat caacaagaac acagaatgag tgcacagcta   18120
agagatcaag tttcagcagg cagctttatc tcaacctgga catattttaa gattcagcat   18180
ttgaaagatt tccctagcct cttccttttt cattagccca aaacggtgca actctattct   18240
ggactttatt acttgattct gtcttctgta taactctgaa gtccaccaaa agtggaccct   18300
ctatatttcc tcccttttta tagtcttata agatacatta tgaaggtga ccgactctat   18360 tttaaatctc agaattttaa gttctagccc catgataacc ttttctttg taatttatgc   18420 tttcatatat ccttggtccc agagatgttt agacaatttt aggctcaaaa attaaagcta   18480
acacaggaaa aggaactgta ctggctatta cataagaaac aatggaccca agagaagaaa   18540
aggaagaaag aaaggttttt tggttttgt tttgttttgt tttgttttt gtttttttga   18600 gatggagtct cactctttcg cccaggctgg agtgcagtgg tatgatctca gctcactgca   18660
agctccacct cccgggttca cgccattctc ctgcctcagc ctcctgagta gctgggacta   18720
caggcgcccg ccaccacacc cggctaattt tttgtatttt ttgtagagac ggggtttcac   18780
catgttagcc aagatggtct cgatctcctg acctcgtgat ccacctgcct cggcctccca   18840
aagtgctggg attacgggtg tgagccaccg tgcccagcct ttttttttt aatagaaaaa   18900 ataatccgac tcccactaca tcaagactaa tcttgttttg tgtgttttc acatgtatta   18960 tagaatgctt ttgcatggac tatcctcttg tttttattaa aaacaaatga tttttttaaa   19020
agtcacaaaa acaattcact aaaaataaat atgtcattgt gctttaaaaa aataacctct   19080
tgtagttata aataaaacg tttgacttct aaactctg                            19118
```

<210> SEQ ID NO 2
<211> LENGTH: 19119
<212> TYPE: DNA
<213> ORGANISM: Homo sapiens

<400> SEQUENCE: 2

```
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catggaatag gcaggcagac tacttatgaa tttgcaaaac    240
gacagagcat attggttctg tgggatatta ataaggtaat gtacacatct tccaactttt    300
taaagtcaca gagtaagata tgtattttaa gaattatttg acttaccatc tacttatctt    360
tgtatttttg tttttcaaag tttgataaat tccctggtcc cttagtctgt atatgtgtca    420
ggttagttag atgaagggaa tgtaattaag aactaagcag cgatttttat gacatggtgt    480
gcaggttgat agaaagactc aggagccagt ctccttccaa gctgctaaat gaggcaagtc    540
acatattatc tctcagcctg ttttcttggc tctgaagtgg ggataataac ttaggggatg    600
ggcaagaacg ggatctgaaa attacagcta caaacaaaag tcaaacgaag aacttgcaac    660
agaaaccttt agtgcctccc ctcatgcaca agcaacacag ttctaaaata tttactgtct    720 gacccctttac agaaaatgtt tgccagtccg tagtcaaaag gattaaataa gtaatatttt    780
cagcacttag catatgataa acgatacgtg gcacatgata aacaataact gtgttaaata    840
aaatatgtgc gcagtgagtc aggctttttcc ttggacatta gtattttttcc tgtgttctta    900 cttgtaaaca ctacattaac aaccccaaat aaaactgaag gaactgaaat cttgtatcat    960
```

```
tttctctaaa cttgtaaatt ctggtaaggc catgaaaata tatgcagaga agtgtttaca     1020
ggattttagg attggaaaaa ttgtgaagta ctccttgaga atcacatttt ctgcaaatta     1080
cagtggtttt aattaccatt atattattac tttctcatgt tctttgctgt catgtttagt     1140
tgaaacctaa aatgtctctt acacttagag aactaattct tttctgtttt ttttctgaat     1200
agtgaagaat actatacaaa aaagctacta cattttattt taacagatat gagcatttat     1260
ataatagagg agttgatgta tataaaaatg atttgccatc tttttggtct ttgaagaaat     1320
tcgaatgaac tttctggaag atagcaagaa tttacaaata gagaaaattg ttgcctgctg     1380
ttctcaggca tttgtccaaa aatataaata agtataaatc tatgaaaagg gcttgatgaa     1440
atctaacctt caaatctctt tccagatgtg tattttggg gaagggcta tatttattaa       1500
gttttttta aattttaaaa tttccagaga caagagaaaa gtaaattaga aggaagtcgt      1560
attaaaaatg acttaagggc gggtgcagtg gctcacacct gtaatcccag cactttggga    1620
gacggaggtg ggcagattgc tggagcccag gagttcaaga ccagcctggg cagcacagca    1680
aaacccccaa ctctacaaaa aatacaaaaa ttagctgggt gcggggtgc acacccgtag     1740
tcccagctac tcgggaggct gaggtgggag gatcgtttca gttcaggaag ccaaggctgc    1800
aatgagctat gatggcatca ttgcactcca agctgggcaa tagagccagg ctctgtctca    1860
aaaaaaataa aaaagactt aagaaaaata ggtaacccaa cctcaaaaat tctctttgaa      1920
tcattaaatt tcatggttaa acatttaagc tactgaatga ttcactctaa ggctgtaatg    1980
taactcagat ctcctttagg cgaggaagat gctggctgag ttttcatcat aactggctcc    2040
ttttgccctg tgagatgaga gacacagtag cagtttggct cttatgcaat ctaaactgtt    2100
gcgttgggaa tacggttcaa aaaacacatt ggagtttaag ctaaagcaag tgttttgcta    2160
acaaaaagac aaggcatcac attttgcaat tgtctagctc agttataaaa cagaagaata    2220
ggccggacgc ggtggctcac gcctgtaatc ccagcacttt gggaggccga gacgggcgga    2280
tcacgaggtc aggagatcga gaccatcctg gataacacag tgaaacccg tctctactaa     2340
aaatacaaaa aaattagcca ggcgtagtgg cgggcgcctg tagtcccagc tactcgggag    2400
gctgaggcag gagaatggtg tgaacccggg aggcggagct tgcagtgagc cgagatgacg    2460
ccactgcact ccagcctggg cgacagagcg agactccgtc tcaaaaaaaa aaaaaaaaa     2520
aaaactgaag aataattaat tcttcaatca aacatctga tgaatgctct ggtaacttat     2580
gctctctact gacctagaaa caaatgagag agtatggtgt ggtttgtgca atctggcagt    2640
gagcaagcta ccaactaaat cagtgaaaga ctctcctatt cttttttac tcttctgcaa     2700
tcccacaaaa ggctatttga ggggatactg actttgagac tgggtcctaa catccatgtt    2760
tggggagttc aggctgctgc tccagggttt agcctacagt agcgaaatac aaaggaccca    2820
gagaccactc attcaaggtt tgccctaaat agcagcaaca ccactgtcat ctcaatacac    2880
gaagaatagg gcttttcagg tatccttgcc tctttgtcac agagaagagt ttacagattg    2940
tgagacggaa aagtataatt tttaaaacct tataatattt tctataaaag tcacctgagg    3000
tgaaaacttg aaaagaatta taattttcca gaatgtgagt caagaaacat tagagcaatt    3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtagcag catggtctcc    3240
ctatgaaagt ccttcttctt taaggagact tctttccctt ccctcctagg aggatgagtc    3300
```

```
agaatcatca agaaaaatat gatgggcaga ggcatacagt ttaccattac cactagttta   3360
gaattactac ttagcactttt actgcctatt acatagttgg tgctcaacaa atgtatgata   3420
aattaatggt tgagtttttc tttcttctcc atattcatct tccatgacac cacgaagagc   3480 aatgttttc aagaatgttc ttcaaggttt gaaagtagcc tgcttagag aaactgccta    3540 ctgtacagcc tccaaccaag aggaaaagct gaaaaaagca tgaagggatt ttgttttgtt   3600
ttgtttgttt tggttttaat atgagcattc cctggcagaa aagccagggg taatctcatt   3660
gcaactaggc aatcactctc aagaaatttt ctaacaaata aggaggccaa ttttatttt    3720 attttgagac gaagtcccac tctgtcaccc aggttggagt gcaatggaat gatttcagct   3780
cactgcaacc tccgcctccc gggttcaagt gattctcctg tctaaacttc ccgagtagct   3840
gggattacag gctcccacca ccacgcccag ctaatttttt gtattttag tagagatggg    3900 gtttcaccat tttggccaga ctggtctcaa actcctgacc tcaagtgatc caccctcctc   3960
ggcctcctaa agtgctggga ttacaggcgt gagccaccac acctgaccca ggaggccaat   4020
ttttaaaagg ttaactaatc ttcatgtcca aaatgaatgt taattgttca ttttggacat   4080
gaatgttaat ttttttttt tttttttttg agacagagtc tcactctgtt gcccaggctg    4140
gagtccagtg gcactatctc cactcactgc aacttcctcc tcccaggttc aagcaattat   4200
cctgcctcag cctcccaagt agctgggatt acaggcccac accatcaggc ctggctaatt   4260
tttgtatttt tagtagagac ggggtttcac catgttggcc aggctggtct tgaactcctg   4320
acctcgtgat ccgcccctcc tcggccaacca aagtgctggg attacaggcg tgagccaccg   4380
cgcctagccg aatgttaatt gtctaaaaat ttttcttctc caatgtcttc tcctccactt   4440
ttttcggaat ttgtttcttc ctaattacag cgcggtgtgg aggaaactgc agctgagtgc   4500
cgaaaactag gcgtcactgc gcatgcgtat gtggtagact gcagcaacag agaagagatc   4560
tatcgctctc taaatcaggt gagactgcag gttcacaaat ttcttcagat tattttgttt   4620
cctaggacgc tgacgtggaa aatgagaaag gtctttatga ctgcctgatt taaattggat   4680
tttagctgct aactgaagta gttatgtcac caaggaagga tatatacttt ttttcttgta   4740
tgtaatccac tcagctctgc ccattattat tgttcatatt attaatcaat ttcattctga   4800
tcagaagtgt gagcagtggc acagagtgac tgacaaaaga tttatcatca gggaatatgg   4860
atcacttcct agttttgttt tagtcctatt aactttgcag taattccagc ttctctttaa   4920
ttatttccct tgtgagattt tattttggtg ttaatgtagt cttctgtaga aaatgtaata   4980
ttaataatta ttatcacaat tattttaaaa gagtaaatac caaataatca caatgaacta   5040
agcactctaa caaactttac attttttaat tcaatcccta caataactct gtaaacttca   5100
ttttacagat aagcaaatta tgactcagag aggttaagcc agaccaggt catgtagtta    5160 ttaggttatg aaaccaggat ttctcaacca gcactttaga ccaggtgcgg tggttcacac   5220
atgtaatccc agcactttgt gaggccaagg tggaaggatc acatgagacc aagagttcaa   5280
gaccagccca ggcaacatag tgagacccta tctctaaaaa aaaaaaaaa aaaaaaaaa    5340 aaagtttaaa gaaaacaca ttttttaaaaa atgaacactt taaaatatt tggtcagaat    5400 ttatatagga atttatcaac ataaatgtta atttcacttt actgataaac ttgcaaaaca   5460
tgatgtgctg ggtactgaaa tttagatgtt aaaagaacag tttatcccac ctttatgaca   5520
gtgttccctt ggcctccacg atttgagctc aacagtctgt cttgcctgaa ctctgagaga   5580
cctcatacaa tagaagaaag actctcatct ttggattata ttggtcccaa aactttgagt   5640
ttgaataata cacccagtga aagtgttctt tcaatttcaa aaggtgaaga aagaagtggg   5700
```

```
tgatgtaaca atcgtggtga ataatgctgg gacagtatat ccagccgatc ttctcagcac    5760
caaggatgaa gagattacca agacatttga ggtcaacatc ctaggacatt tttgggtgag    5820
tgtgagtcag aaacatttct gatttgtgca ccttctctta agatacatga aacttataac    5880
ggagttcaca tacttctgga caggaaactg gccagatctt tgccttaatc aagaatcatt    5940
aaatttgttt gagtagaaga gccacagagt ctctgacaca aggacacaga attcaagtgg    6000
acacaacaca ccagaatgta agctacttgg tctgtcttgt ccaccagtat ctgacacaaa    6060
gcttggcatg taccaggagc tcaacaaatg tttgtggagg tttgttaagg gttgtcagtg    6120
tacatctttt caatgctgtc acttgtgact tcatttttt ccctccacac catgattttg    6180
taatgtgtcc tcattttgtg gaattttaga atggaaagga catcagaagt aattacttgg    6240
atgtatatag gatcgaggac acttttggac gagactctga ggcaagtgtt ctagatccat    6300
ggggtgctgg aactgagaaa tgcagctata cagacctcat ataattggtt agttttgtgg    6360
gagatggaaa tatcaacttc aactgccttt gtatagaaat ttttatgatt aatcttccag    6420
tgcctcaata ttagtgtaga atctagggca gatctggatt ctagaagaaa gaagaaaaaa    6480
aagagatgtg tcccccttac ctttaccagc tcttcacata tgtgaattgg ctcccatgcc    6540
caccaaacta cacggagacc tcatacatta gctacctata gctgcataac aaattataca    6600
aaacttagtg gtttaaagca acaatgtatg ttcactatcc tctcacagtt tctatgggtt    6660
gggaatttgg aggtagcttg ggttgggagt tctagttcta tgaatttgca taggatttat    6720
taaattctta taaaattta ttgatgtttc tcacaaaaga ggttttgga aaaaagaaa    6780 gacttgtttt ctgtaacatc aacatataat atacaatatt acaaataggg agatagtgaa    6840
ttcaatcatg attcattagt gtggtgtaga actctcagct tacactactc aactgtctta    6900
atacagttac acaagatttc actcttttaa ttagaatgat aaagccccaa accaaaaaat    6960
tatatgacac caaattatca taaggaataa ttttagttct gaaaactctg aattttccc    7020 ttaatattgt ttagatgaca tatccaaaaa aggatctatt tgattccttc tgaagggaag    7080 gaggggagt actgagatta gtgttggcat ggggcttacc ataccaataa atttgtatct    7140
ttatttctat catttgtaaa gaattaatca tggaatgctt ggaagtattt tatttcattg    7200
tataagttct ctcaaatgcc tttctgtctt aacaaaaata aaactacctg atttggaaac    7260
ctaacgtcta tgtcattgtc tttcttcttt ctgcaatgat ccttaagatc acaaaagcac    7320
ttcttccatc gatgatggag agaaatcatg gccacatcgt cacagtggct tcagtgtgcg    7380
gccacgaagg gattccttac ctcatcccat attggtaagt atcacatgcc agccatgtta    7440
tatattttta tactttgaag ggagcattac acttcaaatt gttaccactg gagagtcctg    7500
gttcttggca tcttgaacaa agaattggac aaaactcacc aacaaagcca ggaaagaatg    7560
aagcaacaaa agcagagatt tattgaaaat gaaagtacgc tttacagggt gggagtgggc    7620
ccaagcacag gggctcaaga gccaattaca gaattttctg gggtttaaat accccctaga    7680
ggtttccact ggttacttgg tgtacgccct atgtaaatga agaggatgaa ttaaagttac    7740
agagtcgttt actcagtgta caccatatgt aaatggagag atatttcct gtcatagctg    7800 gagtgtttcc atttgattta gttctaggaa gtcagcatga atcggcctta tgttccctgc    7860
ctccagaccc tgttctcctg cctcaagatt acaatgctga gagcagagtg atttggattt    7920
acagaattta aatttatagt agtttagaat gatttttaa atgactttt ctaaaacaat    7980 gaaaccaggt tgtaattata tttaagatat ttttagattt ctgcaaactc ctctgtagaa    8040
```

-continued

```
caatgagaga aaacagtaat gccaagcatg tttccattgt ttcctggaat aagaaacaga    8100
aaccccacag actgagaagc aaaacctaca gaagctaaaa tgaacacatg tctatgtcat    8160
ggccttggtg cccaagataa gacaatcaga gtggtccctg gatcaaaaca ttttacagtg    8220
tgcttgtgcc atgaaagtgt gtgtgtgtgt gtgtgtgtgt gtgtgagaga gagagagaga    8280
gagaaaacga ctctacctga ctaaaagttg cagataccac actccatgca ccaccaaaga    8340
cataaaggga aggaggtgag aggcgttaag gatgtactgc tgtatttgcc aaatatcctt    8400
tcctgtaaac tcttctccag atcctcataa taaaattaag aggccaaagt ggcaaccatt    8460
gtcaagagaa aaactatcaa ccattgtcaa gagataact cagttattga gagagagagg    8520
agaaatgagc agagtcctac agaagtctgt caacacagat accagttttg tagaatttct    8580
aaatgtattt ttcctgattc atattttca aataaaagc agcaataaaa actgattaga    8640
aaacagtttg aagattcaat ggaaaaacct tacatgtagg atggaaaact gaacattaag    8700
ccaatcaata gagttatttt tgttcttttg ttatcattgt tgtttaagaa atgagatacg    8760
ttcacaattc tgcttaatca tgtaagaaaa tgaaaatgaa ttgccattta tactctcaga    8820
aaaatcacaa gtggctgatt tttggcttcc acttgttctt aagccaaatg ataccgcctt    8880
ctcacagaaa gctgaggatt ggtttcactc tcccttagct aacaatgctt aataattctc    8940
ttacagttcc agcaaatttg ccgctgttgg cttttcacaga ggtctgacat cagaacttca    9000
ggccttggga aaaactggta tcaaaacctc atgtctctgc ccagttttg tgaatactgg    9060 gttcaccaaa atccaagca caaggtaagg tcaaaatcaa gttagaatgg gtatgtggta    9120
tgataaattg atatgaaaac taatgagaaa tgtttaggca ggccaactaa tagaagaaaa    9180
tgaagaagga aaaataattt ttcttattat tattattatc ttgaaattaa aggaataaag    9240
ggggaaaaca cattagggac tagcaggaat gatcagccac cgatgaactg ggatatttat    9300
ttgtgtccgg gagaaagcac atacatttga tcaccgttac caccctgtct ttaaaatgca    9360
aatgttccaa ggaccagcaa ataaattgag tatctagctc cttagtcaag gtgaatttct    9420
gcaagaactc ttgtctctgg tgagacagga tttgagacca caagagaaga aaaattagtc    9480
ctgaaaggag aagaaaaaag caggaaggtg tggataagaa cccgaaaatt aagccatctg    9540
cttaacaaat ttttctaatc ctagtatata ttctgctgca ggttaacaaa atatactaag    9600
cttaatgatt cgaaaccaat tttttactgg aagggaatta atcctaaata tattcattca    9660
aaagaactaa acaattctct gttgagtgcc gcctcatttg aggatactga ctcttacagc    9720
ctgagttagc tatgtggtct ctgcagctgg aatcactccc tgccactgga gtccttcatg    9780
gtgttagacc ataggtactg ttgactaaag aaaaaaaaaa gttttgttt ttattttgt    9840 tttttttgag acagagtctc actctgtcac ccaggctgga gtacagtggc gcgatctcag    9900
ctcaccgcaa cctccgcctt tctgggttca agcaattctc cttcctcagc tcctgagta    9960 tttggattac aggcgcccac caccacgcct ggctaatttt tgtatttta gtagagacgg    10020 ggtttcacca tgttggccag gctggtctca aactcctgac ctcaggtgtc ctacctgcct    10080
tggcctccta aaatgctggg attacaggag tgagccacca tgcccggcca aaaaaataag    10140
tttttaaaga attaaaggtc atcctggcta acacagtgaa accccgtctc tactaaaaaa    10200
cacaaaaaaa ttagccgggc gtggtggcgg gcgcctgtag tcccagctgc gcgggaggct    10260
gaggcaggag aatggcgtga acccgggagg cggagcttgc agtgagccga gatcgcgcca    10320
ctgcactcca gcctgggcga cagagcgaga ctccgtctca aaaaaaaaa aaaaaaaaa    10380 aaaaaaaga attaaaggtg ttaatttttat ttagaagcct tactgaagac tacagtcgga    10440
```

```
ggcctatagc ctgagagcag ccctttagag aggttcagtt gaactgttct gatagtgggg    10500
gccatgtgct ctatcctgta ttgtcttcaa agcatctttc cagagagctg cacattgtca    10560
cagagtcagg gactttgtga aattatgctg acaaccagaa gtgagtaaac gtggcttctt    10620
acatttgcta cgttgtctca cagtacttaa taagtatgca atatgtaagt aaatactata    10680
gtactattgc aactcctgat tgttttctta gacaaggaat tgggcccaat aaaaaccctc    10740
ttggtaggca ttcaggcttc gtgtaccatg agctttccta agggtatcct gccactcttg    10800
gggaaggcat gatagatgag gggagtaagg ataatggaac tctgggtaca gggttcctgg    10860
gggctaactt agaggtagac acaggcaatg ctaaatattt gggattgatt ttatagaggt    10920
tgctagattg tgaatttcct tagtaagggc taaggcattg atatgtaatg tcacacttgg    10980
ctccgaggct gggttgttgg atccatgtag atgaaatcag ggagagaaag ggcagaacgg    11040
agtaatttag aaatgtattg atttgtatta ctctctgttg gcttgctatt caaggcagtg    11100
gagaactcaa tcacataata atctgcagca aaccacagat catcccaggg aatgaagttt    11160
taacattcgc tggctcccta actcctcacc cagcctttac attcactggc tgttcagtcc    11220
atgcctggac atcttaattt gaatacaaca ttttaaatcc atttttctgt catcatcttg    11280
cactaacaga caattctaca ctaagcctat gtttatgaat atttctcaag agtacatgta    11340
cacagccttc agtataagga aaactggaag tatgacatac ctccagttgt catactcctt    11400
gggcccctct taaattctca ttaaactgca ggataggcaa gtcagaggtg aatctcaaat    11460
acgaaattct taccggaaag gggttccaat ccagacccca agagagggtt cttagatttc    11520
tcgcaagaaa taattcgggg caaggccaca gtgcaaagca aaagcaagtt tattaggaaa    11580
gtaaaggagt agagaacagc tactccatgg agaagaatgg cttgagctgc tccaccaagg    11640
gtatttagag ttacttcttg attatatgct aaacaagggg tggattattc atgagttttc    11700
cgggaaaagg gtgagcaatt cccagaactg agatttcctc ccctttttag gccatatagg    11760
gtaacttcct gccattgcca tggtatttgt aaactgtcat agtgctggtg gaagtgtctc    11820
ttagcttgct aatgtattat agttagctta taatgagcag tgaggacaac cagaggtcac    11880
tttcatcacc atcttggttt tggtgggttt tggccggctt ctttactgca ccctattta    11940 tcaacaaggt ctttatgacc tgaatcttgt gccaacctcc tatctcatcc tgtgacaaag    12000
aatgccttaa cttcctggga atgcagccca gtaggtgtca gccttatttt acccagaccc    12060
tattcaagat ggagttgctc tgatttaaac gcctctgaca aaatgacgac ctcaaaacaa    12120
tccagcttta tggaatacct ccacaagaaa gaaagtatac ttagctatag aattttctcc    12180
ttgcatccaa caggctttga gatgtcagat gtttccttcc tgtcccatga ttaatcctag    12240
ccattcctct ttcttgtctg gctccactac tccttaccat ctaatgcctc gccaccattt    12300
tgatattttg actaagtgag ctatgaaaca cacctactgg atatgaaagt ataagtttct    12360
gataacaaaa catcaacatg ggatgtggag gaagtgggta gggtggcatt aatgcagcaa    12420
atcctggaat attttaaatc ttcattctaa atttagtaaa aatataggat aattttcctg    12480
ccatcattta cttataaaat taaaatttta gaaataaaaa ataatatttt cctcttttta    12540
atcacagatt atggcctgta ttggagacag atgaagtcgt aagaagtctg atagatggaa    12600
tacttaccaa taagaaaatg atttttgttc catcgtatat caatatcttt ctgagactac    12660
agaagttaag tacagcacag aacacccaaa tactaaaaca ccaatagagc ttttttttt    12720 gcttttttt tttttagaca gagtctcact ctgtcaccct ggctggattg cggtggttgc    12780
```

```
agtggcatga tcttggctca ctgcaacctc cgcctcctgg gttcaagcaa ttctcatgcc   12840
tcagaccccc aagtaactgg gattataggt gtgtgctgcc acactacacc cagctaattt   12900
ttgtattttt tgatagagac aggtttcccc atgttggcca ggctggactc gaactcctga   12960
cctcaagtta tcctcctgtc tcggcctccc aaagtgctgg gattacagtc atgagccacc   13020
atgcctggcc caatagagct attattatgg agcatctttc agttgtgaaa attggcatgg   13080
aaactctcca tccctgggga gaacagttat ttcctctgtt attttcctac ccagtctata   13140 aaagagagt gattcatttt ctctaccaaa tctactgtct ctgcccaaac tttgctgaag   13200
actattctaa ctaaaggaaa cacagtttaa aagaatgca atatagtgaa gtagttaata   13260
ataaagactc cattttttaaa agtctgctgg aagtttggtt gggattgcac tgaatctata   13320
gagcaattgg ggagtattga catatcaaca atattgagtt ttctaatcca agaacataat   13380 atctatttt aaaatcttct tcaaaatctt taaatcttta aattgtattt tgtagttttt   13440
ggtgtttaag tcttgcacat attttgtcag atttattcca aagtatttca cgggttcttt   13500 tttttttt tttttttttt tttgagacag agtttcaccc ttgttgccca ggctggagtg   13560
cagtggcgtg atcttggctc actgcagctt ctgcctcctg gcttcaagtg attctcctgc   13620
ctcagcctcc caagtagctg ggattacagg cacctgcccc ctcgcccaac taactttttg   13680
tgtttgtagt agagacaggg tttcaccatg ttggccaggc tggtctcgaa ctcctgacct   13740
catgtgatcc acctgcctca gcctcccaaa gtgctgggat tacaggcatg agccatcatg   13800
cccagcccta tttgacggtt tttgacgcta atgcaagtgg cattttaaaa aatttatat   13860 ttcccattgt ttgttgtcag tatatattgg attttttgtaa tttgatctca tattttgcag   13920
tcttgctaaa ttgctaaacc tcttttttgct aaactcgata agctttttt tttttggtag   13980 attcctgggc ctctaatttt ctttatggga aagttttaa ttacaaattt aatttcttta   14040
atagctacat ggctattcaa tttacttatt aattcttggt aatgtgtgtc tttcaaggaa   14100
tttgtccatt tcatctaagt tgtagaattt ctttggcata aatttgtaca taacattccc   14160
ttattatcct tttaatgtct ttagaatgtc ttattttattt atttattat ttttattata   14220 tttttttgag acagagtctc gctctgttgc ccaggctgga gtgcagtggc acaatcttgg   14280
ctcactgcaa gctccgcctt ctgggttcat gccattctcc tgcctcagcc tcctagttg   14340 ctgggactac aggcgcctgc aaccatgccc agcttatttt tttttttttt tttttttttt   14400
tttttttttt tttttttttt ttagtagaga cggggtttca ccctgttagc caggatggtc   14460
tcgatctcct gacctggtga tccgcccgcc tcagcctccc aaagtgctgg gattacaggc   14520
gtgagccacc aagcccagcc tatttattta tttagtagag acagtctcac tttgctgccc   14580
aggcaacaaa ggttttgaat gcctggcctc aagcagtcct cctgccttgg cctcccaaag   14640
tgctgggatt acaggcatga gccactgcac ctggccaaat gaatatgctg ataatatctt   14700
ctttataagg atgacataag aataaaataa tgtaatacaa acaaagcccc tgtcactgaa   14760
aatgtataga cttcaaatgt taaagtctta gagaacagaa tttatatgaa atagcaacag   14820
caacaatttc ccagaggaaa tactctctca gctttcttct gaggagcagt ttctaaattg   14880
aaattgtatc agtgagaaga taactatact aacttcataa gccttgggcc ttttgaaac   14940 aaatccatat aaactatgaa caaacttgaa atagaacaat ttgagaacag ggtacaaact   15000
gcattggtgt atcaatttca gtatttggtt ttagcttaaa tagactgact tgagataaca   15060
taaggagaac cttgaccccc aagcaacatc atctcgcgag ttgactaggc cgggtgtggt   15120
gtctcacgcc tgtaattcca gcactttggg aggccacagc aggcagatca cttgaggtca   15180
```

```
ggcattcgag accagcctgg ccaacatggt gaaacctcag ctctactaaa gatacgaaaa    15240
ttagcaggca tagtggcctg cacctgtaat accaggcact cgcaggagaa tcccttgaac    15300
ccggaaggcg gagattgcag taaaccatga ttgtgccact gcactccagc ctgggcaaca    15360
ggagactctg tctcggaaaa ataaattttt taaaaaaatg aaaaaaaata aaagttgact    15420
aaattagtgt cttggtacta agcactgtag gaagtgagtt tcatggaacc ccaactctct    15480
tggggcccaa agcaagtcat attaatattg aaaattacat gcatatacat gcatatgacc    15540
aaggtgataa aaacaattat tctgcctgag ttggagaata gtatcccagt aaaataaaca    15600
agagtctcaa agtcttttgt atcctttgaa gctgtcatgg tggtttgtaa ctaggcaaca    15660
ggtatatatt gttaatcttc tttgcattta attccttttta tagagagaca caattttacg    15720
agcagatgca attactagca tgaaggtttc tttgtgaggg tagttaaaag gcccacatga    15780
gctctcttct tatccttgtc cttctttcag ccagatcttc cctgcccctt tgctcattcc    15840
atctttcacc cacctacccc caaaacaagg aagtaaatct tgcattagtc aacaatacca    15900
aagtgatttt caatatgact ttctctgcag aatgttatta tttctgcctc tttacattca    15960
catactgtct tcctttttttt tttttttttt tttttttttt ttagattggg tctcactctg    16020
ttgcccaggc tggagtgcag tggcttgatc tcagctcact gtaacctcca cctcctgagt    16080
tcaagcaatt ctcctgcctc agcctcctga gtagctggga ttacaggcat gtgccaccac    16140
acctggctag tttttttgta tttttagtag agacagggtt tcaccatgtt ggtcaagctg    16200
gtctcgaact cctgacctca tgatctgacc acctgtgcct ctcaaagtgc tgggattaca    16260
ggcgtgagcc accgggccag ccactctctt cctttcagtt gcctactcat ctcttatgca    16320
ttcctggaca tcagttgtcc ttttgaagct ttcctccact atcccagccc atgtgaatcc    16380
tccttccagt tatagcccctt aattctagat ggctgatatt tttcaataat tgttttaaga    16440
tgaccatttt agcctatcag ctaaacaata tcaaagacaa tagctatttt tcaagtactt    16500
tagtttacct tattatagag tgcataatag atattcagta aatagtaaag gagaggtgaa    16560
ggcttgcata gaatggattc tggtggtgtc tcttggtgag cttttagcat caagattaat    16620
cagcagtttc agcaatgagc tcagaccttc agttttagat ctttactcat atcagataag    16680
agagtgagaa gagtggtatg tatcagtgct ttatttatat ttgcatccaa tttgaactat    16740
gaatattaca aaggtgcaca cataggttca gacagattga tttaaaatga ccaaagatga    16800
cctgtcgtaa gcaacctggg tatcttaaga tgcactcctt ggagagggaa tgttcctaaa    16860 aacatttttca gagggacgaa ctgtatgaaa ttcagtaaaa cataaatcat gaggaaaact    16920
gattactctc ttttttgacat gaaatgagag ttttaatgca tggttacgat tattaacgta    16980
ctccgctgca agacgttaat aaagttactg ttttgcaggc tagaatgtct tgatgctgta    17040
atcagaacac acttttttccc ctttcttcca gcttcaaatg cagattcata attgggctga    17100
cttctaataa ctgcaatgtt ttctgccttg ggcttgcagc agaagcctga caaaatagtg    17160
tttgtttagg caataattta tttatttatt tattgagatg gagtttcatt cttgtcgccc    17220
aggctggagt gcaatggcgt gatctcggct cactgcaacc tctgtgttca ggcaataatt    17280
tagactttac cttacttgtg attactatag caattactat agccacaagg cataatttta    17340
ctgtctcatt tcaattttat gaatttgaat gttttttacac ttttcctaat gaagtccact    17400
atgaagttat gtcaaaaaaa aaaagaaaa agaaagatgc acacgtaaaa gagaggtggt    17460
tgcaagagaa gaaaagaacg gaggaaagtt aaacgcaaac cagataactc tcagcgtatt    17520
```

```
ctaaatgacc aaaaacagaa ctctgttgtc aaagatttta aatggaaaat ttttcaattt    17580
tttttctttt tttgtacagg tttcttcctg aacgcgcctc agcgatttta aatcgtatgc    17640
agaatattca atttgaagca gtggttggcc acaaaatcaa aatgaaatga ataaataagc    17700
tccagccaga gatgtatgca tgataatgat atgaatagtt tcgaatcaat gctgcaaagc    17760
tttatttcac atttttttcag tcctgataat attaaaaaca ttggtttggc actagcagca    17820
gtcaaacgaa caagattaat tacctgtctt cctgtttctc aagaatattt acgtagtttt    17880
tcataggtct gttttttcctt tcatgcctct taaaaacttc tgtgcttaca taaacatact    17940
taaaaggttt tctttaagat atttattttt tccatttaaa ggtggacaaa agctacctcc    18000
ctaaaagtaa atacaaagag aacttattta cacagggaag gtttaagact gttcaagtag    18060
cattccaatc tgtagccatg ccacagaata tcaacaagaa cacagaatga gtgcacagct    18120
aagagatcaa gtttcagcag gcagctttat ctcaacctgg acatatttta agattcagca    18180
tttgaaagat ttccctagcc tcttcctttt tcattagccc aaaacggtgc aactctattc    18240
tggactttat tacttgattc tgtcttctgt ataactctga agtccaccaa aagtggaccc    18300
tctatatttc ctcccttttt atagtcttat aagatacatt atgaaaggtg accgactcta    18360
ttttaaatct cagaattttta agttctagcc ccatgataac cttttttcttt gtaatttatg    18420 ctttcatata tccttggtcc cagagatgtt tagacaattt taggctcaaa aattaaagct    18480
aacacaggaa aaggaactgt actggctatt acataagaaa caatggaccc aagagaagaa    18540
aaggaagaaa gaaaggtttt ttggtttttg ttttgttttg ttttgttttt tgttttttttg    18600 agatggagtc tcactctttc gcccaggctg gagtgcagtg gtatgatctc agctcactgc    18660
aagctccacc tcccgggttc acgccattct cctgcctcag cctcctgagt agctgggact    18720
acaggcgccc gccaccacac ccggctaatt ttttgtattt tttgtagaga cggggtttca    18780
ccatgttagc caagatggtc tcgatctcct gacctcgtga tccacctgcc tcggcctccc    18840
aaagtgctgg gattacgggt gtgagccacc gtgcccagcc tttttttttt taatagaaaa    18900
aataatccga ctcccactac atcaagacta atcttgtttt gtgtgttttt cacatgtatt    18960
atagaatgct tttgcatgga ctatcctctt gtttttatta aaaacaaatg atttttttaa    19020
aagtcacaaa aacaattcac taaaaataaa tatgtcattg tgctttaaaa aaataaacctc    19080 ttgtagttat aaaataaaac gtttgacttc taaactctg                          19119
```

<210> SEQ ID NO 3
<211> LENGTH: 600
<212> TYPE: DNA
<213> ORGANISM: Homo sapiens
<220> FEATURE:
<221> NAME/KEY: misc_feature
<222> LOCATION: (1)..(499)
<223> OTHER INFORMATION: Upstream of TSS

<400> SEQUENCE: 3

```
cactgcacca cgaactcatg gactgaagca atcctcctgc ctcagcctcc tgggtagctg      60
ggactacaga cacatgccac catatccagc taatttttttt ctatagtttt tttttttttt    120
tttgagacag ggtcttacta tgttgcccag actggtctcg aactcctggg ctcaagcaat    180
cctctgcctc agcctcccaa agtgctggga ttacagatgt gagccactgc acctggcccc    240
tagaattgtt tctagaggtg aaacttcaag gtgaaatata gtacataact gcttttcaga    300
taaacaagtc cagagagcac actctcttgt gctcttggca tcacttggca tcacttcata    360
tttgaggtgt ttcaaaccca ttagaacacg tgaacaaggc ctgcttccaa agctggcttc    420
```

-continued

```
catctggtag tcccattaac aactgggcac accccttccc tagagctctg tgtagacagt    480
acctcctccc taggactaca caaggactga accagaagga agaggacaga gcaaagccat    540
gaacatcatc ctagaaatcc ttctgcttct gatcaccatc atctactcct acttggagtc    600
```

<210> SEQ ID NO 4
<211> LENGTH: 2397
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(383)
<223> OTHER INFORMATION: Exon 2
<220> FEATURE:
<221> NAME/KEY: misc_feature
<222> LOCATION: (384)..(515)
<223> OTHER INFORMATION: Exon 3
<220> FEATURE:
<221> NAME/KEY: misc_feature
<222> LOCATION: (516)..(622)
<223> OTHER INFORMATION: Exon 4
<220> FEATURE:
<221> NAME/KEY: misc_feature
<222> LOCATION: (623)..(760)
<223> OTHER INFORMATION: Exon 5
<220> FEATURE:
<221> NAME/KEY: misc_feature
<222> LOCATION: (761)..(877)
<223> OTHER INFORMATION: Exon 6v1
<220> FEATURE:
<221> NAME/KEY: misc_feature
<222> LOCATION: (878)..(2397)
<223> OTHER INFORMATION: Exon 7

<400> SEQUENCE: 4

```
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catggaatag gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga agaagtgggt gatgtaaca atcgtggtga    420 ataatgctgg gacagtatat ccagccgatc ttctcagcac caaggatgaa gagattacca    480
agacatttga ggtcaacatc ctaggacatt tttggatcac aaaagcactt cttccatcga    540
tgatggagag aaatcatggc cacatcgtca gtggcttca gtgtgcggc cacgaaggga    600 ttccttacct catcccatat tgttccagca aatttgccgc tgttggcttt cacagaggtc    660
tgacatcaga acttcaggcc ttgggaaaaa ctggtatcaa acctcatgt ctctgcccag    720 tttttgtgaa tactgggttc accaaaaaatc caagcacaag attatggcct gtattggaga    780
cagatgaagt cgtaagaagt ctgatagatg gaatacttac caataagaaa atgatttttg    840
ttccatcgta tatcaatatc tttctgagac tacagaagtt tcttcctgaa cgcgcctcag    900
cgattttaaa tcgtatgcag aatattcaat ttgaagcagt ggttggccac aaaatcaaaa    960
tgaaatgaat aaataagctc cagccagaga tgtatgcatg ataatgatat gaatagtttc   1020
gaatcaatgc tgcaaagctt tatttcacat tttttcagtc ctgataatat taaaaacatt   1080
```

```
ggtttggcac tagcagcagt caaacgaaca agattaatta cctgtcttcc tgtttctcaa    1140
gaatatttac gtagttttc ataggtctgt ttttcctttc atgcctctta aaaacttctg      1200
tgcttacata aacatactta aaaggttttc tttaagatat tttattttc catttaaagg      1260 tggacaaaag ctacctccct aaaagtaaat acaaagagaa cttatttaca cagggaaggt    1320
ttaagactgt tcaagtagca ttccaatctg tagccatgcc acagaatatc aacaagaaca    1380
cagaatgagt gcacagctaa gagatcaagt ttcagcaggc agctttatct caacctggac    1440 atatttaag attcagcatt tgaaagattt ccctagcctc ttccttttc attagcccaa      1500 aacggtgcaa ctctattctg gactttatta cttgattctg tcttctgtat aactctgaag    1560
tccaccaaaa gtggaccctc tatatttcct cccttttat agtcttataa gatacattat      1620
gaaaggtgac cgactctatt ttaaatctca gaatttaag ttctagcccc atgataacct      1680
ttttctttgt aatttatgct ttcatatatc cttggtccca gagatgttta gacaatttta    1740
ggctcaaaaa ttaaagctaa cacaggaaaa ggaactgtac tggctattac ataagaaaca    1800
atggacccaa gagaagaaaa ggaagaaaga aaggttttt ggttttgtt ttgttttgtt      1860 ttgttttttg tttttttgag atggagtctc actctttcgc ccaggctgga gtgcagtggt    1920
atgatctcag ctcactgcaa gctccacctc ccgggttcac gccattctcc tgcctcagcc    1980
tcctgagtag ctgggactac aggcgcccgc caccacaccc ggctaatttt ttgtattttt    2040
tgtagagacg gggtttcacc atgttagcca agatggtctc gatctcctga cctcgtgatc    2100
cacctgcctc ggcctcccaa agtgctggga ttacgggtgt gagccaccgt gcccagcctt    2160 tttttttta atagaaaaaa taatccgact cccactacat caagactaat cttgttttgt    2220 gtgttttca catgtattat agaatgcttt tgcatggact atcctcttgt ttttattaaa    2280
aacaaatgat tttttaaaa gtcacaaaaa caattcacta aaaataaata tgtcattgtg    2340
ctttaaaaaa ataacctctt gtagttataa aataaaacgt ttgacttcta aactctg      2397
```

<210> SEQ ID NO 5
<211> LENGTH: 2289
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(407)
<223> OTHER INFORMATION: Exon 3
<220> FEATURE:
<221> NAME/KEY: misc_feature
<222> LOCATION: (408)..(514)
<223> OTHER INFORMATION: Exon 4
<220> FEATURE:
<221> NAME/KEY: misc_feature
<222> LOCATION: (515)..(652)
<223> OTHER INFORMATION: Exon 5
<220> FEATURE:
<221> NAME/KEY: misc_feature
<222> LOCATION: (653)..(769)
<223> OTHER INFORMATION: Exon 6v1
<220> FEATURE:
<221> NAME/KEY: misc_feature
<222> LOCATION: (770)..(2289)
<223> OTHER INFORMATION: Exon 7

<400> SEQUENCE: 5

```
agacagtacc tcctccctag gactacacaa ggactgaacc agaaggaaga ggacagagca     60
aagccatgaa catcatccta gaaatccttc tgcttctgat caccatcatc tactcctact    120
```

```
tggagtcgtt ggtgaagttt ttcattcctc agaggagaaa atctgtggct ggggagattg        180
ttctcattac tggagctggg catggaatag gcaggcagac tacttatgaa tttgcaaaac        240
gacagagcat attggttctg tgggatatta ataaggtgaa gaaagaagtg ggtgatgtaa        300
caatcgtggt gaataatgct gggacagtat atccagccga tcttctcagc accaaggatg        360
aagagattac caagacattt gaggtcaaca tcctaggaca ttttggatc acaaaagcac         420
ttcttccatc gatgatggag agaaatcatg gccacatcgt cacagtggct tcagtgtgcg        480
gccacgaagg gattccttac ctcatcccat attgttccag caaatttgcc gctgttggct        540
ttcacagagg tctgacatca gaacttcagg ccttgggaaa aactggtatc aaaacctcat        600
gtctctgccc agttttgtg aatactgggt tcaccaaaaa tccaagcaca agattatggc        660
ctgtattgga gacagatgaa gtcgtaagaa gtctgataga tggaatactt accaataaga       720
aaatgatttt tgttccatcg tatatcaata tcttctgag actacagaag tttcttcctg        780
aacgcgcctc agcgatttta aatcgtatgc agaatattca atttgaagca gtggttggcc       840
acaaaatcaa aatgaaatga ataaataagc tccagccaga gatgtatgca tgataatgat       900
atgaatagtt tcgaatcaat gctgcaaagc tttatttcac attttttcag tcctgataat       960
attaaaaaca ttggtttggc actagcagca gtcaaacgaa caagattaat tacctgtctt       1020
cctgtttctc aagaatattt acgtagtttt tcataggtct gttttccctt tcatgcctct      1080
taaaaacttc tgtgcttaca taaacatact taaaaggttt tctttaagat attttatttt      1140
tccatttaaa ggtggacaaa agctacctcc ctaaaagtaa atacaaagag aacttattta      1200
cacagggaag gtttaagact gttcaagtag cattccaatc tgtagccatg ccacagaata      1260
tcaacaagaa cacagaatga gtgcacagct aagagatcaa gtttcagcag gcagctttat      1320
ctcaacctgg acatatttta agattcagca tttgaaagat ttccctagcc tcttccttt       1380
tcattagccc aaaacggtgc aactctattc tggactttat tacttgattc tgtcttctgt      1440
ataactctga agtccaccaa agtggaccc tctatatttc ctccctttt atagtcttat        1500
aagatacatt atgaaaggtg accgactcta tttaaatct cagaatttta agttctagcc       1560
ccatgataac cttttctt gtaatttatg ctttcatata tccttggtcc cagagatgtt        1620
tagacaattt taggctcaaa aattaaagct aacacaggaa aaggaactgt actggctatt      1680
acataagaaa caatggaccc aagagaagaa aaggaagaaa gaaaggtttt ttggttttg       1740
ttttgttttg ttttgttttt tgttttttg agatggagtc tcactctttc gcccaggctg      1800
gagtgcagtg gtatgatctc agctcactgc aagctccacc tcccgggttc acgccattct      1860
cctgcctcag cctcctgagt agctgggact acaggcgccc gccaccacac ccggctaatt      1920
ttttgtattt tttgtagaga cggggtttca ccatgttagc caagatggtc tcgatctcct      1980
gacctcgtga tccacctgcc tcggcctccc aaagtgctgg gattacgggt gtgagccacc      2040
gtgcccagcc tttttttttt taatagaaaa aataatccga ctcccactac atcaagacta      2100
atcttgtttt gtgtgttttt cacatgtatt atagaatgct tttgcatgga ctatcctctt      2160
gtttttatta aaacaaatg attttttaa aagtcacaaa acaattcac taaaaataaa         2220
tatgtcattg tgctttaaaa aaataaccct ttgtagttat aaaataaaac gtttgacttc      2280
taaactctg                                                              2289
```

<210> SEQ ID NO 6
<211> LENGTH: 2280
<212> TYPE: DNA

```
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(383)
<223> OTHER INFORMATION: Exon 2
<220> FEATURE:
<221> NAME/KEY: misc_feature
<222> LOCATION: (384)..(515)
<223> OTHER INFORMATION: Exon 3
<220> FEATURE:
<221> NAME/KEY: misc_feature
<222> LOCATION: (516)..(622)
<223> OTHER INFORMATION: Exon 4
<220> FEATURE:
<221> NAME/KEY: misc_feature
<222> LOCATION: (623)..(760)
<223> OTHER INFORMATION: Exon 5
<220> FEATURE:
<221> NAME/KEY: misc_feature
<222> LOCATION: (761)..(2280)
<223> OTHER INFORMATION: Exon 7

<400> SEQUENCE: 6
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataagcgcgg tgtggaggaa actgcagctg     300
agtgccgaaa actaggcgtc actgcgcatg cgtatgtggt agactgcagc aacagagaag     360
agatctatcg ctctctaaat caggtgaaga agaagtggg tgatgtaaca atcgtggtga     420
ataatgctgg gacagtatat ccagccgatc ttctcagcac caaggatgaa gagattacca     480
agacatttga ggtcaacatc ctaggacatt tttggatcac aaaagcactt cttccatcga     540
tgatggagag aaatcatggc cacatcgtca cagtggcttc agtgtgcggc cacgaaggga     600
ttccttacct catcccatat tgttccagca aatttgccgc tgttggcttt cacagaggtc     660
tgacatcaga acttcaggcc ttgggaaaaa ctggtatcaa aacctcatgt ctctgcccag     720
tttttgtgaa tactgggttc accaaaaaatc caagcacaag gtttcttcct gaacgcgcct     780
cagcgatttt aaatcgtatg cagaatattc aatttgaagc agtggttggc cacaaaatca     840
aaatgaaatg aataaataag ctccagccag agatgtatgc atgataatga tatgaatagt     900
ttcgaatcaa tgctgcaaag ctttatttca cattttttca gtcctgataa tattaaaaac     960
attggtttgg cactagcagc agtcaaacga acaagattaa ttacctgtct tcctgtttct    1020
caagaatatt tacgtagttt ttcataggtc tgttttttcct ttcatgcctc ttaaaaactt    1080
ctgtgcttac ataaacatac ttaaaaggtt tctttaaga tattttattt ttccatttaa     1140
aggtggacaa aagctacctc cctaaaagta aatacaaaga gaacttattt acacagggaa    1200
ggtttaagac tgttcaagta gcattccaat ctgtagccat gccacagaat atcaacaaga    1260
acacagaatg agtgcacagc taagagatca agtttcagca ggcagcttta tctcaacctg    1320
gacatatttt aagattcagc atttgaaaga tttccctagc ctcttccttt ttcattagcc    1380
caaaacggtg caactctatt ctggacttta ttacttgatt ctgtcttctg tataactctg    1440
aagtccacca aaagtggacc ctctatattt cctccctttt tatagtctta taagatacat    1500
tatgaaaggt gaccgactct attttaaatc tcagaatttt aagttctagc cccatgataa    1560
```

```
ccttttctctt tgtaatttat gctttcatat atccttggtc ccagagatgt ttagacaatt    1620
ttaggctcaa aaattaaagc taacacagga aaaggaactg tactggctat tacataagaa    1680
acaatggacc caagagaaga aaaggaagaa agaaaggttt tttggttttt gttttgtttt    1740
gttttgtttt ttgttttttt gagatggagt ctcactcttt cgcccaggct ggagtgcagt    1800
ggtatgatct cagctcactg caagctccac ctcccgggtt cacgccattc tcctgcctca    1860
gcctcctgag tagctgggac tacaggcgcc cgccaccaca cccggctaat ttttgtatt     1920 ttttgtagag acggggtttc accatgttag ccaagatggt ctcgatctcc tgacctcgtg    1980
atccacctgc ctcggcctcc caaagtgctg ggattacggg tgtgagccac cgtgcccagc    2040
cttttttttt ttaatagaaa aataatccg actcccacta catcaagact aatcttgttt     2100
tgtgtgtttt tcacatgtat tatagaatgc ttttgcatgg actatcctct tgttttttatt   2160 aaaaacaaat gattttttta aaagtcacaa aaacaattca ctaaaaataa atatgtcatt    2220
gtgcttaaaa aaaataaccct cttgtagtta taaaataaaa cgtttgactt ctaaactctg   2280
```

```
<210> SEQ ID NO 7
<211> LENGTH: 2398
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(383)
<223> OTHER INFORMATION: Exon 2
<220> FEATURE:
<221> NAME/KEY: misc_feature
<222> LOCATION: (384)..(515)
<223> OTHER INFORMATION: Exon 3
<220> FEATURE:
<221> NAME/KEY: misc_feature
<222> LOCATION: (516)..(622)
<223> OTHER INFORMATION: Exon 4
<220> FEATURE:
<221> NAME/KEY: misc_feature
<222> LOCATION: (623)..(760)
<223> OTHER INFORMATION: Exon 5
<220> FEATURE:
<221> NAME/KEY: misc_feature
<222> LOCATION: (761)..(878)
<223> OTHER INFORMATION: Exon 6v2 - includes additional residue 878 at
     3' end
<220> FEATURE:
<221> NAME/KEY: misc_feature
<222> LOCATION: (879)..(2398)
<223> OTHER INFORMATION: Exon 7

<400> SEQUENCE: 7
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catggaatag gcaggcagac tacttatgaa tttgcaaaac    240
gacagagcat attggttctg tgggatatta ataagcgcgg tgtggaggaa actgcagctg    300
agtgccgaaa actaggcgtc actgcgcatg cgtatgtggt agactgcagc aacagagaag    360
agatctatcg ctctctaaat caggtgaaga aagaagtggg tgatgtaaca atcgtggtga    420
ataatgctgg gacagtatat ccagccgatc ttctcagcac caaggatgaa gagattacca    480
agacatttga ggtcaacatc ctaggacatt tttggatcac aaaaagcactt cttccatcga    540
```

```
tgatggagag aaatcatggc cacatcgtca cagtggcttc agtgtgcggc cacgaaggga    600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc aagcacaag attatggcct gtattggaga     780
cagatgaagt cgtaagaagt ctgatagatg gaatacttac caataagaaa atgattttg     840 ttccatcgta tatcaatatc tttctgagac tacagaaggt ttcttcctga acgcgcctca    900
gcgattttaa atcgtatgca gaatattcaa tttgaagcag tggttggcca caaaatcaaa    960
atgaaatgaa taaataagct ccagccagag atgtatgcat gataatgata tgaatagttt   1020
cgaatcaatg ctgcaaagct ttatttcaca ttttttcagt cctgataata ttaaaaacat   1080
tggtttggca ctagcagcag tcaaacgaac aagattaatt acctgtcttc ctgtttctca   1140
agaatattta cgtagttttt cataggtctg ttttctcttt catgcctctt aaaaacttct   1200
gtgcttacat aaacatactt aaaaggtttt ctttaagata ttttattttt ccatttaaag   1260
gtggacaaaa gctacctccc taaaagtaaa tacaaagaga acttatttac acagggaagg   1320
tttaagactg ttcaagtagc attccaatct gtagccatgc cacagaatat caacaagaac   1380
acagaatgag tgcacagcta agagatcaag tttcagcagg cagctttatc tcaacctgga   1440
catattttaa gattcagcat ttgaaagatt tccctagcct cttccttttt cattagccca   1500
aaacggtgca actctattct ggactttatt acttgattct gtcttctgta taactctgaa   1560
gtccaccaaa agtggaccct ctatatttcc tcccttttta tagtcttata agatacatta   1620
tgaaaggtga ccgactctat tttaaatctc agaattttaa gttctagccc catgataacc   1680 tttttcttg taatttatgc tttcatatat ccttggtccc agagatgttt agacaatttt    1740
aggctcaaaa attaaagcta acacaggaaa aggaactgta ctggctatta cataagaaac   1800
aatggaccca agagaagaaa aggaagaaag aaaggttttt tggttttgt tttgttttgt    1860 tttgttttt gtttttttga gatggagtct cactctttcg cccaggctgg agtgcagtgg    1920
tatgatctca gctcactgca agctccacct cccgggttca cgccattctc ctgcctcagc   1980
ctcctgagta gctgggacta caggcgcccg ccaccacacc cggctaattt tttgtatttt   2040
ttgtagagac ggggtttcac catgttagcc aagatggtct cgatctcctg acctcgtgat   2100
ccacctgcct cggcctccca aagtgctggg attacgggtg tgagccaccg tgcccagcct   2160 ttttttttt aatagaaaaa ataatccgac tcccactaca tcaagactaa tcttgttttg   2220 tgtgttttc acatgtatta tagaatgctt ttgcatggac tatcctcttg tttttattaa    2280
aaacaaatga ttttttaaa agtcacaaaa acaattcact aaaaataaat atgtcattgt    2340
gctttaaaaa aataacctct tgtagttata aaataaaacg tttgacttct aaactctg     2398
```

<210> SEQ ID NO 8
<211> LENGTH: 2469
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(383)
<223> OTHER INFORMATION: Exon 2
<220> FEATURE:
<221> NAME/KEY: misc_feature
<222> LOCATION: (384)..(515)

```
<223> OTHER INFORMATION: Exon 3
<220> FEATURE:
<221> NAME/KEY: misc_feature
<222> LOCATION: (516)..(587)
<223> OTHER INFORMATION: Exon 3'
<220> FEATURE:
<221> NAME/KEY: misc_feature
<222> LOCATION: (588)..(694)
<223> OTHER INFORMATION: Exon 4
<220> FEATURE:
<221> NAME/KEY: misc_feature
<222> LOCATION: (695)..(832)
<223> OTHER INFORMATION: Exon 5
<220> FEATURE:
<221> NAME/KEY: misc_feature
<222> LOCATION: (833)..(949)
<223> OTHER INFORMATION: Exon 6v1
<220> FEATURE:
<221> NAME/KEY: misc_feature
<222> LOCATION: (950)..(2469)
<223> OTHER INFORMATION: Exon 7

<400> SEQUENCE: 8
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataagcgcgg tgtggaggaa actgcagctg     300
agtgccgaaa actaggcgtc actgcgcatg cgtatgtggt agactgcagc aacagagaag     360
agatctatcg ctctctaaat caggtgaaga agaagtgggg tgatgtaaca atcgtggtga     420
ataatgctgg gacagtatat ccagccgatc ttctcagcac caaggatgaa gagattacca     480
agacatttga ggtcaacatc ctaggacatt tttggaatgg aaaggacatc agaagtaatt     540
acttggatgt atataggatc gaggacactt ttggacgaga ctctgagatc acaaaagcac     600
ttcttccatc gatgatggag agaaatcatg gccacatcgt cacagtggct tcagtgtgcg     660
gccacgaagg gattccttac ctcatcccat attgttccag caaatttgcc gctgttggct     720
ttcacagagg tctgacatca gaacttcagg ccttgggaaa aactggtatc aaaacctcat     780
gtctctgccc agttttttgtg aatactgggt tcaccaaaaa tccaagcaca agattatggc     840
ctgtattgga gacagatgaa gtcgtaagaa gtctgataga tggaatactt accaataaga     900
aaatgatttt tgttccatcg tatatcaata tctttctgag actacagaag tttcttcctg     960
aacgcgcctc agcgatttta aatcgtatgc agaatattca atttgaagca gtggttggcc    1020
acaaaatcaa aatgaaatga ataaataagc tccagccaga gatgtatgca tgataatgat    1080
atgaatagtt tcgaatcaat gctgcaaagc tttatttcac attttttcag tcctgataat    1140
attaaaaaca ttggtttggc actagcagca gtcaaacgaa caagattaat tacctgtctt    1200
cctgtttctc aagaatattt acgtagtttt tcataggtct gttttttcctt tcatgcctct    1260 taaaaacttc tgtgcttaca taaacatact taaaaggttt tctttaagat attttatttt    1320
tccatttaaa ggtggacaaa agctacctcc ctaaaagtaa atacaaagag aacttattta    1380
cacagggaag gtttaagact gttcaagtag cattccaatc tgtagccatg ccacagaata    1440
tcaacaagaa cacagaatga gtgcacagct aagagatcaa gtttcagcag gcagctttat    1500
ctcaacctgg acatatttta agattcagca tttgaaagat ttccctagcc tcttcctttt    1560
tcattagccc aaaacggtgc aactctattc tggactttat tacttgattc tgtcttctgt    1620
ataactctga agtccaccaa aagtggaccc tctatatttc ctccctttttt atagtcttat    1680
```

-continued

```
aagatacatt atgaaaggtg accgactcta ttttaaatct cagaatttta agttctagcc    1740
ccatgataac cttttcttt gtaatttatg ctttcatata tccttggtcc cagagatgtt    1800
tagacaattt taggctcaaa aattaaagct aacacaggaa aaggaactgt actggctatt    1860
acataagaaa caatggaccc aagagaagaa aaggaagaaa gaaaggtttt ttggtttttg    1920
ttttgttttg ttttgttttt tgttttttg agatggagtc tcactctttc gcccaggctg    1980
gagtgcagtg gtatgatctc agctcactgc aagctccacc tcccgggttc acgccattct    2040
cctgcctcag cctcctgagt agctgggact acaggcgccc gccaccacac ccggctaatt    2100
ttttgtattt tttgtagaga cggggtttca ccatgttagc caagatggtc tcgatctcct    2160
gacctcgtga tccacctgcc tcggcctccc aaagtgctgg gattacgggt gtgagccacc    2220
gtgcccagcc tttttttttt taatagaaaa aataatccga ctcccactac atcaagacta    2280
atcttgtttt gtgtgttttt cacatgtatt atagaatgct tttgcatgga ctatcctctt    2340
gtttttatta aaacaaatg atttttttaa aagtcacaaa aacaattcac taaaaataaa    2400
tatgtcattg tgctttaaaa aaataaccctc ttgtagttat aaaataaaac gtttgacttc    2460
taaactctg                                                              2469
```

<210> SEQ ID NO 9
<211> LENGTH: 1715
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(383)
<223> OTHER INFORMATION: Exon 2
<220> FEATURE:
<221> NAME/KEY: misc_feature
<222> LOCATION: (384)..(515)
<223> OTHER INFORMATION: Exon 3
<220> FEATURE:
<221> NAME/KEY: misc_feature
<222> LOCATION: (516)..(622)
<223> OTHER INFORMATION: Exon 4
<220> FEATURE:
<221> NAME/KEY: misc_feature
<222> LOCATION: (623)..(760)
<223> OTHER INFORMATION: Exon 5
<220> FEATURE:
<221> NAME/KEY: misc_feature
<222> LOCATION: (761)..(1715)
<223> OTHER INFORMATION: Exon 6v3
<220> FEATURE:
<221> NAME/KEY: misc_feature
<222> LOCATION: (878)..(1715)
<223> OTHER INFORMATION: Read-through from exon 6 into intron 6
<220> FEATURE:
<221> NAME/KEY: misc_feature
<222> LOCATION: (1716)..(1715)
<223> OTHER INFORMATION: Read-through from exon 6 into intron 6

<400> SEQUENCE: 9

```
agacagtacc tcctccctag gactacacaa ggactgaacc agaaggaaga ggacagagca      60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catggaatag gcaggcagac tacttatgaa tttgcaaaac    240
gacagagcat attggttctg tgggatatta ataagcgcgg tgtggaggaa actgcagctg    300
```

```
agtgccgaaa actaggcgtc actgcgcatg cgtatgtggt agactgcagc aacagagaag      360
agatctatcg ctctctaaat caggtgaaga aagaagtggg tgatgtaaca atcgtggtga      420
ataatgctgg gacagtatat ccagccgatc ttctcagcac caaggatgaa gagattacca      480
agacatttga ggtcaacatc ctaggacatt tttggatcac aaaagcactt cttccatcga      540
tgatggagag aaatcatggc cacatcgtca cagtggcttc agtgtgcggc cacgaaggga      600
ttccttacct catcccatat tgttccagca aatttgccgc tgttggcttt cacagaggtc      660
tgacatcaga acttcaggcc ttgggaaaaa ctggtatcaa aacctcatgt ctctgcccag      720
tttttgtgaa tactgggttc accaaaaatc caagcacaag attatggcct gtattggaga      780
cagatgaagt cgtaagaagt ctgatagatg gaatacttac caataagaaa atgatttttg      840
ttccatcgta tatcaatatc tttctgagac tacagaagtt aagtacagca cagaacaccc      900
aaatactaaa acaccaatag agctttttt tttgcttttt ttttttttag acagagtctc      960
actctgtcac cctggctgga ttgcggtggt tgcagtggca tgatcttggc tcactgcaac     1020
ctccgcctcc tgggttcaag caattctcat gcctcagacc cccaagtaac tgggattata     1080
ggtgtgtgct gccacactac acccagctaa ttttttgtatt ttttgataga cacaggtttc     1140
cccatgttgg ccaggctgga ctcgaactcc tgacctcaag ttatcctcct gtctcggcct     1200
cccaaagtgc tgggattaca gtcatgagcc accatgcctg gcccaataga gctattatta     1260
tggagcatct ttcagttgtg aaaattggca tggaaactct ccatccctgg ggagaacagt     1320
tatttcctct gttatttttcc tacccagtct ataaaagag agtgattcat tttctctacc     1380
aaatctactg tctctgccca aactttgctg aagactattc taactaaagg aaacacagtt     1440 taaaagaat gcaatatagt gaagtagtta ataataaaga ctccatttt aaaagtctgc      1500 tggaagtttg gttgggattg cactgaatct atagagcaat tggggagtat tgacatatca     1560
acaatattga gttttctaat ccaagaacat aatatctatt tttaaaatct tcttcaaaat     1620
ctttaaatct ttaaattgta ttttgtagtt tttggtgttt aagtcttgca catattttgt     1680
cagatttatt ccaaagtatt tcacgggttc ttttt                                1715
```

```
<210> SEQ ID NO 10
<211> LENGTH: 2290
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(407)
<223> OTHER INFORMATION: Exon 3
<220> FEATURE:
<221> NAME/KEY: misc_feature
<222> LOCATION: (408)..(514)
<223> OTHER INFORMATION: Exon 4
<220> FEATURE:
<221> NAME/KEY: misc_feature
<222> LOCATION: (515)..(652)
<223> OTHER INFORMATION: Exon 5
<220> FEATURE:
<221> NAME/KEY: misc_feature
<222> LOCATION: (653)..(770)
<223> OTHER INFORMATION: Exon 6v2 - includes additional residue 770 at
      3' end
<220> FEATURE:
<221> NAME/KEY: misc_feature
<222> LOCATION: (771)..(2290)
<223> OTHER INFORMATION: Exon 7
```

```
<400> SEQUENCE: 10
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta taaggtgaa gaaagaagtg ggtgatgtaa      300
caatcgtggt gaataatgct gggacagtat atccagccga tcttctcagc accaaggatg     360
aagagattac caagacattt gaggtcaaca tcctaggaca tttttggatc acaaaagcac     420
ttcttccatc gatgatggag agaaatcatg gccacatcgt cacagtggct tcagtgtgcg     480
gccacgaagg gattccttac ctcatcccat attgttccag caaatttgcc gctgttggct     540
ttcacagagg tctgacatca gaacttcagg ccttgggaaa aactggtatc aaaacctcat     600
gtctctgccc agttttttgtg aatactgggt tcaccaaaaa tccaagcaca agattatggc     660
ctgtattgga gacagatgaa gtcgtaagaa gtctgataga tggaatactt accaataaga     720
aaatgatttt tgttccatcg tatatcaata tctttctgag actacagaag gtttcttcct     780
gaacgcgcct cagcgatttt aaatcgtatg cagaatattc aatttgaagc agtggttggc     840
cacaaaatca aaatgaaatg aataaataag ctccagccag agatgtatgc atgataatga     900
tatgaatagt ttcgaatcaa tgctgcaaag ctttatttca cattttttca gtcctgataa     960
tattaaaaac attggtttgg cactagcagc agtcaaacga acaagattaa ttacctgtct    1020
tcctgttttct caagaatatt tacgtagttt tccataggtc tgttttttcct ttcatgcctc    1080
ttaaaaactt ctgtgcttac ataaacatac ttaaaaggtt ttctttaaga tattttattt    1140
ttccatttaa aggtggacaa aagctacctc cctaaaagta aatacaaaga gaacttattt    1200
acacagggaa ggtttaagac tgttcaagta gcattccaat ctgtagccat gccacagaat    1260
atcaacaaga acacagaatg agtgcacagc taagagatca agtttcagca ggcagcttta    1320
tctcaacctg gacatatttt aagattcagc atttgaaaga tttccctagc ctcttccttt    1380
ttcattagcc caaaacggtg caactctatt ctggacttta ttacttgatt ctgtcttctg    1440
tataactctg aagtccacca aaagtggacc ctctatattt cctccctttt tatagtctta    1500
taagatacat tatgaaaggt gaccgactct attttaaatc tcagaatttt aagttctagc    1560
cccatgataa ccttttttctt tgtaatttat gctttcatat atccttggtc ccagagatgt    1620
ttagacaatt ttaggctcaa aaattaaagc taacacagga aaaggaactg tactggctat    1680
tacataagaa acaatggacc caagagaaga aaaggaagaa agaaaggttt tttggttttt    1740
gttttgtttt gttttgtttt ttgtttttttt gagatggagt ctcactcttt cgcccaggct    1800
ggagtgcagt ggtatgatct cagctcactg caagctccac ctcccgggtt cacgccattc    1860
tcctgcctca gcctcctgag tagctgggac tacaggcgcc cgccaccaca cccggctaat    1920
ttttttgtatt ttttgtagag acggggtttc accatgttag ccagatggt ctcgatctcc     1980
tgacctcgtg atccacctgc ctcggcctcc caaagtgctg ggattacggg tgtgagccac    2040
cgtgcccagc cttttttttt ttaatagaaa aaataatccg actcccacta catcaagact    2100
aatcttgttt tgtgtgtttt tcacatgtat tatagaatgc ttttgcatgg actatcctct    2160
tgtttttatt aaaaacaaat gatttttta aaagtcacaa aaacaattca ctaaaaataa    2220
atatgtcatt gtgcttaaa aaaataaccct cttgtagtta taaataaaaa cgtttgactt    2280
ctaaactctg                                                          2290
```

<210> SEQ ID NO 11
<211> LENGTH: 2470
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(383)
<223> OTHER INFORMATION: Exon 2
<220> FEATURE:
<221> NAME/KEY: misc_feature
<222> LOCATION: (384)..(515)
<223> OTHER INFORMATION: Exon 3
<220> FEATURE:
<221> NAME/KEY: misc_feature
<222> LOCATION: (516)..(587)
<223> OTHER INFORMATION: Exon 3'
<220> FEATURE:
<221> NAME/KEY: misc_feature
<222> LOCATION: (588)..(694)
<223> OTHER INFORMATION: Exon 4
<220> FEATURE:
<221> NAME/KEY: misc_feature
<222> LOCATION: (695)..(832)
<223> OTHER INFORMATION: Exon 5
<220> FEATURE:
<221> NAME/KEY: misc_feature
<222> LOCATION: (833)..(950)
<223> OTHER INFORMATION: Exon 6v2 - includes additional residue 950 at 3' end
<220> FEATURE:
<221> NAME/KEY: misc_feature
<222> LOCATION: (951)..(2470)
<223> OTHER INFORMATION: Exon 7

<400> SEQUENCE: 11

| | | | | | |
|---|---|---|---|---|---|
| agacagtacc | tcctccctag | gactacacaa | ggactgaacc | agaaggaaga | ggacagagca | 60 |
| aagccatgaa | catcatccta | gaaatccttc | tgcttctgat | caccatcatc | tactcctact | 120 |
| tggagtcgtt | ggtgaagttt | tcattcctc | agaggagaaa | atctgtggct | ggggagattg | 180 |
| ttctcattac | tggagctggg | catggaatag | gcaggcagac | tacttatgaa | tttgcaaaac | 240 |
| gacagagcat | attggttctg | tgggatatta | ataagcgcgg | tgtggaggaa | actgcagctg | 300 |
| agtgccgaaa | actaggcgtc | actgcgcatg | cgtatgtggt | agactgcagc | aacagagaag | 360 |
| agatctatcg | ctctctaaat | caggtgaaga | agaagtgggg | tgatgtaaca | atcgtggtga | 420 |
| ataatgctgg | gacagtatat | ccagccgatc | ttctcagcac | caaggatgaa | gagattacca | 480 |
| agacatttga | ggtcaacatc | ctaggacatt | tttggaatgg | aaaggacatc | agaagtaatt | 540 |
| acttggatgt | ataggatc | gaggacactt | tggacgaga | ctctgagatc | acaaaagcac | 600 |
| ttcttccatc | gatgatggag | agaaatcatg | gccacatcgt | cacagtggct | tcagtgtgcg | 660 |
| gccacgaagg | gattccttac | ctcatcccat | attgttccag | caaatttgcc | gctgttggct | 720 |
| ttacagagg | tctgacatca | gaacttcagg | ccttgggaaa | aactggtatc | aaaacctcat | 780 |
| gtctctgccc | agttttttgtg | aatactgggt | tcaccaaaaa | tccaagcaca | agattatggc | 840 |
| ctgtattgga | gacagatgaa | gtcgtaagaa | gtctgataga | tggaatactt | accaataaga | 900 |
| aaatgatttt | tgttccatcg | tatatcaata | tcttctgag | actacagaag | gtttcttcct | 960 |
| gaacgcgcct | cagcgatttt | aaatcgtatg | cagaatattc | aatttgaagc | agtggttggc | 1020 |
| cacaaaatca | aaatgaaatg | aataaataag | ctccagccag | agatgtatgc | atgataatga | 1080 |
| tatgaatagt | ttcgaatcaa | tgctgcaaag | ctttatttca | cattttttca | gtcctgataa | 1140 |

| | |
|---|---|
| tattaaaaac attggtttgg cactagcagc agtcaaacga acaagattaa ttacctgtct | 1200 |
| tcctgtttct caagaatatt tacgtagttt tcataggtc tgttttcct ttcatgcctc | 1260 |
| ttaaaaactt ctgtgcttac ataaacatac ttaaaaggtt ttctttaaga tatttattt | 1320 |
| ttccatttaa aggtggacaa aagctacctc cctaaaagta aatacaaaga gaacttattt | 1380 |
| acacagggaa ggtttaagac tgttcaagta gcattccaat ctgtagccat gccacagaat | 1440 |
| atcaacaaga acacagaatg agtgcacagc taagagatca agtttcagca ggcagcttta | 1500 |
| tctcaacctg gacatatttt aagattcagc atttgaaaga tttccctagc ctcttccttt | 1560 |
| ttcattagcc caaacggtg caactctatt ctggacttta ttacttgatt ctgtcttctg | 1620 |
| tataactctg aagtccacca aaagtggacc ctctatattt cctcccttt tatagtctta | 1680 |
| taagatacat tatgaaaggt gaccgactct atttaaatc tcagaatttt aagttctagc | 1740 |
| cccatgataa cctttttctt tgtaatttat gctttcatat atccttggtc ccagagatgt | 1800 |
| ttagacaatt ttaggctcaa aaattaaagc taacacagga aaaggaactg tactggctat | 1860 |
| tacataagaa acaatggacc caagagaaga aaaggaagaa agaaaggttt tttggttttt | 1920 |
| gttttgtttt gttttgtttt ttgtttttt gagatggagt ctcactcttt cgcccaggct | 1980 |
| ggagtgcagt ggtatgatct cagctcactg caagctccac ctcccgggtt cacgccattc | 2040 |
| tcctgcctca gcctcctgag tagctgggac tacaggcgcc cgccaccaca cccggctaat | 2100 |
| ttttgtatt ttttgtagag acggggtttc accatgttag ccaagatggt ctcgatctcc | 2160 |
| tgacctcgtg atccacctgc ctcggcctcc caaagtgctg ggattacggg tgtgagccac | 2220 |
| cgtgcccagc ctttttttt ttaatagaaa aaataatccg actcccacta catcaagact | 2280 |
| aatcttgttt tgtgtgtttt tcacatgtat tatagaatgc ttttgcatgg actatcctct | 2340 |
| tgttttatt aaaaacaaat gatttttta aaagtcacaa aaacaattca ctaaaaataa | 2400 |
| atatgtcatt gtgctttaaa aaataaccct cttgtagtta taaaataaaa cgtttgactt | 2460 |
| ctaaactctg | 2470 |

```
<210> SEQ ID NO 12
<211> LENGTH: 300
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(106)
<223> OTHER INFORMATION: Region Encoded by Exon 2
<220> FEATURE:
<221> NAME/KEY: MISC_FEATURE
<222> LOCATION: (107)..(150)
<223> OTHER INFORMATION: Region Encoded by Exon 3
<220> FEATURE:
<221> NAME/KEY: MISC_FEATURE
<222> LOCATION: (151)..(185)
<223> OTHER INFORMATION: Region Encoded by Exon 4
<220> FEATURE:
<221> NAME/KEY: MISC_FEATURE
<222> LOCATION: (186)..(232)
<223> OTHER INFORMATION: Region Encoded by Exon 5
<220> FEATURE:
<221> NAME/KEY: MISC_FEATURE
<222> LOCATION: (233)..(271)
<223> OTHER INFORMATION: Region Encoded by Exon 6v1
<220> FEATURE:
<221> NAME/KEY: MISC_FEATURE
<222> LOCATION: (272)..(300)
```

<223> OTHER INFORMATION: Region Encoded by Exon 7

<400> SEQUENCE: 12

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Phe
            260                 265                 270

Leu Pro Glu Arg Ala Ser Ala Ile Leu Asn Arg Met Gln Asn Ile Gln
        275                 280                 285

Phe Glu Ala Val Val Gly His Lys Ile Lys Met Lys
    290                 295                 300

<210> SEQ ID NO 13
<211> LENGTH: 264
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(114)
<223> OTHER INFORMATION: Region Encoded by Exon 3
<220> FEATURE:
<221> NAME/KEY: MISC_FEATURE
<222> LOCATION: (115)..(149)
<223> OTHER INFORMATION: Region Encoded by Exon 4
<220> FEATURE:

```
<221> NAME/KEY: MISC_FEATURE
<222> LOCATION: (150)..(196)
<223> OTHER INFORMATION: Region Encoded by Exon 5
<220> FEATURE:
<221> NAME/KEY: MISC_FEATURE
<222> LOCATION: (197)..(235)
<223> OTHER INFORMATION: Region Encoded by Exon 6v1
<220> FEATURE:
<221> NAME/KEY: MISC_FEATURE
<222> LOCATION: (236)..(264)
<223> OTHER INFORMATION: Region Encoded by Exon 7

<400> SEQUENCE: 13

Met Asn Ile Ile Leu Glu Ile Leu Leu Leu Ile Thr Ile Ile Tyr
1               5                   10                  15

Ser Tyr Leu Glu Ser Leu Val Lys Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Val Lys Lys Glu Val Gly Asp Val Thr Ile
65              70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
        115                 120                 125

Gly His Ile Val Thr Val Ala Ser Val Cys Gly His Glu Gly Ile Pro
    130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
            180                 185                 190

Pro Ser Thr Arg Leu Trp Pro Val Leu Glu Thr Asp Glu Val Val Arg
        195                 200                 205

Ser Leu Ile Asp Gly Ile Leu Thr Asn Lys Lys Met Ile Phe Val Pro
    210                 215                 220

Ser Tyr Ile Asn Ile Phe Leu Arg Leu Gln Lys Phe Leu Pro Glu Arg
225                 230                 235                 240

Ala Ser Ala Ile Leu Asn Arg Met Gln Asn Ile Gln Phe Glu Ala Val
                245                 250                 255

Val Gly His Lys Ile Lys Met Lys
            260

<210> SEQ ID NO 14
<211> LENGTH: 261
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(106)
<223> OTHER INFORMATION: Region Encoded by Exon 2
<220> FEATURE:
```

```
<221> NAME/KEY: MISC_FEATURE
<222> LOCATION: (107)..(150)
<223> OTHER INFORMATION: Region Encoded by Exon 3
<220> FEATURE:
<221> NAME/KEY: MISC_FEATURE
<222> LOCATION: (151)..(185)
<223> OTHER INFORMATION: Region Encoded by Exon 4
<220> FEATURE:
<221> NAME/KEY: MISC_FEATURE
<222> LOCATION: (186)..(232)
<223> OTHER INFORMATION: Region Encoded by Exon 5
<220> FEATURE:
<221> NAME/KEY: MISC_FEATURE
<222> LOCATION: (233)..(261)
<223> OTHER INFORMATION: Region Encoded by Exon 7

<400> SEQUENCE: 14
```

Met Asn Ile Ile Leu Glu Ile Leu Leu Leu Ile Thr Ile Ile Tyr
1               5                   10                  15

Ser Tyr Leu Glu Ser Leu Val Lys Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Phe Leu Pro Glu Arg Ala Ser Ala
225                 230                 235                 240

Ile Leu Asn Arg Met Gln Asn Ile Gln Phe Glu Ala Val Val Gly His
                245                 250                 255

Lys Ile Lys Met Lys
            260

```
<210> SEQ ID NO 15
<211> LENGTH: 274
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
```

```
<221> NAME/KEY: MISC_FEATURE
<222> LOCATION: (71)..(106)
<223> OTHER INFORMATION: Region Encoded by Exon 2
<220> FEATURE:
<221> NAME/KEY: MISC_FEATURE
<222> LOCATION: (107)..(150)
<223> OTHER INFORMATION: Region Encoded by Exon 3
<220> FEATURE:
<221> NAME/KEY: MISC_FEATURE
<222> LOCATION: (151)..(185)
<223> OTHER INFORMATION: Region Encoded by Exon 4
<220> FEATURE:
<221> NAME/KEY: MISC_FEATURE
<222> LOCATION: (186)..(232)
<223> OTHER INFORMATION: Region Encoded by Exon 5
<220> FEATURE:
<221> NAME/KEY: MISC_FEATURE
<222> LOCATION: (233)..(271)
<223> OTHER INFORMATION: Region Encoded by Exon 6v2
<220> FEATURE:
<221> NAME/KEY: MISC_FEATURE
<222> LOCATION: (272)..(274)
<223> OTHER INFORMATION: Region Encoded by Exon 7

<400> SEQUENCE: 15
```

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Val
            260                 265                 270

Ser Ser

```
<210> SEQ ID NO 16
<211> LENGTH: 324
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(106)
<223> OTHER INFORMATION: Region Encoded by Exon 2
<220> FEATURE:
<221> NAME/KEY: MISC_FEATURE
<222> LOCATION: (107)..(150)
<223> OTHER INFORMATION: Region Encoded by Exon 3
<220> FEATURE:
<221> NAME/KEY: MISC_FEATURE
<222> LOCATION: (151)..(174)
<223> OTHER INFORMATION: Region Encoded by Exon 3'
<220> FEATURE:
<221> NAME/KEY: MISC_FEATURE
<222> LOCATION: (175)..(209)
<223> OTHER INFORMATION: Region Encoded by Exon 4
<220> FEATURE:
<221> NAME/KEY: MISC_FEATURE
<222> LOCATION: (210)..(256)
<223> OTHER INFORMATION: Region Encoded by Exon 5
<220> FEATURE:
<221> NAME/KEY: MISC_FEATURE
<222> LOCATION: (257)..(295)
<223> OTHER INFORMATION: Region Encoded by Exon 6v1
<220> FEATURE:
<221> NAME/KEY: MISC_FEATURE
<222> LOCATION: (296)..(324)
<223> OTHER INFORMATION: Region Encoded by Exon 7

<400> SEQUENCE: 16

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205
```

```
Tyr Cys Ser Ser Lys Phe Ala Ala Val Gly Phe His Arg Gly Leu Thr
    210                 215                 220
Ser Glu Leu Gln Ala Leu Gly Lys Thr Gly Ile Lys Thr Ser Cys Leu
225                 230                 235                 240
Cys Pro Val Phe Val Asn Thr Gly Phe Thr Lys Asn Pro Ser Thr Arg
                245                 250                 255
Leu Trp Pro Val Leu Glu Thr Asp Glu Val Val Arg Ser Leu Ile Asp
            260                 265                 270
Gly Ile Leu Thr Asn Lys Lys Met Ile Phe Val Pro Ser Tyr Ile Asn
        275                 280                 285
Ile Phe Leu Arg Leu Gln Lys Phe Leu Pro Glu Arg Ala Ser Ala Ile
    290                 295                 300
Leu Asn Arg Met Gln Asn Ile Gln Phe Glu Ala Val Val Gly His Lys
305                 310                 315                 320
Ile Lys Met Lys
```

```
<210> SEQ ID NO 17
<211> LENGTH: 284
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(106)
<223> OTHER INFORMATION: Region Encoded by Exon 2
<220> FEATURE:
<221> NAME/KEY: MISC_FEATURE
<222> LOCATION: (107)..(150)
<223> OTHER INFORMATION: Region Encoded by Exon 3
<220> FEATURE:
<221> NAME/KEY: MISC_FEATURE
<222> LOCATION: (151)..(185)
<223> OTHER INFORMATION: Region Encoded by Exon 4
<220> FEATURE:
<221> NAME/KEY: MISC_FEATURE
<222> LOCATION: (186)..(232)
<223> OTHER INFORMATION: Region Encoded by Exon 5
<220> FEATURE:
<221> NAME/KEY: MISC_FEATURE
<222> LOCATION: (233)..(284)
<223> OTHER INFORMATION: Region Encoded by Exon 6v3
<220> FEATURE:
<221> NAME/KEY: MISC_FEATURE
<222> LOCATION: (272)..(284)
<223> OTHER INFORMATION: Region Encoded by Read-Through Into Intron 6

<400> SEQUENCE: 17
```

```
Met Asn Ile Ile Leu Glu Ile Leu Leu Leu Ile Thr Ile Ile Tyr
1               5                   10                  15
Ser Tyr Leu Glu Ser Leu Val Lys Phe Phe Ile Pro Gln Arg Arg Lys
            20                  25                  30
Ser Val Ala Gly Glu Ile Val Leu Ile Thr Gly Ala Gly His Gly Ile
        35                  40                  45
Gly Arg Gln Thr Thr Tyr Glu Phe Ala Lys Arg Gln Ser Ile Leu Val
    50                  55                  60
Leu Trp Asp Ile Asn Lys Arg Gly Val Glu Thr Ala Ala Glu Cys
65                  70                  75                  80
Arg Lys Leu Gly Val Thr Ala His Ala Tyr Val Val Asp Cys Ser Asn
                85                  90                  95
Arg Glu Glu Ile Tyr Arg Ser Leu Asn Gln Val Lys Lys Glu Val Gly
            100                 105                 110
```

```
Asp Val Thr Ile Val Val Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
                180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
        210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Leu
                260                 265                 270

Ser Thr Ala Gln Asn Thr Gln Ile Leu Lys His Gln
        275                 280

<210> SEQ ID NO 18
<211> LENGTH: 238
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(114)
<223> OTHER INFORMATION: Region Encoded by Exon 3
<220> FEATURE:
<221> NAME/KEY: MISC_FEATURE
<222> LOCATION: (115)..(149)
<223> OTHER INFORMATION: Region Encoded by Exon 4
<220> FEATURE:
<221> NAME/KEY: MISC_FEATURE
<222> LOCATION: (150)..(196)
<223> OTHER INFORMATION: Region Encoded by Exon 5
<220> FEATURE:
<221> NAME/KEY: MISC_FEATURE
<222> LOCATION: (197)..(235)
<223> OTHER INFORMATION: Region Encoded by Exon 6v2
<220> FEATURE:
<221> NAME/KEY: MISC_FEATURE
<222> LOCATION: (236)..(238)
<223> OTHER INFORMATION: Region Encoded by Exon 7

<400> SEQUENCE: 18

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Val Lys Lys Glu Val Gly Asp Val Thr Ile
```

```
            65                  70                  75                  80
Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
               100                 105                 110

Phe Trp Ile Thr Lys Ala Leu Leu Pro Ser Met Met Glu Arg Asn His
               115                 120                 125

Gly His Ile Val Thr Val Ala Ser Val Cys Gly His Glu Gly Ile Pro
               130                 135                 140

Tyr Leu Ile Pro Tyr Cys Ser Ser Lys Phe Ala Ala Val Gly Phe His
145                150                 155                 160

Arg Gly Leu Thr Ser Glu Leu Gln Ala Leu Gly Lys Thr Gly Ile Lys
                   165                 170                 175

Thr Ser Cys Leu Cys Pro Val Phe Val Asn Thr Gly Phe Thr Lys Asn
               180                 185                 190

Pro Ser Thr Arg Leu Trp Pro Val Leu Glu Thr Asp Glu Val Val Arg
               195                 200                 205

Ser Leu Ile Asp Gly Ile Leu Thr Asn Lys Lys Met Ile Phe Val Pro
210                215                 220

Ser Tyr Ile Asn Ile Phe Leu Arg Leu Gln Lys Val Ser Ser
225                230                 235

<210> SEQ ID NO 19
<211> LENGTH: 298
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(106)
<223> OTHER INFORMATION: Region Encoded by Exon 2
<220> FEATURE:
<221> NAME/KEY: MISC_FEATURE
<222> LOCATION: (107)..(150)
<223> OTHER INFORMATION: Region Encoded by Exon 3
<220> FEATURE:
<221> NAME/KEY: MISC_FEATURE
<222> LOCATION: (151)..(174)
<223> OTHER INFORMATION: Region Encoded by Exon 3'
<220> FEATURE:
<221> NAME/KEY: MISC_FEATURE
<222> LOCATION: (175)..(209)
<223> OTHER INFORMATION: Region Encoded by Exon 4
<220> FEATURE:
<221> NAME/KEY: MISC_FEATURE
<222> LOCATION: (210)..(256)
<223> OTHER INFORMATION: Region Encoded by Exon 5
<220> FEATURE:
<221> NAME/KEY: MISC_FEATURE
<222> LOCATION: (257)..(295)
<223> OTHER INFORMATION: Region Encoded by Exon 6v2
<220> FEATURE:
<221> NAME/KEY: MISC_FEATURE
<222> LOCATION: (296)..(298)
<223> OTHER INFORMATION: Region Encoded by Exon 7

<400> SEQUENCE: 19

Met Asn Ile Ile Leu Glu Ile Leu Leu Leu Ile Thr Ile Ile Tyr
1               5                  10                  15

Ser Tyr Leu Glu Ser Leu Val Lys Phe Phe Ile Pro Gln Arg Arg Lys
               20                  25                  30

Ser Val Ala Gly Glu Ile Val Leu Ile Thr Gly Ala Gly His Gly Ile
```

```
            35                  40                  45
Gly Arg Gln Thr Thr Tyr Glu Phe Ala Lys Arg Gln Ser Ile Leu Val
 50                  55                  60
Leu Trp Asp Ile Asn Lys Arg Val Glu Glu Thr Ala Ala Glu Cys
 65                  70                  75                  80
Arg Lys Leu Gly Val Thr Ala His Ala Tyr Val Asp Cys Ser Asn
                 85                  90                  95
Arg Glu Glu Ile Tyr Arg Ser Leu Asn Gln Val Lys Lys Glu Val Gly
                100                 105                 110
Asp Val Thr Ile Val Val Asn Asn Ala Gly Thr Val Tyr Pro Ala Asp
            115                 120                 125
Leu Leu Ser Thr Lys Asp Glu Glu Ile Thr Lys Thr Phe Glu Val Asn
130                 135                 140
Ile Leu Gly His Phe Trp Asn Gly Lys Asp Ile Arg Ser Asn Tyr Leu
145                 150                 155                 160
Asp Val Tyr Arg Ile Glu Asp Thr Phe Gly Arg Asp Ser Glu Ile Thr
                165                 170                 175
Lys Ala Leu Leu Pro Ser Met Met Glu Arg Asn His Gly His Ile Val
            180                 185                 190
Thr Val Ala Ser Val Cys Gly His Glu Gly Ile Pro Tyr Leu Ile Pro
        195                 200                 205
Tyr Cys Ser Ser Lys Phe Ala Ala Val Gly Phe His Arg Gly Leu Thr
210                 215                 220
Ser Glu Leu Gln Ala Leu Gly Lys Thr Gly Ile Lys Thr Ser Cys Leu
225                 230                 235                 240
Cys Pro Val Phe Val Asn Thr Gly Phe Thr Lys Asn Pro Ser Thr Arg
                245                 250                 255
Leu Trp Pro Val Leu Glu Thr Asp Glu Val Val Arg Ser Leu Ile Asp
            260                 265                 270
Gly Ile Leu Thr Asn Lys Lys Met Ile Phe Val Pro Ser Tyr Ile Asn
        275                 280                 285
Ile Phe Leu Arg Leu Gln Lys Val Ser Ser
290                 295

<210> SEQ ID NO 20
<211> LENGTH: 20
<212> TYPE: DNA
<213> ORGANISM: Homo sapiens

<400> SEQUENCE: 20
tgaagttttt cattcctcag                                            20

<210> SEQ ID NO 21
<211> LENGTH: 20
<212> TYPE: DNA
<213> ORGANISM: Homo sapiens

<400> SEQUENCE: 21
cttcaccaac gactccaagt                                            20

<210> SEQ ID NO 22
<211> LENGTH: 20
<212> TYPE: DNA
<213> ORGANISM: Homo sapiens

<400> SEQUENCE: 22
ctactcctac ttggagtcgt                                            20
```

<210> SEQ ID NO 23
<211> LENGTH: 20
<212> TYPE: DNA
<213> ORGANISM: Homo sapiens

<400> SEQUENCE: 23
ctccaagtag gagtagatga                                                 20

<210> SEQ ID NO 24
<211> LENGTH: 20
<212> TYPE: DNA
<213> ORGANISM: Homo sapiens

<400> SEQUENCE: 24
caccatcatc tactcctact                                                 20

<210> SEQ ID NO 25
<211> LENGTH: 20
<212> TYPE: DNA
<213> ORGANISM: Homo sapiens

<400> SEQUENCE: 25
tgatggtgat cagaagcaga                                                 20

<210> SEQ ID NO 26
<211> LENGTH: 20
<212> TYPE: DNA
<213> ORGANISM: Homo sapiens

<400> SEQUENCE: 26
tcagaagcag aaggatttct                                                 20

<210> SEQ ID NO 27
<211> LENGTH: 20
<212> TYPE: DNA
<213> ORGANISM: Homo sapiens

<400> SEQUENCE: 27
gatttctagg atgatgttca                                                 20

<210> SEQ ID NO 28
<211> LENGTH: 20
<212> TYPE: DNA
<213> ORGANISM: Homo sapiens

<400> SEQUENCE: 28
ttgctctgtc ctcttccttc                                                 20

<210> SEQ ID NO 29
<211> LENGTH: 20
<212> TYPE: DNA
<213> ORGANISM: Homo sapiens

<400> SEQUENCE: 29
aggactgaac cagaaggaag                                                 20

<210> SEQ ID NO 30
<211> LENGTH: 20
<212> TYPE: DNA
<213> ORGANISM: Homo sapiens

<400> SEQUENCE: 30
tacacaagga ctgaaccaga                                          20

<210> SEQ ID NO 31
<211> LENGTH: 20
<212> TYPE: DNA
<213> ORGANISM: Homo sapiens

<400> SEQUENCE: 31
ttcagtcctt gtgtagtcct                                          20

<210> SEQ ID NO 32
<211> LENGTH: 20
<212> TYPE: DNA
<213> ORGANISM: Homo sapiens

<400> SEQUENCE: 32
tcagtccttg tgtagtccta                                          20

<210> SEQ ID NO 33
<211> LENGTH: 20
<212> TYPE: DNA
<213> ORGANISM: Homo sapiens

<400> SEQUENCE: 33
gtccttgtgt agtcctaggg                                          20

<210> SEQ ID NO 34
<211> LENGTH: 20
<212> TYPE: DNA
<213> ORGANISM: Homo sapiens

<400> SEQUENCE: 34
cttgtgtagt cctagggagg                                          20

<210> SEQ ID NO 35
<211> LENGTH: 20
<212> TYPE: DNA
<213> ORGANISM: Homo sapiens

<400> SEQUENCE: 35
ctcctcccta ggactacaca                                          20

<210> SEQ ID NO 36
<211> LENGTH: 20
<212> TYPE: DNA
<213> ORGANISM: Homo sapiens

<400> SEQUENCE: 36
gtagacagta cctcctccct                                          20

<210> SEQ ID NO 37
<211> LENGTH: 20
<212> TYPE: DNA
<213> ORGANISM: Homo sapiens

<400> SEQUENCE: 37
tactgtctac acagagctct                                          20

<210> SEQ ID NO 38
<211> LENGTH: 20
<212> TYPE: DNA
<213> ORGANISM: Homo sapiens

<400> SEQUENCE: 38
actgtctaca cagagctcta                                               20

<210> SEQ ID NO 39
<211> LENGTH: 20
<212> TYPE: DNA
<213> ORGANISM: Homo sapiens

<400> SEQUENCE: 39
tctacacaga gctctaggga                                               20

<210> SEQ ID NO 40
<211> LENGTH: 20
<212> TYPE: DNA
<213> ORGANISM: Homo sapiens

<400> SEQUENCE: 40
ctacacagag ctctagggaa                                               20

<210> SEQ ID NO 41
<211> LENGTH: 20
<212> TYPE: DNA
<213> ORGANISM: Homo sapiens

<400> SEQUENCE: 41
tacacagagc tctagggaag                                               20

<210> SEQ ID NO 42
<211> LENGTH: 20
<212> TYPE: DNA
<213> ORGANISM: Homo sapiens

<400> SEQUENCE: 42
tgtcaggtta gttagatgaa                                               20

<210> SEQ ID NO 43
<211> LENGTH: 20
<212> TYPE: DNA
<213> ORGANISM: Homo sapiens

<400> SEQUENCE: 43
gtgtcaggtt agttagatga                                               20

<210> SEQ ID NO 44
<211> LENGTH: 20
<212> TYPE: DNA
<213> ORGANISM: Homo sapiens

<400> SEQUENCE: 44
cctgacacat atacagacta                                               20

<210> SEQ ID NO 45
<211> LENGTH: 20
<212> TYPE: DNA
<213> ORGANISM: Homo sapiens

<400> SEQUENCE: 45
ctgacacata tacagactaa                                               20

<210> SEQ ID NO 46
<211> LENGTH: 20
<212> TYPE: DNA
<213> ORGANISM: Homo sapiens

```
<400> SEQUENCE: 46
ccttagtctg tatatgtgtc                                              20

<210> SEQ ID NO 47
<211> LENGTH: 20
<212> TYPE: DNA
<213> ORGANISM: Homo sapiens

<400> SEQUENCE: 47
catatacaga ctaagggacc                                              20

<210> SEQ ID NO 48
<211> LENGTH: 20
<212> TYPE: DNA
<213> ORGANISM: Homo sapiens

<400> SEQUENCE: 48
atatacagac taagggacca                                              20

<210> SEQ ID NO 49
<211> LENGTH: 20
<212> TYPE: DNA
<213> ORGANISM: Homo sapiens

<400> SEQUENCE: 49
tcaaagtttg ataaattccc                                              20

<210> SEQ ID NO 50
<211> LENGTH: 20
<212> TYPE: DNA
<213> ORGANISM: Homo sapiens

<400> SEQUENCE: 50
aaaatacaaa gataagtaga                                              20

<210> SEQ ID NO 51
<211> LENGTH: 20
<212> TYPE: DNA
<213> ORGANISM: Homo sapiens

<400> SEQUENCE: 51
actctgtgac tttaaaaagt                                              20

<210> SEQ ID NO 52
<211> LENGTH: 20
<212> TYPE: DNA
<213> ORGANISM: Homo sapiens

<400> SEQUENCE: 52
ggttctgtgg gatattaata                                              20

<210> SEQ ID NO 53
<211> LENGTH: 20
<212> TYPE: DNA
<213> ORGANISM: Homo sapiens

<400> SEQUENCE: 53
acagagcata ttggttctgt                                              20

<210> SEQ ID NO 54
<211> LENGTH: 20
<212> TYPE: DNA
<213> ORGANISM: Homo sapiens
```

```
<400> SEQUENCE: 54
gacagagcat attggttctg                                              20

<210> SEQ ID NO 55
<211> LENGTH: 20
<212> TYPE: DNA
<213> ORGANISM: Homo sapiens

<400> SEQUENCE: 55
tgcaaaacga cagagcatat                                              20

<210> SEQ ID NO 56
<211> LENGTH: 20
<212> TYPE: DNA
<213> ORGANISM: Homo sapiens

<400> SEQUENCE: 56
gagctgggca tggaataggc                                              20

<210> SEQ ID NO 57
<211> LENGTH: 20
<212> TYPE: DNA
<213> ORGANISM: Homo sapiens

<400> SEQUENCE: 57
actggagctg ggcatggaat                                              20

<210> SEQ ID NO 58
<211> LENGTH: 20
<212> TYPE: DNA
<213> ORGANISM: Homo sapiens

<400> SEQUENCE: 58
ctcattactg gagctgggca                                              20

<210> SEQ ID NO 59
<211> LENGTH: 20
<212> TYPE: DNA
<213> ORGANISM: Homo sapiens

<400> SEQUENCE: 59
ttgttctcat tactggagct                                              20

<210> SEQ ID NO 60
<211> LENGTH: 20
<212> TYPE: DNA
<213> ORGANISM: Homo sapiens

<400> SEQUENCE: 60
attgttctca ttactggagc                                              20

<210> SEQ ID NO 61
<211> LENGTH: 20
<212> TYPE: DNA
<213> ORGANISM: Homo sapiens

<400> SEQUENCE: 61
ggggagattg ttctcattac                                              20

<210> SEQ ID NO 62
<211> LENGTH: 20
<212> TYPE: DNA
```

```
<213> ORGANISM: Homo sapiens

<400> SEQUENCE: 62
gaggagaaaa tctgtggctg                                                 20

<210> SEQ ID NO 63
<211> LENGTH: 20
<212> TYPE: DNA
<213> ORGANISM: Homo sapiens

<400> SEQUENCE: 63
agaggagaaa atctgtggct                                                 20

<210> SEQ ID NO 64
<211> LENGTH: 20
<212> TYPE: DNA
<213> ORGANISM: Homo sapiens

<400> SEQUENCE: 64
cagaggagaa aatctgtggc                                                 20

<210> SEQ ID NO 65
<211> LENGTH: 20
<212> TYPE: DNA
<213> ORGANISM: Homo sapiens

<400> SEQUENCE: 65
tcctcagagg agaaaatctg                                                 20

<210> SEQ ID NO 66
<211> LENGTH: 20
<212> TYPE: DNA
<213> ORGANISM: Homo sapiens

<400> SEQUENCE: 66
ggggtgtgcc cagttgttaa                                                 20

<210> SEQ ID NO 67
<211> LENGTH: 20
<212> TYPE: DNA
<213> ORGANISM: Homo sapiens

<400> SEQUENCE: 67
gggtgtgccc agttgttaat                                                 20

<210> SEQ ID NO 68
<211> LENGTH: 20
<212> TYPE: DNA
<213> ORGANISM: Homo sapiens

<400> SEQUENCE: 68
tggtagtccc attaacaact                                                 20

<210> SEQ ID NO 69
<211> LENGTH: 20
<212> TYPE: DNA
<213> ORGANISM: Homo sapiens

<400> SEQUENCE: 69
ctggtagtcc cattaacaac                                                 20

<210> SEQ ID NO 70
<211> LENGTH: 20
```

<212> TYPE: DNA
<213> ORGANISM: Homo sapiens

<400> SEQUENCE: 70
ttgttaatgg gactaccaga                                              20

<210> SEQ ID NO 71
<211> LENGTH: 20
<212> TYPE: DNA
<213> ORGANISM: Homo sapiens

<400> SEQUENCE: 71
taccagatgg aagccagctt                                              20

<210> SEQ ID NO 72
<211> LENGTH: 20
<212> TYPE: DNA
<213> ORGANISM: Homo sapiens

<400> SEQUENCE: 72
ttccaaagct ggcttccatc                                              20

<210> SEQ ID NO 73
<211> LENGTH: 20
<212> TYPE: DNA
<213> ORGANISM: Homo sapiens

<400> SEQUENCE: 73
tggaagccag ctttggaagc                                              20

<210> SEQ ID NO 74
<211> LENGTH: 20
<212> TYPE: DNA
<213> ORGANISM: Homo sapiens

<400> SEQUENCE: 74
acaaggcctg cttccaaagc                                              20

<210> SEQ ID NO 75
<211> LENGTH: 20
<212> TYPE: DNA
<213> ORGANISM: Homo sapiens

<400> SEQUENCE: 75
gccttgttca cgtgttctaa                                              20

<210> SEQ ID NO 76
<211> LENGTH: 20
<212> TYPE: DNA
<213> ORGANISM: Homo sapiens

<400> SEQUENCE: 76
ccttgttcac gtgttctaat                                              20

<210> SEQ ID NO 77
<211> LENGTH: 20
<212> TYPE: DNA
<213> ORGANISM: Homo sapiens

<400> SEQUENCE: 77
cccattagaa cacgtgaaca                                              20

<210> SEQ ID NO 78

```
<211> LENGTH: 20
<212> TYPE: DNA
<213> ORGANISM: Homo sapiens

<400> SEQUENCE: 78
ttggcatcac ttcatatttg                                              20

<210> SEQ ID NO 79
<211> LENGTH: 20
<212> TYPE: DNA
<213> ORGANISM: Homo sapiens

<400> SEQUENCE: 79
cttgtgctct tggcatcact                                              20

<210> SEQ ID NO 80
<211> LENGTH: 20
<212> TYPE: DNA
<213> ORGANISM: Homo sapiens

<400> SEQUENCE: 80
agcacactct cttgtgctct                                              20

<210> SEQ ID NO 81
<211> LENGTH: 20
<212> TYPE: DNA
<213> ORGANISM: Homo sapiens

<400> SEQUENCE: 81
gcacaagaga gtgtgctctc                                              20

<210> SEQ ID NO 82
<211> LENGTH: 20
<212> TYPE: DNA
<213> ORGANISM: Homo sapiens

<400> SEQUENCE: 82
gcttaatctc acacatagaa                                              20

<210> SEQ ID NO 83
<211> LENGTH: 20
<212> TYPE: DNA
<213> ORGANISM: Homo sapiens

<400> SEQUENCE: 83
cttaatctca cacatagaaa                                              20

<210> SEQ ID NO 84
<211> LENGTH: 20
<212> TYPE: DNA
<213> ORGANISM: Homo sapiens

<400> SEQUENCE: 84
ttaatctcac acatagaaag                                              20

<210> SEQ ID NO 85
<211> LENGTH: 20
<212> TYPE: DNA
<213> ORGANISM: Homo sapiens

<400> SEQUENCE: 85
aggagtgctg gtttatcaac                                              20
```

```
<210> SEQ ID NO 86
<211> LENGTH: 20
<212> TYPE: DNA
<213> ORGANISM: Homo sapiens

<400> SEQUENCE: 86
ttctttgaca gcaggagtgc                                               20

<210> SEQ ID NO 87
<211> LENGTH: 20
<212> TYPE: DNA
<213> ORGANISM: Homo sapiens

<400> SEQUENCE: 87
actctggttt ctttgacagc                                               20

<210> SEQ ID NO 88
<211> LENGTH: 20
<212> TYPE: DNA
<213> ORGANISM: Homo sapiens

<400> SEQUENCE: 88
accagagttg agaaaacccc                                               20

<210> SEQ ID NO 89
<211> LENGTH: 20
<212> TYPE: DNA
<213> ORGANISM: Homo sapiens

<400> SEQUENCE: 89 tccagggtt ttctcaactc                                                20

<210> SEQ ID NO 90
<211> LENGTH: 20
<212> TYPE: DNA
<213> ORGANISM: Homo sapiens

<400> SEQUENCE: 90
cagttattaa atgaatccag                                               20

<210> SEQ ID NO 91
<211> LENGTH: 20
<212> TYPE: DNA
<213> ORGANISM: Homo sapiens

<400> SEQUENCE: 91
gcagttatta aatgaatcca                                               20

<210> SEQ ID NO 92
<211> LENGTH: 20
<212> TYPE: DNA
<213> ORGANISM: Homo sapiens

<400> SEQUENCE: 92
ggcagttatt aaatgaatcc                                               20

<210> SEQ ID NO 93
<211> LENGTH: 20
<212> TYPE: DNA
<213> ORGANISM: Homo sapiens

<400> SEQUENCE: 93
tggatggtaa cagctacatc                                               20
```

```
<210> SEQ ID NO 94
<211> LENGTH: 20
<212> TYPE: DNA
<213> ORGANISM: Homo sapiens

<400> SEQUENCE: 94
gctgttacca tccacatcct                                                 20

<210> SEQ ID NO 95
<211> LENGTH: 20
<212> TYPE: DNA
<213> ORGANISM: Homo sapiens

<400> SEQUENCE: 95
tcaagaacca aggatgtgga                                                 20

<210> SEQ ID NO 96
<211> LENGTH: 20
<212> TYPE: DNA
<213> ORGANISM: Homo sapiens

<400> SEQUENCE: 96
tccttcaaga accaaggatg                                                 20

<210> SEQ ID NO 97
<211> LENGTH: 20
<212> TYPE: DNA
<213> ORGANISM: Homo sapiens

<400> SEQUENCE: 97
tgagtgtcct tcaagaacca                                                 20

<210> SEQ ID NO 98
<211> LENGTH: 20
<212> TYPE: DNA
<213> ORGANISM: Homo sapiens

<400> SEQUENCE: 98
ttttatttta taactacaag                                                 20

<210> SEQ ID NO 99
<211> LENGTH: 20
<212> TYPE: DNA
<213> ORGANISM: Homo sapiens

<400> SEQUENCE: 99
ttgtttttaa taaaaacaag                                                 20

<210> SEQ ID NO 100
<211> LENGTH: 20
<212> TYPE: DNA
<213> ORGANISM: Homo sapiens

<400> SEQUENCE: 100
tattatagaa tgcttttgca                                                 20

<210> SEQ ID NO 101
<211> LENGTH: 20
<212> TYPE: DNA
<213> ORGANISM: Homo sapiens

<400> SEQUENCE: 101
caagattagt cttgatgtag                                                 20
```

```
<210> SEQ ID NO 102
<211> LENGTH: 20
<212> TYPE: DNA
<213> ORGANISM: Homo sapiens

<400> SEQUENCE: 102
aagattagtc ttgatgtagt                                                20

<210> SEQ ID NO 103
<211> LENGTH: 20
<212> TYPE: DNA
<213> ORGANISM: Homo sapiens

<400> SEQUENCE: 103
agtcttgatg tagtgggagt                                                20

<210> SEQ ID NO 104
<211> LENGTH: 20
<212> TYPE: DNA
<213> ORGANISM: Homo sapiens

<400> SEQUENCE: 104
tttttctatt aaaaaaaaaa                                                20

<210> SEQ ID NO 105
<211> LENGTH: 20
<212> TYPE: DNA
<213> ORGANISM: Homo sapiens

<400> SEQUENCE: 105
tctattaaaa aaaaaaggc                                                 20

<210> SEQ ID NO 106
<211> LENGTH: 20
<212> TYPE: DNA
<213> ORGANISM: Homo sapiens

<400> SEQUENCE: 106
ctattaaaaa aaaaaggct                                                 20

<210> SEQ ID NO 107
<211> LENGTH: 20
<212> TYPE: DNA
<213> ORGANISM: Homo sapiens

<400> SEQUENCE: 107
aaaaaaaaaa aggctgggca                                                20

<210> SEQ ID NO 108
<211> LENGTH: 20
<212> TYPE: DNA
<213> ORGANISM: Homo sapiens

<400> SEQUENCE: 108
aaaaaaaagg ctgggcacgg                                                20

<210> SEQ ID NO 109
<211> LENGTH: 20
<212> TYPE: DNA
<213> ORGANISM: Homo sapiens

<400> SEQUENCE: 109
```
cacccgtaat cccagcactt                                              20

<210> SEQ ID NO 110
<211> LENGTH: 20
<212> TYPE: DNA
<213> ORGANISM: Homo sapiens

<400> SEQUENCE: 110
acccgtaatc ccagcacttt                                              20

<210> SEQ ID NO 111
<211> LENGTH: 20
<212> TYPE: DNA
<213> ORGANISM: Homo sapiens

<400> SEQUENCE: 111
cgtaatccca gcactttggg                                              20

<210> SEQ ID NO 112
<211> LENGTH: 20
<212> TYPE: DNA
<213> ORGANISM: Homo sapiens

<400> SEQUENCE: 112
tcccaaagtg ctgggattac                                              20

<210> SEQ ID NO 113
<211> LENGTH: 20
<212> TYPE: DNA
<213> ORGANISM: Homo sapiens

<400> SEQUENCE: 113
ctcccaaagt gctgggatta                                              20

<210> SEQ ID NO 114
<211> LENGTH: 20
<212> TYPE: DNA
<213> ORGANISM: Homo sapiens

<400> SEQUENCE: 114
cccagcactt tgggaggccg                                              20

<210> SEQ ID NO 115
<211> LENGTH: 20
<212> TYPE: DNA
<213> ORGANISM: Homo sapiens

<400> SEQUENCE: 115
cctcggcctc ccaaagtgct                                              20

<210> SEQ ID NO 116
<211> LENGTH: 20
<212> TYPE: DNA
<213> ORGANISM: Homo sapiens

<400> SEQUENCE: 116
gcactttggg aggccgaggc                                              20

<210> SEQ ID NO 117
<211> LENGTH: 20
<212> TYPE: DNA
<213> ORGANISM: Homo sapiens

<400> SEQUENCE: 117
ctttgggagg ccgaggcagg                                          20

<210> SEQ ID NO 118
<211> LENGTH: 20
<212> TYPE: DNA
<213> ORGANISM: Homo sapiens

<400> SEQUENCE: 118
gccgaggcag gtggatcacg                                          20

<210> SEQ ID NO 119
<211> LENGTH: 20
<212> TYPE: DNA
<213> ORGANISM: Homo sapiens

<400> SEQUENCE: 119
acctcgtgat ccacctgcct                                          20

<210> SEQ ID NO 120
<211> LENGTH: 20
<212> TYPE: DNA
<213> ORGANISM: Homo sapiens

<400> SEQUENCE: 120
ggcaggtgga tcacgaggtc                                          20

<210> SEQ ID NO 121
<211> LENGTH: 20
<212> TYPE: DNA
<213> ORGANISM: Homo sapiens

<400> SEQUENCE: 121
tcaggagatc gagaccatct                                          20

<210> SEQ ID NO 122
<211> LENGTH: 20
<212> TYPE: DNA
<213> ORGANISM: Homo sapiens

<400> SEQUENCE: 122
cgagaccatc ttggctaaca                                          20

<210> SEQ ID NO 123
<211> LENGTH: 20
<212> TYPE: DNA
<213> ORGANISM: Homo sapiens

<400> SEQUENCE: 123
tttcaccatg ttagccaaga                                          20

<210> SEQ ID NO 124
<211> LENGTH: 20
<212> TYPE: DNA
<213> ORGANISM: Homo sapiens

<400> SEQUENCE: 124
ttgtattttt tgtagagacg                                          20

<210> SEQ ID NO 125
<211> LENGTH: 20
<212> TYPE: DNA
<213> ORGANISM: Homo sapiens

<400> SEQUENCE: 125 tttgtattttt ttgtagagac                                              20

<210> SEQ ID NO 126
<211> LENGTH: 20
<212> TYPE: DNA
<213> ORGANISM: Homo sapiens

<400> SEQUENCE: 126
ttttgtattt tttgtagaga                                               20

<210> SEQ ID NO 127
<211> LENGTH: 20
<212> TYPE: DNA
<213> ORGANISM: Homo sapiens

<400> SEQUENCE: 127
aaaaaataca aaaaattagc                                               20

<210> SEQ ID NO 128
<211> LENGTH: 20
<212> TYPE: DNA
<213> ORGANISM: Homo sapiens

<400> SEQUENCE: 128
aaaaatacaa aaattagcc                                                20

<210> SEQ ID NO 129
<211> LENGTH: 20
<212> TYPE: DNA
<213> ORGANISM: Homo sapiens

<400> SEQUENCE: 129
tacaaaaaat tagccgggtg                                               20

<210> SEQ ID NO 130
<211> LENGTH: 20
<212> TYPE: DNA
<213> ORGANISM: Homo sapiens

<400> SEQUENCE: 130
aaaaaattag ccgggtgtgg                                               20

<210> SEQ ID NO 131
<211> LENGTH: 20
<212> TYPE: DNA
<213> ORGANISM: Homo sapiens

<400> SEQUENCE: 131
aaattagccg ggtgtggtgg                                               20

<210> SEQ ID NO 132
<211> LENGTH: 20
<212> TYPE: DNA
<213> ORGANISM: Homo sapiens

<400> SEQUENCE: 132
aattagccgg gtgtggtggc                                               20

<210> SEQ ID NO 133
<211> LENGTH: 20
<212> TYPE: DNA
<213> ORGANISM: Homo sapiens

```
<400> SEQUENCE: 133
caggcgcccg ccaccacacc                                                    20

<210> SEQ ID NO 134
<211> LENGTH: 20
<212> TYPE: DNA
<213> ORGANISM: Homo sapiens

<400> SEQUENCE: 134
gcctgtagtc ccagctactc                                                    20

<210> SEQ ID NO 135
<211> LENGTH: 20
<212> TYPE: DNA
<213> ORGANISM: Homo sapiens

<400> SEQUENCE: 135
tgtagtccca gctactcagg                                                    20

<210> SEQ ID NO 136
<211> LENGTH: 20
<212> TYPE: DNA
<213> ORGANISM: Homo sapiens

<400> SEQUENCE: 136
tcctgagtag ctgggactac                                                    20

<210> SEQ ID NO 137
<211> LENGTH: 20
<212> TYPE: DNA
<213> ORGANISM: Homo sapiens

<400> SEQUENCE: 137
cccagctact caggaggctg                                                    20

<210> SEQ ID NO 138
<211> LENGTH: 20
<212> TYPE: DNA
<213> ORGANISM: Homo sapiens

<400> SEQUENCE: 138
cctcagcctc ctgagtagct                                                    20

<210> SEQ ID NO 139
<211> LENGTH: 20
<212> TYPE: DNA
<213> ORGANISM: Homo sapiens

<400> SEQUENCE: 139
gcctcagcct cctgagtagc                                                    20

<210> SEQ ID NO 140
<211> LENGTH: 20
<212> TYPE: DNA
<213> ORGANISM: Homo sapiens

<400> SEQUENCE: 140
aggaggctga ggcaggagaa                                                    20

<210> SEQ ID NO 141
<211> LENGTH: 20
<212> TYPE: DNA
```

<213> ORGANISM: Homo sapiens

<400> SEQUENCE: 141
gcaggagaat ggcgtgaacc                                        20

<210> SEQ ID NO 142
<211> LENGTH: 20
<212> TYPE: DNA
<213> ORGANISM: Homo sapiens

<400> SEQUENCE: 142
caggagaatg gcgtgaaccc                                        20

<210> SEQ ID NO 143
<211> LENGTH: 20
<212> TYPE: DNA
<213> ORGANISM: Homo sapiens

<400> SEQUENCE: 143
gagaatggcg tgaacccggg                                        20

<210> SEQ ID NO 144
<211> LENGTH: 20
<212> TYPE: DNA
<213> ORGANISM: Homo sapiens

<400> SEQUENCE: 144
aatggcgtga acccgggagg                                        20

<210> SEQ ID NO 145
<211> LENGTH: 20
<212> TYPE: DNA
<213> ORGANISM: Homo sapiens

<400> SEQUENCE: 145
cactgcaagc tccacctccc                                        20

<210> SEQ ID NO 146
<211> LENGTH: 20
<212> TYPE: DNA
<213> ORGANISM: Homo sapiens

<400> SEQUENCE: 146
tcactgcaag ctccacctcc                                        20

<210> SEQ ID NO 147
<211> LENGTH: 20
<212> TYPE: DNA
<213> ORGANISM: Homo sapiens

<400> SEQUENCE: 147
cataccactg cactccagcc                                        20

<210> SEQ ID NO 148
<211> LENGTH: 20
<212> TYPE: DNA
<213> ORGANISM: Homo sapiens

<400> SEQUENCE: 148
ataccactgc actccagcct                                        20

<210> SEQ ID NO 149
<211> LENGTH: 20

<212> TYPE: DNA
<213> ORGANISM: Homo sapiens

<400> SEQUENCE: 149
tcgcccaggc tggagtgcag                                           20

<210> SEQ ID NO 150
<211> LENGTH: 20
<212> TYPE: DNA
<213> ORGANISM: Homo sapiens

<400> SEQUENCE: 150
tctcactctt tcgcccaggc                                           20

<210> SEQ ID NO 151
<211> LENGTH: 20
<212> TYPE: DNA
<213> ORGANISM: Homo sapiens

<400> SEQUENCE: 151
ggagtctcac tctttcgccc                                           20

<210> SEQ ID NO 152
<211> LENGTH: 20
<212> TYPE: DNA
<213> ORGANISM: Homo sapiens

<400> SEQUENCE: 152
tgttttttgt tttttgaga                                            20

<210> SEQ ID NO 153
<211> LENGTH: 20
<212> TYPE: DNA
<213> ORGANISM: Homo sapiens

<400> SEQUENCE: 153
aggaagaaag aaaggttttt                                           20

<210> SEQ ID NO 154
<211> LENGTH: 20
<212> TYPE: DNA
<213> ORGANISM: Homo sapiens

<400> SEQUENCE: 154
agaagaaaag gaagaaagaa                                           20

<210> SEQ ID NO 155
<211> LENGTH: 20
<212> TYPE: DNA
<213> ORGANISM: Homo sapiens

<400> SEQUENCE: 155
ctttcttcct tttcttctct                                           20

<210> SEQ ID NO 156
<211> LENGTH: 20
<212> TYPE: DNA
<213> ORGANISM: Homo sapiens

<400> SEQUENCE: 156
tttcttcctt ttcttctctt                                           20

<210> SEQ ID NO 157

```
<211> LENGTH: 20
<212> TYPE: DNA
<213> ORGANISM: Homo sapiens

<400> SEQUENCE: 157
aatggaccca agagaagaaa                                                    20

<210> SEQ ID NO 158
<211> LENGTH: 20
<212> TYPE: DNA
<213> ORGANISM: Homo sapiens

<400> SEQUENCE: 158
ggctattaca taagaaacaa                                                    20

<210> SEQ ID NO 159
<211> LENGTH: 20
<212> TYPE: DNA
<213> ORGANISM: Homo sapiens

<400> SEQUENCE: 159
cacaggaaaa ggaactgtac                                                    20

<210> SEQ ID NO 160
<211> LENGTH: 20
<212> TYPE: DNA
<213> ORGANISM: Homo sapiens

<400> SEQUENCE: 160
attaaagcta acacaggaaa                                                    20

<210> SEQ ID NO 161
<211> LENGTH: 20
<212> TYPE: DNA
<213> ORGANISM: Homo sapiens

<400> SEQUENCE: 161
tcaaaaatta aagctaacac                                                    20

<210> SEQ ID NO 162
<211> LENGTH: 20
<212> TYPE: DNA
<213> ORGANISM: Homo sapiens

<400> SEQUENCE: 162
taaaattgtc taaacatctc                                                    20

<210> SEQ ID NO 163
<211> LENGTH: 20
<212> TYPE: DNA
<213> ORGANISM: Homo sapiens

<400> SEQUENCE: 163
agagatgttt agacaatttt                                                    20

<210> SEQ ID NO 164
<211> LENGTH: 20
<212> TYPE: DNA
<213> ORGANISM: Homo sapiens

<400> SEQUENCE: 164
tctaaacatc tctgggacca                                                    20
```

-continued

```
<210> SEQ ID NO 165
<211> LENGTH: 20
<212> TYPE: DNA
<213> ORGANISM: Homo sapiens

<400> SEQUENCE: 165
tttatgcttt catatatcct                                              20

<210> SEQ ID NO 166
<211> LENGTH: 20
<212> TYPE: DNA
<213> ORGANISM: Homo sapiens

<400> SEQUENCE: 166
agcataaatt acaaagaaaa                                              20

<210> SEQ ID NO 167
<211> LENGTH: 20
<212> TYPE: DNA
<213> ORGANISM: Homo sapiens

<400> SEQUENCE: 167
tacaaagaaa aaggttatca                                              20

<210> SEQ ID NO 168
<211> LENGTH: 20
<212> TYPE: DNA
<213> ORGANISM: Homo sapiens

<400> SEQUENCE: 168
acaaagaaaa aggttatcat                                              20

<210> SEQ ID NO 169
<211> LENGTH: 20
<212> TYPE: DNA
<213> ORGANISM: Homo sapiens

<400> SEQUENCE: 169
caaagaaaaa ggttatcatg                                              20

<210> SEQ ID NO 170
<211> LENGTH: 20
<212> TYPE: DNA
<213> ORGANISM: Homo sapiens

<400> SEQUENCE: 170
tctgagattt aaaatagagt                                              20

<210> SEQ ID NO 171
<211> LENGTH: 20
<212> TYPE: DNA
<213> ORGANISM: Homo sapiens

<400> SEQUENCE: 171
cttataagat acattatgaa                                              20

<210> SEQ ID NO 172
<211> LENGTH: 20
<212> TYPE: DNA
<213> ORGANISM: Homo sapiens

<400> SEQUENCE: 172
tatcttataa gactataaaa                                              20
```

```
<210> SEQ ID NO 173
<211> LENGTH: 20
<212> TYPE: DNA
<213> ORGANISM: Homo sapiens

<400> SEQUENCE: 173
atcttataag actataaaaa                                               20

<210> SEQ ID NO 174
<211> LENGTH: 20
<212> TYPE: DNA
<213> ORGANISM: Homo sapiens

<400> SEQUENCE: 174
ttataagact ataaaagggg                                               20

<210> SEQ ID NO 175
<211> LENGTH: 20
<212> TYPE: DNA
<213> ORGANISM: Homo sapiens

<400> SEQUENCE: 175
taaaaaggga ggaaatatag                                               20

<210> SEQ ID NO 176
<211> LENGTH: 20
<212> TYPE: DNA
<213> ORGANISM: Homo sapiens

<400> SEQUENCE: 176
aaaaagggag gaaatataga                                               20

<210> SEQ ID NO 177
<211> LENGTH: 20
<212> TYPE: DNA
<213> ORGANISM: Homo sapiens

<400> SEQUENCE: 177
aaatatagag ggtccacttt                                               20

<210> SEQ ID NO 178
<211> LENGTH: 20
<212> TYPE: DNA
<213> ORGANISM: Homo sapiens

<400> SEQUENCE: 178
tatagagggt ccacttttgg                                               20

<210> SEQ ID NO 179
<211> LENGTH: 20
<212> TYPE: DNA
<213> ORGANISM: Homo sapiens

<400> SEQUENCE: 179
actctgaagt ccaccaaaag                                               20

<210> SEQ ID NO 180
<211> LENGTH: 20
<212> TYPE: DNA
<213> ORGANISM: Homo sapiens

<400> SEQUENCE: 180
agaatagagt tgcaccgttt                                               20
```

<210> SEQ ID NO 181
<211> LENGTH: 20
<212> TYPE: DNA
<213> ORGANISM: Homo sapiens

<400> SEQUENCE: 181
aaaacggtgc aactctattc                                             20

<210> SEQ ID NO 182
<211> LENGTH: 20
<212> TYPE: DNA
<213> ORGANISM: Homo sapiens

<400> SEQUENCE: 182
ccgttttggg ctaatgaaaa                                             20

<210> SEQ ID NO 183
<211> LENGTH: 20
<212> TYPE: DNA
<213> ORGANISM: Homo sapiens

<400> SEQUENCE: 183 ccttttcat tagcccaaaa                                              20

<210> SEQ ID NO 184
<211> LENGTH: 20
<212> TYPE: DNA
<213> ORGANISM: Homo sapiens

<400> SEQUENCE: 184
tgggctaatg aaaaaggaag                                             20

<210> SEQ ID NO 185
<211> LENGTH: 20
<212> TYPE: DNA
<213> ORGANISM: Homo sapiens

<400> SEQUENCE: 185
taatgaaaaa ggaagaggct                                             20

<210> SEQ ID NO 186
<211> LENGTH: 20
<212> TYPE: DNA
<213> ORGANISM: Homo sapiens

<400> SEQUENCE: 186
aatgaaaaag gaagaggcta                                             20

<210> SEQ ID NO 187
<211> LENGTH: 20
<212> TYPE: DNA
<213> ORGANISM: Homo sapiens

<400> SEQUENCE: 187
ctgaatctta aaatatgtcc                                             20

<210> SEQ ID NO 188
<211> LENGTH: 20
<212> TYPE: DNA
<213> ORGANISM: Homo sapiens

<400> SEQUENCE: 188
caggcagctt tatctcaacc                                           20

<210> SEQ ID NO 189
<211> LENGTH: 20
<212> TYPE: DNA
<213> ORGANISM: Homo sapiens

<400> SEQUENCE: 189
ctaagagatc aagtttcagc                                           20

<210> SEQ ID NO 190
<211> LENGTH: 20
<212> TYPE: DNA
<213> ORGANISM: Homo sapiens

<400> SEQUENCE: 190
gtgttcttgt tgatattctg                                           20

<210> SEQ ID NO 191
<211> LENGTH: 20
<212> TYPE: DNA
<213> ORGANISM: Homo sapiens

<400> SEQUENCE: 191
cttgttgata ttctgtggca                                           20

<210> SEQ ID NO 192
<211> LENGTH: 20
<212> TYPE: DNA
<213> ORGANISM: Homo sapiens

<400> SEQUENCE: 192
tctgtggcat ggctacagat                                           20

<210> SEQ ID NO 193
<211> LENGTH: 20
<212> TYPE: DNA
<213> ORGANISM: Homo sapiens

<400> SEQUENCE: 193
agaacttatt tacacaggga                                           20

<210> SEQ ID NO 194
<211> LENGTH: 20
<212> TYPE: DNA
<213> ORGANISM: Homo sapiens

<400> SEQUENCE: 194
aaagagaact tatttacaca                                           20

<210> SEQ ID NO 195
<211> LENGTH: 20
<212> TYPE: DNA
<213> ORGANISM: Homo sapiens

<400> SEQUENCE: 195
caaagagaac ttatttacac                                           20

<210> SEQ ID NO 196
<211> LENGTH: 20
<212> TYPE: DNA
<213> ORGANISM: Homo sapiens

<400> SEQUENCE: 196

-continued ttctctttgt atttactttt                                           20

<210> SEQ ID NO 197
<211> LENGTH: 20
<212> TYPE: DNA
<213> ORGANISM: Homo sapiens

<400> SEQUENCE: 197
tctctttgta tttactttta                                           20

<210> SEQ ID NO 198
<211> LENGTH: 20
<212> TYPE: DNA
<213> ORGANISM: Homo sapiens

<400> SEQUENCE: 198
ctttgtattt acttttaggg                                           20

<210> SEQ ID NO 199
<211> LENGTH: 20
<212> TYPE: DNA
<213> ORGANISM: Homo sapiens

<400> SEQUENCE: 199
agcttttgtc cacctttaaa                                           20

<210> SEQ ID NO 200
<211> LENGTH: 20
<212> TYPE: DNA
<213> ORGANISM: Homo sapiens

<400> SEQUENCE: 200
tttatttttc catttaaagg                                           20

<210> SEQ ID NO 201
<211> LENGTH: 20
<212> TYPE: DNA
<213> ORGANISM: Homo sapiens

<400> SEQUENCE: 201
tattttattt ttccatttaa                                           20

<210> SEQ ID NO 202
<211> LENGTH: 20
<212> TYPE: DNA
<213> ORGANISM: Homo sapiens

<400> SEQUENCE: 202
cttacataaa catacttaaa                                           20

<210> SEQ ID NO 203
<211> LENGTH: 20
<212> TYPE: DNA
<213> ORGANISM: Homo sapiens

<400> SEQUENCE: 203
taagcacaga agtttttaag                                           20

<210> SEQ ID NO 204
<211> LENGTH: 20
<212> TYPE: DNA
<213> ORGANISM: Homo sapiens -continued

<400> SEQUENCE: 204
aagtttttaa gaggcatgaa                                               20

<210> SEQ ID NO 205
<211> LENGTH: 20
<212> TYPE: DNA
<213> ORGANISM: Homo sapiens

<400> SEQUENCE: 205
atatttacgt agtttttcat                                               20

<210> SEQ ID NO 206
<211> LENGTH: 20
<212> TYPE: DNA
<213> ORGANISM: Homo sapiens

<400> SEQUENCE: 206
cgtaaatatt cttgagaaac                                               20

<210> SEQ ID NO 207
<211> LENGTH: 20
<212> TYPE: DNA
<213> ORGANISM: Homo sapiens

<400> SEQUENCE: 207
ttcttgagaa acaggaagac                                               20

<210> SEQ ID NO 208
<211> LENGTH: 20
<212> TYPE: DNA
<213> ORGANISM: Homo sapiens

<400> SEQUENCE: 208
taatattaaa aacattggtt                                               20

<210> SEQ ID NO 209
<211> LENGTH: 20
<212> TYPE: DNA
<213> ORGANISM: Homo sapiens

<400> SEQUENCE: 209
ccaatgtttt taatattatc                                               20

<210> SEQ ID NO 210
<211> LENGTH: 20
<212> TYPE: DNA
<213> ORGANISM: Homo sapiens

<400> SEQUENCE: 210
cctgataata ttaaaaacat                                               20

<210> SEQ ID NO 211
<211> LENGTH: 20
<212> TYPE: DNA
<213> ORGANISM: Homo sapiens

<400> SEQUENCE: 211
cattatcatg catacatctc                                               20

<210> SEQ ID NO 212
<211> LENGTH: 20
<212> TYPE: DNA
<213> ORGANISM: Homo sapiens

```
<400> SEQUENCE: 212
atcatgcata catctctggc                                               20

<210> SEQ ID NO 213
<211> LENGTH: 20
<212> TYPE: DNA
<213> ORGANISM: Homo sapiens

<400> SEQUENCE: 213
ttcatttcat tttgatttg                                                20

<210> SEQ ID NO 214
<211> LENGTH: 20
<212> TYPE: DNA
<213> ORGANISM: Homo sapiens

<400> SEQUENCE: 214
attcaatttg aagcagtggt                                               20

<210> SEQ ID NO 215
<211> LENGTH: 20
<212> TYPE: DNA
<213> ORGANISM: Homo sapiens

<400> SEQUENCE: 215
gaatattcaa tttgaagcag                                               20

<210> SEQ ID NO 216
<211> LENGTH: 20
<212> TYPE: DNA
<213> ORGANISM: Homo sapiens

<400> SEQUENCE: 216
catacgattt aaaatcgctg                                               20

<210> SEQ ID NO 217
<211> LENGTH: 20
<212> TYPE: DNA
<213> ORGANISM: Homo sapiens

<400> SEQUENCE: 217
aaaatcgctg aggcgcgttc                                               20

<210> SEQ ID NO 218
<211> LENGTH: 20
<212> TYPE: DNA
<213> ORGANISM: Homo sapiens

<400> SEQUENCE: 218 ttttttttc ttttttgtac                                                20

<210> SEQ ID NO 219
<211> LENGTH: 20
<212> TYPE: DNA
<213> ORGANISM: Homo sapiens

<400> SEQUENCE: 219
ctgttgtcaa agattttaaa                                               20

<210> SEQ ID NO 220
<211> LENGTH: 20
<212> TYPE: DNA
```

<213> ORGANISM: Homo sapiens

<400> SEQUENCE: 220
tgacaacaga gttctgtttt                                            20

<210> SEQ ID NO 221
<211> LENGTH: 20
<212> TYPE: DNA
<213> ORGANISM: Homo sapiens

<400> SEQUENCE: 221
agaatacgct gagagttatc                                            20

<210> SEQ ID NO 222
<211> LENGTH: 20
<212> TYPE: DNA
<213> ORGANISM: Homo sapiens

<400> SEQUENCE: 222
gcaagagaag aaaagaacgg                                            20

<210> SEQ ID NO 223
<211> LENGTH: 20
<212> TYPE: DNA
<213> ORGANISM: Homo sapiens

<400> SEQUENCE: 223
gttgcaagag aagaaaagaa                                            20

<210> SEQ ID NO 224
<211> LENGTH: 20
<212> TYPE: DNA
<213> ORGANISM: Homo sapiens

<400> SEQUENCE: 224
atgcacacgt aaaagagagg                                            20

<210> SEQ ID NO 225
<211> LENGTH: 20
<212> TYPE: DNA
<213> ORGANISM: Homo sapiens

<400> SEQUENCE: 225
aagatgcaca cgtaaaagag                                            20

<210> SEQ ID NO 226
<211> LENGTH: 20
<212> TYPE: DNA
<213> ORGANISM: Homo sapiens

<400> SEQUENCE: 226
atcatgcata catctctggc                                            20

<210> SEQ ID NO 227
<211> LENGTH: 20
<212> TYPE: DNA
<213> ORGANISM: Homo sapiens

<400> SEQUENCE: 227
ttcatttcat tttgattttg                                            20

<210> SEQ ID NO 228
<211> LENGTH: 20

```
<212> TYPE: DNA
<213> ORGANISM: Homo sapiens

<400> SEQUENCE: 228
attcaatttg aagcagtggt                                              20

<210> SEQ ID NO 229
<211> LENGTH: 20
<212> TYPE: DNA
<213> ORGANISM: Homo sapiens

<400> SEQUENCE: 229
gaatattcaa tttgaagcag                                              20

<210> SEQ ID NO 230
<211> LENGTH: 20
<212> TYPE: DNA
<213> ORGANISM: Homo sapiens

<400> SEQUENCE: 230
catacgattt aaaatcgctg                                              20

<210> SEQ ID NO 231
<211> LENGTH: 20
<212> TYPE: DNA
<213> ORGANISM: Homo sapiens

<400> SEQUENCE: 231
aaaatcgctg aggcgcgttc                                              20

<210> SEQ ID NO 232
<211> LENGTH: 20
<212> TYPE: DNA
<213> ORGANISM: Homo sapiens

<400> SEQUENCE: 232
tttttttttc tttttttgtac                                             20

<210> SEQ ID NO 233
<211> LENGTH: 20
<212> TYPE: DNA
<213> ORGANISM: Homo sapiens

<400> SEQUENCE: 233
ctgttgtcaa agattttaaa                                              20

<210> SEQ ID NO 234
<211> LENGTH: 20
<212> TYPE: DNA
<213> ORGANISM: Homo sapiens

<400> SEQUENCE: 234
tgacaacaga gttctgtttt                                              20

<210> SEQ ID NO 235
<211> LENGTH: 20
<212> TYPE: DNA
<213> ORGANISM: Homo sapiens

<400> SEQUENCE: 235
agaatacgct gagagttatc                                              20

<210> SEQ ID NO 236
```

```
<211> LENGTH: 20
<212> TYPE: DNA
<213> ORGANISM: Homo sapiens

<400> SEQUENCE: 236
gcaagagaag aaaagaacgg                                               20

<210> SEQ ID NO 237
<211> LENGTH: 20
<212> TYPE: DNA
<213> ORGANISM: Homo sapiens

<400> SEQUENCE: 237
gttgcaagag aagaaaagaa                                               20

<210> SEQ ID NO 238
<211> LENGTH: 20
<212> TYPE: DNA
<213> ORGANISM: Homo sapiens

<400> SEQUENCE: 238
atgcacacgt aaaagagagg                                               20

<210> SEQ ID NO 239
<211> LENGTH: 20
<212> TYPE: DNA
<213> ORGANISM: Homo sapiens

<400> SEQUENCE: 239
aagatgcaca cgtaaaagag                                               20

<210> SEQ ID NO 240
<211> LENGTH: 300
<212> TYPE: PRT
<213> ORGANISM: Homo sapiens

<400> SEQUENCE: 240
```

| Met | Asn | Ile | Ile | Leu | Glu | Ile | Leu | Leu | Leu | Ile | Thr | Ile | Ile | Tyr |
|---|---|---|---|---|---|---|---|---|---|---|---|---|---|---|
| 1 | | | | 5 | | | | | 10 | | | | | 15 |

| Ser | Tyr | Leu | Glu | Ser | Leu | Val | Lys | Phe | Phe | Ile | Pro | Gln | Arg | Lys |
|---|---|---|---|---|---|---|---|---|---|---|---|---|---|---|
| | | | 20 | | | | | 25 | | | | | 30 | |

| Ser | Val | Ala | Gly | Glu | Ile | Val | Leu | Ile | Thr | Gly | Ala | Gly | His | Gly | Ile |
|---|---|---|---|---|---|---|---|---|---|---|---|---|---|---|---|
| | | | 35 | | | | | 40 | | | | 45 | | | |

| Gly | Arg | Gln | Thr | Thr | Tyr | Glu | Phe | Ala | Lys | Arg | Gln | Ser | Ile | Leu | Val |
|---|---|---|---|---|---|---|---|---|---|---|---|---|---|---|---|
| | 50 | | | | | 55 | | | | | 60 | | | | |

| Leu | Trp | Asp | Ile | Asn | Lys | Arg | Gly | Val | Glu | Glu | Thr | Ala | Ala | Glu | Cys |
|---|---|---|---|---|---|---|---|---|---|---|---|---|---|---|---|
| 65 | | | | | 70 | | | | | 75 | | | | | 80 |

| Arg | Lys | Leu | Gly | Val | Thr | Ala | His | Ala | Tyr | Val | Val | Asp | Cys | Ser | Asn |
|---|---|---|---|---|---|---|---|---|---|---|---|---|---|---|---|
| | | | | 85 | | | | | 90 | | | | | 95 | |

| Arg | Glu | Glu | Ile | Tyr | Arg | Ser | Leu | Asn | Gln | Val | Lys | Lys | Glu | Val | Gly |
|---|---|---|---|---|---|---|---|---|---|---|---|---|---|---|---|
| | | | 100 | | | | | 105 | | | | | 110 | | |

| Asp | Val | Thr | Ile | Val | Val | Asn | Asn | Ala | Gly | Thr | Val | Tyr | Pro | Ala | Asp |
|---|---|---|---|---|---|---|---|---|---|---|---|---|---|---|---|
| | | | 115 | | | | | 120 | | | | | 125 | | |

| Leu | Leu | Ser | Thr | Lys | Asp | Glu | Glu | Ile | Thr | Lys | Thr | Phe | Glu | Val | Asn |
|---|---|---|---|---|---|---|---|---|---|---|---|---|---|---|---|
| | | 130 | | | | | 135 | | | | | 140 | | | |

| Ile | Leu | Gly | His | Phe | Trp | Ile | Thr | Lys | Ala | Leu | Leu | Pro | Ser | Met | Met |
|---|---|---|---|---|---|---|---|---|---|---|---|---|---|---|---|
| 145 | | | | | 150 | | | | | 155 | | | | | 160 |

| Glu | Arg | Asn | His | Gly | His | Ile | Val | Thr | Val | Ala | Ser | Val | Cys | Gly | His |
|---|---|---|---|---|---|---|---|---|---|---|---|---|---|---|---|
| | | | | 165 | | | | | 170 | | | | | 175 | |

```
Glu Gly Ile Pro Tyr Leu Ile Pro Tyr Cys Ser Ser Lys Phe Ala Ala
                180                 185                 190

Val Gly Phe His Arg Gly Leu Thr Ser Glu Leu Gln Ala Leu Gly Lys
            195                 200                 205

Thr Gly Ile Lys Thr Ser Cys Leu Cys Pro Val Phe Val Asn Thr Gly
            210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Phe
            260                 265                 270

Leu Pro Glu Arg Ala Ser Ala Ile Leu Asn Arg Met Gln Asn Ile Gln
            275                 280                 285

Phe Glu Ala Val Val Gly His Lys Ile Lys Met Lys
            290                 295                 300

<210> SEQ ID NO 241
<211> LENGTH: 264
<212> TYPE: PRT
<213> ORGANISM: Homo sapiens

<400> SEQUENCE: 241

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
                100                 105                 110

Phe Trp Ile Thr Lys Ala Leu Leu Pro Ser Met Met Glu Arg Asn His
            115                 120                 125

Gly His Ile Val Thr Val Ala Ser Val Cys Gly His Glu Gly Ile Pro
        130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
            180                 185                 190

Pro Ser Thr Arg Leu Trp Pro Val Leu Glu Thr Asp Glu Val Val Arg
            195                 200                 205

Ser Leu Ile Asp Gly Ile Leu Thr Asn Lys Lys Met Ile Phe Val Pro
        210                 215                 220

Ser Tyr Ile Asn Ile Phe Leu Arg Leu Gln Lys Phe Leu Pro Glu Arg
225                 230                 235                 240

Ala Ser Ala Ile Leu Asn Arg Met Gln Asn Ile Gln Phe Glu Ala Val
                245                 250                 255
```

Val Gly His Lys Ile Lys Met Lys
            260

<210> SEQ ID NO 242
<211> LENGTH: 300
<212> TYPE: PRT
<213> ORGANISM: Homo sapiens

<400> SEQUENCE: 242

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Phe
            260                 265                 270

Leu Pro Glu Arg Ala Ser Ala Ile Leu Asn Arg Met Gln Asn Ile Gln
        275                 280                 285

Phe Glu Ala Val Val Gly His Lys Ile Lys Met Lys
        290                 295                 300

<210> SEQ ID NO 243
<211> LENGTH: 264
<212> TYPE: PRT
<213> ORGANISM: Homo sapiens

<400> SEQUENCE: 243

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
50                  55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
        115                 120                 125

Gly His Ile Val Thr Val Ala Ser Val Cys Gly His Glu Gly Ile Pro
    130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
            180                 185                 190

Pro Ser Thr Arg Leu Trp Pro Val Leu Glu Thr Asp Glu Val Val Arg
        195                 200                 205

Ser Leu Ile Asp Gly Ile Leu Thr Asn Lys Lys Met Ile Phe Val Pro
    210                 215                 220

Ser Tyr Ile Asn Ile Phe Leu Arg Leu Gln Lys Phe Leu Pro Glu Arg
225                 230                 235                 240

Ala Ser Ala Ile Leu Asn Arg Met Gln Asn Ile Gln Phe Glu Ala Val
                245                 250                 255

Val Gly His Lys Ile Lys Met Lys
            260

<210> SEQ ID NO 244
<211> LENGTH: 2397
<212> TYPE: DNA
<213> ORGANISM: Homo sapiens

<400> SEQUENCE: 244
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta taagcgcgg tgtggaggaa actgcagctg     300
agtgccgaaa actaggcgtc actgcgcatg cgtatgtggt agactgcagc aacagagaag     360
agatctatcg ctctctaaat caggtgaaga agaagtgggt gatgtaaca atcgtggtga     420 ataatgctgg gacagtatat ccagccgatc ttctcagcac caaggatgaa gagattacca     480
agacatttga ggtcaacatc ctaggacatt tttggatcac aaaagcactt cttccatcga     540
tgatggagag aaatcatggc cacatcgtca cagtggcttc agtgtgcggc acgaagggga     600
ttccttacct catcccatat tgttccagca aatttgccgc tgttggcttt cacagaggtc     660

| | |
|---|---|
| tgacatcaga acttcaggcc ttgggaaaaa ctggtatcaa aacctcatgt ctctgcccag | 720 |
| tttttgtgaa tactgggttc accaaaaatc caagcacaag attatggcct gtattggaga | 780 |
| cagatgaagt cgtaagaagt ctgatagatg aatacttac caataagaaa atgattttg | 840 |
| ttccatcgta tatcaatatc tttctgagac tacagaagtt tcttcctgaa cgcgcctcag | 900 |
| cgattttaaa tcgtatgcag aatattcaat ttgaagcagt ggttggccac aaaatcaaaa | 960 |
| tgaaatgaat aaataagctc cagccagaga tgtatgcatg ataatgatat gaatagtttc | 1020 |
| gaatcaatgc tgcaaagctt tatttcacat tttttcagtc ctgataatat taaaaacatt | 1080 |
| ggtttggcac tagcagcagt caaacgaaca agattaatta cctgtcttcc tgtttctcaa | 1140 |
| gaatatttac gtagtttttc ataggtctgt ttttcctttc atgcctctta aaaacttctg | 1200 |
| tgcttacata aacatactta aaaggttttc tttaagatat tttatttttc catttaaagg | 1260 |
| tggacaaaag ctacctccct aaaagtaaat acaaagagaa cttatttaca cagggaaggt | 1320 |
| ttaagactgt tcaagtagca ttccaatctg tagccatgcc acagaatatc aacaagaaca | 1380 |
| cagaatgagt gcacagctaa gagatcaagt ttcagcaggc agctttatct caacctggac | 1440 |
| atattttaag attcagcatt tgaaagattt ccctagcctc ttcctttttc attagcccaa | 1500 |
| aacggtgcaa ctctattctg gactttatta cttgattctg tcttctgtat aactctgaag | 1560 |
| tccaccaaaa gtggaccctc tatatttcct ccctttttat agtcttataa gatacattat | 1620 |
| gaaaggtgac cgactctatt ttaaatctca gaattttaag ttctagcccc atgataacct | 1680 |
| ttttctttgt aatttatgct ttcatatatc cttggtccca gagatgttta gacaatttta | 1740 |
| ggctcaaaaa ttaaagctaa cacaggaaaa ggaactgtac tggctattac ataagaaaca | 1800 |
| atggacccaa gagaagaaaa ggaagaaaga aaggtttttt ggttttttgtt ttgttttgtt | 1860 |
| ttgttttttg ttttttgag atggagtctc actctttcgc ccaggctgga gtgcagtggt | 1920 |
| atgatctcag ctcactgcaa gctccacctc ccgggttcac gccattctcc tgcctcagcc | 1980 |
| tcctgagtag ctgggactac aggcgcccgc caccacaccc ggctaatttt ttgtattttt | 2040 |
| tgtagagacg gggtttcacc atgttagcca agatggtctc gatctcctga cctcgtgatc | 2100 |
| cacctgcctc ggcctcccaa agtgctggga ttacgggtgt gagccaccgt gcccagcctt | 2160 |
| ttttttttta atagaaaaaa taatccgact cccactacat caagactaat cttgttttgt | 2220 |
| gtgttttca catgtattat agaatgcttt tgcatggact atcctcttgt ttttattaaa | 2280 |
| aacaaatgat ttttttaaaa gtcacaaaaa caattcacta aaaataaata tgtcattgtg | 2340 |
| ctttaaaaaa ataacctctt gtagttataa aataaaacgt ttgacttcta aactctg | 2397 |

<210> SEQ ID NO 245
<211> LENGTH: 2289
<212> TYPE: DNA
<213> ORGANISM: Homo sapiens

<400> SEQUENCE: 245

| | |
|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta ataggtgaa gaagaagtg ggtgatgtaa | 300 |
| caatcgtggt gaataatgct gggacagtat atccagccga tcttctcagc accaaggatg | 360 |
| aagagattac caagacattt gaggtcaaca tcctaggaca ttttggatc acaaaagcac | 420 |

```
ttcttccatc gatgatggag agaaatcatg gccacatcgt cacagtggct tcagtgtgcg    480
gccacgaagg gattccttac ctcatcccat attgttccag caaatttgcc gctgttggct    540
ttcacagagg tctgcatcca gaacttcagg ccttgggaaa aactggtatc aaaacctcat    600
gtctctgccc agttttttgtg aatactgggt tcaccaaaaa tccaagcaca agattatggc    660
ctgtattgga gacagatgaa gtcgtaagaa gtctgataga tggaatactt accaataaga    720
aaatgatttt tgttccatcg tatatcaata tctttctgag actacagaag tttcttcctg    780
aacgcgcctc agcgatttta aatcgtatgc agaatattca atttgaagca gtggttggcc    840
acaaaatcaa aatgaaatga ataaataagc tccagccaga gatgtatgca tgataatgat    900
atgaatagtt tcgaatcaat gctgcaaagc tttatttcac attttttcag tcctgataat    960
attaaaaaca ttggtttggc actagcagca gtcaaacgaa caagattaat tacctgtctt   1020
cctgtttctc aagaatattt acgtagtttt tcataggtct gttttccctt tcatgcctct   1080
taaaaacttc tgtgcttaca taaacatact taaaaggttt tctttaagat attttattt    1140 tccatttaaa ggtggacaaa agctacctcc ctaaaagtaa atacaaagag aacttattta   1200
cacagggaag gtttaagact gttcaagtag cattccaatc tgtagccatg ccacagaata   1260
tcaacaagaa cacagaatga gtgcacagct aagagatcaa gtttcagcag gcagctttat   1320
ctcaacctgg acatatttta agattcagca tttgaaagat ttccctagcc tcttcctttt   1380
tcattagccc aaaacggtgc aactctattc tggactttat tacttgattc tgtcttctgt   1440
ataactctga gtccaccaa aagtggaccc tctatatttc ctcccttttt atagtcttat    1500
aagatacatt atgaaaggtg accgactcta ttttaaatct cagaatttta agttctagcc   1560
ccatgataac ctttttcttt gtaatttatg ctttcatata tccttggtcc cagagatgtt   1620
tagacaattt taggctcaaa aattaaagct aacacaggaa aaggaactgt actggctatt   1680
acataagaaa caatggaccc aagagaagaa aaggaagaaa gaaaggtttt ttggtttttg   1740
ttttgttttg ttttgttttt tgttttttg agatggagtc tcactctttc gcccaggctg   1800
gagtgcagtg gtatgatctc agctcactgc aagctccacc tcccgggttc acgccattct   1860
cctgcctcag cctcctgagt agctgggact acaggcgccc gccaccacac ccggctaatt   1920
ttttgtattt tttgtagaga cggggtttca ccatgttagc caagatggtc tcgatctcct   1980
gacctcgtga tccacctgcc tcggcctccc aaagtgctgg gattacgggt gtgagccacc   2040
gtgcccagcc ttttttttt taatagaaaa aataatccga ctcccactac atcaagacta   2100
atcttgtttt gtgtgttttt cacatgtatt atagaatgct tttgcatgga ctatcctctt   2160
gtttttatta aaacaaatg atttttttaa aagtcacaaa aacaattcac taaaaataaa    2220
tatgtcattg tgctttaaaa aaataaccct ttgtagttat aaaataaaac gtttgacttc   2280
taaactctg                                                           2289
```

<210> SEQ ID NO 246
<211> LENGTH: 1714
<212> TYPE: DNA
<213> ORGANISM: Homo sapiens
<220> FEATURE:
<221> NAME/KEY: misc_feature
<222> LOCATION: (1)..(275)
<223> OTHER INFORMATION: Exon 1
<220> FEATURE:
<221> NAME/KEY: misc_feature
<222> LOCATION: (276)..(383)
<223> OTHER INFORMATION: Exon 2
<220> FEATURE:

```
<221> NAME/KEY: misc_feature
<222> LOCATION: (384)..(515)
<223> OTHER INFORMATION: Exon 3
<220> FEATURE:
<221> NAME/KEY: misc_feature
<222> LOCATION: (516)..(622)
<223> OTHER INFORMATION: Exon 4
<220> FEATURE:
<221> NAME/KEY: misc_feature
<222> LOCATION: (623)..(760)
<223> OTHER INFORMATION: Exon 5
<220> FEATURE:
<221> NAME/KEY: misc_feature
<222> LOCATION: (761)..(1714)
<223> OTHER INFORMATION: Exon 6v4
<220> FEATURE:
<221> NAME/KEY: misc_feature
<222> LOCATION: (878)..(1714)
<223> OTHER INFORMATION: Read-through from exon 6 into intron 6

<400> SEQUENCE: 246
```

| | | |
|---|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta ataagcgcgg tgtggaggaa actgcagctg | 300 |
| agtgccgaaa actaggcgtc actgcgcatg cgtatgtggt agactgcagc aacagagaag | 360 |
| agatctatcg ctctctaaat caggtgaaga agaagtgggg tgatgtaaca atcgtggtga | 420 |
| ataatgctgg gacagtatat ccagccgatc ttctcagcac caaggatgaa gagattacca | 480 |
| agacatttga ggtcaacatc ctaggacatt tttggatcac aaaagcactt cttccatcga | 540 |
| tgatggagag aaatcatggc cacatcgtca cagtggcttc agtgtgcggc cacgaaggga | 600 |
| ttccttacct catcccatat tgttccagca aatttgccgc tgttggcttt cacagaggtc | 660 |
| tgacatcaga acttcaggcc ttgggaaaaa ctggtatcaa aacctcatgt ctctgcccag | 720 |
| tttttgtgaa tactgggttc accaaaaatc aagcacaag attatggcct gtattggaga | 780 |
| cagatgaagt cgtaagaagt ctgatagatg gaatacttac caataagaaa atgatttttg | 840 |
| ttccatcgta tatcaatatc tttctgagac tacagaagta agtacagcac agaacaccca | 900 |
| aatactaaaa caccaataga gctttttttt ttgcttttttt tttttttaga cagagtctca | 960 |
| ctctgtcacc ctggctggat tgcggtggtt gcagtggcat gatcttggct cactgcaacc | 1020 |
| tccgcctcct gggttcaagc aattctcatg cctcagaccc ccaagtaact gggattatag | 1080 |
| gtgtgtgctg ccacactaca cccagctaat ttttgtattt tttgatagag acaggtttcc | 1140 |
| ccatgttggc caggctggac tcgaactcct gacctcaagt tatcctcctg tctcggcctc | 1200 |
| ccaaagtgct gggattacag tcatgagcca ccatgcctgg cccaatagag ctattattat | 1260 |
| ggagcatctt tcagttgtga aaattggcat ggaaactctc catccctggg gagaacagtt | 1320 |
| atttcctctg ttattttcct acccagtcta taaaaagaga gtgattcatt ttctctacca | 1380 |
| aatctactgt ctctgcccaa actttgctga agactattct aactaaagga aacacagttt | 1440 |
| aaaaagaatg caatatagtg aagtagttaa taataaagac tccattttta aaagtctgct | 1500 |
| ggaagtttgg ttgggattgc actgaatcta tagagcaatt ggggagtatt gacatatcaa | 1560 |
| caatattgag ttttctaatc caagaacata atatctattt ttaaaatctt cttcaaaatc | 1620 |
| tttaaatctt taaattgtat tttgtagttt ttggtgttta agtcttgcac atattttgtc | 1680 |
| agatttattc caaagtattt cacgggttct tttt | 1714 |

```
<210> SEQ ID NO 247
<211> LENGTH: 271
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Region Encoded by Exon 1
<220> FEATURE:
<221> NAME/KEY: MISC_FEATURE
<222> LOCATION: (71)..(106)
<223> OTHER INFORMATION: Region Encoded by Exon 2
<220> FEATURE:
<221> NAME/KEY: MISC_FEATURE
<222> LOCATION: (107)..(150)
<223> OTHER INFORMATION: Region Encoded by Exon 3
<220> FEATURE:
<221> NAME/KEY: MISC_FEATURE
<222> LOCATION: (151)..(185)
<223> OTHER INFORMATION: Region Encoded by Exon 4
<220> FEATURE:
<221> NAME/KEY: MISC_FEATURE
<222> LOCATION: (186)..(232)
<223> OTHER INFORMATION: Region Encoded by Exon 5
<220> FEATURE:
<221> NAME/KEY: MISC_FEATURE
<222> LOCATION: (233)..(271)
<223> OTHER INFORMATION: Region Encoded by Exon 6v4

<400> SEQUENCE: 247

Met Asn Ile Ile Leu Glu Ile Leu Leu Leu Ile Thr Ile Thr Ile Tyr
  1               5                  10                  15

Ser Tyr Leu Glu Ser Leu Val Lys Phe Phe Ile Pro Gln Arg Arg Lys
             20                  25                  30

Ser Val Ala Gly Glu Ile Val Leu Ile Thr Gly Ala Gly His Gly Ile
         35                  40                  45

Gly Arg Gln Thr Thr Tyr Glu Phe Ala Lys Arg Gln Ser Ile Leu Val
     50                  55                  60

Leu Trp Asp Ile Asn Lys Arg Gly Val Glu Glu Thr Ala Ala Glu Cys
 65                  70                  75                  80

Arg Lys Leu Gly Val Thr Ala His Ala Tyr Val Val Asp Cys Ser Asn
                 85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
```

```
                    245                 250                 255
Ile Phe Val Pro Ser Tyr Ile Asn Ile Phe Leu Arg Leu Gln Lys
            260                 265                 270
```

<210> SEQ ID NO 248
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 248
gnnnnnnnnn nnnnnnnnnn ngg                                       23

<210> SEQ ID NO 249
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 249
nnnnnnnnnn nnnnnnnnnn ngg                                       23

<210> SEQ ID NO 250
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 250
ggnnnnnnnn nnnnnnnnnn nnngg                                     25

<210> SEQ ID NO 251
<211> LENGTH: 25
<212> TYPE: DNA
<213> ORGANISM: Artificial Sequence
<220> FEATURE:
<223> OTHER INFORMATION: Synthetic

<400> SEQUENCE: 251
atgaacatca tcctagaaat ccttc                                     25

<210> SEQ ID NO 252
<211> LENGTH: 25
<212> TYPE: DNA
<213> ORGANISM: Artificial Sequence
<220> FEATURE:
<223> OTHER INFORMATION: Synthetic

<400> SEQUENCE: 252
atcatgcata catctctggc tggag                                     25

<210> SEQ ID NO 253

```
<211> LENGTH: 20
<212> TYPE: DNA
<213> ORGANISM: Artificial Sequence
<220> FEATURE:
<223> OTHER INFORMATION: Synthetic

<400> SEQUENCE: 253
atcagaactt caggccttgg                                                   20

<210> SEQ ID NO 254
<211> LENGTH: 21
<212> TYPE: DNA
<213> ORGANISM: Artificial Sequence
<220> FEATURE:
<223> OTHER INFORMATION: Synthetic

<400> SEQUENCE: 254
gcaaagccat gaacatcatc c                                                 21

<210> SEQ ID NO 255
<211> LENGTH: 24
<212> TYPE: DNA
<213> ORGANISM: Artificial Sequence
<220> FEATURE:
<223> OTHER INFORMATION: Synthetic

<400> SEQUENCE: 255
tcttgatgta gtgggagtcg gatt                                              24

<210> SEQ ID NO 256
<211> LENGTH: 82
<212> TYPE: RNA
<213> ORGANISM: Artificial Sequence
<220> FEATURE:
<223> OTHER INFORMATION: Synthetic

<400> SEQUENCE: 256
guuggaacca uucaaaacag cauagcaagu uaaaauaagg cuaguccguu aucaacuuga       60
aaaaguggca ccgagucggu gc                                                82

<210> SEQ ID NO 257
<211> LENGTH: 76
<212> TYPE: RNA
<213> ORGANISM: Artificial Sequence
<220> FEATURE:
<223> OTHER INFORMATION: Synthetic

<400> SEQUENCE: 257
guuuuagagc uagaaauagc aaguuaaaau aaggcuaguc cguuaucaac uugaaaagu        60 ggcaccgagu cggugc                                                       76

<210> SEQ ID NO 258
<211> LENGTH: 86
<212> TYPE: RNA
<213> ORGANISM: Artificial Sequence
<220> FEATURE:
<223> OTHER INFORMATION: Synthetic

<400> SEQUENCE: 258
guuuaagagc uaugcuggaa acagcauagc aaguuuaaau aaggcuaguc cguuaucaac       60
uugaaaaagu ggcaccgagu cggugc                                            86

<210> SEQ ID NO 259
<211> LENGTH: 20
```

<212> TYPE: DNA
<213> ORGANISM: Artificial Sequence
<220> FEATURE:
<223> OTHER INFORMATION: Synthetic

<400> SEQUENCE: 259
ggcagaccgt tctcatcacg                                        20

<210> SEQ ID NO 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
ctttaccagt gactccaggt                                        20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
gtcacagatt tccttctccg                                        20

<210> SEQ ID NO 262
<211> LENGTH: 20
<212> TYPE: DNA
<213> ORGANISM: Artificial Sequence
<220> FEATURE:
<223> OTHER INFORMATION: Synthetic

<400> SEQUENCE: 262
agatgatgac gcccaccaga                                        20

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
ggagaaggaa atctgtgacc                                        20

<210> SEQ ID NO 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
tgcgaggaac ttactttcc                                         20

<210> SEQ ID NO 265
<211> LENGTH: 20
<212> TYPE: DNA
<213> ORGANISM: Artificial Sequence
<220> FEATURE:
<223> OTHER INFORMATION: Synthetic

<400> SEQUENCE: 265

```
agagaaatat tgatatagga                                                  20

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
tatcaatatt tctctgatcc                                                  20

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267
atcgctttta aggcacgctc                                                  20

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268
tatacgactg atcgctttta                                                  20

<210> SEQ ID NO 269
<211> LENGTH: 21947
<212> TYPE: DNA
<213> ORGANISM: Mus musculus

<400> SEQUENCE: 269
gcagcagccc ataataccctg acagggctct ctgtggagct ctgagcagag gtgtctgttg      60
tgagaacaga gccatgaacc tcatcctgga atttctcctt ctggtgggcg tcatcatcta     120
ctcctacctg gagtcactgg taaagttctt cattcccgg agaaggaaat ctgtgaccgg      180
gcagaccgtt ctcatcacgg gggccggaca cggaataggc aggctgactg catatgaatt     240
tgcaaagcag aaaagcagac tggttctatg ggatatcaat aaggtaataa taggtgtttc     300
taacaatctt ttaaagtcac aaaataacaa ggcatatgtt tctctagaga cgtaacttag     360
tgctggcttt tctctgtgtt ttcctttttc aaagttttaa taaactcctg ggtcctttct     420
ggatccctgc gacaggtgaa caagatgaa ccaacgagct ggagaactaa gcctgggggg      480
tttcattttg tttgactggt tggttggttg gttggttggt tctactgtgg tgtacaactt     540
gataacaaga gacgcaggag ccagagagct tcccagctgc tgaaattagg caagccacat     600
aacttacctc aacttcaaat ttaaaaaaca aaaacaaac aaaaaactct accattggga      660
taaaatctca gagggagaca aaatctacag gtaatgattg ccagcaacca aattggccaa     720
tatgcagttt attacagcta ggggtgactt ttatacttt agattttcat ttattctgtt      780
attcatttgt tcctttctgt gatagactga agctgggtct tagtacctac cactgagcca     840
cagtacccta gcacgtgcca ggcaagcact ctatcaccga gcaaccgctc aggttttac      900 acatttgagg gattgattct caaacaaac aaacaaaacc acatgaagaa ctaacagcag      960
aaacccatgg tacttccact cacactccag caatcctaaa atacttacat ctgaccttt    1020
```

```
gcagaagaag aaaaaatact tgccgggtcc tgagcaagaa gggtaaagaa taatacttaa    1080
gtgcttagca tggcctggtg cacgcagcat cacatatgga aatgtctaca ccagtgcctg    1140
gctttcacta gtacatttaa gaggttgttg atctctgttt atttataaat gctcttaact    1200
accttaagtc tgaaagtgtt gacgtcctgt gtcactttct cctaaacatg cacattccca    1260
aaaggtcgtg aaaagatgt gccacaacaa actgtctctg ggattgtaat ctttgaagaa     1320
ctggactggg gatgtagccc agcggtacaa caattatcta gaatatacaa actagatatt    1380
agatccagtt gtggctgggt gtgagcctca gcactacaag gaaaccacaa accgctgctg    1440
tcatgtaccg gatacagtgg ctcagactag agagactggg gttttggtgt ttgtttgttt    1500
gtttgtttgt ttgtttgttg agaagcagag tttccaaagc tttccttggg gttttgctcg    1560
gcttcaggta accctctgtt acgttttgc catctgcagt taacaccact tttcccagcc     1620
ttcagaacgc tcttgaacat aaggagctaa atctgctttg gttccttttg agcagtgaag    1680
aatcccgaga ggcaccatgc atctttgctt agcagataca ggcgttggtg ggcaagatga    1740
gctaacacgg tacttggaga tgattctgag attatcaaat cctgcacagg tcccaggcag    1800
tcttcttgga gctgagaaaa ctgagtcagc tgttctcagt ccctcgtaaa aaatataaac    1860
gagaatgaga atacatcatg aagatggtcc acgggtcttc agatcacctc ccaagtgtgc    1920
atggtgggaa gacatcaata cttagtagac tacctttaat ttgaaaattt tcagacacag    1980
aaagagtaaa actagaaaga ggtcacatta aagatgactt ccactttttt tttcctgtgc    2040
ctgaaaactg agtaactcaa ccttgtaaat ttctctttga attcttgaac ttcatgatga    2100
aacatttaag acatcaaatg attgactgaa aagctgcaag tgtaactcca gtttccctgt    2160
tcactgagag gccagctagc tttccatcaa agaaatatgg ctccttttcc ttaaaaggca    2220
agaagcaagg ccacagagaa gcctcctcca cccccagctt taaaaacagt ggcacagaga    2280
tgtgaaacac aactgttagg aagggaattc agcagtgggg agggaggggc tgcaggaagg    2340
taacagggga taaaataata agagcataca tgtgtatgca aggaatgaaa agcaaattta    2400
agaagaacgc aatgacacaa tagcaaaact gtggacccag ccaaggtgcc cacccagaga    2460
catgggttgg aaaatgtggt ttcacacaca ggacatcgtt cagtcttttg gaagaatgac    2520
atcattctgt ttgctggaca gtggaaaaaa ctggcagtca caactttagg tgaaaaggga    2580
gccagactca caaagggaag gatcagtggg gggcgggggg gggggaggt cactctgctc      2640 tggtcccagc attggaccag gaaccaaggc aagagggttg ctgcaagtta gaacccagcc    2700
ctggctacag atgaaattat agcaagagac aaaagagggt aggggaaggc agcaagcatg    2760
ggctctgtca tgcctcgtgt gtgggaatgt catcatggaa catactagtt tgtacgttaa    2820
taaaaaggac acaggggatta gcaatgggca gaggggttga caccccagaa ggtgtttctt    2880
gtgcaaaagt gacgaagaga tacattcttc catgctccag attaattata aggctggata    2940
gttcgcaaat tattagcatc tatcactcat acatgatgct aggtttcacc gtaagctttc    3000
atagatgtgt atattctggt catattcact gttcacccat cattatctct ggtcccctcc    3060
cactcttgct gaccccctt ctaagtgccc ccttgtgctt tcatgtgtgt gtgctaatga     3120
ctttagatag gattgctaac ttgagcctag acgagggctt gttacaggag tagggatggc    3180
ttgctggtgg cgaagaaagt aaccctgata cactgtttct tcagtcacat cttttgctta    3240
tgctactgaa gaaagtaaca ctgataaatt gtttcttctt cagtcaaatc tttgcttgag    3300
gctctggtta ctgcctctct ctacagctct gacgtctgta tgaggctagt gaggagggca    3360
```

-continued

```
gctgggccat ctgacagtaa gcagccttca ttagtggaaa taaagccaac attagtggaa      3420
aactctccta cccagaccac agctctattc cacagcccca cgaggaccta tgctctatgc      3480
ggcagtccat cccaagtcta tgtgaagact atgttggttt cgtaagtgac accttaaccc      3540
tccttaaagt ctgttcttta agacttctat tgttgctttg tggtttagcc aagataagga      3600
aatgcaaagg gtcggagggg aggcaagcag tgtaagccaa acataccatc cactcaggca      3660
aggcccaaat gatggctaca ctattgccat cccagcttgc acaagaaaga gcttcctggg      3720
tgtcctcaca gagaagtggg gacaaccatc agaggaaaaa gtgtgatttt taaaaagaat      3780
ttgaacccca taaatcaat aggtgtcaaa acttggaaag agtccaaatt ttcctgaaat       3840
gtaggttaaa aaaaaaaaa aagccaaggg tagtgactca cacctgtaag tgcttgagga      3900
ggttgaggca ggaggattgg cctgagttga agacccgctt agggttcaca tagtaagcaa      3960
gggatagaga atgacacctg gtctaaaaca ccaagagaga acacacagac acacagacac      4020
acacacacac accacattag gacaatctta ggtaagaggc ttctggattt aggctaaaaa      4080
ttagctgtct ccatgtcttg gaggacttgt gtgcaattct cactttcgtg agaattcagc      4140
tgttggctct tggcctttt ccctccagag cttcagaaga ataaatactc agttaagact       4200
gtcacgtgta gtaagttaca gtttcctcgt gcaagctttt cctggataag attttctcct      4260
cgcatccgcg ggggtgaatc cacgttgtga taagccatct agtgtcactc tagagggctg      4320
cttagcactc tactgccaac aatgggtgat gcccggcaac tgtgtggact agtcttcctt      4380
ctgtcctccg tgctcagaca tcttccctga cactgtgagg agcagcatct tcgataactt      4440
ataggaagcc cttcatgcta ccacagcatg acgctagaca aatcacctac aggcactccc      4500
aggacaagat gcgaagctgc aaaagcctta acccgaaggg cttgtttctc tttgattccg      4560
ctgctgcttt ggccagctaa ttagttaatg tagttagatg agttcacata acgaggctta      4620
ttggacaagg atccgaaagt attttacaga gcctgatctt ttctcaaatt tgcctccccc      4680
ctccttcacc cctcccgccc cccacccgc ccagcgtggt gttgaggaaa ccgcggacaa       4740
atgcaggaaa ctgggggccg tcgtgcacgt gtttgtggtg gactgcagca accgggccga      4800
gatttacaac tctgtggatc aggtgagaac ccgggtgcag gtgtcgcatc agctgacact      4860
gagctgggaa acgaaaaggt gggctaggga aggttgactt ccggtagacg gcagccgccc      4920
tgtcaagttg ctgtgtgacc gaaggagtga atattaatat ccactcagct ctggcctctg      4980
tcactgtttc atattctgag tcaaatctgc tgtgtctaaa aagtttggcc cagaggaaac      5040
gaaagatgat ttatcaagag aaaatttgat ctcttttcta acttttttaa aattagactt      5100
tgttctgctt tttctttaac ttattccctc tgagatttta ttggtttgcg tataatctag      5160
tcttttatga aaaacagagt taatgacttt ttaaacattg tatttgtttt atttactgca      5220
tcgtgtgtgt gtgtgtgtgt gtgtgtgtgt gtgtgtgt gtgtgcgcgc gcgcatggtg        5280
ggggtgtatg tagaatttag atgacaaatt ttgaaagctg gtctctcctt ccatgatggg      5340
gattctgggg gttgttaggt atggcaaaaa cagaagagga ggaggaggag gaggaggagg      5400
aggaggagga ggaggtggtg gtggtggtgg tggtggtgaa gaagaagaag gagcaggagg      5460
aggggaggag gggaggagta agaggagaaa gaggaagggg aaggggaggg gggaggggga      5520
gaagaaaatg cctttaccca ctgagccgtc tccccacccc acaataccta ctctttcaaa      5580
aagtgaacat caagagctta ccaaaaaaaa aaaacaaaa aacaaaaaac aaaaaaacaa       5640 aaacaaacc ctccgctaag ctactgcctt ctttaatctg atttaatttt taaaaatccc       5700
attagcctca ctatagataa gcaaatagaa gcttggaagg tttggcccag acaaagacca      5760
```

```
cgtggccagt gggtagcaaa accaagatta attacttaac actttaaaaa tatcttaaca    5820
gaacttaagt attatttacc agcacaaaca ttaattcttg tttatttaag ttcataagtt    5880
ttcaccctac ctatcacata ctgagcacag aatttagggt tttaaccaaa acaggttagc    5940
cctacctcat gacaggtttc ccttcctgtc actgcttggg ctggttcttt cacgcctgaa    6000
ctctgagacc tcgtgcactg gaataacaaa agcctagatg gcatagtgac caagctagct    6060
gtcaccaaag ccagtgagcc cagacagaaa tgcatcgtaa agctattctt tattcttgga    6120
agtcagatcg atatcttgga tatctgtctt ccatgtcacg ctgtgatgtc tgtgtgtctc    6180
tcattatcat cccttggaca acttcctcct tttgtgttat tgggctcagg catttcttgg    6240
agttgagttg gcctagttta tgctggtatc aatcttagac tcttgggatg gctagggta    6300 gggtgtggag tggttagctc agaacacatg gtgtggagtt gctgagctat aaatattgtg    6360
tatgctctgg tttctttta catggtggag tatatatatc cttataatat agaacataaa    6420
aatgcctcta cccatctgtc tcctatcaac atgagctttg tgagaatgac cggtcctgtg    6480
tgtgcatttt aaaaggtaaa gagagaagta ggtgatgtcg agatcgtggt aaacaacgcc    6540
ggggcgatat atccagcaga ccttcttagt gccaaggacg aggagatcac caagaccttt    6600
gaggtcaata tcctcggaca tttttgggta agtcagaaac atttctgggt gtgtgtgtct    6660
gacatctctt cggtacagga aactcattga ggtcacaata tttgtggagg gaggtgtttt    6720
tggttttgtt tcttaagatt tatttattta tttatttat gtatgtgagt acactgtagc    6780
tgtcttcaga cacaccagaa gagggcatcc gatcccgtta cagatggttg tgagccacca    6840
tgaggttgtt gggaattgaa ctcagtacct ctgggagtgc tattaaccac tgagccatct    6900
ctccagcctt gttttttgtt ttgcaagtca ggaatcttat aatgtgtttg aatagaagag    6960
ccacaggtct ctggcaacag ggttcagagt tcaaggagac acaggacacc caaaagagag    7020
agccatttgg tttattttgt caaacaaaat ctaacatagg gcctgatgaa taccagatct    7080 acaaaagta aattaataat aaaaaattta ttaattaaaa atatttgtaa aggtttactg    7140
atatttcctc tgtacatctt ttcactattt tagaggaaat gtatgctgca tacattggtc    7200
tgcatcttcc tttcataggt gtttagagct gaaaggacat agaatactta gatttgtgca    7260
gaagttgggg acactagag ttaggctctg agataagtag acattttgac ataacattat    7320
tatctacaaa gttcctgcct gagaacttca caattgagtt accaataggg gggggaaaca    7380
atctcaaaat gttttactgt agctcacaaa tttgcattga tctatattcc cagctaatct    7440
cagtcataag cagcctatgg gcggtgggat gagcatgcct attagttctg gagtgtagag    7500
agaatgaatc caattcctta ctattgggag tttgtgagaa actgaagtac ccttctcagc    7560
cctttggagg gagcatttgt atgaattaat accgtgggac ctcaaaatta ctatagcacc    7620
tggagcaaac ctggatttga agaacatcct tcatcctcat gacccagcta acatgacagt    7680
cacacaacac agggacccta tatactagtt atctaataat taataggaaa ttataactat    7740
gtcacaaaat atatcaaaag gtagaggttt agagaaccag gagccctcat tacctccata    7800
cagatctgca ggcagggctg atagggggat tatcttggca acctgggctc taggaattta    7860
cacagaattt gaagagtggg tctgtaaaat tctcataaaa tgttctgata tttcccactg    7920
tacagtgagg cttttgtttc ccataatgta tcctatactg tatactgtta caagagagag    7980
atttgggtct gctccctgtg cacggtggtt gtgggccagg atagagcttc caccgctttg    8040
acgtgagtaa agatccccat tcttcaaatt ggagccaaga acttgtaaaa cggtaaacca    8100
```

```
tcctccagtt cccgcactgg tggatctctc ccttgacaat attgcttagg gctcagcagc   8160
accaggcttg cctggcatgc acaaagtcct ctggttaatt cctagcacgg cggaaaagta   8220
acaatgttgc ttctgtggca aatcccggaa ggagctactt aattcttcct ggagggatga   8280
aggggcatgc tcgcccgcta gcactggtcc tcagcacaat ctaggggact cagctctgag   8340
tgctgtatgc acgcttgcac aggtcctctg catgatctaa gggacactct gagtactgcc   8400
tggaaccatc acagttactc tctctttctg tcactgtgtg gaaggaacct cagggtctta   8460
caagtgtgta atttccaatg cctcctcctc cgctatggtg gaggcattgg aaatgaaaga   8520
gcctggcctg gaatccacct aataaccgtg tcattgtttc tgttcttttt acgtggacct   8580
taagatcata aaagcactcc ttccatcgat gctgagaaga aactctggcc acattgtcac   8640
agtggcttcg gtgtgcggcc atggagtgat tccttatctc atcccttatt ggtaggtgtc   8700
tcttgctcac agcgctgtgc atttctgctt attagtttgg ggattattta tagggattat   8760
tataattagt atatttatgt gttttataaa tattatatac tataatttta taaatgtatt   8820
catatattat ataactaaat aattataggg attaattata ggaaattatt agggattatt   8880
agttttcagg cctcaatgcc cacagcctag taaagtgccc agaagctaac acaagcacag   8940
aggtatagcg tggtctatgt gtgtgcatgt gtgagagaag agaacggagc agccctgcct   9000
tcccaggaga tgcacacact gcacaccatg tcccagggac ccagacacac tcgcagtctg   9060
cagcatatcc ctgagaagtc tgctattgcc atcttgtttc cttactgcta tacgatgatc   9120
tcagaaacac ttttaccaag atctgtggat gtagcagatg caggtgttat ttctttatag   9180
gcatattcaa agctaaactt gaccatggac taagcaatct ctcacactat acatggtcac   9240
agatgagtta aatttcagtg tagttcaggt ttccattaca cgcacacact cacacacata   9300
cacatacaca cacaatacac acacatgcac acacatacac cacacacacc atacacaaca   9360
catacacaca caacacacat tcacatatgc acacacatat acacacacac acatcacaca   9420
tgcacacagg agaggaagac agagacagca ataacttcta acactgatat ttttgtcac   9480
ctggacaaaa actacaatta aaacttatat agctccatat atgcatatgc taatttattg   9540
aattctccaa gacagcctta tattttgtta tctatatttt ataatcagaa aaatgaaaga   9600
acaaaaggtt aaaggttgca catgcaaaca caaccctacc aatgccatct ggagcccctt   9660
tgctccaaat actcgttgtg acattaggac acacatgaga ctgccagtgt caagggagaa   9720
aacatcagct ctttaatcaa gagaagagaa atgagctcag acccacaagt tgtcgatgt    9780
tggtttcaca gtgttttaag tgtgtttttc tgactcacat ttttggagat aaaaactaat   9840
aaaacctgat taagaagcac ttggaaggtt gcctggacca tagagaaggg tcacacatac   9900
agtgagaaac attaagccta tctgtaaagt ggtccttttg ctatctttgc tagttagaag   9960
ttagaaacag gggctttggg gttagcaatg gttgaagaca tgcatgtgtc aatccctgag  10020
ttcaatcccc agcacctaaa agaaaaaagg aaaaagaaac aggtattttg catgctcaga  10080
attctgcttc ctacataaga aaataaactc gagcggcagg tgacaggtct ggacacatga  10140
agctgccttc tctcaggcag ctgagactgt ccccaccacc accaccacca ccaccaccac  10200
cacacacaca cacacacaca cacacacaca cacacacaca cacacacaca cacctttgct  10260
gatggctgat tttctcacag ctccagcaag tttgctgctg tgggcttcca ccgagcactg  10320
accgcagaac tggacacctt ggggaaaacc ggtatccaaa cctcgtgtct ctgccctgtg  10380
ttcgtgaata ctggcttcac caaaaacccg agtacaaggt gagatggaag acctttaagc  10440
gggagccccc ccctccaggc aatggagtct tgagtaggtc ataggtactt aacaagcatg  10500
```

```
tcacgatcat ttaaataagt ccagtagcat gatctcaacc cctaggctga cactgaggtg   10560
cccatgtcag atgtggctct aaggctggat tgaagactcc attgcaaaat taggaagggg   10620
agagacagag gcaggataat ctaaaaagaa ttgatttgtg ctgctgtgtg atggtttgct   10680
agtccacatc acaggcatca caatcgcacg ggagtctgcg gaaaccacag actatctcat   10740
gggattcagt tccaacaccc acacagcctt gcctcggcat gctaaccttg gtgtgacatc   10800
taaaatccat ttttatgctt tgattttttcc ctcctcttca ttaatgggca aggctccaac   10860
actggacatg ggttatacgc atttctcagt tatacacggg tgcaacttttt gaatcacgaa   10920 acgccccagt gctgtaacag aacactcctt gtacaaatct taaattccca taaaattgca   10980
ggagaagcaa atcttagtac gagatgcctc agaacaactc agctctgtgg atacccacac   11040
acaacgggaa gtgtactcag acatagaata ttcttttttac atacagcagg cattggagat   11100
ccggtgtttc cttcctggcc attttgtccc ctggctcctc agtccctccc catcttgtac   11160
cttgttgtga tttaattatt ttgacctggt gaggtaacag acagacctac tggacccaag   11220
agtacaagaa catgataaca agttatcagt gtgggatgtg ggaaggggag agggtgatgt   11280
tcactcaggg aagcctggaa cattgtaaat cctaattcta aatttggtga agagacagga   11340 taattttcctt catttgttaa ttaaaaacaa tataaatcaa gaggctgggg ttttacctca   11400
acatcagggt atgtgtgaaa gttctggatt taattccagc atccaaagga agaaataaaa   11460
tataaacgga gataaactct ttccccccttt ccttcaggtt atggcctgta ttagagccgg   11520
aagaagttgc aaggagtctg atcaatggaa tacttaccaa caagaaaatg atcttcgttc   11580
catcctatat caatatttct ctgatcctgg aaaagtaagt tcctcgcaga accctgaaac   11640
actcaaacac aaatgttaga aatgttgcta tggaaactcc ccatggctgc agtgaaagtc   11700
acgttttcca tgttgcctta cccatgagtc tttgattccc tgatacccctt tctggaatac   11760 atctaccatc ttggcccaaa ttttgttcaa gtctatttaa cagaaagaaa gaaaaactac   11820
agggtatggg cacaccataa aggctctgtg tgtgtgttca tgtggtgtat gtgggggata   11880
gagatgtggt acttgtggag acagaggcaa agctctcagg aaccatccac ctaggtttct   11940
gatttgggtt tatttctctt ctctccttcc cctcccctcc cctcccctcc cttcccctcc   12000
cttcccctcc cctcccctcc tctcttcctt ttcctttcct ttcctttcct tttctttcct   12060
tttcttctct tctcttctct tctcttctct tctcttctct tctcttctct tctcttcctc   12120
ttccttccct ccctccctcc ctctctttcc tctctctctt ttttctgat acaatctctt   12180 attgagacct ggactcacca gcttggctag gatagatatg catcaccagg gatatcccag   12240
gccctctatt cccacagtac tggggttaca agtgctgaca gctatgccca gctgtgtgtg   12300
tgttctgagg attgaactca ggccctcctg ttgtcgtggc aatctcccta aaccctcggg   12360
tgctcagttt tgcagttctt tgtgacagtg tgcatctcga atgtctcata acatgctttc   12420
acatgtttct atttcacttc atttataacc caagagcctt atgatagaat cacttctttt   12480
catctcaggc ttgtgagccc ccaaagaggg caaaatccca caaattgaat ttcctcaaca   12540
cagctcaaaa caggtctcat taaaagttga aaaaaaattc caaaattggc atgtatatga   12600
ccaaagtgca aaaatggttg actgctctgc ctggataggg accagttacc tgtctccaaag   12660 cccttgccac actgtgggtg atttgttacg ctggcaacag ggattttttgt tgctccttgc   12720 atttaactcc ttttggagag agacagttct gtgatcagaa gcaatcacta gtctctgggc   12780
ttgttgttca atggcctgag caagctctct ccttaccacc tcacagcagg gtccccacct   12840
```

```
cccagtctct tctcccacct tctgccctct atccagggaa gtaaatgttg ctttagtaaa   12900
caataccaat gtgatctgaa atttggcttt ctctgtagaa atcgcacctc ctgcctcttt   12960
cacttcactc acacccttcc ctattctgtc aactcagacc taaccctccg acatgctgag   13020
aggtattcag cccctgtaaa cccttccttc cacatcttgt tatagtcagc tgatggtttt   13080
ctgtattcat ttccagttgg ccatgtttaa ccgctgggca gcgcaataca ctaagaggca   13140
gtagcttttg aaaaggctct ttagttttc tttctctaaa ataataggtc tggacacagg    13200 cagaggggg aaggggtgt atgtggtgga ctctcagttc ttggccccag aatacactgc     13260
cgttttttgg aagtgagctt ggtgtcggtt ttaggttgtc attggtagaa gacgtcatcc    13320
aattttgctg ttctgagaga acaacgctat attatatata gataactgta gatggggtgg    13380
gggaggggag actaaacaat aagcaaagag tagaggaaaa ctggacttga gtaagtatgc    13440
tcttggcgct ttttaaattg acaacaaaaa ggaacactgg catcaaaact tcaaactgaa    13500
atttctcatt ttattttaa tgtaggtttc ttcctgagcg tgccttaaaa gcgatcagtc     13560
gtatacagaa cattcaattt gaagcaattg tgggccacaa aaccaagatg aagtagtgca    13620
tgcagagacg tgtggacacc aatgatgtga agccaagttt agagggaca cacagctttc     13680 tttcacatgt tttaagtgtt ccacatgttt aaaatgtagg cttgacccta gcagccatcg    13740
agtgcataag cgtggtcaac tgtccttcta gtttcctata cttatagatg tctcagctcc    13800
tggtagtggg ttctggcaat ggatatgtaa aggagggaaa aggcaatcca tgtgttttta    13860
taaaataaat tactaaatag aaatgtgggc aaaagggcaa gataataaag tcttgggcaa    13920
atgttggcac gctgtagtga tttctctttc gatggagaga ttggtggtgt tttaaatttg    13980
ctctttgtgg acaggatgaa aactctacct ggtttccttg acatatgaat taggaaggag    14040 tattttgtt ccacattttt tttctcagtg tgaggttttc ttcacatcat gtgaatggac     14100
aatgaggtca ttttatttac ctaacttggg gaagcaaata ttgacacaga tttgcaactg    14160
tgaaatctca acaccttgtt ctttgcttta gaaagacctt ggacacattt gttttctttt    14220
ttattctatt aggcaataac tgaaaatacc caaccgtata catagtaaca gtgacatgac    14280
ctcccacaca gatcccatta tgaagcagga aaccttcctg ggttttcctt tggcttctgt    14340
attttgctgc aggggactga tcccacagac taagacaggt tacataggca gtctgtgttg    14400
acctcctgtc tatcaacttg cagagttact tccacatttt gctttgatac ctttaaagtg    14460
aagctcagag ggatgcctca gtatgtgaca atgatctctt ttgcccacgt ctgcatattt    14520
tgagtgtaaa tatcttccct acaaggtcca gctccatttc taaatatttt tctatgataa    14580
tcttcacagt cacagttctc actcctgcta accattgcag ccgcttaggc taccccagga    14640
agcacagatc cctaagtaag accccatcta cacaaatcat ttagttagag acacatcata    14700
gaattcctag gtccctgcga gcacggggtc atgatttatt gatgagtatt tcagaatggt    14760
ggaagtattt gttattgtc tactcagttc atggaaacaa ccttttttggt aagcagacag    14820 tatctcctct ttttttttaat ggtagaatat gatattgcat atacataagc acattttgaa   14880
catagctgaa tataagtatc actgtttcat ccttcttctt cttcttcttc ttcttcttct    14940
tcttcttctt cttcttcttc ttcttccgga gcatataatt ttattgctct tctttttaa     15000 agaatagaag aatatctttt atactaggtc catgggctat ctagtgtctg gttttttgttc    15060 acccaagcag tgctagatac aagctccatc ttgtgtagta ggctttaagt caaaacagat    15120
ttggttggtt actctcacaa cattgggcta ccatttttcct accatatctt ttaggcacaa    15180
caccaatgtt gatccatggg tgtgtggctt tgtttgttgt tcttttccta ggagcatgca    15240
```

```
gaatgacttc ctacacctaa gatactagta gataggagtg aagagtctat gtagtcacca    15300
gattgacttc tagatgttca gtgagttgag ttgcctttag caataggacc ttgttgacag    15360
gtggtgtaga gaaacatatg gccatggtaa cagcttgagt tctttgcaga ttcccatgta    15420
aacatttgga caacatctca gtaaaatgta attgagtttg aatactggaa gcttcttttg    15480
gtgaggaaag ataccctgtt agaaacaagt ctcctttgtt atagggtgat ttcatttata    15540
tgtgtaattg cctttgtatg tgtatatttt tctatcaatc tgtctatgta tcatctatct    15600
aatctctctg tcatctaata tatgtatcat ctgtcagtta tccacctatc acacatatat    15660
agctattgtc tatcaatcac cttttaatct acctttcat tctatcaaac tattaatata    15720
tcaatcactt atgtatttgt gattgatcta tcttttaacc atctaattat cacatatctt    15780
tcttctattg atgatctatt ttcatctgtt tctctgtctg cctctcattt cctttgaat    15840 agctctagct atcatatgca aagggaagac attttcacaa aaataagcag tcttgagggt    15900
cctcatgatg ttttcagtcc ctcagtgtct cattccaaaa gcccaaagac accatagaat    15960
tcagacagaa tgccatgtaa caaagcccca cactcaatac ccagttacaa ccaccttagc    16020
agaacactaa agagattaaa ctatccttgg ctgccactaa aatcaggtag tcttcatggt    16080
aagtgtggat ctagcttttg gggaagtcct gtattctttg ctaacccact ttcatttcaa    16140
gattgaacaa aacacaggaa gatggtgccc tgtgaggcct tgacactcac atagcctcag    16200
tccagttagc tccctgtcca tgtgttcaca acagatgctt gtgataaaga aagcccaca    16260 ggatgggtga ggtctgagtt tctgaccaca gatccttcct gttatttttg atgttatttt    16320
tatgtttgtg tggttatctt cttttgggtt tgttgaaaga ggatttcttt ttctttttct    16380
aaggtgtagt ttcccttctt gtgttggcat tttccatcta ttatcctta tagggctgga    16440 tttgtggaaa gatattgtgt aaatttggtt tgtcatggaa tatcttggtc tctctgtcta    16500
tggtaattga gagttttgct gggtatagta gcctaggctg gcatttgtgt tctcttagga    16560
tctgtatgac atctgcctag gatcttctag cttttcatagt ctctggtaag aagtctggtg    16620
gaattctgat aggtctgcct tttacttgac cttttcccct tactgctttt aatattcttt    16680
ctttgttttg tgcatttgat gttttgatta ttatgtgaca ggaggaattt cttttctggt    16740
caagtctctt tggagttctg taggcttctt gtatgtttat gggcatctct ttctttagat    16800
tagggaagtt ttcttctata actttgttaa agatatttac tggccctta agttgggat    16860 cttcactctc ttctataccct attatcctta ggtttggtct tctcattgtg tcctggattt    16920
ccaggatgtt ttgggttagg agcttttgc tttttgcatt ttctttgact gttgtgtcaa    16980
tgttttctat ggtatcttct gcacctgaga ttctctcttc tacctcttgt atactgctgg    17040
tgatgcttgc atctataact actgatctct ttcctaggtt ttctatctcc agggttgtcc    17100
ctttgtgatt tctttattgt ttctatttcc attttcagat cctggatagt tttgttcaac    17160
tccttcacct atttggttgt gttttcctgt aattctttaa gggagttttg tgtttcctct    17220
ttaagggttt ctagacattt acctgtgttt ctttaaagga gttatttatg tccttaaagt    17280
cctctatcat catcatgaga tgtgatttta actcagggtc ttgcttttct ggtgtgttgg    17340
gatatccagg gctcactgtg ttgggagaac tgggttctga tgatgccaag tagccttggt    17400
ttctgttgct tatgttcttg ctcttacctc ttgccacctg gttatctctg tgttaactg    17460 gtctggctgt ctctgactgt ggcttgtccc ttctgcaagt ctgcattgtt agtacttctg    17520
ggagaccagt tctctcagga ggaatttggg tatggagatc tgtggcacag ggtcagctct    17580
```

```
ggagtgtaga cagaaaccag aaggatcctg tgcctggttg ttccttgatt cctgtgtcct   17640
gatggctctg ggaaggtttc gcttgggcca cgagtttgaa cagaagtggt gctcttacct   17700
gtgctcgggg gtgtgtcagc actcctggca aaccagctct ctcctggccg tatttgggta   17760
tgtagcggtg tggcacagga tcagctccgg gcacagacgc aaaccagaaa gcttctgtcc   17820
caggccgctc ctggttcctg tgtcctgaga gttccaggag ggtccttctg agcagcagtg   17880
gtggttttac ctgagttcaa aggcttgtcc acactcctgg gaggcaagct ctctcccagc   17940
actatttggg tatggagccc tgtggcagag gatcagctct gggccaaaca taaaccggaa   18000
ggctgacatc tttcaaaagg agtcttttt tcttctttt tttttggggg ggggggggtt      18060
gatttttttt ttttcgaga cagggtgtct ctgtatagcc ctggctgtcc tggaactcac    18120
tctgtagacc aggctggtct cgaactcaga atctgcctg cctctgcctc ccgcatgctg     18180
ggattaaagg tgtgcgccac cacgacccgc tcaaaaggac ttaatgttct ttatttaaca   18240
atgttatata ttttctagca acctatcttc tctccctctc tccctttctg cttctctctt   18300
tcttcctctt tcttttttctg caccttttctc tctctgcctc tctctcttcc tttctctctg  18360
tctctgtctc tctctctctc tcttttctctc tctctctctc tctctctctc tctctctcgt  18420
gtgtgtgtgt gtgtgtgtgt gtgtgtgtgt gtgtgtgtgt gtgtattaaa ggctgcatta   18480
caccaggcaa aggctgtgtt acaccaggta aaggctacat tacacaggta aaggttgtgt   18540
tatgccaagc aaaggagttt ctttgaactt taatctcatt gcacccacaa gagagtaagc   18600
atacctcagg ctaggtgtgt tcactggaat acgtgaagta aaggttgaaa cttctgttta   18660
tgactaattc tttatcttaa aactttgttt tttacagtat atacgatatg tgattatatt   18720
atgacacgat atatactaag taaatattag gtacacactg aagtttagct gcaatgctca   18780
gtcagaccca cagtcctttg cccactcctg ttctctctct ctctctctcc ctctctgtct    18840
ctctctctct ctcgctctgt actctatagc tgtctttgag caaagatcac aggaaccaaa  18900
aaactgagag gtccagagca tgagcctagt gcacatttta gtattcctac atggtttatag  18960 gtgcactgtc tcctgtccat ggtgtctacc acccttaggaa aagctgcagg gtctagagat   19020
cttagaaata gaataagcca ggctaaatac acagaccact gggtaaatca gtgcagtggt   19080
cactgttgtg ggctagtcac cagagaagac tgttcaagcc aatggaaagt cattactagc   19140
tgactggtga ctacactgga tgttcaggat cccagtgtag cactgagcct tcctcaggtt    19200
gagcttttaa gcacaaaaac catgttcttg gttgacgtac ttcagttaac aagaacagtt   19260
agctggaaga ggaactacag aagctaaaag gcaacattag tacattatga gactttacca   19320
aaacaatgaa ccctaatgaa ttatgccttt tagttttgac aggtagggct gtctaagtgc   19380
tgagttttac agcctgaaca gtacttccat catggagtca gatatgctaa gatctgggac  19440
cctgttacat tccacactgt tcttagtgaa tgagtcaaat catggattca tcctgttta    19500 gtttaagatg aagaatgaga attaaagtgc tgacacaaaa tcattagcca gggagaccac   19560
gagaatggag actggtactg actacttcct caaccatgtc tatattttct ctaattattc   19620
cttaccaatt agtatagaaa caataggttt cttttcagagc catgtatagt ttcctttatg   19680
tcatttgaag tctaggcctc tccaattttg tagggagaat ctacctgcaa gggaatctaa   19740
ctgttgtttt aattcagaaa ctgaaacttc aaatacctgt aggtcctgat caacctatcc   19800
tcttagtttg gaaagcctca gaagaggcat atttagtcaa accattaata tatgctcacc   19860
aagtagtctc agaggtttgg taatattgct gttgtccaga tgaattaaac catcgggcag   19920
aataacacac cttggaatgt ggggaagtgc gtaggttaaa aattttggat attagacagg   19980
```

```
ttttagcccc ttctaagtcc tctagcatta atctgggctg ccccagtca cagtgagttt      20040 tgtcagtcaa tagattggtt agtccccatt tctctgtcct acagcagatg ggtgtctaag     20100
cagtttcatc aaccctggat ggttttgact gggcatgatt acctctgcct cccagggact     20160 cttctgtgg catagagtct gatgctccag gccttttgg ttttacaaag accagaatct       20220
tttaaagagt tttgggggcc tagtgagatg gttaagaaca ctgactgttc ttccaaaggt     20280
cctgagttca attcccagcg accacatggt gggtcacaac catccgtaat gagatctgac     20340
accctcttct ggtgtgtctg aagacagcta cagtgtagtg tacttagata taataataaa     20400
taaatctaaa agaattttct gtaggaagct tcggttttaa gttccaattt ttggaatgga     20460
aactcctctg ttttaagctg tggtacaggg tcagctctgg ggttcagaca gaaaccagaa     20520
ggatcctgtc cccaactgtt ctttggttcc agtgtcctga tggctctggg catgtccctc     20580
ttgggccagg aatttgagca gaaatggtgg tcttacctgt ccacactcac aggcatgtcc     20640
acactcctgg gagaccagtt ctctcctggt ggtatttggg tatggagcgc tgtggcacag     20700
gatcaagctc tgggtacagg cggccagtat ctcctctcgt ttgatcctga attgttaaat     20760 tcttattat caaataaacc attcttggcc aatcttgtgg ccacactgaa tgccagtagt      20820
aaggagccta tgaacatctg acatcactgt gcaacaataa aagacggcac catgttcaga    20880
cataaccaat ggaattggat tcatagatgt acacatgtgg agtgaagatc aatagtccag    20940
agccagaaga ggaccagagg ccccagcaac attgctccca gacctgctaa cactttggtt    21000
tcctccatac actgctgaac aagagagtac ttactccaga aagctatgag ctgggtgatg    21060
aggagagggc tcaggtttta aaagcacttc tctttctttc agaggacctg gattcagttc    21120
caagcaccca catggtggtt ctcaacagcc tgttactcca atcccagggg atttgacacc    21180
ctcttcagac tttctcaaac actaggcact cgtggggtac gcatacgtca ttcaggcaag    21240
ccctcataca cataaaatag aataagcaca tattttaaat gtgctactat tactgatgtt    21300
ttaagccagt taaattatgt gattttctta acagcaataa aatattgtag ataatgtcat    21360
catgctagct gcatcactct gactgtataa acccaagaga atttcactcc atctccttct    21420
gccaaaatat ttacaacact taagaaataa gggctgattt ttatttttt taacataaaa      21480 tatatgagac agttgtatcc tgtcagctaa aaatgttttc tctggcctgt gagttggctc     21540
agtagatgaa gacacttgct gccaagccta acaacctgaa ttcaactccc agaacccatg    21600
taatgggaag acagatggga ttcagagaaa ttgtcctctg atcattgtac ccatgccttg     21660
gtatatgagt atctgtgatg gtttgtatat gctcagtcca gggagtggca ctactagaag    21720
gtgtggtcct gttggagtag atgtatcact gtgggtgtgg gctttaataa cctcatccta    21780
gctgcctgga agccagtatt ctgctagcag ccttcatatg aagatacaga actctcagct    21840
gtgtttgcac catgcctgca tgaacgctgc catgctccca ccttgatgat aatggactga    21900
acctctgaac ctgtaagcca gccccgatta aatgttgtca cttataa                  21947
```

<210> SEQ ID NO 270
<211> LENGTH: 36
<212> TYPE: RNA
<213> ORGANISM: Artificial Sequence
<220> FEATURE:
<223> OTHER INFORMATION: Synthetic

<400> SEQUENCE: 270
ugucagguua guuagaugaa guuuuagagc uaugcu                               36

```
<210> SEQ ID NO 271
<211> LENGTH: 36
<212> TYPE: RNA
<213> ORGANISM: Artificial Sequence
<220> FEATURE:
<223> OTHER INFORMATION: Synthetic

<400> SEQUENCE: 271
gugucagguu aguuagauga guuuuagagc uaugcu                                 36

<210> SEQ ID NO 272
<211> LENGTH: 36
<212> TYPE: RNA
<213> ORGANISM: Artificial Sequence
<220> FEATURE:
<223> OTHER INFORMATION: Synthetic

<400> SEQUENCE: 272
ccugacacau auacagacua guuuuagagc uaugcu                                 36

<210> SEQ ID NO 273
<211> LENGTH: 36
<212> TYPE: RNA
<213> ORGANISM: Artificial Sequence
<220> FEATURE:
<223> OTHER INFORMATION: Synthetic

<400> SEQUENCE: 273
cugacacaua uacagacuaa guuuuagagc uaugcu                                 36

<210> SEQ ID NO 274
<211> LENGTH: 36
<212> TYPE: RNA
<213> ORGANISM: Artificial Sequence
<220> FEATURE:
<223> OTHER INFORMATION: Synthetic

<400> SEQUENCE: 274
ccuuagucug uauauguguc guuuuagagc uaugcu                                 36

<210> SEQ ID NO 275
<211> LENGTH: 36
<212> TYPE: RNA
<213> ORGANISM: Artificial Sequence
<220> FEATURE:
<223> OTHER INFORMATION: Synthetic

<400> SEQUENCE: 275
cauauacaga cuaagggacc guuuuagagc uaugcu                                 36

<210> SEQ ID NO 276
<211> LENGTH: 36
<212> TYPE: RNA
<213> ORGANISM: Artificial Sequence
<220> FEATURE:
<223> OTHER INFORMATION: Synthetic

<400> SEQUENCE: 276
auauacagac uaagggacca guuuuagagc uaugcu                                 36

<210> SEQ ID NO 277
<211> LENGTH: 36
<212> TYPE: RNA
<213> ORGANISM: Artificial Sequence
<220> FEATURE:
<223> OTHER INFORMATION: Synthetic
```

<400> SEQUENCE: 277
ucaaaguuug auaaauuccc guuuuagagc uaugcu                36

<210> SEQ ID NO 278
<211> LENGTH: 36
<212> TYPE: RNA
<213> ORGANISM: Artificial Sequence
<220> FEATURE:
<223> OTHER INFORMATION: Synthetic

<400> SEQUENCE: 278
aaaauacaaa gauaaguaga guuuuagagc uaugcu                36

<210> SEQ ID NO 279
<211> LENGTH: 36
<212> TYPE: RNA
<213> ORGANISM: Artificial Sequence
<220> FEATURE:
<223> OTHER INFORMATION: Synthetic

<400> SEQUENCE: 279
acucugugac uuuaaaaagu guuuuagagc uaugcu                36

<210> SEQ ID NO 280
<211> LENGTH: 36
<212> TYPE: RNA
<213> ORGANISM: Artificial Sequence
<220> FEATURE:
<223> OTHER INFORMATION: Synthetic

<400> SEQUENCE: 280
gguucugugg gauauuaaua guuuuagagc uaugcu                36

<210> SEQ ID NO 281
<211> LENGTH: 36
<212> TYPE: RNA
<213> ORGANISM: Artificial Sequence
<220> FEATURE:
<223> OTHER INFORMATION: Synthetic

<400> SEQUENCE: 281
acagagcaua uugguucugu guuuuagagc uaugcu                36

<210> SEQ ID NO 282
<211> LENGTH: 36
<212> TYPE: RNA
<213> ORGANISM: Artificial Sequence
<220> FEATURE:
<223> OTHER INFORMATION: Synthetic

<400> SEQUENCE: 282
gacagagcau auugguucug guuuuagagc uaugcu                36

<210> SEQ ID NO 283
<211> LENGTH: 36
<212> TYPE: RNA
<213> ORGANISM: Artificial Sequence
<220> FEATURE:
<223> OTHER INFORMATION: Synthetic

<400> SEQUENCE: 283
ugcaaaacga cagagcauau guuuuagagc uaugcu                36

<210> SEQ ID NO 284

```
<211> LENGTH: 36
<212> TYPE: RNA
<213> ORGANISM: Artificial Sequence
<220> FEATURE:
<223> OTHER INFORMATION: Synthetic

<400> SEQUENCE: 284
gagcugggca uggaauaggc guuuuagagc uaugcu                              36

<210> SEQ ID NO 285
<211> LENGTH: 36
<212> TYPE: RNA
<213> ORGANISM: Artificial Sequence
<220> FEATURE:
<223> OTHER INFORMATION: Synthetic

<400> SEQUENCE: 285
acuggagcug ggcauggaau guuuuagagc uaugcu                              36

<210> SEQ ID NO 286
<211> LENGTH: 36
<212> TYPE: RNA
<213> ORGANISM: Artificial Sequence
<220> FEATURE:
<223> OTHER INFORMATION: Synthetic

<400> SEQUENCE: 286
cucauuacug gagcugggca guuuuagagc uaugcu                              36

<210> SEQ ID NO 287
<211> LENGTH: 36
<212> TYPE: RNA
<213> ORGANISM: Artificial Sequence
<220> FEATURE:
<223> OTHER INFORMATION: Synthetic

<400> SEQUENCE: 287
uuguucucau uacuggagcu guuuuagagc uaugcu                              36

<210> SEQ ID NO 288
<211> LENGTH: 36
<212> TYPE: RNA
<213> ORGANISM: Artificial Sequence
<220> FEATURE:
<223> OTHER INFORMATION: Synthetic

<400> SEQUENCE: 288
auuguucuca uuacuggagc guuuuagagc uaugcu                              36

<210> SEQ ID NO 289
<211> LENGTH: 36
<212> TYPE: RNA
<213> ORGANISM: Artificial Sequence
<220> FEATURE:
<223> OTHER INFORMATION: Synthetic

<400> SEQUENCE: 289
ggggagauug uucucauuac guuuuagagc uaugcu                              36

<210> SEQ ID NO 290
<211> LENGTH: 36
<212> TYPE: RNA
<213> ORGANISM: Artificial Sequence
<220> FEATURE:
<223> OTHER INFORMATION: Synthetic

<400> SEQUENCE: 290
```
gaggagaaaa ucguggcug guuuuagagc uaugcu                          36

<210> SEQ ID NO 291
<211> LENGTH: 36
<212> TYPE: RNA
<213> ORGANISM: Artificial Sequence
<220> FEATURE:
<223> OTHER INFORMATION: Synthetic

<400> SEQUENCE: 291
agaggagaaa aucguggcu guuuuagagc uaugcu                          36

<210> SEQ ID NO 292
<211> LENGTH: 36
<212> TYPE: RNA
<213> ORGANISM: Artificial Sequence
<220> FEATURE:
<223> OTHER INFORMATION: Synthetic

<400> SEQUENCE: 292
cagaggagaa aaucguggc guuuuagagc uaugcu                          36

<210> SEQ ID NO 293
<211> LENGTH: 36
<212> TYPE: RNA
<213> ORGANISM: Artificial Sequence
<220> FEATURE:
<223> OTHER INFORMATION: Synthetic

<400> SEQUENCE: 293
uccucagagg agaaaaucug guuuuagagc uaugcu                         36

<210> SEQ ID NO 294
<211> LENGTH: 36
<212> TYPE: RNA
<213> ORGANISM: Artificial Sequence
<220> FEATURE:
<223> OTHER INFORMATION: Synthetic

<400> SEQUENCE: 294
ugaaguuuuu cauuccucag guuuuagagc uaugcu                         36

<210> SEQ ID NO 295
<211> LENGTH: 36
<212> TYPE: RNA
<213> ORGANISM: Artificial Sequence
<220> FEATURE:
<223> OTHER INFORMATION: Synthetic

<400> SEQUENCE: 295
cuucaccaac gacuccaagu guuuuagagc uaugcu                         36

<210> SEQ ID NO 296
<211> LENGTH: 36
<212> TYPE: RNA
<213> ORGANISM: Artificial Sequence
<220> FEATURE:
<223> OTHER INFORMATION: Synthetic

<400> SEQUENCE: 296
cuacuccuac uuggagucgu guuuuagagc uaugcu                         36

<210> SEQ ID NO 297
<211> LENGTH: 36
<212> TYPE: RNA

```
<213> ORGANISM: Artificial Sequence
<220> FEATURE:
<223> OTHER INFORMATION: Synthetic

<400> SEQUENCE: 297
cuccaaguag gaguagauga guuuuagagc uaugcu                                   36

<210> SEQ ID NO 298
<211> LENGTH: 36
<212> TYPE: RNA
<213> ORGANISM: Artificial Sequence
<220> FEATURE:
<223> OTHER INFORMATION: Synthetic

<400> SEQUENCE: 298
caccaucauc uacuccuacu guuuuagagc uaugcu                                   36

<210> SEQ ID NO 299
<211> LENGTH: 36
<212> TYPE: RNA
<213> ORGANISM: Artificial Sequence
<220> FEATURE:
<223> OTHER INFORMATION: Synthetic

<400> SEQUENCE: 299
ugauggugau cagaagcaga guuuuagagc uaugcu                                   36

<210> SEQ ID NO 300
<211> LENGTH: 36
<212> TYPE: RNA
<213> ORGANISM: Artificial Sequence
<220> FEATURE:
<223> OTHER INFORMATION: Synthetic

<400> SEQUENCE: 300
ucagaagcag aaggauuucu guuuuagagc uaugcu                                   36

<210> SEQ ID NO 301
<211> LENGTH: 36
<212> TYPE: RNA
<213> ORGANISM: Artificial Sequence
<220> FEATURE:
<223> OTHER INFORMATION: Synthetic

<400> SEQUENCE: 301
gauuucuagg augauguuca guuuuagagc uaugcu                                   36

<210> SEQ ID NO 302
<211> LENGTH: 36
<212> TYPE: RNA
<213> ORGANISM: Artificial Sequence
<220> FEATURE:
<223> OTHER INFORMATION: Synthetic

<400> SEQUENCE: 302
uugcucuguc cucuuccuuc guuuuagagc uaugcu                                   36

<210> SEQ ID NO 303
<211> LENGTH: 36
<212> TYPE: RNA
<213> ORGANISM: Artificial Sequence
<220> FEATURE:
<223> OTHER INFORMATION: Synthetic

<400> SEQUENCE: 303
aggacugaac cagaaggaag guuuuagagc uaugcu                                   36
```

<210> SEQ ID NO 304
<211> LENGTH: 36
<212> TYPE: RNA
<213> ORGANISM: Artificial Sequence
<220> FEATURE:
<223> OTHER INFORMATION: Synthetic

<400> SEQUENCE: 304
uacacaagga cugaaccaga guuuuagagc uaugcu         36

<210> SEQ ID NO 305
<211> LENGTH: 36
<212> TYPE: RNA
<213> ORGANISM: Artificial Sequence
<220> FEATURE:
<223> OTHER INFORMATION: Synthetic

<400> SEQUENCE: 305
uucaguccuu guguaguccu guuuuagagc uaugcu         36

<210> SEQ ID NO 306
<211> LENGTH: 36
<212> TYPE: RNA
<213> ORGANISM: Artificial Sequence
<220> FEATURE:
<223> OTHER INFORMATION: Synthetic

<400> SEQUENCE: 306
ucaguccuug uguaguccua guuuuagagc uaugcu         36

<210> SEQ ID NO 307
<211> LENGTH: 36
<212> TYPE: RNA
<213> ORGANISM: Artificial Sequence
<220> FEATURE:
<223> OTHER INFORMATION: Synthetic

<400> SEQUENCE: 307
guccuugugu aguccuaggg guuuuagagc uaugcu         36

<210> SEQ ID NO 308
<211> LENGTH: 36
<212> TYPE: RNA
<213> ORGANISM: Artificial Sequence
<220> FEATURE:
<223> OTHER INFORMATION: Synthetic

<400> SEQUENCE: 308
cuuguguagu ccuagggagg guuuuagagc uaugcu         36

<210> SEQ ID NO 309
<211> LENGTH: 36
<212> TYPE: RNA
<213> ORGANISM: Artificial Sequence
<220> FEATURE:
<223> OTHER INFORMATION: Synthetic

<400> SEQUENCE: 309
cuccucccua ggacuacaca guuuuagagc uaugcu         36

<210> SEQ ID NO 310
<211> LENGTH: 36
<212> TYPE: RNA
<213> ORGANISM: Artificial Sequence
<220> FEATURE:

<223> OTHER INFORMATION: Synthetic

<400> SEQUENCE: 310
guagacagua ccuccucccu guuuuagagc uaugcu                              36

<210> SEQ ID NO 311
<211> LENGTH: 36
<212> TYPE: RNA
<213> ORGANISM: Artificial Sequence
<220> FEATURE:
<223> OTHER INFORMATION: Synthetic

<400> SEQUENCE: 311
uacugucuac acagagcucu guuuuagagc uaugcu                              36

<210> SEQ ID NO 312
<211> LENGTH: 36
<212> TYPE: RNA
<213> ORGANISM: Artificial Sequence
<220> FEATURE:
<223> OTHER INFORMATION: Synthetic

<400> SEQUENCE: 312
acugucuaca cagagcucua guuuuagagc uaugcu                              36

<210> SEQ ID NO 313
<211> LENGTH: 36
<212> TYPE: RNA
<213> ORGANISM: Artificial Sequence
<220> FEATURE:
<223> OTHER INFORMATION: Synthetic

<400> SEQUENCE: 313
ucuacacaga gcucuaggga guuuuagagc uaugcu                              36

<210> SEQ ID NO 314
<211> LENGTH: 36
<212> TYPE: RNA
<213> ORGANISM: Artificial Sequence
<220> FEATURE:
<223> OTHER INFORMATION: Synthetic

<400> SEQUENCE: 314
cuacacagag cucuagggaa guuuuagagc uaugcu                              36

<210> SEQ ID NO 315
<211> LENGTH: 36
<212> TYPE: RNA
<213> ORGANISM: Artificial Sequence
<220> FEATURE:
<223> OTHER INFORMATION: Synthetic

<400> SEQUENCE: 315
uacacagagc ucuagggaag guuuuagagc uaugcu                              36

<210> SEQ ID NO 316
<211> LENGTH: 36
<212> TYPE: RNA
<213> ORGANISM: Artificial Sequence
<220> FEATURE:
<223> OTHER INFORMATION: Synthetic

<400> SEQUENCE: 316
gggguguguu caguuguuaa guuuuagagc uaugcu                              36

```
<210> SEQ ID NO 317
<211> LENGTH: 36
<212> TYPE: RNA
<213> ORGANISM: Artificial Sequence
<220> FEATURE:
<223> OTHER INFORMATION: Synthetic

<400> SEQUENCE: 317
gggugugccc aguuguuaau guuuuagagc uaugcu                              36

<210> SEQ ID NO 318
<211> LENGTH: 36
<212> TYPE: RNA
<213> ORGANISM: Artificial Sequence
<220> FEATURE:
<223> OTHER INFORMATION: Synthetic

<400> SEQUENCE: 318
ugguaguccc auuaacaacu guuuuagagc uaugcu                              36

<210> SEQ ID NO 319
<211> LENGTH: 36
<212> TYPE: RNA
<213> ORGANISM: Artificial Sequence
<220> FEATURE:
<223> OTHER INFORMATION: Synthetic

<400> SEQUENCE: 319
cugguagucc cauuaacaac guuuuagagc uaugcu                              36

<210> SEQ ID NO 320
<211> LENGTH: 36
<212> TYPE: RNA
<213> ORGANISM: Artificial Sequence
<220> FEATURE:
<223> OTHER INFORMATION: Synthetic

<400> SEQUENCE: 320
uuguuaaugg gacuaccaga guuuuagagc uaugcu                              36

<210> SEQ ID NO 321
<211> LENGTH: 36
<212> TYPE: RNA
<213> ORGANISM: Artificial Sequence
<220> FEATURE:
<223> OTHER INFORMATION: Synthetic

<400> SEQUENCE: 321
uaccagaugg aagccagcuu guuuuagagc uaugcu                              36

<210> SEQ ID NO 322
<211> LENGTH: 36
<212> TYPE: RNA
<213> ORGANISM: Artificial Sequence
<220> FEATURE:
<223> OTHER INFORMATION: Synthetic

<400> SEQUENCE: 322
uuccaaagcu ggcuuccauc guuuuagagc uaugcu                              36

<210> SEQ ID NO 323
<211> LENGTH: 36
<212> TYPE: RNA
<213> ORGANISM: Artificial Sequence
<220> FEATURE:
<223> OTHER INFORMATION: Synthetic
```

-continued

```
<400> SEQUENCE: 323
uggaagccag cuuuggaagc guuuuagagc uaugcu                           36

<210> SEQ ID NO 324
<211> LENGTH: 36
<212> TYPE: RNA
<213> ORGANISM: Artificial Sequence
<220> FEATURE:
<223> OTHER INFORMATION: Synthetic

<400> SEQUENCE: 324
acaaggccug cuuccaaagc guuuuagagc uaugcu                           36

<210> SEQ ID NO 325
<211> LENGTH: 36
<212> TYPE: RNA
<213> ORGANISM: Artificial Sequence
<220> FEATURE:
<223> OTHER INFORMATION: Synthetic

<400> SEQUENCE: 325
gccuuguuca cguguucuaa guuuuagagc uaugcu                           36

<210> SEQ ID NO 326
<211> LENGTH: 36
<212> TYPE: RNA
<213> ORGANISM: Artificial Sequence
<220> FEATURE:
<223> OTHER INFORMATION: Synthetic

<400> SEQUENCE: 326 ccuguucac guguucuaau guuuuagagc uaugcu                            36

<210> SEQ ID NO 327
<211> LENGTH: 36
<212> TYPE: RNA
<213> ORGANISM: Artificial Sequence
<220> FEATURE:
<223> OTHER INFORMATION: Synthetic

<400> SEQUENCE: 327
cccauuagaa cacgugaaca guuuuagagc uaugcu                           36

<210> SEQ ID NO 328
<211> LENGTH: 36
<212> TYPE: RNA
<213> ORGANISM: Artificial Sequence
<220> FEATURE:
<223> OTHER INFORMATION: Synthetic

<400> SEQUENCE: 328
uuggcaucac uucauauuug guuuuagagc uaugcu                           36

<210> SEQ ID NO 329
<211> LENGTH: 36
<212> TYPE: RNA
<213> ORGANISM: Artificial Sequence
<220> FEATURE:
<223> OTHER INFORMATION: Synthetic

<400> SEQUENCE: 329
cuugugcucu uggcaucacu guuuuagagc uaugcu                           36

<210> SEQ ID NO 330
<211> LENGTH: 36
```

```
<212> TYPE: RNA
<213> ORGANISM: Artificial Sequence
<220> FEATURE:
<223> OTHER INFORMATION: Synthetic

<400> SEQUENCE: 330
agcacacucu cuugugcucu guuuuagagc uaugcu                                   36

<210> SEQ ID NO 331
<211> LENGTH: 36
<212> TYPE: RNA
<213> ORGANISM: Artificial Sequence
<220> FEATURE:
<223> OTHER INFORMATION: Synthetic

<400> SEQUENCE: 331
gcacaagaga gugugcucuc guuuuagagc uaugcu                                   36

<210> SEQ ID NO 332
<211> LENGTH: 36
<212> TYPE: RNA
<213> ORGANISM: Artificial Sequence
<220> FEATURE:
<223> OTHER INFORMATION: Synthetic

<400> SEQUENCE: 332
gcuuaaucuc acacauagaa guuuuagagc uaugcu                                   36

<210> SEQ ID NO 333
<211> LENGTH: 36
<212> TYPE: RNA
<213> ORGANISM: Artificial Sequence
<220> FEATURE:
<223> OTHER INFORMATION: Synthetic

<400> SEQUENCE: 333
cuuaaucuca cacauagaaa guuuuagagc uaugcu                                   36

<210> SEQ ID NO 334
<211> LENGTH: 36
<212> TYPE: RNA
<213> ORGANISM: Artificial Sequence
<220> FEATURE:
<223> OTHER INFORMATION: Synthetic

<400> SEQUENCE: 334
uuaaucucac acauagaaag guuuuagagc uaugcu                                   36

<210> SEQ ID NO 335
<211> LENGTH: 36
<212> TYPE: RNA
<213> ORGANISM: Artificial Sequence
<220> FEATURE:
<223> OTHER INFORMATION: Synthetic

<400> SEQUENCE: 335
aggagugcug guuuaucaac guuuuagagc uaugcu                                   36

<210> SEQ ID NO 336
<211> LENGTH: 36
<212> TYPE: RNA
<213> ORGANISM: Artificial Sequence
<220> FEATURE:
<223> OTHER INFORMATION: Synthetic

<400> SEQUENCE: 336
```
uucuuugaca gcaggagugc guuuuagagc uaugcu                                    36

<210> SEQ ID NO 337
<211> LENGTH: 36
<212> TYPE: RNA
<213> ORGANISM: Artificial Sequence
<220> FEATURE:
<223> OTHER INFORMATION: Synthetic

<400> SEQUENCE: 337
acucugguuu cuuugacagc guuuuagagc uaugcu                                    36

<210> SEQ ID NO 338
<211> LENGTH: 36
<212> TYPE: RNA
<213> ORGANISM: Artificial Sequence
<220> FEATURE:
<223> OTHER INFORMATION: Synthetic

<400> SEQUENCE: 338
accagaguug agaaaacccc guuuuagagc uaugcu                                    36

<210> SEQ ID NO 339
<211> LENGTH: 36
<212> TYPE: RNA
<213> ORGANISM: Artificial Sequence
<220> FEATURE:
<223> OTHER INFORMATION: Synthetic

<400> SEQUENCE: 339 uccaggguu uucucaacuc guuuuagagc uaugcu                                     36

<210> SEQ ID NO 340
<211> LENGTH: 36
<212> TYPE: RNA
<213> ORGANISM: Artificial Sequence
<220> FEATURE:
<223> OTHER INFORMATION: Synthetic

<400> SEQUENCE: 340
caguuauuaa augaauccag guuuuagagc uaugcu                                    36

<210> SEQ ID NO 341
<211> LENGTH: 36
<212> TYPE: RNA
<213> ORGANISM: Artificial Sequence
<220> FEATURE:
<223> OTHER INFORMATION: Synthetic

<400> SEQUENCE: 341
gcaguuauua aaugaaucca guuuuagagc uaugcu                                    36

<210> SEQ ID NO 342
<211> LENGTH: 36
<212> TYPE: RNA
<213> ORGANISM: Artificial Sequence
<220> FEATURE:
<223> OTHER INFORMATION: Synthetic

<400> SEQUENCE: 342
ggcaguuauu aaaugaaucc guuuuagagc uaugcu                                    36

<210> SEQ ID NO 343
<211> LENGTH: 36
<212> TYPE: RNA
<213> ORGANISM: Artificial Sequence
<220> FEATURE:
<223> OTHER INFORMATION: Synthetic

<400> SEQUENCE: 343
uggaugguaa cagcuacauc guuuuagagc uaugcu         36

<210> SEQ ID NO 344
<211> LENGTH: 36
<212> TYPE: RNA
<213> ORGANISM: Artificial Sequence
<220> FEATURE:
<223> OTHER INFORMATION: Synthetic

<400> SEQUENCE: 344
gcuguuacca uccacauccu guuuuagagc uaugcu         36

<210> SEQ ID NO 345
<211> LENGTH: 36
<212> TYPE: RNA
<213> ORGANISM: Artificial Sequence
<220> FEATURE:
<223> OTHER INFORMATION: Synthetic

<400> SEQUENCE: 345
ucaagaacca aggaugugga guuuuagagc uaugcu         36

<210> SEQ ID NO 346
<211> LENGTH: 36
<212> TYPE: RNA
<213> ORGANISM: Artificial Sequence
<220> FEATURE:
<223> OTHER INFORMATION: Synthetic

<400> SEQUENCE: 346
uccuucaaga accaaggaug guuuuagagc uaugcu         36

<210> SEQ ID NO 347
<211> LENGTH: 36
<212> TYPE: RNA
<213> ORGANISM: Artificial Sequence
<220> FEATURE:
<223> OTHER INFORMATION: Synthetic

<400> SEQUENCE: 347
ugaguguccu ucaagaacca guuuuagagc uaugcu         36

<210> SEQ ID NO 348
<211> LENGTH: 36
<212> TYPE: RNA
<213> ORGANISM: Artificial Sequence
<220> FEATURE:
<223> OTHER INFORMATION: Synthetic

<400> SEQUENCE: 348
uuuuauuuua uaacuacaag guuuuagagc uaugcu         36

<210> SEQ ID NO 349
<211> LENGTH: 36
<212> TYPE: RNA
<213> ORGANISM: Artificial Sequence
<220> FEATURE:
<223> OTHER INFORMATION: Synthetic

<400> SEQUENCE: 349
uuguuuuuaa uaaaaacaag guuuuagagc uaugcu         36

<210> SEQ ID NO 350
<211> LENGTH: 36
<212> TYPE: RNA
<213> ORGANISM: Artificial Sequence
<220> FEATURE:
<223> OTHER INFORMATION: Synthetic

<400> SEQUENCE: 350
uauuauagaa ugcuuuugca guuuuagagc uaugcu                                    36

<210> SEQ ID NO 351
<211> LENGTH: 36
<212> TYPE: RNA
<213> ORGANISM: Artificial Sequence
<220> FEATURE:
<223> OTHER INFORMATION: Synthetic

<400> SEQUENCE: 351
caagauuagu cuugauguag guuuuagagc uaugcu                                    36

<210> SEQ ID NO 352
<211> LENGTH: 36
<212> TYPE: RNA
<213> ORGANISM: Artificial Sequence
<220> FEATURE:
<223> OTHER INFORMATION: Synthetic

<400> SEQUENCE: 352
aagauuaguc uugauguagu guuuuagagc uaugcu                                    36

<210> SEQ ID NO 353
<211> LENGTH: 36
<212> TYPE: RNA
<213> ORGANISM: Artificial Sequence
<220> FEATURE:
<223> OTHER INFORMATION: Synthetic

<400> SEQUENCE: 353
agucuugaug uagugggagu guuuuagagc uaugcu                                    36

<210> SEQ ID NO 354
<211> LENGTH: 36
<212> TYPE: RNA
<213> ORGANISM: Artificial Sequence
<220> FEATURE:
<223> OTHER INFORMATION: Synthetic

<400> SEQUENCE: 354
uuuuucuauu aaaaaaaaaa guuuuagagc uaugcu                                    36

<210> SEQ ID NO 355
<211> LENGTH: 36
<212> TYPE: RNA
<213> ORGANISM: Artificial Sequence
<220> FEATURE:
<223> OTHER INFORMATION: Synthetic

<400> SEQUENCE: 355
ucuauuaaaa aaaaaaggc guuuuagagc uaugcu                                     36

<210> SEQ ID NO 356
<211> LENGTH: 36
<212> TYPE: RNA
<213> ORGANISM: Artificial Sequence
<220> FEATURE:
<223> OTHER INFORMATION: Synthetic

```
<400> SEQUENCE: 356
cuauuaaaaa aaaaaaggcu guuuuagagc uaugcu                                  36

<210> SEQ ID NO 357
<211> LENGTH: 36
<212> TYPE: RNA
<213> ORGANISM: Artificial Sequence
<220> FEATURE:
<223> OTHER INFORMATION: Synthetic

<400> SEQUENCE: 357
aaaaaaaaaa aggcugggca guuuuagagc uaugcu                                  36

<210> SEQ ID NO 358
<211> LENGTH: 36
<212> TYPE: RNA
<213> ORGANISM: Artificial Sequence
<220> FEATURE:
<223> OTHER INFORMATION: Synthetic

<400> SEQUENCE: 358
aaaaaaaagg cugggcacgg guuuuagagc uaugcu                                  36

<210> SEQ ID NO 359
<211> LENGTH: 36
<212> TYPE: RNA
<213> ORGANISM: Artificial Sequence
<220> FEATURE:
<223> OTHER INFORMATION: Synthetic

<400> SEQUENCE: 359
cacccguaau cccagcacuu guuuuagagc uaugcu                                  36

<210> SEQ ID NO 360
<211> LENGTH: 36
<212> TYPE: RNA
<213> ORGANISM: Artificial Sequence
<220> FEATURE:
<223> OTHER INFORMATION: Synthetic

<400> SEQUENCE: 360
acccguaauc ccagcacuuu guuuuagagc uaugcu                                  36

<210> SEQ ID NO 361
<211> LENGTH: 36
<212> TYPE: RNA
<213> ORGANISM: Artificial Sequence
<220> FEATURE:
<223> OTHER INFORMATION: Synthetic

<400> SEQUENCE: 361
cguaauccca gcacuuuggg guuuuagagc uaugcu                                  36

<210> SEQ ID NO 362
<211> LENGTH: 36
<212> TYPE: RNA
<213> ORGANISM: Artificial Sequence
<220> FEATURE:
<223> OTHER INFORMATION: Synthetic

<400> SEQUENCE: 362
ucccaaagug cugggauuac guuuuagagc uaugcu                                  36

<210> SEQ ID NO 363
```

```
<211> LENGTH: 36
<212> TYPE: RNA
<213> ORGANISM: Artificial Sequence
<220> FEATURE:
<223> OTHER INFORMATION: Synthetic

<400> SEQUENCE: 363
cucccaaagu gcugggauua guuuuagagc uaugcu                              36

<210> SEQ ID NO 364
<211> LENGTH: 36
<212> TYPE: RNA
<213> ORGANISM: Artificial Sequence
<220> FEATURE:
<223> OTHER INFORMATION: Synthetic

<400> SEQUENCE: 364
cccagcacuu ugggaggccg guuuuagagc uaugcu                              36

<210> SEQ ID NO 365
<211> LENGTH: 36
<212> TYPE: RNA
<213> ORGANISM: Artificial Sequence
<220> FEATURE:
<223> OTHER INFORMATION: Synthetic

<400> SEQUENCE: 365
ccucggccuc ccaaagugcu guuuuagagc uaugcu                              36

<210> SEQ ID NO 366
<211> LENGTH: 36
<212> TYPE: RNA
<213> ORGANISM: Artificial Sequence
<220> FEATURE:
<223> OTHER INFORMATION: Synthetic

<400> SEQUENCE: 366
gcacuuuggg aggccgaggc guuuuagagc uaugcu                              36

<210> SEQ ID NO 367
<211> LENGTH: 36
<212> TYPE: RNA
<213> ORGANISM: Artificial Sequence
<220> FEATURE:
<223> OTHER INFORMATION: Synthetic

<400> SEQUENCE: 367
cuuugggagg ccgaggcagg guuuuagagc uaugcu                              36

<210> SEQ ID NO 368
<211> LENGTH: 36
<212> TYPE: RNA
<213> ORGANISM: Artificial Sequence
<220> FEATURE:
<223> OTHER INFORMATION: Synthetic

<400> SEQUENCE: 368
gccgaggcag guggaucacg guuuuagagc uaugcu                              36

<210> SEQ ID NO 369
<211> LENGTH: 36
<212> TYPE: RNA
<213> ORGANISM: Artificial Sequence
<220> FEATURE:
<223> OTHER INFORMATION: Synthetic

<400> SEQUENCE: 369
```
accucgugau ccaccugccu guuuuagagc uaugcu         36

<210> SEQ ID NO 370
<211> LENGTH: 36
<212> TYPE: RNA
<213> ORGANISM: Artificial Sequence
<220> FEATURE:
<223> OTHER INFORMATION: Synthetic

<400> SEQUENCE: 370
ggcaggugga ucacgagguc guuuuagagc uaugcu         36

<210> SEQ ID NO 371
<211> LENGTH: 36
<212> TYPE: RNA
<213> ORGANISM: Artificial Sequence
<220> FEATURE:
<223> OTHER INFORMATION: Synthetic

<400> SEQUENCE: 371
ucaggagauc gagaccaucu guuuuagagc uaugcu         36

<210> SEQ ID NO 372
<211> LENGTH: 36
<212> TYPE: RNA
<213> ORGANISM: Artificial Sequence
<220> FEATURE:
<223> OTHER INFORMATION: Synthetic

<400> SEQUENCE: 372
cgagaccauc uuggcuaaca guuuuagagc uaugcu         36

<210> SEQ ID NO 373
<211> LENGTH: 36
<212> TYPE: RNA
<213> ORGANISM: Artificial Sequence
<220> FEATURE:
<223> OTHER INFORMATION: Synthetic

<400> SEQUENCE: 373
uuucaccaug uuagccaaga guuuuagagc uaugcu         36

<210> SEQ ID NO 374
<211> LENGTH: 36
<212> TYPE: RNA
<213> ORGANISM: Artificial Sequence
<220> FEATURE:
<223> OTHER INFORMATION: Synthetic

<400> SEQUENCE: 374
uuguauuuuu uguagagacg guuuuagagc uaugcu         36

<210> SEQ ID NO 375
<211> LENGTH: 36
<212> TYPE: RNA
<213> ORGANISM: Artificial Sequence
<220> FEATURE:
<223> OTHER INFORMATION: Synthetic

<400> SEQUENCE: 375
uuuguauuuu uuguagagac guuuuagagc uaugcu         36

<210> SEQ ID NO 376
<211> LENGTH: 36
<212> TYPE: RNA

```
<213> ORGANISM: Artificial Sequence
<220> FEATURE:
<223> OTHER INFORMATION: Synthetic

<400> SEQUENCE: 376
uuuuguauuu uuguagaga guuuuagagc uaugcu                           36

<210> SEQ ID NO 377
<211> LENGTH: 36
<212> TYPE: RNA
<213> ORGANISM: Artificial Sequence
<220> FEATURE:
<223> OTHER INFORMATION: Synthetic

<400> SEQUENCE: 377
aaaaaauaca aaaaauuagc guuuuagagc uaugcu                          36

<210> SEQ ID NO 378
<211> LENGTH: 36
<212> TYPE: RNA
<213> ORGANISM: Artificial Sequence
<220> FEATURE:
<223> OTHER INFORMATION: Synthetic

<400> SEQUENCE: 378
aaaaauacaa aaauuagcc guuuuagagc uaugcu                           36

<210> SEQ ID NO 379
<211> LENGTH: 36
<212> TYPE: RNA
<213> ORGANISM: Artificial Sequence
<220> FEATURE:
<223> OTHER INFORMATION: Synthetic

<400> SEQUENCE: 379
uacaaaaaau uagccgggug guuuuagagc uaugcu                          36

<210> SEQ ID NO 380
<211> LENGTH: 36
<212> TYPE: RNA
<213> ORGANISM: Artificial Sequence
<220> FEATURE:
<223> OTHER INFORMATION: Synthetic

<400> SEQUENCE: 380
aaaaaauuag ccggguguhg guuuuagagc uaugcu                          36

<210> SEQ ID NO 381
<211> LENGTH: 36
<212> TYPE: RNA
<213> ORGANISM: Artificial Sequence
<220> FEATURE:
<223> OTHER INFORMATION: Synthetic

<400> SEQUENCE: 381
aaauuagccg ggguggugg guuuuagagc uaugcu                           36

<210> SEQ ID NO 382
<211> LENGTH: 36
<212> TYPE: RNA
<213> ORGANISM: Artificial Sequence
<220> FEATURE:
<223> OTHER INFORMATION: Synthetic

<400> SEQUENCE: 382
aauuagccgg gugugguggc guuuuagagc uaugcu                          36
```

<210> SEQ ID NO 383
<211> LENGTH: 36
<212> TYPE: RNA
<213> ORGANISM: Artificial Sequence
<220> FEATURE:
<223> OTHER INFORMATION: Synthetic

<400> SEQUENCE: 383
caggcgcccg ccaccacacc guuuuagagc uaugcu                                    36

<210> SEQ ID NO 384
<211> LENGTH: 36
<212> TYPE: RNA
<213> ORGANISM: Artificial Sequence
<220> FEATURE:
<223> OTHER INFORMATION: Synthetic

<400> SEQUENCE: 384
gccuguaguc ccagcuacuc guuuuagagc uaugcu                                    36

<210> SEQ ID NO 385
<211> LENGTH: 36
<212> TYPE: RNA
<213> ORGANISM: Artificial Sequence
<220> FEATURE:
<223> OTHER INFORMATION: Synthetic

<400> SEQUENCE: 385
uguaguccca gcuacucagg guuuuagagc uaugcu                                    36

<210> SEQ ID NO 386
<211> LENGTH: 36
<212> TYPE: RNA
<213> ORGANISM: Artificial Sequence
<220> FEATURE:
<223> OTHER INFORMATION: Synthetic

<400> SEQUENCE: 386
uccugaguag cugggacuac guuuuagagc uaugcu                                    36

<210> SEQ ID NO 387
<211> LENGTH: 36
<212> TYPE: RNA
<213> ORGANISM: Artificial Sequence
<220> FEATURE:
<223> OTHER INFORMATION: Synthetic

<400> SEQUENCE: 387
cccagcuacu caggaggcug guuuuagagc uaugcu                                    36

<210> SEQ ID NO 388
<211> LENGTH: 36
<212> TYPE: RNA
<213> ORGANISM: Artificial Sequence
<220> FEATURE:
<223> OTHER INFORMATION: Synthetic

<400> SEQUENCE: 388
ccucagccuc cugaguagcu guuuuagagc uaugcu                                    36

<210> SEQ ID NO 389
<211> LENGTH: 36
<212> TYPE: RNA
<213> ORGANISM: Artificial Sequence
<220> FEATURE:

<223> OTHER INFORMATION: Synthetic

<400> SEQUENCE: 389
gccucagccu ccugaguagc guuuuagagc uaugcu                36

<210> SEQ ID NO 390
<211> LENGTH: 36
<212> TYPE: RNA
<213> ORGANISM: Artificial Sequence
<220> FEATURE:
<223> OTHER INFORMATION: Synthetic

<400> SEQUENCE: 390
aggaggcuga ggcaggagaa guuuuagagc uaugcu                36

<210> SEQ ID NO 391
<211> LENGTH: 36
<212> TYPE: RNA
<213> ORGANISM: Artificial Sequence
<220> FEATURE:
<223> OTHER INFORMATION: Synthetic

<400> SEQUENCE: 391
gcaggagaau ggcgugaacc guuuuagagc uaugcu                36

<210> SEQ ID NO 392
<211> LENGTH: 36
<212> TYPE: RNA
<213> ORGANISM: Artificial Sequence
<220> FEATURE:
<223> OTHER INFORMATION: Synthetic

<400> SEQUENCE: 392
caggagaaug gcgugaaccc guuuuagagc uaugcu                36

<210> SEQ ID NO 393
<211> LENGTH: 36
<212> TYPE: RNA
<213> ORGANISM: Artificial Sequence
<220> FEATURE:
<223> OTHER INFORMATION: Synthetic

<400> SEQUENCE: 393
gagaauggcg ugaacccggg guuuuagagc uaugcu                36

<210> SEQ ID NO 394
<211> LENGTH: 36
<212> TYPE: RNA
<213> ORGANISM: Artificial Sequence
<220> FEATURE:
<223> OTHER INFORMATION: Synthetic

<400> SEQUENCE: 394
aauggcguga acccgggagg guuuuagagc uaugcu                36

<210> SEQ ID NO 395
<211> LENGTH: 36
<212> TYPE: RNA
<213> ORGANISM: Artificial Sequence
<220> FEATURE:
<223> OTHER INFORMATION: Synthetic

<400> SEQUENCE: 395
cacugcaagc uccaccuccc guuuuagagc uaugcu                36

```
<210> SEQ ID NO 396
<211> LENGTH: 36
<212> TYPE: RNA
<213> ORGANISM: Artificial Sequence
<220> FEATURE:
<223> OTHER INFORMATION: Synthetic

<400> SEQUENCE: 396
ucacugcaag cuccaccucc guuuuagagc uaugcu                                 36

<210> SEQ ID NO 397
<211> LENGTH: 36
<212> TYPE: RNA
<213> ORGANISM: Artificial Sequence
<220> FEATURE:
<223> OTHER INFORMATION: Synthetic

<400> SEQUENCE: 397
cauaccacug cacuccagcc guuuuagagc uaugcu                                 36

<210> SEQ ID NO 398
<211> LENGTH: 36
<212> TYPE: RNA
<213> ORGANISM: Artificial Sequence
<220> FEATURE:
<223> OTHER INFORMATION: Synthetic

<400> SEQUENCE: 398
auaccacugc acuccagccu guuuuagagc uaugcu                                 36

<210> SEQ ID NO 399
<211> LENGTH: 36
<212> TYPE: RNA
<213> ORGANISM: Artificial Sequence
<220> FEATURE:
<223> OTHER INFORMATION: Synthetic

<400> SEQUENCE: 399
ucgcccaggc uggagugcag guuuuagagc uaugcu                                 36

<210> SEQ ID NO 400
<211> LENGTH: 36
<212> TYPE: RNA
<213> ORGANISM: Artificial Sequence
<220> FEATURE:
<223> OTHER INFORMATION: Synthetic

<400> SEQUENCE: 400
ucucacucuu ucgcccaggc guuuuagagc uaugcu                                 36

<210> SEQ ID NO 401
<211> LENGTH: 36
<212> TYPE: RNA
<213> ORGANISM: Artificial Sequence
<220> FEATURE:
<223> OTHER INFORMATION: Synthetic

<400> SEQUENCE: 401
ggagucucac ucuuucgccc guuuuagagc uaugcu                                 36

<210> SEQ ID NO 402
<211> LENGTH: 36
<212> TYPE: RNA
<213> ORGANISM: Artificial Sequence
<220> FEATURE:
<223> OTHER INFORMATION: Synthetic
```

```
<400> SEQUENCE: 402
uguuuuuugu uuuuuugaga guuuuagagc uaugcu                               36

<210> SEQ ID NO 403
<211> LENGTH: 36
<212> TYPE: RNA
<213> ORGANISM: Artificial Sequence
<220> FEATURE:
<223> OTHER INFORMATION: Synthetic

<400> SEQUENCE: 403
aggaagaaag aaagguuuuu guuuuagagc uaugcu                               36

<210> SEQ ID NO 404
<211> LENGTH: 36
<212> TYPE: RNA
<213> ORGANISM: Artificial Sequence
<220> FEATURE:
<223> OTHER INFORMATION: Synthetic

<400> SEQUENCE: 404
agaagaaaag gaagaaagaa guuuuagagc uaugcu                               36

<210> SEQ ID NO 405
<211> LENGTH: 36
<212> TYPE: RNA
<213> ORGANISM: Artificial Sequence
<220> FEATURE:
<223> OTHER INFORMATION: Synthetic

<400> SEQUENCE: 405
cuuucuuccu uuucuucucu guuuuagagc uaugcu                               36

<210> SEQ ID NO 406
<211> LENGTH: 36
<212> TYPE: RNA
<213> ORGANISM: Artificial Sequence
<220> FEATURE:
<223> OTHER INFORMATION: Synthetic

<400> SEQUENCE: 406
uuucuuccuu uucuucucuu guuuuagagc uaugcu                               36

<210> SEQ ID NO 407
<211> LENGTH: 36
<212> TYPE: RNA
<213> ORGANISM: Artificial Sequence
<220> FEATURE:
<223> OTHER INFORMATION: Synthetic

<400> SEQUENCE: 407
aauggaccca agagaagaaa guuuuagagc uaugcu                               36

<210> SEQ ID NO 408
<211> LENGTH: 36
<212> TYPE: RNA
<213> ORGANISM: Artificial Sequence
<220> FEATURE:
<223> OTHER INFORMATION: Synthetic

<400> SEQUENCE: 408
ggcuauuaca uaagaaacaa guuuuagagc uaugcu                               36

<210> SEQ ID NO 409
<211> LENGTH: 36
```

```
<212> TYPE: RNA
<213> ORGANISM: Artificial Sequence
<220> FEATURE:
<223> OTHER INFORMATION: Synthetic

<400> SEQUENCE: 409
cacaggaaaa ggaacuguac guuuuagagc uaugcu                                 36

<210> SEQ ID NO 410
<211> LENGTH: 36
<212> TYPE: RNA
<213> ORGANISM: Artificial Sequence
<220> FEATURE:
<223> OTHER INFORMATION: Synthetic

<400> SEQUENCE: 410
auuaaagcua acacaggaaa guuuuagagc uaugcu                                 36

<210> SEQ ID NO 411
<211> LENGTH: 36
<212> TYPE: RNA
<213> ORGANISM: Artificial Sequence
<220> FEATURE:
<223> OTHER INFORMATION: Synthetic

<400> SEQUENCE: 411
ucaaaaauua aagcuaacac guuuuagagc uaugcu                                 36

<210> SEQ ID NO 412
<211> LENGTH: 36
<212> TYPE: RNA
<213> ORGANISM: Artificial Sequence
<220> FEATURE:
<223> OTHER INFORMATION: Synthetic

<400> SEQUENCE: 412
uaaaauuguc uaaacaucuc guuuuagagc uaugcu                                 36

<210> SEQ ID NO 413
<211> LENGTH: 36
<212> TYPE: RNA
<213> ORGANISM: Artificial Sequence
<220> FEATURE:
<223> OTHER INFORMATION: Synthetic

<400> SEQUENCE: 413
agagauguuu agacaauuuu guuuuagagc uaugcu                                 36

<210> SEQ ID NO 414
<211> LENGTH: 36
<212> TYPE: RNA
<213> ORGANISM: Artificial Sequence
<220> FEATURE:
<223> OTHER INFORMATION: Synthetic

<400> SEQUENCE: 414
ucuaaacauc ucugggacca guuuuagagc uaugcu                                 36

<210> SEQ ID NO 415
<211> LENGTH: 36
<212> TYPE: RNA
<213> ORGANISM: Artificial Sequence
<220> FEATURE:
<223> OTHER INFORMATION: Synthetic

<400> SEQUENCE: 415
```
uuuaugcuuu cauauauccu guuuuagagc uaugcu 36

<210> SEQ ID NO 416
<211> LENGTH: 36
<212> TYPE: RNA
<213> ORGANISM: Artificial Sequence
<220> FEATURE:
<223> OTHER INFORMATION: Synthetic

<400> SEQUENCE: 416
agcauaaauu acaaagaaaa guuuuagagc uaugcu 36

<210> SEQ ID NO 417
<211> LENGTH: 36
<212> TYPE: RNA
<213> ORGANISM: Artificial Sequence
<220> FEATURE:
<223> OTHER INFORMATION: Synthetic

<400> SEQUENCE: 417
uacaaagaaa aagguuauca guuuuagagc uaugcu 36

<210> SEQ ID NO 418
<211> LENGTH: 36
<212> TYPE: RNA
<213> ORGANISM: Artificial Sequence
<220> FEATURE:
<223> OTHER INFORMATION: Synthetic

<400> SEQUENCE: 418
acaaagaaaa agguuaucau guuuuagagc uaugcu 36

<210> SEQ ID NO 419
<211> LENGTH: 36
<212> TYPE: RNA
<213> ORGANISM: Artificial Sequence
<220> FEATURE:
<223> OTHER INFORMATION: Synthetic

<400> SEQUENCE: 419
caaagaaaaa gguuaucaug guuuuagagc uaugcu 36

<210> SEQ ID NO 420
<211> LENGTH: 36
<212> TYPE: RNA
<213> ORGANISM: Artificial Sequence
<220> FEATURE:
<223> OTHER INFORMATION: Synthetic

<400> SEQUENCE: 420
ucugagauuu aaaauagagu guuuuagagc uaugcu 36

<210> SEQ ID NO 421
<211> LENGTH: 36
<212> TYPE: RNA
<213> ORGANISM: Artificial Sequence
<220> FEATURE:
<223> OTHER INFORMATION: Synthetic

<400> SEQUENCE: 421
cuuauaagau acauuaugaa guuuuagagc uaugcu 36

<210> SEQ ID NO 422
<211> LENGTH: 36
<212> TYPE: RNA
<213> ORGANISM: Artificial Sequence

```
<220> FEATURE:
<223> OTHER INFORMATION: Synthetic

<400> SEQUENCE: 422
uaucuuauaa gacuauaaaa guuuuagagc uaugcu                                    36

<210> SEQ ID NO 423
<211> LENGTH: 36
<212> TYPE: RNA
<213> ORGANISM: Artificial Sequence
<220> FEATURE:
<223> OTHER INFORMATION: Synthetic

<400> SEQUENCE: 423
aucuuauaag acuauaaaaa guuuuagagc uaugcu                                    36

<210> SEQ ID NO 424
<211> LENGTH: 36
<212> TYPE: RNA
<213> ORGANISM: Artificial Sequence
<220> FEATURE:
<223> OTHER INFORMATION: Synthetic

<400> SEQUENCE: 424
uuauaagacu auaaaaaggg guuuuagagc uaugcu                                    36

<210> SEQ ID NO 425
<211> LENGTH: 36
<212> TYPE: RNA
<213> ORGANISM: Artificial Sequence
<220> FEATURE:
<223> OTHER INFORMATION: Synthetic

<400> SEQUENCE: 425
uaaaaaggga ggaaauauag guuuuagagc uaugcu                                    36

<210> SEQ ID NO 426
<211> LENGTH: 36
<212> TYPE: RNA
<213> ORGANISM: Artificial Sequence
<220> FEATURE:
<223> OTHER INFORMATION: Synthetic

<400> SEQUENCE: 426
aaaaagggag gaaauauaga guuuuagagc uaugcu                                    36

<210> SEQ ID NO 427
<211> LENGTH: 36
<212> TYPE: RNA
<213> ORGANISM: Artificial Sequence
<220> FEATURE:
<223> OTHER INFORMATION: Synthetic

<400> SEQUENCE: 427
aaauauagag gguccacuuu guuuuagagc uaugcu                                    36

<210> SEQ ID NO 428
<211> LENGTH: 36
<212> TYPE: RNA
<213> ORGANISM: Artificial Sequence
<220> FEATURE:
<223> OTHER INFORMATION: Synthetic

<400> SEQUENCE: 428
uauagagggu ccacuuuugg guuuuagagc uaugcu                                    36
```

<210> SEQ ID NO 429
<211> LENGTH: 36
<212> TYPE: RNA
<213> ORGANISM: Artificial Sequence
<220> FEATURE:
<223> OTHER INFORMATION: Synthetic

<400> SEQUENCE: 429
acucugaagu ccaccaaaag guuuuagagc uaugcu                         36

<210> SEQ ID NO 430
<211> LENGTH: 36
<212> TYPE: RNA
<213> ORGANISM: Artificial Sequence
<220> FEATURE:
<223> OTHER INFORMATION: Synthetic

<400> SEQUENCE: 430
agaauagagu ugcaccguuu guuuuagagc uaugcu                         36

<210> SEQ ID NO 431
<211> LENGTH: 36
<212> TYPE: RNA
<213> ORGANISM: Artificial Sequence
<220> FEATURE:
<223> OTHER INFORMATION: Synthetic

<400> SEQUENCE: 431
aaaacggugc aacucuauuc guuuuagagc uaugcu                         36

<210> SEQ ID NO 432
<211> LENGTH: 36
<212> TYPE: RNA
<213> ORGANISM: Artificial Sequence
<220> FEATURE:
<223> OTHER INFORMATION: Synthetic

<400> SEQUENCE: 432
ccguuuuggg cuaaugaaaa guuuuagagc uaugcu                         36

<210> SEQ ID NO 433
<211> LENGTH: 36
<212> TYPE: RNA
<213> ORGANISM: Artificial Sequence
<220> FEATURE:
<223> OTHER INFORMATION: Synthetic

<400> SEQUENCE: 433
ccuuuuucau uagcccaaaa guuuuagagc uaugcu                         36

<210> SEQ ID NO 434
<211> LENGTH: 36
<212> TYPE: RNA
<213> ORGANISM: Artificial Sequence
<220> FEATURE:
<223> OTHER INFORMATION: Synthetic

<400> SEQUENCE: 434
ugggcuaaug aaaaggaag guuuuagagc uaugcu                          36

<210> SEQ ID NO 435
<211> LENGTH: 36
<212> TYPE: RNA
<213> ORGANISM: Artificial Sequence
<220> FEATURE:
<223> OTHER INFORMATION: Synthetic

```
<400> SEQUENCE: 435
uaaugaaaaa ggaagaggcu guuuuagagc uaugcu                             36

<210> SEQ ID NO 436
<211> LENGTH: 36
<212> TYPE: RNA
<213> ORGANISM: Artificial Sequence
<220> FEATURE:
<223> OTHER INFORMATION: Synthetic

<400> SEQUENCE: 436
aaugaaaaag gaagaggcua guuuuagagc uaugcu                             36

<210> SEQ ID NO 437
<211> LENGTH: 36
<212> TYPE: RNA
<213> ORGANISM: Artificial Sequence
<220> FEATURE:
<223> OTHER INFORMATION: Synthetic

<400> SEQUENCE: 437
cugaaucuua aaauaugucc guuuuagagc uaugcu                             36

<210> SEQ ID NO 438
<211> LENGTH: 36
<212> TYPE: RNA
<213> ORGANISM: Artificial Sequence
<220> FEATURE:
<223> OTHER INFORMATION: Synthetic

<400> SEQUENCE: 438
caggcagcuu uaucucaacc guuuuagagc uaugcu                             36

<210> SEQ ID NO 439
<211> LENGTH: 36
<212> TYPE: RNA
<213> ORGANISM: Artificial Sequence
<220> FEATURE:
<223> OTHER INFORMATION: Synthetic

<400> SEQUENCE: 439
cuaagagauc aaguuucagc guuuuagagc uaugcu                             36

<210> SEQ ID NO 440
<211> LENGTH: 36
<212> TYPE: RNA
<213> ORGANISM: Artificial Sequence
<220> FEATURE:
<223> OTHER INFORMATION: Synthetic

<400> SEQUENCE: 440
guguucuugu ugauauucug guuuuagagc uaugcu                             36

<210> SEQ ID NO 441
<211> LENGTH: 36
<212> TYPE: RNA
<213> ORGANISM: Artificial Sequence
<220> FEATURE:
<223> OTHER INFORMATION: Synthetic

<400> SEQUENCE: 441
cuuguugaua uucuguggca guuuuagagc uaugcu                             36

<210> SEQ ID NO 442
```

```
<211> LENGTH: 36
<212> TYPE: RNA
<213> ORGANISM: Artificial Sequence
<220> FEATURE:
<223> OTHER INFORMATION: Synthetic

<400> SEQUENCE: 442
ucuguggcau ggcuacagau guuuuagagc uaugcu                              36

<210> SEQ ID NO 443
<211> LENGTH: 36
<212> TYPE: RNA
<213> ORGANISM: Artificial Sequence
<220> FEATURE:
<223> OTHER INFORMATION: Synthetic

<400> SEQUENCE: 443
agaacuuauu uacacaggga guuuuagagc uaugcu                              36

<210> SEQ ID NO 444
<211> LENGTH: 36
<212> TYPE: RNA
<213> ORGANISM: Artificial Sequence
<220> FEATURE:
<223> OTHER INFORMATION: Synthetic

<400> SEQUENCE: 444
aaagagaacu uauuuacaca guuuuagagc uaugcu                              36

<210> SEQ ID NO 445
<211> LENGTH: 36
<212> TYPE: RNA
<213> ORGANISM: Artificial Sequence
<220> FEATURE:
<223> OTHER INFORMATION: Synthetic

<400> SEQUENCE: 445
caaagagaac uuauuuacac guuuuagagc uaugcu                              36

<210> SEQ ID NO 446
<211> LENGTH: 36
<212> TYPE: RNA
<213> ORGANISM: Artificial Sequence
<220> FEATURE:
<223> OTHER INFORMATION: Synthetic

<400> SEQUENCE: 446
uucucuuugu auuuacuuuu guuuuagagc uaugcu                              36

<210> SEQ ID NO 447
<211> LENGTH: 36
<212> TYPE: RNA
<213> ORGANISM: Artificial Sequence
<220> FEATURE:
<223> OTHER INFORMATION: Synthetic

<400> SEQUENCE: 447
ucucuuugua uuuacuuuua guuuuagagc uaugcu                              36

<210> SEQ ID NO 448
<211> LENGTH: 36
<212> TYPE: RNA
<213> ORGANISM: Artificial Sequence
<220> FEATURE:
<223> OTHER INFORMATION: Synthetic

<400> SEQUENCE: 448
```
cuuuguauuu acuuuuaggg guuuuagagc uaugcu    36

<210> SEQ ID NO 449
<211> LENGTH: 36
<212> TYPE: RNA
<213> ORGANISM: Artificial Sequence
<220> FEATURE:
<223> OTHER INFORMATION: Synthetic

<400> SEQUENCE: 449
agcuuuuguc caccuuuaaa guuuuagagc uaugcu    36

<210> SEQ ID NO 450
<211> LENGTH: 36
<212> TYPE: RNA
<213> ORGANISM: Artificial Sequence
<220> FEATURE:
<223> OTHER INFORMATION: Synthetic

<400> SEQUENCE: 450
uuuauuuuuc cauuuaaagg guuuuagagc uaugcu    36

<210> SEQ ID NO 451
<211> LENGTH: 36
<212> TYPE: RNA
<213> ORGANISM: Artificial Sequence
<220> FEATURE:
<223> OTHER INFORMATION: Synthetic

<400> SEQUENCE: 451
uauuuuauuu uuccauuuaa guuuuagagc uaugcu    36

<210> SEQ ID NO 452
<211> LENGTH: 36
<212> TYPE: RNA
<213> ORGANISM: Artificial Sequence
<220> FEATURE:
<223> OTHER INFORMATION: Synthetic

<400> SEQUENCE: 452
cuuacauaaa cauacuuaaa guuuuagagc uaugcu    36

<210> SEQ ID NO 453
<211> LENGTH: 36
<212> TYPE: RNA
<213> ORGANISM: Artificial Sequence
<220> FEATURE:
<223> OTHER INFORMATION: Synthetic

<400> SEQUENCE: 453
uaagcacaga aguuuuuaag guuuuagagc uaugcu    36

<210> SEQ ID NO 454
<211> LENGTH: 36
<212> TYPE: RNA
<213> ORGANISM: Artificial Sequence
<220> FEATURE:
<223> OTHER INFORMATION: Synthetic

<400> SEQUENCE: 454 aaguuuuaa gaggcaugaa guuuuagagc uaugcu    36

<210> SEQ ID NO 455
<211> LENGTH: 36
<212> TYPE: RNA

```
<213> ORGANISM: Artificial Sequence
<220> FEATURE:
<223> OTHER INFORMATION: Synthetic

<400> SEQUENCE: 455
auauuuacgu aguuuucau guuuuagagc uaugcu                                  36

<210> SEQ ID NO 456
<211> LENGTH: 36
<212> TYPE: RNA
<213> ORGANISM: Artificial Sequence
<220> FEATURE:
<223> OTHER INFORMATION: Synthetic

<400> SEQUENCE: 456
cguaaauauu cuugagaaac guuuuagagc uaugcu                                 36

<210> SEQ ID NO 457
<211> LENGTH: 36
<212> TYPE: RNA
<213> ORGANISM: Artificial Sequence
<220> FEATURE:
<223> OTHER INFORMATION: Synthetic

<400> SEQUENCE: 457
uucuugagaa acaggaagac guuuuagagc uaugcu                                 36

<210> SEQ ID NO 458
<211> LENGTH: 36
<212> TYPE: RNA
<213> ORGANISM: Artificial Sequence
<220> FEATURE:
<223> OTHER INFORMATION: Synthetic

<400> SEQUENCE: 458
uaauauuaaa aacauugguu guuuuagagc uaugcu                                 36

<210> SEQ ID NO 459
<211> LENGTH: 36
<212> TYPE: RNA
<213> ORGANISM: Artificial Sequence
<220> FEATURE:
<223> OTHER INFORMATION: Synthetic

<400> SEQUENCE: 459
ccaauguuuu uaauauuauc guuuuagagc uaugcu                                 36

<210> SEQ ID NO 460
<211> LENGTH: 36
<212> TYPE: RNA
<213> ORGANISM: Artificial Sequence
<220> FEATURE:
<223> OTHER INFORMATION: Synthetic

<400> SEQUENCE: 460
ccugauaaua uuaaaaacau guuuuagagc uaugcu                                 36

<210> SEQ ID NO 461
<211> LENGTH: 36
<212> TYPE: RNA
<213> ORGANISM: Artificial Sequence
<220> FEATURE:
<223> OTHER INFORMATION: Synthetic

<400> SEQUENCE: 461
cauuaucaug cauacaucuc guuuuagagc uaugcu                                 36
```

<210> SEQ ID NO 462
<211> LENGTH: 36
<212> TYPE: RNA
<213> ORGANISM: Artificial Sequence
<220> FEATURE:
<223> OTHER INFORMATION: Synthetic

<400> SEQUENCE: 462
aucaugcaua caucucuggc guuuuagagc uaugcu                                    36

<210> SEQ ID NO 463
<211> LENGTH: 36
<212> TYPE: RNA
<213> ORGANISM: Artificial Sequence
<220> FEATURE:
<223> OTHER INFORMATION: Synthetic

<400> SEQUENCE: 463
uucauuucau uuugauuuug guuuuagagc uaugcu                                    36

<210> SEQ ID NO 464
<211> LENGTH: 36
<212> TYPE: RNA
<213> ORGANISM: Artificial Sequence
<220> FEATURE:
<223> OTHER INFORMATION: Synthetic

<400> SEQUENCE: 464
auucaauuug aagcaguggu guuuuagagc uaugcu                                    36

<210> SEQ ID NO 465
<211> LENGTH: 36
<212> TYPE: RNA
<213> ORGANISM: Artificial Sequence
<220> FEATURE:
<223> OTHER INFORMATION: Synthetic

<400> SEQUENCE: 465
gaauauucaa uuugaagcag guuuuagagc uaugcu                                    36

<210> SEQ ID NO 466
<211> LENGTH: 36
<212> TYPE: RNA
<213> ORGANISM: Artificial Sequence
<220> FEATURE:
<223> OTHER INFORMATION: Synthetic

<400> SEQUENCE: 466
cauacgauuu aaaaucgcug guuuuagagc uaugcu                                    36

<210> SEQ ID NO 467
<211> LENGTH: 36
<212> TYPE: RNA
<213> ORGANISM: Artificial Sequence
<220> FEATURE:
<223> OTHER INFORMATION: Synthetic

<400> SEQUENCE: 467
aaaaucgcug aggcgcguuc guuuuagagc uaugcu                                    36

<210> SEQ ID NO 468
<211> LENGTH: 36
<212> TYPE: RNA
<213> ORGANISM: Artificial Sequence
<220> FEATURE:

```
<223> OTHER INFORMATION: Synthetic

<400> SEQUENCE: 468
uuuuuuuuuc uuuuuuguac guuuuagagc uaugcu                                      36

<210> SEQ ID NO 469
<211> LENGTH: 36
<212> TYPE: RNA
<213> ORGANISM: Artificial Sequence
<220> FEATURE:
<223> OTHER INFORMATION: Synthetic

<400> SEQUENCE: 469
cuguugucaa agauuuuaaa guuuuagagc uaugcu                                      36

<210> SEQ ID NO 470
<211> LENGTH: 36
<212> TYPE: RNA
<213> ORGANISM: Artificial Sequence
<220> FEATURE:
<223> OTHER INFORMATION: Synthetic

<400> SEQUENCE: 470
ugacaacaga guucuguuuu guuuuagagc uaugcu                                      36

<210> SEQ ID NO 471
<211> LENGTH: 36
<212> TYPE: RNA
<213> ORGANISM: Artificial Sequence
<220> FEATURE:
<223> OTHER INFORMATION: Synthetic

<400> SEQUENCE: 471
agaauacgcu gagaguuauc guuuuagagc uaugcu                                      36

<210> SEQ ID NO 472
<211> LENGTH: 36
<212> TYPE: RNA
<213> ORGANISM: Artificial Sequence
<220> FEATURE:
<223> OTHER INFORMATION: Synthetic

<400> SEQUENCE: 472
gcaagagaag aaaagaacgg guuuuagagc uaugcu                                      36

<210> SEQ ID NO 473
<211> LENGTH: 36
<212> TYPE: RNA
<213> ORGANISM: Artificial Sequence
<220> FEATURE:
<223> OTHER INFORMATION: Synthetic

<400> SEQUENCE: 473
guugcaagag aagaaaagaa guuuuagagc uaugcu                                      36

<210> SEQ ID NO 474
<211> LENGTH: 36
<212> TYPE: RNA
<213> ORGANISM: Artificial Sequence
<220> FEATURE:
<223> OTHER INFORMATION: Synthetic

<400> SEQUENCE: 474
augcacacgu aaaagagagg guuuuagagc uaugcu                                      36
```

```
<210> SEQ ID NO 475
<211> LENGTH: 36
<212> TYPE: RNA
<213> ORGANISM: Artificial Sequence
<220> FEATURE:
<223> OTHER INFORMATION: Synthetic

<400> SEQUENCE: 475
aagaugcaca cguaaaagag guuuuagagc uaugcu                                    36

<210> SEQ ID NO 476
<211> LENGTH: 36
<212> TYPE: RNA
<213> ORGANISM: Artificial Sequence
<220> FEATURE:
<223> OTHER INFORMATION: Synthetic

<400> SEQUENCE: 476
aucaugcaua caucucuggc guuuuagagc uaugcu                                    36

<210> SEQ ID NO 477
<211> LENGTH: 36
<212> TYPE: RNA
<213> ORGANISM: Artificial Sequence
<220> FEATURE:
<223> OTHER INFORMATION: Synthetic

<400> SEQUENCE: 477
uucauuucau uuugauuuug guuuuagagc uaugcu                                    36

<210> SEQ ID NO 478
<211> LENGTH: 36
<212> TYPE: RNA
<213> ORGANISM: Artificial Sequence
<220> FEATURE:
<223> OTHER INFORMATION: Synthetic

<400> SEQUENCE: 478
auucaauuug aagcaguggu guuuuagagc uaugcu                                    36

<210> SEQ ID NO 479
<211> LENGTH: 36
<212> TYPE: RNA
<213> ORGANISM: Artificial Sequence
<220> FEATURE:
<223> OTHER INFORMATION: Synthetic

<400> SEQUENCE: 479
gaauauucaa uuugaagcag guuuuagagc uaugcu                                    36

<210> SEQ ID NO 480
<211> LENGTH: 36
<212> TYPE: RNA
<213> ORGANISM: Artificial Sequence
<220> FEATURE:
<223> OTHER INFORMATION: Synthetic

<400> SEQUENCE: 480
cauacgauuu aaaaucgcug guuuuagagc uaugcu                                    36

<210> SEQ ID NO 481
<211> LENGTH: 36
<212> TYPE: RNA
<213> ORGANISM: Artificial Sequence
<220> FEATURE:
<223> OTHER INFORMATION: Synthetic
```

```
<400> SEQUENCE: 481
aaaaucgcug aggcgcguuc guuuuagagc uaugcu                              36

<210> SEQ ID NO 482
<211> LENGTH: 36
<212> TYPE: RNA
<213> ORGANISM: Artificial Sequence
<220> FEATURE:
<223> OTHER INFORMATION: Synthetic

<400> SEQUENCE: 482
uuuuuuuuuc uuuuuuguac guuuuagagc uaugcu                              36

<210> SEQ ID NO 483
<211> LENGTH: 36
<212> TYPE: RNA
<213> ORGANISM: Artificial Sequence
<220> FEATURE:
<223> OTHER INFORMATION: Synthetic

<400> SEQUENCE: 483
cuguugucaa agauuuaaaa guuuuagagc uaugcu                              36

<210> SEQ ID NO 484
<211> LENGTH: 36
<212> TYPE: RNA
<213> ORGANISM: Artificial Sequence
<220> FEATURE:
<223> OTHER INFORMATION: Synthetic

<400> SEQUENCE: 484
ugacaacaga guucuguuuu guuuuagagc uaugcu                              36

<210> SEQ ID NO 485
<211> LENGTH: 36
<212> TYPE: RNA
<213> ORGANISM: Artificial Sequence
<220> FEATURE:
<223> OTHER INFORMATION: Synthetic

<400> SEQUENCE: 485
agaauacgcu gagaguuauc guuuuagagc uaugcu                              36

<210> SEQ ID NO 486
<211> LENGTH: 36
<212> TYPE: RNA
<213> ORGANISM: Artificial Sequence
<220> FEATURE:
<223> OTHER INFORMATION: Synthetic

<400> SEQUENCE: 486
gcaagagaag aaaagaacgg guuuuagagc uaugcu                              36

<210> SEQ ID NO 487
<211> LENGTH: 36
<212> TYPE: RNA
<213> ORGANISM: Artificial Sequence
<220> FEATURE:
<223> OTHER INFORMATION: Synthetic

<400> SEQUENCE: 487
guugcaagag aagaaaagaa guuuuagagc uaugcu                              36

<210> SEQ ID NO 488
<211> LENGTH: 36
```

```
<212> TYPE: RNA
<213> ORGANISM: Artificial Sequence
<220> FEATURE:
<223> OTHER INFORMATION: Synthetic

<400> SEQUENCE: 488
augcacacgu aaaagagagg guuuuagagc uaugcu                                    36

<210> SEQ ID NO 489
<211> LENGTH: 36
<212> TYPE: RNA
<213> ORGANISM: Artificial Sequence
<220> FEATURE:
<223> OTHER INFORMATION: Synthetic

<400> SEQUENCE: 489
aagaugcaca cguaaaagag guuuuagagc uaugcu                                    36

<210> SEQ ID NO 490
<211> LENGTH: 36
<212> TYPE: RNA
<213> ORGANISM: Artificial Sequence
<220> FEATURE:
<223> OTHER INFORMATION: Synthetic

<400> SEQUENCE: 490
ggcagaccgu ucucaucacg guuuuagagc uaugcu                                    36

<210> SEQ ID NO 491
<211> LENGTH: 36
<212> TYPE: RNA
<213> ORGANISM: Artificial Sequence
<220> FEATURE:
<223> OTHER INFORMATION: Synthetic

<400> SEQUENCE: 491
cuuuaccagu gacuccaggu guuuuagagc uaugcu                                    36

<210> SEQ ID NO 492
<211> LENGTH: 36
<212> TYPE: RNA
<213> ORGANISM: Artificial Sequence
<220> FEATURE:
<223> OTHER INFORMATION: Synthetic

<400> SEQUENCE: 492
gucacagauu uccuucuccg guuuuagagc uaugcu                                    36

<210> SEQ ID NO 493
<211> LENGTH: 36
<212> TYPE: RNA
<213> ORGANISM: Artificial Sequence
<220> FEATURE:
<223> OTHER INFORMATION: Synthetic

<400> SEQUENCE: 493
agaugaugac gcccaccaga guuuuagagc uaugcu                                    36

<210> SEQ ID NO 494
<211> LENGTH: 36
<212> TYPE: RNA
<213> ORGANISM: Artificial Sequence
<220> FEATURE:
<223> OTHER INFORMATION: Synthetic

<400> SEQUENCE: 494
```
ggagaaggaa aucugugacc guuuuagagc uaugcu       36

<210> SEQ ID NO 495
<211> LENGTH: 36
<212> TYPE: RNA
<213> ORGANISM: Artificial Sequence
<220> FEATURE:
<223> OTHER INFORMATION: Synthetic

<400> SEQUENCE: 495
ugcgaggaac uuacuuuucc guuuuagagc uaugcu       36

<210> SEQ ID NO 496
<211> LENGTH: 36
<212> TYPE: RNA
<213> ORGANISM: Artificial Sequence
<220> FEATURE:
<223> OTHER INFORMATION: Synthetic

<400> SEQUENCE: 496
agagaaauau ugauauagga guuuuagagc uaugcu       36

<210> SEQ ID NO 497
<211> LENGTH: 36
<212> TYPE: RNA
<213> ORGANISM: Artificial Sequence
<220> FEATURE:
<223> OTHER INFORMATION: Synthetic

<400> SEQUENCE: 497
uaucaauauu ucucugaucc guuuuagagc uaugcu       36

<210> SEQ ID NO 498
<211> LENGTH: 36
<212> TYPE: RNA
<213> ORGANISM: Artificial Sequence
<220> FEATURE:
<223> OTHER INFORMATION: Synthetic

<400> SEQUENCE: 498
aucgcuuuua aggcacgcuc guuuuagagc uaugcu       36

<210> SEQ ID NO 499
<211> LENGTH: 36
<212> TYPE: RNA
<213> ORGANISM: Artificial Sequence
<220> FEATURE:
<223> OTHER INFORMATION: Synthetic

<400> SEQUENCE: 499
uauacgacug aucgcuuuua guuuuagagc uaugcu       36

<210> SEQ ID NO 500
<211> LENGTH: 97
<212> TYPE: RNA
<213> ORGANISM: Artificial Sequence
<220> FEATURE:
<223> OTHER INFORMATION: Synthetic

<400> SEQUENCE: 500
ugucagguua guuagaugaa guuuuagagc uagaaauagc aaguuaaaau aaggcuaguc       60
cguuaucaac uugaaaaagu ggcaccgagu cggugcu       97

<210> SEQ ID NO 501
<211> LENGTH: 97

```
<212> TYPE: RNA
<213> ORGANISM: Artificial Sequence
<220> FEATURE:
<223> OTHER INFORMATION: Synthetic

<400> SEQUENCE: 501
gugucagguu aguuagauga guuuuagagc uagaaauagc aaguuaaaau aaggcuaguc    60
cguuaucaac uugaaaaagu ggcaccgagu cggugcu                            97

<210> SEQ ID NO 502
<211> LENGTH: 97
<212> TYPE: RNA
<213> ORGANISM: Artificial Sequence
<220> FEATURE:
<223> OTHER INFORMATION: Synthetic

<400> SEQUENCE: 502
ccugacacau auacagacua guuuuagagc uagaaauagc aaguuaaaau aaggcuaguc    60
cguuaucaac uugaaaaagu ggcaccgagu cggugcu                            97

<210> SEQ ID NO 503
<211> LENGTH: 97
<212> TYPE: RNA
<213> ORGANISM: Artificial Sequence
<220> FEATURE:
<223> OTHER INFORMATION: Synthetic

<400> SEQUENCE: 503
cugacacaua uacagacuaa guuuuagagc uagaaauagc aaguuaaaau aaggcuaguc    60
cguuaucaac uugaaaaagu ggcaccgagu cggugcu                            97

<210> SEQ ID NO 504
<211> LENGTH: 97
<212> TYPE: RNA
<213> ORGANISM: Artificial Sequence
<220> FEATURE:
<223> OTHER INFORMATION: Synthetic

<400> SEQUENCE: 504
ccuuagucug uauauguguc guuuuagagc uagaaauagc aaguuaaaau aaggcuaguc    60
cguuaucaac uugaaaaagu ggcaccgagu cggugcu                            97

<210> SEQ ID NO 505
<211> LENGTH: 97
<212> TYPE: RNA
<213> ORGANISM: Artificial Sequence
<220> FEATURE:
<223> OTHER INFORMATION: Synthetic

<400> SEQUENCE: 505
cauauacaga cuaagggacc guuuuagagc uagaaauagc aaguuaaaau aaggcuaguc    60
cguuaucaac uugaaaaagu ggcaccgagu cggugcu                            97

<210> SEQ ID NO 506
<211> LENGTH: 97
<212> TYPE: RNA
<213> ORGANISM: Artificial Sequence
<220> FEATURE:
<223> OTHER INFORMATION: Synthetic

<400> SEQUENCE: 506
auauacagac uaagggacca guuuuagagc uagaaauagc aaguuaaaau aaggcuaguc    60
```
cguuaucaac uugaaaaagu ggcaccgagu cggugcu    97

<210> SEQ ID NO 507
<211> LENGTH: 97
<212> TYPE: RNA
<213> ORGANISM: Artificial Sequence
<220> FEATURE:
<223> OTHER INFORMATION: Synthetic

<400> SEQUENCE: 507
ucaaaguuug auaaauuccc guuuuagagc uagaaauagc aaguuaaaau aaggcuaguc    60
cguuaucaac uugaaaaagu ggcaccgagu cggugcu    97

<210> SEQ ID NO 508
<211> LENGTH: 97
<212> TYPE: RNA
<213> ORGANISM: Artificial Sequence
<220> FEATURE:
<223> OTHER INFORMATION: Synthetic

<400> SEQUENCE: 508
aaaauacaaa gauaaguaga guuuuagagc uagaaauagc aaguuaaaau aaggcuaguc    60
cguuaucaac uugaaaaagu ggcaccgagu cggugcu    97

<210> SEQ ID NO 509
<211> LENGTH: 97
<212> TYPE: RNA
<213> ORGANISM: Artificial Sequence
<220> FEATURE:
<223> OTHER INFORMATION: Synthetic

<400> SEQUENCE: 509
acucugugac uuuaaaaagu guuuuagagc uagaaauagc aaguuaaaau aaggcuaguc    60
cguuaucaac uugaaaaagu ggcaccgagu cggugcu    97

<210> SEQ ID NO 510
<211> LENGTH: 97
<212> TYPE: RNA
<213> ORGANISM: Artificial Sequence
<220> FEATURE:
<223> OTHER INFORMATION: Synthetic

<400> SEQUENCE: 510
gguucugugg gauauuaaua guuuuagagc uagaaauagc aaguuaaaau aaggcuaguc    60
cguuaucaac uugaaaaagu ggcaccgagu cggugcu    97

<210> SEQ ID NO 511
<211> LENGTH: 97
<212> TYPE: RNA
<213> ORGANISM: Artificial Sequence
<220> FEATURE:
<223> OTHER INFORMATION: Synthetic

<400> SEQUENCE: 511
acagagcaua uugguucugu guuuuagagc uagaaauagc aaguuaaaau aaggcuaguc    60
cguuaucaac uugaaaaagu ggcaccgagu cggugcu    97

<210> SEQ ID NO 512
<211> LENGTH: 97
<212> TYPE: RNA
<213> ORGANISM: Artificial Sequence
<220> FEATURE:
<223> OTHER INFORMATION: Synthetic

<400> SEQUENCE: 512
gacagagcau auugguucug guuuuagagc uagaaauagc aaguuaaaau aaggcuaguc    60
cguuaucaac uugaaaaagu ggcaccgagu cggugcu                            97

<210> SEQ ID NO 513
<211> LENGTH: 97
<212> TYPE: RNA
<213> ORGANISM: Artificial Sequence
<220> FEATURE:
<223> OTHER INFORMATION: Synthetic

<400> SEQUENCE: 513
ugcaaaacga cagagcauau guuuuagagc uagaaauagc aaguuaaaau aaggcuaguc    60
cguuaucaac uugaaaaagu ggcaccgagu cggugcu                            97

<210> SEQ ID NO 514
<211> LENGTH: 97
<212> TYPE: RNA
<213> ORGANISM: Artificial Sequence
<220> FEATURE:
<223> OTHER INFORMATION: Synthetic

<400> SEQUENCE: 514
gagcugggca uggaauaggc guuuuagagc uagaaauagc aaguuaaaau aaggcuaguc    60
cguuaucaac uugaaaaagu ggcaccgagu cggugcu                            97

<210> SEQ ID NO 515
<211> LENGTH: 97
<212> TYPE: RNA
<213> ORGANISM: Artificial Sequence
<220> FEATURE:
<223> OTHER INFORMATION: Synthetic

<400> SEQUENCE: 515
acuggagcug ggcauggaau guuuuagagc uagaaauagc aaguuaaaau aaggcuaguc    60
cguuaucaac uugaaaaagu ggcaccgagu cggugcu                            97

<210> SEQ ID NO 516
<211> LENGTH: 97
<212> TYPE: RNA
<213> ORGANISM: Artificial Sequence
<220> FEATURE:
<223> OTHER INFORMATION: Synthetic

<400> SEQUENCE: 516
cucauuacug gagcugggca guuuuagagc uagaaauagc aaguuaaaau aaggcuaguc    60
cguuaucaac uugaaaaagu ggcaccgagu cggugcu                            97

<210> SEQ ID NO 517
<211> LENGTH: 97
<212> TYPE: RNA
<213> ORGANISM: Artificial Sequence
<220> FEATURE:
<223> OTHER INFORMATION: Synthetic

<400> SEQUENCE: 517
uuguucucau uacuggagcu guuuuagagc uagaaauagc aaguuaaaau aaggcuaguc    60
cguuaucaac uugaaaaagu ggcaccgagu cggugcu                            97

<210> SEQ ID NO 518

```
<211> LENGTH: 97
<212> TYPE: RNA
<213> ORGANISM: Artificial Sequence
<220> FEATURE:
<223> OTHER INFORMATION: Synthetic

<400> SEQUENCE: 518
auuguucuca uuacuggagc guuuuagagc uagaaauagc aaguuaaaau aaggcuaguc    60
cguuaucaac uugaaaaagu ggcaccgagu cggugcu                             97

<210> SEQ ID NO 519
<211> LENGTH: 97
<212> TYPE: RNA
<213> ORGANISM: Artificial Sequence
<220> FEATURE:
<223> OTHER INFORMATION: Synthetic

<400> SEQUENCE: 519
ggggagauug uucucauuac guuuuagagc uagaaauagc aaguuaaaau aaggcuaguc    60
cguuaucaac uugaaaaagu ggcaccgagu cggugcu                             97

<210> SEQ ID NO 520
<211> LENGTH: 97
<212> TYPE: RNA
<213> ORGANISM: Artificial Sequence
<220> FEATURE:
<223> OTHER INFORMATION: Synthetic

<400> SEQUENCE: 520
gaggagaaaa ucuguggcug guuuuagagc uagaaauagc aaguuaaaau aaggcuaguc    60
cguuaucaac uugaaaaagu ggcaccgagu cggugcu                             97

<210> SEQ ID NO 521
<211> LENGTH: 97
<212> TYPE: RNA
<213> ORGANISM: Artificial Sequence
<220> FEATURE:
<223> OTHER INFORMATION: Synthetic

<400> SEQUENCE: 521
agaggagaaa aucuguggcu guuuuagagc uagaaauagc aaguuaaaau aaggcuaguc    60
cguuaucaac uugaaaaagu ggcaccgagu cggugcu                             97

<210> SEQ ID NO 522
<211> LENGTH: 97
<212> TYPE: RNA
<213> ORGANISM: Artificial Sequence
<220> FEATURE:
<223> OTHER INFORMATION: Synthetic

<400> SEQUENCE: 522
cagaggagaa aaucuguggc guuuuagagc uagaaauagc aaguuaaaau aaggcuaguc    60
cguuaucaac uugaaaaagu ggcaccgagu cggugcu                             97

<210> SEQ ID NO 523
<211> LENGTH: 97
<212> TYPE: RNA
<213> ORGANISM: Artificial Sequence
<220> FEATURE:
<223> OTHER INFORMATION: Synthetic

<400> SEQUENCE: 523
uccucagagg agaaaaucug guuuuagagc uagaaauagc aaguuaaaau aaggcuaguc    60
```
cguuaucaac uugaaaaagu ggcaccgagu cggugcu          97

<210> SEQ ID NO 524
<211> LENGTH: 97
<212> TYPE: RNA
<213> ORGANISM: Artificial Sequence
<220> FEATURE:
<223> OTHER INFORMATION: Synthetic

<400> SEQUENCE: 524
ugaaguuuuu cauuccucag guuuuagagc uagaaauagc aaguuaaaau aaggcuaguc          60
cguuaucaac uugaaaaagu ggcaccgagu cggugcu          97

<210> SEQ ID NO 525
<211> LENGTH: 97
<212> TYPE: RNA
<213> ORGANISM: Artificial Sequence
<220> FEATURE:
<223> OTHER INFORMATION: Synthetic

<400> SEQUENCE: 525
cuucaccaac gacuccaagu guuuuagagc uagaaauagc aaguuaaaau aaggcuaguc          60
cguuaucaac uugaaaaagu ggcaccgagu cggugcu          97

<210> SEQ ID NO 526
<211> LENGTH: 97
<212> TYPE: RNA
<213> ORGANISM: Artificial Sequence
<220> FEATURE:
<223> OTHER INFORMATION: Synthetic

<400> SEQUENCE: 526
cuacuccuac uuggagucgu guuuuagagc uagaaauagc aaguuaaaau aaggcuaguc          60
cguuaucaac uugaaaaagu ggcaccgagu cggugcu          97

<210> SEQ ID NO 527
<211> LENGTH: 97
<212> TYPE: RNA
<213> ORGANISM: Artificial Sequence
<220> FEATURE:
<223> OTHER INFORMATION: Synthetic

<400> SEQUENCE: 527
cuccaaguag gaguagauga guuuuagagc uagaaauagc aaguuaaaau aaggcuaguc          60
cguuaucaac uugaaaaagu ggcaccgagu cggugcu          97

<210> SEQ ID NO 528
<211> LENGTH: 97
<212> TYPE: RNA
<213> ORGANISM: Artificial Sequence
<220> FEATURE:
<223> OTHER INFORMATION: Synthetic

<400> SEQUENCE: 528
caccaucauc uacuccuacu guuuuagagc uagaaauagc aaguuaaaau aaggcuaguc          60
cguuaucaac uugaaaaagu ggcaccgagu cggugcu          97

<210> SEQ ID NO 529
<211> LENGTH: 97
<212> TYPE: RNA
<213> ORGANISM: Artificial Sequence
<220> FEATURE:

<223> OTHER INFORMATION: Synthetic

<400> SEQUENCE: 529
ugauggugau cagaagcaga guuuuagagc uagaaauagc aaguuaaaau aaggcuaguc    60
cguuaucaac uugaaaaagu ggcaccgagu cggugcu    97

<210> SEQ ID NO 530
<211> LENGTH: 97
<212> TYPE: RNA
<213> ORGANISM: Artificial Sequence
<220> FEATURE:
<223> OTHER INFORMATION: Synthetic

<400> SEQUENCE: 530
ucagaagcag aaggauuucu guuuuagagc uagaaauagc aaguuaaaau aaggcuaguc    60
cguuaucaac uugaaaaagu ggcaccgagu cggugcu    97

<210> SEQ ID NO 531
<211> LENGTH: 97
<212> TYPE: RNA
<213> ORGANISM: Artificial Sequence
<220> FEATURE:
<223> OTHER INFORMATION: Synthetic

<400> SEQUENCE: 531
gauuucuagg augauguuca guuuuagagc uagaaauagc aaguuaaaau aaggcuaguc    60
cguuaucaac uugaaaaagu ggcaccgagu cggugcu    97

<210> SEQ ID NO 532
<211> LENGTH: 97
<212> TYPE: RNA
<213> ORGANISM: Artificial Sequence
<220> FEATURE:
<223> OTHER INFORMATION: Synthetic

<400> SEQUENCE: 532
uugcucuguc cucuuccuuc guuuuagagc uagaaauagc aaguuaaaau aaggcuaguc    60
cguuaucaac uugaaaaagu ggcaccgagu cggugcu    97

<210> SEQ ID NO 533
<211> LENGTH: 97
<212> TYPE: RNA
<213> ORGANISM: Artificial Sequence
<220> FEATURE:
<223> OTHER INFORMATION: Synthetic

<400> SEQUENCE: 533
aggacugaac cagaaggaag guuuuagagc uagaaauagc aaguuaaaau aaggcuaguc    60
cguuaucaac uugaaaaagu ggcaccgagu cggugcu    97

<210> SEQ ID NO 534
<211> LENGTH: 97
<212> TYPE: RNA
<213> ORGANISM: Artificial Sequence
<220> FEATURE:
<223> OTHER INFORMATION: Synthetic

<400> SEQUENCE: 534
uacacaagga cugaaccaga guuuuagagc uagaaauagc aaguuaaaau aaggcuaguc    60
cguuaucaac uugaaaaagu ggcaccgagu cggugcu    97

```
<210> SEQ ID NO 535
<211> LENGTH: 97
<212> TYPE: RNA
<213> ORGANISM: Artificial Sequence
<220> FEATURE:
<223> OTHER INFORMATION: Synthetic

<400> SEQUENCE: 535
uucaguccuu guguagaguccu guuuuagagc uagaaauagc aaguuaaaau aaggcuaguc    60
cguuaucaac uugaaaaagu ggcaccgagu cggugcu                              97

<210> SEQ ID NO 536
<211> LENGTH: 97
<212> TYPE: RNA
<213> ORGANISM: Artificial Sequence
<220> FEATURE:
<223> OTHER INFORMATION: Synthetic

<400> SEQUENCE: 536 ucagccuug uguagccua guuuuagagc uagaaauagc aaguuaaaau aaggcuaguc       60
cguuaucaac uugaaaaagu ggcaccgagu cggugcu                              97

<210> SEQ ID NO 537
<211> LENGTH: 97
<212> TYPE: RNA
<213> ORGANISM: Artificial Sequence
<220> FEATURE:
<223> OTHER INFORMATION: Synthetic

<400> SEQUENCE: 537
guccuugugu aguccuaggg guuuuagagc uagaaauagc aaguuaaaau aaggcuaguc     60
cguuaucaac uugaaaaagu ggcaccgagu cggugcu                              97

<210> SEQ ID NO 538
<211> LENGTH: 97
<212> TYPE: RNA
<213> ORGANISM: Artificial Sequence
<220> FEATURE:
<223> OTHER INFORMATION: Synthetic

<400> SEQUENCE: 538
cuuguguagu ccuagggagg guuuuagagc uagaaauagc aaguuaaaau aaggcuaguc     60
cguuaucaac uugaaaaagu ggcaccgagu cggugcu                              97

<210> SEQ ID NO 539
<211> LENGTH: 97
<212> TYPE: RNA
<213> ORGANISM: Artificial Sequence
<220> FEATURE:
<223> OTHER INFORMATION: Synthetic

<400> SEQUENCE: 539
cuccucccua ggacuacaca guuuuagagc uagaaauagc aaguuaaaau aaggcuaguc     60
cguuaucaac uugaaaaagu ggcaccgagu cggugcu                              97

<210> SEQ ID NO 540
<211> LENGTH: 97
<212> TYPE: RNA
<213> ORGANISM: Artificial Sequence
<220> FEATURE:
<223> OTHER INFORMATION: Synthetic

<400> SEQUENCE: 540
```
guagacagua ccuccuccccu guuuuagagc uagaaauagc aaguuaaaau aaggcuaguc    60
cguuaucaac uugaaaaagu ggcaccgagu cggugcu                              97

<210> SEQ ID NO 541
<211> LENGTH: 97
<212> TYPE: RNA
<213> ORGANISM: Artificial Sequence
<220> FEATURE:
<223> OTHER INFORMATION: Synthetic

<400> SEQUENCE: 541
uacugucuac acagagcucu guuuuagagc uagaaauagc aaguuaaaau aaggcuaguc    60
cguuaucaac uugaaaaagu ggcaccgagu cggugcu                              97

<210> SEQ ID NO 542
<211> LENGTH: 97
<212> TYPE: RNA
<213> ORGANISM: Artificial Sequence
<220> FEATURE:
<223> OTHER INFORMATION: Synthetic

<400> SEQUENCE: 542
acugucuaca cagagcucua guuuuagagc uagaaauagc aaguuaaaau aaggcuaguc    60
cguuaucaac uugaaaaagu ggcaccgagu cggugcu                              97

<210> SEQ ID NO 543
<211> LENGTH: 97
<212> TYPE: RNA
<213> ORGANISM: Artificial Sequence
<220> FEATURE:
<223> OTHER INFORMATION: Synthetic

<400> SEQUENCE: 543
ucuacacaga gcucuaggga guuuuagagc uagaaauagc aaguuaaaau aaggcuaguc    60
cguuaucaac uugaaaaagu ggcaccgagu cggugcu                              97

<210> SEQ ID NO 544
<211> LENGTH: 97
<212> TYPE: RNA
<213> ORGANISM: Artificial Sequence
<220> FEATURE:
<223> OTHER INFORMATION: Synthetic

<400> SEQUENCE: 544
cuacacagag cucuagggaa guuuuagagc uagaaauagc aaguuaaaau aaggcuaguc    60
cguuaucaac uugaaaaagu ggcaccgagu cggugcu                              97

<210> SEQ ID NO 545
<211> LENGTH: 97
<212> TYPE: RNA
<213> ORGANISM: Artificial Sequence
<220> FEATURE:
<223> OTHER INFORMATION: Synthetic

<400> SEQUENCE: 545
uacacagagc ucugggaag guuuuagagc uagaaauagc aaguuaaaau aaggcuaguc    60
cguuaucaac uugaaaaagu ggcaccgagu cggugcu                              97

<210> SEQ ID NO 546
<211> LENGTH: 97
<212> TYPE: RNA
<213> ORGANISM: Artificial Sequence

```
<220> FEATURE:
<223> OTHER INFORMATION: Synthetic

<400> SEQUENCE: 546
ggggugugcc caguuguuaa guuuuagagc uagaaauagc aaguuaaaau aaggcuaguc      60
cguuaucaac uugaaaaagu ggcaccgagu cggugcu                              97

<210> SEQ ID NO 547
<211> LENGTH: 97
<212> TYPE: RNA
<213> ORGANISM: Artificial Sequence
<220> FEATURE:
<223> OTHER INFORMATION: Synthetic

<400> SEQUENCE: 547
gggugugccc aguuguuaau guuuuagagc uagaaauagc aaguuaaaau aaggcuaguc      60
cguuaucaac uugaaaaagu ggcaccgagu cggugcu                              97

<210> SEQ ID NO 548
<211> LENGTH: 97
<212> TYPE: RNA
<213> ORGANISM: Artificial Sequence
<220> FEATURE:
<223> OTHER INFORMATION: Synthetic

<400> SEQUENCE: 548
ugguaguccc auuaacaacu guuuuagagc uagaaauagc aaguuaaaau aaggcuaguc      60
cguuaucaac uugaaaaagu ggcaccgagu cggugcu                              97

<210> SEQ ID NO 549
<211> LENGTH: 97
<212> TYPE: RNA
<213> ORGANISM: Artificial Sequence
<220> FEATURE:
<223> OTHER INFORMATION: Synthetic

<400> SEQUENCE: 549
cugguagucc cauuaacaac guuuuagagc uagaaauagc aaguuaaaau aaggcuaguc      60
cguuaucaac uugaaaaagu ggcaccgagu cggugcu                              97

<210> SEQ ID NO 550
<211> LENGTH: 97
<212> TYPE: RNA
<213> ORGANISM: Artificial Sequence
<220> FEATURE:
<223> OTHER INFORMATION: Synthetic

<400> SEQUENCE: 550
uuguuaaugg dacuaccaga guuuuagagc uagaaauagc aaguuaaaau aaggcuaguc      60
cguuaucaac uugaaaaagu ggcaccgagu cggugcu                              97

<210> SEQ ID NO 551
<211> LENGTH: 97
<212> TYPE: RNA
<213> ORGANISM: Artificial Sequence
<220> FEATURE:
<223> OTHER INFORMATION: Synthetic

<400> SEQUENCE: 551
uaccagaugg aagccagcuu guuuuagagc uagaaauagc aaguuaaaau aaggcuaguc      60
cguuaucaac uugaaaaagu ggcaccgagu cggugcu                              97
```

```
<210> SEQ ID NO 552
<211> LENGTH: 97
<212> TYPE: RNA
<213> ORGANISM: Artificial Sequence
<220> FEATURE:
<223> OTHER INFORMATION: Synthetic

<400> SEQUENCE: 552
uuccaaagcu ggcuuccauc guuuuagagc uagaaauagc aaguuaaaau aaggcuaguc    60
cguuaucaac uugaaaaagu ggcaccgagu cggugcu                            97

<210> SEQ ID NO 553
<211> LENGTH: 97
<212> TYPE: RNA
<213> ORGANISM: Artificial Sequence
<220> FEATURE:
<223> OTHER INFORMATION: Synthetic

<400> SEQUENCE: 553
uggaagccag cuuuggaagc guuuuagagc uagaaauagc aaguuaaaau aaggcuaguc    60
cguuaucaac uugaaaaagu ggcaccgagu cggugcu                            97

<210> SEQ ID NO 554
<211> LENGTH: 97
<212> TYPE: RNA
<213> ORGANISM: Artificial Sequence
<220> FEATURE:
<223> OTHER INFORMATION: Synthetic

<400> SEQUENCE: 554
acaaggccug cuuccaaagc guuuuagagc uagaaauagc aaguuaaaau aaggcuaguc    60
cguuaucaac uugaaaaagu ggcaccgagu cggugcu                            97

<210> SEQ ID NO 555
<211> LENGTH: 97
<212> TYPE: RNA
<213> ORGANISM: Artificial Sequence
<220> FEATURE:
<223> OTHER INFORMATION: Synthetic

<400> SEQUENCE: 555
gccuuguuca cguguucuaa guuuuagagc uagaaauagc aaguuaaaau aaggcuaguc    60
cguuaucaac uugaaaaagu ggcaccgagu cggugcu                            97

<210> SEQ ID NO 556
<211> LENGTH: 97
<212> TYPE: RNA
<213> ORGANISM: Artificial Sequence
<220> FEATURE:
<223> OTHER INFORMATION: Synthetic

<400> SEQUENCE: 556
ccuuguucac guguucuaau guuuuagagc uagaaauagc aaguuaaaau aaggcuaguc    60
cguuaucaac uugaaaaagu ggcaccgagu cggugcu                            97

<210> SEQ ID NO 557
<211> LENGTH: 97
<212> TYPE: RNA
<213> ORGANISM: Artificial Sequence
<220> FEATURE:
<223> OTHER INFORMATION: Synthetic

<400> SEQUENCE: 557
```

```
cccauuagaa cacgugaaca guuuuagagc uagaaauagc aaguuaaaau aaggcuaguc    60
cguuaucaac uugaaaaagu ggcaccgagu cggugcu                            97

<210> SEQ ID NO 558
<211> LENGTH: 97
<212> TYPE: RNA
<213> ORGANISM: Artificial Sequence
<220> FEATURE:
<223> OTHER INFORMATION: Synthetic

<400> SEQUENCE: 558
uuggcaucac uucauauuug guuuuagagc uagaaauagc aaguuaaaau aaggcuaguc    60
cguuaucaac uugaaaaagu ggcaccgagu cggugcu                            97

<210> SEQ ID NO 559
<211> LENGTH: 97
<212> TYPE: RNA
<213> ORGANISM: Artificial Sequence
<220> FEATURE:
<223> OTHER INFORMATION: Synthetic

<400> SEQUENCE: 559
cuugugcucu uggcaucacu guuuuagagc uagaaauagc aaguuaaaau aaggcuaguc    60
cguuaucaac uugaaaaagu ggcaccgagu cggugcu                            97

<210> SEQ ID NO 560
<211> LENGTH: 97
<212> TYPE: RNA
<213> ORGANISM: Artificial Sequence
<220> FEATURE:
<223> OTHER INFORMATION: Synthetic

<400> SEQUENCE: 560
agcacacucu cuugugcucu guuuuagagc uagaaauagc aaguuaaaau aaggcuaguc    60
cguuaucaac uugaaaaagu ggcaccgagu cggugcu                            97

<210> SEQ ID NO 561
<211> LENGTH: 97
<212> TYPE: RNA
<213> ORGANISM: Artificial Sequence
<220> FEATURE:
<223> OTHER INFORMATION: Synthetic

<400> SEQUENCE: 561
gcacaagaga gugugcucuc guuuuagagc uagaaauagc aaguuaaaau aaggcuaguc    60
cguuaucaac uugaaaaagu ggcaccgagu cggugcu                            97

<210> SEQ ID NO 562
<211> LENGTH: 97
<212> TYPE: RNA
<213> ORGANISM: Artificial Sequence
<220> FEATURE:
<223> OTHER INFORMATION: Synthetic

<400> SEQUENCE: 562
gcuuaaucuc acacauagaa guuuuagagc uagaaauagc aaguuaaaau aaggcuaguc    60
cguuaucaac uugaaaaagu ggcaccgagu cggugcu                            97

<210> SEQ ID NO 563
<211> LENGTH: 97
<212> TYPE: RNA
```

<213> ORGANISM: Artificial Sequence
<220> FEATURE:
<223> OTHER INFORMATION: Synthetic

<400> SEQUENCE: 563
cuuaaucuca cacauagaaa guuuuagagc uagaaauagc aaguuaaaau aaggcuaguc    60
cguuaucaac uugaaaaagu ggcaccgagu cggugcu                            97

<210> SEQ ID NO 564
<211> LENGTH: 97
<212> TYPE: RNA
<213> ORGANISM: Artificial Sequence
<220> FEATURE:
<223> OTHER INFORMATION: Synthetic

<400> SEQUENCE: 564
uuaaucucac acauagaaag guuuuagagc uagaaauagc aaguuaaaau aaggcuaguc    60
cguuaucaac uugaaaaagu ggcaccgagu cggugcu                            97

<210> SEQ ID NO 565
<211> LENGTH: 97
<212> TYPE: RNA
<213> ORGANISM: Artificial Sequence
<220> FEATURE:
<223> OTHER INFORMATION: Synthetic

<400> SEQUENCE: 565
aggagugcug guuuaucaac guuuuagagc uagaaauagc aaguuaaaau aaggcuaguc    60
cguuaucaac uugaaaaagu ggcaccgagu cggugcu                            97

<210> SEQ ID NO 566
<211> LENGTH: 97
<212> TYPE: RNA
<213> ORGANISM: Artificial Sequence
<220> FEATURE:
<223> OTHER INFORMATION: Synthetic

<400> SEQUENCE: 566
uucuuugaca gcaggagugc guuuuagagc uagaaauagc aaguuaaaau aaggcuaguc    60
cguuaucaac uugaaaaagu ggcaccgagu cggugcu                            97

<210> SEQ ID NO 567
<211> LENGTH: 97
<212> TYPE: RNA
<213> ORGANISM: Artificial Sequence
<220> FEATURE:
<223> OTHER INFORMATION: Synthetic

<400> SEQUENCE: 567
acucugguuu cuuugacagc guuuuagagc uagaaauagc aaguuaaaau aaggcuaguc    60
cguuaucaac uugaaaaagu ggcaccgagu cggugcu                            97

<210> SEQ ID NO 568
<211> LENGTH: 97
<212> TYPE: RNA
<213> ORGANISM: Artificial Sequence
<220> FEATURE:
<223> OTHER INFORMATION: Synthetic

<400> SEQUENCE: 568
accagaguug agaaaacccc guuuuagagc uagaaauagc aaguuaaaau aaggcuaguc    60
cguuaucaac uugaaaaagu ggcaccgagu cggugcu                            97

<210> SEQ ID NO 569
<211> LENGTH: 97
<212> TYPE: RNA
<213> ORGANISM: Artificial Sequence
<220> FEATURE:
<223> OTHER INFORMATION: Synthetic

<400> SEQUENCE: 569
uccagggguu uucucaacuc guuuuagagc uagaaauagc aaguuaaaau aaggcuaguc    60
cguuaucaac uugaaaaagu ggcaccgagu cggugcu                             97

<210> SEQ ID NO 570
<211> LENGTH: 97
<212> TYPE: RNA
<213> ORGANISM: Artificial Sequence
<220> FEATURE:
<223> OTHER INFORMATION: Synthetic

<400> SEQUENCE: 570
caguuauuaa augaauccag guuuuagagc uagaaauagc aaguuaaaau aaggcuaguc    60
cguuaucaac uugaaaaagu ggcaccgagu cggugcu                             97

<210> SEQ ID NO 571
<211> LENGTH: 97
<212> TYPE: RNA
<213> ORGANISM: Artificial Sequence
<220> FEATURE:
<223> OTHER INFORMATION: Synthetic

<400> SEQUENCE: 571
gcaguuauua aaugaaucca guuuuagagc uagaaauagc aaguuaaaau aaggcuaguc    60
cguuaucaac uugaaaaagu ggcaccgagu cggugcu                             97

<210> SEQ ID NO 572
<211> LENGTH: 97
<212> TYPE: RNA
<213> ORGANISM: Artificial Sequence
<220> FEATURE:
<223> OTHER INFORMATION: Synthetic

<400> SEQUENCE: 572
ggcaguuauu aaaugaaucc guuuuagagc uagaaauagc aaguuaaaau aaggcuaguc    60
cguuaucaac uugaaaaagu ggcaccgagu cggugcu                             97

<210> SEQ ID NO 573
<211> LENGTH: 97
<212> TYPE: RNA
<213> ORGANISM: Artificial Sequence
<220> FEATURE:
<223> OTHER INFORMATION: Synthetic

<400> SEQUENCE: 573
uggaugguaa cagcuacauc guuuuagagc uagaaauagc aaguuaaaau aaggcuaguc    60
cguuaucaac uugaaaaagu ggcaccgagu cggugcu                             97

<210> SEQ ID NO 574
<211> LENGTH: 97
<212> TYPE: RNA
<213> ORGANISM: Artificial Sequence
<220> FEATURE:
<223> OTHER INFORMATION: Synthetic -continued

<400> SEQUENCE: 574
gcuguuacca uccacauccu guuuuagagc uagaaauagc aaguuaaaau aaggcuaguc    60
cguuaucaac uugaaaaagu ggcaccgagu cggugcu                              97

<210> SEQ ID NO 575
<211> LENGTH: 97
<212> TYPE: RNA
<213> ORGANISM: Artificial Sequence
<220> FEATURE:
<223> OTHER INFORMATION: Synthetic

<400> SEQUENCE: 575
ucaagaacca aggaugugga guuuuagagc uagaaauagc aaguuaaaau aaggcuaguc    60
cguuaucaac uugaaaaagu ggcaccgagu cggugcu                              97

<210> SEQ ID NO 576
<211> LENGTH: 97
<212> TYPE: RNA
<213> ORGANISM: Artificial Sequence
<220> FEATURE:
<223> OTHER INFORMATION: Synthetic

<400> SEQUENCE: 576
uccuucaaga accaaggaug guuuuagagc uagaaauagc aaguuaaaau aaggcuaguc    60
cguuaucaac uugaaaaagu ggcaccgagu cggugcu                              97

<210> SEQ ID NO 577
<211> LENGTH: 97
<212> TYPE: RNA
<213> ORGANISM: Artificial Sequence
<220> FEATURE:
<223> OTHER INFORMATION: Synthetic

<400> SEQUENCE: 577 ugagguguccu ucaagaacca guuuuagagc uagaaauagc aaguuaaaau aaggcuaguc   60
cguuaucaac uugaaaaagu ggcaccgagu cggugcu                              97

<210> SEQ ID NO 578
<211> LENGTH: 97
<212> TYPE: RNA
<213> ORGANISM: Artificial Sequence
<220> FEATURE:
<223> OTHER INFORMATION: Synthetic

<400> SEQUENCE: 578
uuuuauuuua uaacuacaag guuuuagagc uagaaauagc aaguuaaaau aaggcuaguc    60
cguuaucaac uugaaaaagu ggcaccgagu cggugcu                              97

<210> SEQ ID NO 579
<211> LENGTH: 97
<212> TYPE: RNA
<213> ORGANISM: Artificial Sequence
<220> FEATURE:
<223> OTHER INFORMATION: Synthetic

<400> SEQUENCE: 579
uuguuuuuaa uaaaaacaag guuuuagagc uagaaauagc aaguuaaaau aaggcuaguc    60
cguuaucaac uugaaaaagu ggcaccgagu cggugcu                              97

<210> SEQ ID NO 580
<211> LENGTH: 97

```
<212> TYPE: RNA
<213> ORGANISM: Artificial Sequence
<220> FEATURE:
<223> OTHER INFORMATION: Synthetic

<400> SEQUENCE: 580
uauuauagaa ugcuuuugca guuuuagagc uagaaauagc aaguuaaaau aaggcuaguc    60
cguuaucaac uugaaaaagu ggcaccgagu cggugcu                             97

<210> SEQ ID NO 581
<211> LENGTH: 97
<212> TYPE: RNA
<213> ORGANISM: Artificial Sequence
<220> FEATURE:
<223> OTHER INFORMATION: Synthetic

<400> SEQUENCE: 581
caagauuagu cuugauguag guuuuagagc uagaaauagc aaguuaaaau aaggcuaguc    60
cguuaucaac uugaaaaagu ggcaccgagu cggugcu                             97

<210> SEQ ID NO 582
<211> LENGTH: 97
<212> TYPE: RNA
<213> ORGANISM: Artificial Sequence
<220> FEATURE:
<223> OTHER INFORMATION: Synthetic

<400> SEQUENCE: 582
aagauuaguc uugauguagu guuuuagagc uagaaauagc aaguuaaaau aaggcuaguc    60
cguuaucaac uugaaaaagu ggcaccgagu cggugcu                             97

<210> SEQ ID NO 583
<211> LENGTH: 97
<212> TYPE: RNA
<213> ORGANISM: Artificial Sequence
<220> FEATURE:
<223> OTHER INFORMATION: Synthetic

<400> SEQUENCE: 583
agucuugaug uagugggagu guuuuagagc uagaaauagc aaguuaaaau aaggcuaguc    60
cguuaucaac uugaaaaagu ggcaccgagu cggugcu                             97

<210> SEQ ID NO 584
<211> LENGTH: 97
<212> TYPE: RNA
<213> ORGANISM: Artificial Sequence
<220> FEATURE:
<223> OTHER INFORMATION: Synthetic

<400> SEQUENCE: 584
uuuuucuauu aaaaaaaaaa guuuuagagc uagaaauagc aaguuaaaau aaggcuaguc    60
cguuaucaac uugaaaaagu ggcaccgagu cggugcu                             97

<210> SEQ ID NO 585
<211> LENGTH: 97
<212> TYPE: RNA
<213> ORGANISM: Artificial Sequence
<220> FEATURE:
<223> OTHER INFORMATION: Synthetic

<400> SEQUENCE: 585
ucuauuaaaa aaaaaaggc guuuuagagc uagaaauagc aaguuaaaau aaggcuaguc     60
```
cguuaucaac uugaaaaagu ggcaccgagu cggugcu                                    97

<210> SEQ ID NO 586
<211> LENGTH: 97
<212> TYPE: RNA
<213> ORGANISM: Artificial Sequence
<220> FEATURE:
<223> OTHER INFORMATION: Synthetic

<400> SEQUENCE: 586
cuauuaaaaa aaaaaaggcu guuuuagagc uagaaauagc aaguuaaaau aaggcuaguc           60
cguuaucaac uugaaaaagu ggcaccgagu cggugcu                                    97

<210> SEQ ID NO 587
<211> LENGTH: 97
<212> TYPE: RNA
<213> ORGANISM: Artificial Sequence
<220> FEATURE:
<223> OTHER INFORMATION: Synthetic

<400> SEQUENCE: 587
aaaaaaaaaa aggcugggca guuuuagagc uagaaauagc aaguuaaaau aaggcuaguc           60
cguuaucaac uugaaaaagu ggcaccgagu cggugcu                                    97

<210> SEQ ID NO 588
<211> LENGTH: 97
<212> TYPE: RNA
<213> ORGANISM: Artificial Sequence
<220> FEATURE:
<223> OTHER INFORMATION: Synthetic

<400> SEQUENCE: 588
aaaaaaaagg cugggcacgg guuuuagagc uagaaauagc aaguuaaaau aaggcuaguc           60
cguuaucaac uugaaaaagu ggcaccgagu cggugcu                                    97

<210> SEQ ID NO 589
<211> LENGTH: 97
<212> TYPE: RNA
<213> ORGANISM: Artificial Sequence
<220> FEATURE:
<223> OTHER INFORMATION: Synthetic

<400> SEQUENCE: 589
cacccguaau cccagcacuu guuuuagagc uagaaauagc aaguuaaaau aaggcuaguc           60
cguuaucaac uugaaaaagu ggcaccgagu cggugcu                                    97

<210> SEQ ID NO 590
<211> LENGTH: 97
<212> TYPE: RNA
<213> ORGANISM: Artificial Sequence
<220> FEATURE:
<223> OTHER INFORMATION: Synthetic

<400> SEQUENCE: 590
acccguaauc ccagcacuuu guuuuagagc uagaaauagc aaguuaaaau aaggcuaguc           60
cguuaucaac uugaaaaagu ggcaccgagu cggugcu                                    97

<210> SEQ ID NO 591
<211> LENGTH: 97
<212> TYPE: RNA
<213> ORGANISM: Artificial Sequence
<220> FEATURE:
<223> OTHER INFORMATION: Synthetic

<400> SEQUENCE: 591
cguaauccca gcacuuuggg guuuuagagc uagaaauagc aaguuaaaau aaggcuaguc    60
cguuaucaac uugaaaaagu ggcaccgagu cggugcu                            97

<210> SEQ ID NO 592
<211> LENGTH: 97
<212> TYPE: RNA
<213> ORGANISM: Artificial Sequence
<220> FEATURE:
<223> OTHER INFORMATION: Synthetic

<400> SEQUENCE: 592
ucccaaagug cugggauuac guuuuagagc uagaaauagc aaguuaaaau aaggcuaguc    60
cguuaucaac uugaaaaagu ggcaccgagu cggugcu                            97

<210> SEQ ID NO 593
<211> LENGTH: 97
<212> TYPE: RNA
<213> ORGANISM: Artificial Sequence
<220> FEATURE:
<223> OTHER INFORMATION: Synthetic

<400> SEQUENCE: 593
cucccaaagu gcugggauua guuuuagagc uagaaauagc aaguuaaaau aaggcuaguc    60
cguuaucaac uugaaaaagu ggcaccgagu cggugcu                            97

<210> SEQ ID NO 594
<211> LENGTH: 97
<212> TYPE: RNA
<213> ORGANISM: Artificial Sequence
<220> FEATURE:
<223> OTHER INFORMATION: Synthetic

<400> SEQUENCE: 594
cccagcacuu ugggaggccg guuuuagagc uagaaauagc aaguuaaaau aaggcuaguc    60
cguuaucaac uugaaaaagu ggcaccgagu cggugcu                            97

<210> SEQ ID NO 595
<211> LENGTH: 97
<212> TYPE: RNA
<213> ORGANISM: Artificial Sequence
<220> FEATURE:
<223> OTHER INFORMATION: Synthetic

<400> SEQUENCE: 595
ccucggccuc ccaaagugcu guuuuagagc uagaaauagc aaguuaaaau aaggcuaguc    60
cguuaucaac uugaaaaagu ggcaccgagu cggugcu                            97

<210> SEQ ID NO 596
<211> LENGTH: 97
<212> TYPE: RNA
<213> ORGANISM: Artificial Sequence
<220> FEATURE:
<223> OTHER INFORMATION: Synthetic

<400> SEQUENCE: 596
gcacuuuggg aggccgaggc guuuuagagc uagaaauagc aaguuaaaau aaggcuaguc    60
cguuaucaac uugaaaaagu ggcaccgagu cggugcu                            97

<210> SEQ ID NO 597

```
<211> LENGTH: 97
<212> TYPE: RNA
<213> ORGANISM: Artificial Sequence
<220> FEATURE:
<223> OTHER INFORMATION: Synthetic

<400> SEQUENCE: 597
cuuugggagg ccgaggcagg guuuuagagc uagaaauagc aaguuaaaau aaggcuaguc    60
cguuaucaac uugaaaaagu ggcaccgagu cggugcu                            97

<210> SEQ ID NO 598
<211> LENGTH: 97
<212> TYPE: RNA
<213> ORGANISM: Artificial Sequence
<220> FEATURE:
<223> OTHER INFORMATION: Synthetic

<400> SEQUENCE: 598
gccgaggcag guggaucacg guuuuagagc uagaaauagc aaguuaaaau aaggcuaguc    60
cguuaucaac uugaaaaagu ggcaccgagu cggugcu                            97

<210> SEQ ID NO 599
<211> LENGTH: 97
<212> TYPE: RNA
<213> ORGANISM: Artificial Sequence
<220> FEATURE:
<223> OTHER INFORMATION: Synthetic

<400> SEQUENCE: 599
accucgugau ccaccugccu guuuuagagc uagaaauagc aaguuaaaau aaggcuaguc    60
cguuaucaac uugaaaaagu ggcaccgagu cggugcu                            97

<210> SEQ ID NO 600
<211> LENGTH: 97
<212> TYPE: RNA
<213> ORGANISM: Artificial Sequence
<220> FEATURE:
<223> OTHER INFORMATION: Synthetic

<400> SEQUENCE: 600
ggcaggugga ucacgagguc guuuuagagc uagaaauagc aaguuaaaau aaggcuaguc    60
cguuaucaac uugaaaaagu ggcaccgagu cggugcu                            97

<210> SEQ ID NO 601
<211> LENGTH: 97
<212> TYPE: RNA
<213> ORGANISM: Artificial Sequence
<220> FEATURE:
<223> OTHER INFORMATION: Synthetic

<400> SEQUENCE: 601
ucaggagauc gagaccaucu guuuuagagc uagaaauagc aaguuaaaau aaggcuaguc    60
cguuaucaac uugaaaaagu ggcaccgagu cggugcu                            97

<210> SEQ ID NO 602
<211> LENGTH: 97
<212> TYPE: RNA
<213> ORGANISM: Artificial Sequence
<220> FEATURE:
<223> OTHER INFORMATION: Synthetic

<400> SEQUENCE: 602
cgagaccauc uuggcuaaca guuuuagagc uagaaauagc aaguuaaaau aaggcuaguc    60
```

```
cguuaucaac uugaaaaagu ggcaccgagu cggugcu                              97
```

<210> SEQ ID NO 603
<211> LENGTH: 97
<212> TYPE: RNA
<213> ORGANISM: Artificial Sequence
<220> FEATURE:
<223> OTHER INFORMATION: Synthetic

<400> SEQUENCE: 603

```
uuucaccaug uuagccaaga guuuagagc uagaaauagc aaguuaaaau aaggcuaguc      60
cguuaucaac uugaaaaagu ggcaccgagu cggugcu                              97
```

<210> SEQ ID NO 604
<211> LENGTH: 97
<212> TYPE: RNA
<213> ORGANISM: Artificial Sequence
<220> FEATURE:
<223> OTHER INFORMATION: Synthetic

<400> SEQUENCE: 604

```
uuguauuuuu uguagagacg guuuagagc uagaaauagc aaguuaaaau aaggcuaguc      60
cguuaucaac uugaaaaagu ggcaccgagu cggugcu                              97
```

<210> SEQ ID NO 605
<211> LENGTH: 97
<212> TYPE: RNA
<213> ORGANISM: Artificial Sequence
<220> FEATURE:
<223> OTHER INFORMATION: Synthetic

<400> SEQUENCE: 605

```
uuuguauuuu uuguagagac guuuagagc uagaaauagc aaguuaaaau aaggcuaguc      60
cguuaucaac uugaaaaagu ggcaccgagu cggugcu                              97
```

<210> SEQ ID NO 606
<211> LENGTH: 97
<212> TYPE: RNA
<213> ORGANISM: Artificial Sequence
<220> FEATURE:
<223> OTHER INFORMATION: Synthetic

<400> SEQUENCE: 606

```
uuuuguauuu uuuguagaga guuuagagc uagaaauagc aaguuaaaau aaggcuaguc      60
cguuaucaac uugaaaaagu ggcaccgagu cggugcu                              97
```

<210> SEQ ID NO 607
<211> LENGTH: 97
<212> TYPE: RNA
<213> ORGANISM: Artificial Sequence
<220> FEATURE:
<223> OTHER INFORMATION: Synthetic

<400> SEQUENCE: 607

```
aaaaaauaca aaaauuagc guuuagagc uagaaauagc aaguuaaaau aaggcuaguc       60
cguuaucaac uugaaaaagu ggcaccgagu cggugcu                              97
```

<210> SEQ ID NO 608
<211> LENGTH: 97
<212> TYPE: RNA
<213> ORGANISM: Artificial Sequence
<220> FEATURE:

<223> OTHER INFORMATION: Synthetic

<400> SEQUENCE: 608
aaaaauacaa aaaauuagcc guuuuagagc uagaaauagc aaguuaaaau aaggcuaguc    60
cguuaucaac uugaaaaagu ggcaccgagu cggugcu                            97

<210> SEQ ID NO 609
<211> LENGTH: 97
<212> TYPE: RNA
<213> ORGANISM: Artificial Sequence
<220> FEATURE:
<223> OTHER INFORMATION: Synthetic

<400> SEQUENCE: 609
uacaaaaaau uagccgggug guuuuagagc uagaaauagc aaguuaaaau aaggcuaguc    60
cguuaucaac uugaaaaagu ggcaccgagu cggugcu                            97

<210> SEQ ID NO 610
<211> LENGTH: 97
<212> TYPE: RNA
<213> ORGANISM: Artificial Sequence
<220> FEATURE:
<223> OTHER INFORMATION: Synthetic

<400> SEQUENCE: 610 aaaaauuag ccggguguggu guuuuagagc uagaaauagc aaguuaaaau aaggcuaguc    60
cguuaucaac uugaaaaagu ggcaccgagu cggugcu                            97

<210> SEQ ID NO 611
<211> LENGTH: 97
<212> TYPE: RNA
<213> ORGANISM: Artificial Sequence
<220> FEATURE:
<223> OTHER INFORMATION: Synthetic

<400> SEQUENCE: 611
aaauuagccg ggguguggugg guuuuagagc uagaaauagc aaguuaaaau aaggcuaguc    60
cguuaucaac uugaaaaagu ggcaccgagu cggugcu                            97

<210> SEQ ID NO 612
<211> LENGTH: 97
<212> TYPE: RNA
<213> ORGANISM: Artificial Sequence
<220> FEATURE:
<223> OTHER INFORMATION: Synthetic

<400> SEQUENCE: 612
aauuagccgg guguggguggc guuuuagagc uagaaauagc aaguuaaaau aaggcuaguc    60
cguuaucaac uugaaaaagu ggcaccgagu cggugcu                            97

<210> SEQ ID NO 613
<211> LENGTH: 97
<212> TYPE: RNA
<213> ORGANISM: Artificial Sequence
<220> FEATURE:
<223> OTHER INFORMATION: Synthetic

<400> SEQUENCE: 613
caggcgcccg ccaccacacc guuuuagagc uagaaauagc aaguuaaaau aaggcuaguc    60
cguuaucaac uugaaaaagu ggcaccgagu cggugcu                            97

```
<210> SEQ ID NO 614
<211> LENGTH: 97
<212> TYPE: RNA
<213> ORGANISM: Artificial Sequence
<220> FEATURE:
<223> OTHER INFORMATION: Synthetic

<400> SEQUENCE: 614
gccuguaguc ccagcuacuc guuuuagagc uagaaauagc aaguuaaaau aaggcuaguc    60
cguuaucaac uugaaaaagu ggcaccgagu cggugcu                             97

<210> SEQ ID NO 615
<211> LENGTH: 97
<212> TYPE: RNA
<213> ORGANISM: Artificial Sequence
<220> FEATURE:
<223> OTHER INFORMATION: Synthetic

<400> SEQUENCE: 615
uguaguccca gcuacucagg guuuuagagc uagaaauagc aaguuaaaau aaggcuaguc    60
cguuaucaac uugaaaaagu ggcaccgagu cggugcu                             97

<210> SEQ ID NO 616
<211> LENGTH: 97
<212> TYPE: RNA
<213> ORGANISM: Artificial Sequence
<220> FEATURE:
<223> OTHER INFORMATION: Synthetic

<400> SEQUENCE: 616
uccugaguag cugggacuac guuuuagagc uagaaauagc aaguuaaaau aaggcuaguc    60
cguuaucaac uugaaaaagu ggcaccgagu cggugcu                             97

<210> SEQ ID NO 617
<211> LENGTH: 97
<212> TYPE: RNA
<213> ORGANISM: Artificial Sequence
<220> FEATURE:
<223> OTHER INFORMATION: Synthetic

<400> SEQUENCE: 617
cccagcuacu caggaggcug guuuuagagc uagaaauagc aaguuaaaau aaggcuaguc    60
cguuaucaac uugaaaaagu ggcaccgagu cggugcu                             97

<210> SEQ ID NO 618
<211> LENGTH: 97
<212> TYPE: RNA
<213> ORGANISM: Artificial Sequence
<220> FEATURE:
<223> OTHER INFORMATION: Synthetic

<400> SEQUENCE: 618
ccucagccuc cugaguagcu guuuuagagc uagaaauagc aaguuaaaau aaggcuaguc    60
cguuaucaac uugaaaaagu ggcaccgagu cggugcu                             97

<210> SEQ ID NO 619
<211> LENGTH: 97
<212> TYPE: RNA
<213> ORGANISM: Artificial Sequence
<220> FEATURE:
<223> OTHER INFORMATION: Synthetic

<400> SEQUENCE: 619
```

```
gccucagccu ccugaguagc guuuuagagc uagaaauagc aaguuaaaau aaggcuaguc    60
cguuaucaac uugaaaaagu ggcaccgagu cggugcu                             97
```

<210> SEQ ID NO 620
<211> LENGTH: 97
<212> TYPE: RNA
<213> ORGANISM: Artificial Sequence
<220> FEATURE:
<223> OTHER INFORMATION: Synthetic

<400> SEQUENCE: 620

```
aggaggcuga ggcaggagaa guuuuagagc uagaaauagc aaguuaaaau aaggcuaguc    60
cguuaucaac uugaaaaagu ggcaccgagu cggugcu                             97
```

<210> SEQ ID NO 621
<211> LENGTH: 97
<212> TYPE: RNA
<213> ORGANISM: Artificial Sequence
<220> FEATURE:
<223> OTHER INFORMATION: Synthetic

<400> SEQUENCE: 621

```
gcaggagaau ggcgugaacc guuuuagagc uagaaauagc aaguuaaaau aaggcuaguc    60
cguuaucaac uugaaaaagu ggcaccgagu cggugcu                             97
```

<210> SEQ ID NO 622
<211> LENGTH: 97
<212> TYPE: RNA
<213> ORGANISM: Artificial Sequence
<220> FEATURE:
<223> OTHER INFORMATION: Synthetic

<400> SEQUENCE: 622

```
caggagaaug gcgugaaccc guuuuagagc uagaaauagc aaguuaaaau aaggcuaguc    60
cguuaucaac uugaaaaagu ggcaccgagu cggugcu                             97
```

<210> SEQ ID NO 623
<211> LENGTH: 97
<212> TYPE: RNA
<213> ORGANISM: Artificial Sequence
<220> FEATURE:
<223> OTHER INFORMATION: Synthetic

<400> SEQUENCE: 623

```
gagaauggcg ugaacccggg guuuuagagc uagaaauagc aaguuaaaau aaggcuaguc    60
cguuaucaac uugaaaaagu ggcaccgagu cggugcu                             97
```

<210> SEQ ID NO 624
<211> LENGTH: 97
<212> TYPE: RNA
<213> ORGANISM: Artificial Sequence
<220> FEATURE:
<223> OTHER INFORMATION: Synthetic

<400> SEQUENCE: 624

```
aauggcguga acccgggagg guuuuagagc uagaaauagc aaguuaaaau aaggcuaguc    60
cguuaucaac uugaaaaagu ggcaccgagu cggugcu                             97
```

<210> SEQ ID NO 625
<211> LENGTH: 97
<212> TYPE: RNA
<213> ORGANISM: Artificial Sequence

```
<220> FEATURE:
<223> OTHER INFORMATION: Synthetic

<400> SEQUENCE: 625
cacugcaagc uccaccuccc guuuuagagc uagaaauagc aaguuaaaau aaggcuaguc    60
cguuaucaac uugaaaaagu ggcaccgagu cggugcu                              97

<210> SEQ ID NO 626
<211> LENGTH: 97
<212> TYPE: RNA
<213> ORGANISM: Artificial Sequence
<220> FEATURE:
<223> OTHER INFORMATION: Synthetic

<400> SEQUENCE: 626
ucacugcaag cuccaccucc guuuuagagc uagaaauagc aaguuaaaau aaggcuaguc    60
cguuaucaac uugaaaaagu ggcaccgagu cggugcu                              97

<210> SEQ ID NO 627
<211> LENGTH: 97
<212> TYPE: RNA
<213> ORGANISM: Artificial Sequence
<220> FEATURE:
<223> OTHER INFORMATION: Synthetic

<400> SEQUENCE: 627
cauaccacug cacuccagcc guuuuagagc uagaaauagc aaguuaaaau aaggcuaguc    60
cguuaucaac uugaaaaagu ggcaccgagu cggugcu                              97

<210> SEQ ID NO 628
<211> LENGTH: 97
<212> TYPE: RNA
<213> ORGANISM: Artificial Sequence
<220> FEATURE:
<223> OTHER INFORMATION: Synthetic

<400> SEQUENCE: 628
auaccacugc acuccagccu guuuuagagc uagaaauagc aaguuaaaau aaggcuaguc    60
cguuaucaac uugaaaaagu ggcaccgagu cggugcu                              97

<210> SEQ ID NO 629
<211> LENGTH: 97
<212> TYPE: RNA
<213> ORGANISM: Artificial Sequence
<220> FEATURE:
<223> OTHER INFORMATION: Synthetic

<400> SEQUENCE: 629
ucgcccaggc uggagugcag guuuuagagc uagaaauagc aaguuaaaau aaggcuaguc    60
cguuaucaac uugaaaaagu ggcaccgagu cggugcu                              97

<210> SEQ ID NO 630
<211> LENGTH: 97
<212> TYPE: RNA
<213> ORGANISM: Artificial Sequence
<220> FEATURE:
<223> OTHER INFORMATION: Synthetic

<400> SEQUENCE: 630
ucucacucuu ucgcccaggc guuuuagagc uagaaauagc aaguuaaaau aaggcuaguc    60
cguuaucaac uugaaaaagu ggcaccgagu cggugcu                              97
```

<210> SEQ ID NO 631
<211> LENGTH: 97
<212> TYPE: RNA
<213> ORGANISM: Artificial Sequence
<220> FEATURE:
<223> OTHER INFORMATION: Synthetic

<400> SEQUENCE: 631

```
ggagucucac ucuuucgccc guuuuagagc uagaaauagc aaguuaaaau aaggcuaguc     60
cguuaucaac uugaaaaagu ggcaccgagu cggugcu                             97
```

<210> SEQ ID NO 632
<211> LENGTH: 97
<212> TYPE: RNA
<213> ORGANISM: Artificial Sequence
<220> FEATURE:
<223> OTHER INFORMATION: Synthetic

<400> SEQUENCE: 632

```
uguuuuuugu uuuuugaga guuuuagagc uagaaauagc aaguuaaaau aaggcuaguc      60
cguuaucaac uugaaaaagu ggcaccgagu cggugcu                             97
```

<210> SEQ ID NO 633
<211> LENGTH: 97
<212> TYPE: RNA
<213> ORGANISM: Artificial Sequence
<220> FEATURE:
<223> OTHER INFORMATION: Synthetic

<400> SEQUENCE: 633

```
aggaagaaag aaagguuuuu guuuuagagc uagaaauagc aaguuaaaau aaggcuaguc     60
cguuaucaac uugaaaaagu ggcaccgagu cggugcu                             97
```

<210> SEQ ID NO 634
<211> LENGTH: 97
<212> TYPE: RNA
<213> ORGANISM: Artificial Sequence
<220> FEATURE:
<223> OTHER INFORMATION: Synthetic

<400> SEQUENCE: 634

```
agaagaaaag gaagaaagaa guuuuagagc uagaaauagc aaguuaaaau aaggcuaguc     60
cguuaucaac uugaaaaagu ggcaccgagu cggugcu                             97
```

<210> SEQ ID NO 635
<211> LENGTH: 97
<212> TYPE: RNA
<213> ORGANISM: Artificial Sequence
<220> FEATURE:
<223> OTHER INFORMATION: Synthetic

<400> SEQUENCE: 635

```
cuuucuuccu uuucuucucu guuuuagagc uagaaauagc aaguuaaaau aaggcuaguc     60
cguuaucaac uugaaaaagu ggcaccgagu cggugcu                             97
```

<210> SEQ ID NO 636
<211> LENGTH: 97
<212> TYPE: RNA
<213> ORGANISM: Artificial Sequence
<220> FEATURE:
<223> OTHER INFORMATION: Synthetic

<400> SEQUENCE: 636

```
uuucuuccuu uucuucucuu guuuuagagc uagaaauagc aaguuaaaau aaggcuaguc    60
cguuaucaac uugaaaaagu ggcaccgagu cggugcu                             97

<210> SEQ ID NO 637
<211> LENGTH: 97
<212> TYPE: RNA
<213> ORGANISM: Artificial Sequence
<220> FEATURE:
<223> OTHER INFORMATION: Synthetic

<400> SEQUENCE: 637
aauggaccca agagaagaaa guuuuagagc uagaaauagc aaguuaaaau aaggcuaguc    60
cguuaucaac uugaaaaagu ggcaccgagu cggugcu                             97

<210> SEQ ID NO 638
<211> LENGTH: 97
<212> TYPE: RNA
<213> ORGANISM: Artificial Sequence
<220> FEATURE:
<223> OTHER INFORMATION: Synthetic

<400> SEQUENCE: 638
ggcuauuaca uaagaaacaa guuuuagagc uagaaauagc aaguuaaaau aaggcuaguc    60
cguuaucaac uugaaaaagu ggcaccgagu cggugcu                             97

<210> SEQ ID NO 639
<211> LENGTH: 97
<212> TYPE: RNA
<213> ORGANISM: Artificial Sequence
<220> FEATURE:
<223> OTHER INFORMATION: Synthetic

<400> SEQUENCE: 639
cacaggaaaa ggaacuguac guuuuagagc uagaaauagc aaguuaaaau aaggcuaguc    60
cguuaucaac uugaaaaagu ggcaccgagu cggugcu                             97

<210> SEQ ID NO 640
<211> LENGTH: 97
<212> TYPE: RNA
<213> ORGANISM: Artificial Sequence
<220> FEATURE:
<223> OTHER INFORMATION: Synthetic

<400> SEQUENCE: 640
auuaaagcua acacaggaaa guuuuagagc uagaaauagc aaguuaaaau aaggcuaguc    60
cguuaucaac uugaaaaagu ggcaccgagu cggugcu                             97

<210> SEQ ID NO 641
<211> LENGTH: 97
<212> TYPE: RNA
<213> ORGANISM: Artificial Sequence
<220> FEATURE:
<223> OTHER INFORMATION: Synthetic

<400> SEQUENCE: 641
ucaaaaauua aagcuaacac guuuuagagc uagaaauagc aaguuaaaau aaggcuaguc    60
cguuaucaac uugaaaaagu ggcaccgagu cggugcu                             97

<210> SEQ ID NO 642
<211> LENGTH: 97
<212> TYPE: RNA
```

```
<213> ORGANISM: Artificial Sequence
<220> FEATURE:
<223> OTHER INFORMATION: Synthetic

<400> SEQUENCE: 642
uaaaauuguc uaaacaucuc guuuuagagc uagaaauagc aaguuaaaau aaggcuaguc    60
cguuaucaac uugaaaaagu ggcaccgagu cggugcu                             97

<210> SEQ ID NO 643
<211> LENGTH: 97
<212> TYPE: RNA
<213> ORGANISM: Artificial Sequence
<220> FEATURE:
<223> OTHER INFORMATION: Synthetic

<400> SEQUENCE: 643
agagauguuu agacaauuuu guuuuagagc uagaaauagc aaguuaaaau aaggcuaguc    60
cguuaucaac uugaaaaagu ggcaccgagu cggugcu                             97

<210> SEQ ID NO 644
<211> LENGTH: 97
<212> TYPE: RNA
<213> ORGANISM: Artificial Sequence
<220> FEATURE:
<223> OTHER INFORMATION: Synthetic

<400> SEQUENCE: 644
ucuaaacauc ucugggacca guuuuagagc uagaaauagc aaguuaaaau aaggcuaguc    60
cguuaucaac uugaaaaagu ggcaccgagu cggugcu                             97

<210> SEQ ID NO 645
<211> LENGTH: 97
<212> TYPE: RNA
<213> ORGANISM: Artificial Sequence
<220> FEATURE:
<223> OTHER INFORMATION: Synthetic

<400> SEQUENCE: 645
uuuaugcuuu cauauauccu guuuuagagc uagaaauagc aaguuaaaau aaggcuaguc    60
cguuaucaac uugaaaaagu ggcaccgagu cggugcu                             97

<210> SEQ ID NO 646
<211> LENGTH: 97
<212> TYPE: RNA
<213> ORGANISM: Artificial Sequence
<220> FEATURE:
<223> OTHER INFORMATION: Synthetic

<400> SEQUENCE: 646
agcauaaauu acaaagaaaa guuuuagagc uagaaauagc aaguuaaaau aaggcuaguc    60
cguuaucaac uugaaaaagu ggcaccgagu cggugcu                             97

<210> SEQ ID NO 647
<211> LENGTH: 97
<212> TYPE: RNA
<213> ORGANISM: Artificial Sequence
<220> FEATURE:
<223> OTHER INFORMATION: Synthetic

<400> SEQUENCE: 647
uacaaagaaa aagguuauca guuuuagagc uagaaauagc aaguuaaaau aaggcuaguc    60
cguuaucaac uugaaaaagu ggcaccgagu cggugcu                             97
```

<210> SEQ ID NO 648
<211> LENGTH: 97
<212> TYPE: RNA
<213> ORGANISM: Artificial Sequence
<220> FEATURE:
<223> OTHER INFORMATION: Synthetic

<400> SEQUENCE: 648
acaaagaaaa agguuaucau guuuuagagc uagaaauagc aaguuaaaau aaggcuaguc    60
cguuaucaac uugaaaaagu ggcaccgagu cggugcu                            97

<210> SEQ ID NO 649
<211> LENGTH: 97
<212> TYPE: RNA
<213> ORGANISM: Artificial Sequence
<220> FEATURE:
<223> OTHER INFORMATION: Synthetic

<400> SEQUENCE: 649
caaagaaaaa gguuaucaug guuuuagagc uagaaauagc aaguuaaaau aaggcuaguc    60
cguuaucaac uugaaaaagu ggcaccgagu cggugcu                            97

<210> SEQ ID NO 650
<211> LENGTH: 97
<212> TYPE: RNA
<213> ORGANISM: Artificial Sequence
<220> FEATURE:
<223> OTHER INFORMATION: Synthetic

<400> SEQUENCE: 650
ucugagauuu aaaauagagu guuuuagagc uagaaauagc aaguuaaaau aaggcuaguc    60
cguuaucaac uugaaaaagu ggcaccgagu cggugcu                            97

<210> SEQ ID NO 651
<211> LENGTH: 97
<212> TYPE: RNA
<213> ORGANISM: Artificial Sequence
<220> FEATURE:
<223> OTHER INFORMATION: Synthetic

<400> SEQUENCE: 651
cuuauaagau acauuaugaa guuuuagagc uagaaauagc aaguuaaaau aaggcuaguc    60
cguuaucaac uugaaaaagu ggcaccgagu cggugcu                            97

<210> SEQ ID NO 652
<211> LENGTH: 97
<212> TYPE: RNA
<213> ORGANISM: Artificial Sequence
<220> FEATURE:
<223> OTHER INFORMATION: Synthetic

<400> SEQUENCE: 652
uaucuuauaa gacuauaaaa guuuuagagc uagaaauagc aaguuaaaau aaggcuaguc    60
cguuaucaac uugaaaaagu ggcaccgagu cggugcu                            97

<210> SEQ ID NO 653
<211> LENGTH: 97
<212> TYPE: RNA
<213> ORGANISM: Artificial Sequence
<220> FEATURE:
<223> OTHER INFORMATION: Synthetic

```
<400> SEQUENCE: 653
aucuuauaag acuauaaaaa guuuuagagc uagaaauagc aaguuaaaau aaggcuaguc    60
cguuaucaac uugaaaaagu ggcaccgagu cggugcu                            97

<210> SEQ ID NO 654
<211> LENGTH: 97
<212> TYPE: RNA
<213> ORGANISM: Artificial Sequence
<220> FEATURE:
<223> OTHER INFORMATION: Synthetic

<400> SEQUENCE: 654
uuauaagacu auaaaaaggg guuuuagagc uagaaauagc aaguuaaaau aaggcuaguc    60
cguuaucaac uugaaaaagu ggcaccgagu cggugcu                            97

<210> SEQ ID NO 655
<211> LENGTH: 97
<212> TYPE: RNA
<213> ORGANISM: Artificial Sequence
<220> FEATURE:
<223> OTHER INFORMATION: Synthetic

<400> SEQUENCE: 655
uaaaaaggga ggaaauauag guuuuagagc uagaaauagc aaguuaaaau aaggcuaguc    60
cguuaucaac uugaaaaagu ggcaccgagu cggugcu                            97

<210> SEQ ID NO 656
<211> LENGTH: 97
<212> TYPE: RNA
<213> ORGANISM: Artificial Sequence
<220> FEATURE:
<223> OTHER INFORMATION: Synthetic

<400> SEQUENCE: 656
aaaaagggag gaaauauaga guuuuagagc uagaaauagc aaguuaaaau aaggcuaguc    60
cguuaucaac uugaaaaagu ggcaccgagu cggugcu                            97

<210> SEQ ID NO 657
<211> LENGTH: 97
<212> TYPE: RNA
<213> ORGANISM: Artificial Sequence
<220> FEATURE:
<223> OTHER INFORMATION: Synthetic

<400> SEQUENCE: 657
aaauauagag gguccacuuu guuuuagagc uagaaauagc aaguuaaaau aaggcuaguc    60
cguuaucaac uugaaaaagu ggcaccgagu cggugcu                            97

<210> SEQ ID NO 658
<211> LENGTH: 97
<212> TYPE: RNA
<213> ORGANISM: Artificial Sequence
<220> FEATURE:
<223> OTHER INFORMATION: Synthetic

<400> SEQUENCE: 658
uauagagggu ccacuuuugg guuuuagagc uagaaauagc aaguuaaaau aaggcuaguc    60
cguuaucaac uugaaaaagu ggcaccgagu cggugcu                            97

<210> SEQ ID NO 659
<211> LENGTH: 97
```

<212> TYPE: RNA
<213> ORGANISM: Artificial Sequence
<220> FEATURE:
<223> OTHER INFORMATION: Synthetic

<400> SEQUENCE: 659
acucugaagu ccaccaaaag guuuuagagc uagaaauagc aaguuaaaau aaggcuaguc    60
cguuaucaac uugaaaaagu ggcaccgagu cggugcu                            97

<210> SEQ ID NO 660
<211> LENGTH: 97
<212> TYPE: RNA
<213> ORGANISM: Artificial Sequence
<220> FEATURE:
<223> OTHER INFORMATION: Synthetic

<400> SEQUENCE: 660
agaauagagu ugcaccguuu guuuuagagc uagaaauagc aaguuaaaau aaggcuaguc    60
cguuaucaac uugaaaaagu ggcaccgagu cggugcu                            97

<210> SEQ ID NO 661
<211> LENGTH: 97
<212> TYPE: RNA
<213> ORGANISM: Artificial Sequence
<220> FEATURE:
<223> OTHER INFORMATION: Synthetic

<400> SEQUENCE: 661
aaaacggugc aacucuauuc guuuuagagc uagaaauagc aaguuaaaau aaggcuaguc    60
cguuaucaac uugaaaaagu ggcaccgagu cggugcu                            97

<210> SEQ ID NO 662
<211> LENGTH: 97
<212> TYPE: RNA
<213> ORGANISM: Artificial Sequence
<220> FEATURE:
<223> OTHER INFORMATION: Synthetic

<400> SEQUENCE: 662
ccguuuuggg cuaaugaaaa guuuuagagc uagaaauagc aaguuaaaau aaggcuaguc    60
cguuaucaac uugaaaaagu ggcaccgagu cggugcu                            97

<210> SEQ ID NO 663
<211> LENGTH: 97
<212> TYPE: RNA
<213> ORGANISM: Artificial Sequence
<220> FEATURE:
<223> OTHER INFORMATION: Synthetic

<400> SEQUENCE: 663
ccuuuuucau uagcccaaaa guuuuagagc uagaaauagc aaguuaaaau aaggcuaguc    60
cguuaucaac uugaaaaagu ggcaccgagu cggugcu                            97

<210> SEQ ID NO 664
<211> LENGTH: 97
<212> TYPE: RNA
<213> ORGANISM: Artificial Sequence
<220> FEATURE:
<223> OTHER INFORMATION: Synthetic

<400> SEQUENCE: 664
ugggcuaaug aaaaaggaag guuuuagagc uagaaauagc aaguuaaaau aaggcuaguc    60
cguuaucaac uugaaaaagu ggcaccgagu cggugcu 97

<210> SEQ ID NO 665
<211> LENGTH: 97
<212> TYPE: RNA
<213> ORGANISM: Artificial Sequence
<220> FEATURE:
<223> OTHER INFORMATION: Synthetic

<400> SEQUENCE: 665
uaaugaaaaa ggaagaggcu guuuuagagc uagaaauagc aaguuaaaau aaggcuaguc 60
cguuaucaac uugaaaaagu ggcaccgagu cggugcu 97

<210> SEQ ID NO 666
<211> LENGTH: 97
<212> TYPE: RNA
<213> ORGANISM: Artificial Sequence
<220> FEATURE:
<223> OTHER INFORMATION: Synthetic

<400> SEQUENCE: 666
aaugaaaaag gaagaggcua guuuuagagc uagaaauagc aaguuaaaau aaggcuaguc 60
cguuaucaac uugaaaaagu ggcaccgagu cggugcu 97

<210> SEQ ID NO 667
<211> LENGTH: 97
<212> TYPE: RNA
<213> ORGANISM: Artificial Sequence
<220> FEATURE:
<223> OTHER INFORMATION: Synthetic

<400> SEQUENCE: 667
cugaaucuua aaauaugucc guuuuagagc uagaaauagc aaguuaaaau aaggcuaguc 60
cguuaucaac uugaaaaagu ggcaccgagu cggugcu 97

<210> SEQ ID NO 668
<211> LENGTH: 97
<212> TYPE: RNA
<213> ORGANISM: Artificial Sequence
<220> FEATURE:
<223> OTHER INFORMATION: Synthetic

<400> SEQUENCE: 668
caggcagcuu uaucucaacc guuuuagagc uagaaauagc aaguuaaaau aaggcuaguc 60
cguuaucaac uugaaaaagu ggcaccgagu cggugcu 97

<210> SEQ ID NO 669
<211> LENGTH: 97
<212> TYPE: RNA
<213> ORGANISM: Artificial Sequence
<220> FEATURE:
<223> OTHER INFORMATION: Synthetic

<400> SEQUENCE: 669
cuaagagauc aaguuucagc guuuuagagc uagaaauagc aaguuaaaau aaggcuaguc 60
cguuaucaac uugaaaaagu ggcaccgagu cggugcu 97

<210> SEQ ID NO 670
<211> LENGTH: 97
<212> TYPE: RNA
<213> ORGANISM: Artificial Sequence
<220> FEATURE:
<223> OTHER INFORMATION: Synthetic

<400> SEQUENCE: 670
guguucuugu ugauauucug guuuuagagc uagaaauagc aaguuaaaau aaggcuaguc    60
cguuaucaac uugaaaaagu ggcaccgagu cggugcu                              97

<210> SEQ ID NO 671
<211> LENGTH: 97
<212> TYPE: RNA
<213> ORGANISM: Artificial Sequence
<220> FEATURE:
<223> OTHER INFORMATION: Synthetic

<400> SEQUENCE: 671
cuuguugaua uucuguggca guuuuagagc uagaaauagc aaguuaaaau aaggcuaguc    60
cguuaucaac uugaaaaagu ggcaccgagu cggugcu                              97

<210> SEQ ID NO 672
<211> LENGTH: 97
<212> TYPE: RNA
<213> ORGANISM: Artificial Sequence
<220> FEATURE:
<223> OTHER INFORMATION: Synthetic

<400> SEQUENCE: 672
ucuguggcau ggcuacagau guuuuagagc uagaaauagc aaguuaaaau aaggcuaguc    60
cguuaucaac uugaaaaagu ggcaccgagu cggugcu                              97

<210> SEQ ID NO 673
<211> LENGTH: 97
<212> TYPE: RNA
<213> ORGANISM: Artificial Sequence
<220> FEATURE:
<223> OTHER INFORMATION: Synthetic

<400> SEQUENCE: 673
agaacuuauu uacacaggga guuuuagagc uagaaauagc aaguuaaaau aaggcuaguc    60
cguuaucaac uugaaaaagu ggcaccgagu cggugcu                              97

<210> SEQ ID NO 674
<211> LENGTH: 97
<212> TYPE: RNA
<213> ORGANISM: Artificial Sequence
<220> FEATURE:
<223> OTHER INFORMATION: Synthetic

<400> SEQUENCE: 674
aaagagaacu uauuuacaca guuuuagagc uagaaauagc aaguuaaaau aaggcuaguc    60
cguuaucaac uugaaaaagu ggcaccgagu cggugcu                              97

<210> SEQ ID NO 675
<211> LENGTH: 97
<212> TYPE: RNA
<213> ORGANISM: Artificial Sequence
<220> FEATURE:
<223> OTHER INFORMATION: Synthetic

<400> SEQUENCE: 675
caaagagaac uuauuuacac guuuuagagc uagaaauagc aaguuaaaau aaggcuaguc    60
cguuaucaac uugaaaaagu ggcaccgagu cggugcu                              97

<210> SEQ ID NO 676

```
<211> LENGTH: 97
<212> TYPE: RNA
<213> ORGANISM: Artificial Sequence
<220> FEATURE:
<223> OTHER INFORMATION: Synthetic

<400> SEQUENCE: 676
uucucuuugu auuuacuuuu guuuuagagc uagaaauagc aaguuaaaau aaggcuaguc      60
cguuaucaac uugaaaaagu ggcaccgagu cggugcu                              97

<210> SEQ ID NO 677
<211> LENGTH: 97
<212> TYPE: RNA
<213> ORGANISM: Artificial Sequence
<220> FEATURE:
<223> OTHER INFORMATION: Synthetic

<400> SEQUENCE: 677
ucucuuugua uuuacuuuua guuuuagagc uagaaauagc aaguuaaaau aaggcuaguc      60
cguuaucaac uugaaaaagu ggcaccgagu cggugcu                              97

<210> SEQ ID NO 678
<211> LENGTH: 97
<212> TYPE: RNA
<213> ORGANISM: Artificial Sequence
<220> FEATURE:
<223> OTHER INFORMATION: Synthetic

<400> SEQUENCE: 678
cuuuguauuu acuuuaaggg guuuuagagc uagaaauagc aaguuaaaau aaggcuaguc      60
cguuaucaac uugaaaaagu ggcaccgagu cggugcu                              97

<210> SEQ ID NO 679
<211> LENGTH: 97
<212> TYPE: RNA
<213> ORGANISM: Artificial Sequence
<220> FEATURE:
<223> OTHER INFORMATION: Synthetic

<400> SEQUENCE: 679
agcuuuuguc caccuuuaaa guuuuagagc uagaaauagc aaguuaaaau aaggcuaguc      60
cguuaucaac uugaaaaagu ggcaccgagu cggugcu                              97

<210> SEQ ID NO 680
<211> LENGTH: 97
<212> TYPE: RNA
<213> ORGANISM: Artificial Sequence
<220> FEATURE:
<223> OTHER INFORMATION: Synthetic

<400> SEQUENCE: 680
uuuauuuuuc cauuuaaagg guuuuagagc uagaaauagc aaguuaaaau aaggcuaguc      60
cguuaucaac uugaaaaagu ggcaccgagu cggugcu                              97

<210> SEQ ID NO 681
<211> LENGTH: 97
<212> TYPE: RNA
<213> ORGANISM: Artificial Sequence
<220> FEATURE:
<223> OTHER INFORMATION: Synthetic

<400> SEQUENCE: 681
uauuuuauuu uuccauuuaa guuuuagagc uagaaauagc aaguuaaaau aaggcuaguc      60
```
cguuaucaac uugaaaaagu ggcaccgagu cggugcu                                    97

<210> SEQ ID NO 682
<211> LENGTH: 97
<212> TYPE: RNA
<213> ORGANISM: Artificial Sequence
<220> FEATURE:
<223> OTHER INFORMATION: Synthetic

<400> SEQUENCE: 682
cuuacauaaa cauacuuaaa guuuuagagc uagaaauagc aaguuaaaau aaggcuaguc            60
cguuaucaac uugaaaaagu ggcaccgagu cggugcu                                    97

<210> SEQ ID NO 683
<211> LENGTH: 97
<212> TYPE: RNA
<213> ORGANISM: Artificial Sequence
<220> FEATURE:
<223> OTHER INFORMATION: Synthetic

<400> SEQUENCE: 683
uaagcacaga aguuuuuaag guuuuagagc uagaaauagc aaguuaaaau aaggcuaguc            60
cguuaucaac uugaaaaagu ggcaccgagu cggugcu                                    97

<210> SEQ ID NO 684
<211> LENGTH: 97
<212> TYPE: RNA
<213> ORGANISM: Artificial Sequence
<220> FEATURE:
<223> OTHER INFORMATION: Synthetic

<400> SEQUENCE: 684
aaguuuuuaa gaggcaugaa guuuuagagc uagaaauagc aaguuaaaau aaggcuaguc            60
cguuaucaac uugaaaaagu ggcaccgagu cggugcu                                    97

<210> SEQ ID NO 685
<211> LENGTH: 97
<212> TYPE: RNA
<213> ORGANISM: Artificial Sequence
<220> FEATURE:
<223> OTHER INFORMATION: Synthetic

<400> SEQUENCE: 685
auauuuacgu aguuuuucau guuuuagagc uagaaauagc aaguuaaaau aaggcuaguc            60
cguuaucaac uugaaaaagu ggcaccgagu cggugcu                                    97

<210> SEQ ID NO 686
<211> LENGTH: 97
<212> TYPE: RNA
<213> ORGANISM: Artificial Sequence
<220> FEATURE:
<223> OTHER INFORMATION: Synthetic

<400> SEQUENCE: 686
cguaaauauu cuugagaaac guuuuagagc uagaaauagc aaguuaaaau aaggcuaguc            60
cguuaucaac uugaaaaagu ggcaccgagu cggugcu                                    97

<210> SEQ ID NO 687
<211> LENGTH: 97
<212> TYPE: RNA
<213> ORGANISM: Artificial Sequence
<220> FEATURE:

<223> OTHER INFORMATION: Synthetic

<400> SEQUENCE: 687
uucuugagaa acaggaagac guuuuagagc uagaaauagc aaguuaaaau aaggcuaguc    60
cguuaucaac uugaaaaagu ggcaccgagu cggugcu    97

<210> SEQ ID NO 688
<211> LENGTH: 97
<212> TYPE: RNA
<213> ORGANISM: Artificial Sequence
<220> FEATURE:
<223> OTHER INFORMATION: Synthetic

<400> SEQUENCE: 688
uaauauuaaa aacauugguu guuuuagagc uagaaauagc aaguuaaaau aaggcuaguc    60
cguuaucaac uugaaaaagu ggcaccgagu cggugcu    97

<210> SEQ ID NO 689
<211> LENGTH: 97
<212> TYPE: RNA
<213> ORGANISM: Artificial Sequence
<220> FEATURE:
<223> OTHER INFORMATION: Synthetic

<400> SEQUENCE: 689
ccaauguuuu uaauauuauc guuuuagagc uagaaauagc aaguuaaaau aaggcuaguc    60
cguuaucaac uugaaaaagu ggcaccgagu cggugcu    97

<210> SEQ ID NO 690
<211> LENGTH: 97
<212> TYPE: RNA
<213> ORGANISM: Artificial Sequence
<220> FEATURE:
<223> OTHER INFORMATION: Synthetic

<400> SEQUENCE: 690
ccugauaaua uuaaaaacau guuuuagagc uagaaauagc aaguuaaaau aaggcuaguc    60
cguuaucaac uugaaaaagu ggcaccgagu cggugcu    97

<210> SEQ ID NO 691
<211> LENGTH: 97
<212> TYPE: RNA
<213> ORGANISM: Artificial Sequence
<220> FEATURE:
<223> OTHER INFORMATION: Synthetic

<400> SEQUENCE: 691
cauuaucaug cauacaucuc guuuuagagc uagaaauagc aaguuaaaau aaggcuaguc    60
cguuaucaac uugaaaaagu ggcaccgagu cggugcu    97

<210> SEQ ID NO 692
<211> LENGTH: 97
<212> TYPE: RNA
<213> ORGANISM: Artificial Sequence
<220> FEATURE:
<223> OTHER INFORMATION: Synthetic

<400> SEQUENCE: 692
aucaugcaua caucucuggc guuuuagagc uagaaauagc aaguuaaaau aaggcuaguc    60
cguuaucaac uugaaaaagu ggcaccgagu cggugcu    97

<210> SEQ ID NO 693
<211> LENGTH: 97
<212> TYPE: RNA
<213> ORGANISM: Artificial Sequence
<220> FEATURE:
<223> OTHER INFORMATION: Synthetic

<400> SEQUENCE: 693
uucauuucau uuugauuuug guuuuagagc uagaaauagc aaguuaaaau aaggcuaguc    60
cguuaucaac uugaaaaagu ggcaccgagu cggugcu    97

<210> SEQ ID NO 694
<211> LENGTH: 97
<212> TYPE: RNA
<213> ORGANISM: Artificial Sequence
<220> FEATURE:
<223> OTHER INFORMATION: Synthetic

<400> SEQUENCE: 694
auucaauuug aagcaguggu guuuuagagc uagaaauagc aaguuaaaau aaggcuaguc    60
cguuaucaac uugaaaaagu ggcaccgagu cggugcu    97

<210> SEQ ID NO 695
<211> LENGTH: 97
<212> TYPE: RNA
<213> ORGANISM: Artificial Sequence
<220> FEATURE:
<223> OTHER INFORMATION: Synthetic

<400> SEQUENCE: 695
gaauauucaa uuugaagcag guuuuagagc uagaaauagc aaguuaaaau aaggcuaguc    60
cguuaucaac uugaaaaagu ggcaccgagu cggugcu    97

<210> SEQ ID NO 696
<211> LENGTH: 97
<212> TYPE: RNA
<213> ORGANISM: Artificial Sequence
<220> FEATURE:
<223> OTHER INFORMATION: Synthetic

<400> SEQUENCE: 696
cauacgauuu aaaaucgcug guuuuagagc uagaaauagc aaguuaaaau aaggcuaguc    60
cguuaucaac uugaaaaagu ggcaccgagu cggugcu    97

<210> SEQ ID NO 697
<211> LENGTH: 97
<212> TYPE: RNA
<213> ORGANISM: Artificial Sequence
<220> FEATURE:
<223> OTHER INFORMATION: Synthetic

<400> SEQUENCE: 697
aaaaucgcug aggcgcguuc guuuuagagc uagaaauagc aaguuaaaau aaggcuaguc    60
cguuaucaac uugaaaaagu ggcaccgagu cggugcu    97

<210> SEQ ID NO 698
<211> LENGTH: 97
<212> TYPE: RNA
<213> ORGANISM: Artificial Sequence
<220> FEATURE:
<223> OTHER INFORMATION: Synthetic

<400> SEQUENCE: 698
uuuuuuuuuc uuuuuuguac guuuuagagc uagaaauagc aaguuaaaau aaggcuaguc    60
cguuaucaac uugaaaaagu ggcaccgagu cggugcu                              97

<210> SEQ ID NO 699
<211> LENGTH: 97
<212> TYPE: RNA
<213> ORGANISM: Artificial Sequence
<220> FEATURE:
<223> OTHER INFORMATION: Synthetic

<400> SEQUENCE: 699
cuguugucaa agauuuuaaa guuuuagagc uagaaauagc aaguuaaaau aaggcuaguc    60
cguuaucaac uugaaaaagu ggcaccgagu cggugcu                              97

<210> SEQ ID NO 700
<211> LENGTH: 97
<212> TYPE: RNA
<213> ORGANISM: Artificial Sequence
<220> FEATURE:
<223> OTHER INFORMATION: Synthetic

<400> SEQUENCE: 700
ugacaacaga guucuguuuu guuuuagagc uagaaauagc aaguuaaaau aaggcuaguc    60
cguuaucaac uugaaaaagu ggcaccgagu cggugcu                              97

<210> SEQ ID NO 701
<211> LENGTH: 97
<212> TYPE: RNA
<213> ORGANISM: Artificial Sequence
<220> FEATURE:
<223> OTHER INFORMATION: Synthetic

<400> SEQUENCE: 701
agaauacgcu gagaguuauc guuuuagagc uagaaauagc aaguuaaaau aaggcuaguc    60
cguuaucaac uugaaaaagu ggcaccgagu cggugcu                              97

<210> SEQ ID NO 702
<211> LENGTH: 97
<212> TYPE: RNA
<213> ORGANISM: Artificial Sequence
<220> FEATURE:
<223> OTHER INFORMATION: Synthetic

<400> SEQUENCE: 702
gcaagagaag aaaagaacgg guuuuagagc uagaaauagc aaguuaaaau aaggcuaguc    60
cguuaucaac uugaaaaagu ggcaccgagu cggugcu                              97

<210> SEQ ID NO 703
<211> LENGTH: 97
<212> TYPE: RNA
<213> ORGANISM: Artificial Sequence
<220> FEATURE:
<223> OTHER INFORMATION: Synthetic

<400> SEQUENCE: 703
guugcaagag aagaaaagaa guuuuagagc uagaaauagc aaguuaaaau aaggcuaguc    60
cguuaucaac uugaaaaagu ggcaccgagu cggugcu                              97

<210> SEQ ID NO 704
<211> LENGTH: 97
<212> TYPE: RNA
<213> ORGANISM: Artificial Sequence

```
<220> FEATURE:
<223> OTHER INFORMATION: Synthetic

<400> SEQUENCE: 704
augcacacgu aaaagagagg guuuuagagc uagaaauagc aaguuaaaau aaggcuaguc    60
cguuaucaac uugaaaaagu ggcaccgagu cggugcu                            97

<210> SEQ ID NO 705
<211> LENGTH: 97
<212> TYPE: RNA
<213> ORGANISM: Artificial Sequence
<220> FEATURE:
<223> OTHER INFORMATION: Synthetic

<400> SEQUENCE: 705
aagaugcaca cguaaaagag guuuuagagc uagaaauagc aaguuaaaau aaggcuaguc    60
cguuaucaac uugaaaaagu ggcaccgagu cggugcu                            97

<210> SEQ ID NO 706
<211> LENGTH: 97
<212> TYPE: RNA
<213> ORGANISM: Artificial Sequence
<220> FEATURE:
<223> OTHER INFORMATION: Synthetic

<400> SEQUENCE: 706
aucaugcaua caucucuggc guuuuagagc uagaaauagc aaguuaaaau aaggcuaguc    60
cguuaucaac uugaaaaagu ggcaccgagu cggugcu                            97

<210> SEQ ID NO 707
<211> LENGTH: 97
<212> TYPE: RNA
<213> ORGANISM: Artificial Sequence
<220> FEATURE:
<223> OTHER INFORMATION: Synthetic

<400> SEQUENCE: 707
uucauuucau uuugauuuug guuuuagagc uagaaauagc aaguuaaaau aaggcuaguc    60
cguuaucaac uugaaaaagu ggcaccgagu cggugcu                            97

<210> SEQ ID NO 708
<211> LENGTH: 97
<212> TYPE: RNA
<213> ORGANISM: Artificial Sequence
<220> FEATURE:
<223> OTHER INFORMATION: Synthetic

<400> SEQUENCE: 708
auucaauuug aagcaguggu guuuuagagc uagaaauagc aaguuaaaau aaggcuaguc    60
cguuaucaac uugaaaaagu ggcaccgagu cggugcu                            97

<210> SEQ ID NO 709
<211> LENGTH: 97
<212> TYPE: RNA
<213> ORGANISM: Artificial Sequence
<220> FEATURE:
<223> OTHER INFORMATION: Synthetic

<400> SEQUENCE: 709
gaauauucaa uuugaagcag guuuuagagc uagaaauagc aaguuaaaau aaggcuaguc    60
cguuaucaac uugaaaaagu ggcaccgagu cggugcu                            97
```

<210> SEQ ID NO 710
<211> LENGTH: 97
<212> TYPE: RNA
<213> ORGANISM: Artificial Sequence
<220> FEATURE:
<223> OTHER INFORMATION: Synthetic

<400> SEQUENCE: 710
cauacgauuu aaaaucgcug guuuuagagc uagaaauagc aaguuaaaau aaggcuaguc      60
cguuaucaac uugaaaaagu ggcaccgagu cggugcu                              97

<210> SEQ ID NO 711
<211> LENGTH: 97
<212> TYPE: RNA
<213> ORGANISM: Artificial Sequence
<220> FEATURE:
<223> OTHER INFORMATION: Synthetic

<400> SEQUENCE: 711
aaaaucgcug aggcgcguuc guuuuagagc uagaaauagc aaguuaaaau aaggcuaguc      60
cguuaucaac uugaaaaagu ggcaccgagu cggugcu                              97

<210> SEQ ID NO 712
<211> LENGTH: 97
<212> TYPE: RNA
<213> ORGANISM: Artificial Sequence
<220> FEATURE:
<223> OTHER INFORMATION: Synthetic

<400> SEQUENCE: 712
uuuuuuuuuc uuuuuuguac guuuuagagc uagaaauagc aaguuaaaau aaggcuaguc      60
cguuaucaac uugaaaaagu ggcaccgagu cggugcu                              97

<210> SEQ ID NO 713
<211> LENGTH: 97
<212> TYPE: RNA
<213> ORGANISM: Artificial Sequence
<220> FEATURE:
<223> OTHER INFORMATION: Synthetic

<400> SEQUENCE: 713
cuguugucaa agauuuuaaa guuuuagagc uagaaauagc aaguuaaaau aaggcuaguc      60
cguuaucaac uugaaaaagu ggcaccgagu cggugcu                              97

<210> SEQ ID NO 714
<211> LENGTH: 97
<212> TYPE: RNA
<213> ORGANISM: Artificial Sequence
<220> FEATURE:
<223> OTHER INFORMATION: Synthetic

<400> SEQUENCE: 714
ugacaacaga guucuguuuu guuuuagagc uagaaauagc aaguuaaaau aaggcuaguc      60
cguuaucaac uugaaaaagu ggcaccgagu cggugcu                              97

<210> SEQ ID NO 715
<211> LENGTH: 97
<212> TYPE: RNA
<213> ORGANISM: Artificial Sequence
<220> FEATURE:
<223> OTHER INFORMATION: Synthetic

<400> SEQUENCE: 715
agaauacgcu gagaguuauc guuuuagagc uagaaauagc aaguuaaaau aaggcuaguc    60
cguuaucaac uugaaaaagu ggcaccgagu cggugcu                             97

<210> SEQ ID NO 716
<211> LENGTH: 97
<212> TYPE: RNA
<213> ORGANISM: Artificial Sequence
<220> FEATURE:
<223> OTHER INFORMATION: Synthetic

<400> SEQUENCE: 716
gcaagagaag aaaagaacgg guuuuagagc uagaaauagc aaguuaaaau aaggcuaguc    60
cguuaucaac uugaaaaagu ggcaccgagu cggugcu                             97

<210> SEQ ID NO 717
<211> LENGTH: 97
<212> TYPE: RNA
<213> ORGANISM: Artificial Sequence
<220> FEATURE:
<223> OTHER INFORMATION: Synthetic

<400> SEQUENCE: 717
guugcaagag aagaaaagaa guuuuagagc uagaaauagc aaguuaaaau aaggcuaguc    60
cguuaucaac uugaaaaagu ggcaccgagu cggugcu                             97

<210> SEQ ID NO 718
<211> LENGTH: 97
<212> TYPE: RNA
<213> ORGANISM: Artificial Sequence
<220> FEATURE:
<223> OTHER INFORMATION: Synthetic

<400> SEQUENCE: 718
augcacacgu aaaagagagg guuuuagagc uagaaauagc aaguuaaaau aaggcuaguc    60
cguuaucaac uugaaaaagu ggcaccgagu cggugcu                             97

<210> SEQ ID NO 719
<211> LENGTH: 97
<212> TYPE: RNA
<213> ORGANISM: Artificial Sequence
<220> FEATURE:
<223> OTHER INFORMATION: Synthetic

<400> SEQUENCE: 719
aagaugcaca cguaaaagag guuuuagagc uagaaauagc aaguuaaaau aaggcuaguc    60
cguuaucaac uugaaaaagu ggcaccgagu cggugcu                             97

<210> SEQ ID NO 720
<211> LENGTH: 97
<212> TYPE: RNA
<213> ORGANISM: Artificial Sequence
<220> FEATURE:
<223> OTHER INFORMATION: Synthetic

<400> SEQUENCE: 720
ggcagaccgu ucucaucacg guuuuagagc uagaaauagc aaguuaaaau aaggcuaguc    60
cguuaucaac uugaaaaagu ggcaccgagu cggugcu                             97

<210> SEQ ID NO 721
<211> LENGTH: 97
<212> TYPE: RNA

<213> ORGANISM: Artificial Sequence
<220> FEATURE:
<223> OTHER INFORMATION: Synthetic

<400> SEQUENCE: 721
cuuuaccagu gacuccaggu guuuuagagc uagaaauagc aaguuaaaau aaggcuaguc    60
cguuaucaac uugaaaaagu ggcaccgagu cggugcu    97

<210> SEQ ID NO 722
<211> LENGTH: 97
<212> TYPE: RNA
<213> ORGANISM: Artificial Sequence
<220> FEATURE:
<223> OTHER INFORMATION: Synthetic

<400> SEQUENCE: 722
gucacagauu uccuucuccg guuuuagagc uagaaauagc aaguuaaaau aaggcuaguc    60
cguuaucaac uugaaaaagu ggcaccgagu cggugcu    97

<210> SEQ ID NO 723
<211> LENGTH: 97
<212> TYPE: RNA
<213> ORGANISM: Artificial Sequence
<220> FEATURE:
<223> OTHER INFORMATION: Synthetic

<400> SEQUENCE: 723
agaugaugac gcccaccaga guuuuagagc uagaaauagc aaguuaaaau aaggcuaguc    60
cguuaucaac uugaaaaagu ggcaccgagu cggugcu    97

<210> SEQ ID NO 724
<211> LENGTH: 97
<212> TYPE: RNA
<213> ORGANISM: Artificial Sequence
<220> FEATURE:
<223> OTHER INFORMATION: Synthetic

<400> SEQUENCE: 724
ggagaaggaa aucugugacc guuuuagagc uagaaauagc aaguuaaaau aaggcuaguc    60
cguuaucaac uugaaaaagu ggcaccgagu cggugcu    97

<210> SEQ ID NO 725
<211> LENGTH: 97
<212> TYPE: RNA
<213> ORGANISM: Artificial Sequence
<220> FEATURE:
<223> OTHER INFORMATION: Synthetic

<400> SEQUENCE: 725
ugcgaggaac uuacuuuucc guuuuagagc uagaaauagc aaguuaaaau aaggcuaguc    60
cguuaucaac uugaaaaagu ggcaccgagu cggugcu    97

<210> SEQ ID NO 726
<211> LENGTH: 97
<212> TYPE: RNA
<213> ORGANISM: Artificial Sequence
<220> FEATURE:
<223> OTHER INFORMATION: Synthetic

<400> SEQUENCE: 726
agagaaauau ugauauagga guuuuagagc uagaaauagc aaguuaaaau aaggcuaguc    60
cguuaucaac uugaaaaagu ggcaccgagu cggugcu    97

<210> SEQ ID NO 727
<211> LENGTH: 97
<212> TYPE: RNA
<213> ORGANISM: Artificial Sequence
<220> FEATURE:
<223> OTHER INFORMATION: Synthetic

<400> SEQUENCE: 727
uaucaauauu ucucugaucc guuuuagagc uagaaauagc aaguuaaaau aaggcuaguc    60
cguuaucaac uugaaaaagu ggcaccgagu cggugcu    97

<210> SEQ ID NO 728
<211> LENGTH: 97
<212> TYPE: RNA
<213> ORGANISM: Artificial Sequence
<220> FEATURE:
<223> OTHER INFORMATION: Synthetic

<400> SEQUENCE: 728
aucgcuuuua aggcacgcuc guuuuagagc uagaaauagc aaguuaaaau aaggcuaguc    60
cguuaucaac uugaaaaagu ggcaccgagu cggugcu    97

<210> SEQ ID NO 729
<211> LENGTH: 97
<212> TYPE: RNA
<213> ORGANISM: Artificial Sequence
<220> FEATURE:
<223> OTHER INFORMATION: Synthetic

<400> SEQUENCE: 729
uauacgacug aucgcuuuua guuuuagagc uagaaauagc aaguuaaaau aaggcuaguc    60
cguuaucaac uugaaaaagu ggcaccgagu cggugcu    97

<210> SEQ ID NO 730
<211> LENGTH: 102
<212> TYPE: RNA
<213> ORGANISM: Artificial Sequence
<220> FEATURE:
<223> OTHER INFORMATION: Synthetic

<400> SEQUENCE: 730
ugucagguua guuagaugaa guuggaacca uucaaaacag cauagcaagu uaaaauaagg    60
cuaguccguu aucaacuuga aaaguggca ccgagucggu gc    102

<210> SEQ ID NO 731
<211> LENGTH: 102
<212> TYPE: RNA
<213> ORGANISM: Artificial Sequence
<220> FEATURE:
<223> OTHER INFORMATION: Synthetic

<400> SEQUENCE: 731
gugucagguu aguuagauga guuggaacca uucaaaacag cauagcaagu uaaaauaagg    60
cuaguccguu aucaacuuga aaaguggca ccgagucggu gc    102

<210> SEQ ID NO 732
<211> LENGTH: 102
<212> TYPE: RNA
<213> ORGANISM: Artificial Sequence
<220> FEATURE:
<223> OTHER INFORMATION: Synthetic

<400> SEQUENCE: 732
ccugacacau auacagacua guuggaacca uucaaaacag cauagcaagu uaaaauaagg    60
cuaguccguu aucaacuuga aaaaguggca ccgagucggu gc    102

<210> SEQ ID NO 733
<211> LENGTH: 102
<212> TYPE: RNA
<213> ORGANISM: Artificial Sequence
<220> FEATURE:
<223> OTHER INFORMATION: Synthetic

<400> SEQUENCE: 733
cugacacaua uacagacuaa guuggaacca uucaaaacag cauagcaagu uaaaauaagg    60
cuaguccguu aucaacuuga aaaaguggca ccgagucggu gc    102

<210> SEQ ID NO 734
<211> LENGTH: 102
<212> TYPE: RNA
<213> ORGANISM: Artificial Sequence
<220> FEATURE:
<223> OTHER INFORMATION: Synthetic

<400> SEQUENCE: 734
ccuuagucug uauauguguc guuggaacca uucaaaacag cauagcaagu uaaaauaagg    60
cuaguccguu aucaacuuga aaaaguggca ccgagucggu gc    102

<210> SEQ ID NO 735
<211> LENGTH: 102
<212> TYPE: RNA
<213> ORGANISM: Artificial Sequence
<220> FEATURE:
<223> OTHER INFORMATION: Synthetic

<400> SEQUENCE: 735
cauauacaga cuaagggacc guuggaacca uucaaaacag cauagcaagu uaaaauaagg    60
cuaguccguu aucaacuuga aaaaguggca ccgagucggu gc    102

<210> SEQ ID NO 736
<211> LENGTH: 102
<212> TYPE: RNA
<213> ORGANISM: Artificial Sequence
<220> FEATURE:
<223> OTHER INFORMATION: Synthetic

<400> SEQUENCE: 736
auauacagac uaagggacca guuggaacca uucaaaacag cauagcaagu uaaaauaagg    60
cuaguccguu aucaacuuga aaaaguggca ccgagucggu gc    102

<210> SEQ ID NO 737
<211> LENGTH: 102
<212> TYPE: RNA
<213> ORGANISM: Artificial Sequence
<220> FEATURE:
<223> OTHER INFORMATION: Synthetic

<400> SEQUENCE: 737
ucaaaguuug auaaauuccc guuggaacca uucaaaacag cauagcaagu uaaaauaagg    60
cuaguccguu aucaacuuga aaaaguggca ccgagucggu gc    102

<210> SEQ ID NO 738
<211> LENGTH: 102

```
<212> TYPE: RNA
<213> ORGANISM: Artificial Sequence
<220> FEATURE:
<223> OTHER INFORMATION: Synthetic

<400> SEQUENCE: 738
aaaaaucaaa gauaaguaga guuggaacca uucaaaacag cauagcaagu uaaaauaagg      60
cuaguccguu aucaacuuga aaaaguggca ccgagucggu gc                       102

<210> SEQ ID NO 739
<211> LENGTH: 102
<212> TYPE: RNA
<213> ORGANISM: Artificial Sequence
<220> FEATURE:
<223> OTHER INFORMATION: Synthetic

<400> SEQUENCE: 739
acucugugac uuuaaaaagu guuggaacca uucaaaacag cauagcaagu uaaaauaagg      60
cuaguccguu aucaacuuga aaaaguggca ccgagucggu gc                       102

<210> SEQ ID NO 740
<211> LENGTH: 102
<212> TYPE: RNA
<213> ORGANISM: Artificial Sequence
<220> FEATURE:
<223> OTHER INFORMATION: Synthetic

<400> SEQUENCE: 740
gguucugugg gauauuaaua guuggaacca uucaaaacag cauagcaagu uaaaauaagg      60
cuaguccguu aucaacuuga aaaaguggca ccgagucggu gc                       102

<210> SEQ ID NO 741
<211> LENGTH: 102
<212> TYPE: RNA
<213> ORGANISM: Artificial Sequence
<220> FEATURE:
<223> OTHER INFORMATION: Synthetic

<400> SEQUENCE: 741
acagagcaua uugguucugu guuggaacca uucaaaacag cauagcaagu uaaaauaagg      60
cuaguccguu aucaacuuga aaaaguggca ccgagucggu gc                       102

<210> SEQ ID NO 742
<211> LENGTH: 102
<212> TYPE: RNA
<213> ORGANISM: Artificial Sequence
<220> FEATURE:
<223> OTHER INFORMATION: Synthetic

<400> SEQUENCE: 742
gacagagcau auugguucug guuggaacca uucaaaacag cauagcaagu uaaaauaagg      60
cuaguccguu aucaacuuga aaaaguggca ccgagucggu gc                       102

<210> SEQ ID NO 743
<211> LENGTH: 102
<212> TYPE: RNA
<213> ORGANISM: Artificial Sequence
<220> FEATURE:
<223> OTHER INFORMATION: Synthetic

<400> SEQUENCE: 743
ugcaaaacga cagagcauau guuggaacca uucaaaacag cauagcaagu uaaaauaagg      60
```
cuaguccguu aucaacuuga aaaaguggca ccgagucggu gc 102

<210> SEQ ID NO 744
<211> LENGTH: 102
<212> TYPE: RNA
<213> ORGANISM: Artificial Sequence
<220> FEATURE:
<223> OTHER INFORMATION: Synthetic

<400> SEQUENCE: 744
gagcugggca uggaauaggc guuggaacca uucaaaacag cauagcaagu uaaaauaagg 60
cuaguccguu aucaacuuga aaaaguggca ccgagucggu gc 102

<210> SEQ ID NO 745
<211> LENGTH: 102
<212> TYPE: RNA
<213> ORGANISM: Artificial Sequence
<220> FEATURE:
<223> OTHER INFORMATION: Synthetic

<400> SEQUENCE: 745
acuggagcug ggcauggaau guuggaacca uucaaaacag cauagcaagu uaaaauaagg 60
cuaguccguu aucaacuuga aaaaguggca ccgagucggu gc 102

<210> SEQ ID NO 746
<211> LENGTH: 102
<212> TYPE: RNA
<213> ORGANISM: Artificial Sequence
<220> FEATURE:
<223> OTHER INFORMATION: Synthetic

<400> SEQUENCE: 746
cucauuacug gagcugggca guuggaacca uucaaaacag cauagcaagu uaaaauaagg 60
cuaguccguu aucaacuuga aaaaguggca ccgagucggu gc 102

<210> SEQ ID NO 747
<211> LENGTH: 102
<212> TYPE: RNA
<213> ORGANISM: Artificial Sequence
<220> FEATURE:
<223> OTHER INFORMATION: Synthetic

<400> SEQUENCE: 747
uuguucucau uacuggagcu guuggaacca uucaaaacag cauagcaagu uaaaauaagg 60
cuaguccguu aucaacuuga aaaaguggca ccgagucggu gc 102

<210> SEQ ID NO 748
<211> LENGTH: 102
<212> TYPE: RNA
<213> ORGANISM: Artificial Sequence
<220> FEATURE:
<223> OTHER INFORMATION: Synthetic

<400> SEQUENCE: 748
auuguucuca uuacuggagc guuggaacca uucaaaacag cauagcaagu uaaaauaagg 60
cuaguccguu aucaacuuga aaaaguggca ccgagucggu gc 102

<210> SEQ ID NO 749
<211> LENGTH: 102
<212> TYPE: RNA
<213> ORGANISM: Artificial Sequence
<220> FEATURE:
<223> OTHER INFORMATION: Synthetic

<400> SEQUENCE: 749 gggagauug uucucauuac guuggaacca uucaaaacag cauagcaagu uaaaauaagg    60
cuaguccguu aucaacuuga aaaaguggca ccgagucggu gc                      102

<210> SEQ ID NO 750
<211> LENGTH: 102
<212> TYPE: RNA
<213> ORGANISM: Artificial Sequence
<220> FEATURE:
<223> OTHER INFORMATION: Synthetic

<400> SEQUENCE: 750
gaggagaaaa ucuguggcug guuggaacca uucaaaacag cauagcaagu uaaaauaagg    60
cuaguccguu aucaacuuga aaaaguggca ccgagucggu gc                      102

<210> SEQ ID NO 751
<211> LENGTH: 102
<212> TYPE: RNA
<213> ORGANISM: Artificial Sequence
<220> FEATURE:
<223> OTHER INFORMATION: Synthetic

<400> SEQUENCE: 751
agaggagaaa aucuguggcu guuggaacca uucaaaacag cauagcaagu uaaaauaagg    60
cuaguccguu aucaacuuga aaaaguggca ccgagucggu gc                      102

<210> SEQ ID NO 752
<211> LENGTH: 102
<212> TYPE: RNA
<213> ORGANISM: Artificial Sequence
<220> FEATURE:
<223> OTHER INFORMATION: Synthetic

<400> SEQUENCE: 752
cagaggagaa aaucuguggc guuggaacca uucaaaacag cauagcaagu uaaaauaagg    60
cuaguccguu aucaacuuga aaaaguggca ccgagucggu gc                      102

<210> SEQ ID NO 753
<211> LENGTH: 102
<212> TYPE: RNA
<213> ORGANISM: Artificial Sequence
<220> FEATURE:
<223> OTHER INFORMATION: Synthetic

<400> SEQUENCE: 753
uccucagagg agaaaaucug guuggaacca uucaaaacag cauagcaagu uaaaauaagg    60
cuaguccguu aucaacuuga aaaaguggca ccgagucggu gc                      102

<210> SEQ ID NO 754
<211> LENGTH: 102
<212> TYPE: RNA
<213> ORGANISM: Artificial Sequence
<220> FEATURE:
<223> OTHER INFORMATION: Synthetic

<400> SEQUENCE: 754
ugaaguuuuu cauuccucag guuggaacca uucaaaacag cauagcaagu uaaaauaagg    60
cuaguccguu aucaacuuga aaaaguggca ccgagucggu gc                      102

<210> SEQ ID NO 755

```
<211> LENGTH: 102
<212> TYPE: RNA
<213> ORGANISM: Artificial Sequence
<220> FEATURE:
<223> OTHER INFORMATION: Synthetic

<400> SEQUENCE: 755
cuucaccaac gacuccaagu guuggaacca uucaaaacag cauagcaagu uaaaauaagg      60
cuaguccguu aucaacuuga aaaguggca ccgagucggu gc                        102

<210> SEQ ID NO 756
<211> LENGTH: 102
<212> TYPE: RNA
<213> ORGANISM: Artificial Sequence
<220> FEATURE:
<223> OTHER INFORMATION: Synthetic

<400> SEQUENCE: 756
cuacuccuac uuggagucgu guuggaacca uucaaaacag cauagcaagu uaaaauaagg      60
cuaguccguu aucaacuuga aaaguggca ccgagucggu gc                        102

<210> SEQ ID NO 757
<211> LENGTH: 102
<212> TYPE: RNA
<213> ORGANISM: Artificial Sequence
<220> FEATURE:
<223> OTHER INFORMATION: Synthetic

<400> SEQUENCE: 757
cuccaaguag gaguagauga guuggaacca uucaaaacag cauagcaagu uaaaauaagg      60
cuaguccguu aucaacuuga aaaguggca ccgagucggu gc                        102

<210> SEQ ID NO 758
<211> LENGTH: 102
<212> TYPE: RNA
<213> ORGANISM: Artificial Sequence
<220> FEATURE:
<223> OTHER INFORMATION: Synthetic

<400> SEQUENCE: 758
caccaucauc uacuccuacu guuggaacca uucaaaacag cauagcaagu uaaaauaagg      60
cuaguccguu aucaacuuga aaaguggca ccgagucggu gc                        102

<210> SEQ ID NO 759
<211> LENGTH: 102
<212> TYPE: RNA
<213> ORGANISM: Artificial Sequence
<220> FEATURE:
<223> OTHER INFORMATION: Synthetic

<400> SEQUENCE: 759
ugauggugau cagaagcaga guuggaacca uucaaaacag cauagcaagu uaaaauaagg      60
cuaguccguu aucaacuuga aaaguggca ccgagucggu gc                        102

<210> SEQ ID NO 760
<211> LENGTH: 102
<212> TYPE: RNA
<213> ORGANISM: Artificial Sequence
<220> FEATURE:
<223> OTHER INFORMATION: Synthetic

<400> SEQUENCE: 760
ucagaagcag aaggauuucu guuggaacca uucaaaacag cauagcaagu uaaaauaagg      60
```
cuaguccguu aucaacuuga aaaaguggca ccgagucggu gc        102

<210> SEQ ID NO 761
<211> LENGTH: 102
<212> TYPE: RNA
<213> ORGANISM: Artificial Sequence
<220> FEATURE:
<223> OTHER INFORMATION: Synthetic

<400> SEQUENCE: 761
gauuucuagg augauguuca guuggaacca uucaaaacag cauagcaagu uaaaauaagg        60
cuaguccguu aucaacuuga aaaaguggca ccgagucggu gc        102

<210> SEQ ID NO 762
<211> LENGTH: 102
<212> TYPE: RNA
<213> ORGANISM: Artificial Sequence
<220> FEATURE:
<223> OTHER INFORMATION: Synthetic

<400> SEQUENCE: 762
uugcucuguc cucuuccuuc guuggaacca uucaaaacag cauagcaagu uaaaauaagg        60
cuaguccguu aucaacuuga aaaaguggca ccgagucggu gc        102

<210> SEQ ID NO 763
<211> LENGTH: 102
<212> TYPE: RNA
<213> ORGANISM: Artificial Sequence
<220> FEATURE:
<223> OTHER INFORMATION: Synthetic

<400> SEQUENCE: 763
aggacugaac cagaaggaag guuggaacca uucaaaacag cauagcaagu uaaaauaagg        60
cuaguccguu aucaacuuga aaaaguggca ccgagucggu gc        102

<210> SEQ ID NO 764
<211> LENGTH: 102
<212> TYPE: RNA
<213> ORGANISM: Artificial Sequence
<220> FEATURE:
<223> OTHER INFORMATION: Synthetic

<400> SEQUENCE: 764
uacacaagga cugaaccaga guuggaacca uucaaaacag cauagcaagu uaaaauaagg        60
cuaguccguu aucaacuuga aaaaguggca ccgagucggu gc        102

<210> SEQ ID NO 765
<211> LENGTH: 102
<212> TYPE: RNA
<213> ORGANISM: Artificial Sequence
<220> FEATURE:
<223> OTHER INFORMATION: Synthetic

<400> SEQUENCE: 765
uucagaccuu guguaguccu guuggaacca uucaaaacag cauagcaagu uaaaauaagg        60
cuaguccguu aucaacuuga aaaaguggca ccgagucggu gc        102

<210> SEQ ID NO 766
<211> LENGTH: 102
<212> TYPE: RNA
<213> ORGANISM: Artificial Sequence
<220> FEATURE:

<223> OTHER INFORMATION: Synthetic

<400> SEQUENCE: 766 ucagccuug uguaguccua guuggaacca uucaaaacag cauagcaagu uaaaauaagg    60
cuaguccguu aucaacuuga aaaaguggca ccgagucggu gc    102

<210> SEQ ID NO 767
<211> LENGTH: 102
<212> TYPE: RNA
<213> ORGANISM: Artificial Sequence
<220> FEATURE:
<223> OTHER INFORMATION: Synthetic

<400> SEQUENCE: 767
guccuugugu aguccuaggg guuggaacca uucaaaacag cauagcaagu uaaaauaagg    60
cuaguccguu aucaacuuga aaaaguggca ccgagucggu gc    102

<210> SEQ ID NO 768
<211> LENGTH: 102
<212> TYPE: RNA
<213> ORGANISM: Artificial Sequence
<220> FEATURE:
<223> OTHER INFORMATION: Synthetic

<400> SEQUENCE: 768
cuuguguagu ccuagggagg guuggaacca uucaaaacag cauagcaagu uaaaauaagg    60
cuaguccguu aucaacuuga aaaaguggca ccgagucggu gc    102

<210> SEQ ID NO 769
<211> LENGTH: 102
<212> TYPE: RNA
<213> ORGANISM: Artificial Sequence
<220> FEATURE:
<223> OTHER INFORMATION: Synthetic

<400> SEQUENCE: 769
cuccucccua ggacuacaca guuggaacca uucaaaacag cauagcaagu uaaaauaagg    60
cuaguccguu aucaacuuga aaaaguggca ccgagucggu gc    102

<210> SEQ ID NO 770
<211> LENGTH: 102
<212> TYPE: RNA
<213> ORGANISM: Artificial Sequence
<220> FEATURE:
<223> OTHER INFORMATION: Synthetic

<400> SEQUENCE: 770
guagacagua ccuccucccu guuggaacca uucaaaacag cauagcaagu uaaaauaagg    60
cuaguccguu aucaacuuga aaaaguggca ccgagucggu gc    102

<210> SEQ ID NO 771
<211> LENGTH: 102
<212> TYPE: RNA
<213> ORGANISM: Artificial Sequence
<220> FEATURE:
<223> OTHER INFORMATION: Synthetic

<400> SEQUENCE: 771
uacugucuac acagagcucu guuggaacca uucaaaacag cauagcaagu uaaaauaagg    60
cuaguccguu aucaacuuga aaaaguggca ccgagucggu gc    102

-continued

```
<210> SEQ ID NO 772
<211> LENGTH: 102
<212> TYPE: RNA
<213> ORGANISM: Artificial Sequence
<220> FEATURE:
<223> OTHER INFORMATION: Synthetic

<400> SEQUENCE: 772
acugucuaca cagagcucua guuggaacca uucaaaacag cauagcaagu uaaaauaagg      60
cuaguccguu aucaacuuga aaaaguggca ccgagucggu gc                       102

<210> SEQ ID NO 773
<211> LENGTH: 102
<212> TYPE: RNA
<213> ORGANISM: Artificial Sequence
<220> FEATURE:
<223> OTHER INFORMATION: Synthetic

<400> SEQUENCE: 773
ucuacacaga gcucuaggga guuggaacca uucaaaacag cauagcaagu uaaaauaagg      60
cuaguccguu aucaacuuga aaaaguggca ccgagucggu gc                       102

<210> SEQ ID NO 774
<211> LENGTH: 102
<212> TYPE: RNA
<213> ORGANISM: Artificial Sequence
<220> FEATURE:
<223> OTHER INFORMATION: Synthetic

<400> SEQUENCE: 774
cuacacagag cucugggaa guuggaacca uucaaaacag cauagcaagu uaaaauaagg       60
cuaguccguu aucaacuuga aaaaguggca ccgagucggu gc                       102

<210> SEQ ID NO 775
<211> LENGTH: 102
<212> TYPE: RNA
<213> ORGANISM: Artificial Sequence
<220> FEATURE:
<223> OTHER INFORMATION: Synthetic

<400> SEQUENCE: 775
uacacagagc ucugggaag guuggaacca uucaaaacag cauagcaagu uaaaauaagg       60
cuaguccguu aucaacuuga aaaaguggca ccgagucggu gc                       102

<210> SEQ ID NO 776
<211> LENGTH: 102
<212> TYPE: RNA
<213> ORGANISM: Artificial Sequence
<220> FEATURE:
<223> OTHER INFORMATION: Synthetic

<400> SEQUENCE: 776
ggggugugcc caguuguuaa guuggaacca uucaaaacag cauagcaagu uaaaauaagg      60
cuaguccguu aucaacuuga aaaaguggca ccgagucggu gc                       102

<210> SEQ ID NO 777
<211> LENGTH: 102
<212> TYPE: RNA
<213> ORGANISM: Artificial Sequence
<220> FEATURE:
<223> OTHER INFORMATION: Synthetic

<400> SEQUENCE: 777
```

```
gggugugccc aguuguuaau guuggaacca uucaaaacag cauagcaagu uaaaauaagg      60
cuaguccguu aucaacuuga aaaaguggca ccgagucggu gc                        102

<210> SEQ ID NO 778
<211> LENGTH: 102
<212> TYPE: RNA
<213> ORGANISM: Artificial Sequence
<220> FEATURE:
<223> OTHER INFORMATION: Synthetic

<400> SEQUENCE: 778
ugguaguccc auuaacaacu guuggaacca uucaaaacag cauagcaagu uaaaauaagg      60
cuaguccguu aucaacuuga aaaaguggca ccgagucggu gc                        102

<210> SEQ ID NO 779
<211> LENGTH: 102
<212> TYPE: RNA
<213> ORGANISM: Artificial Sequence
<220> FEATURE:
<223> OTHER INFORMATION: Synthetic

<400> SEQUENCE: 779
cugguagucc cauuaacaac guuggaacca uucaaaacag cauagcaagu uaaaauaagg      60
cuaguccguu aucaacuuga aaaaguggca ccgagucggu gc                        102

<210> SEQ ID NO 780
<211> LENGTH: 102
<212> TYPE: RNA
<213> ORGANISM: Artificial Sequence
<220> FEATURE:
<223> OTHER INFORMATION: Synthetic

<400> SEQUENCE: 780
uuguuaaugg gacuaccaga guuggaacca uucaaaacag cauagcaagu uaaaauaagg      60
cuaguccguu aucaacuuga aaaaguggca ccgagucggu gc                        102

<210> SEQ ID NO 781
<211> LENGTH: 102
<212> TYPE: RNA
<213> ORGANISM: Artificial Sequence
<220> FEATURE:
<223> OTHER INFORMATION: Synthetic

<400> SEQUENCE: 781
uaccagaugg aagccagcuu guuggaacca uucaaaacag cauagcaagu uaaaauaagg      60
cuaguccguu aucaacuuga aaaaguggca ccgagucggu gc                        102

<210> SEQ ID NO 782
<211> LENGTH: 102
<212> TYPE: RNA
<213> ORGANISM: Artificial Sequence
<220> FEATURE:
<223> OTHER INFORMATION: Synthetic

<400> SEQUENCE: 782
uuccaaagcu ggcuuccauc guuggaacca uucaaaacag cauagcaagu uaaaauaagg      60
cuaguccguu aucaacuuga aaaaguggca ccgagucggu gc                        102

<210> SEQ ID NO 783
<211> LENGTH: 102
<212> TYPE: RNA
<213> ORGANISM: Artificial Sequence
```

```
<220> FEATURE:
<223> OTHER INFORMATION: Synthetic

<400> SEQUENCE: 783
uggaagccag cuuuggaagc guuggaacca uucaaaacag cauagcaagu uaaaauaagg      60
cuaguccguu aucaacuuga aaaguggca ccgagucggu gc                        102

<210> SEQ ID NO 784
<211> LENGTH: 102
<212> TYPE: RNA
<213> ORGANISM: Artificial Sequence
<220> FEATURE:
<223> OTHER INFORMATION: Synthetic

<400> SEQUENCE: 784
acaaggccug cuuccaaagc guuggaacca uucaaaacag cauagcaagu uaaaauaagg      60
cuaguccguu aucaacuuga aaaguggca ccgagucggu gc                        102

<210> SEQ ID NO 785
<211> LENGTH: 102
<212> TYPE: RNA
<213> ORGANISM: Artificial Sequence
<220> FEATURE:
<223> OTHER INFORMATION: Synthetic

<400> SEQUENCE: 785
gccuuguuca cguguucuaa guuggaacca uucaaaacag cauagcaagu uaaaauaagg      60
cuaguccguu aucaacuuga aaaguggca ccgagucggu gc                        102

<210> SEQ ID NO 786
<211> LENGTH: 102
<212> TYPE: RNA
<213> ORGANISM: Artificial Sequence
<220> FEATURE:
<223> OTHER INFORMATION: Synthetic

<400> SEQUENCE: 786 ccuguucac guguucuaau guuggaacca uucaaaacag cauagcaagu uaaaauaagg       60
cuaguccguu aucaacuuga aaaguggca ccgagucggu gc                        102

<210> SEQ ID NO 787
<211> LENGTH: 102
<212> TYPE: RNA
<213> ORGANISM: Artificial Sequence
<220> FEATURE:
<223> OTHER INFORMATION: Synthetic

<400> SEQUENCE: 787
cccauuagaa cacgugaaca guuggaacca uucaaaacag cauagcaagu uaaaauaagg      60
cuaguccguu aucaacuuga aaaguggca ccgagucggu gc                        102

<210> SEQ ID NO 788
<211> LENGTH: 102
<212> TYPE: RNA
<213> ORGANISM: Artificial Sequence
<220> FEATURE:
<223> OTHER INFORMATION: Synthetic

<400> SEQUENCE: 788
uuggcaucac uucauauuug guuggaacca uucaaaacag cauagcaagu uaaaauaagg      60
cuaguccguu aucaacuuga aaaguggca ccgagucggu gc                        102
```

<210> SEQ ID NO 789
<211> LENGTH: 102
<212> TYPE: RNA
<213> ORGANISM: Artificial Sequence
<220> FEATURE:
<223> OTHER INFORMATION: Synthetic

<400> SEQUENCE: 789
cuugugcucu uggcaucacu guuggaacca uucaaaacag cauagcaagu uaaaauaagg    60
cuaguccguu aucaacuuga aaaguggca ccgagucggu gc    102

<210> SEQ ID NO 790
<211> LENGTH: 102
<212> TYPE: RNA
<213> ORGANISM: Artificial Sequence
<220> FEATURE:
<223> OTHER INFORMATION: Synthetic

<400> SEQUENCE: 790
agcacacucu cuugugcucu guuggaacca uucaaaacag cauagcaagu uaaaauaagg    60
cuaguccguu aucaacuuga aaaguggca ccgagucggu gc    102

<210> SEQ ID NO 791
<211> LENGTH: 102
<212> TYPE: RNA
<213> ORGANISM: Artificial Sequence
<220> FEATURE:
<223> OTHER INFORMATION: Synthetic

<400> SEQUENCE: 791
gcacaagaga gugugcucuc guuggaacca uucaaaacag cauagcaagu uaaaauaagg    60
cuaguccguu aucaacuuga aaaguggca ccgagucggu gc    102

<210> SEQ ID NO 792
<211> LENGTH: 102
<212> TYPE: RNA
<213> ORGANISM: Artificial Sequence
<220> FEATURE:
<223> OTHER INFORMATION: Synthetic

<400> SEQUENCE: 792
gcuuaaucuc acacauagaa guuggaacca uucaaaacag cauagcaagu uaaaauaagg    60
cuaguccguu aucaacuuga aaaguggca ccgagucggu gc    102

<210> SEQ ID NO 793
<211> LENGTH: 102
<212> TYPE: RNA
<213> ORGANISM: Artificial Sequence
<220> FEATURE:
<223> OTHER INFORMATION: Synthetic

<400> SEQUENCE: 793
cuuaaucuca cacauagaaa guuggaacca uucaaaacag cauagcaagu uaaaauaagg    60
cuaguccguu aucaacuuga aaaguggca ccgagucggu gc    102

<210> SEQ ID NO 794
<211> LENGTH: 102
<212> TYPE: RNA
<213> ORGANISM: Artificial Sequence
<220> FEATURE:
<223> OTHER INFORMATION: Synthetic

<400> SEQUENCE: 794

```
uuaaucucac acauagaaag guuggaacca uucaaaacag cauagcaagu uaaaauaagg    60
cuaguccguu aucaacuuga aaaaguggca ccgagucggu gc                      102

<210> SEQ ID NO 795
<211> LENGTH: 102
<212> TYPE: RNA
<213> ORGANISM: Artificial Sequence
<220> FEATURE:
<223> OTHER INFORMATION: Synthetic

<400> SEQUENCE: 795
aggagugcug guuuaucaac guuggaacca uucaaaacag cauagcaagu uaaaauaagg    60
cuaguccguu aucaacuuga aaaaguggca ccgagucggu gc                      102

<210> SEQ ID NO 796
<211> LENGTH: 102
<212> TYPE: RNA
<213> ORGANISM: Artificial Sequence
<220> FEATURE:
<223> OTHER INFORMATION: Synthetic

<400> SEQUENCE: 796
uucuuugaca gcaggagugc guuggaacca uucaaaacag cauagcaagu uaaaauaagg    60
cuaguccguu aucaacuuga aaaaguggca ccgagucggu gc                      102

<210> SEQ ID NO 797
<211> LENGTH: 102
<212> TYPE: RNA
<213> ORGANISM: Artificial Sequence
<220> FEATURE:
<223> OTHER INFORMATION: Synthetic

<400> SEQUENCE: 797
acucugguuu cuuugacagc guuggaacca uucaaaacag cauagcaagu uaaaauaagg    60
cuaguccguu aucaacuuga aaaaguggca ccgagucggu gc                      102

<210> SEQ ID NO 798
<211> LENGTH: 102
<212> TYPE: RNA
<213> ORGANISM: Artificial Sequence
<220> FEATURE:
<223> OTHER INFORMATION: Synthetic

<400> SEQUENCE: 798
accagaguug agaaaacccc guuggaacca uucaaaacag cauagcaagu uaaaauaagg    60
cuaguccguu aucaacuuga aaaaguggca ccgagucggu gc                      102

<210> SEQ ID NO 799
<211> LENGTH: 102
<212> TYPE: RNA
<213> ORGANISM: Artificial Sequence
<220> FEATURE:
<223> OTHER INFORMATION: Synthetic

<400> SEQUENCE: 799 uccaggggu uucucaacuc guuggaacca uucaaaacag cauagcaagu uaaaauaagg     60
cuaguccguu aucaacuuga aaaaguggca ccgagucggu gc                      102

<210> SEQ ID NO 800
<211> LENGTH: 102
<212> TYPE: RNA
```

```
<213> ORGANISM: Artificial Sequence
<220> FEATURE:
<223> OTHER INFORMATION: Synthetic

<400> SEQUENCE: 800
caguuauuaa augaauccag guuggaacca uucaaaacag cauagcaagu uaaaauaagg     60
cuaguccguu aucaacuuga aaaguggca ccgagucggu gc                        102

<210> SEQ ID NO 801
<211> LENGTH: 102
<212> TYPE: RNA
<213> ORGANISM: Artificial Sequence
<220> FEATURE:
<223> OTHER INFORMATION: Synthetic

<400> SEQUENCE: 801
gcaguuauua aaugaaucca guuggaacca uucaaaacag cauagcaagu uaaaauaagg     60
cuaguccguu aucaacuuga aaaguggca ccgagucggu gc                        102

<210> SEQ ID NO 802
<211> LENGTH: 102
<212> TYPE: RNA
<213> ORGANISM: Artificial Sequence
<220> FEATURE:
<223> OTHER INFORMATION: Synthetic

<400> SEQUENCE: 802
ggcaguuauu aaaugaaucc guuggaacca uucaaaacag cauagcaagu uaaaauaagg     60
cuaguccguu aucaacuuga aaaguggca ccgagucggu gc                        102

<210> SEQ ID NO 803
<211> LENGTH: 102
<212> TYPE: RNA
<213> ORGANISM: Artificial Sequence
<220> FEATURE:
<223> OTHER INFORMATION: Synthetic

<400> SEQUENCE: 803
uggaugguaa cagcuacauc guuggaacca uucaaaacag cauagcaagu uaaaauaagg     60
cuaguccguu aucaacuuga aaaguggca ccgagucggu gc                        102

<210> SEQ ID NO 804
<211> LENGTH: 102
<212> TYPE: RNA
<213> ORGANISM: Artificial Sequence
<220> FEATURE:
<223> OTHER INFORMATION: Synthetic

<400> SEQUENCE: 804
gcuguuacca uccacauccu guuggaacca uucaaaacag cauagcaagu uaaaauaagg     60
cuaguccguu aucaacuuga aaaguggca ccgagucggu gc                        102

<210> SEQ ID NO 805
<211> LENGTH: 102
<212> TYPE: RNA
<213> ORGANISM: Artificial Sequence
<220> FEATURE:
<223> OTHER INFORMATION: Synthetic

<400> SEQUENCE: 805
ucaagaacca aggaugugga guuggaacca uucaaaacag cauagcaagu uaaaauaagg     60
cuaguccguu aucaacuuga aaaguggca ccgagucggu gc                        102
```

<210> SEQ ID NO 806
<211> LENGTH: 102
<212> TYPE: RNA
<213> ORGANISM: Artificial Sequence
<220> FEATURE:
<223> OTHER INFORMATION: Synthetic

<400> SEQUENCE: 806
uccuucaaga accaaggaug guuggaacca uucaaaacag cauagcaagu uaaaauaagg    60
cuaguccguu aucaacuuga aaaaguggca ccgagucggu gc                      102

<210> SEQ ID NO 807
<211> LENGTH: 102
<212> TYPE: RNA
<213> ORGANISM: Artificial Sequence
<220> FEATURE:
<223> OTHER INFORMATION: Synthetic

<400> SEQUENCE: 807
ugaguguccu ucaagaacca guuggaacca uucaaaacag cauagcaagu uaaaauaagg    60
cuaguccguu aucaacuuga aaaaguggca ccgagucggu gc                      102

<210> SEQ ID NO 808
<211> LENGTH: 102
<212> TYPE: RNA
<213> ORGANISM: Artificial Sequence
<220> FEATURE:
<223> OTHER INFORMATION: Synthetic

<400> SEQUENCE: 808
uuuuauuuua uaacuacaag guuggaacca uucaaaacag cauagcaagu uaaaauaagg    60
cuaguccguu aucaacuuga aaaaguggca ccgagucggu gc                      102

<210> SEQ ID NO 809
<211> LENGTH: 102
<212> TYPE: RNA
<213> ORGANISM: Artificial Sequence
<220> FEATURE:
<223> OTHER INFORMATION: Synthetic

<400> SEQUENCE: 809
uuguuuuuaa uaaaaacaag guuggaacca uucaaaacag cauagcaagu uaaaauaagg    60
cuaguccguu aucaacuuga aaaaguggca ccgagucggu gc                      102

<210> SEQ ID NO 810
<211> LENGTH: 102
<212> TYPE: RNA
<213> ORGANISM: Artificial Sequence
<220> FEATURE:
<223> OTHER INFORMATION: Synthetic

<400> SEQUENCE: 810
uauuauagaa ugcuuuugca guuggaacca uucaaaacag cauagcaagu uaaaauaagg    60
cuaguccguu aucaacuuga aaaaguggca ccgagucggu gc                      102

<210> SEQ ID NO 811
<211> LENGTH: 102
<212> TYPE: RNA
<213> ORGANISM: Artificial Sequence
<220> FEATURE:
<223> OTHER INFORMATION: Synthetic

```
<400> SEQUENCE: 811
caagauuagu cuugauguag guuggaacca uucaaaacag cauagcaagu uaaaauaagg      60
cuaguccguu aucaacuuga aaaguggca ccgagucggu gc                         102

<210> SEQ ID NO 812
<211> LENGTH: 102
<212> TYPE: RNA
<213> ORGANISM: Artificial Sequence
<220> FEATURE:
<223> OTHER INFORMATION: Synthetic

<400> SEQUENCE: 812
aagauuaguc uugauguagu guuggaacca uucaaaacag cauagcaagu uaaaauaagg      60
cuaguccguu aucaacuuga aaaguggca ccgagucggu gc                         102

<210> SEQ ID NO 813
<211> LENGTH: 102
<212> TYPE: RNA
<213> ORGANISM: Artificial Sequence
<220> FEATURE:
<223> OTHER INFORMATION: Synthetic

<400> SEQUENCE: 813
agucuugaug uagugggagu guuggaacca uucaaaacag cauagcaagu uaaaauaagg      60
cuaguccguu aucaacuuga aaaguggca ccgagucggu gc                         102

<210> SEQ ID NO 814
<211> LENGTH: 102
<212> TYPE: RNA
<213> ORGANISM: Artificial Sequence
<220> FEATURE:
<223> OTHER INFORMATION: Synthetic

<400> SEQUENCE: 814
uuuuucuauu aaaaaaaaaa guuggaacca uucaaaacag cauagcaagu uaaaauaagg      60
cuaguccguu aucaacuuga aaaguggca ccgagucggu gc                         102

<210> SEQ ID NO 815
<211> LENGTH: 102
<212> TYPE: RNA
<213> ORGANISM: Artificial Sequence
<220> FEATURE:
<223> OTHER INFORMATION: Synthetic

<400> SEQUENCE: 815
ucuauuaaaa aaaaaaaggc guuggaacca uucaaaacag cauagcaagu uaaaauaagg      60
cuaguccguu aucaacuuga aaaguggca ccgagucggu gc                         102

<210> SEQ ID NO 816
<211> LENGTH: 102
<212> TYPE: RNA
<213> ORGANISM: Artificial Sequence
<220> FEATURE:
<223> OTHER INFORMATION: Synthetic

<400> SEQUENCE: 816
cuauuaaaaa aaaaaaggcu guuggaacca uucaaaacag cauagcaagu uaaaauaagg      60
cuaguccguu aucaacuuga aaaguggca ccgagucggu gc                         102

<210> SEQ ID NO 817
<211> LENGTH: 102
```

```
<212> TYPE: RNA
<213> ORGANISM: Artificial Sequence
<220> FEATURE:
<223> OTHER INFORMATION: Synthetic

<400> SEQUENCE: 817
aaaaaaaaaa aggcugggca guuggaacca uucaaaacag cauagcaagu uaaaauaagg      60
cuaguccguu aucaacuuga aaaaguggca ccgagucggu gc                       102

<210> SEQ ID NO 818
<211> LENGTH: 102
<212> TYPE: RNA
<213> ORGANISM: Artificial Sequence
<220> FEATURE:
<223> OTHER INFORMATION: Synthetic

<400> SEQUENCE: 818
aaaaaaaagg cugggcacgg guuggaacca uucaaaacag cauagcaagu uaaaauaagg      60
cuaguccguu aucaacuuga aaaaguggca ccgagucggu gc                       102

<210> SEQ ID NO 819
<211> LENGTH: 102
<212> TYPE: RNA
<213> ORGANISM: Artificial Sequence
<220> FEATURE:
<223> OTHER INFORMATION: Synthetic

<400> SEQUENCE: 819
cacccguaau cccagcacuu guuggaacca uucaaaacag cauagcaagu uaaaauaagg      60
cuaguccguu aucaacuuga aaaaguggca ccgagucggu gc                       102

<210> SEQ ID NO 820
<211> LENGTH: 102
<212> TYPE: RNA
<213> ORGANISM: Artificial Sequence
<220> FEATURE:
<223> OTHER INFORMATION: Synthetic

<400> SEQUENCE: 820
acccguaauc ccagcacuuu guuggaacca uucaaaacag cauagcaagu uaaaauaagg      60
cuaguccguu aucaacuuga aaaaguggca ccgagucggu gc                       102

<210> SEQ ID NO 821
<211> LENGTH: 102
<212> TYPE: RNA
<213> ORGANISM: Artificial Sequence
<220> FEATURE:
<223> OTHER INFORMATION: Synthetic

<400> SEQUENCE: 821
cguaauccca gcacuuuggg guuggaacca uucaaaacag cauagcaagu uaaaauaagg      60
cuaguccguu aucaacuuga aaaaguggca ccgagucggu gc                       102

<210> SEQ ID NO 822
<211> LENGTH: 102
<212> TYPE: RNA
<213> ORGANISM: Artificial Sequence
<220> FEATURE:
<223> OTHER INFORMATION: Synthetic

<400> SEQUENCE: 822
ucccaaagug cugggauuac guuggaacca uucaaaacag cauagcaagu uaaaauaagg      60
```
cuaguccguu aucaacuuga aaaaguggca ccgagucggu gc        102

<210> SEQ ID NO 823
<211> LENGTH: 102
<212> TYPE: RNA
<213> ORGANISM: Artificial Sequence
<220> FEATURE:
<223> OTHER INFORMATION: Synthetic

<400> SEQUENCE: 823
cucccaaagu gcugggauua guuggaacca uucaaaacag cauagcaagu uaaaauaagg    60
cuaguccguu aucaacuuga aaaaguggca ccgagucggu gc        102

<210> SEQ ID NO 824
<211> LENGTH: 102
<212> TYPE: RNA
<213> ORGANISM: Artificial Sequence
<220> FEATURE:
<223> OTHER INFORMATION: Synthetic

<400> SEQUENCE: 824
cccagcacuu ugggaggccg guuggaacca uucaaaacag cauagcaagu uaaaauaagg    60
cuaguccguu aucaacuuga aaaaguggca ccgagucggu gc        102

<210> SEQ ID NO 825
<211> LENGTH: 102
<212> TYPE: RNA
<213> ORGANISM: Artificial Sequence
<220> FEATURE:
<223> OTHER INFORMATION: Synthetic

<400> SEQUENCE: 825
ccucggccuc ccaaagugcu guuggaacca uucaaaacag cauagcaagu uaaaauaagg    60
cuaguccguu aucaacuuga aaaaguggca ccgagucggu gc        102

<210> SEQ ID NO 826
<211> LENGTH: 102
<212> TYPE: RNA
<213> ORGANISM: Artificial Sequence
<220> FEATURE:
<223> OTHER INFORMATION: Synthetic

<400> SEQUENCE: 826
gcacuuuggg aggccgaggc guuggaacca uucaaaacag cauagcaagu uaaaauaagg    60
cuaguccguu aucaacuuga aaaaguggca ccgagucggu gc        102

<210> SEQ ID NO 827
<211> LENGTH: 102
<212> TYPE: RNA
<213> ORGANISM: Artificial Sequence
<220> FEATURE:
<223> OTHER INFORMATION: Synthetic

<400> SEQUENCE: 827
cuuugggagg ccgaggcagg guuggaacca uucaaaacag cauagcaagu uaaaauaagg    60
cuaguccguu aucaacuuga aaaaguggca ccgagucggu gc        102

<210> SEQ ID NO 828
<211> LENGTH: 102
<212> TYPE: RNA
<213> ORGANISM: Artificial Sequence
<220> FEATURE:
<223> OTHER INFORMATION: Synthetic -continued

<400> SEQUENCE: 828
gccgaggcag guggaucacg guuggaacca uucaaaacag cauagcaagu uaaaauaagg      60
cuaguccguu aucaacuuga aaaaguggca ccgagucggu gc                        102

<210> SEQ ID NO 829
<211> LENGTH: 102
<212> TYPE: RNA
<213> ORGANISM: Artificial Sequence
<220> FEATURE:
<223> OTHER INFORMATION: Synthetic

<400> SEQUENCE: 829
accucgugau ccaccugccu guuggaacca uucaaaacag cauagcaagu uaaaauaagg      60
cuaguccguu aucaacuuga aaaaguggca ccgagucggu gc                        102

<210> SEQ ID NO 830
<211> LENGTH: 102
<212> TYPE: RNA
<213> ORGANISM: Artificial Sequence
<220> FEATURE:
<223> OTHER INFORMATION: Synthetic

<400> SEQUENCE: 830
ggcaggugga ucacgagguc guuggaacca uucaaaacag cauagcaagu uaaaauaagg      60
cuaguccguu aucaacuuga aaaaguggca ccgagucggu gc                        102

<210> SEQ ID NO 831
<211> LENGTH: 102
<212> TYPE: RNA
<213> ORGANISM: Artificial Sequence
<220> FEATURE:
<223> OTHER INFORMATION: Synthetic

<400> SEQUENCE: 831
ucaggagauc gagaccaucu guuggaacca uucaaaacag cauagcaagu uaaaauaagg      60
cuaguccguu aucaacuuga aaaaguggca ccgagucggu gc                        102

<210> SEQ ID NO 832
<211> LENGTH: 102
<212> TYPE: RNA
<213> ORGANISM: Artificial Sequence
<220> FEATURE:
<223> OTHER INFORMATION: Synthetic

<400> SEQUENCE: 832
cgagaccauc uuggcuaaca guuggaacca uucaaaacag cauagcaagu uaaaauaagg      60
cuaguccguu aucaacuuga aaaaguggca ccgagucggu gc                        102

<210> SEQ ID NO 833
<211> LENGTH: 102
<212> TYPE: RNA
<213> ORGANISM: Artificial Sequence
<220> FEATURE:
<223> OTHER INFORMATION: Synthetic

<400> SEQUENCE: 833
uuucaccaug uuagccaaga guuggaacca uucaaaacag cauagcaagu uaaaauaagg      60
cuaguccguu aucaacuuga aaaaguggca ccgagucggu gc                        102

<210> SEQ ID NO 834

```
<211> LENGTH: 102
<212> TYPE: RNA
<213> ORGANISM: Artificial Sequence
<220> FEATURE:
<223> OTHER INFORMATION: Synthetic

<400> SEQUENCE: 834
uuguauuuuu uguagagacg guuggaacca uucaaaacag cauagcaagu uaaaauaagg      60
cuaguccguu aucaacuuga aaaguggca ccgagucggu gc                        102

<210> SEQ ID NO 835
<211> LENGTH: 102
<212> TYPE: RNA
<213> ORGANISM: Artificial Sequence
<220> FEATURE:
<223> OTHER INFORMATION: Synthetic

<400> SEQUENCE: 835
uuuguauuuu uuguagagac guuggaacca uucaaaacag cauagcaagu uaaaauaagg      60
cuaguccguu aucaacuuga aaaguggca ccgagucggu gc                        102

<210> SEQ ID NO 836
<211> LENGTH: 102
<212> TYPE: RNA
<213> ORGANISM: Artificial Sequence
<220> FEATURE:
<223> OTHER INFORMATION: Synthetic

<400> SEQUENCE: 836
uuuuguauuu uuguagaga guuggaacca uucaaaacag cauagcaagu uaaaauaagg      60
cuaguccguu aucaacuuga aaaguggca ccgagucggu gc                        102

<210> SEQ ID NO 837
<211> LENGTH: 102
<212> TYPE: RNA
<213> ORGANISM: Artificial Sequence
<220> FEATURE:
<223> OTHER INFORMATION: Synthetic

<400> SEQUENCE: 837
aaaaaauaca aaaaauuagc guuggaacca uucaaaacag cauagcaagu uaaaauaagg      60
cuaguccguu aucaacuuga aaaguggca ccgagucggu gc                        102

<210> SEQ ID NO 838
<211> LENGTH: 102
<212> TYPE: RNA
<213> ORGANISM: Artificial Sequence
<220> FEATURE:
<223> OTHER INFORMATION: Synthetic

<400> SEQUENCE: 838
aaaaauacaa aaaauuagcc guuggaacca uucaaaacag cauagcaagu uaaaauaagg      60
cuaguccguu aucaacuuga aaaguggca ccgagucggu gc                        102

<210> SEQ ID NO 839
<211> LENGTH: 102
<212> TYPE: RNA
<213> ORGANISM: Artificial Sequence
<220> FEATURE:
<223> OTHER INFORMATION: Synthetic

<400> SEQUENCE: 839
uacaaaaaau uagccggguu guuggaacca uucaaaacag cauagcaagu uaaaauaagg      60
```
cuaguccguu aucaacuuga aaaaguggca ccgagucggu gc        102

<210> SEQ ID NO 840
<211> LENGTH: 102
<212> TYPE: RNA
<213> ORGANISM: Artificial Sequence
<220> FEATURE:
<223> OTHER INFORMATION: Synthetic

<400> SEQUENCE: 840
aaaaaauuag ccgggugugg guuggaacca uucaaaacag cauagcaagu uaaaauaagg        60
cuaguccguu aucaacuuga aaaaguggca ccgagucggu gc        102

<210> SEQ ID NO 841
<211> LENGTH: 102
<212> TYPE: RNA
<213> ORGANISM: Artificial Sequence
<220> FEATURE:
<223> OTHER INFORMATION: Synthetic

<400> SEQUENCE: 841
aaauuagccg ggugggugg guuggaacca uucaaaacag cauagcaagu uaaaauaagg        60
cuaguccguu aucaacuuga aaaaguggca ccgagucggu gc        102

<210> SEQ ID NO 842
<211> LENGTH: 102
<212> TYPE: RNA
<213> ORGANISM: Artificial Sequence
<220> FEATURE:
<223> OTHER INFORMATION: Synthetic

<400> SEQUENCE: 842
aauuagccgg gugugguggc guuggaacca uucaaaacag cauagcaagu uaaaauaagg        60
cuaguccguu aucaacuuga aaaaguggca ccgagucggu gc        102

<210> SEQ ID NO 843
<211> LENGTH: 102
<212> TYPE: RNA
<213> ORGANISM: Artificial Sequence
<220> FEATURE:
<223> OTHER INFORMATION: Synthetic

<400> SEQUENCE: 843
caggcgcccg ccaccacacc guuggaacca uucaaaacag cauagcaagu uaaaauaagg        60
cuaguccguu aucaacuuga aaaaguggca ccgagucggu gc        102

<210> SEQ ID NO 844
<211> LENGTH: 102
<212> TYPE: RNA
<213> ORGANISM: Artificial Sequence
<220> FEATURE:
<223> OTHER INFORMATION: Synthetic

<400> SEQUENCE: 844
gccuguaguc ccagcuacuc guuggaacca uucaaaacag cauagcaagu uaaaauaagg        60
cuaguccguu aucaacuuga aaaaguggca ccgagucggu gc        102

<210> SEQ ID NO 845
<211> LENGTH: 102
<212> TYPE: RNA
<213> ORGANISM: Artificial Sequence
<220> FEATURE:

<223> OTHER INFORMATION: Synthetic

<400> SEQUENCE: 845
uguaguccca gcuacucagg guuggaacca uucaaaacag cauagcaagu uaaaauaagg        60
cuaguccguu aucaacuuga aaaguggca ccgagucggu gc        102

<210> SEQ ID NO 846
<211> LENGTH: 102
<212> TYPE: RNA
<213> ORGANISM: Artificial Sequence
<220> FEATURE:
<223> OTHER INFORMATION: Synthetic

<400> SEQUENCE: 846
uccugaguag cugggacuac guuggaacca uucaaaacag cauagcaagu uaaaauaagg        60
cuaguccguu aucaacuuga aaaguggca ccgagucggu gc        102

<210> SEQ ID NO 847
<211> LENGTH: 102
<212> TYPE: RNA
<213> ORGANISM: Artificial Sequence
<220> FEATURE:
<223> OTHER INFORMATION: Synthetic

<400> SEQUENCE: 847
cccagcuacu caggaggcug guuggaacca uucaaaacag cauagcaagu uaaaauaagg        60
cuaguccguu aucaacuuga aaaguggca ccgagucggu gc        102

<210> SEQ ID NO 848
<211> LENGTH: 102
<212> TYPE: RNA
<213> ORGANISM: Artificial Sequence
<220> FEATURE:
<223> OTHER INFORMATION: Synthetic

<400> SEQUENCE: 848
ccucagccuc cugaguagcu guuggaacca uucaaaacag cauagcaagu uaaaauaagg        60
cuaguccguu aucaacuuga aaaguggca ccgagucggu gc        102

<210> SEQ ID NO 849
<211> LENGTH: 102
<212> TYPE: RNA
<213> ORGANISM: Artificial Sequence
<220> FEATURE:
<223> OTHER INFORMATION: Synthetic

<400> SEQUENCE: 849
gccucagccu ccugaguagc guuggaacca uucaaaacag cauagcaagu uaaaauaagg        60
cuaguccguu aucaacuuga aaaguggca ccgagucggu gc        102

<210> SEQ ID NO 850
<211> LENGTH: 102
<212> TYPE: RNA
<213> ORGANISM: Artificial Sequence
<220> FEATURE:
<223> OTHER INFORMATION: Synthetic

<400> SEQUENCE: 850
aggaggcuga ggcaggagaa guuggaacca uucaaaacag cauagcaagu uaaaauaagg        60
cuaguccguu aucaacuuga aaaguggca ccgagucggu gc        102

```
<210> SEQ ID NO 851
<211> LENGTH: 102
<212> TYPE: RNA
<213> ORGANISM: Artificial Sequence
<220> FEATURE:
<223> OTHER INFORMATION: Synthetic

<400> SEQUENCE: 851
gcaggagaau ggcgugaacc guuggaacca uucaaaacag cauagcaagu uaaaauaagg      60
cuaguccguu aucaacuuga aaaguggca ccgagucggu gc                         102

<210> SEQ ID NO 852
<211> LENGTH: 102
<212> TYPE: RNA
<213> ORGANISM: Artificial Sequence
<220> FEATURE:
<223> OTHER INFORMATION: Synthetic

<400> SEQUENCE: 852
caggagaaug gcgugaaccc guuggaacca uucaaaacag cauagcaagu uaaaauaagg      60
cuaguccguu aucaacuuga aaaguggca ccgagucggu gc                         102

<210> SEQ ID NO 853
<211> LENGTH: 102
<212> TYPE: RNA
<213> ORGANISM: Artificial Sequence
<220> FEATURE:
<223> OTHER INFORMATION: Synthetic

<400> SEQUENCE: 853
gagaauggcg ugaacccggg guuggaacca uucaaaacag cauagcaagu uaaaauaagg      60
cuaguccguu aucaacuuga aaaguggca ccgagucggu gc                         102

<210> SEQ ID NO 854
<211> LENGTH: 102
<212> TYPE: RNA
<213> ORGANISM: Artificial Sequence
<220> FEATURE:
<223> OTHER INFORMATION: Synthetic

<400> SEQUENCE: 854
aauggcguga acccgggagg guuggaacca uucaaaacag cauagcaagu uaaaauaagg      60
cuaguccguu aucaacuuga aaaguggca ccgagucggu gc                         102

<210> SEQ ID NO 855
<211> LENGTH: 102
<212> TYPE: RNA
<213> ORGANISM: Artificial Sequence
<220> FEATURE:
<223> OTHER INFORMATION: Synthetic

<400> SEQUENCE: 855
cacugcaagc uccaccuccc guuggaacca uucaaaacag cauagcaagu uaaaauaagg      60
cuaguccguu aucaacuuga aaaguggca ccgagucggu gc                         102

<210> SEQ ID NO 856
<211> LENGTH: 102
<212> TYPE: RNA
<213> ORGANISM: Artificial Sequence
<220> FEATURE:
<223> OTHER INFORMATION: Synthetic

<400> SEQUENCE: 856
```
ucacugcaag cucccaccucc guuggaacca uucaaaacag cauagcaagu uaaaauaagg    60
cuaguccguu aucaacuuga aaaaguggca ccgagucggu gc    102

<210> SEQ ID NO 857
<211> LENGTH: 102
<212> TYPE: RNA
<213> ORGANISM: Artificial Sequence
<220> FEATURE:
<223> OTHER INFORMATION: Synthetic

<400> SEQUENCE: 857
cauaccacug cacuccagcc guuggaacca uucaaaacag cauagcaagu uaaaauaagg    60
cuaguccguu aucaacuuga aaaaguggca ccgagucggu gc    102

<210> SEQ ID NO 858
<211> LENGTH: 102
<212> TYPE: RNA
<213> ORGANISM: Artificial Sequence
<220> FEATURE:
<223> OTHER INFORMATION: Synthetic

<400> SEQUENCE: 858
auaccacugc acuccagccu guuggaacca uucaaaacag cauagcaagu uaaaauaagg    60
cuaguccguu aucaacuuga aaaaguggca ccgagucggu gc    102

<210> SEQ ID NO 859
<211> LENGTH: 102
<212> TYPE: RNA
<213> ORGANISM: Artificial Sequence
<220> FEATURE:
<223> OTHER INFORMATION: Synthetic

<400> SEQUENCE: 859
ucgcccaggc uggagugcag guuggaacca uucaaaacag cauagcaagu uaaaauaagg    60
cuaguccguu aucaacuuga aaaaguggca ccgagucggu gc    102

<210> SEQ ID NO 860
<211> LENGTH: 102
<212> TYPE: RNA
<213> ORGANISM: Artificial Sequence
<220> FEATURE:
<223> OTHER INFORMATION: Synthetic

<400> SEQUENCE: 860
ucucacucuu ucgcccaggc guuggaacca uucaaaacag cauagcaagu uaaaauaagg    60
cuaguccguu aucaacuuga aaaaguggca ccgagucggu gc    102

<210> SEQ ID NO 861
<211> LENGTH: 102
<212> TYPE: RNA
<213> ORGANISM: Artificial Sequence
<220> FEATURE:
<223> OTHER INFORMATION: Synthetic

<400> SEQUENCE: 861
ggagucucac ucuuucgccc guuggaacca uucaaaacag cauagcaagu uaaaauaagg    60
cuaguccguu aucaacuuga aaaaguggca ccgagucggu gc    102

<210> SEQ ID NO 862
<211> LENGTH: 102
<212> TYPE: RNA
<213> ORGANISM: Artificial Sequence

```
<220> FEATURE:
<223> OTHER INFORMATION: Synthetic

<400> SEQUENCE: 862 uguuuuugu uuuuugaga guuggaacca uucaaaacag cauagcaagu uaaaauaagg      60
cuaguccguu aucaacuuga aaaguggca ccgagucggu gc                       102

<210> SEQ ID NO 863
<211> LENGTH: 102
<212> TYPE: RNA
<213> ORGANISM: Artificial Sequence
<220> FEATURE:
<223> OTHER INFORMATION: Synthetic

<400> SEQUENCE: 863
aggaagaaag aaagguuuuu guuggaacca uucaaaacag cauagcaagu uaaaauaagg     60
cuaguccguu aucaacuuga aaaguggca ccgagucggu gc                       102

<210> SEQ ID NO 864
<211> LENGTH: 102
<212> TYPE: RNA
<213> ORGANISM: Artificial Sequence
<220> FEATURE:
<223> OTHER INFORMATION: Synthetic

<400> SEQUENCE: 864
agaagaaaag gaagaaagaa guuggaacca uucaaaacag cauagcaagu uaaaauaagg     60
cuaguccguu aucaacuuga aaaguggca ccgagucggu gc                       102

<210> SEQ ID NO 865
<211> LENGTH: 102
<212> TYPE: RNA
<213> ORGANISM: Artificial Sequence
<220> FEATURE:
<223> OTHER INFORMATION: Synthetic

<400> SEQUENCE: 865 cuucuuccu uuucuucucu guuggaacca uucaaaacag cauagcaagu uaaaauaagg      60
cuaguccguu aucaacuuga aaaguggca ccgagucggu gc                       102

<210> SEQ ID NO 866
<211> LENGTH: 102
<212> TYPE: RNA
<213> ORGANISM: Artificial Sequence
<220> FEATURE:
<223> OTHER INFORMATION: Synthetic

<400> SEQUENCE: 866
uuucuuccuu uucuucucuu guuggaacca uucaaaacag cauagcaagu uaaaauaagg     60
cuaguccguu aucaacuuga aaaguggca ccgagucggu gc                       102

<210> SEQ ID NO 867
<211> LENGTH: 102
<212> TYPE: RNA
<213> ORGANISM: Artificial Sequence
<220> FEATURE:
<223> OTHER INFORMATION: Synthetic

<400> SEQUENCE: 867
aauggaccca agagaagaaa guuggaacca uucaaaacag cauagcaagu uaaaauaagg     60
cuaguccguu aucaacuuga aaaguggca ccgagucggu gc                       102
```

<210> SEQ ID NO 868
<211> LENGTH: 102
<212> TYPE: RNA
<213> ORGANISM: Artificial Sequence
<220> FEATURE:
<223> OTHER INFORMATION: Synthetic

<400> SEQUENCE: 868
ggcuauuaca uaagaaacaa guuggaacca uucaaaacag cauagcaagu uaaaauaagg    60
cuaguccguu aucaacuuga aaaaguggca ccgagucggu gc                     102

<210> SEQ ID NO 869
<211> LENGTH: 102
<212> TYPE: RNA
<213> ORGANISM: Artificial Sequence
<220> FEATURE:
<223> OTHER INFORMATION: Synthetic

<400> SEQUENCE: 869
cacaggaaaa ggaacuguac guuggaacca uucaaaacag cauagcaagu uaaaauaagg    60
cuaguccguu aucaacuuga aaaaguggca ccgagucggu gc                     102

<210> SEQ ID NO 870
<211> LENGTH: 102
<212> TYPE: RNA
<213> ORGANISM: Artificial Sequence
<220> FEATURE:
<223> OTHER INFORMATION: Synthetic

<400> SEQUENCE: 870
auuaaagcua acacaggaaa guuggaacca uucaaaacag cauagcaagu uaaaauaagg    60
cuaguccguu aucaacuuga aaaaguggca ccgagucggu gc                     102

<210> SEQ ID NO 871
<211> LENGTH: 102
<212> TYPE: RNA
<213> ORGANISM: Artificial Sequence
<220> FEATURE:
<223> OTHER INFORMATION: Synthetic

<400> SEQUENCE: 871
ucaaaaauua aagcuaacac guuggaacca uucaaaacag cauagcaagu uaaaauaagg    60
cuaguccguu aucaacuuga aaaaguggca ccgagucggu gc                     102

<210> SEQ ID NO 872
<211> LENGTH: 102
<212> TYPE: RNA
<213> ORGANISM: Artificial Sequence
<220> FEATURE:
<223> OTHER INFORMATION: Synthetic

<400> SEQUENCE: 872
uaaaauuguc uaaacaucuc guuggaacca uucaaaacag cauagcaagu uaaaauaagg    60
cuaguccguu aucaacuuga aaaaguggca ccgagucggu gc                     102

<210> SEQ ID NO 873
<211> LENGTH: 102
<212> TYPE: RNA
<213> ORGANISM: Artificial Sequence
<220> FEATURE:
<223> OTHER INFORMATION: Synthetic

<400> SEQUENCE: 873

```
agagauguuu agacaauuuu guuggaacca uucaaaacag cauagcaagu uaaaauaagg    60
cuaguccguu aucaacuuga aaaaguggca ccgagucggu gc                      102

<210> SEQ ID NO 874
<211> LENGTH: 102
<212> TYPE: RNA
<213> ORGANISM: Artificial Sequence
<220> FEATURE:
<223> OTHER INFORMATION: Synthetic

<400> SEQUENCE: 874
ucuaaacauc ucugggacca guuggaacca uucaaaacag cauagcaagu uaaaauaagg    60
cuaguccguu aucaacuuga aaaaguggca ccgagucggu gc                      102

<210> SEQ ID NO 875
<211> LENGTH: 102
<212> TYPE: RNA
<213> ORGANISM: Artificial Sequence
<220> FEATURE:
<223> OTHER INFORMATION: Synthetic

<400> SEQUENCE: 875
uuuaugcuuu cauauauccu guuggaacca uucaaaacag cauagcaagu uaaaauaagg    60
cuaguccguu aucaacuuga aaaaguggca ccgagucggu gc                      102

<210> SEQ ID NO 876
<211> LENGTH: 102
<212> TYPE: RNA
<213> ORGANISM: Artificial Sequence
<220> FEATURE:
<223> OTHER INFORMATION: Synthetic

<400> SEQUENCE: 876
agcauaaauu acaaagaaaa guuggaacca uucaaaacag cauagcaagu uaaaauaagg    60
cuaguccguu aucaacuuga aaaaguggca ccgagucggu gc                      102

<210> SEQ ID NO 877
<211> LENGTH: 102
<212> TYPE: RNA
<213> ORGANISM: Artificial Sequence
<220> FEATURE:
<223> OTHER INFORMATION: Synthetic

<400> SEQUENCE: 877
uacaaagaaa aagguuauca guuggaacca uucaaaacag cauagcaagu uaaaauaagg    60
cuaguccguu aucaacuuga aaaaguggca ccgagucggu gc                      102

<210> SEQ ID NO 878
<211> LENGTH: 102
<212> TYPE: RNA
<213> ORGANISM: Artificial Sequence
<220> FEATURE:
<223> OTHER INFORMATION: Synthetic

<400> SEQUENCE: 878
acaaagaaaa agguuaucau guuggaacca uucaaaacag cauagcaagu uaaaauaagg    60
cuaguccguu aucaacuuga aaaaguggca ccgagucggu gc                      102

<210> SEQ ID NO 879
<211> LENGTH: 102
<212> TYPE: RNA
```

```
<213> ORGANISM: Artificial Sequence
<220> FEATURE:
<223> OTHER INFORMATION: Synthetic

<400> SEQUENCE: 879
caaagaaaaa gguuaucaug guuggaacca uucaaaacag cauagcaagu uaaaauaagg      60
cuaguccguu aucaacuuga aaaguggca ccgagucggu gc                         102

<210> SEQ ID NO 880
<211> LENGTH: 102
<212> TYPE: RNA
<213> ORGANISM: Artificial Sequence
<220> FEATURE:
<223> OTHER INFORMATION: Synthetic

<400> SEQUENCE: 880
ucugagauuu aaauagagu guuggaacca uucaaaacag cauagcaagu uaaaauaagg       60
cuaguccguu aucaacuuga aaaguggca ccgagucggu gc                         102

<210> SEQ ID NO 881
<211> LENGTH: 102
<212> TYPE: RNA
<213> ORGANISM: Artificial Sequence
<220> FEATURE:
<223> OTHER INFORMATION: Synthetic

<400> SEQUENCE: 881
cuuauaagau acauuaugaa guuggaacca uucaaaacag cauagcaagu uaaaauaagg      60
cuaguccguu aucaacuuga aaaguggca ccgagucggu gc                         102

<210> SEQ ID NO 882
<211> LENGTH: 102
<212> TYPE: RNA
<213> ORGANISM: Artificial Sequence
<220> FEATURE:
<223> OTHER INFORMATION: Synthetic

<400> SEQUENCE: 882
uaucuuauaa gacuauaaaa guuggaacca uucaaaacag cauagcaagu uaaaauaagg      60
cuaguccguu aucaacuuga aaaguggca ccgagucggu gc                         102

<210> SEQ ID NO 883
<211> LENGTH: 102
<212> TYPE: RNA
<213> ORGANISM: Artificial Sequence
<220> FEATURE:
<223> OTHER INFORMATION: Synthetic

<400> SEQUENCE: 883
aucuuauaag acuauaaaaa guuggaacca uucaaaacag cauagcaagu uaaaauaagg      60
cuaguccguu aucaacuuga aaaguggca ccgagucggu gc                         102

<210> SEQ ID NO 884
<211> LENGTH: 102
<212> TYPE: RNA
<213> ORGANISM: Artificial Sequence
<220> FEATURE:
<223> OTHER INFORMATION: Synthetic

<400> SEQUENCE: 884
uuauaagacu auaaaaggg guuggaacca uucaaaacag cauagcaagu uaaaauaagg       60
cuaguccguu aucaacuuga aaaguggca ccgagucggu gc                         102
```

<210> SEQ ID NO 885
<211> LENGTH: 102
<212> TYPE: RNA
<213> ORGANISM: Artificial Sequence
<220> FEATURE:
<223> OTHER INFORMATION: Synthetic

<400> SEQUENCE: 885
uaaaaaggga ggaaauauag guuggaacca uucaaaacag cauagcaagu uaaaauaagg    60
cuaguccguu aucaacuuga aaaaguggca ccgagucggu gc                     102

<210> SEQ ID NO 886
<211> LENGTH: 102
<212> TYPE: RNA
<213> ORGANISM: Artificial Sequence
<220> FEATURE:
<223> OTHER INFORMATION: Synthetic

<400> SEQUENCE: 886
aaaaagggag gaaauauaga guuggaacca uucaaaacag cauagcaagu uaaaauaagg    60
cuaguccguu aucaacuuga aaaaguggca ccgagucggu gc                     102

<210> SEQ ID NO 887
<211> LENGTH: 102
<212> TYPE: RNA
<213> ORGANISM: Artificial Sequence
<220> FEATURE:
<223> OTHER INFORMATION: Synthetic

<400> SEQUENCE: 887
aaauauagag gguccacuuu guuggaacca uucaaaacag cauagcaagu uaaaauaagg    60
cuaguccguu aucaacuuga aaaaguggca ccgagucggu gc                     102

<210> SEQ ID NO 888
<211> LENGTH: 102
<212> TYPE: RNA
<213> ORGANISM: Artificial Sequence
<220> FEATURE:
<223> OTHER INFORMATION: Synthetic

<400> SEQUENCE: 888
uauagagggu ccacuuuugg guuggaacca uucaaaacag cauagcaagu uaaaauaagg    60
cuaguccguu aucaacuuga aaaaguggca ccgagucggu gc                     102

<210> SEQ ID NO 889
<211> LENGTH: 102
<212> TYPE: RNA
<213> ORGANISM: Artificial Sequence
<220> FEATURE:
<223> OTHER INFORMATION: Synthetic

<400> SEQUENCE: 889
acucugaagu ccaccaaaag guuggaacca uucaaaacag cauagcaagu uaaaauaagg    60
cuaguccguu aucaacuuga aaaaguggca ccgagucggu gc                     102

<210> SEQ ID NO 890
<211> LENGTH: 102
<212> TYPE: RNA
<213> ORGANISM: Artificial Sequence
<220> FEATURE:
<223> OTHER INFORMATION: Synthetic

```
<400> SEQUENCE: 890
agaauagagu ugcaccguuu guuggaacca uucaaaacag cauagcaagu uaaaauaagg    60
cuaguccguu aucaacuuga aaaguggca ccgagucggu gc                      102

<210> SEQ ID NO 891
<211> LENGTH: 102
<212> TYPE: RNA
<213> ORGANISM: Artificial Sequence
<220> FEATURE:
<223> OTHER INFORMATION: Synthetic

<400> SEQUENCE: 891
aaaacggugc aacucuauuc guuggaacca uucaaaacag cauagcaagu uaaaauaagg    60
cuaguccguu aucaacuuga aaaguggca ccgagucggu gc                      102

<210> SEQ ID NO 892
<211> LENGTH: 102
<212> TYPE: RNA
<213> ORGANISM: Artificial Sequence
<220> FEATURE:
<223> OTHER INFORMATION: Synthetic

<400> SEQUENCE: 892 ccguuuggg cuaaugaaaa guuggaacca uucaaaacag cauagcaagu uaaaauaagg    60
cuaguccguu aucaacuuga aaaguggca ccgagucggu gc                      102

<210> SEQ ID NO 893
<211> LENGTH: 102
<212> TYPE: RNA
<213> ORGANISM: Artificial Sequence
<220> FEATURE:
<223> OTHER INFORMATION: Synthetic

<400> SEQUENCE: 893 ccuuuucau uagcccaaaa guuggaacca uucaaaacag cauagcaagu uaaaauaagg    60
cuaguccguu aucaacuuga aaaguggca ccgagucggu gc                      102

<210> SEQ ID NO 894
<211> LENGTH: 102
<212> TYPE: RNA
<213> ORGANISM: Artificial Sequence
<220> FEATURE:
<223> OTHER INFORMATION: Synthetic

<400> SEQUENCE: 894
ugggcuaaug aaaaaggaag guuggaacca uucaaaacag cauagcaagu uaaaauaagg    60
cuaguccguu aucaacuuga aaaguggca ccgagucggu gc                      102

<210> SEQ ID NO 895
<211> LENGTH: 102
<212> TYPE: RNA
<213> ORGANISM: Artificial Sequence
<220> FEATURE:
<223> OTHER INFORMATION: Synthetic

<400> SEQUENCE: 895
uaaugaaaaa ggaagaggcu guuggaacca uucaaaacag cauagcaagu uaaaauaagg    60
cuaguccguu aucaacuuga aaaguggca ccgagucggu gc                      102

<210> SEQ ID NO 896
<211> LENGTH: 102
```

```
<212> TYPE: RNA
<213> ORGANISM: Artificial Sequence
<220> FEATURE:
<223> OTHER INFORMATION: Synthetic

<400> SEQUENCE: 896
aaugaaaaag gaagaggcua guuggaacca uucaaaacag cauagcaagu uaaaauaagg      60
cuaguccguu aucaacuuga aaaguggca ccgagucggu gc                        102

<210> SEQ ID NO 897
<211> LENGTH: 102
<212> TYPE: RNA
<213> ORGANISM: Artificial Sequence
<220> FEATURE:
<223> OTHER INFORMATION: Synthetic

<400> SEQUENCE: 897
cugaaucuua aaauaugucc guuggaacca uucaaaacag cauagcaagu uaaaauaagg      60
cuaguccguu aucaacuuga aaaguggca ccgagucggu gc                        102

<210> SEQ ID NO 898
<211> LENGTH: 102
<212> TYPE: RNA
<213> ORGANISM: Artificial Sequence
<220> FEATURE:
<223> OTHER INFORMATION: Synthetic

<400> SEQUENCE: 898
caggcagcuu uaucucaacc guuggaacca uucaaaacag cauagcaagu uaaaauaagg      60
cuaguccguu aucaacuuga aaaguggca ccgagucggu gc                        102

<210> SEQ ID NO 899
<211> LENGTH: 102
<212> TYPE: RNA
<213> ORGANISM: Artificial Sequence
<220> FEATURE:
<223> OTHER INFORMATION: Synthetic

<400> SEQUENCE: 899
cuaagagauc aaguuucagc guuggaacca uucaaaacag cauagcaagu uaaaauaagg      60
cuaguccguu aucaacuuga aaaguggca ccgagucggu gc                        102

<210> SEQ ID NO 900
<211> LENGTH: 102
<212> TYPE: RNA
<213> ORGANISM: Artificial Sequence
<220> FEATURE:
<223> OTHER INFORMATION: Synthetic

<400> SEQUENCE: 900
guguucuugu ugauauucug guuggaacca uucaaaacag cauagcaagu uaaaauaagg      60
cuaguccguu aucaacuuga aaaguggca ccgagucggu gc                        102

<210> SEQ ID NO 901
<211> LENGTH: 102
<212> TYPE: RNA
<213> ORGANISM: Artificial Sequence
<220> FEATURE:
<223> OTHER INFORMATION: Synthetic

<400> SEQUENCE: 901
cuuguugaua uucuguggca guuggaacca uucaaaacag cauagcaagu uaaaauaagg      60
```
cuaguccguu aucaacuuga aaaaguggca ccgagucggu gc                              102

<210> SEQ ID NO 902
<211> LENGTH: 102
<212> TYPE: RNA
<213> ORGANISM: Artificial Sequence
<220> FEATURE:
<223> OTHER INFORMATION: Synthetic

<400> SEQUENCE: 902
ucuguggcau ggcuacagau guuggaacca uucaaaacag cauagcaagu uaaaauaagg            60
cuaguccguu aucaacuuga aaaaguggca ccgagucggu gc                              102

<210> SEQ ID NO 903
<211> LENGTH: 102
<212> TYPE: RNA
<213> ORGANISM: Artificial Sequence
<220> FEATURE:
<223> OTHER INFORMATION: Synthetic

<400> SEQUENCE: 903
agaacuuauu uacacaggga guuggaacca uucaaaacag cauagcaagu uaaaauaagg            60
cuaguccguu aucaacuuga aaaaguggca ccgagucggu gc                              102

<210> SEQ ID NO 904
<211> LENGTH: 102
<212> TYPE: RNA
<213> ORGANISM: Artificial Sequence
<220> FEATURE:
<223> OTHER INFORMATION: Synthetic

<400> SEQUENCE: 904
aaagagaacu uauuuacaca guuggaacca uucaaaacag cauagcaagu uaaaauaagg            60
cuaguccguu aucaacuuga aaaaguggca ccgagucggu gc                              102

<210> SEQ ID NO 905
<211> LENGTH: 102
<212> TYPE: RNA
<213> ORGANISM: Artificial Sequence
<220> FEATURE:
<223> OTHER INFORMATION: Synthetic

<400> SEQUENCE: 905
caaagagaac uuauuuacac guuggaacca uucaaaacag cauagcaagu uaaaauaagg            60
cuaguccguu aucaacuuga aaaaguggca ccgagucggu gc                              102

<210> SEQ ID NO 906
<211> LENGTH: 102
<212> TYPE: RNA
<213> ORGANISM: Artificial Sequence
<220> FEATURE:
<223> OTHER INFORMATION: Synthetic

<400> SEQUENCE: 906
uucucuuugu auuuacuuuu guuggaacca uucaaaacag cauagcaagu uaaaauaagg            60
cuaguccguu aucaacuuga aaaaguggca ccgagucggu gc                              102

<210> SEQ ID NO 907
<211> LENGTH: 102
<212> TYPE: RNA
<213> ORGANISM: Artificial Sequence
<220> FEATURE:
<223> OTHER INFORMATION: Synthetic

<400> SEQUENCE: 907
ucucuuugua uuuacuuuua guuggaacca uucaaaacag cauagcaagu uaaaauaagg    60
cuaguccguu aucaacuuga aaaaguggca ccgagucggu gc    102

<210> SEQ ID NO 908
<211> LENGTH: 102
<212> TYPE: RNA
<213> ORGANISM: Artificial Sequence
<220> FEATURE:
<223> OTHER INFORMATION: Synthetic

<400> SEQUENCE: 908
cuuuguauuu acuuuuaggg guuggaacca uucaaaacag cauagcaagu uaaaauaagg    60
cuaguccguu aucaacuuga aaaaguggca ccgagucggu gc    102

<210> SEQ ID NO 909
<211> LENGTH: 102
<212> TYPE: RNA
<213> ORGANISM: Artificial Sequence
<220> FEATURE:
<223> OTHER INFORMATION: Synthetic

<400> SEQUENCE: 909
agcuuuuguc caccuuuaaa guuggaacca uucaaaacag cauagcaagu uaaaauaagg    60
cuaguccguu aucaacuuga aaaaguggca ccgagucggu gc    102

<210> SEQ ID NO 910
<211> LENGTH: 102
<212> TYPE: RNA
<213> ORGANISM: Artificial Sequence
<220> FEATURE:
<223> OTHER INFORMATION: Synthetic

<400> SEQUENCE: 910
uuuauuuuuc cauuuaaagg guuggaacca uucaaaacag cauagcaagu uaaaauaagg    60
cuaguccguu aucaacuuga aaaaguggca ccgagucggu gc    102

<210> SEQ ID NO 911
<211> LENGTH: 102
<212> TYPE: RNA
<213> ORGANISM: Artificial Sequence
<220> FEATURE:
<223> OTHER INFORMATION: Synthetic

<400> SEQUENCE: 911
uauuuuauuu uuccauuuaa guuggaacca uucaaaacag cauagcaagu uaaaauaagg    60
cuaguccguu aucaacuuga aaaaguggca ccgagucggu gc    102

<210> SEQ ID NO 912
<211> LENGTH: 102
<212> TYPE: RNA
<213> ORGANISM: Artificial Sequence
<220> FEATURE:
<223> OTHER INFORMATION: Synthetic

<400> SEQUENCE: 912
cuuacauaaa cauacuuaaa guuggaacca uucaaaacag cauagcaagu uaaaauaagg    60
cuaguccguu aucaacuuga aaaaguggca ccgagucggu gc    102

<210> SEQ ID NO 913

```
<211> LENGTH: 102
<212> TYPE: RNA
<213> ORGANISM: Artificial Sequence
<220> FEATURE:
<223> OTHER INFORMATION: Synthetic

<400> SEQUENCE: 913
uaagcacaga aguuuuuaag guuggaacca uucaaaacag cauagcaagu uaaaauaagg    60
cuaguccguu aucaacuuga aaaaguggca ccgagucggu gc                     102

<210> SEQ ID NO 914
<211> LENGTH: 102
<212> TYPE: RNA
<213> ORGANISM: Artificial Sequence
<220> FEATURE:
<223> OTHER INFORMATION: Synthetic

<400> SEQUENCE: 914
aaguuuuuaa gaggcaugaa guuggaacca uucaaaacag cauagcaagu uaaaauaagg    60
cuaguccguu aucaacuuga aaaaguggca ccgagucggu gc                     102

<210> SEQ ID NO 915
<211> LENGTH: 102
<212> TYPE: RNA
<213> ORGANISM: Artificial Sequence
<220> FEATURE:
<223> OTHER INFORMATION: Synthetic

<400> SEQUENCE: 915
auauuuacgu aguuuucau guuggaacca uucaaaacag cauagcaagu uaaaauaagg    60
cuaguccguu aucaacuuga aaaaguggca ccgagucggu gc                     102

<210> SEQ ID NO 916
<211> LENGTH: 102
<212> TYPE: RNA
<213> ORGANISM: Artificial Sequence
<220> FEATURE:
<223> OTHER INFORMATION: Synthetic

<400> SEQUENCE: 916
cguaaauauu cuugagaaac guuggaacca uucaaaacag cauagcaagu uaaaauaagg    60
cuaguccguu aucaacuuga aaaaguggca ccgagucggu gc                     102

<210> SEQ ID NO 917
<211> LENGTH: 102
<212> TYPE: RNA
<213> ORGANISM: Artificial Sequence
<220> FEATURE:
<223> OTHER INFORMATION: Synthetic

<400> SEQUENCE: 917
uucuugagaa acaggaagac guuggaacca uucaaaacag cauagcaagu uaaaauaagg    60
cuaguccguu aucaacuuga aaaaguggca ccgagucggu gc                     102

<210> SEQ ID NO 918
<211> LENGTH: 102
<212> TYPE: RNA
<213> ORGANISM: Artificial Sequence
<220> FEATURE:
<223> OTHER INFORMATION: Synthetic

<400> SEQUENCE: 918
uaauauuaaa aacauugguu guuggaacca uucaaaacag cauagcaagu uaaaauaagg    60
```

```
cuaguccguu aucaacuuga aaaaguggca ccgagucggu gc                        102

<210> SEQ ID NO 919
<211> LENGTH: 102
<212> TYPE: RNA
<213> ORGANISM: Artificial Sequence
<220> FEATURE:
<223> OTHER INFORMATION: Synthetic

<400> SEQUENCE: 919
ccaauguuuu uaauauuauc guuggaacca uucaaaacag cauagcaagu uaaaauaagg      60
cuaguccguu aucaacuuga aaaaguggca ccgagucggu gc                        102

<210> SEQ ID NO 920
<211> LENGTH: 102
<212> TYPE: RNA
<213> ORGANISM: Artificial Sequence
<220> FEATURE:
<223> OTHER INFORMATION: Synthetic

<400> SEQUENCE: 920
ccugauaaua uuaaaaacau guuggaacca uucaaaacag cauagcaagu uaaaauaagg      60
cuaguccguu aucaacuuga aaaaguggca ccgagucggu gc                        102

<210> SEQ ID NO 921
<211> LENGTH: 102
<212> TYPE: RNA
<213> ORGANISM: Artificial Sequence
<220> FEATURE:
<223> OTHER INFORMATION: Synthetic

<400> SEQUENCE: 921
cauuaucaug cauacaucuc guuggaacca uucaaaacag cauagcaagu uaaaauaagg      60
cuaguccguu aucaacuuga aaaaguggca ccgagucggu gc                        102

<210> SEQ ID NO 922
<211> LENGTH: 102
<212> TYPE: RNA
<213> ORGANISM: Artificial Sequence
<220> FEATURE:
<223> OTHER INFORMATION: Synthetic

<400> SEQUENCE: 922
aucaugcaua caucucuggc guuggaacca uucaaaacag cauagcaagu uaaaauaagg      60
cuaguccguu aucaacuuga aaaaguggca ccgagucggu gc                        102

<210> SEQ ID NO 923
<211> LENGTH: 102
<212> TYPE: RNA
<213> ORGANISM: Artificial Sequence
<220> FEATURE:
<223> OTHER INFORMATION: Synthetic

<400> SEQUENCE: 923
uucauuucau uuugauuuug guuggaacca uucaaaacag cauagcaagu uaaaauaagg      60
cuaguccguu aucaacuuga aaaaguggca ccgagucggu gc                        102

<210> SEQ ID NO 924
<211> LENGTH: 102
<212> TYPE: RNA
<213> ORGANISM: Artificial Sequence
<220> FEATURE:
```

<223> OTHER INFORMATION: Synthetic

<400> SEQUENCE: 924
auucaauuug aagcaguggu guuggaacca uucaaaacag cauagcaagu uaaaauaagg    60
cuaguccguu aucaacuuga aaaaguggca ccgagucggu gc    102

<210> SEQ ID NO 925
<211> LENGTH: 102
<212> TYPE: RNA
<213> ORGANISM: Artificial Sequence
<220> FEATURE:
<223> OTHER INFORMATION: Synthetic

<400> SEQUENCE: 925
gaauauucaa uuugaagcag guuggaacca uucaaaacag cauagcaagu uaaaauaagg    60
cuaguccguu aucaacuuga aaaaguggca ccgagucggu gc    102

<210> SEQ ID NO 926
<211> LENGTH: 102
<212> TYPE: RNA
<213> ORGANISM: Artificial Sequence
<220> FEATURE:
<223> OTHER INFORMATION: Synthetic

<400> SEQUENCE: 926
cauacgauuu aaaaucgcug guuggaacca uucaaaacag cauagcaagu uaaaauaagg    60
cuaguccguu aucaacuuga aaaaguggca ccgagucggu gc    102

<210> SEQ ID NO 927
<211> LENGTH: 102
<212> TYPE: RNA
<213> ORGANISM: Artificial Sequence
<220> FEATURE:
<223> OTHER INFORMATION: Synthetic

<400> SEQUENCE: 927
aaaaucgcug aggcgcguuc guuggaacca uucaaaacag cauagcaagu uaaaauaagg    60
cuaguccguu aucaacuuga aaaaguggca ccgagucggu gc    102

<210> SEQ ID NO 928
<211> LENGTH: 102
<212> TYPE: RNA
<213> ORGANISM: Artificial Sequence
<220> FEATURE:
<223> OTHER INFORMATION: Synthetic

<400> SEQUENCE: 928 uuuuuuuuc uuuuuuguac guuggaacca uucaaaacag cauagcaagu uaaaauaagg    60
cuaguccguu aucaacuuga aaaaguggca ccgagucggu gc    102

<210> SEQ ID NO 929
<211> LENGTH: 102
<212> TYPE: RNA
<213> ORGANISM: Artificial Sequence
<220> FEATURE:
<223> OTHER INFORMATION: Synthetic

<400> SEQUENCE: 929
cuguugucaa agauuuuaaa guuggaacca uucaaaacag cauagcaagu uaaaauaagg    60
cuaguccguu aucaacuuga aaaaguggca ccgagucggu gc    102

```
<210> SEQ ID NO 930
<211> LENGTH: 102
<212> TYPE: RNA
<213> ORGANISM: Artificial Sequence
<220> FEATURE:
<223> OTHER INFORMATION: Synthetic

<400> SEQUENCE: 930
ugacaacaga guucuguuuu guuggaacca uucaaaacag cauagcaagu uaaaauaagg     60
cuaguccguu aucaacuuga aaaaguggca ccgagucggu gc                      102

<210> SEQ ID NO 931
<211> LENGTH: 102
<212> TYPE: RNA
<213> ORGANISM: Artificial Sequence
<220> FEATURE:
<223> OTHER INFORMATION: Synthetic

<400> SEQUENCE: 931
agaauacgcu gagaguuauc guuggaacca uucaaaacag cauagcaagu uaaaauaagg     60
cuaguccguu aucaacuuga aaaaguggca ccgagucggu gc                      102

<210> SEQ ID NO 932
<211> LENGTH: 102
<212> TYPE: RNA
<213> ORGANISM: Artificial Sequence
<220> FEATURE:
<223> OTHER INFORMATION: Synthetic

<400> SEQUENCE: 932
gcaagagaag aaaagaacgg guuggaacca uucaaaacag cauagcaagu uaaaauaagg     60
cuaguccguu aucaacuuga aaaaguggca ccgagucggu gc                      102

<210> SEQ ID NO 933
<211> LENGTH: 102
<212> TYPE: RNA
<213> ORGANISM: Artificial Sequence
<220> FEATURE:
<223> OTHER INFORMATION: Synthetic

<400> SEQUENCE: 933
guugcaagag aagaaaagaa guuggaacca uucaaaacag cauagcaagu uaaaauaagg     60
cuaguccguu aucaacuuga aaaaguggca ccgagucggu gc                      102

<210> SEQ ID NO 934
<211> LENGTH: 102
<212> TYPE: RNA
<213> ORGANISM: Artificial Sequence
<220> FEATURE:
<223> OTHER INFORMATION: Synthetic

<400> SEQUENCE: 934
augcacacgu aaaagagagg guuggaacca uucaaaacag cauagcaagu uaaaauaagg     60
cuaguccguu aucaacuuga aaaaguggca ccgagucggu gc                      102

<210> SEQ ID NO 935
<211> LENGTH: 102
<212> TYPE: RNA
<213> ORGANISM: Artificial Sequence
<220> FEATURE:
<223> OTHER INFORMATION: Synthetic

<400> SEQUENCE: 935
```

-continued aagaugcaca cguaaaagag guuggaacca uucaaaacag cauagcaagu uaaaauaagg    60
cuaguccguu aucaacuuga aaaaguggca ccgagucggu gc    102

<210> SEQ ID NO 936
<211> LENGTH: 102
<212> TYPE: RNA
<213> ORGANISM: Artificial Sequence
<220> FEATURE:
<223> OTHER INFORMATION: Synthetic

<400> SEQUENCE: 936
aucaugcaua caucucuggc guuggaacca uucaaaacag cauagcaagu uaaaauaagg    60
cuaguccguu aucaacuuga aaaaguggca ccgagucggu gc    102

<210> SEQ ID NO 937
<211> LENGTH: 102
<212> TYPE: RNA
<213> ORGANISM: Artificial Sequence
<220> FEATURE:
<223> OTHER INFORMATION: Synthetic

<400> SEQUENCE: 937
uucauuucau uuugauuuug guuggaacca uucaaaacag cauagcaagu uaaaauaagg    60
cuaguccguu aucaacuuga aaaaguggca ccgagucggu gc    102

<210> SEQ ID NO 938
<211> LENGTH: 102
<212> TYPE: RNA
<213> ORGANISM: Artificial Sequence
<220> FEATURE:
<223> OTHER INFORMATION: Synthetic

<400> SEQUENCE: 938
auucaauuug aagcaguggu guuggaacca uucaaaacag cauagcaagu uaaaauaagg    60
cuaguccguu aucaacuuga aaaaguggca ccgagucggu gc    102

<210> SEQ ID NO 939
<211> LENGTH: 102
<212> TYPE: RNA
<213> ORGANISM: Artificial Sequence
<220> FEATURE:
<223> OTHER INFORMATION: Synthetic

<400> SEQUENCE: 939
gaauauucaa uuugaagcag guuggaacca uucaaaacag cauagcaagu uaaaauaagg    60
cuaguccguu aucaacuuga aaaaguggca ccgagucggu gc    102

<210> SEQ ID NO 940
<211> LENGTH: 102
<212> TYPE: RNA
<213> ORGANISM: Artificial Sequence
<220> FEATURE:
<223> OTHER INFORMATION: Synthetic

<400> SEQUENCE: 940
cauacgauuu aaaaucgcug guuggaacca uucaaaacag cauagcaagu uaaaauaagg    60
cuaguccguu aucaacuuga aaaaguggca ccgagucggu gc    102

<210> SEQ ID NO 941
<211> LENGTH: 102
<212> TYPE: RNA
<213> ORGANISM: Artificial Sequence

```
<220> FEATURE:
<223> OTHER INFORMATION: Synthetic

<400> SEQUENCE: 941
aaaaucgcug aggcgcguuc guuggaacca uucaaaacag cauagcaagu uaaaauaagg    60
cuaguccguu aucaacuuga aaaguggca ccgagucggu gc                       102

<210> SEQ ID NO 942
<211> LENGTH: 102
<212> TYPE: RNA
<213> ORGANISM: Artificial Sequence
<220> FEATURE:
<223> OTHER INFORMATION: Synthetic

<400> SEQUENCE: 942
uuuuuuuuuc uuuuuguac guuggaacca uucaaaacag cauagcaagu uaaaauaagg     60
cuaguccguu aucaacuuga aaaguggca ccgagucggu gc                       102

<210> SEQ ID NO 943
<211> LENGTH: 102
<212> TYPE: RNA
<213> ORGANISM: Artificial Sequence
<220> FEATURE:
<223> OTHER INFORMATION: Synthetic

<400> SEQUENCE: 943
cuguugucaa agauuuaaa guuggaacca uucaaaacag cauagcaagu uaaaauaagg     60
cuaguccguu aucaacuuga aaaguggca ccgagucggu gc                       102

<210> SEQ ID NO 944
<211> LENGTH: 102
<212> TYPE: RNA
<213> ORGANISM: Artificial Sequence
<220> FEATURE:
<223> OTHER INFORMATION: Synthetic

<400> SEQUENCE: 944
ugacaacaga guucuguuuu guuggaacca uucaaaacag cauagcaagu uaaaauaagg    60
cuaguccguu aucaacuuga aaaguggca ccgagucggu gc                       102

<210> SEQ ID NO 945
<211> LENGTH: 102
<212> TYPE: RNA
<213> ORGANISM: Artificial Sequence
<220> FEATURE:
<223> OTHER INFORMATION: Synthetic

<400> SEQUENCE: 945
agaauacgcu gagaguuauc guuggaacca uucaaaacag cauagcaagu uaaaauaagg    60
cuaguccguu aucaacuuga aaaguggca ccgagucggu gc                       102

<210> SEQ ID NO 946
<211> LENGTH: 102
<212> TYPE: RNA
<213> ORGANISM: Artificial Sequence
<220> FEATURE:
<223> OTHER INFORMATION: Synthetic

<400> SEQUENCE: 946
gcaagagaag aaaagaacgg guuggaacca uucaaaacag cauagcaagu uaaaauaagg    60
cuaguccguu aucaacuuga aaaguggca ccgagucggu gc                       102
```

```
<210> SEQ ID NO 947
<211> LENGTH: 102
<212> TYPE: RNA
<213> ORGANISM: Artificial Sequence
<220> FEATURE:
<223> OTHER INFORMATION: Synthetic

<400> SEQUENCE: 947
guugcaagag aagaaaagaa guuggaacca uucaaaacag cauagcaagu uaaaauaagg      60
cuaguccguu aucaacuuga aaaaguggca ccgagucggu gc                       102

<210> SEQ ID NO 948
<211> LENGTH: 102
<212> TYPE: RNA
<213> ORGANISM: Artificial Sequence
<220> FEATURE:
<223> OTHER INFORMATION: Synthetic

<400> SEQUENCE: 948
augcacacgu aaaagagagg guuggaacca uucaaaacag cauagcaagu uaaaauaagg      60
cuaguccguu aucaacuuga aaaaguggca ccgagucggu gc                       102

<210> SEQ ID NO 949
<211> LENGTH: 102
<212> TYPE: RNA
<213> ORGANISM: Artificial Sequence
<220> FEATURE:
<223> OTHER INFORMATION: Synthetic

<400> SEQUENCE: 949
aagaugcaca cguaaaagag guuggaacca uucaaaacag cauagcaagu uaaaauaagg      60
cuaguccguu aucaacuuga aaaaguggca ccgagucggu gc                       102

<210> SEQ ID NO 950
<211> LENGTH: 102
<212> TYPE: RNA
<213> ORGANISM: Artificial Sequence
<220> FEATURE:
<223> OTHER INFORMATION: Synthetic

<400> SEQUENCE: 950
ggcagaccgu ucucaucacg guuggaacca uucaaaacag cauagcaagu uaaaauaagg      60
cuaguccguu aucaacuuga aaaaguggca ccgagucggu gc                       102

<210> SEQ ID NO 951
<211> LENGTH: 102
<212> TYPE: RNA
<213> ORGANISM: Artificial Sequence
<220> FEATURE:
<223> OTHER INFORMATION: Synthetic

<400> SEQUENCE: 951
cuuuaccagu gacuccaggu guuggaacca uucaaaacag cauagcaagu uaaaauaagg      60
cuaguccguu aucaacuuga aaaaguggca ccgagucggu gc                       102

<210> SEQ ID NO 952
<211> LENGTH: 102
<212> TYPE: RNA
<213> ORGANISM: Artificial Sequence
<220> FEATURE:
<223> OTHER INFORMATION: Synthetic

<400> SEQUENCE: 952
```

-continued

```
gucacagauu uccuucuccg guuggaacca uucaaaacag cauagcaagu uaaaauaagg    60
cuaguccguu aucaacuuga aaaaguggca ccgagucggu gc                       102

<210> SEQ ID NO 953
<211> LENGTH: 102
<212> TYPE: RNA
<213> ORGANISM: Artificial Sequence
<220> FEATURE:
<223> OTHER INFORMATION: Synthetic

<400> SEQUENCE: 953
agaugaugac gcccaccaga guuggaacca uucaaaacag cauagcaagu uaaaauaagg    60
cuaguccguu aucaacuuga aaaaguggca ccgagucggu gc                       102

<210> SEQ ID NO 954
<211> LENGTH: 102
<212> TYPE: RNA
<213> ORGANISM: Artificial Sequence
<220> FEATURE:
<223> OTHER INFORMATION: Synthetic

<400> SEQUENCE: 954
ggagaaggaa aucugugacc guuggaacca uucaaaacag cauagcaagu uaaaauaagg    60
cuaguccguu aucaacuuga aaaaguggca ccgagucggu gc                       102

<210> SEQ ID NO 955
<211> LENGTH: 102
<212> TYPE: RNA
<213> ORGANISM: Artificial Sequence
<220> FEATURE:
<223> OTHER INFORMATION: Synthetic

<400> SEQUENCE: 955
ugcgaggaac uuacuuuucc guuggaacca uucaaaacag cauagcaagu uaaaauaagg    60
cuaguccguu aucaacuuga aaaaguggca ccgagucggu gc                       102

<210> SEQ ID NO 956
<211> LENGTH: 102
<212> TYPE: RNA
<213> ORGANISM: Artificial Sequence
<220> FEATURE:
<223> OTHER INFORMATION: Synthetic

<400> SEQUENCE: 956
agagaaauau ugauauagga guuggaacca uucaaaacag cauagcaagu uaaaauaagg    60
cuaguccguu aucaacuuga aaaaguggca ccgagucggu gc                       102

<210> SEQ ID NO 957
<211> LENGTH: 102
<212> TYPE: RNA
<213> ORGANISM: Artificial Sequence
<220> FEATURE:
<223> OTHER INFORMATION: Synthetic

<400> SEQUENCE: 957
uaucaauauu ucucugaucc guuggaacca uucaaaacag cauagcaagu uaaaauaagg    60
cuaguccguu aucaacuuga aaaaguggca ccgagucggu gc                       102

<210> SEQ ID NO 958
<211> LENGTH: 102
<212> TYPE: RNA
```

```
<213> ORGANISM: Artificial Sequence
<220> FEATURE:
<223> OTHER INFORMATION: Synthetic

<400> SEQUENCE: 958
aucgcuuuua aggcacgcuc guuggaacca uucaaaacag cauagcaagu uaaaauaagg    60
cuaguccguu aucaacuuga aaaguggca ccgagucggu gc                       102

<210> SEQ ID NO 959
<211> LENGTH: 102
<212> TYPE: RNA
<213> ORGANISM: Artificial Sequence
<220> FEATURE:
<223> OTHER INFORMATION: Synthetic

<400> SEQUENCE: 959
uauacgacug aucgcuuuua guuggaacca uucaaaacag cauagcaagu uaaaauaagg    60
cuaguccguu aucaacuuga aaaguggca ccgagucggu gc                       102

<210> SEQ ID NO 960
<211> LENGTH: 96
<212> TYPE: RNA
<213> ORGANISM: Artificial Sequence
<220> FEATURE:
<223> OTHER INFORMATION: Synthetic

<400> SEQUENCE: 960
ugucagguua guuagaugaa guuuuagagc uagaaauagc aaguuaaaau aaggcuaguc    60
cguuaucaac uugaaaaagu ggcaccgagu cggugc                              96

<210> SEQ ID NO 961
<211> LENGTH: 96
<212> TYPE: RNA
<213> ORGANISM: Artificial Sequence
<220> FEATURE:
<223> OTHER INFORMATION: Synthetic

<400> SEQUENCE: 961
gugucagguu aguuagauga guuuuagagc uagaaauagc aaguuaaaau aaggcuaguc    60
cguuaucaac uugaaaaagu ggcaccgagu cggugc                              96

<210> SEQ ID NO 962
<211> LENGTH: 96
<212> TYPE: RNA
<213> ORGANISM: Artificial Sequence
<220> FEATURE:
<223> OTHER INFORMATION: Synthetic

<400> SEQUENCE: 962
ccugacacau auacagacua guuuuagagc uagaaauagc aaguuaaaau aaggcuaguc    60
cguuaucaac uugaaaaagu ggcaccgagu cggugc                              96

<210> SEQ ID NO 963
<211> LENGTH: 96
<212> TYPE: RNA
<213> ORGANISM: Artificial Sequence
<220> FEATURE:
<223> OTHER INFORMATION: Synthetic

<400> SEQUENCE: 963
cugacacaua uacagacuaa guuuuagagc uagaaauagc aaguuaaaau aaggcuaguc    60
cguuaucaac uugaaaaagu ggcaccgagu cggugc                              96
```

<210> SEQ ID NO 964
<211> LENGTH: 96
<212> TYPE: RNA
<213> ORGANISM: Artificial Sequence
<220> FEATURE:
<223> OTHER INFORMATION: Synthetic

<400> SEQUENCE: 964
ccuuagucug uauauguguc guuuuagagc uagaaauagc aaguuaaaau aaggcuaguc    60
cguuaucaac uugaaaaagu ggcaccgagu cggugc                             96

<210> SEQ ID NO 965
<211> LENGTH: 96
<212> TYPE: RNA
<213> ORGANISM: Artificial Sequence
<220> FEATURE:
<223> OTHER INFORMATION: Synthetic

<400> SEQUENCE: 965
cauauacaga cuaagggacc guuuuagagc uagaaauagc aaguuaaaau aaggcuaguc    60
cguuaucaac uugaaaaagu ggcaccgagu cggugc                             96

<210> SEQ ID NO 966
<211> LENGTH: 96
<212> TYPE: RNA
<213> ORGANISM: Artificial Sequence
<220> FEATURE:
<223> OTHER INFORMATION: Synthetic

<400> SEQUENCE: 966
auauacagac uaagggacca guuuuagagc uagaaauagc aaguuaaaau aaggcuaguc    60
cguuaucaac uugaaaaagu ggcaccgagu cggugc                             96

<210> SEQ ID NO 967
<211> LENGTH: 96
<212> TYPE: RNA
<213> ORGANISM: Artificial Sequence
<220> FEATURE:
<223> OTHER INFORMATION: Synthetic

<400> SEQUENCE: 967
ucaaaguuug auaaauuccc guuuuagagc uagaaauagc aaguuaaaau aaggcuaguc    60
cguuaucaac uugaaaaagu ggcaccgagu cggugc                             96

<210> SEQ ID NO 968
<211> LENGTH: 96
<212> TYPE: RNA
<213> ORGANISM: Artificial Sequence
<220> FEATURE:
<223> OTHER INFORMATION: Synthetic

<400> SEQUENCE: 968
aaaauacaaa gauaaguaga guuuuagagc uagaaauagc aaguuaaaau aaggcuaguc    60
cguuaucaac uugaaaaagu ggcaccgagu cggugc                             96

<210> SEQ ID NO 969
<211> LENGTH: 96
<212> TYPE: RNA
<213> ORGANISM: Artificial Sequence
<220> FEATURE:
<223> OTHER INFORMATION: Synthetic

```
<400> SEQUENCE: 969
acucugugac uuuaaaaagu guuuuagagc uagaaauagc aaguuaaaau aaggcuaguc      60
cguuaucaac uugaaaaagu ggcaccgagu cggugc                               96

<210> SEQ ID NO 970
<211> LENGTH: 96
<212> TYPE: RNA
<213> ORGANISM: Artificial Sequence
<220> FEATURE:
<223> OTHER INFORMATION: Synthetic

<400> SEQUENCE: 970
gguucugugg gauauuaaua guuuuagagc uagaaauagc aaguuaaaau aaggcuaguc      60
cguuaucaac uugaaaaagu ggcaccgagu cggugc                               96

<210> SEQ ID NO 971
<211> LENGTH: 96
<212> TYPE: RNA
<213> ORGANISM: Artificial Sequence
<220> FEATURE:
<223> OTHER INFORMATION: Synthetic

<400> SEQUENCE: 971
acagagcaua uugguucugu guuuuagagc uagaaauagc aaguuaaaau aaggcuaguc      60
cguuaucaac uugaaaaagu ggcaccgagu cggugc                               96

<210> SEQ ID NO 972
<211> LENGTH: 96
<212> TYPE: RNA
<213> ORGANISM: Artificial Sequence
<220> FEATURE:
<223> OTHER INFORMATION: Synthetic

<400> SEQUENCE: 972
gacagagcau auugguucug guuuuagagc uagaaauagc aaguuaaaau aaggcuaguc      60
cguuaucaac uugaaaaagu ggcaccgagu cggugc                               96

<210> SEQ ID NO 973
<211> LENGTH: 96
<212> TYPE: RNA
<213> ORGANISM: Artificial Sequence
<220> FEATURE:
<223> OTHER INFORMATION: Synthetic

<400> SEQUENCE: 973
ugcaaaacga cagagcauau guuuuagagc uagaaauagc aaguuaaaau aaggcuaguc      60
cguuaucaac uugaaaaagu ggcaccgagu cggugc                               96

<210> SEQ ID NO 974
<211> LENGTH: 96
<212> TYPE: RNA
<213> ORGANISM: Artificial Sequence
<220> FEATURE:
<223> OTHER INFORMATION: Synthetic

<400> SEQUENCE: 974
gagcugggca uggaauaggc guuuuagagc uagaaauagc aaguuaaaau aaggcuaguc      60
cguuaucaac uugaaaaagu ggcaccgagu cggugc                               96

<210> SEQ ID NO 975
<211> LENGTH: 96
```

```
<212> TYPE: RNA
<213> ORGANISM: Artificial Sequence
<220> FEATURE:
<223> OTHER INFORMATION: Synthetic

<400> SEQUENCE: 975
acuggagcug ggcauggaau guuuuagagc uagaaauagc aaguuaaaau aaggcuaguc    60
cguuaucaac uugaaaaagu ggcaccgagu cggugc                              96

<210> SEQ ID NO 976
<211> LENGTH: 96
<212> TYPE: RNA
<213> ORGANISM: Artificial Sequence
<220> FEATURE:
<223> OTHER INFORMATION: Synthetic

<400> SEQUENCE: 976
cucauuacug gagcugggca guuuuagagc uagaaauagc aaguuaaaau aaggcuaguc    60
cguuaucaac uugaaaaagu ggcaccgagu cggugc                              96

<210> SEQ ID NO 977
<211> LENGTH: 96
<212> TYPE: RNA
<213> ORGANISM: Artificial Sequence
<220> FEATURE:
<223> OTHER INFORMATION: Synthetic

<400> SEQUENCE: 977
uuguucucau uacuggagcu guuuuagagc uagaaauagc aaguuaaaau aaggcuaguc    60
cguuaucaac uugaaaaagu ggcaccgagu cggugc                              96

<210> SEQ ID NO 978
<211> LENGTH: 96
<212> TYPE: RNA
<213> ORGANISM: Artificial Sequence
<220> FEATURE:
<223> OTHER INFORMATION: Synthetic

<400> SEQUENCE: 978
auuguucuca uuacuggagc guuuuagagc uagaaauagc aaguuaaaau aaggcuaguc    60
cguuaucaac uugaaaaagu ggcaccgagu cggugc                              96

<210> SEQ ID NO 979
<211> LENGTH: 96
<212> TYPE: RNA
<213> ORGANISM: Artificial Sequence
<220> FEATURE:
<223> OTHER INFORMATION: Synthetic

<400> SEQUENCE: 979
ggggagauug uucucauuac guuuuagagc uagaaauagc aaguuaaaau aaggcuaguc    60
cguuaucaac uugaaaaagu ggcaccgagu cggugc                              96

<210> SEQ ID NO 980
<211> LENGTH: 96
<212> TYPE: RNA
<213> ORGANISM: Artificial Sequence
<220> FEATURE:
<223> OTHER INFORMATION: Synthetic

<400> SEQUENCE: 980
gaggagaaaa ucuguggcug guuuuagagc uagaaauagc aaguuaaaau aaggcuaguc    60
```
cguuaucaac uugaaaaagu ggcaccgagu cggugc        96

<210> SEQ ID NO 981
<211> LENGTH: 96
<212> TYPE: RNA
<213> ORGANISM: Artificial Sequence
<220> FEATURE:
<223> OTHER INFORMATION: Synthetic

<400> SEQUENCE: 981
agaggagaaa aucuguggcu guuuuagagc uagaaauagc aaguuaaaau aaggcuaguc        60
cguuaucaac uugaaaaagu ggcaccgagu cggugc        96

<210> SEQ ID NO 982
<211> LENGTH: 96
<212> TYPE: RNA
<213> ORGANISM: Artificial Sequence
<220> FEATURE:
<223> OTHER INFORMATION: Synthetic

<400> SEQUENCE: 982
cagaggagaa aaucguggc guuuuagagc uagaaauagc aaguuaaaau aaggcuaguc        60
cguuaucaac uugaaaaagu ggcaccgagu cggugc        96

<210> SEQ ID NO 983
<211> LENGTH: 96
<212> TYPE: RNA
<213> ORGANISM: Artificial Sequence
<220> FEATURE:
<223> OTHER INFORMATION: Synthetic

<400> SEQUENCE: 983
uccucagagg agaaaaucug guuuuagagc uagaaauagc aaguuaaaau aaggcuaguc        60
cguuaucaac uugaaaaagu ggcaccgagu cggugc        96

<210> SEQ ID NO 984
<211> LENGTH: 96
<212> TYPE: RNA
<213> ORGANISM: Artificial Sequence
<220> FEATURE:
<223> OTHER INFORMATION: Synthetic

<400> SEQUENCE: 984
ugaaguuuuu cauuccucag guuuuagagc uagaaauagc aaguuaaaau aaggcuaguc        60
cguuaucaac uugaaaaagu ggcaccgagu cggugc        96

<210> SEQ ID NO 985
<211> LENGTH: 96
<212> TYPE: RNA
<213> ORGANISM: Artificial Sequence
<220> FEATURE:
<223> OTHER INFORMATION: Synthetic

<400> SEQUENCE: 985
cuucaccaac gacuccaagu guuuuagagc uagaaauagc aaguuaaaau aaggcuaguc        60
cguuaucaac uugaaaaagu ggcaccgagu cggugc        96

<210> SEQ ID NO 986
<211> LENGTH: 96
<212> TYPE: RNA
<213> ORGANISM: Artificial Sequence
<220> FEATURE:
<223> OTHER INFORMATION: Synthetic -continued

<400> SEQUENCE: 986
cuacuccuac uuggagucgu guuuuagagc uagaaauagc aaguuaaaau aaggcuaguc    60
cguuaucaac uugaaaaagu ggcaccgagu cggugc    96

<210> SEQ ID NO 987
<211> LENGTH: 96
<212> TYPE: RNA
<213> ORGANISM: Artificial Sequence
<220> FEATURE:
<223> OTHER INFORMATION: Synthetic

<400> SEQUENCE: 987
cuccaaguag gaguagauga guuuuagagc uagaaauagc aaguuaaaau aaggcuaguc    60
cguuaucaac uugaaaaagu ggcaccgagu cggugc    96

<210> SEQ ID NO 988
<211> LENGTH: 96
<212> TYPE: RNA
<213> ORGANISM: Artificial Sequence
<220> FEATURE:
<223> OTHER INFORMATION: Synthetic

<400> SEQUENCE: 988
caccaucauc uacuccuacu guuuuagagc uagaaauagc aaguuaaaau aaggcuaguc    60
cguuaucaac uugaaaaagu ggcaccgagu cggugc    96

<210> SEQ ID NO 989
<211> LENGTH: 96
<212> TYPE: RNA
<213> ORGANISM: Artificial Sequence
<220> FEATURE:
<223> OTHER INFORMATION: Synthetic

<400> SEQUENCE: 989
ugauggugau cagaagcaga guuuuagagc uagaaauagc aaguuaaaau aaggcuaguc    60
cguuaucaac uugaaaaagu ggcaccgagu cggugc    96

<210> SEQ ID NO 990
<211> LENGTH: 96
<212> TYPE: RNA
<213> ORGANISM: Artificial Sequence
<220> FEATURE:
<223> OTHER INFORMATION: Synthetic

<400> SEQUENCE: 990
ucagaagcag aaggauuucu guuuuagagc uagaaauagc aaguuaaaau aaggcuaguc    60
cguuaucaac uugaaaaagu ggcaccgagu cggugc    96

<210> SEQ ID NO 991
<211> LENGTH: 96
<212> TYPE: RNA
<213> ORGANISM: Artificial Sequence
<220> FEATURE:
<223> OTHER INFORMATION: Synthetic

<400> SEQUENCE: 991
gauuucuagg augauguuca guuuuagagc uagaaauagc aaguuaaaau aaggcuaguc    60
cguuaucaac uugaaaaagu ggcaccgagu cggugc    96

<210> SEQ ID NO 992

```
<211> LENGTH: 96
<212> TYPE: RNA
<213> ORGANISM: Artificial Sequence
<220> FEATURE:
<223> OTHER INFORMATION: Synthetic

<400> SEQUENCE: 992
uugcucuguc cucuuccuuc guuuuagagc uagaaauagc aaguuaaaau aaggcuaguc    60
cguuaucaac uugaaaaagu ggcaccgagu cggugc                              96

<210> SEQ ID NO 993
<211> LENGTH: 96
<212> TYPE: RNA
<213> ORGANISM: Artificial Sequence
<220> FEATURE:
<223> OTHER INFORMATION: Synthetic

<400> SEQUENCE: 993
aggacugaac cagaaggaag guuuuagagc uagaaauagc aaguuaaaau aaggcuaguc    60
cguuaucaac uugaaaaagu ggcaccgagu cggugc                              96

<210> SEQ ID NO 994
<211> LENGTH: 96
<212> TYPE: RNA
<213> ORGANISM: Artificial Sequence
<220> FEATURE:
<223> OTHER INFORMATION: Synthetic

<400> SEQUENCE: 994
uacacaagga cugaaccaga guuuuagagc uagaaauagc aaguuaaaau aaggcuaguc    60
cguuaucaac uugaaaaagu ggcaccgagu cggugc                              96

<210> SEQ ID NO 995
<211> LENGTH: 96
<212> TYPE: RNA
<213> ORGANISM: Artificial Sequence
<220> FEATURE:
<223> OTHER INFORMATION: Synthetic

<400> SEQUENCE: 995
uucaguccuu guguaguccu guuuuagagc uagaaauagc aaguuaaaau aaggcuaguc    60
cguuaucaac uugaaaaagu ggcaccgagu cggugc                              96

<210> SEQ ID NO 996
<211> LENGTH: 96
<212> TYPE: RNA
<213> ORGANISM: Artificial Sequence
<220> FEATURE:
<223> OTHER INFORMATION: Synthetic

<400> SEQUENCE: 996
ucaguccuug uguaguccua guuuuagagc uagaaauagc aaguuaaaau aaggcuaguc    60
cguuaucaac uugaaaaagu ggcaccgagu cggugc                              96

<210> SEQ ID NO 997
<211> LENGTH: 96
<212> TYPE: RNA
<213> ORGANISM: Artificial Sequence
<220> FEATURE:
<223> OTHER INFORMATION: Synthetic

<400> SEQUENCE: 997
guccuugugu aguccuaggg guuuuagagc uagaaauagc aaguuaaaau aaggcuaguc    60
```

```
cguuaucaac uugaaaaagu ggcaccgagu cggugc                                  96
```

<210> SEQ ID NO 998
<211> LENGTH: 96
<212> TYPE: RNA
<213> ORGANISM: Artificial Sequence
<220> FEATURE:
<223> OTHER INFORMATION: Synthetic

<400> SEQUENCE: 998

```
cuuguguagu ccuagggagg guuuuagagc uagaaauagc aaguuaaaau aaggcuaguc        60
cguuaucaac uugaaaaagu ggcaccgagu cggugc                                  96
```

<210> SEQ ID NO 999
<211> LENGTH: 96
<212> TYPE: RNA
<213> ORGANISM: Artificial Sequence
<220> FEATURE:
<223> OTHER INFORMATION: Synthetic

<400> SEQUENCE: 999

```
cuccucccua ggacuacaca guuuuagagc uagaaauagc aaguuaaaau aaggcuaguc        60
cguuaucaac uugaaaaagu ggcaccgagu cggugc                                  96
```

<210> SEQ ID NO 1000
<211> LENGTH: 96
<212> TYPE: RNA
<213> ORGANISM: Artificial Sequence
<220> FEATURE:
<223> OTHER INFORMATION: Synthetic

<400> SEQUENCE: 1000

```
guagacagua ccuccucccu guuuuagagc uagaaauagc aaguuaaaau aaggcuaguc        60
cguuaucaac uugaaaaagu ggcaccgagu cggugc                                  96
```

<210> SEQ ID NO 1001
<211> LENGTH: 96
<212> TYPE: RNA
<213> ORGANISM: Artificial Sequence
<220> FEATURE:
<223> OTHER INFORMATION: Synthetic

<400> SEQUENCE: 1001

```
uacugucuac acagagcucu guuuuagagc uagaaauagc aaguuaaaau aaggcuaguc        60
cguuaucaac uugaaaaagu ggcaccgagu cggugc                                  96
```

<210> SEQ ID NO 1002
<211> LENGTH: 96
<212> TYPE: RNA
<213> ORGANISM: Artificial Sequence
<220> FEATURE:
<223> OTHER INFORMATION: Synthetic

<400> SEQUENCE: 1002

```
acugucuaca cagagcucua guuuuagagc uagaaauagc aaguuaaaau aaggcuaguc        60
cguuaucaac uugaaaaagu ggcaccgagu cggugc                                  96
```

<210> SEQ ID NO 1003
<211> LENGTH: 96
<212> TYPE: RNA
<213> ORGANISM: Artificial Sequence
<220> FEATURE:

<223> OTHER INFORMATION: Synthetic

<400> SEQUENCE: 1003
ucuacacaga gcucuaggga guuuuagagc uagaaauagc aaguuaaaau aaggcuaguc    60
cguuaucaac uugaaaaagu ggcaccgagu cggugc    96

<210> SEQ ID NO 1004
<211> LENGTH: 96
<212> TYPE: RNA
<213> ORGANISM: Artificial Sequence
<220> FEATURE:
<223> OTHER INFORMATION: Synthetic

<400> SEQUENCE: 1004
cuacacagag cucuagggaa guuuuagagc uagaaauagc aaguuaaaau aaggcuaguc    60
cguuaucaac uugaaaaagu ggcaccgagu cggugc    96

<210> SEQ ID NO 1005
<211> LENGTH: 96
<212> TYPE: RNA
<213> ORGANISM: Artificial Sequence
<220> FEATURE:
<223> OTHER INFORMATION: Synthetic

<400> SEQUENCE: 1005
uacacagagc ucugggaag guuuuagagc uagaaauagc aaguuaaaau aaggcuaguc    60
cguuaucaac uugaaaaagu ggcaccgagu cggugc    96

<210> SEQ ID NO 1006
<211> LENGTH: 96
<212> TYPE: RNA
<213> ORGANISM: Artificial Sequence
<220> FEATURE:
<223> OTHER INFORMATION: Synthetic

<400> SEQUENCE: 1006
ggggugugcc caguuguuaa guuuuagagc uagaaauagc aaguuaaaau aaggcuaguc    60
cguuaucaac uugaaaaagu ggcaccgagu cggugc    96

<210> SEQ ID NO 1007
<211> LENGTH: 96
<212> TYPE: RNA
<213> ORGANISM: Artificial Sequence
<220> FEATURE:
<223> OTHER INFORMATION: Synthetic

<400> SEQUENCE: 1007
gggugugccc aguuguuaau guuuuagagc uagaaauagc aaguuaaaau aaggcuaguc    60
cguuaucaac uugaaaaagu ggcaccgagu cggugc    96

<210> SEQ ID NO 1008
<211> LENGTH: 96
<212> TYPE: RNA
<213> ORGANISM: Artificial Sequence
<220> FEATURE:
<223> OTHER INFORMATION: Synthetic

<400> SEQUENCE: 1008
ugguaguccc auuaacaacu guuuuagagc uagaaauagc aaguuaaaau aaggcuaguc    60
cguuaucaac uugaaaaagu ggcaccgagu cggugc    96

```
<210> SEQ ID NO 1009
<211> LENGTH: 96
<212> TYPE: RNA
<213> ORGANISM: Artificial Sequence
<220> FEATURE:
<223> OTHER INFORMATION: Synthetic

<400> SEQUENCE: 1009
cugguagucc cauuaacaac guuuuagagc uagaaauagc aaguuaaaau aaggcuaguc      60
cguuaucaac uugaaaaagu ggcaccgagu cggugc                               96

<210> SEQ ID NO 1010
<211> LENGTH: 96
<212> TYPE: RNA
<213> ORGANISM: Artificial Sequence
<220> FEATURE:
<223> OTHER INFORMATION: Synthetic

<400> SEQUENCE: 1010
uuguuaaugg gacuaccaga guuuuagagc uagaaauagc aaguuaaaau aaggcuaguc      60
cguuaucaac uugaaaaagu ggcaccgagu cggugc                               96

<210> SEQ ID NO 1011
<211> LENGTH: 96
<212> TYPE: RNA
<213> ORGANISM: Artificial Sequence
<220> FEATURE:
<223> OTHER INFORMATION: Synthetic

<400> SEQUENCE: 1011
uaccagaugg aagccagcuu guuuuagagc uagaaauagc aaguuaaaau aaggcuaguc      60
cguuaucaac uugaaaaagu ggcaccgagu cggugc                               96

<210> SEQ ID NO 1012
<211> LENGTH: 96
<212> TYPE: RNA
<213> ORGANISM: Artificial Sequence
<220> FEATURE:
<223> OTHER INFORMATION: Synthetic

<400> SEQUENCE: 1012
uuccaaagcu ggcuuccauc guuuuagagc uagaaauagc aaguuaaaau aaggcuaguc      60
cguuaucaac uugaaaaagu ggcaccgagu cggugc                               96

<210> SEQ ID NO 1013
<211> LENGTH: 96
<212> TYPE: RNA
<213> ORGANISM: Artificial Sequence
<220> FEATURE:
<223> OTHER INFORMATION: Synthetic

<400> SEQUENCE: 1013
uggaagccag cuuuggaagc guuuuagagc uagaaauagc aaguuaaaau aaggcuaguc      60
cguuaucaac uugaaaaagu ggcaccgagu cggugc                               96

<210> SEQ ID NO 1014
<211> LENGTH: 96
<212> TYPE: RNA
<213> ORGANISM: Artificial Sequence
<220> FEATURE:
<223> OTHER INFORMATION: Synthetic

<400> SEQUENCE: 1014
```

```
acaaggccug cuuccaaagc guuuuagagc uagaaauagc aaguuaaaau aaggcuaguc        60
cguuaucaac uugaaaaagu ggcaccgagu cggugc                                 96
```

<210> SEQ ID NO 1015
<211> LENGTH: 96
<212> TYPE: RNA
<213> ORGANISM: Artificial Sequence
<220> FEATURE:
<223> OTHER INFORMATION: Synthetic

<400> SEQUENCE: 1015

```
gccuuguuca cguguucuaa guuuuagagc uagaaauagc aaguuaaaau aaggcuaguc        60
cguuaucaac uugaaaaagu ggcaccgagu cggugc                                 96
```

<210> SEQ ID NO 1016
<211> LENGTH: 96
<212> TYPE: RNA
<213> ORGANISM: Artificial Sequence
<220> FEATURE:
<223> OTHER INFORMATION: Synthetic

<400> SEQUENCE: 1016

```
ccuguucac guguucuaau guuuuagagc uagaaauagc aaguuaaaau aaggcuaguc         60
cguuaucaac uugaaaaagu ggcaccgagu cggugc                                 96
```

<210> SEQ ID NO 1017
<211> LENGTH: 96
<212> TYPE: RNA
<213> ORGANISM: Artificial Sequence
<220> FEATURE:
<223> OTHER INFORMATION: Synthetic

<400> SEQUENCE: 1017

```
cccauuagaa cacgugaaca guuuuagagc uagaaauagc aaguuaaaau aaggcuaguc        60
cguuaucaac uugaaaaagu ggcaccgagu cggugc                                 96
```

<210> SEQ ID NO 1018
<211> LENGTH: 96
<212> TYPE: RNA
<213> ORGANISM: Artificial Sequence
<220> FEATURE:
<223> OTHER INFORMATION: Synthetic

<400> SEQUENCE: 1018

```
uuggcaucac uucauauuug guuuuagagc uagaaauagc aaguuaaaau aaggcuaguc        60
cguuaucaac uugaaaaagu ggcaccgagu cggugc                                 96
```

<210> SEQ ID NO 1019
<211> LENGTH: 96
<212> TYPE: RNA
<213> ORGANISM: Artificial Sequence
<220> FEATURE:
<223> OTHER INFORMATION: Synthetic

<400> SEQUENCE: 1019

```
cuugugcucu uggcaucacu guuuuagagc uagaaauagc aaguuaaaau aaggcuaguc        60
cguuaucaac uugaaaaagu ggcaccgagu cggugc                                 96
```

<210> SEQ ID NO 1020
<211> LENGTH: 96
<212> TYPE: RNA
<213> ORGANISM: Artificial Sequence

```
<220> FEATURE:
<223> OTHER INFORMATION: Synthetic

<400> SEQUENCE: 1020
agcacacucu cuugugcucu guuuuagagc uagaaauagc aaguuaaaau aaggcuaguc    60
cguuaucaac uugaaaaagu ggcaccgagu cggugc                              96

<210> SEQ ID NO 1021
<211> LENGTH: 96
<212> TYPE: RNA
<213> ORGANISM: Artificial Sequence
<220> FEATURE:
<223> OTHER INFORMATION: Synthetic

<400> SEQUENCE: 1021
gcacaagaga gugugcucuc guuuuagagc uagaaauagc aaguuaaaau aaggcuaguc    60
cguuaucaac uugaaaaagu ggcaccgagu cggugc                              96

<210> SEQ ID NO 1022
<211> LENGTH: 96
<212> TYPE: RNA
<213> ORGANISM: Artificial Sequence
<220> FEATURE:
<223> OTHER INFORMATION: Synthetic

<400> SEQUENCE: 1022
gcuuaaucuc acacauagaa guuuuagagc uagaaauagc aaguuaaaau aaggcuaguc    60
cguuaucaac uugaaaaagu ggcaccgagu cggugc                              96

<210> SEQ ID NO 1023
<211> LENGTH: 96
<212> TYPE: RNA
<213> ORGANISM: Artificial Sequence
<220> FEATURE:
<223> OTHER INFORMATION: Synthetic

<400> SEQUENCE: 1023
cuuaaucuca cacauagaaa guuuuagagc uagaaauagc aaguuaaaau aaggcuaguc    60
cguuaucaac uugaaaaagu ggcaccgagu cggugc                              96

<210> SEQ ID NO 1024
<211> LENGTH: 96
<212> TYPE: RNA
<213> ORGANISM: Artificial Sequence
<220> FEATURE:
<223> OTHER INFORMATION: Synthetic

<400> SEQUENCE: 1024
uuaaucucac acaugaaag guuuuagagc uagaaauagc aaguuaaaau aaggcuaguc    60
cguuaucaac uugaaaaagu ggcaccgagu cggugc                              96

<210> SEQ ID NO 1025
<211> LENGTH: 96
<212> TYPE: RNA
<213> ORGANISM: Artificial Sequence
<220> FEATURE:
<223> OTHER INFORMATION: Synthetic

<400> SEQUENCE: 1025
aggagugcug guuuaucaac guuuuagagc uagaaauagc aaguuaaaau aaggcuaguc    60
cguuaucaac uugaaaaagu ggcaccgagu cggugc                              96
```

```
<210> SEQ ID NO 1026
<211> LENGTH: 96
<212> TYPE: RNA
<213> ORGANISM: Artificial Sequence
<220> FEATURE:
<223> OTHER INFORMATION: Synthetic

<400> SEQUENCE: 1026
uucuuugaca gcaggagugc guuuuagagc uagaaauagc aaguuaaaau aaggcuaguc    60
cguuaucaac uugaaaaagu ggcaccgagu cggugc                              96

<210> SEQ ID NO 1027
<211> LENGTH: 96
<212> TYPE: RNA
<213> ORGANISM: Artificial Sequence
<220> FEATURE:
<223> OTHER INFORMATION: Synthetic

<400> SEQUENCE: 1027
acucugguuu cuuugacagc guuuuagagc uagaaauagc aaguuaaaau aaggcuaguc    60
cguuaucaac uugaaaaagu ggcaccgagu cggugc                              96

<210> SEQ ID NO 1028
<211> LENGTH: 96
<212> TYPE: RNA
<213> ORGANISM: Artificial Sequence
<220> FEATURE:
<223> OTHER INFORMATION: Synthetic

<400> SEQUENCE: 1028
accagaguug agaaaacccc guuuuagagc uagaaauagc aaguuaaaau aaggcuaguc    60
cguuaucaac uugaaaaagu ggcaccgagu cggugc                              96

<210> SEQ ID NO 1029
<211> LENGTH: 96
<212> TYPE: RNA
<213> ORGANISM: Artificial Sequence
<220> FEATURE:
<223> OTHER INFORMATION: Synthetic

<400> SEQUENCE: 1029
uccaggaguu uucucaacuc guuuuagagc uagaaauagc aaguuaaaau aaggcuaguc    60
cguuaucaac uugaaaaagu ggcaccgagu cggugc                              96

<210> SEQ ID NO 1030
<211> LENGTH: 96
<212> TYPE: RNA
<213> ORGANISM: Artificial Sequence
<220> FEATURE:
<223> OTHER INFORMATION: Synthetic

<400> SEQUENCE: 1030
caguuauuaa augaauccag guuuuagagc uagaaauagc aaguuaaaau aaggcuaguc    60
cguuaucaac uugaaaaagu ggcaccgagu cggugc                              96

<210> SEQ ID NO 1031
<211> LENGTH: 96
<212> TYPE: RNA
<213> ORGANISM: Artificial Sequence
<220> FEATURE:
<223> OTHER INFORMATION: Synthetic

<400> SEQUENCE: 1031
```

```
gcaguuauua aaugaauccaa guuuuagagc uagaaauagc aaguuaaaau aaggcuaguc    60
cguuaucaac uugaaaaagu ggcaccgagu cggugc                              96

<210> SEQ ID NO 1032
<211> LENGTH: 96
<212> TYPE: RNA
<213> ORGANISM: Artificial Sequence
<220> FEATURE:
<223> OTHER INFORMATION: Synthetic

<400> SEQUENCE: 1032
ggcaguuauu aaaugaaucc guuuuagagc uagaaauagc aaguuaaaau aaggcuaguc    60
cguuaucaac uugaaaaagu ggcaccgagu cggugc                              96

<210> SEQ ID NO 1033
<211> LENGTH: 96
<212> TYPE: RNA
<213> ORGANISM: Artificial Sequence
<220> FEATURE:
<223> OTHER INFORMATION: Synthetic

<400> SEQUENCE: 1033 uggauggua cagcuacauc guuuuagagc uagaaauagc aaguuaaaau aaggcuaguc     60
cguuaucaac uugaaaaagu ggcaccgagu cggugc                              96

<210> SEQ ID NO 1034
<211> LENGTH: 96
<212> TYPE: RNA
<213> ORGANISM: Artificial Sequence
<220> FEATURE:
<223> OTHER INFORMATION: Synthetic

<400> SEQUENCE: 1034
gcuguuacca uccacauccu guuuuagagc uagaaauagc aaguuaaaau aaggcuaguc    60
cguuaucaac uugaaaaagu ggcaccgagu cggugc                              96

<210> SEQ ID NO 1035
<211> LENGTH: 96
<212> TYPE: RNA
<213> ORGANISM: Artificial Sequence
<220> FEATURE:
<223> OTHER INFORMATION: Synthetic

<400> SEQUENCE: 1035
ucaagaacca aggaugugga guuuuagagc uagaaauagc aaguuaaaau aaggcuaguc    60
cguuaucaac uugaaaaagu ggcaccgagu cggugc                              96

<210> SEQ ID NO 1036
<211> LENGTH: 96
<212> TYPE: RNA
<213> ORGANISM: Artificial Sequence
<220> FEATURE:
<223> OTHER INFORMATION: Synthetic

<400> SEQUENCE: 1036
uccuucaaga accaaggaug guuuuagagc uagaaauagc aaguuaaaau aaggcuaguc    60
cguuaucaac uugaaaaagu ggcaccgagu cggugc                              96

<210> SEQ ID NO 1037
<211> LENGTH: 96
<212> TYPE: RNA
```

<213> ORGANISM: Artificial Sequence
<220> FEATURE:
<223> OTHER INFORMATION: Synthetic

<400> SEQUENCE: 1037 ugagguccu ucaagaacca guuuuagagc uagaaauagc aaguuaaaau aaggcuaguc    60
cguuaucaac uugaaaaagu ggcaccgagu cggugc                              96

<210> SEQ ID NO 1038
<211> LENGTH: 96
<212> TYPE: RNA
<213> ORGANISM: Artificial Sequence
<220> FEATURE:
<223> OTHER INFORMATION: Synthetic

<400> SEQUENCE: 1038
uuuuauuuua uaacuacaag guuuuagagc uagaaauagc aaguuaaaau aaggcuaguc    60
cguuaucaac uugaaaaagu ggcaccgagu cggugc                              96

<210> SEQ ID NO 1039
<211> LENGTH: 96
<212> TYPE: RNA
<213> ORGANISM: Artificial Sequence
<220> FEATURE:
<223> OTHER INFORMATION: Synthetic

<400> SEQUENCE: 1039
uuguuuuuaa uaaaaacaag guuuuagagc uagaaauagc aaguuaaaau aaggcuaguc    60
cguuaucaac uugaaaaagu ggcaccgagu cggugc                              96

<210> SEQ ID NO 1040
<211> LENGTH: 96
<212> TYPE: RNA
<213> ORGANISM: Artificial Sequence
<220> FEATURE:
<223> OTHER INFORMATION: Synthetic

<400> SEQUENCE: 1040
uauuauagaa ugcuuuugca guuuuagagc uagaaauagc aaguuaaaau aaggcuaguc    60
cguuaucaac uugaaaaagu ggcaccgagu cggugc                              96

<210> SEQ ID NO 1041
<211> LENGTH: 96
<212> TYPE: RNA
<213> ORGANISM: Artificial Sequence
<220> FEATURE:
<223> OTHER INFORMATION: Synthetic

<400> SEQUENCE: 1041
caagauuagu cuugauguag guuuuagagc uagaaauagc aaguuaaaau aaggcuaguc    60
cguuaucaac uugaaaaagu ggcaccgagu cggugc                              96

<210> SEQ ID NO 1042
<211> LENGTH: 96
<212> TYPE: RNA
<213> ORGANISM: Artificial Sequence
<220> FEATURE:
<223> OTHER INFORMATION: Synthetic

<400> SEQUENCE: 1042
aagauuaguc uugauguagu guuuuagagc uagaaauagc aaguuaaaau aaggcuaguc    60
cguuaucaac uugaaaaagu ggcaccgagu cggugc                              96

<210> SEQ ID NO 1043
<211> LENGTH: 96
<212> TYPE: RNA
<213> ORGANISM: Artificial Sequence
<220> FEATURE:
<223> OTHER INFORMATION: Synthetic

<400> SEQUENCE: 1043
agucuugaug uagugggagu guuuuagagc uagaaauagc aaguuaaaau aaggcuaguc    60
cguuaucaac uugaaaaagu ggcaccgagu cggugc                              96

<210> SEQ ID NO 1044
<211> LENGTH: 96
<212> TYPE: RNA
<213> ORGANISM: Artificial Sequence
<220> FEATURE:
<223> OTHER INFORMATION: Synthetic

<400> SEQUENCE: 1044
uuuuucuauu aaaaaaaaaa guuuuagagc uagaaauagc aaguuaaaau aaggcuaguc    60
cguuaucaac uugaaaaagu ggcaccgagu cggugc                              96

<210> SEQ ID NO 1045
<211> LENGTH: 96
<212> TYPE: RNA
<213> ORGANISM: Artificial Sequence
<220> FEATURE:
<223> OTHER INFORMATION: Synthetic

<400> SEQUENCE: 1045
ucuauuaaaa aaaaaaggc guuuuagagc uagaaauagc aaguuaaaau aaggcuaguc     60
cguuaucaac uugaaaaagu ggcaccgagu cggugc                              96

<210> SEQ ID NO 1046
<211> LENGTH: 96
<212> TYPE: RNA
<213> ORGANISM: Artificial Sequence
<220> FEATURE:
<223> OTHER INFORMATION: Synthetic

<400> SEQUENCE: 1046
cuauuaaaaa aaaaaaggcu guuuuagagc uagaaauagc aaguuaaaau aaggcuaguc    60
cguuaucaac uugaaaaagu ggcaccgagu cggugc                              96

<210> SEQ ID NO 1047
<211> LENGTH: 96
<212> TYPE: RNA
<213> ORGANISM: Artificial Sequence
<220> FEATURE:
<223> OTHER INFORMATION: Synthetic

<400> SEQUENCE: 1047
aaaaaaaaaa aggcugggca guuuuagagc uagaaauagc aaguuaaaau aaggcuaguc    60
cguuaucaac uugaaaaagu ggcaccgagu cggugc                              96

<210> SEQ ID NO 1048
<211> LENGTH: 96
<212> TYPE: RNA
<213> ORGANISM: Artificial Sequence
<220> FEATURE:
<223> OTHER INFORMATION: Synthetic

<400> SEQUENCE: 1048
aaaaaaaagg cugggcacgg guuuuagagc uagaaauagc aaguuaaaau aaggcuaguc    60
cguuaucaac uugaaaaagu ggcaccgagu cggugc                              96

<210> SEQ ID NO 1049
<211> LENGTH: 96
<212> TYPE: RNA
<213> ORGANISM: Artificial Sequence
<220> FEATURE:
<223> OTHER INFORMATION: Synthetic

<400> SEQUENCE: 1049
cacccguaau cccagcacuu guuuuagagc uagaaauagc aaguuaaaau aaggcuaguc    60
cguuaucaac uugaaaaagu ggcaccgagu cggugc                              96

<210> SEQ ID NO 1050
<211> LENGTH: 96
<212> TYPE: RNA
<213> ORGANISM: Artificial Sequence
<220> FEATURE:
<223> OTHER INFORMATION: Synthetic

<400> SEQUENCE: 1050
acccguaauc ccagcacuuu guuuuagagc uagaaauagc aaguuaaaau aaggcuaguc    60
cguuaucaac uugaaaaagu ggcaccgagu cggugc                              96

<210> SEQ ID NO 1051
<211> LENGTH: 96
<212> TYPE: RNA
<213> ORGANISM: Artificial Sequence
<220> FEATURE:
<223> OTHER INFORMATION: Synthetic

<400> SEQUENCE: 1051
cguaauccca gcacuuuggg guuuuagagc uagaaauagc aaguuaaaau aaggcuaguc    60
cguuaucaac uugaaaaagu ggcaccgagu cggugc                              96

<210> SEQ ID NO 1052
<211> LENGTH: 96
<212> TYPE: RNA
<213> ORGANISM: Artificial Sequence
<220> FEATURE:
<223> OTHER INFORMATION: Synthetic

<400> SEQUENCE: 1052
ucccaaagug cugggauuac guuuuagagc uagaaauagc aaguuaaaau aaggcuaguc    60
cguuaucaac uugaaaaagu ggcaccgagu cggugc                              96

<210> SEQ ID NO 1053
<211> LENGTH: 96
<212> TYPE: RNA
<213> ORGANISM: Artificial Sequence
<220> FEATURE:
<223> OTHER INFORMATION: Synthetic

<400> SEQUENCE: 1053
cucccaaagu gcugggauua guuuuagagc uagaaauagc aaguuaaaau aaggcuaguc    60
cguuaucaac uugaaaaagu ggcaccgagu cggugc                              96

<210> SEQ ID NO 1054
<211> LENGTH: 96

```
<212> TYPE: RNA
<213> ORGANISM: Artificial Sequence
<220> FEATURE:
<223> OTHER INFORMATION: Synthetic

<400> SEQUENCE: 1054
cccagcacuu ugggaggccg guuuuagagc uagaaauagc aaguuaaaau aaggcuaguc    60
cguuaucaac uugaaaaagu ggcaccgagu cggugc                              96

<210> SEQ ID NO 1055
<211> LENGTH: 96
<212> TYPE: RNA
<213> ORGANISM: Artificial Sequence
<220> FEATURE:
<223> OTHER INFORMATION: Synthetic

<400> SEQUENCE: 1055
ccucggccuc ccaaagugcu guuuuagagc uagaaauagc aaguuaaaau aaggcuaguc    60
cguuaucaac uugaaaaagu ggcaccgagu cggugc                              96

<210> SEQ ID NO 1056
<211> LENGTH: 96
<212> TYPE: RNA
<213> ORGANISM: Artificial Sequence
<220> FEATURE:
<223> OTHER INFORMATION: Synthetic

<400> SEQUENCE: 1056
gcacuuuggg aggccgaggc guuuuagagc uagaaauagc aaguuaaaau aaggcuaguc    60
cguuaucaac uugaaaaagu ggcaccgagu cggugc                              96

<210> SEQ ID NO 1057
<211> LENGTH: 96
<212> TYPE: RNA
<213> ORGANISM: Artificial Sequence
<220> FEATURE:
<223> OTHER INFORMATION: Synthetic

<400> SEQUENCE: 1057 cuugggagg ccgaggcagg guuuuagagc uagaaauagc aaguuaaaau aaggcuaguc     60
cguuaucaac uugaaaaagu ggcaccgagu cggugc                              96

<210> SEQ ID NO 1058
<211> LENGTH: 96
<212> TYPE: RNA
<213> ORGANISM: Artificial Sequence
<220> FEATURE:
<223> OTHER INFORMATION: Synthetic

<400> SEQUENCE: 1058
gccgaggcag guggaucacg guuuuagagc uagaaauagc aaguuaaaau aaggcuaguc    60
cguuaucaac uugaaaaagu ggcaccgagu cggugc                              96

<210> SEQ ID NO 1059
<211> LENGTH: 96
<212> TYPE: RNA
<213> ORGANISM: Artificial Sequence
<220> FEATURE:
<223> OTHER INFORMATION: Synthetic

<400> SEQUENCE: 1059
accucgugau ccaccugccu guuuuagagc uagaaauagc aaguuaaaau aaggcuaguc    60
```

```
cguuaucaac uugaaaaagu ggcaccgagu cggugc                                  96

<210> SEQ ID NO 1060
<211> LENGTH: 96
<212> TYPE: RNA
<213> ORGANISM: Artificial Sequence
<220> FEATURE:
<223> OTHER INFORMATION: Synthetic

<400> SEQUENCE: 1060
ggcaggugga ucacgagguc guuuuagagc uagaaauagc aaguuaaaau aaggcuaguc        60
cguuaucaac uugaaaaagu ggcaccgagu cggugc                                  96

<210> SEQ ID NO 1061
<211> LENGTH: 96
<212> TYPE: RNA
<213> ORGANISM: Artificial Sequence
<220> FEATURE:
<223> OTHER INFORMATION: Synthetic

<400> SEQUENCE: 1061
ucaggagauc gagaccaucu guuuuagagc uagaaauagc aaguuaaaau aaggcuaguc        60
cguuaucaac uugaaaaagu ggcaccgagu cggugc                                  96

<210> SEQ ID NO 1062
<211> LENGTH: 96
<212> TYPE: RNA
<213> ORGANISM: Artificial Sequence
<220> FEATURE:
<223> OTHER INFORMATION: Synthetic

<400> SEQUENCE: 1062
cgagaccauc uuggcuaaca guuuuagagc uagaaauagc aaguuaaaau aaggcuaguc        60
cguuaucaac uugaaaaagu ggcaccgagu cggugc                                  96

<210> SEQ ID NO 1063
<211> LENGTH: 96
<212> TYPE: RNA
<213> ORGANISM: Artificial Sequence
<220> FEATURE:
<223> OTHER INFORMATION: Synthetic

<400> SEQUENCE: 1063
uuucaccaug uuagccaaga guuuuagagc uagaaauagc aaguuaaaau aaggcuaguc        60
cguuaucaac uugaaaaagu ggcaccgagu cggugc                                  96

<210> SEQ ID NO 1064
<211> LENGTH: 96
<212> TYPE: RNA
<213> ORGANISM: Artificial Sequence
<220> FEATURE:
<223> OTHER INFORMATION: Synthetic

<400> SEQUENCE: 1064
uuguauuuuu uguagagacg guuuuagagc uagaaauagc aaguuaaaau aaggcuaguc        60
cguuaucaac uugaaaaagu ggcaccgagu cggugc                                  96

<210> SEQ ID NO 1065
<211> LENGTH: 96
<212> TYPE: RNA
<213> ORGANISM: Artificial Sequence
<220> FEATURE:
<223> OTHER INFORMATION: Synthetic
```

<400> SEQUENCE: 1065
uuuguauuuu uuguagagac guuuuagagc uagaaauagc aaguuaaaau aaggcuaguc    60
cguuaucaac uugaaaaagu ggcaccgagu cggugc    96

<210> SEQ ID NO 1066
<211> LENGTH: 96
<212> TYPE: RNA
<213> ORGANISM: Artificial Sequence
<220> FEATURE:
<223> OTHER INFORMATION: Synthetic

<400> SEQUENCE: 1066
uuuuguauuu uuuguagaga guuuuagagc uagaaauagc aaguuaaaau aaggcuaguc    60
cguuaucaac uugaaaaagu ggcaccgagu cggugc    96

<210> SEQ ID NO 1067
<211> LENGTH: 96
<212> TYPE: RNA
<213> ORGANISM: Artificial Sequence
<220> FEATURE:
<223> OTHER INFORMATION: Synthetic

<400> SEQUENCE: 1067
aaaaaauaca aaaauuagc guuuuagagc uagaaauagc aaguuaaaau aaggcuaguc    60
cguuaucaac uugaaaaagu ggcaccgagu cggugc    96

<210> SEQ ID NO 1068
<211> LENGTH: 96
<212> TYPE: RNA
<213> ORGANISM: Artificial Sequence
<220> FEATURE:
<223> OTHER INFORMATION: Synthetic

<400> SEQUENCE: 1068
aaaaauacaa aaauuagcc guuuuagagc uagaaauagc aaguuaaaau aaggcuaguc    60
cguuaucaac uugaaaaagu ggcaccgagu cggugc    96

<210> SEQ ID NO 1069
<211> LENGTH: 96
<212> TYPE: RNA
<213> ORGANISM: Artificial Sequence
<220> FEATURE:
<223> OTHER INFORMATION: Synthetic

<400> SEQUENCE: 1069
uacaaaaaau uagccgggug guuuuagagc uagaaauagc aaguuaaaau aaggcuaguc    60
cguuaucaac uugaaaaagu ggcaccgagu cggugc    96

<210> SEQ ID NO 1070
<211> LENGTH: 96
<212> TYPE: RNA
<213> ORGANISM: Artificial Sequence
<220> FEATURE:
<223> OTHER INFORMATION: Synthetic

<400> SEQUENCE: 1070
aaaaaauuag ccgggugugg guuuuagagc uagaaauagc aaguuaaaau aaggcuaguc    60
cguuaucaac uugaaaaagu ggcaccgagu cggugc    96

<210> SEQ ID NO 1071

```
<211> LENGTH: 96
<212> TYPE: RNA
<213> ORGANISM: Artificial Sequence
<220> FEATURE:
<223> OTHER INFORMATION: Synthetic

<400> SEQUENCE: 1071
aaauuagccg ggugugguggg guuuuagagc uagaaauagc aaguuaaaau aaggcuaguc    60
cguuaucaac uugaaaaagu ggcaccgagu cggugc                              96

<210> SEQ ID NO 1072
<211> LENGTH: 96
<212> TYPE: RNA
<213> ORGANISM: Artificial Sequence
<220> FEATURE:
<223> OTHER INFORMATION: Synthetic

<400> SEQUENCE: 1072
aauuagccgg guguggtuggc guuuuagagc uagaaauagc aaguuaaaau aaggcuaguc    60
cguuaucaac uugaaaaagu ggcaccgagu cggugc                              96

<210> SEQ ID NO 1073
<211> LENGTH: 96
<212> TYPE: RNA
<213> ORGANISM: Artificial Sequence
<220> FEATURE:
<223> OTHER INFORMATION: Synthetic

<400> SEQUENCE: 1073
caggcgcccg ccaccacacc guuuuagagc uagaaauagc aaguuaaaau aaggcuaguc    60
cguuaucaac uugaaaaagu ggcaccgagu cggugc                              96

<210> SEQ ID NO 1074
<211> LENGTH: 96
<212> TYPE: RNA
<213> ORGANISM: Artificial Sequence
<220> FEATURE:
<223> OTHER INFORMATION: Synthetic

<400> SEQUENCE: 1074
gccuguaguc ccagcuacuc guuuuagagc uagaaauagc aaguuaaaau aaggcuaguc    60
cguuaucaac uugaaaaagu ggcaccgagu cggugc                              96

<210> SEQ ID NO 1075
<211> LENGTH: 96
<212> TYPE: RNA
<213> ORGANISM: Artificial Sequence
<220> FEATURE:
<223> OTHER INFORMATION: Synthetic

<400> SEQUENCE: 1075 uguagucccca gcuacucagg guuuuagagc uagaaauagc aaguuaaaau aaggcuaguc    60
cguuaucaac uugaaaaagu ggcaccgagu cggugc                              96

<210> SEQ ID NO 1076
<211> LENGTH: 96
<212> TYPE: RNA
<213> ORGANISM: Artificial Sequence
<220> FEATURE:
<223> OTHER INFORMATION: Synthetic

<400> SEQUENCE: 1076
uccugaguag cuggggacuac guuuuagagc uagaaauagc aaguuaaaau aaggcuaguc    60
```
cguuaucaac uugaaaaagu ggcaccgagu cggugc        96

<210> SEQ ID NO 1077
<211> LENGTH: 96
<212> TYPE: RNA
<213> ORGANISM: Artificial Sequence
<220> FEATURE:
<223> OTHER INFORMATION: Synthetic

<400> SEQUENCE: 1077
cccagcuacu caggaggcug guuuuagagc uagaaauagc aaguuaaaau aaggcuaguc        60
cguuaucaac uugaaaaagu ggcaccgagu cggugc        96

<210> SEQ ID NO 1078
<211> LENGTH: 96
<212> TYPE: RNA
<213> ORGANISM: Artificial Sequence
<220> FEATURE:
<223> OTHER INFORMATION: Synthetic

<400> SEQUENCE: 1078
ccucagccuc cugaguagcu guuuuagagc uagaaauagc aaguuaaaau aaggcuaguc        60
cguuaucaac uugaaaaagu ggcaccgagu cggugc        96

<210> SEQ ID NO 1079
<211> LENGTH: 96
<212> TYPE: RNA
<213> ORGANISM: Artificial Sequence
<220> FEATURE:
<223> OTHER INFORMATION: Synthetic

<400> SEQUENCE: 1079
gccucagccu ccugaguagc guuuuagagc uagaaauagc aaguuaaaau aaggcuaguc        60
cguuaucaac uugaaaaagu ggcaccgagu cggugc        96

<210> SEQ ID NO 1080
<211> LENGTH: 96
<212> TYPE: RNA
<213> ORGANISM: Artificial Sequence
<220> FEATURE:
<223> OTHER INFORMATION: Synthetic

<400> SEQUENCE: 1080
aggaggcuga ggcaggagaa guuuuagagc uagaaauagc aaguuaaaau aaggcuaguc        60
cguuaucaac uugaaaaagu ggcaccgagu cggugc        96

<210> SEQ ID NO 1081
<211> LENGTH: 96
<212> TYPE: RNA
<213> ORGANISM: Artificial Sequence
<220> FEATURE:
<223> OTHER INFORMATION: Synthetic

<400> SEQUENCE: 1081
gcaggagaau ggcgugaacc guuuuagagc uagaaauagc aaguuaaaau aaggcuaguc        60
cguuaucaac uugaaaaagu ggcaccgagu cggugc        96

<210> SEQ ID NO 1082
<211> LENGTH: 96
<212> TYPE: RNA
<213> ORGANISM: Artificial Sequence
<220> FEATURE:

```
<223> OTHER INFORMATION: Synthetic

<400> SEQUENCE: 1082
caggagaaug gcgugaaccc guuuuagagc uagaaauagc aaguuaaaau aaggcuaguc      60
cguuaucaac uugaaaaagu ggcaccgagu cggugc                                96

<210> SEQ ID NO 1083
<211> LENGTH: 96
<212> TYPE: RNA
<213> ORGANISM: Artificial Sequence
<220> FEATURE:
<223> OTHER INFORMATION: Synthetic

<400> SEQUENCE: 1083
gagaauggcg ugaacccggg guuuuagagc uagaaauagc aaguuaaaau aaggcuaguc      60
cguuaucaac uugaaaaagu ggcaccgagu cggugc                                96

<210> SEQ ID NO 1084
<211> LENGTH: 96
<212> TYPE: RNA
<213> ORGANISM: Artificial Sequence
<220> FEATURE:
<223> OTHER INFORMATION: Synthetic

<400> SEQUENCE: 1084
aauggcguga acccgggagg guuuuagagc uagaaauagc aaguuaaaau aaggcuaguc      60
cguuaucaac uugaaaaagu ggcaccgagu cggugc                                96

<210> SEQ ID NO 1085
<211> LENGTH: 96
<212> TYPE: RNA
<213> ORGANISM: Artificial Sequence
<220> FEATURE:
<223> OTHER INFORMATION: Synthetic

<400> SEQUENCE: 1085
cacugcaagc uccaccuccc guuuuagagc uagaaauagc aaguuaaaau aaggcuaguc      60
cguuaucaac uugaaaaagu ggcaccgagu cggugc                                96

<210> SEQ ID NO 1086
<211> LENGTH: 96
<212> TYPE: RNA
<213> ORGANISM: Artificial Sequence
<220> FEATURE:
<223> OTHER INFORMATION: Synthetic

<400> SEQUENCE: 1086
ucacugcaag cuccaccucc guuuuagagc uagaaauagc aaguuaaaau aaggcuaguc      60
cguuaucaac uugaaaaagu ggcaccgagu cggugc                                96

<210> SEQ ID NO 1087
<211> LENGTH: 96
<212> TYPE: RNA
<213> ORGANISM: Artificial Sequence
<220> FEATURE:
<223> OTHER INFORMATION: Synthetic

<400> SEQUENCE: 1087
cauaccacug cacuccagcc guuuuagagc uagaaauagc aaguuaaaau aaggcuaguc      60
cguuaucaac uugaaaaagu ggcaccgagu cggugc                                96
```

```
<210> SEQ ID NO 1088
<211> LENGTH: 96
<212> TYPE: RNA
<213> ORGANISM: Artificial Sequence
<220> FEATURE:
<223> OTHER INFORMATION: Synthetic

<400> SEQUENCE: 1088
auaccacugc acuccagccu guuuuagagc uagaaauagc aaguuaaaau aaggcuaguc    60
cguuaucaac uugaaaaagu ggcaccgagu cggugc                             96

<210> SEQ ID NO 1089
<211> LENGTH: 96
<212> TYPE: RNA
<213> ORGANISM: Artificial Sequence
<220> FEATURE:
<223> OTHER INFORMATION: Synthetic

<400> SEQUENCE: 1089
ucgcccaggc uggagugcag guuuuagagc uagaaauagc aaguuaaaau aaggcuaguc    60
cguuaucaac uugaaaaagu ggcaccgagu cggugc                             96

<210> SEQ ID NO 1090
<211> LENGTH: 96
<212> TYPE: RNA
<213> ORGANISM: Artificial Sequence
<220> FEATURE:
<223> OTHER INFORMATION: Synthetic

<400> SEQUENCE: 1090
ucucacucuu ucgcccaggc guuuuagagc uagaaauagc aaguuaaaau aaggcuaguc    60
cguuaucaac uugaaaaagu ggcaccgagu cggugc                             96

<210> SEQ ID NO 1091
<211> LENGTH: 96
<212> TYPE: RNA
<213> ORGANISM: Artificial Sequence
<220> FEATURE:
<223> OTHER INFORMATION: Synthetic

<400> SEQUENCE: 1091
ggagucucac ucuuucgccc guuuuagagc uagaaauagc aaguuaaaau aaggcuaguc    60
cguuaucaac uugaaaaagu ggcaccgagu cggugc                             96

<210> SEQ ID NO 1092
<211> LENGTH: 96
<212> TYPE: RNA
<213> ORGANISM: Artificial Sequence
<220> FEATURE:
<223> OTHER INFORMATION: Synthetic

<400> SEQUENCE: 1092 uguuuuugu uuuuugaga guuuuagagc uagaaauagc aaguuaaaau aaggcuaguc     60
cguuaucaac uugaaaaagu ggcaccgagu cggugc                             96

<210> SEQ ID NO 1093
<211> LENGTH: 96
<212> TYPE: RNA
<213> ORGANISM: Artificial Sequence
<220> FEATURE:
<223> OTHER INFORMATION: Synthetic

<400> SEQUENCE: 1093
```

```
aggaagaaag aaagguuuuu guuuuagagc uagaaauagc aaguuaaaau aaggcuaguc    60
cguuaucaac uugaaaaagu ggcaccgagu cggugc                               96
```

<210> SEQ ID NO 1094
<211> LENGTH: 96
<212> TYPE: RNA
<213> ORGANISM: Artificial Sequence
<220> FEATURE:
<223> OTHER INFORMATION: Synthetic

<400> SEQUENCE: 1094

```
agaagaaaag gaagaaagaa guuuuagagc uagaaauagc aaguuaaaau aaggcuaguc    60
cguuaucaac uugaaaaagu ggcaccgagu cggugc                               96
```

<210> SEQ ID NO 1095
<211> LENGTH: 96
<212> TYPE: RNA
<213> ORGANISM: Artificial Sequence
<220> FEATURE:
<223> OTHER INFORMATION: Synthetic

<400> SEQUENCE: 1095

```
cuuucuuccu uuucuucucu guuuuagagc uagaaauagc aaguuaaaau aaggcuaguc    60
cguuaucaac uugaaaaagu ggcaccgagu cggugc                               96
```

<210> SEQ ID NO 1096
<211> LENGTH: 96
<212> TYPE: RNA
<213> ORGANISM: Artificial Sequence
<220> FEATURE:
<223> OTHER INFORMATION: Synthetic

<400> SEQUENCE: 1096

```
uuucuuccuu uucuucucuu guuuuagagc uagaaauagc aaguuaaaau aaggcuaguc    60
cguuaucaac uugaaaaagu ggcaccgagu cggugc                               96
```

<210> SEQ ID NO 1097
<211> LENGTH: 96
<212> TYPE: RNA
<213> ORGANISM: Artificial Sequence
<220> FEATURE:
<223> OTHER INFORMATION: Synthetic

<400> SEQUENCE: 1097

```
aauggaccca agagaagaaa guuuuagagc uagaaauagc aaguuaaaau aaggcuaguc    60
cguuaucaac uugaaaaagu ggcaccgagu cggugc                               96
```

<210> SEQ ID NO 1098
<211> LENGTH: 96
<212> TYPE: RNA
<213> ORGANISM: Artificial Sequence
<220> FEATURE:
<223> OTHER INFORMATION: Synthetic

<400> SEQUENCE: 1098

```
ggcuauuaca uaagaaacaa guuuuagagc uagaaauagc aaguuaaaau aaggcuaguc    60
cguuaucaac uugaaaaagu ggcaccgagu cggugc                               96
```

<210> SEQ ID NO 1099
<211> LENGTH: 96
<212> TYPE: RNA
<213> ORGANISM: Artificial Sequence

```
<220> FEATURE:
<223> OTHER INFORMATION: Synthetic

<400> SEQUENCE: 1099
cacaggaaaa ggaacuguac guuuuagagc uagaaauagc aaguuaaaau aaggcuaguc      60
cguuaucaac uugaaaaagu ggcaccgagu cggugc                               96

<210> SEQ ID NO 1100
<211> LENGTH: 96
<212> TYPE: RNA
<213> ORGANISM: Artificial Sequence
<220> FEATURE:
<223> OTHER INFORMATION: Synthetic

<400> SEQUENCE: 1100
auuaaagcua acacaggaaa guuuuagagc uagaaauagc aaguuaaaau aaggcuaguc      60
cguuaucaac uugaaaaagu ggcaccgagu cggugc                               96

<210> SEQ ID NO 1101
<211> LENGTH: 96
<212> TYPE: RNA
<213> ORGANISM: Artificial Sequence
<220> FEATURE:
<223> OTHER INFORMATION: Synthetic

<400> SEQUENCE: 1101
ucaaaaauua aagcuaacac guuuuagagc uagaaauagc aaguuaaaau aaggcuaguc      60
cguuaucaac uugaaaaagu ggcaccgagu cggugc                               96

<210> SEQ ID NO 1102
<211> LENGTH: 96
<212> TYPE: RNA
<213> ORGANISM: Artificial Sequence
<220> FEATURE:
<223> OTHER INFORMATION: Synthetic

<400> SEQUENCE: 1102
uaaaauuguc uaaacaucuc guuuuagagc uagaaauagc aaguuaaaau aaggcuaguc      60
cguuaucaac uugaaaaagu ggcaccgagu cggugc                               96

<210> SEQ ID NO 1103
<211> LENGTH: 96
<212> TYPE: RNA
<213> ORGANISM: Artificial Sequence
<220> FEATURE:
<223> OTHER INFORMATION: Synthetic

<400> SEQUENCE: 1103
agagauguuu agacaauuuu guuuuagagc uagaaauagc aaguuaaaau aaggcuaguc      60
cguuaucaac uugaaaaagu ggcaccgagu cggugc                               96

<210> SEQ ID NO 1104
<211> LENGTH: 96
<212> TYPE: RNA
<213> ORGANISM: Artificial Sequence
<220> FEATURE:
<223> OTHER INFORMATION: Synthetic

<400> SEQUENCE: 1104
ucuaaacauc ucugggacca guuuuagagc uagaaauagc aaguuaaaau aaggcuaguc      60
cguuaucaac uugaaaaagu ggcaccgagu cggugc                               96
```

<210> SEQ ID NO 1105
<211> LENGTH: 96
<212> TYPE: RNA
<213> ORGANISM: Artificial Sequence
<220> FEATURE:
<223> OTHER INFORMATION: Synthetic

<400> SEQUENCE: 1105
uuuaugcuuu cauauauccu guuuuagagc uagaaauagc aaguuaaaau aaggcuaguc    60
cguuaucaac uugaaaaagu ggcaccgagu cggugc    96

<210> SEQ ID NO 1106
<211> LENGTH: 96
<212> TYPE: RNA
<213> ORGANISM: Artificial Sequence
<220> FEATURE:
<223> OTHER INFORMATION: Synthetic

<400> SEQUENCE: 1106
agcauaaauu acaaagaaaa guuuuagagc uagaaauagc aaguuaaaau aaggcuaguc    60
cguuaucaac uugaaaaagu ggcaccgagu cggugc    96

<210> SEQ ID NO 1107
<211> LENGTH: 96
<212> TYPE: RNA
<213> ORGANISM: Artificial Sequence
<220> FEATURE:
<223> OTHER INFORMATION: Synthetic

<400> SEQUENCE: 1107
uacaaagaaa aagguuauca guuuuagagc uagaaauagc aaguuaaaau aaggcuaguc    60
cguuaucaac uugaaaaagu ggcaccgagu cggugc    96

<210> SEQ ID NO 1108
<211> LENGTH: 96
<212> TYPE: RNA
<213> ORGANISM: Artificial Sequence
<220> FEATURE:
<223> OTHER INFORMATION: Synthetic

<400> SEQUENCE: 1108
acaaagaaaa agguuaucau guuuuagagc uagaaauagc aaguuaaaau aaggcuaguc    60
cguuaucaac uugaaaaagu ggcaccgagu cggugc    96

<210> SEQ ID NO 1109
<211> LENGTH: 96
<212> TYPE: RNA
<213> ORGANISM: Artificial Sequence
<220> FEATURE:
<223> OTHER INFORMATION: Synthetic

<400> SEQUENCE: 1109
caaagaaaaa gguuaucaug guuuuagagc uagaaauagc aaguuaaaau aaggcuaguc    60
cguuaucaac uugaaaaagu ggcaccgagu cggugc    96

<210> SEQ ID NO 1110
<211> LENGTH: 96
<212> TYPE: RNA
<213> ORGANISM: Artificial Sequence
<220> FEATURE:
<223> OTHER INFORMATION: Synthetic

<400> SEQUENCE: 1110

```
ucgagauuu aaaauagagu guuuuagagc uagaaauagc aaguuaaaau aaggcuaguc    60
cguuaucaac uugaaaaagu ggcaccgagu cggugc                            96

<210> SEQ ID NO 1111
<211> LENGTH: 96
<212> TYPE: RNA
<213> ORGANISM: Artificial Sequence
<220> FEATURE:
<223> OTHER INFORMATION: Synthetic

<400> SEQUENCE: 1111
cuuauaagau acauuaugaa guuuuagagc uagaaauagc aaguuaaaau aaggcuaguc    60
cguuaucaac uugaaaaagu ggcaccgagu cggugc                            96

<210> SEQ ID NO 1112
<211> LENGTH: 96
<212> TYPE: RNA
<213> ORGANISM: Artificial Sequence
<220> FEATURE:
<223> OTHER INFORMATION: Synthetic

<400> SEQUENCE: 1112
uaucuuauaa gacuauaaaa guuuuagagc uagaaauagc aaguuaaaau aaggcuaguc    60
cguuaucaac uugaaaaagu ggcaccgagu cggugc                            96

<210> SEQ ID NO 1113
<211> LENGTH: 96
<212> TYPE: RNA
<213> ORGANISM: Artificial Sequence
<220> FEATURE:
<223> OTHER INFORMATION: Synthetic

<400> SEQUENCE: 1113
aucuuauaag acuauaaaaa guuuuagagc uagaaauagc aaguuaaaau aaggcuaguc    60
cguuaucaac uugaaaaagu ggcaccgagu cggugc                            96

<210> SEQ ID NO 1114
<211> LENGTH: 96
<212> TYPE: RNA
<213> ORGANISM: Artificial Sequence
<220> FEATURE:
<223> OTHER INFORMATION: Synthetic

<400> SEQUENCE: 1114
uuauaagacu auaaaagggg guuuuagagc uagaaauagc aaguuaaaau aaggcuaguc    60
cguuaucaac uugaaaaagu ggcaccgagu cggugc                            96

<210> SEQ ID NO 1115
<211> LENGTH: 96
<212> TYPE: RNA
<213> ORGANISM: Artificial Sequence
<220> FEATURE:
<223> OTHER INFORMATION: Synthetic

<400> SEQUENCE: 1115
uaaaagggga ggaaauauag guuuuagagc uagaaauagc aaguuaaaau aaggcuaguc    60
cguuaucaac uugaaaaagu ggcaccgagu cggugc                            96

<210> SEQ ID NO 1116
<211> LENGTH: 96
<212> TYPE: RNA
```

```
<213> ORGANISM: Artificial Sequence
<220> FEATURE:
<223> OTHER INFORMATION: Synthetic

<400> SEQUENCE: 1116
aaaaagggag gaaauauaga guuuuagagc uagaaauagc aaguuaaaau aaggcuaguc    60
cguuaucaac uugaaaaagu ggcaccgagu cggugc                              96

<210> SEQ ID NO 1117
<211> LENGTH: 96
<212> TYPE: RNA
<213> ORGANISM: Artificial Sequence
<220> FEATURE:
<223> OTHER INFORMATION: Synthetic

<400> SEQUENCE: 1117
aaauauagag gguccacuuu guuuuagagc uagaaauagc aaguuaaaau aaggcuaguc    60
cguuaucaac uugaaaaagu ggcaccgagu cggugc                              96

<210> SEQ ID NO 1118
<211> LENGTH: 96
<212> TYPE: RNA
<213> ORGANISM: Artificial Sequence
<220> FEATURE:
<223> OTHER INFORMATION: Synthetic

<400> SEQUENCE: 1118
uauagagggu ccacuuuugg guuuuagagc uagaaauagc aaguuaaaau aaggcuaguc    60
cguuaucaac uugaaaaagu ggcaccgagu cggugc                              96

<210> SEQ ID NO 1119
<211> LENGTH: 96
<212> TYPE: RNA
<213> ORGANISM: Artificial Sequence
<220> FEATURE:
<223> OTHER INFORMATION: Synthetic

<400> SEQUENCE: 1119
acucugaagu ccaccaaaag guuuuagagc uagaaauagc aaguuaaaau aaggcuaguc    60
cguuaucaac uugaaaaagu ggcaccgagu cggugc                              96

<210> SEQ ID NO 1120
<211> LENGTH: 96
<212> TYPE: RNA
<213> ORGANISM: Artificial Sequence
<220> FEATURE:
<223> OTHER INFORMATION: Synthetic

<400> SEQUENCE: 1120
agaauagagu ugcaccguuu guuuuagagc uagaaauagc aaguuaaaau aaggcuaguc    60
cguuaucaac uugaaaaagu ggcaccgagu cggugc                              96

<210> SEQ ID NO 1121
<211> LENGTH: 96
<212> TYPE: RNA
<213> ORGANISM: Artificial Sequence
<220> FEATURE:
<223> OTHER INFORMATION: Synthetic

<400> SEQUENCE: 1121
aaaacggugc aacucuauuc guuuuagagc uagaaauagc aaguuaaaau aaggcuaguc    60
cguuaucaac uugaaaaagu ggcaccgagu cggugc                              96
```

```
<210> SEQ ID NO 1122
<211> LENGTH: 96
<212> TYPE: RNA
<213> ORGANISM: Artificial Sequence
<220> FEATURE:
<223> OTHER INFORMATION: Synthetic

<400> SEQUENCE: 1122
ccguuuuggg cuaaugaaaa guuuuagagc uagaaauagc aaguuaaaau aaggcuaguc    60
cguuaucaac uugaaaaagu ggcaccgagu cggugc                             96

<210> SEQ ID NO 1123
<211> LENGTH: 96
<212> TYPE: RNA
<213> ORGANISM: Artificial Sequence
<220> FEATURE:
<223> OTHER INFORMATION: Synthetic

<400> SEQUENCE: 1123
ccuuuuucau uagcccaaaa guuuuagagc uagaaauagc aaguuaaaau aaggcuaguc    60
cguuaucaac uugaaaaagu ggcaccgagu cggugc                             96

<210> SEQ ID NO 1124
<211> LENGTH: 96
<212> TYPE: RNA
<213> ORGANISM: Artificial Sequence
<220> FEATURE:
<223> OTHER INFORMATION: Synthetic

<400> SEQUENCE: 1124
ugggcuaaug aaaaggaag guuuuagagc uagaaauagc aaguuaaaau aaggcuaguc    60
cguuaucaac uugaaaaagu ggcaccgagu cggugc                             96

<210> SEQ ID NO 1125
<211> LENGTH: 96
<212> TYPE: RNA
<213> ORGANISM: Artificial Sequence
<220> FEATURE:
<223> OTHER INFORMATION: Synthetic

<400> SEQUENCE: 1125
uaaugaaaaa ggaagaggcu guuuuagagc uagaaauagc aaguuaaaau aaggcuaguc    60
cguuaucaac uugaaaaagu ggcaccgagu cggugc                             96

<210> SEQ ID NO 1126
<211> LENGTH: 96
<212> TYPE: RNA
<213> ORGANISM: Artificial Sequence
<220> FEATURE:
<223> OTHER INFORMATION: Synthetic

<400> SEQUENCE: 1126
aaugaaaaag gaagaggcua guuuuagagc uagaaauagc aaguuaaaau aaggcuaguc    60
cguuaucaac uugaaaaagu ggcaccgagu cggugc                             96

<210> SEQ ID NO 1127
<211> LENGTH: 96
<212> TYPE: RNA
<213> ORGANISM: Artificial Sequence
<220> FEATURE:
<223> OTHER INFORMATION: Synthetic
```

```
<400> SEQUENCE: 1127
cugaaucuua aaauaugucc guuuuagagc uagaaauagc aaguuaaaau aaggcuaguc    60
cguuaucaac uugaaaaagu ggcaccgagu cggugc                              96

<210> SEQ ID NO 1128
<211> LENGTH: 96
<212> TYPE: RNA
<213> ORGANISM: Artificial Sequence
<220> FEATURE:
<223> OTHER INFORMATION: Synthetic

<400> SEQUENCE: 1128
caggcagcuu uaucucaacc guuuuagagc uagaaauagc aaguuaaaau aaggcuaguc    60
cguuaucaac uugaaaaagu ggcaccgagu cggugc                              96

<210> SEQ ID NO 1129
<211> LENGTH: 96
<212> TYPE: RNA
<213> ORGANISM: Artificial Sequence
<220> FEATURE:
<223> OTHER INFORMATION: Synthetic

<400> SEQUENCE: 1129
cuaagagauc aaguuucagc guuuuagagc uagaaauagc aaguuaaaau aaggcuaguc    60
cguuaucaac uugaaaaagu ggcaccgagu cggugc                              96

<210> SEQ ID NO 1130
<211> LENGTH: 96
<212> TYPE: RNA
<213> ORGANISM: Artificial Sequence
<220> FEATURE:
<223> OTHER INFORMATION: Synthetic

<400> SEQUENCE: 1130
guguucuugu ugauauucug guuuuagagc uagaaauagc aaguuaaaau aaggcuaguc    60
cguuaucaac uugaaaaagu ggcaccgagu cggugc                              96

<210> SEQ ID NO 1131
<211> LENGTH: 96
<212> TYPE: RNA
<213> ORGANISM: Artificial Sequence
<220> FEATURE:
<223> OTHER INFORMATION: Synthetic

<400> SEQUENCE: 1131
cuuguugaua uucuguggca guuuuagagc uagaaauagc aaguuaaaau aaggcuaguc    60
cguuaucaac uugaaaaagu ggcaccgagu cggugc                              96

<210> SEQ ID NO 1132
<211> LENGTH: 96
<212> TYPE: RNA
<213> ORGANISM: Artificial Sequence
<220> FEATURE:
<223> OTHER INFORMATION: Synthetic

<400> SEQUENCE: 1132
ucuguggcau ggcuacagau guuuuagagc uagaaauagc aaguuaaaau aaggcuaguc    60
cguuaucaac uugaaaaagu ggcaccgagu cggugc                              96

<210> SEQ ID NO 1133
<211> LENGTH: 96
```

```
<212> TYPE: RNA
<213> ORGANISM: Artificial Sequence
<220> FEATURE:
<223> OTHER INFORMATION: Synthetic

<400> SEQUENCE: 1133
agaacuuauu uacacaggga guuuuagagc uagaaauagc aaguuaaaau aaggcuaguc    60
cguuaucaac uugaaaaagu ggcaccgagu cggugc                              96

<210> SEQ ID NO 1134
<211> LENGTH: 96
<212> TYPE: RNA
<213> ORGANISM: Artificial Sequence
<220> FEATURE:
<223> OTHER INFORMATION: Synthetic

<400> SEQUENCE: 1134
aaagagaacu uauuuacaca guuuuagagc uagaaauagc aaguuaaaau aaggcuaguc    60
cguuaucaac uugaaaaagu ggcaccgagu cggugc                              96

<210> SEQ ID NO 1135
<211> LENGTH: 96
<212> TYPE: RNA
<213> ORGANISM: Artificial Sequence
<220> FEATURE:
<223> OTHER INFORMATION: Synthetic

<400> SEQUENCE: 1135
caaagagaac uuauuuacac guuuuagagc uagaaauagc aaguuaaaau aaggcuaguc    60
cguuaucaac uugaaaaagu ggcaccgagu cggugc                              96

<210> SEQ ID NO 1136
<211> LENGTH: 96
<212> TYPE: RNA
<213> ORGANISM: Artificial Sequence
<220> FEATURE:
<223> OTHER INFORMATION: Synthetic

<400> SEQUENCE: 1136
uucucuuugu auuuacuuuu guuuuagagc uagaaauagc aaguuaaaau aaggcuaguc    60
cguuaucaac uugaaaaagu ggcaccgagu cggugc                              96

<210> SEQ ID NO 1137
<211> LENGTH: 96
<212> TYPE: RNA
<213> ORGANISM: Artificial Sequence
<220> FEATURE:
<223> OTHER INFORMATION: Synthetic

<400> SEQUENCE: 1137
ucucuuugua uuuacuuuua guuuuagagc uagaaauagc aaguuaaaau aaggcuaguc    60
cguuaucaac uugaaaaagu ggcaccgagu cggugc                              96

<210> SEQ ID NO 1138
<211> LENGTH: 96
<212> TYPE: RNA
<213> ORGANISM: Artificial Sequence
<220> FEATURE:
<223> OTHER INFORMATION: Synthetic

<400> SEQUENCE: 1138
cuuuguauuu acuuuagggg guuuuagagc uagaaauagc aaguuaaaau aaggcuaguc    60
```

```
cguuaucaac uugaaaaagu ggcaccgagu cggugc                                96
```

<210> SEQ ID NO 1139
<211> LENGTH: 96
<212> TYPE: RNA
<213> ORGANISM: Artificial Sequence
<220> FEATURE:
<223> OTHER INFORMATION: Synthetic

<400> SEQUENCE: 1139

```
agcuuuuguc caccuuuaaa guuuuagagc uagaaauagc aaguuaaaau aaggcuaguc    60
cguuaucaac uugaaaaagu ggcaccgagu cggugc                                96
```

<210> SEQ ID NO 1140
<211> LENGTH: 96
<212> TYPE: RNA
<213> ORGANISM: Artificial Sequence
<220> FEATURE:
<223> OTHER INFORMATION: Synthetic

<400> SEQUENCE: 1140

```
uuuauuuuuc cauuuaaagg guuuuagagc uagaaauagc aaguuaaaau aaggcuaguc    60
cguuaucaac uugaaaaagu ggcaccgagu cggugc                                96
```

<210> SEQ ID NO 1141
<211> LENGTH: 96
<212> TYPE: RNA
<213> ORGANISM: Artificial Sequence
<220> FEATURE:
<223> OTHER INFORMATION: Synthetic

<400> SEQUENCE: 1141

```
uauuuuauuu uuccauuuaa guuuuagagc uagaaauagc aaguuaaaau aaggcuaguc    60
cguuaucaac uugaaaaagu ggcaccgagu cggugc                                96
```

<210> SEQ ID NO 1142
<211> LENGTH: 96
<212> TYPE: RNA
<213> ORGANISM: Artificial Sequence
<220> FEATURE:
<223> OTHER INFORMATION: Synthetic

<400> SEQUENCE: 1142

```
cuuacauaaa cauacuuaaa guuuuagagc uagaaauagc aaguuaaaau aaggcuaguc    60
cguuaucaac uugaaaaagu ggcaccgagu cggugc                                96
```

<210> SEQ ID NO 1143
<211> LENGTH: 96
<212> TYPE: RNA
<213> ORGANISM: Artificial Sequence
<220> FEATURE:
<223> OTHER INFORMATION: Synthetic

<400> SEQUENCE: 1143

```
uaagcacaga aguuuuuaag guuuuagagc uagaaauagc aaguuaaaau aaggcuaguc    60
cguuaucaac uugaaaaagu ggcaccgagu cggugc                                96
```

<210> SEQ ID NO 1144
<211> LENGTH: 96
<212> TYPE: RNA
<213> ORGANISM: Artificial Sequence
<220> FEATURE:
<223> OTHER INFORMATION: Synthetic

<400> SEQUENCE: 1144
aaguuuuuaa gaggcaugaa guuuuagagc uagaaauagc aaguuaaaau aaggcuaguc    60
cguuaucaac uugaaaaagu ggcaccgagu cggugc                             96

<210> SEQ ID NO 1145
<211> LENGTH: 96
<212> TYPE: RNA
<213> ORGANISM: Artificial Sequence
<220> FEATURE:
<223> OTHER INFORMATION: Synthetic

<400> SEQUENCE: 1145
auauuuacgu aguuuuucau guuuuagagc uagaaauagc aaguuaaaau aaggcuaguc    60
cguuaucaac uugaaaaagu ggcaccgagu cggugc                             96

<210> SEQ ID NO 1146
<211> LENGTH: 96
<212> TYPE: RNA
<213> ORGANISM: Artificial Sequence
<220> FEATURE:
<223> OTHER INFORMATION: Synthetic

<400> SEQUENCE: 1146
cguaaauauu cuugagaaac guuuuagagc uagaaauagc aaguuaaaau aaggcuaguc    60
cguuaucaac uugaaaaagu ggcaccgagu cggugc                             96

<210> SEQ ID NO 1147
<211> LENGTH: 96
<212> TYPE: RNA
<213> ORGANISM: Artificial Sequence
<220> FEATURE:
<223> OTHER INFORMATION: Synthetic

<400> SEQUENCE: 1147
uucuugagaa acaggaagac guuuuagagc uagaaauagc aaguuaaaau aaggcuaguc    60
cguuaucaac uugaaaaagu ggcaccgagu cggugc                             96

<210> SEQ ID NO 1148
<211> LENGTH: 96
<212> TYPE: RNA
<213> ORGANISM: Artificial Sequence
<220> FEATURE:
<223> OTHER INFORMATION: Synthetic

<400> SEQUENCE: 1148
uaauauuaaa aacauugguu guuuuagagc uagaaauagc aaguuaaaau aaggcuaguc    60
cguuaucaac uugaaaaagu ggcaccgagu cggugc                             96

<210> SEQ ID NO 1149
<211> LENGTH: 96
<212> TYPE: RNA
<213> ORGANISM: Artificial Sequence
<220> FEATURE:
<223> OTHER INFORMATION: Synthetic

<400> SEQUENCE: 1149
ccaauguuuu uaauauuauc guuuuagagc uagaaauagc aaguuaaaau aaggcuaguc    60
cguuaucaac uugaaaaagu ggcaccgagu cggugc                             96

<210> SEQ ID NO 1150

-continued

```
<211> LENGTH: 96
<212> TYPE: RNA
<213> ORGANISM: Artificial Sequence
<220> FEATURE:
<223> OTHER INFORMATION: Synthetic

<400> SEQUENCE: 1150
ccugauaaua uuaaaaacau guuuuagagc uagaaauagc aaguuaaaau aaggcuaguc       60
cguuaucaac uugaaaaagu ggcaccgagu cggugc                                96

<210> SEQ ID NO 1151
<211> LENGTH: 96
<212> TYPE: RNA
<213> ORGANISM: Artificial Sequence
<220> FEATURE:
<223> OTHER INFORMATION: Synthetic

<400> SEQUENCE: 1151
cauuaucaug cauacaucuc guuuuagagc uagaaauagc aaguuaaaau aaggcuaguc       60
cguuaucaac uugaaaaagu ggcaccgagu cggugc                                96

<210> SEQ ID NO 1152
<211> LENGTH: 96
<212> TYPE: RNA
<213> ORGANISM: Artificial Sequence
<220> FEATURE:
<223> OTHER INFORMATION: Synthetic

<400> SEQUENCE: 1152
aucaugcaua caucucuggc guuuuagagc uagaaauagc aaguuaaaau aaggcuaguc       60
cguuaucaac uugaaaaagu ggcaccgagu cggugc                                96

<210> SEQ ID NO 1153
<211> LENGTH: 96
<212> TYPE: RNA
<213> ORGANISM: Artificial Sequence
<220> FEATURE:
<223> OTHER INFORMATION: Synthetic

<400> SEQUENCE: 1153
uucauuucau uuugauuuug guuuuagagc uagaaauagc aaguuaaaau aaggcuaguc       60
cguuaucaac uugaaaaagu ggcaccgagu cggugc                                96

<210> SEQ ID NO 1154
<211> LENGTH: 96
<212> TYPE: RNA
<213> ORGANISM: Artificial Sequence
<220> FEATURE:
<223> OTHER INFORMATION: Synthetic

<400> SEQUENCE: 1154
auucaauuug aagcaguggu guuuuagagc uagaaauagc aaguuaaaau aaggcuaguc       60
cguuaucaac uugaaaaagu ggcaccgagu cggugc                                96

<210> SEQ ID NO 1155
<211> LENGTH: 96
<212> TYPE: RNA
<213> ORGANISM: Artificial Sequence
<220> FEATURE:
<223> OTHER INFORMATION: Synthetic

<400> SEQUENCE: 1155
gaauauucaa uuugaagcag guuuuagagc uagaaauagc aaguuaaaau aaggcuaguc       60
```

```
cguuaucaac uugaaaaagu ggcaccgagu cggugc                                     96

<210> SEQ ID NO 1156
<211> LENGTH: 96
<212> TYPE: RNA
<213> ORGANISM: Artificial Sequence
<220> FEATURE:
<223> OTHER INFORMATION: Synthetic

<400> SEQUENCE: 1156
cauacgauuu aaaaucgcug guuuuagagc uagaaauagc aaguuaaaau aaggcuaguc           60
cguuaucaac uugaaaaagu ggcaccgagu cggugc                                     96

<210> SEQ ID NO 1157
<211> LENGTH: 96
<212> TYPE: RNA
<213> ORGANISM: Artificial Sequence
<220> FEATURE:
<223> OTHER INFORMATION: Synthetic

<400> SEQUENCE: 1157
aaaaucgcug aggcgcguuc guuuuagagc uagaaauagc aaguuaaaau aaggcuaguc           60
cguuaucaac uugaaaaagu ggcaccgagu cggugc                                     96

<210> SEQ ID NO 1158
<211> LENGTH: 96
<212> TYPE: RNA
<213> ORGANISM: Artificial Sequence
<220> FEATURE:
<223> OTHER INFORMATION: Synthetic

<400> SEQUENCE: 1158
uuuuuuuuuc uuuuuuguac guuuuagagc uagaaauagc aaguuaaaau aaggcuaguc           60
cguuaucaac uugaaaaagu ggcaccgagu cggugc                                     96

<210> SEQ ID NO 1159
<211> LENGTH: 96
<212> TYPE: RNA
<213> ORGANISM: Artificial Sequence
<220> FEATURE:
<223> OTHER INFORMATION: Synthetic

<400> SEQUENCE: 1159
cuguugucaa agauuuuaaa guuuuagagc uagaaauagc aaguuaaaau aaggcuaguc           60
cguuaucaac uugaaaaagu ggcaccgagu cggugc                                     96

<210> SEQ ID NO 1160
<211> LENGTH: 96
<212> TYPE: RNA
<213> ORGANISM: Artificial Sequence
<220> FEATURE:
<223> OTHER INFORMATION: Synthetic

<400> SEQUENCE: 1160
ugacaacaga guucuguuuu guuuuagagc uagaaauagc aaguuaaaau aaggcuaguc           60
cguuaucaac uugaaaaagu ggcaccgagu cggugc                                     96

<210> SEQ ID NO 1161
<211> LENGTH: 96
<212> TYPE: RNA
<213> ORGANISM: Artificial Sequence
<220> FEATURE:
```

<223> OTHER INFORMATION: Synthetic

<400> SEQUENCE: 1161
agaauacgcu gagaguuauc guuuuagagc uagaaauagc aaguuaaaau aaggcuaguc    60
cguuaucaac uugaaaaagu ggcaccgagu cggugc                              96

<210> SEQ ID NO 1162
<211> LENGTH: 96
<212> TYPE: RNA
<213> ORGANISM: Artificial Sequence
<220> FEATURE:
<223> OTHER INFORMATION: Synthetic

<400> SEQUENCE: 1162
gcaagagaag aaaagaacgg guuuuagagc uagaaauagc aaguuaaaau aaggcuaguc    60
cguuaucaac uugaaaaagu ggcaccgagu cggugc                              96

<210> SEQ ID NO 1163
<211> LENGTH: 96
<212> TYPE: RNA
<213> ORGANISM: Artificial Sequence
<220> FEATURE:
<223> OTHER INFORMATION: Synthetic

<400> SEQUENCE: 1163
guugcaagag aagaaaagaa guuuuagagc uagaaauagc aaguuaaaau aaggcuaguc    60
cguuaucaac uugaaaaagu ggcaccgagu cggugc                              96

<210> SEQ ID NO 1164
<211> LENGTH: 96
<212> TYPE: RNA
<213> ORGANISM: Artificial Sequence
<220> FEATURE:
<223> OTHER INFORMATION: Synthetic

<400> SEQUENCE: 1164
augcacacgu aaaagagagg guuuuagagc uagaaauagc aaguuaaaau aaggcuaguc    60
cguuaucaac uugaaaaagu ggcaccgagu cggugc                              96

<210> SEQ ID NO 1165
<211> LENGTH: 96
<212> TYPE: RNA
<213> ORGANISM: Artificial Sequence
<220> FEATURE:
<223> OTHER INFORMATION: Synthetic

<400> SEQUENCE: 1165
aagaugcaca cguaaaagag guuuuagagc uagaaauagc aaguuaaaau aaggcuaguc    60
cguuaucaac uugaaaaagu ggcaccgagu cggugc                              96

<210> SEQ ID NO 1166
<211> LENGTH: 96
<212> TYPE: RNA
<213> ORGANISM: Artificial Sequence
<220> FEATURE:
<223> OTHER INFORMATION: Synthetic

<400> SEQUENCE: 1166
aucaugcaua caucucuggc guuuuagagc uagaaauagc aaguuaaaau aaggcuaguc    60
cguuaucaac uugaaaaagu ggcaccgagu cggugc                              96

```
<210> SEQ ID NO 1167
<211> LENGTH: 96
<212> TYPE: RNA
<213> ORGANISM: Artificial Sequence
<220> FEATURE:
<223> OTHER INFORMATION: Synthetic

<400> SEQUENCE: 1167
uucauuucau uuugauuuug guuuuagagc uagaaauagc aaguuaaaau aaggcuaguc    60
cguuaucaac uugaaaaagu ggcaccgagu cggugc                              96

<210> SEQ ID NO 1168
<211> LENGTH: 96
<212> TYPE: RNA
<213> ORGANISM: Artificial Sequence
<220> FEATURE:
<223> OTHER INFORMATION: Synthetic

<400> SEQUENCE: 1168
auucaauuug aagcaguggu guuuuagagc uagaaauagc aaguuaaaau aaggcuaguc    60
cguuaucaac uugaaaaagu ggcaccgagu cggugc                              96

<210> SEQ ID NO 1169
<211> LENGTH: 96
<212> TYPE: RNA
<213> ORGANISM: Artificial Sequence
<220> FEATURE:
<223> OTHER INFORMATION: Synthetic

<400> SEQUENCE: 1169
gaauauucaa uuugaagcag guuuuagagc uagaaauagc aaguuaaaau aaggcuaguc    60
cguuaucaac uugaaaaagu ggcaccgagu cggugc                              96

<210> SEQ ID NO 1170
<211> LENGTH: 96
<212> TYPE: RNA
<213> ORGANISM: Artificial Sequence
<220> FEATURE:
<223> OTHER INFORMATION: Synthetic

<400> SEQUENCE: 1170
cauacgauuu aaaaucgcug guuuuagagc uagaaauagc aaguuaaaau aaggcuaguc    60
cguuaucaac uugaaaaagu ggcaccgagu cggugc                              96

<210> SEQ ID NO 1171
<211> LENGTH: 96
<212> TYPE: RNA
<213> ORGANISM: Artificial Sequence
<220> FEATURE:
<223> OTHER INFORMATION: Synthetic

<400> SEQUENCE: 1171
aaaaucgcug aggcgcguuc guuuuagagc uagaaauagc aaguuaaaau aaggcuaguc    60
cguuaucaac uugaaaaagu ggcaccgagu cggugc                              96

<210> SEQ ID NO 1172
<211> LENGTH: 96
<212> TYPE: RNA
<213> ORGANISM: Artificial Sequence
<220> FEATURE:
<223> OTHER INFORMATION: Synthetic

<400> SEQUENCE: 1172
```
uuuuuuuuuc uuuuuguac guuuuagagc uagaaauagc aaguuaaaau aaggcuaguc      60
cguuaucaac uugaaaaagu ggcaccgagu cggugc                                96

<210> SEQ ID NO 1173
<211> LENGTH: 96
<212> TYPE: RNA
<213> ORGANISM: Artificial Sequence
<220> FEATURE:
<223> OTHER INFORMATION: Synthetic

<400> SEQUENCE: 1173 cguugucaa agauuuaaa guuuuagagc uagaaauagc aaguuaaaau aaggcuaguc        60
cguuaucaac uugaaaaagu ggcaccgagu cggugc                                96

<210> SEQ ID NO 1174
<211> LENGTH: 96
<212> TYPE: RNA
<213> ORGANISM: Artificial Sequence
<220> FEATURE:
<223> OTHER INFORMATION: Synthetic

<400> SEQUENCE: 1174
ugacaacaga guucuguuuu guuuuagagc uagaaauagc aaguuaaaau aaggcuaguc      60
cguuaucaac uugaaaaagu ggcaccgagu cggugc                                96

<210> SEQ ID NO 1175
<211> LENGTH: 96
<212> TYPE: RNA
<213> ORGANISM: Artificial Sequence
<220> FEATURE:
<223> OTHER INFORMATION: Synthetic

<400> SEQUENCE: 1175
agaauacgcu gagaguuauc guuuuagagc uagaaauagc aaguuaaaau aaggcuaguc      60
cguuaucaac uugaaaaagu ggcaccgagu cggugc                                96

<210> SEQ ID NO 1176
<211> LENGTH: 96
<212> TYPE: RNA
<213> ORGANISM: Artificial Sequence
<220> FEATURE:
<223> OTHER INFORMATION: Synthetic

<400> SEQUENCE: 1176
gcaagagaag aaaagaacgg guuuuagagc uagaaauagc aaguuaaaau aaggcuaguc      60
cguuaucaac uugaaaaagu ggcaccgagu cggugc                                96

<210> SEQ ID NO 1177
<211> LENGTH: 96
<212> TYPE: RNA
<213> ORGANISM: Artificial Sequence
<220> FEATURE:
<223> OTHER INFORMATION: Synthetic

<400> SEQUENCE: 1177
guugcaagag aagaaaagaa guuuuagagc uagaaauagc aaguuaaaau aaggcuaguc      60
cguuaucaac uugaaaaagu ggcaccgagu cggugc                                96

<210> SEQ ID NO 1178
<211> LENGTH: 96
<212> TYPE: RNA
<213> ORGANISM: Artificial Sequence

```
<220> FEATURE:
<223> OTHER INFORMATION: Synthetic

<400> SEQUENCE: 1178
augcacacgu aaaagagagg guuuuagagc uagaaauagc aaguuaaaau aaggcuaguc    60
cguuaucaac uugaaaaagu ggcaccgagu cggugc                              96

<210> SEQ ID NO 1179
<211> LENGTH: 96
<212> TYPE: RNA
<213> ORGANISM: Artificial Sequence
<220> FEATURE:
<223> OTHER INFORMATION: Synthetic

<400> SEQUENCE: 1179
aagaugcaca cguaaaagag guuuuagagc uagaaauagc aaguuaaaau aaggcuaguc    60
cguuaucaac uugaaaaagu ggcaccgagu cggugc                              96

<210> SEQ ID NO 1180
<211> LENGTH: 96
<212> TYPE: RNA
<213> ORGANISM: Artificial Sequence
<220> FEATURE:
<223> OTHER INFORMATION: Synthetic

<400> SEQUENCE: 1180
ggcagaccgu ucucaucacg guuuuagagc uagaaauagc aaguuaaaau aaggcuaguc    60
cguuaucaac uugaaaaagu ggcaccgagu cggugc                              96

<210> SEQ ID NO 1181
<211> LENGTH: 96
<212> TYPE: RNA
<213> ORGANISM: Artificial Sequence
<220> FEATURE:
<223> OTHER INFORMATION: Synthetic

<400> SEQUENCE: 1181
cuuuaccagu gacuccaggu guuuuagagc uagaaauagc aaguuaaaau aaggcuaguc    60
cguuaucaac uugaaaaagu ggcaccgagu cggugc                              96

<210> SEQ ID NO 1182
<211> LENGTH: 96
<212> TYPE: RNA
<213> ORGANISM: Artificial Sequence
<220> FEATURE:
<223> OTHER INFORMATION: Synthetic

<400> SEQUENCE: 1182
gucacagauu uccuucuccg guuuuagagc uagaaauagc aaguuaaaau aaggcuaguc    60
cguuaucaac uugaaaaagu ggcaccgagu cggugc                              96

<210> SEQ ID NO 1183
<211> LENGTH: 96
<212> TYPE: RNA
<213> ORGANISM: Artificial Sequence
<220> FEATURE:
<223> OTHER INFORMATION: Synthetic

<400> SEQUENCE: 1183
agaugaugac gcccaccaga guuuuagagc uagaaauagc aaguuaaaau aaggcuaguc    60
cguuaucaac uugaaaaagu ggcaccgagu cggugc                              96
```

<210> SEQ ID NO 1184
<211> LENGTH: 96
<212> TYPE: RNA
<213> ORGANISM: Artificial Sequence
<220> FEATURE:
<223> OTHER INFORMATION: Synthetic

<400> SEQUENCE: 1184

```
ggagaaggaa aucugugacc guuuuagagc uagaaauagc aaguuaaaau aaggcuaguc    60
cguuaucaac uugaaaaagu ggcaccgagu cggugc                              96
```

<210> SEQ ID NO 1185
<211> LENGTH: 96
<212> TYPE: RNA
<213> ORGANISM: Artificial Sequence
<220> FEATURE:
<223> OTHER INFORMATION: Synthetic

<400> SEQUENCE: 1185

```
ugcgaggaac uuacuuuucc guuuuagagc uagaaauagc aaguuaaaau aaggcuaguc    60
cguuaucaac uugaaaaagu ggcaccgagu cggugc                              96
```

<210> SEQ ID NO 1186
<211> LENGTH: 96
<212> TYPE: RNA
<213> ORGANISM: Artificial Sequence
<220> FEATURE:
<223> OTHER INFORMATION: Synthetic

<400> SEQUENCE: 1186

```
agagaaauau ugauauagga guuuuagagc uagaaauagc aaguuaaaau aaggcuaguc    60
cguuaucaac uugaaaaagu ggcaccgagu cggugc                              96
```

<210> SEQ ID NO 1187
<211> LENGTH: 96
<212> TYPE: RNA
<213> ORGANISM: Artificial Sequence
<220> FEATURE:
<223> OTHER INFORMATION: Synthetic

<400> SEQUENCE: 1187

```
uaucaauauu ucucugaucc guuuuagagc uagaaauagc aaguuaaaau aaggcuaguc    60
cguuaucaac uugaaaaagu ggcaccgagu cggugc                              96
```

<210> SEQ ID NO 1188
<211> LENGTH: 96
<212> TYPE: RNA
<213> ORGANISM: Artificial Sequence
<220> FEATURE:
<223> OTHER INFORMATION: Synthetic

<400> SEQUENCE: 1188

```
aucgcuuuua aggcacgcuc guuuuagagc uagaaauagc aaguuaaaau aaggcuaguc    60
cguuaucaac uugaaaaagu ggcaccgagu cggugc                              96
```

<210> SEQ ID NO 1189
<211> LENGTH: 96
<212> TYPE: RNA
<213> ORGANISM: Artificial Sequence
<220> FEATURE:
<223> OTHER INFORMATION: Synthetic

<400> SEQUENCE: 1189

```
uauacgacug aucgcuuuua guuuuagagc uagaaauagc aaguuaaaau aaggcuaguc    60
cguuaucaac uugaaaaagu ggcaccgagu cggugc                              96

<210> SEQ ID NO 1190
<211> LENGTH: 106
<212> TYPE: RNA
<213> ORGANISM: Artificial Sequence
<220> FEATURE:
<223> OTHER INFORMATION: Synthetic

<400> SEQUENCE: 1190
ugucagguua guuagaugaa guuuaagagc uaugcuggaa acagcauagc aaguuuaaau    60
aaggcuaguc cguuaucaac uugaaaaagu ggcaccgagu cggugc                  106

<210> SEQ ID NO 1191
<211> LENGTH: 106
<212> TYPE: RNA
<213> ORGANISM: Artificial Sequence
<220> FEATURE:
<223> OTHER INFORMATION: Synthetic

<400> SEQUENCE: 1191
gugucagguu aguuagauga guuuaagagc uaugcuggaa acagcauagc aaguuuaaau    60
aaggcuaguc cguuaucaac uugaaaaagu ggcaccgagu cggugc                  106

<210> SEQ ID NO 1192
<211> LENGTH: 106
<212> TYPE: RNA
<213> ORGANISM: Artificial Sequence
<220> FEATURE:
<223> OTHER INFORMATION: Synthetic

<400> SEQUENCE: 1192
ccugacacau auacagacua guuuaagagc uaugcuggaa acagcauagc aaguuuaaau    60
aaggcuaguc cguuaucaac uugaaaaagu ggcaccgagu cggugc                  106

<210> SEQ ID NO 1193
<211> LENGTH: 106
<212> TYPE: RNA
<213> ORGANISM: Artificial Sequence
<220> FEATURE:
<223> OTHER INFORMATION: Synthetic

<400> SEQUENCE: 1193
cugacacaua uacagacuaa guuuaagagc uaugcuggaa acagcauagc aaguuuaaau    60
aaggcuaguc cguuaucaac uugaaaaagu ggcaccgagu cggugc                  106

<210> SEQ ID NO 1194
<211> LENGTH: 106
<212> TYPE: RNA
<213> ORGANISM: Artificial Sequence
<220> FEATURE:
<223> OTHER INFORMATION: Synthetic

<400> SEQUENCE: 1194
ccuuagucug uauauguguc guuuaagagc uaugcuggaa acagcauagc aaguuuaaau    60
aaggcuaguc cguuaucaac uugaaaaagu ggcaccgagu cggugc                  106

<210> SEQ ID NO 1195
<211> LENGTH: 106
<212> TYPE: RNA
```

<213> ORGANISM: Artificial Sequence
<220> FEATURE:
<223> OTHER INFORMATION: Synthetic

<400> SEQUENCE: 1195
cauauacaga cuaagggacc guuuaagagc uaugcuggaa acagcauagc aaguuuaaau    60
aaggcuaguc cguuaucaac uugaaaaagu ggcaccgagu cggugc                  106

<210> SEQ ID NO 1196
<211> LENGTH: 106
<212> TYPE: RNA
<213> ORGANISM: Artificial Sequence
<220> FEATURE:
<223> OTHER INFORMATION: Synthetic

<400> SEQUENCE: 1196
auauacagac uaagggacca guuuaagagc uaugcuggaa acagcauagc aaguuuaaau    60
aaggcuaguc cguuaucaac uugaaaaagu ggcaccgagu cggugc                  106

<210> SEQ ID NO 1197
<211> LENGTH: 106
<212> TYPE: RNA
<213> ORGANISM: Artificial Sequence
<220> FEATURE:
<223> OTHER INFORMATION: Synthetic

<400> SEQUENCE: 1197
ucaaaguuug auaaauuccc guuuaagagc uaugcuggaa acagcauagc aaguuuaaau    60
aaggcuaguc cguuaucaac uugaaaaagu ggcaccgagu cggugc                  106

<210> SEQ ID NO 1198
<211> LENGTH: 106
<212> TYPE: RNA
<213> ORGANISM: Artificial Sequence
<220> FEATURE:
<223> OTHER INFORMATION: Synthetic

<400> SEQUENCE: 1198
aaaauacaaa gauaaguaga guuuaagagc uaugcuggaa acagcauagc aaguuuaaau    60
aaggcuaguc cguuaucaac uugaaaaagu ggcaccgagu cggugc                  106

<210> SEQ ID NO 1199
<211> LENGTH: 106
<212> TYPE: RNA
<213> ORGANISM: Artificial Sequence
<220> FEATURE:
<223> OTHER INFORMATION: Synthetic

<400> SEQUENCE: 1199
acucugugac uuuaaaaagu guuuaagagc uaugcuggaa acagcauagc aaguuuaaau    60
aaggcuaguc cguuaucaac uugaaaaagu ggcaccgagu cggugc                  106

<210> SEQ ID NO 1200
<211> LENGTH: 106
<212> TYPE: RNA
<213> ORGANISM: Artificial Sequence
<220> FEATURE:
<223> OTHER INFORMATION: Synthetic

<400> SEQUENCE: 1200
gguucugugg gauauuaaua guuuaagagc uaugcuggaa acagcauagc aaguuuaaau    60
aaggcuaguc cguuaucaac uugaaaaagu ggcaccgagu cggugc                  106

<210> SEQ ID NO 1201
<211> LENGTH: 106
<212> TYPE: RNA
<213> ORGANISM: Artificial Sequence
<220> FEATURE:
<223> OTHER INFORMATION: Synthetic

<400> SEQUENCE: 1201
acagagcaua uugguucugu guuuaagagc uaugcuggaa acagcauagc aaguuuaaau    60
aaggcuaguc cguuaucaac uugaaaaagu ggcaccgagu cggugc                 106

<210> SEQ ID NO 1202
<211> LENGTH: 106
<212> TYPE: RNA
<213> ORGANISM: Artificial Sequence
<220> FEATURE:
<223> OTHER INFORMATION: Synthetic

<400> SEQUENCE: 1202
gacagagcau auugguucug guuuaagagc uaugcuggaa acagcauagc aaguuuaaau    60
aaggcuaguc cguuaucaac uugaaaaagu ggcaccgagu cggugc                 106

<210> SEQ ID NO 1203
<211> LENGTH: 106
<212> TYPE: RNA
<213> ORGANISM: Artificial Sequence
<220> FEATURE:
<223> OTHER INFORMATION: Synthetic

<400> SEQUENCE: 1203
ugcaaaacga cagagcauau guuuaagagc uaugcuggaa acagcauagc aaguuuaaau    60
aaggcuaguc cguuaucaac uugaaaaagu ggcaccgagu cggugc                 106

<210> SEQ ID NO 1204
<211> LENGTH: 106
<212> TYPE: RNA
<213> ORGANISM: Artificial Sequence
<220> FEATURE:
<223> OTHER INFORMATION: Synthetic

<400> SEQUENCE: 1204
gagcugggca uggaauaggc guuuaagagc uaugcuggaa acagcauagc aaguuuaaau    60
aaggcuaguc cguuaucaac uugaaaaagu ggcaccgagu cggugc                 106

<210> SEQ ID NO 1205
<211> LENGTH: 106
<212> TYPE: RNA
<213> ORGANISM: Artificial Sequence
<220> FEATURE:
<223> OTHER INFORMATION: Synthetic

<400> SEQUENCE: 1205
acuggagcug ggcauggaau guuuaagagc uaugcuggaa acagcauagc aaguuuaaau    60
aaggcuaguc cguuaucaac uugaaaaagu ggcaccgagu cggugc                 106

<210> SEQ ID NO 1206
<211> LENGTH: 106
<212> TYPE: RNA
<213> ORGANISM: Artificial Sequence
<220> FEATURE:
<223> OTHER INFORMATION: Synthetic

<400> SEQUENCE: 1206
cucauuacug gagcugggca guuuaagagc uaugcuggaa acagcauagc aaguuuaaau      60
aaggcuaguc cguuaucaac uugaaaaagu ggcaccgagu cggugc                   106

<210> SEQ ID NO 1207
<211> LENGTH: 106
<212> TYPE: RNA
<213> ORGANISM: Artificial Sequence
<220> FEATURE:
<223> OTHER INFORMATION: Synthetic

<400> SEQUENCE: 1207
uuguucucau uacuggagcu guuuaagagc uaugcuggaa acagcauagc aaguuuaaau      60
aaggcuaguc cguuaucaac uugaaaaagu ggcaccgagu cggugc                   106

<210> SEQ ID NO 1208
<211> LENGTH: 106
<212> TYPE: RNA
<213> ORGANISM: Artificial Sequence
<220> FEATURE:
<223> OTHER INFORMATION: Synthetic

<400> SEQUENCE: 1208
auuguucuca uuacuggagc guuuaagagc uaugcuggaa acagcauagc aaguuuaaau      60
aaggcuaguc cguuaucaac uugaaaaagu ggcaccgagu cggugc                   106

<210> SEQ ID NO 1209
<211> LENGTH: 106
<212> TYPE: RNA
<213> ORGANISM: Artificial Sequence
<220> FEATURE:
<223> OTHER INFORMATION: Synthetic

<400> SEQUENCE: 1209
ggggagauug uucucauuac guuuaagagc uaugcuggaa acagcauagc aaguuuaaau      60
aaggcuaguc cguuaucaac uugaaaaagu ggcaccgagu cggugc                   106

<210> SEQ ID NO 1210
<211> LENGTH: 106
<212> TYPE: RNA
<213> ORGANISM: Artificial Sequence
<220> FEATURE:
<223> OTHER INFORMATION: Synthetic

<400> SEQUENCE: 1210
gaggagaaaa ucuguggcug guuuaagagc uaugcuggaa acagcauagc aaguuuaaau      60
aaggcuaguc cguuaucaac uugaaaaagu ggcaccgagu cggugc                   106

<210> SEQ ID NO 1211
<211> LENGTH: 106
<212> TYPE: RNA
<213> ORGANISM: Artificial Sequence
<220> FEATURE:
<223> OTHER INFORMATION: Synthetic

<400> SEQUENCE: 1211
agaggagaaa aucuguggcu guuuaagagc uaugcuggaa acagcauagc aaguuuaaau      60
aaggcuaguc cguuaucaac uugaaaaagu ggcaccgagu cggugc                   106

<210> SEQ ID NO 1212
<211> LENGTH: 106

```
<212> TYPE: RNA
<213> ORGANISM: Artificial Sequence
<220> FEATURE:
<223> OTHER INFORMATION: Synthetic

<400> SEQUENCE: 1212
cagaggagaa aaucugnggc guuuaagagc uaugcuggaa acagcauagc aaguuuaaau      60
aaggcuaguc cguuaucaac uugaaaaagu ggcaccgagu cggugc                   106

<210> SEQ ID NO 1213
<211> LENGTH: 106
<212> TYPE: RNA
<213> ORGANISM: Artificial Sequence
<220> FEATURE:
<223> OTHER INFORMATION: Synthetic

<400> SEQUENCE: 1213
uccucagagg agaaaaucug guuuaagagc uaugcuggaa acagcauagc aaguuuaaau      60
aaggcuaguc cguuaucaac uugaaaaagu ggcaccgagu cggugc                   106

<210> SEQ ID NO 1214
<211> LENGTH: 106
<212> TYPE: RNA
<213> ORGANISM: Artificial Sequence
<220> FEATURE:
<223> OTHER INFORMATION: Synthetic

<400> SEQUENCE: 1214
ugaaguuuuu cauuccucag guuuaagagc uaugcuggaa acagcauagc aaguuuaaau      60
aaggcuaguc cguuaucaac uugaaaaagu ggcaccgagu cggugc                   106

<210> SEQ ID NO 1215
<211> LENGTH: 106
<212> TYPE: RNA
<213> ORGANISM: Artificial Sequence
<220> FEATURE:
<223> OTHER INFORMATION: Synthetic

<400> SEQUENCE: 1215
cuucaccaac gacuccaagu guuuaagagc uaugcuggaa acagcauagc aaguuuaaau      60
aaggcuaguc cguuaucaac uugaaaaagu ggcaccgagu cggugc                   106

<210> SEQ ID NO 1216
<211> LENGTH: 106
<212> TYPE: RNA
<213> ORGANISM: Artificial Sequence
<220> FEATURE:
<223> OTHER INFORMATION: Synthetic

<400> SEQUENCE: 1216
cuacuccuac uuggagucgu guuuaagagc uaugcuggaa acagcauagc aaguuuaaau      60
aaggcuaguc cguuaucaac uugaaaaagu ggcaccgagu cggugc                   106

<210> SEQ ID NO 1217
<211> LENGTH: 106
<212> TYPE: RNA
<213> ORGANISM: Artificial Sequence
<220> FEATURE:
<223> OTHER INFORMATION: Synthetic

<400> SEQUENCE: 1217
cuccaaguag gaguagauga guuuaagagc uaugcuggaa acagcauagc aaguuuaaau      60
```
aaggcuaguc cguuaucaac uugaaaaagu ggcaccgagu cgguqc        106

<210> SEQ ID NO 1218
<211> LENGTH: 106
<212> TYPE: RNA
<213> ORGANISM: Artificial Sequence
<220> FEATURE:
<223> OTHER INFORMATION: Synthetic

<400> SEQUENCE: 1218
caccaucauc uacuccuacu guuuaagagc uaugcuggaa acagcauagc aaguuuaaau        60
aaggcuaguc cguuaucaac uugaaaaagu ggcaccgagu cggugc        106

<210> SEQ ID NO 1219
<211> LENGTH: 106
<212> TYPE: RNA
<213> ORGANISM: Artificial Sequence
<220> FEATURE:
<223> OTHER INFORMATION: Synthetic

<400> SEQUENCE: 1219
ugauggugau cagaagcaga guuuaagagc uaugcuggaa acagcauagc aaguuuaaau        60
aaggcuaguc cguuaucaac uugaaaaagu ggcaccgagu cggugc        106

<210> SEQ ID NO 1220
<211> LENGTH: 106
<212> TYPE: RNA
<213> ORGANISM: Artificial Sequence
<220> FEATURE:
<223> OTHER INFORMATION: Synthetic

<400> SEQUENCE: 1220
ucagaagcag aaggauuucu guuuaagagc uaugcuggaa acagcauagc aaguuuaaau        60
aaggcuaguc cguuaucaac uugaaaaagu ggcaccgagu cggugc        106

<210> SEQ ID NO 1221
<211> LENGTH: 106
<212> TYPE: RNA
<213> ORGANISM: Artificial Sequence
<220> FEATURE:
<223> OTHER INFORMATION: Synthetic

<400> SEQUENCE: 1221
gauuucuagg augauguuca guuuaagagc uaugcuggaa acagcauagc aaguuuaaau        60
aaggcuaguc cguuaucaac uugaaaaagu ggcaccgagu cggugc        106

<210> SEQ ID NO 1222
<211> LENGTH: 106
<212> TYPE: RNA
<213> ORGANISM: Artificial Sequence
<220> FEATURE:
<223> OTHER INFORMATION: Synthetic

<400> SEQUENCE: 1222
uugcucuguc cucuuccuuc guuuaagagc uaugcuggaa acagcauagc aaguuuaaau        60
aaggcuaguc cguuaucaac uugaaaaagu ggcaccgagu cggugc        106

<210> SEQ ID NO 1223
<211> LENGTH: 106
<212> TYPE: RNA
<213> ORGANISM: Artificial Sequence
<220> FEATURE:
<223> OTHER INFORMATION: Synthetic

<400> SEQUENCE: 1223
aggacugaac cagaaggaag guuuaagagc uaugcuggaa acagcauagc aaguuuaaau    60
aaggcuaguc cguuaucaac uugaaaaagu ggcaccgagu cggugc                   106

<210> SEQ ID NO 1224
<211> LENGTH: 106
<212> TYPE: RNA
<213> ORGANISM: Artificial Sequence
<220> FEATURE:
<223> OTHER INFORMATION: Synthetic

<400> SEQUENCE: 1224
uacacaagga cugaaccaga guuuaagagc uaugcuggaa acagcauagc aaguuuaaau    60
aaggcuaguc cguuaucaac uugaaaaagu ggcaccgagu cggugc                   106

<210> SEQ ID NO 1225
<211> LENGTH: 106
<212> TYPE: RNA
<213> ORGANISM: Artificial Sequence
<220> FEATURE:
<223> OTHER INFORMATION: Synthetic

<400> SEQUENCE: 1225
uucaguccuu guguaguccu guuuaagagc uaugcuggaa acagcauagc aaguuuaaau    60
aaggcuaguc cguuaucaac uugaaaaagu ggcaccgagu cggugc                   106

<210> SEQ ID NO 1226
<211> LENGTH: 106
<212> TYPE: RNA
<213> ORGANISM: Artificial Sequence
<220> FEATURE:
<223> OTHER INFORMATION: Synthetic

<400> SEQUENCE: 1226
ucaguccuug uguaguccua guuuaagagc uaugcuggaa acagcauagc aaguuuaaau    60
aaggcuaguc cguuaucaac uugaaaaagu ggcaccgagu cggugc                   106

<210> SEQ ID NO 1227
<211> LENGTH: 106
<212> TYPE: RNA
<213> ORGANISM: Artificial Sequence
<220> FEATURE:
<223> OTHER INFORMATION: Synthetic

<400> SEQUENCE: 1227
guccuugugu aguccuaggg guuuaagagc uaugcuggaa acagcauagc aaguuuaaau    60
aaggcuaguc cguuaucaac uugaaaaagu ggcaccgagu cggugc                   106

<210> SEQ ID NO 1228
<211> LENGTH: 106
<212> TYPE: RNA
<213> ORGANISM: Artificial Sequence
<220> FEATURE:
<223> OTHER INFORMATION: Synthetic

<400> SEQUENCE: 1228
cuuguguagu ccuagggagg guuuaagagc uaugcuggaa acagcauagc aaguuuaaau    60
aaggcuaguc cguuaucaac uugaaaaagu ggcaccgagu cggugc                   106

<210> SEQ ID NO 1229

```
<211> LENGTH: 106
<212> TYPE: RNA
<213> ORGANISM: Artificial Sequence
<220> FEATURE:
<223> OTHER INFORMATION: Synthetic

<400> SEQUENCE: 1229
cuccucccua ggacuacaca guuuaagagc uaugcuggaa acagcauagc aaguuuaaau     60
aaggcuaguc cguuaucaac uugaaaaagu ggcaccgagu cggugc                  106

<210> SEQ ID NO 1230
<211> LENGTH: 106
<212> TYPE: RNA
<213> ORGANISM: Artificial Sequence
<220> FEATURE:
<223> OTHER INFORMATION: Synthetic

<400> SEQUENCE: 1230
guagacagua ccuccucccu guuuaagagc uaugcuggaa acagcauagc aaguuuaaau     60
aaggcuaguc cguuaucaac uugaaaaagu ggcaccgagu cggugc                  106

<210> SEQ ID NO 1231
<211> LENGTH: 106
<212> TYPE: RNA
<213> ORGANISM: Artificial Sequence
<220> FEATURE:
<223> OTHER INFORMATION: Synthetic

<400> SEQUENCE: 1231
uacugucuac acagagcucu guuuaagagc uaugcuggaa acagcauagc aaguuuaaau     60
aaggcuaguc cguuaucaac uugaaaaagu ggcaccgagu cggugc                  106

<210> SEQ ID NO 1232
<211> LENGTH: 106
<212> TYPE: RNA
<213> ORGANISM: Artificial Sequence
<220> FEATURE:
<223> OTHER INFORMATION: Synthetic

<400> SEQUENCE: 1232
acugucuaca cagagcucua guuuaagagc uaugcuggaa acagcauagc aaguuuaaau     60
aaggcuaguc cguuaucaac uugaaaaagu ggcaccgagu cggugc                  106

<210> SEQ ID NO 1233
<211> LENGTH: 106
<212> TYPE: RNA
<213> ORGANISM: Artificial Sequence
<220> FEATURE:
<223> OTHER INFORMATION: Synthetic

<400> SEQUENCE: 1233
ucuacacaga gcucuaggga guuuaagagc uaugcuggaa acagcauagc aaguuuaaau     60
aaggcuaguc cguuaucaac uugaaaaagu ggcaccgagu cggugc                  106

<210> SEQ ID NO 1234
<211> LENGTH: 106
<212> TYPE: RNA
<213> ORGANISM: Artificial Sequence
<220> FEATURE:
<223> OTHER INFORMATION: Synthetic

<400> SEQUENCE: 1234
cuacacagag cucuagggaa guuuaagagc uaugcuggaa acagcauagc aaguuuaaau     60
```
aaggcuaguc cguuaucaac uugaaaaagu ggcaccgagu cggugc                   106

<210> SEQ ID NO 1235
<211> LENGTH: 106
<212> TYPE: RNA
<213> ORGANISM: Artificial Sequence
<220> FEATURE:
<223> OTHER INFORMATION: Synthetic

<400> SEQUENCE: 1235
uacacagagc ucuagggaag guuuaagagc uaugcuggaa acagcauagc aaguuuaaau   60
aaggcuaguc cguuaucaac uugaaaaagu ggcaccgagu cggugc                  106

<210> SEQ ID NO 1236
<211> LENGTH: 106
<212> TYPE: RNA
<213> ORGANISM: Artificial Sequence
<220> FEATURE:
<223> OTHER INFORMATION: Synthetic

<400> SEQUENCE: 1236
ggggugugcc caguuguuaa guuuaagagc uaugcuggaa acagcauagc aaguuuaaau   60
aaggcuaguc cguuaucaac uugaaaaagu ggcaccgagu cggugc                  106

<210> SEQ ID NO 1237
<211> LENGTH: 106
<212> TYPE: RNA
<213> ORGANISM: Artificial Sequence
<220> FEATURE:
<223> OTHER INFORMATION: Synthetic

<400> SEQUENCE: 1237
gggugugccc aguuguuaau guuuaagagc uaugcuggaa acagcauagc aaguuuaaau   60
aaggcuaguc cguuaucaac uugaaaaagu ggcaccgagu cggugc                  106

<210> SEQ ID NO 1238
<211> LENGTH: 106
<212> TYPE: RNA
<213> ORGANISM: Artificial Sequence
<220> FEATURE:
<223> OTHER INFORMATION: Synthetic

<400> SEQUENCE: 1238
ugguaguccc auuaacaacu guuuaagagc uaugcuggaa acagcauagc aaguuuaaau   60
aaggcuaguc cguuaucaac uugaaaaagu ggcaccgagu cggugc                  106

<210> SEQ ID NO 1239
<211> LENGTH: 106
<212> TYPE: RNA
<213> ORGANISM: Artificial Sequence
<220> FEATURE:
<223> OTHER INFORMATION: Synthetic

<400> SEQUENCE: 1239 cugguaguccc cauuaacaac guuuaagagc uaugcuggaa acagcauagc aaguuuaaau  60 aagguaguc cguuaucaac uugaaaaagu ggcaccgagu cggugc                   106

<210> SEQ ID NO 1240
<211> LENGTH: 106
<212> TYPE: RNA
<213> ORGANISM: Artificial Sequence
<220> FEATURE:

<223> OTHER INFORMATION: Synthetic

<400> SEQUENCE: 1240
uuguuaaugg gacuaccaga guuuaagagc uaugcuggaa acagcauagc aaguuuaaau       60
aaggcuaguc cguuaucaac uugaaaaagu ggcaccgagu cggugc                    106

<210> SEQ ID NO 1241
<211> LENGTH: 106
<212> TYPE: RNA
<213> ORGANISM: Artificial Sequence
<220> FEATURE:
<223> OTHER INFORMATION: Synthetic

<400> SEQUENCE: 1241
uaccagaugg aagccagcuu guuuaagagc uaugcuggaa acagcauagc aaguuuaaau       60
aaggcuaguc cguuaucaac uugaaaaagu ggcaccgagu cggugc                    106

<210> SEQ ID NO 1242
<211> LENGTH: 106
<212> TYPE: RNA
<213> ORGANISM: Artificial Sequence
<220> FEATURE:
<223> OTHER INFORMATION: Synthetic

<400> SEQUENCE: 1242
uuccaaagcu ggcuuccauc guuuaagagc uaugcuggaa acagcauagc aaguuuaaau       60
aaggcuaguc cguuaucaac uugaaaaagu ggcaccgagu cggugc                    106

<210> SEQ ID NO 1243
<211> LENGTH: 106
<212> TYPE: RNA
<213> ORGANISM: Artificial Sequence
<220> FEATURE:
<223> OTHER INFORMATION: Synthetic

<400> SEQUENCE: 1243
uggaagccag cuuuggaagc guuuaagagc uaugcuggaa acagcauagc aaguuuaaau       60
aaggcuaguc cguuaucaac uugaaaaagu ggcaccgagu cggugc                    106

<210> SEQ ID NO 1244
<211> LENGTH: 106
<212> TYPE: RNA
<213> ORGANISM: Artificial Sequence
<220> FEATURE:
<223> OTHER INFORMATION: Synthetic

<400> SEQUENCE: 1244
acaaggccug cuuccaaagc guuuaagagc uaugcuggaa acagcauagc aaguuuaaau       60
aaggcuaguc cguuaucaac uugaaaaagu ggcaccgagu cggugc                    106

<210> SEQ ID NO 1245
<211> LENGTH: 106
<212> TYPE: RNA
<213> ORGANISM: Artificial Sequence
<220> FEATURE:
<223> OTHER INFORMATION: Synthetic

<400> SEQUENCE: 1245
gccuuguuca cguguucuaa guuuaagagc uaugcuggaa acagcauagc aaguuuaaau       60
aaggcuaguc cguuaucaac uugaaaaagu ggcaccgagu cggugc                    106

<210> SEQ ID NO 1246
<211> LENGTH: 106
<212> TYPE: RNA
<213> ORGANISM: Artificial Sequence
<220> FEATURE:
<223> OTHER INFORMATION: Synthetic

<400> SEQUENCE: 1246
ccuuguucac guguucuaau guuuaagagc uaugcuggaa acagcauagc aaguuuaaau      60
aaggcuaguc cguuaucaac uugaaaaagu ggcaccgagu cggugc                   106

<210> SEQ ID NO 1247
<211> LENGTH: 106
<212> TYPE: RNA
<213> ORGANISM: Artificial Sequence
<220> FEATURE:
<223> OTHER INFORMATION: Synthetic

<400> SEQUENCE: 1247
cccauuagaa cacgugaaca guuuaagagc uaugcuggaa acagcauagc aaguuuaaau      60
aaggcuaguc cguuaucaac uugaaaaagu ggcaccgagu cggugc                   106

<210> SEQ ID NO 1248
<211> LENGTH: 106
<212> TYPE: RNA
<213> ORGANISM: Artificial Sequence
<220> FEATURE:
<223> OTHER INFORMATION: Synthetic

<400> SEQUENCE: 1248
uuggcaucac uucauauuug guuuaagagc uaugcuggaa acagcauagc aaguuuaaau      60
aaggcuaguc cguuaucaac uugaaaaagu ggcaccgagu cggugc                   106

<210> SEQ ID NO 1249
<211> LENGTH: 106
<212> TYPE: RNA
<213> ORGANISM: Artificial Sequence
<220> FEATURE:
<223> OTHER INFORMATION: Synthetic

<400> SEQUENCE: 1249
cuugugcucu uggcaucacu guuuaagagc uaugcuggaa acagcauagc aaguuuaaau      60
aaggcuaguc cguuaucaac uugaaaaagu ggcaccgagu cggugc                   106

<210> SEQ ID NO 1250
<211> LENGTH: 106
<212> TYPE: RNA
<213> ORGANISM: Artificial Sequence
<220> FEATURE:
<223> OTHER INFORMATION: Synthetic

<400> SEQUENCE: 1250
agcacacucu cuugugcucu guuuaagagc uaugcuggaa acagcauagc aaguuuaaau      60
aaggcuaguc cguuaucaac uugaaaaagu ggcaccgagu cggugc                   106

<210> SEQ ID NO 1251
<211> LENGTH: 106
<212> TYPE: RNA
<213> ORGANISM: Artificial Sequence
<220> FEATURE:
<223> OTHER INFORMATION: Synthetic

<400> SEQUENCE: 1251
gcacaagaga gugugcucuc guuuaagagc uaugcuggaa acagcauagc aaguuuaaau    60
aaggcuaguc cguuaucaac uugaaaaagu ggcaccgagu cggugc                  106

<210> SEQ ID NO 1252
<211> LENGTH: 106
<212> TYPE: RNA
<213> ORGANISM: Artificial Sequence
<220> FEATURE:
<223> OTHER INFORMATION: Synthetic

<400> SEQUENCE: 1252
gcuuaaucuc acacauagaa guuuaagagc uaugcuggaa acagcauagc aaguuuaaau    60
aaggcuaguc cguuaucaac uugaaaaagu ggcaccgagu cggugc                  106

<210> SEQ ID NO 1253
<211> LENGTH: 106
<212> TYPE: RNA
<213> ORGANISM: Artificial Sequence
<220> FEATURE:
<223> OTHER INFORMATION: Synthetic

<400> SEQUENCE: 1253
cuuaaucuca cacauagaaa guuuaagagc uaugcuggaa acagcauagc aaguuuaaau    60
aaggcuaguc cguuaucaac uugaaaaagu ggcaccgagu cggugc                  106

<210> SEQ ID NO 1254
<211> LENGTH: 106
<212> TYPE: RNA
<213> ORGANISM: Artificial Sequence
<220> FEATURE:
<223> OTHER INFORMATION: Synthetic

<400> SEQUENCE: 1254
uuaaucucac acauagaaag guuuaagagc uaugcuggaa acagcauagc aaguuuaaau    60
aaggcuaguc cguuaucaac uugaaaaagu ggcaccgagu cggugc                  106

<210> SEQ ID NO 1255
<211> LENGTH: 106
<212> TYPE: RNA
<213> ORGANISM: Artificial Sequence
<220> FEATURE:
<223> OTHER INFORMATION: Synthetic

<400> SEQUENCE: 1255
aggagugcug guuaucaac guuuaagagc uaugcuggaa acagcauagc aaguuuaaau    60
aaggcuaguc cguuaucaac uugaaaaagu ggcaccgagu cggugc                  106

<210> SEQ ID NO 1256
<211> LENGTH: 106
<212> TYPE: RNA
<213> ORGANISM: Artificial Sequence
<220> FEATURE:
<223> OTHER INFORMATION: Synthetic

<400> SEQUENCE: 1256
uucuuugaca gcaggagugc guuuaagagc uaugcuggaa acagcauagc aaguuuaaau    60
aaggcuaguc cguuaucaac uugaaaaagu ggcaccgagu cggugc                  106

<210> SEQ ID NO 1257
<211> LENGTH: 106
<212> TYPE: RNA
<213> ORGANISM: Artificial Sequence -continued
<220> FEATURE:
<223> OTHER INFORMATION: Synthetic

<400> SEQUENCE: 1257
acucugguuu cuuugacagc guuuaagagc uaugcuggaa acagcauagc aaguuuaaau    60
aaggcuaguc cguuaucaac uugaaaaagu ggcaccgagu cggugc                  106

<210> SEQ ID NO 1258
<211> LENGTH: 106
<212> TYPE: RNA
<213> ORGANISM: Artificial Sequence
<220> FEATURE:
<223> OTHER INFORMATION: Synthetic

<400> SEQUENCE: 1258
accagaguug agaaaacccc guuuaagagc uaugcuggaa acagcauagc aaguuuaaau    60
aaggcuaguc cguuaucaac uugaaaaagu ggcaccgagu cggugc                  106

<210> SEQ ID NO 1259
<211> LENGTH: 106
<212> TYPE: RNA
<213> ORGANISM: Artificial Sequence
<220> FEATURE:
<223> OTHER INFORMATION: Synthetic

<400> SEQUENCE: 1259
uccaggggug uucucaacuc guuuaagagc uaugcuggaa acagcauagc aaguuuaaau    60
aaggcuaguc cguuaucaac uugaaaaagu ggcaccgagu cggugc                  106

<210> SEQ ID NO 1260
<211> LENGTH: 106
<212> TYPE: RNA
<213> ORGANISM: Artificial Sequence
<220> FEATURE:
<223> OTHER INFORMATION: Synthetic

<400> SEQUENCE: 1260
caguuauuaa augaauccag guuuaagagc uaugcuggaa acagcauagc aaguuuaaau    60
aaggcuaguc cguuaucaac uugaaaaagu ggcaccgagu cggugc                  106

<210> SEQ ID NO 1261
<211> LENGTH: 106
<212> TYPE: RNA
<213> ORGANISM: Artificial Sequence
<220> FEATURE:
<223> OTHER INFORMATION: Synthetic

<400> SEQUENCE: 1261
gcaguuauua aaugaaucca guuuaagagc uaugcuggaa acagcauagc aaguuuaaau    60
aaggcuaguc cguuaucaac uugaaaaagu ggcaccgagu cggugc                  106

<210> SEQ ID NO 1262
<211> LENGTH: 106
<212> TYPE: RNA
<213> ORGANISM: Artificial Sequence
<220> FEATURE:
<223> OTHER INFORMATION: Synthetic

<400> SEQUENCE: 1262
ggcaguuauu aaaugaaucc guuuaagagc uaugcuggaa acagcauagc aaguuuaaau    60
aaggcuaguc cguuaucaac uugaaaaagu ggcaccgagu cggugc                  106

<210> SEQ ID NO 1263
<211> LENGTH: 106
<212> TYPE: RNA
<213> ORGANISM: Artificial Sequence
<220> FEATURE:
<223> OTHER INFORMATION: Synthetic

<400> SEQUENCE: 1263
uggaugguaa cagcuacauc guuuaagagc uaugcuggaa acagcauagc aaguuuaaau    60
aaggcuaguc cguuaucaac uugaaaaagu ggcaccgagu cggugc                  106

<210> SEQ ID NO 1264
<211> LENGTH: 106
<212> TYPE: RNA
<213> ORGANISM: Artificial Sequence
<220> FEATURE:
<223> OTHER INFORMATION: Synthetic

<400> SEQUENCE: 1264
gcuguuacca uccacauccu guuuaagagc uaugcuggaa acagcauagc aaguuuaaau    60
aaggcuaguc cguuaucaac uugaaaaagu ggcaccgagu cggugc                  106

<210> SEQ ID NO 1265
<211> LENGTH: 106
<212> TYPE: RNA
<213> ORGANISM: Artificial Sequence
<220> FEATURE:
<223> OTHER INFORMATION: Synthetic

<400> SEQUENCE: 1265
ucaagaacca aggaugugga guuuaagagc uaugcuggaa acagcauagc aaguuuaaau    60
aaggcuaguc cguuaucaac uugaaaaagu ggcaccgagu cggugc                  106

<210> SEQ ID NO 1266
<211> LENGTH: 106
<212> TYPE: RNA
<213> ORGANISM: Artificial Sequence
<220> FEATURE:
<223> OTHER INFORMATION: Synthetic

<400> SEQUENCE: 1266
uccuucaaga accaaggaug guuuaagagc uaugcuggaa acagcauagc aaguuuaaau    60
aaggcuaguc cguuaucaac uugaaaaagu ggcaccgagu cggugc                  106

<210> SEQ ID NO 1267
<211> LENGTH: 106
<212> TYPE: RNA
<213> ORGANISM: Artificial Sequence
<220> FEATURE:
<223> OTHER INFORMATION: Synthetic

<400> SEQUENCE: 1267
ugaguguccu ucaagaacca guuuaagagc uaugcuggaa acagcauagc aaguuuaaau    60
aaggcuaguc cguuaucaac uugaaaaagu ggcaccgagu cggugc                  106

<210> SEQ ID NO 1268
<211> LENGTH: 106
<212> TYPE: RNA
<213> ORGANISM: Artificial Sequence
<220> FEATURE:
<223> OTHER INFORMATION: Synthetic

<400> SEQUENCE: 1268
uuuuauuuua uaacuacaag guuuaagagc uaugcuggaa acagcauagc aaguuuaaau    60
aaggcuaguc cguuaucaac uugaaaaagu ggcaccgagu cggugc                  106

<210> SEQ ID NO 1269
<211> LENGTH: 106
<212> TYPE: RNA
<213> ORGANISM: Artificial Sequence
<220> FEATURE:
<223> OTHER INFORMATION: Synthetic

<400> SEQUENCE: 1269
uuguuuuuaa uaaaaacaag guuuaagagc uaugcuggaa acagcauagc aaguuuaaau    60
aaggcuaguc cguuaucaac uugaaaaagu ggcaccgagu cggugc                  106

<210> SEQ ID NO 1270
<211> LENGTH: 106
<212> TYPE: RNA
<213> ORGANISM: Artificial Sequence
<220> FEATURE:
<223> OTHER INFORMATION: Synthetic

<400> SEQUENCE: 1270
uauuauagaa ugcuuuugca guuuaagagc uaugcuggaa acagcauagc aaguuuaaau    60
aaggcuaguc cguuaucaac uugaaaaagu ggcaccgagu cggugc                  106

<210> SEQ ID NO 1271
<211> LENGTH: 106
<212> TYPE: RNA
<213> ORGANISM: Artificial Sequence
<220> FEATURE:
<223> OTHER INFORMATION: Synthetic

<400> SEQUENCE: 1271
caagauuagu cuugauguag guuuaagagc uaugcuggaa acagcauagc aaguuuaaau    60
aaggcuaguc cguuaucaac uugaaaaagu ggcaccgagu cggugc                  106

<210> SEQ ID NO 1272
<211> LENGTH: 106
<212> TYPE: RNA
<213> ORGANISM: Artificial Sequence
<220> FEATURE:
<223> OTHER INFORMATION: Synthetic

<400> SEQUENCE: 1272
aagauuaguc uugauguagu guuuaagagc uaugcuggaa acagcauagc aaguuuaaau    60
aaggcuaguc cguuaucaac uugaaaaagu ggcaccgagu cggugc                  106

<210> SEQ ID NO 1273
<211> LENGTH: 106
<212> TYPE: RNA
<213> ORGANISM: Artificial Sequence
<220> FEATURE:
<223> OTHER INFORMATION: Synthetic

<400> SEQUENCE: 1273
agucuugaug uagugggagu guuuaagagc uaugcuggaa acagcauagc aaguuuaaau    60
aaggcuaguc cguuaucaac uugaaaaagu ggcaccgagu cggugc                  106

<210> SEQ ID NO 1274
<211> LENGTH: 106
<212> TYPE: RNA

<213> ORGANISM: Artificial Sequence
<220> FEATURE:
<223> OTHER INFORMATION: Synthetic

<400> SEQUENCE: 1274
uuuuucuauu aaaaaaaaaa guuuaagagc uaugcuggaa acagcauagc aaguuuaaau    60
aaggcuaguc cguuaucaac uugaaaaagu ggcaccgagu cggugc                   106

<210> SEQ ID NO 1275
<211> LENGTH: 106
<212> TYPE: RNA
<213> ORGANISM: Artificial Sequence
<220> FEATURE:
<223> OTHER INFORMATION: Synthetic

<400> SEQUENCE: 1275
ucuauuaaaa aaaaaaggc guuuaagagc uaugcuggaa acagcauagc aaguuuaaau    60
aaggcuaguc cguuaucaac uugaaaaagu ggcaccgagu cggugc                   106

<210> SEQ ID NO 1276
<211> LENGTH: 106
<212> TYPE: RNA
<213> ORGANISM: Artificial Sequence
<220> FEATURE:
<223> OTHER INFORMATION: Synthetic

<400> SEQUENCE: 1276
cuauuaaaaa aaaaaaggcu guuuaagagc uaugcuggaa acagcauagc aaguuuaaau    60
aaggcuaguc cguuaucaac uugaaaaagu ggcaccgagu cggugc                   106

<210> SEQ ID NO 1277
<211> LENGTH: 106
<212> TYPE: RNA
<213> ORGANISM: Artificial Sequence
<220> FEATURE:
<223> OTHER INFORMATION: Synthetic

<400> SEQUENCE: 1277
aaaaaaaaaa aggcugggca guuuaagagc uaugcuggaa acagcauagc aaguuuaaau    60
aaggcuaguc cguuaucaac uugaaaaagu ggcaccgagu cggugc                   106

<210> SEQ ID NO 1278
<211> LENGTH: 106
<212> TYPE: RNA
<213> ORGANISM: Artificial Sequence
<220> FEATURE:
<223> OTHER INFORMATION: Synthetic

<400> SEQUENCE: 1278
aaaaaaaagg cugggcacgg guuuaagagc uaugcuggaa acagcauagc aaguuuaaau    60
aaggcuaguc cguuaucaac uugaaaaagu ggcaccgagu cggugc                   106

<210> SEQ ID NO 1279
<211> LENGTH: 106
<212> TYPE: RNA
<213> ORGANISM: Artificial Sequence
<220> FEATURE:
<223> OTHER INFORMATION: Synthetic

<400> SEQUENCE: 1279
cacccguaau cccagcacuu guuuaagagc uaugcuggaa acagcauagc aaguuuaaau    60
aaggcuaguc cguuaucaac uugaaaaagu ggcaccgagu cggugc                   106

<210> SEQ ID NO 1280
<211> LENGTH: 106
<212> TYPE: RNA
<213> ORGANISM: Artificial Sequence
<220> FEATURE:
<223> OTHER INFORMATION: Synthetic

<400> SEQUENCE: 1280
acccguaauc ccagcacuuu guuuaagagc uaugcuggaa acagcauagc aaguuuaaau    60
aaggcuaguc cguuaucaac uugaaaaagu ggcaccgagu cggugc                  106

<210> SEQ ID NO 1281
<211> LENGTH: 106
<212> TYPE: RNA
<213> ORGANISM: Artificial Sequence
<220> FEATURE:
<223> OTHER INFORMATION: Synthetic

<400> SEQUENCE: 1281
cguaauccca gcacuuuggg guuuaagagc uaugcuggaa acagcauagc aaguuuaaau    60
aaggcuaguc cguuaucaac uugaaaaagu ggcaccgagu cggugc                  106

<210> SEQ ID NO 1282
<211> LENGTH: 106
<212> TYPE: RNA
<213> ORGANISM: Artificial Sequence
<220> FEATURE:
<223> OTHER INFORMATION: Synthetic

<400> SEQUENCE: 1282
ucccaaagug cugggauuac guuuaagagc uaugcuggaa acagcauagc aaguuuaaau    60
aaggcuaguc cguuaucaac uugaaaaagu ggcaccgagu cggugc                  106

<210> SEQ ID NO 1283
<211> LENGTH: 106
<212> TYPE: RNA
<213> ORGANISM: Artificial Sequence
<220> FEATURE:
<223> OTHER INFORMATION: Synthetic

<400> SEQUENCE: 1283
cucccaaagu gcugggauua guuuaagagc uaugcuggaa acagcauagc aaguuuaaau    60
aaggcuaguc cguuaucaac uugaaaaagu ggcaccgagu cggugc                  106

<210> SEQ ID NO 1284
<211> LENGTH: 106
<212> TYPE: RNA
<213> ORGANISM: Artificial Sequence
<220> FEATURE:
<223> OTHER INFORMATION: Synthetic

<400> SEQUENCE: 1284
cccagcacuu ugggaggccg guuuaagagc uaugcuggaa acagcauagc aaguuuaaau    60
aaggcuaguc cguuaucaac uugaaaaagu ggcaccgagu cggugc                  106

<210> SEQ ID NO 1285
<211> LENGTH: 106
<212> TYPE: RNA
<213> ORGANISM: Artificial Sequence
<220> FEATURE:
<223> OTHER INFORMATION: Synthetic

```
<400> SEQUENCE: 1285
ccucggccuc caaagugcu guuuaagagc uaugcuggaa acagcauagc aaguuuaaau      60
aaggcuaguc cguuaucaac uugaaaaagu ggcaccgagu cggugc                  106

<210> SEQ ID NO 1286
<211> LENGTH: 106
<212> TYPE: RNA
<213> ORGANISM: Artificial Sequence
<220> FEATURE:
<223> OTHER INFORMATION: Synthetic

<400> SEQUENCE: 1286
gcacuuuggg aggccgaggc guuuaagagc uaugcuggaa acagcauagc aaguuuaaau      60
aaggcuaguc cguuaucaac uugaaaaagu ggcaccgagu cggugc                  106

<210> SEQ ID NO 1287
<211> LENGTH: 106
<212> TYPE: RNA
<213> ORGANISM: Artificial Sequence
<220> FEATURE:
<223> OTHER INFORMATION: Synthetic

<400> SEQUENCE: 1287
cuuugggagg ccgaggcagg guuuaagagc uaugcuggaa acagcauagc aaguuuaaau      60
aaggcuaguc cguuaucaac uugaaaaagu ggcaccgagu cggugc                  106

<210> SEQ ID NO 1288
<211> LENGTH: 106
<212> TYPE: RNA
<213> ORGANISM: Artificial Sequence
<220> FEATURE:
<223> OTHER INFORMATION: Synthetic

<400> SEQUENCE: 1288
gccgaggcag guggaucacg guuuaagagc uaugcuggaa acagcauagc aaguuuaaau      60
aaggcuaguc cguuaucaac uugaaaaagu ggcaccgagu cggugc                  106

<210> SEQ ID NO 1289
<211> LENGTH: 106
<212> TYPE: RNA
<213> ORGANISM: Artificial Sequence
<220> FEATURE:
<223> OTHER INFORMATION: Synthetic

<400> SEQUENCE: 1289
accucgugau ccaccugccu guuuaagagc uaugcuggaa acagcauagc aaguuuaaau      60
aaggcuaguc cguuaucaac uugaaaaagu ggcaccgagu cggugc                  106

<210> SEQ ID NO 1290
<211> LENGTH: 106
<212> TYPE: RNA
<213> ORGANISM: Artificial Sequence
<220> FEATURE:
<223> OTHER INFORMATION: Synthetic

<400> SEQUENCE: 1290
ggcaggugga ucacgagguc guuuaagagc uaugcuggaa acagcauagc aaguuuaaau      60
aaggcuaguc cguuaucaac uugaaaaagu ggcaccgagu cggugc                  106

<210> SEQ ID NO 1291
<211> LENGTH: 106
```

<212> TYPE: RNA
<213> ORGANISM: Artificial Sequence
<220> FEATURE:
<223> OTHER INFORMATION: Synthetic

<400> SEQUENCE: 1291
ucaggagauc gagaccaucu guuuaagagc uaugcuggaa acagcauagc aaguuuaaau    60
aaggcuaguc cguuaucaac uugaaaaagu ggcaccgagu cggugc    106

<210> SEQ ID NO 1292
<211> LENGTH: 106
<212> TYPE: RNA
<213> ORGANISM: Artificial Sequence
<220> FEATURE:
<223> OTHER INFORMATION: Synthetic

<400> SEQUENCE: 1292
cgagaccauc uuggcuaaca guuuaagagc uaugcuggaa acagcauagc aaguuuaaau    60
aaggcuaguc cguuaucaac uugaaaaagu ggcaccgagu cggugc    106

<210> SEQ ID NO 1293
<211> LENGTH: 106
<212> TYPE: RNA
<213> ORGANISM: Artificial Sequence
<220> FEATURE:
<223> OTHER INFORMATION: Synthetic

<400> SEQUENCE: 1293
uuucaccaug uuagccaaga guuuaagagc uaugcuggaa acagcauagc aaguuuaaau    60
aaggcuaguc cguuaucaac uugaaaaagu ggcaccgagu cggugc    106

<210> SEQ ID NO 1294
<211> LENGTH: 106
<212> TYPE: RNA
<213> ORGANISM: Artificial Sequence
<220> FEATURE:
<223> OTHER INFORMATION: Synthetic

<400> SEQUENCE: 1294
uuguauuuuu uguagagacg guuuaagagc uaugcuggaa acagcauagc aaguuuaaau    60
aaggcuaguc cguuaucaac uugaaaaagu ggcaccgagu cggugc    106

<210> SEQ ID NO 1295
<211> LENGTH: 106
<212> TYPE: RNA
<213> ORGANISM: Artificial Sequence
<220> FEATURE:
<223> OTHER INFORMATION: Synthetic

<400> SEQUENCE: 1295
uuuguauuuu uuguagagac guuuaagagc uaugcuggaa acagcauagc aaguuuaaau    60
aaggcuaguc cguuaucaac uugaaaaagu ggcaccgagu cggugc    106

<210> SEQ ID NO 1296
<211> LENGTH: 106
<212> TYPE: RNA
<213> ORGANISM: Artificial Sequence
<220> FEATURE:
<223> OTHER INFORMATION: Synthetic

<400> SEQUENCE: 1296
uuuuguauuu uuuguagaga guuuaagagc uaugcuggaa acagcauagc aaguuuaaau    60
aaggcuaguc cguuaucaac uugaaaaagu ggcaccgagu cgguqc    106

<210> SEQ ID NO 1297
<211> LENGTH: 106
<212> TYPE: RNA
<213> ORGANISM: Artificial Sequence
<220> FEATURE:
<223> OTHER INFORMATION: Synthetic

<400> SEQUENCE: 1297
aaaaaauaca aaaauuagc guuuaagagc uaugcuggaa acagcauagc aaguuuaaau    60
aaggcuaguc cguuaucaac uugaaaaagu ggcaccgagu cgguqc    106

<210> SEQ ID NO 1298
<211> LENGTH: 106
<212> TYPE: RNA
<213> ORGANISM: Artificial Sequence
<220> FEATURE:
<223> OTHER INFORMATION: Synthetic

<400> SEQUENCE: 1298
aaaaauacaa aaauuagcc guuuaagagc uaugcuggaa acagcauagc aaguuuaaau    60
aaggcuaguc cguuaucaac uugaaaaagu ggcaccgagu cgguqc    106

<210> SEQ ID NO 1299
<211> LENGTH: 106
<212> TYPE: RNA
<213> ORGANISM: Artificial Sequence
<220> FEATURE:
<223> OTHER INFORMATION: Synthetic

<400> SEQUENCE: 1299
uacaaaaaau uagccgggug guuuaagagc uaugcuggaa acagcauagc aaguuuaaau    60
aaggcuaguc cguuaucaac uugaaaaagu ggcaccgagu cgguqc    106

<210> SEQ ID NO 1300
<211> LENGTH: 106
<212> TYPE: RNA
<213> ORGANISM: Artificial Sequence
<220> FEATURE:
<223> OTHER INFORMATION: Synthetic

<400> SEQUENCE: 1300 aaaaauuag ccgggugugg guuuaagagc uaugcuggaa acagcauagc aaguuuaaau    60
aaggcuaguc cguuaucaac uugaaaaagu ggcaccgagu cgguqc    106

<210> SEQ ID NO 1301
<211> LENGTH: 106
<212> TYPE: RNA
<213> ORGANISM: Artificial Sequence
<220> FEATURE:
<223> OTHER INFORMATION: Synthetic

<400> SEQUENCE: 1301
aaauuagccg ggguggugg guuuaagagc uaugcuggaa acagcauagc aaguuuaaau    60
aaggcuaguc cguuaucaac uugaaaaagu ggcaccgagu cgguqc    106

<210> SEQ ID NO 1302
<211> LENGTH: 106
<212> TYPE: RNA
<213> ORGANISM: Artificial Sequence
<220> FEATURE:
<223> OTHER INFORMATION: Synthetic

<400> SEQUENCE: 1302
aauuagccgg gugguggugc guuuaagagc uaugcuggaa acagcauagc aaguuuaaau    60
aaggcuaguc cguuaucaac uugaaaaagu ggcaccgagu cggugc                  106

<210> SEQ ID NO 1303
<211> LENGTH: 106
<212> TYPE: RNA
<213> ORGANISM: Artificial Sequence
<220> FEATURE:
<223> OTHER INFORMATION: Synthetic

<400> SEQUENCE: 1303
caggcgcccg ccaccacacc guuuaagagc uaugcuggaa acagcauagc aaguuuaaau    60
aaggcuaguc cguuaucaac uugaaaaagu ggcaccgagu cggugc                  106

<210> SEQ ID NO 1304
<211> LENGTH: 106
<212> TYPE: RNA
<213> ORGANISM: Artificial Sequence
<220> FEATURE:
<223> OTHER INFORMATION: Synthetic

<400> SEQUENCE: 1304
gccuguaguc ccagcuacuc guuuaagagc uaugcuggaa acagcauagc aaguuuaaau    60
aaggcuaguc cguuaucaac uugaaaaagu ggcaccgagu cggugc                  106

<210> SEQ ID NO 1305
<211> LENGTH: 106
<212> TYPE: RNA
<213> ORGANISM: Artificial Sequence
<220> FEATURE:
<223> OTHER INFORMATION: Synthetic

<400> SEQUENCE: 1305
uguaguccca gcuacucagg guuuaagagc uaugcuggaa acagcauagc aaguuuaaau    60
aaggcuaguc cguuaucaac uugaaaaagu ggcaccgagu cggugc                  106

<210> SEQ ID NO 1306
<211> LENGTH: 106
<212> TYPE: RNA
<213> ORGANISM: Artificial Sequence
<220> FEATURE:
<223> OTHER INFORMATION: Synthetic

<400> SEQUENCE: 1306
uccugaguag cugggacuac guuuaagagc uaugcuggaa acagcauagc aaguuuaaau    60
aaggcuaguc cguuaucaac uugaaaaagu ggcaccgagu cggugc                  106

<210> SEQ ID NO 1307
<211> LENGTH: 106
<212> TYPE: RNA
<213> ORGANISM: Artificial Sequence
<220> FEATURE:
<223> OTHER INFORMATION: Synthetic

<400> SEQUENCE: 1307
cccagcuacu caggaggcug guuuaagagc uaugcuggaa acagcauagc aaguuuaaau    60
aaggcuaguc cguuaucaac uugaaaaagu ggcaccgagu cggugc                  106

<210> SEQ ID NO 1308

```
<211> LENGTH: 106
<212> TYPE: RNA
<213> ORGANISM: Artificial Sequence
<220> FEATURE:
<223> OTHER INFORMATION: Synthetic

<400> SEQUENCE: 1308
ccucagccuc cugaguagcu guuuaagagc uaugcuggaa acagcauagc aaguuuaaau      60
aaggcuaguc cguuaucaac uugaaaaagu ggcaccgagu cggugc                   106

<210> SEQ ID NO 1309
<211> LENGTH: 106
<212> TYPE: RNA
<213> ORGANISM: Artificial Sequence
<220> FEATURE:
<223> OTHER INFORMATION: Synthetic

<400> SEQUENCE: 1309
gccucagccu ccugaguagc guuuaagagc uaugcuggaa acagcauagc aaguuuaaau      60
aaggcuaguc cguuaucaac uugaaaaagu ggcaccgagu cggugc                   106

<210> SEQ ID NO 1310
<211> LENGTH: 106
<212> TYPE: RNA
<213> ORGANISM: Artificial Sequence
<220> FEATURE:
<223> OTHER INFORMATION: Synthetic

<400> SEQUENCE: 1310
aggaggcuga ggcaggagaa guuuaagagc uaugcuggaa acagcauagc aaguuuaaau      60
aaggcuaguc cguuaucaac uugaaaaagu ggcaccgagu cggugc                   106

<210> SEQ ID NO 1311
<211> LENGTH: 106
<212> TYPE: RNA
<213> ORGANISM: Artificial Sequence
<220> FEATURE:
<223> OTHER INFORMATION: Synthetic

<400> SEQUENCE: 1311
gcaggagaau ggcgugaacc guuuaagagc uaugcuggaa acagcauagc aaguuuaaau      60
aaggcuaguc cguuaucaac uugaaaaagu ggcaccgagu cggugc                   106

<210> SEQ ID NO 1312
<211> LENGTH: 106
<212> TYPE: RNA
<213> ORGANISM: Artificial Sequence
<220> FEATURE:
<223> OTHER INFORMATION: Synthetic

<400> SEQUENCE: 1312
caggagaaug gcgugaaccc guuuaagagc uaugcuggaa acagcauagc aaguuuaaau      60
aaggcuaguc cguuaucaac uugaaaaagu ggcaccgagu cggugc                   106

<210> SEQ ID NO 1313
<211> LENGTH: 106
<212> TYPE: RNA
<213> ORGANISM: Artificial Sequence
<220> FEATURE:
<223> OTHER INFORMATION: Synthetic

<400> SEQUENCE: 1313
gagaauggcg ugaacccggg guuuaagagc uaugcuggaa acagcauagc aaguuuaaau      60
```
aaggcuaguc cguuaucaac uugaaaaagu ggcaccgagu cgguge                    106

<210> SEQ ID NO 1314
<211> LENGTH: 106
<212> TYPE: RNA
<213> ORGANISM: Artificial Sequence
<220> FEATURE:
<223> OTHER INFORMATION: Synthetic

<400> SEQUENCE: 1314
aauggcguga acccgggagg guuuaagagc uaugcuggaa acagcauagc aaguuuaaau     60
aaggcuaguc cguuaucaac uugaaaaagu ggcaccgagu cgguge                    106

<210> SEQ ID NO 1315
<211> LENGTH: 106
<212> TYPE: RNA
<213> ORGANISM: Artificial Sequence
<220> FEATURE:
<223> OTHER INFORMATION: Synthetic

<400> SEQUENCE: 1315
cacugcaagc uccaccuccc guuuaagagc uaugcuggaa acagcauagc aaguuuaaau     60
aaggcuaguc cguuaucaac uugaaaaagu ggcaccgagu cgguge                    106

<210> SEQ ID NO 1316
<211> LENGTH: 106
<212> TYPE: RNA
<213> ORGANISM: Artificial Sequence
<220> FEATURE:
<223> OTHER INFORMATION: Synthetic

<400> SEQUENCE: 1316
ucacugcaag cuccaccucc guuuaagagc uaugcuggaa acagcauagc aaguuuaaau     60
aaggcuaguc cguuaucaac uugaaaaagu ggcaccgagu cgguge                    106

<210> SEQ ID NO 1317
<211> LENGTH: 106
<212> TYPE: RNA
<213> ORGANISM: Artificial Sequence
<220> FEATURE:
<223> OTHER INFORMATION: Synthetic

<400> SEQUENCE: 1317
cauaccacug cacuccagcc guuuaagagc uaugcuggaa acagcauagc aaguuuaaau     60
aaggcuaguc cguuaucaac uugaaaaagu ggcaccgagu cgguge                    106

<210> SEQ ID NO 1318
<211> LENGTH: 106
<212> TYPE: RNA
<213> ORGANISM: Artificial Sequence
<220> FEATURE:
<223> OTHER INFORMATION: Synthetic

<400> SEQUENCE: 1318
auaccacugc acuccagccu guuuaagagc uaugcuggaa acagcauagc aaguuuaaau     60
aaggcuaguc cguuaucaac uugaaaaagu ggcaccgagu cgguge                    106

<210> SEQ ID NO 1319
<211> LENGTH: 106
<212> TYPE: RNA
<213> ORGANISM: Artificial Sequence
<220> FEATURE:

<223> OTHER INFORMATION: Synthetic

<400> SEQUENCE: 1319
ucgcccaggc uggagugcag guuuaagagc uaugcuggaa acagcauagc aaguuuaaau    60
aaggcuaguc cguuaucaac uugaaaaagu ggcaccgagu cggugc    106

<210> SEQ ID NO 1320
<211> LENGTH: 106
<212> TYPE: RNA
<213> ORGANISM: Artificial Sequence
<220> FEATURE:
<223> OTHER INFORMATION: Synthetic

<400> SEQUENCE: 1320
ucucacucuu ucgcccaggc guuuaagagc uaugcuggaa acagcauagc aaguuuaaau    60
aaggcuaguc cguuaucaac uugaaaaagu ggcaccgagu cggugc    106

<210> SEQ ID NO 1321
<211> LENGTH: 106
<212> TYPE: RNA
<213> ORGANISM: Artificial Sequence
<220> FEATURE:
<223> OTHER INFORMATION: Synthetic

<400> SEQUENCE: 1321
ggagucucac ucuuucgccc guuuaagagc uaugcuggaa acagcauagc aaguuuaaau    60
aaggcuaguc cguuaucaac uugaaaaagu ggcaccgagu cggugc    106

<210> SEQ ID NO 1322
<211> LENGTH: 106
<212> TYPE: RNA
<213> ORGANISM: Artificial Sequence
<220> FEATURE:
<223> OTHER INFORMATION: Synthetic

<400> SEQUENCE: 1322
uguuuuuugu uuuuugaga guuuaagagc uaugcuggaa acagcauagc aaguuuaaau    60
aaggcuaguc cguuaucaac uugaaaaagu ggcaccgagu cggugc    106

<210> SEQ ID NO 1323
<211> LENGTH: 106
<212> TYPE: RNA
<213> ORGANISM: Artificial Sequence
<220> FEATURE:
<223> OTHER INFORMATION: Synthetic

<400> SEQUENCE: 1323
aggaagaaag aaagguuuuu guuuaagagc uaugcuggaa acagcauagc aaguuuaaau    60
aaggcuaguc cguuaucaac uugaaaaagu ggcaccgagu cggugc    106

<210> SEQ ID NO 1324
<211> LENGTH: 106
<212> TYPE: RNA
<213> ORGANISM: Artificial Sequence
<220> FEATURE:
<223> OTHER INFORMATION: Synthetic

<400> SEQUENCE: 1324
agaagaaaag gaagaaagaa guuuaagagc uaugcuggaa acagcauagc aaguuuaaau    60
aaggcuaguc cguuaucaac uugaaaaagu ggcaccgagu cggugc    106

<210> SEQ ID NO 1325
<211> LENGTH: 106
<212> TYPE: RNA
<213> ORGANISM: Artificial Sequence
<220> FEATURE:
<223> OTHER INFORMATION: Synthetic

<400> SEQUENCE: 1325
cuuucuuccu uuucuucucu guuuaagagc uaugcuggaa acagcauagc aaguuuaaau    60
aaggcuaguc cguuaucaac uugaaaaagu ggcaccgagu cggugc                 106

<210> SEQ ID NO 1326
<211> LENGTH: 106
<212> TYPE: RNA
<213> ORGANISM: Artificial Sequence
<220> FEATURE:
<223> OTHER INFORMATION: Synthetic

<400> SEQUENCE: 1326
uuucuuccuu uucuucucuu guuuaagagc uaugcuggaa acagcauagc aaguuuaaau    60
aaggcuaguc cguuaucaac uugaaaaagu ggcaccgagu cggugc                 106

<210> SEQ ID NO 1327
<211> LENGTH: 106
<212> TYPE: RNA
<213> ORGANISM: Artificial Sequence
<220> FEATURE:
<223> OTHER INFORMATION: Synthetic

<400> SEQUENCE: 1327
aauggaccca agagaagaaa guuuaagagc uaugcuggaa acagcauagc aaguuuaaau    60
aaggcuaguc cguuaucaac uugaaaaagu ggcaccgagu cggugc                 106

<210> SEQ ID NO 1328
<211> LENGTH: 106
<212> TYPE: RNA
<213> ORGANISM: Artificial Sequence
<220> FEATURE:
<223> OTHER INFORMATION: Synthetic

<400> SEQUENCE: 1328
ggcuauuaca uaagaaacaa guuuaagagc uaugcuggaa acagcauagc aaguuuaaau    60
aaggcuaguc cguuaucaac uugaaaaagu ggcaccgagu cggugc                 106

<210> SEQ ID NO 1329
<211> LENGTH: 106
<212> TYPE: RNA
<213> ORGANISM: Artificial Sequence
<220> FEATURE:
<223> OTHER INFORMATION: Synthetic

<400> SEQUENCE: 1329
cacaggaaaa ggaacuguac guuuaagagc uaugcuggaa acagcauagc aaguuuaaau    60
aaggcuaguc cguuaucaac uugaaaaagu ggcaccgagu cggugc                 106

<210> SEQ ID NO 1330
<211> LENGTH: 106
<212> TYPE: RNA
<213> ORGANISM: Artificial Sequence
<220> FEATURE:
<223> OTHER INFORMATION: Synthetic

<400> SEQUENCE: 1330

```
auuaaagcua acacaggaaa guuuagagc uaugcuggaa acagcauagc aaguuuaaau    60
aaggcuaguc cguuaucaac uugaaaaagu ggcaccgagu cggugc                 106
```

<210> SEQ ID NO 1331
<211> LENGTH: 106
<212> TYPE: RNA
<213> ORGANISM: Artificial Sequence
<220> FEATURE:
<223> OTHER INFORMATION: Synthetic

<400> SEQUENCE: 1331

```
ucaaaaauua aagcuaacac guuuagagc uaugcuggaa acagcauagc aaguuuaaau    60
aaggcuaguc cguuaucaac uugaaaaagu ggcaccgagu cggugc                 106
```

<210> SEQ ID NO 1332
<211> LENGTH: 106
<212> TYPE: RNA
<213> ORGANISM: Artificial Sequence
<220> FEATURE:
<223> OTHER INFORMATION: Synthetic

<400> SEQUENCE: 1332

```
uaaaauuguc uaaacaucuc guuuagagc uaugcuggaa acagcauagc aaguuuaaau    60
aaggcuaguc cguuaucaac uugaaaaagu ggcaccgagu cggugc                 106
```

<210> SEQ ID NO 1333
<211> LENGTH: 106
<212> TYPE: RNA
<213> ORGANISM: Artificial Sequence
<220> FEATURE:
<223> OTHER INFORMATION: Synthetic

<400> SEQUENCE: 1333

```
agagauguuu agacaauuuu guuuagagc uaugcuggaa acagcauagc aaguuuaaau    60
aaggcuaguc cguuaucaac uugaaaaagu ggcaccgagu cggugc                 106
```

<210> SEQ ID NO 1334
<211> LENGTH: 106
<212> TYPE: RNA
<213> ORGANISM: Artificial Sequence
<220> FEATURE:
<223> OTHER INFORMATION: Synthetic

<400> SEQUENCE: 1334

```
ucuaaacauc ucugggacca guuuagagc uaugcuggaa acagcauagc aaguuuaaau    60
aaggcuaguc cguuaucaac uugaaaaagu ggcaccgagu cggugc                 106
```

<210> SEQ ID NO 1335
<211> LENGTH: 106
<212> TYPE: RNA
<213> ORGANISM: Artificial Sequence
<220> FEATURE:
<223> OTHER INFORMATION: Synthetic

<400> SEQUENCE: 1335

```
uuuaugcuuu cauauauccu guuuagagc uaugcuggaa acagcauagc aaguuuaaau    60
aaggcuaguc cguuaucaac uugaaaaagu ggcaccgagu cggugc                 106
```

<210> SEQ ID NO 1336
<211> LENGTH: 106
<212> TYPE: RNA
<213> ORGANISM: Artificial Sequence

```
<220> FEATURE:
<223> OTHER INFORMATION: Synthetic

<400> SEQUENCE: 1336
agcauaaauu acaaagaaaa guuuaagagc uaugcuggaa acagcauagc aaguuuaaau      60
aaggcuaguc cguuaucaac uugaaaaagu ggcaccgagu cggugc                    106

<210> SEQ ID NO 1337
<211> LENGTH: 106
<212> TYPE: RNA
<213> ORGANISM: Artificial Sequence
<220> FEATURE:
<223> OTHER INFORMATION: Synthetic

<400> SEQUENCE: 1337
uacaaagaaa aagguuauca guuuaagagc uaugcuggaa acagcauagc aaguuuaaau      60
aaggcuaguc cguuaucaac uugaaaaagu ggcaccgagu cggugc                    106

<210> SEQ ID NO 1338
<211> LENGTH: 106
<212> TYPE: RNA
<213> ORGANISM: Artificial Sequence
<220> FEATURE:
<223> OTHER INFORMATION: Synthetic

<400> SEQUENCE: 1338
acaaagaaaa agguuaucau guuuaagagc uaugcuggaa acagcauagc aaguuuaaau      60
aaggcuaguc cguuaucaac uugaaaaagu ggcaccgagu cggugc                    106

<210> SEQ ID NO 1339
<211> LENGTH: 106
<212> TYPE: RNA
<213> ORGANISM: Artificial Sequence
<220> FEATURE:
<223> OTHER INFORMATION: Synthetic

<400> SEQUENCE: 1339
caaagaaaaa gguuaucaug guuuaagagc uaugcuggaa acagcauagc aaguuuaaau      60
aaggcuaguc cguuaucaac uugaaaaagu ggcaccgagu cggugc                    106

<210> SEQ ID NO 1340
<211> LENGTH: 106
<212> TYPE: RNA
<213> ORGANISM: Artificial Sequence
<220> FEATURE:
<223> OTHER INFORMATION: Synthetic

<400> SEQUENCE: 1340
ucugagauuu aaaauagagu guuuaagagc uaugcuggaa acagcauagc aaguuuaaau      60
aaggcuaguc cguuaucaac uugaaaaagu ggcaccgagu cggugc                    106

<210> SEQ ID NO 1341
<211> LENGTH: 106
<212> TYPE: RNA
<213> ORGANISM: Artificial Sequence
<220> FEATURE:
<223> OTHER INFORMATION: Synthetic

<400> SEQUENCE: 1341
cuuauaagau acauuaugaa guuuaagagc uaugcuggaa acagcauagc aaguuuaaau      60
aaggcuaguc cguuaucaac uugaaaaagu ggcaccgagu cggugc                    106
```

```
<210> SEQ ID NO 1342
<211> LENGTH: 106
<212> TYPE: RNA
<213> ORGANISM: Artificial Sequence
<220> FEATURE:
<223> OTHER INFORMATION: Synthetic

<400> SEQUENCE: 1342
uaucuuauaa gacuauaaaa guuuaagagc uaugcuggaa acagcauagc aaguuuaaau    60
aaggcuaguc cguuaucaac uugaaaaagu ggcaccgagu cggugc                  106

<210> SEQ ID NO 1343
<211> LENGTH: 106
<212> TYPE: RNA
<213> ORGANISM: Artificial Sequence
<220> FEATURE:
<223> OTHER INFORMATION: Synthetic

<400> SEQUENCE: 1343
aucuuauaag acuauaaaaa guuuaagagc uaugcuggaa acagcauagc aaguuuaaau    60
aaggcuaguc cguuaucaac uugaaaaagu ggcaccgagu cggugc                  106

<210> SEQ ID NO 1344
<211> LENGTH: 106
<212> TYPE: RNA
<213> ORGANISM: Artificial Sequence
<220> FEATURE:
<223> OTHER INFORMATION: Synthetic

<400> SEQUENCE: 1344
uuauaagacu auaaaaaggg guuuaagagc uaugcuggaa acagcauagc aaguuuaaau    60
aaggcuaguc cguuaucaac uugaaaaagu ggcaccgagu cggugc                  106

<210> SEQ ID NO 1345
<211> LENGTH: 106
<212> TYPE: RNA
<213> ORGANISM: Artificial Sequence
<220> FEATURE:
<223> OTHER INFORMATION: Synthetic

<400> SEQUENCE: 1345
uaaaaaggga ggaaauauag guuuaagagc uaugcuggaa acagcauagc aaguuuaaau    60
aaggcuaguc cguuaucaac uugaaaaagu ggcaccgagu cggugc                  106

<210> SEQ ID NO 1346
<211> LENGTH: 106
<212> TYPE: RNA
<213> ORGANISM: Artificial Sequence
<220> FEATURE:
<223> OTHER INFORMATION: Synthetic

<400> SEQUENCE: 1346
aaaaagggag gaaauauaga guuuaagagc uaugcuggaa acagcauagc aaguuuaaau    60
aaggcuaguc cguuaucaac uugaaaaagu ggcaccgagu cggugc                  106

<210> SEQ ID NO 1347
<211> LENGTH: 106
<212> TYPE: RNA
<213> ORGANISM: Artificial Sequence
<220> FEATURE:
<223> OTHER INFORMATION: Synthetic

<400> SEQUENCE: 1347
```

```
aaauauagag gguccacuuu guuuaagagc uaugcuggaa acagcauagc aaguuuaaau       60
aaggcuaguc cguuaucaac uugaaaaagu ggcaccgagu cggugc                    106

<210> SEQ ID NO 1348
<211> LENGTH: 106
<212> TYPE: RNA
<213> ORGANISM: Artificial Sequence
<220> FEATURE:
<223> OTHER INFORMATION: Synthetic

<400> SEQUENCE: 1348
uauagagggu ccacuuuugg guuuaagagc uaugcuggaa acagcauagc aaguuuaaau       60
aaggcuaguc cguuaucaac uugaaaaagu ggcaccgagu cggugc                    106

<210> SEQ ID NO 1349
<211> LENGTH: 106
<212> TYPE: RNA
<213> ORGANISM: Artificial Sequence
<220> FEATURE:
<223> OTHER INFORMATION: Synthetic

<400> SEQUENCE: 1349
acucugaagu ccaccaaaag guuuaagagc uaugcuggaa acagcauagc aaguuuaaau       60
aaggcuaguc cguuaucaac uugaaaaagu ggcaccgagu cggugc                    106

<210> SEQ ID NO 1350
<211> LENGTH: 106
<212> TYPE: RNA
<213> ORGANISM: Artificial Sequence
<220> FEATURE:
<223> OTHER INFORMATION: Synthetic

<400> SEQUENCE: 1350
agaauagagu ugcaccguuu guuuaagagc uaugcuggaa acagcauagc aaguuuaaau       60
aaggcuaguc cguuaucaac uugaaaaagu ggcaccgagu cggugc                    106

<210> SEQ ID NO 1351
<211> LENGTH: 106
<212> TYPE: RNA
<213> ORGANISM: Artificial Sequence
<220> FEATURE:
<223> OTHER INFORMATION: Synthetic

<400> SEQUENCE: 1351
aaaacggugc aacucuauuc guuuaagagc uaugcuggaa acagcauagc aaguuuaaau       60
aaggcuaguc cguuaucaac uugaaaaagu ggcaccgagu cggugc                    106

<210> SEQ ID NO 1352
<211> LENGTH: 106
<212> TYPE: RNA
<213> ORGANISM: Artificial Sequence
<220> FEATURE:
<223> OTHER INFORMATION: Synthetic

<400> SEQUENCE: 1352
ccguuuuggg cuaaugaaaa guuuaagagc uaugcuggaa acagcauagc aaguuuaaau       60
aaggcuaguc cguuaucaac uugaaaaagu ggcaccgagu cggugc                    106

<210> SEQ ID NO 1353
<211> LENGTH: 106
<212> TYPE: RNA
```

```
<213> ORGANISM: Artificial Sequence
<220> FEATURE:
<223> OTHER INFORMATION: Synthetic

<400> SEQUENCE: 1353
ccuuuuucau uagcccaaaa guuuaagagc uaugcuggaa acagcauagc aaguuuaaau    60
aaggcuaguc cguuaucaac uugaaaaagu ggcaccgagu cggugc                 106

<210> SEQ ID NO 1354
<211> LENGTH: 106
<212> TYPE: RNA
<213> ORGANISM: Artificial Sequence
<220> FEATURE:
<223> OTHER INFORMATION: Synthetic

<400> SEQUENCE: 1354
ugggcuaaug aaaaggaag guuuaagagc uaugcuggaa acagcauagc aaguuuaaau     60
aaggcuaguc cguuaucaac uugaaaaagu ggcaccgagu cggugc                 106

<210> SEQ ID NO 1355
<211> LENGTH: 106
<212> TYPE: RNA
<213> ORGANISM: Artificial Sequence
<220> FEATURE:
<223> OTHER INFORMATION: Synthetic

<400> SEQUENCE: 1355
uaaugaaaaa ggaagaggcu guuuaagagc uaugcuggaa acagcauagc aaguuuaaau    60
aaggcuaguc cguuaucaac uugaaaaagu ggcaccgagu cggugc                 106

<210> SEQ ID NO 1356
<211> LENGTH: 106
<212> TYPE: RNA
<213> ORGANISM: Artificial Sequence
<220> FEATURE:
<223> OTHER INFORMATION: Synthetic

<400> SEQUENCE: 1356
aaugaaaaag gaagaggcua guuuaagagc uaugcuggaa acagcauagc aaguuuaaau    60
aaggcuaguc cguuaucaac uugaaaaagu ggcaccgagu cggugc                 106

<210> SEQ ID NO 1357
<211> LENGTH: 106
<212> TYPE: RNA
<213> ORGANISM: Artificial Sequence
<220> FEATURE:
<223> OTHER INFORMATION: Synthetic

<400> SEQUENCE: 1357
cugaaucuua aaauaugucc guuuaagagc uaugcuggaa acagcauagc aaguuuaaau    60
aaggcuaguc cguuaucaac uugaaaaagu ggcaccgagu cggugc                 106

<210> SEQ ID NO 1358
<211> LENGTH: 106
<212> TYPE: RNA
<213> ORGANISM: Artificial Sequence
<220> FEATURE:
<223> OTHER INFORMATION: Synthetic

<400> SEQUENCE: 1358
caggcagcuu uaucucaacc guuuaagagc uaugcuggaa acagcauagc aaguuuaaau    60
aaggcuaguc cguuaucaac uugaaaaagu ggcaccgagu cggugc                 106
```

<210> SEQ ID NO 1359
<211> LENGTH: 106
<212> TYPE: RNA
<213> ORGANISM: Artificial Sequence
<220> FEATURE:
<223> OTHER INFORMATION: Synthetic

<400> SEQUENCE: 1359
cuaagagauc aaguuucagc guuuaagagc uaugcuggaa acagcauagc aaguuuaaau      60
aaggcuaguc cguuaucaac uugaaaaagu ggcaccgagu cggugc                    106

<210> SEQ ID NO 1360
<211> LENGTH: 106
<212> TYPE: RNA
<213> ORGANISM: Artificial Sequence
<220> FEATURE:
<223> OTHER INFORMATION: Synthetic

<400> SEQUENCE: 1360
guguucuugu ugauauucug guuuaagagc uaugcuggaa acagcauagc aaguuuaaau      60
aaggcuaguc cguuaucaac uugaaaaagu ggcaccgagu cggugc                    106

<210> SEQ ID NO 1361
<211> LENGTH: 106
<212> TYPE: RNA
<213> ORGANISM: Artificial Sequence
<220> FEATURE:
<223> OTHER INFORMATION: Synthetic

<400> SEQUENCE: 1361
cuuguugaua uucuguggca guuuaagagc uaugcuggaa acagcauagc aaguuuaaau      60
aaggcuaguc cguuaucaac uugaaaaagu ggcaccgagu cggugc                    106

<210> SEQ ID NO 1362
<211> LENGTH: 106
<212> TYPE: RNA
<213> ORGANISM: Artificial Sequence
<220> FEATURE:
<223> OTHER INFORMATION: Synthetic

<400> SEQUENCE: 1362
ucuguggcau ggcuacagau guuuaagagc uaugcuggaa acagcauagc aaguuuaaau      60
aaggcuaguc cguuaucaac uugaaaaagu ggcaccgagu cggugc                    106

<210> SEQ ID NO 1363
<211> LENGTH: 106
<212> TYPE: RNA
<213> ORGANISM: Artificial Sequence
<220> FEATURE:
<223> OTHER INFORMATION: Synthetic

<400> SEQUENCE: 1363
agaacuuauu uacacaggga guuuaagagc uaugcuggaa acagcauagc aaguuuaaau      60
aaggcuaguc cguuaucaac uugaaaaagu ggcaccgagu cggugc                    106

<210> SEQ ID NO 1364
<211> LENGTH: 106
<212> TYPE: RNA
<213> ORGANISM: Artificial Sequence
<220> FEATURE:
<223> OTHER INFORMATION: Synthetic -continued

```
<400> SEQUENCE: 1364
aaagagaacu uauuuacaca guuuaagagc uaugcuggaa acagcauagc aaguuuaaau     60
aaggcuaguc cguuaucaac uugaaaaagu ggcaccgagu cggugc                  106

<210> SEQ ID NO 1365
<211> LENGTH: 106
<212> TYPE: RNA
<213> ORGANISM: Artificial Sequence
<220> FEATURE:
<223> OTHER INFORMATION: Synthetic

<400> SEQUENCE: 1365
caaagagaac uuauuuacac guuuaagagc uaugcuggaa acagcauagc aaguuuaaau     60
aaggcuaguc cguuaucaac uugaaaaagu ggcaccgagu cggugc                  106

<210> SEQ ID NO 1366
<211> LENGTH: 106
<212> TYPE: RNA
<213> ORGANISM: Artificial Sequence
<220> FEATURE:
<223> OTHER INFORMATION: Synthetic

<400> SEQUENCE: 1366
uucucuuugu auuuacuuuu guuuaagagc uaugcuggaa acagcauagc aaguuuaaau     60
aaggcuaguc cguuaucaac uugaaaaagu ggcaccgagu cggugc                  106

<210> SEQ ID NO 1367
<211> LENGTH: 106
<212> TYPE: RNA
<213> ORGANISM: Artificial Sequence
<220> FEATURE:
<223> OTHER INFORMATION: Synthetic

<400> SEQUENCE: 1367
ucucuuugua uuuacuuuua guuuaagagc uaugcuggaa acagcauagc aaguuuaaau     60
aaggcuaguc cguuaucaac uugaaaaagu ggcaccgagu cggugc                  106

<210> SEQ ID NO 1368
<211> LENGTH: 106
<212> TYPE: RNA
<213> ORGANISM: Artificial Sequence
<220> FEATURE:
<223> OTHER INFORMATION: Synthetic

<400> SEQUENCE: 1368
cuuuguauuu acuuuuaggg guuuaagagc uaugcuggaa acagcauagc aaguuuaaau     60
aaggcuaguc cguuaucaac uugaaaaagu ggcaccgagu cggugc                  106

<210> SEQ ID NO 1369
<211> LENGTH: 106
<212> TYPE: RNA
<213> ORGANISM: Artificial Sequence
<220> FEATURE:
<223> OTHER INFORMATION: Synthetic

<400> SEQUENCE: 1369
agcuuuuguc caccuuuaaa guuuaagagc uaugcuggaa acagcauagc aaguuuaaau     60
aaggcuaguc cguuaucaac uugaaaaagu ggcaccgagu cggugc                  106

<210> SEQ ID NO 1370
<211> LENGTH: 106
```

```
<212> TYPE: RNA
<213> ORGANISM: Artificial Sequence
<220> FEATURE:
<223> OTHER INFORMATION: Synthetic

<400> SEQUENCE: 1370
uuuauuuuuc cauuuaaagg guuuaagagc uaugcuggaa acagcauagc aaguuuaaau      60
aaggcuaguc cguuaucaac uugaaaaagu ggcaccgagu cggugc                   106

<210> SEQ ID NO 1371
<211> LENGTH: 106
<212> TYPE: RNA
<213> ORGANISM: Artificial Sequence
<220> FEATURE:
<223> OTHER INFORMATION: Synthetic

<400> SEQUENCE: 1371
uauuuuauuu uuccauuuaa guuuaagagc uaugcuggaa acagcauagc aaguuuaaau      60
aaggcuaguc cguuaucaac uugaaaaagu ggcaccgagu cggugc                   106

<210> SEQ ID NO 1372
<211> LENGTH: 106
<212> TYPE: RNA
<213> ORGANISM: Artificial Sequence
<220> FEATURE:
<223> OTHER INFORMATION: Synthetic

<400> SEQUENCE: 1372
cuuacauaaa cauacuuaaa guuuaagagc uaugcuggaa acagcauagc aaguuuaaau      60
aaggcuaguc cguuaucaac uugaaaaagu ggcaccgagu cggugc                   106

<210> SEQ ID NO 1373
<211> LENGTH: 106
<212> TYPE: RNA
<213> ORGANISM: Artificial Sequence
<220> FEATURE:
<223> OTHER INFORMATION: Synthetic

<400> SEQUENCE: 1373
uaagcacaga aguuuuuaag guuuaagagc uaugcuggaa acagcauagc aaguuuaaau      60
aaggcuaguc cguuaucaac uugaaaaagu ggcaccgagu cggugc                   106

<210> SEQ ID NO 1374
<211> LENGTH: 106
<212> TYPE: RNA
<213> ORGANISM: Artificial Sequence
<220> FEATURE:
<223> OTHER INFORMATION: Synthetic

<400> SEQUENCE: 1374
aaguuuuuaa gaggcaugaa guuuaagagc uaugcuggaa acagcauagc aaguuuaaau      60
aaggcuaguc cguuaucaac uugaaaaagu ggcaccgagu cggugc                   106

<210> SEQ ID NO 1375
<211> LENGTH: 106
<212> TYPE: RNA
<213> ORGANISM: Artificial Sequence
<220> FEATURE:
<223> OTHER INFORMATION: Synthetic

<400> SEQUENCE: 1375
auauuuacgu aguuuuucau guuuaagagc uaugcuggaa acagcauagc aaguuuaaau      60
```
aaggcuaguc cguuaucaac uugaaaaagu ggcaccgagu cgguqc       106

<210> SEQ ID NO 1376
<211> LENGTH: 106
<212> TYPE: RNA
<213> ORGANISM: Artificial Sequence
<220> FEATURE:
<223> OTHER INFORMATION: Synthetic

<400> SEQUENCE: 1376
cguaaauauu cuugagaaac guuuaagagc uaugcuggaa acagcauagc aaguuuaaau       60
aaggcuaguc cguuaucaac uugaaaaagu ggcaccgagu cgguqc       106

<210> SEQ ID NO 1377
<211> LENGTH: 106
<212> TYPE: RNA
<213> ORGANISM: Artificial Sequence
<220> FEATURE:
<223> OTHER INFORMATION: Synthetic

<400> SEQUENCE: 1377
uucuugagaa acaggaagac guuuaagagc uaugcuggaa acagcauagc aaguuuaaau       60
aaggcuaguc cguuaucaac uugaaaaagu ggcaccgagu cgguqc       106

<210> SEQ ID NO 1378
<211> LENGTH: 106
<212> TYPE: RNA
<213> ORGANISM: Artificial Sequence
<220> FEATURE:
<223> OTHER INFORMATION: Synthetic

<400> SEQUENCE: 1378
uaauauuaaa aacauugguu guuuaagagc uaugcuggaa acagcauagc aaguuuaaau       60
aaggcuaguc cguuaucaac uugaaaaagu ggcaccgagu cgguqc       106

<210> SEQ ID NO 1379
<211> LENGTH: 106
<212> TYPE: RNA
<213> ORGANISM: Artificial Sequence
<220> FEATURE:
<223> OTHER INFORMATION: Synthetic

<400> SEQUENCE: 1379
ccaauguuuu uaauauuauc guuuaagagc uaugcuggaa acagcauagc aaguuuaaau       60
aaggcuaguc cguuaucaac uugaaaaagu ggcaccgagu cgguqc       106

<210> SEQ ID NO 1380
<211> LENGTH: 106
<212> TYPE: RNA
<213> ORGANISM: Artificial Sequence
<220> FEATURE:
<223> OTHER INFORMATION: Synthetic

<400> SEQUENCE: 1380
ccugauaaua uuaaaaacau guuuaagagc uaugcuggaa acagcauagc aaguuuaaau       60
aaggcuaguc cguuaucaac uugaaaaagu ggcaccgagu cgguqc       106

<210> SEQ ID NO 1381
<211> LENGTH: 106
<212> TYPE: RNA
<213> ORGANISM: Artificial Sequence
<220> FEATURE:
<223> OTHER INFORMATION: Synthetic

<400> SEQUENCE: 1381
cauuaucaug cauacaucuc guuuaagagc uaugcuggaa acagcauagc aaguuuaaau    60
aaggcuaguc cguuaucaac uugaaaaagu ggcaccgagu cggugc                  106

<210> SEQ ID NO 1382
<211> LENGTH: 106
<212> TYPE: RNA
<213> ORGANISM: Artificial Sequence
<220> FEATURE:
<223> OTHER INFORMATION: Synthetic

<400> SEQUENCE: 1382
aucaugcaua caucucuggc guuuaagagc uaugcuggaa acagcauagc aaguuuaaau    60
aaggcuaguc cguuaucaac uugaaaaagu ggcaccgagu cggugc                  106

<210> SEQ ID NO 1383
<211> LENGTH: 106
<212> TYPE: RNA
<213> ORGANISM: Artificial Sequence
<220> FEATURE:
<223> OTHER INFORMATION: Synthetic

<400> SEQUENCE: 1383
uucauuucau uuugauuuug guuuaagagc uaugcuggaa acagcauagc aaguuuaaau    60
aaggcuaguc cguuaucaac uugaaaaagu ggcaccgagu cggugc                  106

<210> SEQ ID NO 1384
<211> LENGTH: 106
<212> TYPE: RNA
<213> ORGANISM: Artificial Sequence
<220> FEATURE:
<223> OTHER INFORMATION: Synthetic

<400> SEQUENCE: 1384
auucaauuug aagcaguggu guuuaagagc uaugcuggaa acagcauagc aaguuuaaau    60
aaggcuaguc cguuaucaac uugaaaaagu ggcaccgagu cggugc                  106

<210> SEQ ID NO 1385
<211> LENGTH: 106
<212> TYPE: RNA
<213> ORGANISM: Artificial Sequence
<220> FEATURE:
<223> OTHER INFORMATION: Synthetic

<400> SEQUENCE: 1385
gaauauucaa uuugaagcag guuuaagagc uaugcuggaa acagcauagc aaguuuaaau    60
aaggcuaguc cguuaucaac uugaaaaagu ggcaccgagu cggugc                  106

<210> SEQ ID NO 1386
<211> LENGTH: 106
<212> TYPE: RNA
<213> ORGANISM: Artificial Sequence
<220> FEATURE:
<223> OTHER INFORMATION: Synthetic

<400> SEQUENCE: 1386
cauacgauuu aaaaucgcug guuuaagagc uaugcuggaa acagcauagc aaguuuaaau    60
aaggcuaguc cguuaucaac uugaaaaagu ggcaccgagu cggugc                  106

<210> SEQ ID NO 1387

```
<210> SEQ ID NO 1387
<211> LENGTH: 106
<212> TYPE: RNA
<213> ORGANISM: Artificial Sequence
<220> FEATURE:
<223> OTHER INFORMATION: Synthetic

<400> SEQUENCE: 1387
aaaaucgcug aggcgcguuc guuuaagagc uaugcuggaa acagcauagc aaguuuaaau      60
aaggcuaguc cguuaucaac uugaaaaagu ggcaccgagu cggugc                    106

<210> SEQ ID NO 1388
<211> LENGTH: 106
<212> TYPE: RNA
<213> ORGANISM: Artificial Sequence
<220> FEATURE:
<223> OTHER INFORMATION: Synthetic

<400> SEQUENCE: 1388
uuuuuuuuuc uuuuuuguac guuuaagagc uaugcuggaa acagcauagc aaguuuaaau      60
aaggcuaguc cguuaucaac uugaaaaagu ggcaccgagu cggugc                    106

<210> SEQ ID NO 1389
<211> LENGTH: 106
<212> TYPE: RNA
<213> ORGANISM: Artificial Sequence
<220> FEATURE:
<223> OTHER INFORMATION: Synthetic

<400> SEQUENCE: 1389
cuguugucaa agauuuuaaa guuuaagagc uaugcuggaa acagcauagc aaguuuaaau      60
aaggcuaguc cguuaucaac uugaaaaagu ggcaccgagu cggugc                    106

<210> SEQ ID NO 1390
<211> LENGTH: 106
<212> TYPE: RNA
<213> ORGANISM: Artificial Sequence
<220> FEATURE:
<223> OTHER INFORMATION: Synthetic

<400> SEQUENCE: 1390
ugacaacaga guucuguuuu guuuaagagc uaugcuggaa acagcauagc aaguuuaaau      60
aaggcuaguc cguuaucaac uugaaaaagu ggcaccgagu cggugc                    106

<210> SEQ ID NO 1391
<211> LENGTH: 106
<212> TYPE: RNA
<213> ORGANISM: Artificial Sequence
<220> FEATURE:
<223> OTHER INFORMATION: Synthetic

<400> SEQUENCE: 1391
agaauacgcu gagaguuauc guuuaagagc uaugcuggaa acagcauagc aaguuuaaau      60
aaggcuaguc cguuaucaac uugaaaaagu ggcaccgagu cggugc                    106

<210> SEQ ID NO 1392
<211> LENGTH: 106
<212> TYPE: RNA
<213> ORGANISM: Artificial Sequence
<220> FEATURE:
<223> OTHER INFORMATION: Synthetic

<400> SEQUENCE: 1392
gcaagagaag aaaagaacgg guuuaagagc uaugcuggaa acagcauagc aaguuuaaau      60
```

```
aaggcuaguc cguuaucaac uugaaaaagu ggcaccgagu cgguqc         106

<210> SEQ ID NO 1393
<211> LENGTH: 106
<212> TYPE: RNA
<213> ORGANISM: Artificial Sequence
<220> FEATURE:
<223> OTHER INFORMATION: Synthetic

<400> SEQUENCE: 1393
guugcaagag aagaaaagaa guuuaagagc uaugcuggaa acagcauagc aaguuuaaau    60
aaggcuaguc cguuaucaac uugaaaaagu ggcaccgagu cggugc                  106

<210> SEQ ID NO 1394
<211> LENGTH: 106
<212> TYPE: RNA
<213> ORGANISM: Artificial Sequence
<220> FEATURE:
<223> OTHER INFORMATION: Synthetic

<400> SEQUENCE: 1394
augcacacgu aaaagagagg guuuaagagc uaugcuggaa acagcauagc aaguuuaaau    60
aaggcuaguc cguuaucaac uugaaaaagu ggcaccgagu cggugc                  106

<210> SEQ ID NO 1395
<211> LENGTH: 106
<212> TYPE: RNA
<213> ORGANISM: Artificial Sequence
<220> FEATURE:
<223> OTHER INFORMATION: Synthetic

<400> SEQUENCE: 1395
aagaugcaca cguaaaagag guuuaagagc uaugcuggaa acagcauagc aaguuuaaau    60
aaggcuaguc cguuaucaac uugaaaaagu ggcaccgagu cggugc                  106

<210> SEQ ID NO 1396
<211> LENGTH: 106
<212> TYPE: RNA
<213> ORGANISM: Artificial Sequence
<220> FEATURE:
<223> OTHER INFORMATION: Synthetic

<400> SEQUENCE: 1396
aucaugcaua caucucuggc guuuaagagc uaugcuggaa acagcauagc aaguuuaaau    60
aaggcuaguc cguuaucaac uugaaaaagu ggcaccgagu cggugc                  106

<210> SEQ ID NO 1397
<211> LENGTH: 106
<212> TYPE: RNA
<213> ORGANISM: Artificial Sequence
<220> FEATURE:
<223> OTHER INFORMATION: Synthetic

<400> SEQUENCE: 1397
uucauuucau uuugauuuug guuuaagagc uaugcuggaa acagcauagc aaguuuaaau    60
aaggcuaguc cguuaucaac uugaaaaagu ggcaccgagu cggugc                  106

<210> SEQ ID NO 1398
<211> LENGTH: 106
<212> TYPE: RNA
<213> ORGANISM: Artificial Sequence
<220> FEATURE:
```

<223> OTHER INFORMATION: Synthetic

<400> SEQUENCE: 1398
auucaauuug aagcaguggu guuuaagagc uaugcuggaa acagcauagc aaguuuaaau    60
aaggcuaguc cguuaucaac uugaaaaagu ggcaccgagu cggugc    106

<210> SEQ ID NO 1399
<211> LENGTH: 106
<212> TYPE: RNA
<213> ORGANISM: Artificial Sequence
<220> FEATURE:
<223> OTHER INFORMATION: Synthetic

<400> SEQUENCE: 1399
gaauauucaa uuugaagcag guuuaagagc uaugcuggaa acagcauagc aaguuuaaau    60
aaggcuaguc cguuaucaac uugaaaaagu ggcaccgagu cggugc    106

<210> SEQ ID NO 1400
<211> LENGTH: 106
<212> TYPE: RNA
<213> ORGANISM: Artificial Sequence
<220> FEATURE:
<223> OTHER INFORMATION: Synthetic

<400> SEQUENCE: 1400
cauacgauuu aaaaucgcug guuuaagagc uaugcuggaa acagcauagc aaguuuaaau    60
aaggcuaguc cguuaucaac uugaaaaagu ggcaccgagu cggugc    106

<210> SEQ ID NO 1401
<211> LENGTH: 106
<212> TYPE: RNA
<213> ORGANISM: Artificial Sequence
<220> FEATURE:
<223> OTHER INFORMATION: Synthetic

<400> SEQUENCE: 1401
aaaaucgcug aggcgcguuc guuuaagagc uaugcuggaa acagcauagc aaguuuaaau    60
aaggcuaguc cguuaucaac uugaaaaagu ggcaccgagu cggugc    106

<210> SEQ ID NO 1402
<211> LENGTH: 106
<212> TYPE: RNA
<213> ORGANISM: Artificial Sequence
<220> FEATURE:
<223> OTHER INFORMATION: Synthetic

<400> SEQUENCE: 1402
uuuuuuuuuc uuuuuuguac guuuaagagc uaugcuggaa acagcauagc aaguuuaaau    60
aaggcuaguc cguuaucaac uugaaaaagu ggcaccgagu cggugc    106

<210> SEQ ID NO 1403
<211> LENGTH: 106
<212> TYPE: RNA
<213> ORGANISM: Artificial Sequence
<220> FEATURE:
<223> OTHER INFORMATION: Synthetic

<400> SEQUENCE: 1403
cuguugucaa agauuuuaaa guuuaagagc uaugcuggaa acagcauagc aaguuuaaau    60
aaggcuaguc cguuaucaac uugaaaaagu ggcaccgagu cggugc    106

<210> SEQ ID NO 1404
<211> LENGTH: 106
<212> TYPE: RNA
<213> ORGANISM: Artificial Sequence
<220> FEATURE:
<223> OTHER INFORMATION: Synthetic

<400> SEQUENCE: 1404
ugacaacaga guucuguuuu guuuaagagc uaugcuggaa acagcauagc aaguuuaaau    60
aaggcuaguc cguuaucaac uugaaaaagu ggcaccgagu cggugc                  106

<210> SEQ ID NO 1405
<211> LENGTH: 106
<212> TYPE: RNA
<213> ORGANISM: Artificial Sequence
<220> FEATURE:
<223> OTHER INFORMATION: Synthetic

<400> SEQUENCE: 1405
agaauacgcu gagaguuauc guuuaagagc uaugcuggaa acagcauagc aaguuuaaau    60
aaggcuaguc cguuaucaac uugaaaaagu ggcaccgagu cggugc                  106

<210> SEQ ID NO 1406
<211> LENGTH: 106
<212> TYPE: RNA
<213> ORGANISM: Artificial Sequence
<220> FEATURE:
<223> OTHER INFORMATION: Synthetic

<400> SEQUENCE: 1406
gcaagagaag aaaagaacgg guuuaagagc uaugcuggaa acagcauagc aaguuuaaau    60
aaggcuaguc cguuaucaac uugaaaaagu ggcaccgagu cggugc                  106

<210> SEQ ID NO 1407
<211> LENGTH: 106
<212> TYPE: RNA
<213> ORGANISM: Artificial Sequence
<220> FEATURE:
<223> OTHER INFORMATION: Synthetic

<400> SEQUENCE: 1407
guugcaagag aagaaaagaa guuuaagagc uaugcuggaa acagcauagc aaguuuaaau    60
aaggcuaguc cguuaucaac uugaaaaagu ggcaccgagu cggugc                  106

<210> SEQ ID NO 1408
<211> LENGTH: 106
<212> TYPE: RNA
<213> ORGANISM: Artificial Sequence
<220> FEATURE:
<223> OTHER INFORMATION: Synthetic

<400> SEQUENCE: 1408
augcacacgu aaaagagagg guuuaagagc uaugcuggaa acagcauagc aaguuuaaau    60
aaggcuaguc cguuaucaac uugaaaaagu ggcaccgagu cggugc                  106

<210> SEQ ID NO 1409
<211> LENGTH: 106
<212> TYPE: RNA
<213> ORGANISM: Artificial Sequence
<220> FEATURE:
<223> OTHER INFORMATION: Synthetic

<400> SEQUENCE: 1409
aagaugcaca cguaaaagag guuuaagagc uaugcuggaa acagcauagc aaguuuaaau    60
aaggcuaguc cguuaucaac uugaaaaagu ggcaccgagu cggugc                  106

<210> SEQ ID NO 1410
<211> LENGTH: 106
<212> TYPE: RNA
<213> ORGANISM: Artificial Sequence
<220> FEATURE:
<223> OTHER INFORMATION: Synthetic

<400> SEQUENCE: 1410
ggcagaccgu ucucaucacg guuuaagagc uaugcuggaa acagcauagc aaguuuaaau    60
aaggcuaguc cguuaucaac uugaaaaagu ggcaccgagu cggugc                  106

<210> SEQ ID NO 1411
<211> LENGTH: 106
<212> TYPE: RNA
<213> ORGANISM: Artificial Sequence
<220> FEATURE:
<223> OTHER INFORMATION: Synthetic

<400> SEQUENCE: 1411
cuuuaccagu gacuccaggu guuuaagagc uaugcuggaa acagcauagc aaguuuaaau    60
aaggcuaguc cguuaucaac uugaaaaagu ggcaccgagu cggugc                  106

<210> SEQ ID NO 1412
<211> LENGTH: 106
<212> TYPE: RNA
<213> ORGANISM: Artificial Sequence
<220> FEATURE:
<223> OTHER INFORMATION: Synthetic

<400> SEQUENCE: 1412
gucacagauu uccuucuccg guuuaagagc uaugcuggaa acagcauagc aaguuuaaau    60
aaggcuaguc cguuaucaac uugaaaaagu ggcaccgagu cggugc                  106

<210> SEQ ID NO 1413
<211> LENGTH: 106
<212> TYPE: RNA
<213> ORGANISM: Artificial Sequence
<220> FEATURE:
<223> OTHER INFORMATION: Synthetic

<400> SEQUENCE: 1413
agaugaugac gcccaccaga guuuaagagc uaugcuggaa acagcauagc aaguuuaaau    60
aaggcuaguc cguuaucaac uugaaaaagu ggcaccgagu cggugc                  106

<210> SEQ ID NO 1414
<211> LENGTH: 106
<212> TYPE: RNA
<213> ORGANISM: Artificial Sequence
<220> FEATURE:
<223> OTHER INFORMATION: Synthetic

<400> SEQUENCE: 1414
ggagaaggaa aucugugacc guuuaagagc uaugcuggaa acagcauagc aaguuuaaau    60
aaggcuaguc cguuaucaac uugaaaaagu ggcaccgagu cggugc                  106

<210> SEQ ID NO 1415
<211> LENGTH: 106
<212> TYPE: RNA
<213> ORGANISM: Artificial Sequence

```
<220> FEATURE:
<223> OTHER INFORMATION: Synthetic

<400> SEQUENCE: 1415
ugcgaggaac uuacuuuucc guuuagagc uaugcuggaa acagcauagc aaguuuaaau      60
aaggcuaguc cguuaucaac uugaaaaagu ggcaccgagu cggugc                   106

<210> SEQ ID NO 1416
<211> LENGTH: 106
<212> TYPE: RNA
<213> ORGANISM: Artificial Sequence
<220> FEATURE:
<223> OTHER INFORMATION: Synthetic

<400> SEQUENCE: 1416
agagaaauau ugauauagga guuuagagc uaugcuggaa acagcauagc aaguuuaaau      60
aaggcuaguc cguuaucaac uugaaaaagu ggcaccgagu cggugc                   106

<210> SEQ ID NO 1417
<211> LENGTH: 106
<212> TYPE: RNA
<213> ORGANISM: Artificial Sequence
<220> FEATURE:
<223> OTHER INFORMATION: Synthetic

<400> SEQUENCE: 1417
uaucaauauu ucucugaucc guuuagagc uaugcuggaa acagcauagc aaguuuaaau      60
aaggcuaguc cguuaucaac uugaaaaagu ggcaccgagu cggugc                   106

<210> SEQ ID NO 1418
<211> LENGTH: 106
<212> TYPE: RNA
<213> ORGANISM: Artificial Sequence
<220> FEATURE:
<223> OTHER INFORMATION: Synthetic

<400> SEQUENCE: 1418
aucgcuuuua aggcacgcuc guuuagagc uaugcuggaa acagcauagc aaguuuaaau      60
aaggcuaguc cguuaucaac uugaaaaagu ggcaccgagu cggugc                   106

<210> SEQ ID NO 1419
<211> LENGTH: 106
<212> TYPE: RNA
<213> ORGANISM: Artificial Sequence
<220> FEATURE:
<223> OTHER INFORMATION: Synthetic

<400> SEQUENCE: 1419
uauacgacug aucgcuuuua guuuagagc uaugcuggaa acagcauagc aaguuuaaau      60
aaggcuaguc cguuaucaac uugaaaaagu ggcaccgagu cggugc                   106

<210> SEQ ID NO 1420
<211> LENGTH: 77
<212> TYPE: RNA
<213> ORGANISM: Artificial Sequence
<220> FEATURE:
<223> OTHER INFORMATION: Synthetic

<400> SEQUENCE: 1420 guuuagagc uagaaauagc aaguuaaaau aaggcuaguc cguuaucaac uugaaaaagu      60
ggcaccgagu cggugcu                                                    77
```

<210> SEQ ID NO 1421
<211> LENGTH: 16
<212> TYPE: RNA
<213> ORGANISM: Artificial Sequence
<220> FEATURE:
<223> OTHER INFORMATION: Synthetic

<400> SEQUENCE: 1421
guuuuagagc uaugcu    16

<210> SEQ ID NO 1422
<211> LENGTH: 67
<212> TYPE: RNA
<213> ORGANISM: Artificial Sequence
<220> FEATURE:
<223> OTHER INFORMATION: Synthetic

<400> SEQUENCE: 1422
agcauagcaa guuaaaauaa ggcuaguccg uuaucaacuu gaaaaagugg caccgagucg    60
gugcuuu    67

<210> SEQ ID NO 1423
<211> LENGTH: 20
<212> TYPE: RNA
<213> ORGANISM: Artificial Sequence
<220> FEATURE:
<223> OTHER INFORMATION: Synthetic

<400> SEQUENCE: 1423
ugucagguua guuagaugaa    20

<210> SEQ ID NO 1424
<211> LENGTH: 20
<212> TYPE: RNA
<213> ORGANISM: Artificial Sequence
<220> FEATURE:
<223> OTHER INFORMATION: Synthetic

<400> SEQUENCE: 1424
gugucagguu aguuagauga    20

<210> SEQ ID NO 1425
<211> LENGTH: 20
<212> TYPE: RNA
<213> ORGANISM: Artificial Sequence
<220> FEATURE:
<223> OTHER INFORMATION: Synthetic

<400> SEQUENCE: 1425
ccugacacau auacagacua    20

<210> SEQ ID NO 1426
<211> LENGTH: 20
<212> TYPE: RNA
<213> ORGANISM: Artificial Sequence
<220> FEATURE:
<223> OTHER INFORMATION: Synthetic

<400> SEQUENCE: 1426
cugacacaua uacagacuaa    20

<210> SEQ ID NO 1427
<211> LENGTH: 20
<212> TYPE: RNA
<213> ORGANISM: Artificial Sequence

```
<220> FEATURE:
<223> OTHER INFORMATION: Synthetic

<400> SEQUENCE: 1427
ccuuagucug uauauguguc                                                  20

<210> SEQ ID NO 1428
<211> LENGTH: 20
<212> TYPE: RNA
<213> ORGANISM: Artificial Sequence
<220> FEATURE:
<223> OTHER INFORMATION: Synthetic

<400> SEQUENCE: 1428
cauauacaga cuaagggacc                                                  20

<210> SEQ ID NO 1429
<211> LENGTH: 20
<212> TYPE: RNA
<213> ORGANISM: Artificial Sequence
<220> FEATURE:
<223> OTHER INFORMATION: Synthetic

<400> SEQUENCE: 1429
auauacagac uaagggacca                                                  20

<210> SEQ ID NO 1430
<211> LENGTH: 20
<212> TYPE: RNA
<213> ORGANISM: Artificial Sequence
<220> FEATURE:
<223> OTHER INFORMATION: Synthetic

<400> SEQUENCE: 1430
ucaaaguuug auaaauuccc                                                  20

<210> SEQ ID NO 1431
<211> LENGTH: 20
<212> TYPE: RNA
<213> ORGANISM: Artificial Sequence
<220> FEATURE:
<223> OTHER INFORMATION: Synthetic

<400> SEQUENCE: 1431
aaaauacaaa gauaaguaga                                                  20

<210> SEQ ID NO 1432
<211> LENGTH: 20
<212> TYPE: RNA
<213> ORGANISM: Artificial Sequence
<220> FEATURE:
<223> OTHER INFORMATION: Synthetic

<400> SEQUENCE: 1432
acucugugac uuuaaaaagu                                                  20

<210> SEQ ID NO 1433
<211> LENGTH: 20
<212> TYPE: RNA
<213> ORGANISM: Artificial Sequence
<220> FEATURE:
<223> OTHER INFORMATION: Synthetic

<400> SEQUENCE: 1433
gguucugugg gauauuaaua                                                  20
```

<210> SEQ ID NO 1434
<211> LENGTH: 20
<212> TYPE: RNA
<213> ORGANISM: Artificial Sequence
<220> FEATURE:
<223> OTHER INFORMATION: Synthetic

<400> SEQUENCE: 1434
acagagcaua uugguucugu                                              20

<210> SEQ ID NO 1435
<211> LENGTH: 20
<212> TYPE: RNA
<213> ORGANISM: Artificial Sequence
<220> FEATURE:
<223> OTHER INFORMATION: Synthetic

<400> SEQUENCE: 1435
gacagagcau auugguucug                                              20

<210> SEQ ID NO 1436
<211> LENGTH: 20
<212> TYPE: RNA
<213> ORGANISM: Artificial Sequence
<220> FEATURE:
<223> OTHER INFORMATION: Synthetic

<400> SEQUENCE: 1436
ugcaaaacga cagagcauau                                              20

<210> SEQ ID NO 1437
<211> LENGTH: 20
<212> TYPE: RNA
<213> ORGANISM: Artificial Sequence
<220> FEATURE:
<223> OTHER INFORMATION: Synthetic

<400> SEQUENCE: 1437
gagcugggca uggaauaggc                                              20

<210> SEQ ID NO 1438
<211> LENGTH: 20
<212> TYPE: RNA
<213> ORGANISM: Artificial Sequence
<220> FEATURE:
<223> OTHER INFORMATION: Synthetic

<400> SEQUENCE: 1438
acuggagcug ggcauggaau                                              20

<210> SEQ ID NO 1439
<211> LENGTH: 20
<212> TYPE: RNA
<213> ORGANISM: Artificial Sequence
<220> FEATURE:
<223> OTHER INFORMATION: Synthetic

<400> SEQUENCE: 1439
cucauuacug gagcugggca                                              20

<210> SEQ ID NO 1440
<211> LENGTH: 20
<212> TYPE: RNA
<213> ORGANISM: Artificial Sequence
<220> FEATURE:
<223> OTHER INFORMATION: Synthetic

<400> SEQUENCE: 1440
uuguucucau uacuggagcu                                               20

<210> SEQ ID NO 1441
<211> LENGTH: 20
<212> TYPE: RNA
<213> ORGANISM: Artificial Sequence
<220> FEATURE:
<223> OTHER INFORMATION: Synthetic

<400> SEQUENCE: 1441
auuguucuca uuacuggagc                                               20

<210> SEQ ID NO 1442
<211> LENGTH: 20
<212> TYPE: RNA
<213> ORGANISM: Artificial Sequence
<220> FEATURE:
<223> OTHER INFORMATION: Synthetic

<400> SEQUENCE: 1442
ggggagauug uucucauuac                                               20

<210> SEQ ID NO 1443
<211> LENGTH: 20
<212> TYPE: RNA
<213> ORGANISM: Artificial Sequence
<220> FEATURE:
<223> OTHER INFORMATION: Synthetic

<400> SEQUENCE: 1443
gaggagaaaa ucuguggcug                                               20

<210> SEQ ID NO 1444
<211> LENGTH: 20
<212> TYPE: RNA
<213> ORGANISM: Artificial Sequence
<220> FEATURE:
<223> OTHER INFORMATION: Synthetic

<400> SEQUENCE: 1444
agaggagaaa aucuguggcu                                               20

<210> SEQ ID NO 1445
<211> LENGTH: 20
<212> TYPE: RNA
<213> ORGANISM: Artificial Sequence
<220> FEATURE:
<223> OTHER INFORMATION: Synthetic

<400> SEQUENCE: 1445
cagaggagaa aaucuguggc                                               20

<210> SEQ ID NO 1446
<211> LENGTH: 20
<212> TYPE: RNA
<213> ORGANISM: Artificial Sequence
<220> FEATURE:
<223> OTHER INFORMATION: Synthetic

<400> SEQUENCE: 1446
uccucagagg agaaaaucug                                               20

<210> SEQ ID NO 1447

```
<211> LENGTH: 20
<212> TYPE: RNA
<213> ORGANISM: Artificial Sequence
<220> FEATURE:
<223> OTHER INFORMATION: Synthetic

<400> SEQUENCE: 1447
ugaaguuuuu cauuccucag                                                     20

<210> SEQ ID NO 1448
<211> LENGTH: 20
<212> TYPE: RNA
<213> ORGANISM: Artificial Sequence
<220> FEATURE:
<223> OTHER INFORMATION: Synthetic

<400> SEQUENCE: 1448
cuucaccaac gacuccaagu                                                     20

<210> SEQ ID NO 1449
<211> LENGTH: 20
<212> TYPE: RNA
<213> ORGANISM: Artificial Sequence
<220> FEATURE:
<223> OTHER INFORMATION: Synthetic

<400> SEQUENCE: 1449
cuacuccuac uuggagucgu                                                     20

<210> SEQ ID NO 1450
<211> LENGTH: 20
<212> TYPE: RNA
<213> ORGANISM: Artificial Sequence
<220> FEATURE:
<223> OTHER INFORMATION: Synthetic

<400> SEQUENCE: 1450
cuccaaguag gaguagauga                                                     20

<210> SEQ ID NO 1451
<211> LENGTH: 20
<212> TYPE: RNA
<213> ORGANISM: Artificial Sequence
<220> FEATURE:
<223> OTHER INFORMATION: Synthetic

<400> SEQUENCE: 1451
caccaucauc uacuccuacu                                                     20

<210> SEQ ID NO 1452
<211> LENGTH: 20
<212> TYPE: RNA
<213> ORGANISM: Artificial Sequence
<220> FEATURE:
<223> OTHER INFORMATION: Synthetic

<400> SEQUENCE: 1452
ugauggugau cagaagcaga                                                     20

<210> SEQ ID NO 1453
<211> LENGTH: 20
<212> TYPE: RNA
<213> ORGANISM: Artificial Sequence
<220> FEATURE:
<223> OTHER INFORMATION: Synthetic

<400> SEQUENCE: 1453
```
ucagaagcag aaggauuucu                                              20

<210> SEQ ID NO 1454
<211> LENGTH: 20
<212> TYPE: RNA
<213> ORGANISM: Artificial Sequence
<220> FEATURE:
<223> OTHER INFORMATION: Synthetic

<400> SEQUENCE: 1454
gauuucuagg augauguuca                                              20

<210> SEQ ID NO 1455
<211> LENGTH: 20
<212> TYPE: RNA
<213> ORGANISM: Artificial Sequence
<220> FEATURE:
<223> OTHER INFORMATION: Synthetic

<400> SEQUENCE: 1455
uugcucuguc cucuuccuuc                                              20

<210> SEQ ID NO 1456
<211> LENGTH: 20
<212> TYPE: RNA
<213> ORGANISM: Artificial Sequence
<220> FEATURE:
<223> OTHER INFORMATION: Synthetic

<400> SEQUENCE: 1456
aggacugaac cagaaggaag                                              20

<210> SEQ ID NO 1457
<211> LENGTH: 20
<212> TYPE: RNA
<213> ORGANISM: Artificial Sequence
<220> FEATURE:
<223> OTHER INFORMATION: Synthetic

<400> SEQUENCE: 1457
uacacaagga cugaaccaga                                              20

<210> SEQ ID NO 1458
<211> LENGTH: 20
<212> TYPE: RNA
<213> ORGANISM: Artificial Sequence
<220> FEATURE:
<223> OTHER INFORMATION: Synthetic

<400> SEQUENCE: 1458
uucaguccuu guguaguccu                                              20

<210> SEQ ID NO 1459
<211> LENGTH: 20
<212> TYPE: RNA
<213> ORGANISM: Artificial Sequence
<220> FEATURE:
<223> OTHER INFORMATION: Synthetic

<400> SEQUENCE: 1459
ucaguccuug uguaguccua                                              20

<210> SEQ ID NO 1460
<211> LENGTH: 20
<212> TYPE: RNA

```
<213> ORGANISM: Artificial Sequence
<220> FEATURE:
<223> OTHER INFORMATION: Synthetic

<400> SEQUENCE: 1460
guccuugugu aguccuaggg                                              20

<210> SEQ ID NO 1461
<211> LENGTH: 20
<212> TYPE: RNA
<213> ORGANISM: Artificial Sequence
<220> FEATURE:
<223> OTHER INFORMATION: Synthetic

<400> SEQUENCE: 1461
cuuguguagu ccuagggagg                                              20

<210> SEQ ID NO 1462
<211> LENGTH: 20
<212> TYPE: RNA
<213> ORGANISM: Artificial Sequence
<220> FEATURE:
<223> OTHER INFORMATION: Synthetic

<400> SEQUENCE: 1462
cuccucccua ggacuacaca                                              20

<210> SEQ ID NO 1463
<211> LENGTH: 20
<212> TYPE: RNA
<213> ORGANISM: Artificial Sequence
<220> FEATURE:
<223> OTHER INFORMATION: Synthetic

<400> SEQUENCE: 1463
guagacagua ccuccucccu                                              20

<210> SEQ ID NO 1464
<211> LENGTH: 20
<212> TYPE: RNA
<213> ORGANISM: Artificial Sequence
<220> FEATURE:
<223> OTHER INFORMATION: Synthetic

<400> SEQUENCE: 1464
uacugucuac acagagcucu                                              20

<210> SEQ ID NO 1465
<211> LENGTH: 20
<212> TYPE: RNA
<213> ORGANISM: Artificial Sequence
<220> FEATURE:
<223> OTHER INFORMATION: Synthetic

<400> SEQUENCE: 1465
acugucuaca cagagcucua                                              20

<210> SEQ ID NO 1466
<211> LENGTH: 20
<212> TYPE: RNA
<213> ORGANISM: Artificial Sequence
<220> FEATURE:
<223> OTHER INFORMATION: Synthetic

<400> SEQUENCE: 1466
ucuacacaga gcucuaggga                                              20
```

<210> SEQ ID NO 1467
<211> LENGTH: 20
<212> TYPE: RNA
<213> ORGANISM: Artificial Sequence
<220> FEATURE:
<223> OTHER INFORMATION: Synthetic

<400> SEQUENCE: 1467
cuacacagag cucuagggaa                                           20

<210> SEQ ID NO 1468
<211> LENGTH: 20
<212> TYPE: RNA
<213> ORGANISM: Artificial Sequence
<220> FEATURE:
<223> OTHER INFORMATION: Synthetic

<400> SEQUENCE: 1468
uacacagagc ucuagggaag                                           20

<210> SEQ ID NO 1469
<211> LENGTH: 20
<212> TYPE: RNA
<213> ORGANISM: Artificial Sequence
<220> FEATURE:
<223> OTHER INFORMATION: Synthetic

<400> SEQUENCE: 1469
ggggugugcc caguuguuaa                                           20

<210> SEQ ID NO 1470
<211> LENGTH: 20
<212> TYPE: RNA
<213> ORGANISM: Artificial Sequence
<220> FEATURE:
<223> OTHER INFORMATION: Synthetic

<400> SEQUENCE: 1470
gggugugccc aguuguuaau                                           20

<210> SEQ ID NO 1471
<211> LENGTH: 20
<212> TYPE: RNA
<213> ORGANISM: Artificial Sequence
<220> FEATURE:
<223> OTHER INFORMATION: Synthetic

<400> SEQUENCE: 1471
ugguaguccc auuaacaacu                                           20

<210> SEQ ID NO 1472
<211> LENGTH: 20
<212> TYPE: RNA
<213> ORGANISM: Artificial Sequence
<220> FEATURE:
<223> OTHER INFORMATION: Synthetic

<400> SEQUENCE: 1472
cugguagucc cauuaacaac                                           20

<210> SEQ ID NO 1473
<211> LENGTH: 20
<212> TYPE: RNA
<213> ORGANISM: Artificial Sequence
<220> FEATURE:

<223> OTHER INFORMATION: Synthetic

<400> SEQUENCE: 1473
uuguuaaugg gacuaccaga                                               20

<210> SEQ ID NO 1474
<211> LENGTH: 20
<212> TYPE: RNA
<213> ORGANISM: Artificial Sequence
<220> FEATURE:
<223> OTHER INFORMATION: Synthetic

<400> SEQUENCE: 1474
uaccagaugg aagccagcuu                                               20

<210> SEQ ID NO 1475
<211> LENGTH: 20
<212> TYPE: RNA
<213> ORGANISM: Artificial Sequence
<220> FEATURE:
<223> OTHER INFORMATION: Synthetic

<400> SEQUENCE: 1475
uuccaaagcu ggcuuccauc                                               20

<210> SEQ ID NO 1476
<211> LENGTH: 20
<212> TYPE: RNA
<213> ORGANISM: Artificial Sequence
<220> FEATURE:
<223> OTHER INFORMATION: Synthetic

<400> SEQUENCE: 1476
uggaagccag cuuuggaagc                                               20

<210> SEQ ID NO 1477
<211> LENGTH: 20
<212> TYPE: RNA
<213> ORGANISM: Artificial Sequence
<220> FEATURE:
<223> OTHER INFORMATION: Synthetic

<400> SEQUENCE: 1477
acaaggccug cuuccaaagc                                               20

<210> SEQ ID NO 1478
<211> LENGTH: 20
<212> TYPE: RNA
<213> ORGANISM: Artificial Sequence
<220> FEATURE:
<223> OTHER INFORMATION: Synthetic

<400> SEQUENCE: 1478
gccuuguuca cguguucuaa                                               20

<210> SEQ ID NO 1479
<211> LENGTH: 20
<212> TYPE: RNA
<213> ORGANISM: Artificial Sequence
<220> FEATURE:
<223> OTHER INFORMATION: Synthetic

<400> SEQUENCE: 1479
ccuuguucac guguucuaau                                               20

<210> SEQ ID NO 1480
<211> LENGTH: 20
<212> TYPE: RNA
<213> ORGANISM: Artificial Sequence
<220> FEATURE:
<223> OTHER INFORMATION: Synthetic

<400> SEQUENCE: 1480
cccauuagaa cacgugaaca                                               20

<210> SEQ ID NO 1481
<211> LENGTH: 20
<212> TYPE: RNA
<213> ORGANISM: Artificial Sequence
<220> FEATURE:
<223> OTHER INFORMATION: Synthetic

<400> SEQUENCE: 1481
uuggcaucac uucauauuug                                               20

<210> SEQ ID NO 1482
<211> LENGTH: 20
<212> TYPE: RNA
<213> ORGANISM: Artificial Sequence
<220> FEATURE:
<223> OTHER INFORMATION: Synthetic

<400> SEQUENCE: 1482
cuugugcucu uggcaucacu                                               20

<210> SEQ ID NO 1483
<211> LENGTH: 20
<212> TYPE: RNA
<213> ORGANISM: Artificial Sequence
<220> FEATURE:
<223> OTHER INFORMATION: Synthetic

<400> SEQUENCE: 1483
agcacacucu cuugugcucu                                               20

<210> SEQ ID NO 1484
<211> LENGTH: 20
<212> TYPE: RNA
<213> ORGANISM: Artificial Sequence
<220> FEATURE:
<223> OTHER INFORMATION: Synthetic

<400> SEQUENCE: 1484
gcacaagaga gugugcucuc                                               20

<210> SEQ ID NO 1485
<211> LENGTH: 20
<212> TYPE: RNA
<213> ORGANISM: Artificial Sequence
<220> FEATURE:
<223> OTHER INFORMATION: Synthetic

<400> SEQUENCE: 1485
gcuuaaucuc acacauagaa                                               20

<210> SEQ ID NO 1486
<211> LENGTH: 20
<212> TYPE: RNA
<213> ORGANISM: Artificial Sequence
<220> FEATURE:
<223> OTHER INFORMATION: Synthetic

```
<400> SEQUENCE: 1486
cuuaaucuca cacauagaaa                                                   20

<210> SEQ ID NO 1487
<211> LENGTH: 20
<212> TYPE: RNA
<213> ORGANISM: Artificial Sequence
<220> FEATURE:
<223> OTHER INFORMATION: Synthetic

<400> SEQUENCE: 1487
uuaaucucac acauagaaag                                                   20

<210> SEQ ID NO 1488
<211> LENGTH: 20
<212> TYPE: RNA
<213> ORGANISM: Artificial Sequence
<220> FEATURE:
<223> OTHER INFORMATION: Synthetic

<400> SEQUENCE: 1488
aggagugcug guuuaucaac                                                   20

<210> SEQ ID NO 1489
<211> LENGTH: 20
<212> TYPE: RNA
<213> ORGANISM: Artificial Sequence
<220> FEATURE:
<223> OTHER INFORMATION: Synthetic

<400> SEQUENCE: 1489
uucuuugaca gcaggagugc                                                   20

<210> SEQ ID NO 1490
<211> LENGTH: 20
<212> TYPE: RNA
<213> ORGANISM: Artificial Sequence
<220> FEATURE:
<223> OTHER INFORMATION: Synthetic

<400> SEQUENCE: 1490
acucugguuu cuuugacagc                                                   20

<210> SEQ ID NO 1491
<211> LENGTH: 20
<212> TYPE: RNA
<213> ORGANISM: Artificial Sequence
<220> FEATURE:
<223> OTHER INFORMATION: Synthetic

<400> SEQUENCE: 1491
accagaguug agaaaacccc                                                   20

<210> SEQ ID NO 1492
<211> LENGTH: 20
<212> TYPE: RNA
<213> ORGANISM: Artificial Sequence
<220> FEATURE:
<223> OTHER INFORMATION: Synthetic

<400> SEQUENCE: 1492 uccaggggu uuucucaacuc                                                   20

<210> SEQ ID NO 1493
<211> LENGTH: 20
```

```
<212> TYPE: RNA
<213> ORGANISM: Artificial Sequence
<220> FEATURE:
<223> OTHER INFORMATION: Synthetic

<400> SEQUENCE: 1493
caguuauuaa augaauccag                                                    20

<210> SEQ ID NO 1494
<211> LENGTH: 20
<212> TYPE: RNA
<213> ORGANISM: Artificial Sequence
<220> FEATURE:
<223> OTHER INFORMATION: Synthetic

<400> SEQUENCE: 1494
gcaguuauua aaugaaucca                                                    20

<210> SEQ ID NO 1495
<211> LENGTH: 20
<212> TYPE: RNA
<213> ORGANISM: Artificial Sequence
<220> FEATURE:
<223> OTHER INFORMATION: Synthetic

<400> SEQUENCE: 1495
ggcaguuauu aaaugaaucc                                                    20

<210> SEQ ID NO 1496
<211> LENGTH: 20
<212> TYPE: RNA
<213> ORGANISM: Artificial Sequence
<220> FEATURE:
<223> OTHER INFORMATION: Synthetic

<400> SEQUENCE: 1496
uggaugguaa cagcuacauc                                                    20

<210> SEQ ID NO 1497
<211> LENGTH: 20
<212> TYPE: RNA
<213> ORGANISM: Artificial Sequence
<220> FEATURE:
<223> OTHER INFORMATION: Synthetic

<400> SEQUENCE: 1497
gcuguuacca uccacauccu                                                    20

<210> SEQ ID NO 1498
<211> LENGTH: 20
<212> TYPE: RNA
<213> ORGANISM: Artificial Sequence
<220> FEATURE:
<223> OTHER INFORMATION: Synthetic

<400> SEQUENCE: 1498
ucaagaacca aggaugugga                                                    20

<210> SEQ ID NO 1499
<211> LENGTH: 20
<212> TYPE: RNA
<213> ORGANISM: Artificial Sequence
<220> FEATURE:
<223> OTHER INFORMATION: Synthetic

<400> SEQUENCE: 1499
```
uccuucaaga accaaggaug                                            20

<210> SEQ ID NO 1500
<211> LENGTH: 20
<212> TYPE: RNA
<213> ORGANISM: Artificial Sequence
<220> FEATURE:
<223> OTHER INFORMATION: Synthetic

<400> SEQUENCE: 1500
ugaguguccu ucaagaacca                                            20

<210> SEQ ID NO 1501
<211> LENGTH: 20
<212> TYPE: RNA
<213> ORGANISM: Artificial Sequence
<220> FEATURE:
<223> OTHER INFORMATION: Synthetic

<400> SEQUENCE: 1501
uuuuauuuua uaacuacaag                                            20

<210> SEQ ID NO 1502
<211> LENGTH: 20
<212> TYPE: RNA
<213> ORGANISM: Artificial Sequence
<220> FEATURE:
<223> OTHER INFORMATION: Synthetic

<400> SEQUENCE: 1502
uuguuuuuaa uaaaaacaag                                            20

<210> SEQ ID NO 1503
<211> LENGTH: 20
<212> TYPE: RNA
<213> ORGANISM: Artificial Sequence
<220> FEATURE:
<223> OTHER INFORMATION: Synthetic

<400> SEQUENCE: 1503
uauuauagaa ugcuuuugca                                            20

<210> SEQ ID NO 1504
<211> LENGTH: 20
<212> TYPE: RNA
<213> ORGANISM: Artificial Sequence
<220> FEATURE:
<223> OTHER INFORMATION: Synthetic

<400> SEQUENCE: 1504
caagauuagu cuugauguag                                            20

<210> SEQ ID NO 1505
<211> LENGTH: 20
<212> TYPE: RNA
<213> ORGANISM: Artificial Sequence
<220> FEATURE:
<223> OTHER INFORMATION: Synthetic

<400> SEQUENCE: 1505
aagauuaguc uugauguagu                                            20

<210> SEQ ID NO 1506
<211> LENGTH: 20
<212> TYPE: RNA
<213> ORGANISM: Artificial Sequence

```
<220> FEATURE:
<223> OTHER INFORMATION: Synthetic

<400> SEQUENCE: 1506
agucuugaug uagugggagu                                              20

<210> SEQ ID NO 1507
<211> LENGTH: 20
<212> TYPE: RNA
<213> ORGANISM: Artificial Sequence
<220> FEATURE:
<223> OTHER INFORMATION: Synthetic

<400> SEQUENCE: 1507
uuuuucuauu aaaaaaaaaa                                              20

<210> SEQ ID NO 1508
<211> LENGTH: 20
<212> TYPE: RNA
<213> ORGANISM: Artificial Sequence
<220> FEATURE:
<223> OTHER INFORMATION: Synthetic

<400> SEQUENCE: 1508
ucuauuaaaa aaaaaaaggc                                              20

<210> SEQ ID NO 1509
<211> LENGTH: 20
<212> TYPE: RNA
<213> ORGANISM: Artificial Sequence
<220> FEATURE:
<223> OTHER INFORMATION: Synthetic

<400> SEQUENCE: 1509
cuauuaaaaa aaaaaaggcu                                              20

<210> SEQ ID NO 1510
<211> LENGTH: 20
<212> TYPE: RNA
<213> ORGANISM: Artificial Sequence
<220> FEATURE:
<223> OTHER INFORMATION: Synthetic

<400> SEQUENCE: 1510
aaaaaaaaaa aggcugggca                                              20

<210> SEQ ID NO 1511
<211> LENGTH: 20
<212> TYPE: RNA
<213> ORGANISM: Artificial Sequence
<220> FEATURE:
<223> OTHER INFORMATION: Synthetic

<400> SEQUENCE: 1511
aaaaaaaagg cugggcacgg                                              20

<210> SEQ ID NO 1512
<211> LENGTH: 20
<212> TYPE: RNA
<213> ORGANISM: Artificial Sequence
<220> FEATURE:
<223> OTHER INFORMATION: Synthetic

<400> SEQUENCE: 1512
cacccguaau cccagcacuu                                              20
```

<210> SEQ ID NO 1513
<211> LENGTH: 20
<212> TYPE: RNA
<213> ORGANISM: Artificial Sequence
<220> FEATURE:
<223> OTHER INFORMATION: Synthetic

<400> SEQUENCE: 1513
acccguaauc ccagcacuuu                                               20

<210> SEQ ID NO 1514
<211> LENGTH: 20
<212> TYPE: RNA
<213> ORGANISM: Artificial Sequence
<220> FEATURE:
<223> OTHER INFORMATION: Synthetic

<400> SEQUENCE: 1514
cguaauccca gcacuuuggg                                               20

<210> SEQ ID NO 1515
<211> LENGTH: 20
<212> TYPE: RNA
<213> ORGANISM: Artificial Sequence
<220> FEATURE:
<223> OTHER INFORMATION: Synthetic

<400> SEQUENCE: 1515
ucccaaagug cugggauuac                                               20

<210> SEQ ID NO 1516
<211> LENGTH: 20
<212> TYPE: RNA
<213> ORGANISM: Artificial Sequence
<220> FEATURE:
<223> OTHER INFORMATION: Synthetic

<400> SEQUENCE: 1516
cucccaaagu gcugggauua                                               20

<210> SEQ ID NO 1517
<211> LENGTH: 20
<212> TYPE: RNA
<213> ORGANISM: Artificial Sequence
<220> FEATURE:
<223> OTHER INFORMATION: Synthetic

<400> SEQUENCE: 1517
cccagcacuu ugggaggccg                                               20

<210> SEQ ID NO 1518
<211> LENGTH: 20
<212> TYPE: RNA
<213> ORGANISM: Artificial Sequence
<220> FEATURE:
<223> OTHER INFORMATION: Synthetic

<400> SEQUENCE: 1518
ccucggccuc ccaaagugcu                                               20

<210> SEQ ID NO 1519
<211> LENGTH: 20
<212> TYPE: RNA
<213> ORGANISM: Artificial Sequence
<220> FEATURE:
<223> OTHER INFORMATION: Synthetic

```
<400> SEQUENCE: 1519
gcacuuuggg aggccgaggc                                            20

<210> SEQ ID NO 1520
<211> LENGTH: 20
<212> TYPE: RNA
<213> ORGANISM: Artificial Sequence
<220> FEATURE:
<223> OTHER INFORMATION: Synthetic

<400> SEQUENCE: 1520
cuuugggagg ccgaggcagg                                            20

<210> SEQ ID NO 1521
<211> LENGTH: 20
<212> TYPE: RNA
<213> ORGANISM: Artificial Sequence
<220> FEATURE:
<223> OTHER INFORMATION: Synthetic

<400> SEQUENCE: 1521
gccgaggcag guggaucacg                                            20

<210> SEQ ID NO 1522
<211> LENGTH: 20
<212> TYPE: RNA
<213> ORGANISM: Artificial Sequence
<220> FEATURE:
<223> OTHER INFORMATION: Synthetic

<400> SEQUENCE: 1522
accucgugau ccaccugccu                                            20

<210> SEQ ID NO 1523
<211> LENGTH: 20
<212> TYPE: RNA
<213> ORGANISM: Artificial Sequence
<220> FEATURE:
<223> OTHER INFORMATION: Synthetic

<400> SEQUENCE: 1523
ggcaggugga ucacgagguc                                            20

<210> SEQ ID NO 1524
<211> LENGTH: 20
<212> TYPE: RNA
<213> ORGANISM: Artificial Sequence
<220> FEATURE:
<223> OTHER INFORMATION: Synthetic

<400> SEQUENCE: 1524
ucaggagauc gagaccaucu                                            20

<210> SEQ ID NO 1525
<211> LENGTH: 20
<212> TYPE: RNA
<213> ORGANISM: Artificial Sequence
<220> FEATURE:
<223> OTHER INFORMATION: Synthetic

<400> SEQUENCE: 1525
cgagaccauc uuggcuaaca                                            20

<210> SEQ ID NO 1526
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 1526
uuucaccaug uuagccaaga                                                   20

<210> SEQ ID NO 1527
<211> LENGTH: 20
<212> TYPE: RNA
<213> ORGANISM: Artificial Sequence
<220> FEATURE:
<223> OTHER INFORMATION: Synthetic

<400> SEQUENCE: 1527
uuguauuuuu uguagagacg                                                   20

<210> SEQ ID NO 1528
<211> LENGTH: 20
<212> TYPE: RNA
<213> ORGANISM: Artificial Sequence
<220> FEATURE:
<223> OTHER INFORMATION: Synthetic

<400> SEQUENCE: 1528
uuuguauuuu uuguagagac                                                   20

<210> SEQ ID NO 1529
<211> LENGTH: 20
<212> TYPE: RNA
<213> ORGANISM: Artificial Sequence
<220> FEATURE:
<223> OTHER INFORMATION: Synthetic

<400> SEQUENCE: 1529
uuuuguauuu uuuguagaga                                                   20

<210> SEQ ID NO 1530
<211> LENGTH: 20
<212> TYPE: RNA
<213> ORGANISM: Artificial Sequence
<220> FEATURE:
<223> OTHER INFORMATION: Synthetic

<400> SEQUENCE: 1530
aaaaaauaca aaaaauuagc                                                   20

<210> SEQ ID NO 1531
<211> LENGTH: 20
<212> TYPE: RNA
<213> ORGANISM: Artificial Sequence
<220> FEATURE:
<223> OTHER INFORMATION: Synthetic

<400> SEQUENCE: 1531
aaaaauacaa aaauuagcc                                                    20

<210> SEQ ID NO 1532
<211> LENGTH: 20
<212> TYPE: RNA
<213> ORGANISM: Artificial Sequence
<220> FEATURE:
<223> OTHER INFORMATION: Synthetic

<400> SEQUENCE: 1532
```
uacaaaaaau uagccggguq                                      20

<210> SEQ ID NO 1533
<211> LENGTH: 20
<212> TYPE: RNA
<213> ORGANISM: Artificial Sequence
<220> FEATURE:
<223> OTHER INFORMATION: Synthetic

<400> SEQUENCE: 1533
aaaaaauuag ccggguguqg                                      20

<210> SEQ ID NO 1534
<211> LENGTH: 20
<212> TYPE: RNA
<213> ORGANISM: Artificial Sequence
<220> FEATURE:
<223> OTHER INFORMATION: Synthetic

<400> SEQUENCE: 1534
aaauuagccg gguguggugg                                      20

<210> SEQ ID NO 1535
<211> LENGTH: 20
<212> TYPE: RNA
<213> ORGANISM: Artificial Sequence
<220> FEATURE:
<223> OTHER INFORMATION: Synthetic

<400> SEQUENCE: 1535
aauuagccgg guguggu ggc                                     20

<210> SEQ ID NO 1536
<211> LENGTH: 20
<212> TYPE: RNA
<213> ORGANISM: Artificial Sequence
<220> FEATURE:
<223> OTHER INFORMATION: Synthetic

<400> SEQUENCE: 1536
caggcgcccg ccaccacacc                                      20

<210> SEQ ID NO 1537
<211> LENGTH: 20
<212> TYPE: RNA
<213> ORGANISM: Artificial Sequence
<220> FEATURE:
<223> OTHER INFORMATION: Synthetic

<400> SEQUENCE: 1537
gccuguaguc ccagcuacuc                                      20

<210> SEQ ID NO 1538
<211> LENGTH: 20
<212> TYPE: RNA
<213> ORGANISM: Artificial Sequence
<220> FEATURE:
<223> OTHER INFORMATION: Synthetic

<400> SEQUENCE: 1538
uguagcccca gcuacucagg                                      20

<210> SEQ ID NO 1539
<211> LENGTH: 20
<212> TYPE: RNA

```
<213> ORGANISM: Artificial Sequence
<220> FEATURE:
<223> OTHER INFORMATION: Synthetic

<400> SEQUENCE: 1539
uccugaguag cugggacuac                                               20

<210> SEQ ID NO 1540
<211> LENGTH: 20
<212> TYPE: RNA
<213> ORGANISM: Artificial Sequence
<220> FEATURE:
<223> OTHER INFORMATION: Synthetic

<400> SEQUENCE: 1540
cccagcuacu caggaggcug                                               20

<210> SEQ ID NO 1541
<211> LENGTH: 20
<212> TYPE: RNA
<213> ORGANISM: Artificial Sequence
<220> FEATURE:
<223> OTHER INFORMATION: Synthetic

<400> SEQUENCE: 1541
ccucagccuc cugaguagcu                                               20

<210> SEQ ID NO 1542
<211> LENGTH: 20
<212> TYPE: RNA
<213> ORGANISM: Artificial Sequence
<220> FEATURE:
<223> OTHER INFORMATION: Synthetic

<400> SEQUENCE: 1542
gccucagccu ccugaguagc                                               20

<210> SEQ ID NO 1543
<211> LENGTH: 20
<212> TYPE: RNA
<213> ORGANISM: Artificial Sequence
<220> FEATURE:
<223> OTHER INFORMATION: Synthetic

<400> SEQUENCE: 1543
aggaggcuga ggcaggagaa                                               20

<210> SEQ ID NO 1544
<211> LENGTH: 20
<212> TYPE: RNA
<213> ORGANISM: Artificial Sequence
<220> FEATURE:
<223> OTHER INFORMATION: Synthetic

<400> SEQUENCE: 1544
gcaggagaau ggcgugaacc                                               20

<210> SEQ ID NO 1545
<211> LENGTH: 20
<212> TYPE: RNA
<213> ORGANISM: Artificial Sequence
<220> FEATURE:
<223> OTHER INFORMATION: Synthetic

<400> SEQUENCE: 1545
caggagaaug gcgugaaccc                                               20
```

<210> SEQ ID NO 1546
<211> LENGTH: 20
<212> TYPE: RNA
<213> ORGANISM: Artificial Sequence
<220> FEATURE:
<223> OTHER INFORMATION: Synthetic

<400> SEQUENCE: 1546
gagaauggcg ugaacccggg                                           20

<210> SEQ ID NO 1547
<211> LENGTH: 20
<212> TYPE: RNA
<213> ORGANISM: Artificial Sequence
<220> FEATURE:
<223> OTHER INFORMATION: Synthetic

<400> SEQUENCE: 1547
aauggcguga acccgggagg                                           20

<210> SEQ ID NO 1548
<211> LENGTH: 20
<212> TYPE: RNA
<213> ORGANISM: Artificial Sequence
<220> FEATURE:
<223> OTHER INFORMATION: Synthetic

<400> SEQUENCE: 1548
cacugcaagc uccaccuccc                                           20

<210> SEQ ID NO 1549
<211> LENGTH: 20
<212> TYPE: RNA
<213> ORGANISM: Artificial Sequence
<220> FEATURE:
<223> OTHER INFORMATION: Synthetic

<400> SEQUENCE: 1549
ucacugcaag cuccaccucc                                           20

<210> SEQ ID NO 1550
<211> LENGTH: 20
<212> TYPE: RNA
<213> ORGANISM: Artificial Sequence
<220> FEATURE:
<223> OTHER INFORMATION: Synthetic

<400> SEQUENCE: 1550
cauaccacug cacuccagcc                                           20

<210> SEQ ID NO 1551
<211> LENGTH: 20
<212> TYPE: RNA
<213> ORGANISM: Artificial Sequence
<220> FEATURE:
<223> OTHER INFORMATION: Synthetic

<400> SEQUENCE: 1551
auaccacugc acuccagccu                                           20

<210> SEQ ID NO 1552
<211> LENGTH: 20
<212> TYPE: RNA
<213> ORGANISM: Artificial Sequence
<220> FEATURE:

<223> OTHER INFORMATION: Synthetic

<400> SEQUENCE: 1552
ucgcccaggc uggagugcag                                          20

<210> SEQ ID NO 1553
<211> LENGTH: 20
<212> TYPE: RNA
<213> ORGANISM: Artificial Sequence
<220> FEATURE:
<223> OTHER INFORMATION: Synthetic

<400> SEQUENCE: 1553
ucucacucuu ucgcccaggc                                          20

<210> SEQ ID NO 1554
<211> LENGTH: 20
<212> TYPE: RNA
<213> ORGANISM: Artificial Sequence
<220> FEATURE:
<223> OTHER INFORMATION: Synthetic

<400> SEQUENCE: 1554
ggagucucac ucuuucgccc                                          20

<210> SEQ ID NO 1555
<211> LENGTH: 20
<212> TYPE: RNA
<213> ORGANISM: Artificial Sequence
<220> FEATURE:
<223> OTHER INFORMATION: Synthetic

<400> SEQUENCE: 1555 uguuuuugu uuuuugaga                                            20

<210> SEQ ID NO 1556
<211> LENGTH: 20
<212> TYPE: RNA
<213> ORGANISM: Artificial Sequence
<220> FEATURE:
<223> OTHER INFORMATION: Synthetic

<400> SEQUENCE: 1556
aggaagaaag aaagguuuuu                                          20

<210> SEQ ID NO 1557
<211> LENGTH: 20
<212> TYPE: RNA
<213> ORGANISM: Artificial Sequence
<220> FEATURE:
<223> OTHER INFORMATION: Synthetic

<400> SEQUENCE: 1557
agaagaaaag gaagaaagaa                                          20

<210> SEQ ID NO 1558
<211> LENGTH: 20
<212> TYPE: RNA
<213> ORGANISM: Artificial Sequence
<220> FEATURE:
<223> OTHER INFORMATION: Synthetic

<400> SEQUENCE: 1558
cuuucuuccu uuucuucucu                                          20

```
<210> SEQ ID NO 1559
<211> LENGTH: 20
<212> TYPE: RNA
<213> ORGANISM: Artificial Sequence
<220> FEATURE:
<223> OTHER INFORMATION: Synthetic

<400> SEQUENCE: 1559
uuucuuccuu uucuucucuu                                              20

<210> SEQ ID NO 1560
<211> LENGTH: 20
<212> TYPE: RNA
<213> ORGANISM: Artificial Sequence
<220> FEATURE:
<223> OTHER INFORMATION: Synthetic

<400> SEQUENCE: 1560
aauggaccca agagaagaaa                                              20

<210> SEQ ID NO 1561
<211> LENGTH: 20
<212> TYPE: RNA
<213> ORGANISM: Artificial Sequence
<220> FEATURE:
<223> OTHER INFORMATION: Synthetic

<400> SEQUENCE: 1561
ggcuauuaca uaagaaacaa                                              20

<210> SEQ ID NO 1562
<211> LENGTH: 20
<212> TYPE: RNA
<213> ORGANISM: Artificial Sequence
<220> FEATURE:
<223> OTHER INFORMATION: Synthetic

<400> SEQUENCE: 1562
cacaggaaaa ggaacuguac                                              20

<210> SEQ ID NO 1563
<211> LENGTH: 20
<212> TYPE: RNA
<213> ORGANISM: Artificial Sequence
<220> FEATURE:
<223> OTHER INFORMATION: Synthetic

<400> SEQUENCE: 1563
auuaaagcua acacaggaaa                                              20

<210> SEQ ID NO 1564
<211> LENGTH: 20
<212> TYPE: RNA
<213> ORGANISM: Artificial Sequence
<220> FEATURE:
<223> OTHER INFORMATION: Synthetic

<400> SEQUENCE: 1564
ucaaaaauua aagcuaacac                                              20

<210> SEQ ID NO 1565
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 1565
uaaaauuguc uaaacaucuc                                              20

<210> SEQ ID NO 1566
<211> LENGTH: 20
<212> TYPE: RNA
<213> ORGANISM: Artificial Sequence
<220> FEATURE:
<223> OTHER INFORMATION: Synthetic

<400> SEQUENCE: 1566
agagauguuu agacaauuuu                                              20

<210> SEQ ID NO 1567
<211> LENGTH: 20
<212> TYPE: RNA
<213> ORGANISM: Artificial Sequence
<220> FEATURE:
<223> OTHER INFORMATION: Synthetic

<400> SEQUENCE: 1567
ucuaaacauc ucugggacca                                              20

<210> SEQ ID NO 1568
<211> LENGTH: 20
<212> TYPE: RNA
<213> ORGANISM: Artificial Sequence
<220> FEATURE:
<223> OTHER INFORMATION: Synthetic

<400> SEQUENCE: 1568
uuuaugcuuu cauauauccu                                              20

<210> SEQ ID NO 1569
<211> LENGTH: 20
<212> TYPE: RNA
<213> ORGANISM: Artificial Sequence
<220> FEATURE:
<223> OTHER INFORMATION: Synthetic

<400> SEQUENCE: 1569
agcauaaauu acaaagaaaa                                              20

<210> SEQ ID NO 1570
<211> LENGTH: 20
<212> TYPE: RNA
<213> ORGANISM: Artificial Sequence
<220> FEATURE:
<223> OTHER INFORMATION: Synthetic

<400> SEQUENCE: 1570
uacaaagaaa aagguuauca                                              20

<210> SEQ ID NO 1571
<211> LENGTH: 20
<212> TYPE: RNA
<213> ORGANISM: Artificial Sequence
<220> FEATURE:
<223> OTHER INFORMATION: Synthetic

<400> SEQUENCE: 1571
acaaagaaaa agguuaucau                                              20

<210> SEQ ID NO 1572
<211> LENGTH: 20
```

```
<212> TYPE: RNA
<213> ORGANISM: Artificial Sequence
<220> FEATURE:
<223> OTHER INFORMATION: Synthetic

<400> SEQUENCE: 1572
caaagaaaaa gguuaucaug                                               20

<210> SEQ ID NO 1573
<211> LENGTH: 20
<212> TYPE: RNA
<213> ORGANISM: Artificial Sequence
<220> FEATURE:
<223> OTHER INFORMATION: Synthetic

<400> SEQUENCE: 1573
ucugagauuu aaaauagagu                                               20

<210> SEQ ID NO 1574
<211> LENGTH: 20
<212> TYPE: RNA
<213> ORGANISM: Artificial Sequence
<220> FEATURE:
<223> OTHER INFORMATION: Synthetic

<400> SEQUENCE: 1574
cuuauaagau acauuaugaa                                               20

<210> SEQ ID NO 1575
<211> LENGTH: 20
<212> TYPE: RNA
<213> ORGANISM: Artificial Sequence
<220> FEATURE:
<223> OTHER INFORMATION: Synthetic

<400> SEQUENCE: 1575
uaucuuauaa gacuauaaaa                                               20

<210> SEQ ID NO 1576
<211> LENGTH: 20
<212> TYPE: RNA
<213> ORGANISM: Artificial Sequence
<220> FEATURE:
<223> OTHER INFORMATION: Synthetic

<400> SEQUENCE: 1576
aucuuauaag acuauaaaaa                                               20

<210> SEQ ID NO 1577
<211> LENGTH: 20
<212> TYPE: RNA
<213> ORGANISM: Artificial Sequence
<220> FEATURE:
<223> OTHER INFORMATION: Synthetic

<400> SEQUENCE: 1577
uuauaagacu auaaaaaggg                                               20

<210> SEQ ID NO 1578
<211> LENGTH: 20
<212> TYPE: RNA
<213> ORGANISM: Artificial Sequence
<220> FEATURE:
<223> OTHER INFORMATION: Synthetic

<400> SEQUENCE: 1578
```

```
uaaaaaggga ggaaauauag                                              20

<210> SEQ ID NO 1579
<211> LENGTH: 20
<212> TYPE: RNA
<213> ORGANISM: Artificial Sequence
<220> FEATURE:
<223> OTHER INFORMATION: Synthetic

<400> SEQUENCE: 1579
aaaaagggag gaaauauaga                                              20

<210> SEQ ID NO 1580
<211> LENGTH: 20
<212> TYPE: RNA
<213> ORGANISM: Artificial Sequence
<220> FEATURE:
<223> OTHER INFORMATION: Synthetic

<400> SEQUENCE: 1580
aaauauagag gguccacuuu                                              20

<210> SEQ ID NO 1581
<211> LENGTH: 20
<212> TYPE: RNA
<213> ORGANISM: Artificial Sequence
<220> FEATURE:
<223> OTHER INFORMATION: Synthetic

<400> SEQUENCE: 1581
uauagagggu ccacuuuugg                                              20

<210> SEQ ID NO 1582
<211> LENGTH: 20
<212> TYPE: RNA
<213> ORGANISM: Artificial Sequence
<220> FEATURE:
<223> OTHER INFORMATION: Synthetic

<400> SEQUENCE: 1582
acucugaagu ccaccaaaag                                              20

<210> SEQ ID NO 1583
<211> LENGTH: 20
<212> TYPE: RNA
<213> ORGANISM: Artificial Sequence
<220> FEATURE:
<223> OTHER INFORMATION: Synthetic

<400> SEQUENCE: 1583
agaauagagu ugcaccguuu                                              20

<210> SEQ ID NO 1584
<211> LENGTH: 20
<212> TYPE: RNA
<213> ORGANISM: Artificial Sequence
<220> FEATURE:
<223> OTHER INFORMATION: Synthetic

<400> SEQUENCE: 1584
aaaacggugc aacucuauuc                                              20

<210> SEQ ID NO 1585
<211> LENGTH: 20
<212> TYPE: RNA
<213> ORGANISM: Artificial Sequence
```

```
<220> FEATURE:
<223> OTHER INFORMATION: Synthetic

<400> SEQUENCE: 1585
ccguuuuggg cuaaugaaaa                                                      20

<210> SEQ ID NO 1586
<211> LENGTH: 20
<212> TYPE: RNA
<213> ORGANISM: Artificial Sequence
<220> FEATURE:
<223> OTHER INFORMATION: Synthetic

<400> SEQUENCE: 1586
ccuuuuucau uagcccaaaa                                                      20

<210> SEQ ID NO 1587
<211> LENGTH: 20
<212> TYPE: RNA
<213> ORGANISM: Artificial Sequence
<220> FEATURE:
<223> OTHER INFORMATION: Synthetic

<400> SEQUENCE: 1587
ugggcuaaug aaaaaggaag                                                      20

<210> SEQ ID NO 1588
<211> LENGTH: 20
<212> TYPE: RNA
<213> ORGANISM: Artificial Sequence
<220> FEATURE:
<223> OTHER INFORMATION: Synthetic

<400> SEQUENCE: 1588
uaaugaaaaa ggaagaggcu                                                      20

<210> SEQ ID NO 1589
<211> LENGTH: 20
<212> TYPE: RNA
<213> ORGANISM: Artificial Sequence
<220> FEATURE:
<223> OTHER INFORMATION: Synthetic

<400> SEQUENCE: 1589
aaugaaaaag gaagaggcua                                                      20

<210> SEQ ID NO 1590
<211> LENGTH: 20
<212> TYPE: RNA
<213> ORGANISM: Artificial Sequence
<220> FEATURE:
<223> OTHER INFORMATION: Synthetic

<400> SEQUENCE: 1590
cugaaucuua aaauaugucc                                                      20

<210> SEQ ID NO 1591
<211> LENGTH: 20
<212> TYPE: RNA
<213> ORGANISM: Artificial Sequence
<220> FEATURE:
<223> OTHER INFORMATION: Synthetic

<400> SEQUENCE: 1591
caggcagcuu uaucucaacc                                                      20
```

<210> SEQ ID NO 1592
<211> LENGTH: 20
<212> TYPE: RNA
<213> ORGANISM: Artificial Sequence
<220> FEATURE:
<223> OTHER INFORMATION: Synthetic

<400> SEQUENCE: 1592
cuaagagauc aaguuucagc								20

<210> SEQ ID NO 1593
<211> LENGTH: 20
<212> TYPE: RNA
<213> ORGANISM: Artificial Sequence
<220> FEATURE:
<223> OTHER INFORMATION: Synthetic

<400> SEQUENCE: 1593
guguucuugu ugauauucug								20

<210> SEQ ID NO 1594
<211> LENGTH: 20
<212> TYPE: RNA
<213> ORGANISM: Artificial Sequence
<220> FEATURE:
<223> OTHER INFORMATION: Synthetic

<400> SEQUENCE: 1594
cuuguugaua uucuguggca								20

<210> SEQ ID NO 1595
<211> LENGTH: 20
<212> TYPE: RNA
<213> ORGANISM: Artificial Sequence
<220> FEATURE:
<223> OTHER INFORMATION: Synthetic

<400> SEQUENCE: 1595
ucuguggcau ggcuacagau								20

<210> SEQ ID NO 1596
<211> LENGTH: 20
<212> TYPE: RNA
<213> ORGANISM: Artificial Sequence
<220> FEATURE:
<223> OTHER INFORMATION: Synthetic

<400> SEQUENCE: 1596
agaacuuauu uacacaggga								20

<210> SEQ ID NO 1597
<211> LENGTH: 20
<212> TYPE: RNA
<213> ORGANISM: Artificial Sequence
<220> FEATURE:
<223> OTHER INFORMATION: Synthetic

<400> SEQUENCE: 1597
aaagagaacu uauuuacaca								20

<210> SEQ ID NO 1598
<211> LENGTH: 20
<212> TYPE: RNA
<213> ORGANISM: Artificial Sequence
<220> FEATURE:
<223> OTHER INFORMATION: Synthetic -continued

<400> SEQUENCE: 1598
caaagagaac uuauuuacac                                                    20

<210> SEQ ID NO 1599
<211> LENGTH: 20
<212> TYPE: RNA
<213> ORGANISM: Artificial Sequence
<220> FEATURE:
<223> OTHER INFORMATION: Synthetic

<400> SEQUENCE: 1599
uucucuuugu auuuacuuuu                                                    20

<210> SEQ ID NO 1600
<211> LENGTH: 20
<212> TYPE: RNA
<213> ORGANISM: Artificial Sequence
<220> FEATURE:
<223> OTHER INFORMATION: Synthetic

<400> SEQUENCE: 1600
ucucuuugua uuuacuuuua                                                    20

<210> SEQ ID NO 1601
<211> LENGTH: 20
<212> TYPE: RNA
<213> ORGANISM: Artificial Sequence
<220> FEATURE:
<223> OTHER INFORMATION: Synthetic

<400> SEQUENCE: 1601
cuuuguauuu acuuuuaggg                                                    20

<210> SEQ ID NO 1602
<211> LENGTH: 20
<212> TYPE: RNA
<213> ORGANISM: Artificial Sequence
<220> FEATURE:
<223> OTHER INFORMATION: Synthetic

<400> SEQUENCE: 1602
agcuuuuguc caccuuuaaa                                                    20

<210> SEQ ID NO 1603
<211> LENGTH: 20
<212> TYPE: RNA
<213> ORGANISM: Artificial Sequence
<220> FEATURE:
<223> OTHER INFORMATION: Synthetic

<400> SEQUENCE: 1603
uuuauuuuuc cauuuaaagg                                                    20

<210> SEQ ID NO 1604
<211> LENGTH: 20
<212> TYPE: RNA
<213> ORGANISM: Artificial Sequence
<220> FEATURE:
<223> OTHER INFORMATION: Synthetic

<400> SEQUENCE: 1604 uauuuauuu uuccauuuaa                                                     20

<210> SEQ ID NO 1605

```
<211> LENGTH: 20
<212> TYPE: RNA
<213> ORGANISM: Artificial Sequence
<220> FEATURE:
<223> OTHER INFORMATION: Synthetic

<400> SEQUENCE: 1605
cuuacauaaa cauacuuaaa                                              20

<210> SEQ ID NO 1606
<211> LENGTH: 20
<212> TYPE: RNA
<213> ORGANISM: Artificial Sequence
<220> FEATURE:
<223> OTHER INFORMATION: Synthetic

<400> SEQUENCE: 1606
uaagcacaga aguuuuuaag                                              20

<210> SEQ ID NO 1607
<211> LENGTH: 20
<212> TYPE: RNA
<213> ORGANISM: Artificial Sequence
<220> FEATURE:
<223> OTHER INFORMATION: Synthetic

<400> SEQUENCE: 1607
aaguuuuuaa gaggcaugaa                                              20

<210> SEQ ID NO 1608
<211> LENGTH: 20
<212> TYPE: RNA
<213> ORGANISM: Artificial Sequence
<220> FEATURE:
<223> OTHER INFORMATION: Synthetic

<400> SEQUENCE: 1608
auauuuacgu aguuuuucau                                              20

<210> SEQ ID NO 1609
<211> LENGTH: 20
<212> TYPE: RNA
<213> ORGANISM: Artificial Sequence
<220> FEATURE:
<223> OTHER INFORMATION: Synthetic

<400> SEQUENCE: 1609
cguaaauauu cuugagaaac                                              20

<210> SEQ ID NO 1610
<211> LENGTH: 20
<212> TYPE: RNA
<213> ORGANISM: Artificial Sequence
<220> FEATURE:
<223> OTHER INFORMATION: Synthetic

<400> SEQUENCE: 1610
uucuugagaa acaggaagac                                              20

<210> SEQ ID NO 1611
<211> LENGTH: 20
<212> TYPE: RNA
<213> ORGANISM: Artificial Sequence
<220> FEATURE:
<223> OTHER INFORMATION: Synthetic

<400> SEQUENCE: 1611
```
uaauauuaaa aacauugguu                                    20

<210> SEQ ID NO 1612
<211> LENGTH: 20
<212> TYPE: RNA
<213> ORGANISM: Artificial Sequence
<220> FEATURE:
<223> OTHER INFORMATION: Synthetic

<400> SEQUENCE: 1612
ccaauguuuu uaauauuauc                                    20

<210> SEQ ID NO 1613
<211> LENGTH: 20
<212> TYPE: RNA
<213> ORGANISM: Artificial Sequence
<220> FEATURE:
<223> OTHER INFORMATION: Synthetic

<400> SEQUENCE: 1613
ccugauaaua uuaaaaacau                                    20

<210> SEQ ID NO 1614
<211> LENGTH: 20
<212> TYPE: RNA
<213> ORGANISM: Artificial Sequence
<220> FEATURE:
<223> OTHER INFORMATION: Synthetic

<400> SEQUENCE: 1614
cauuaucaug cauacaucuc                                    20

<210> SEQ ID NO 1615
<211> LENGTH: 20
<212> TYPE: RNA
<213> ORGANISM: Artificial Sequence
<220> FEATURE:
<223> OTHER INFORMATION: Synthetic

<400> SEQUENCE: 1615
aucaugcaua caucucuggc                                    20

<210> SEQ ID NO 1616
<211> LENGTH: 20
<212> TYPE: RNA
<213> ORGANISM: Artificial Sequence
<220> FEATURE:
<223> OTHER INFORMATION: Synthetic

<400> SEQUENCE: 1616
uucauuucau uuugauuuug                                    20

<210> SEQ ID NO 1617
<211> LENGTH: 20
<212> TYPE: RNA
<213> ORGANISM: Artificial Sequence
<220> FEATURE:
<223> OTHER INFORMATION: Synthetic

<400> SEQUENCE: 1617
auucaauuug aagcaguggu                                    20

<210> SEQ ID NO 1618
<211> LENGTH: 20
<212> TYPE: RNA

<213> ORGANISM: Artificial Sequence
<220> FEATURE:
<223> OTHER INFORMATION: Synthetic

<400> SEQUENCE: 1618
gaauauucaa uuugaagcag                                               20

<210> SEQ ID NO 1619
<211> LENGTH: 20
<212> TYPE: RNA
<213> ORGANISM: Artificial Sequence
<220> FEATURE:
<223> OTHER INFORMATION: Synthetic

<400> SEQUENCE: 1619
cauacgauuu aaaaucgcug                                               20

<210> SEQ ID NO 1620
<211> LENGTH: 20
<212> TYPE: RNA
<213> ORGANISM: Artificial Sequence
<220> FEATURE:
<223> OTHER INFORMATION: Synthetic

<400> SEQUENCE: 1620
aaaaucgcug aggcgcguuc                                               20

<210> SEQ ID NO 1621
<211> LENGTH: 20
<212> TYPE: RNA
<213> ORGANISM: Artificial Sequence
<220> FEATURE:
<223> OTHER INFORMATION: Synthetic

<400> SEQUENCE: 1621
uuuuuuuuuc uuuuuuguac                                               20

<210> SEQ ID NO 1622
<211> LENGTH: 20
<212> TYPE: RNA
<213> ORGANISM: Artificial Sequence
<220> FEATURE:
<223> OTHER INFORMATION: Synthetic

<400> SEQUENCE: 1622
cuguugucaa agauuuuaaa                                               20

<210> SEQ ID NO 1623
<211> LENGTH: 20
<212> TYPE: RNA
<213> ORGANISM: Artificial Sequence
<220> FEATURE:
<223> OTHER INFORMATION: Synthetic

<400> SEQUENCE: 1623
ugacaacaga guucuguuuu                                               20

<210> SEQ ID NO 1624
<211> LENGTH: 20
<212> TYPE: RNA
<213> ORGANISM: Artificial Sequence
<220> FEATURE:
<223> OTHER INFORMATION: Synthetic

<400> SEQUENCE: 1624
agaauacgcu gagaguuauc                                               20

<210> SEQ ID NO 1625
<211> LENGTH: 20
<212> TYPE: RNA
<213> ORGANISM: Artificial Sequence
<220> FEATURE:
<223> OTHER INFORMATION: Synthetic

<400> SEQUENCE: 1625
gcaagagaag aaaagaacgg                                              20

<210> SEQ ID NO 1626
<211> LENGTH: 20
<212> TYPE: RNA
<213> ORGANISM: Artificial Sequence
<220> FEATURE:
<223> OTHER INFORMATION: Synthetic

<400> SEQUENCE: 1626
guugcaagag aagaaaagaa                                              20

<210> SEQ ID NO 1627
<211> LENGTH: 20
<212> TYPE: RNA
<213> ORGANISM: Artificial Sequence
<220> FEATURE:
<223> OTHER INFORMATION: Synthetic

<400> SEQUENCE: 1627
augcacacgu aaaagagagg                                              20

<210> SEQ ID NO 1628
<211> LENGTH: 20
<212> TYPE: RNA
<213> ORGANISM: Artificial Sequence
<220> FEATURE:
<223> OTHER INFORMATION: Synthetic

<400> SEQUENCE: 1628
aagaugcaca cguaaaagag                                              20

<210> SEQ ID NO 1629
<211> LENGTH: 20
<212> TYPE: RNA
<213> ORGANISM: Artificial Sequence
<220> FEATURE:
<223> OTHER INFORMATION: Synthetic

<400> SEQUENCE: 1629
aucaugcaua caucucuggc                                              20

<210> SEQ ID NO 1630
<211> LENGTH: 20
<212> TYPE: RNA
<213> ORGANISM: Artificial Sequence
<220> FEATURE:
<223> OTHER INFORMATION: Synthetic

<400> SEQUENCE: 1630
uucauuucau uuugauuuug                                              20

<210> SEQ ID NO 1631
<211> LENGTH: 20
<212> TYPE: RNA
<213> ORGANISM: Artificial Sequence
<220> FEATURE:

<223> OTHER INFORMATION: Synthetic

<400> SEQUENCE: 1631
auucaauuug aagcaguggu					20

<210> SEQ ID NO 1632
<211> LENGTH: 20
<212> TYPE: RNA
<213> ORGANISM: Artificial Sequence
<220> FEATURE:
<223> OTHER INFORMATION: Synthetic

<400> SEQUENCE: 1632
gaauauucaa uuugaagcag					20

<210> SEQ ID NO 1633
<211> LENGTH: 20
<212> TYPE: RNA
<213> ORGANISM: Artificial Sequence
<220> FEATURE:
<223> OTHER INFORMATION: Synthetic

<400> SEQUENCE: 1633
cauacgauuu aaaaucgcug					20

<210> SEQ ID NO 1634
<211> LENGTH: 20
<212> TYPE: RNA
<213> ORGANISM: Artificial Sequence
<220> FEATURE:
<223> OTHER INFORMATION: Synthetic

<400> SEQUENCE: 1634
aaaaucgcug aggcgcguuc					20

<210> SEQ ID NO 1635
<211> LENGTH: 20
<212> TYPE: RNA
<213> ORGANISM: Artificial Sequence
<220> FEATURE:
<223> OTHER INFORMATION: Synthetic

<400> SEQUENCE: 1635
uuuuuuuuuc uuuuuuguac					20

<210> SEQ ID NO 1636
<211> LENGTH: 20
<212> TYPE: RNA
<213> ORGANISM: Artificial Sequence
<220> FEATURE:
<223> OTHER INFORMATION: Synthetic

<400> SEQUENCE: 1636
cuguugucaa agauuuuaaa					20

<210> SEQ ID NO 1637
<211> LENGTH: 20
<212> TYPE: RNA
<213> ORGANISM: Artificial Sequence
<220> FEATURE:
<223> OTHER INFORMATION: Synthetic

<400> SEQUENCE: 1637
ugacaacaga guucuguuuu					20

<210> SEQ ID NO 1638
<211> LENGTH: 20
<212> TYPE: RNA
<213> ORGANISM: Artificial Sequence
<220> FEATURE:
<223> OTHER INFORMATION: Synthetic

<400> SEQUENCE: 1638
agaauacgcu gagaguuauc            20

<210> SEQ ID NO 1639
<211> LENGTH: 20
<212> TYPE: RNA
<213> ORGANISM: Artificial Sequence
<220> FEATURE:
<223> OTHER INFORMATION: Synthetic

<400> SEQUENCE: 1639
gcaagagaag aaaagaacgg            20

<210> SEQ ID NO 1640
<211> LENGTH: 20
<212> TYPE: RNA
<213> ORGANISM: Artificial Sequence
<220> FEATURE:
<223> OTHER INFORMATION: Synthetic

<400> SEQUENCE: 1640
guugcaagag aagaaaagaa            20

<210> SEQ ID NO 1641
<211> LENGTH: 20
<212> TYPE: RNA
<213> ORGANISM: Artificial Sequence
<220> FEATURE:
<223> OTHER INFORMATION: Synthetic

<400> SEQUENCE: 1641
augcacacgu aaaagagagg            20

<210> SEQ ID NO 1642
<211> LENGTH: 20
<212> TYPE: RNA
<213> ORGANISM: Artificial Sequence
<220> FEATURE:
<223> OTHER INFORMATION: Synthetic

<400> SEQUENCE: 1642
aagaugcaca cguaaaagag            20

<210> SEQ ID NO 1643
<211> LENGTH: 20
<212> TYPE: RNA
<213> ORGANISM: Artificial Sequence
<220> FEATURE:
<223> OTHER INFORMATION: Synthetic

<400> SEQUENCE: 1643
ggcagaccgu ucucaucacg            20

<210> SEQ ID NO 1644
<211> LENGTH: 20
<212> TYPE: RNA
<213> ORGANISM: Artificial Sequence
<220> FEATURE:
<223> OTHER INFORMATION: Synthetic

<400> SEQUENCE: 1644
cuuuaccagu gacuccaggu                                               20

<210> SEQ ID NO 1645
<211> LENGTH: 20
<212> TYPE: RNA
<213> ORGANISM: Artificial Sequence
<220> FEATURE:
<223> OTHER INFORMATION: Synthetic

<400> SEQUENCE: 1645
gucacagauu uccuucuccg                                               20

<210> SEQ ID NO 1646
<211> LENGTH: 20
<212> TYPE: RNA
<213> ORGANISM: Artificial Sequence
<220> FEATURE:
<223> OTHER INFORMATION: Synthetic

<400> SEQUENCE: 1646
agaugaugac gcccaccaga                                               20

<210> SEQ ID NO 1647
<211> LENGTH: 20
<212> TYPE: RNA
<213> ORGANISM: Artificial Sequence
<220> FEATURE:
<223> OTHER INFORMATION: Synthetic

<400> SEQUENCE: 1647
ggagaaggaa aucugugacc                                               20

<210> SEQ ID NO 1648
<211> LENGTH: 20
<212> TYPE: RNA
<213> ORGANISM: Artificial Sequence
<220> FEATURE:
<223> OTHER INFORMATION: Synthetic

<400> SEQUENCE: 1648
ugcgaggaac uuacuuuucc                                               20

<210> SEQ ID NO 1649
<211> LENGTH: 20
<212> TYPE: RNA
<213> ORGANISM: Artificial Sequence
<220> FEATURE:
<223> OTHER INFORMATION: Synthetic

<400> SEQUENCE: 1649
agagaaauau ugauauagga                                               20

<210> SEQ ID NO 1650
<211> LENGTH: 20
<212> TYPE: RNA
<213> ORGANISM: Artificial Sequence
<220> FEATURE:
<223> OTHER INFORMATION: Synthetic

<400> SEQUENCE: 1650
uaucaauauu ucucugaucc                                               20

<210> SEQ ID NO 1651
<211> LENGTH: 20

```
<212> TYPE: RNA
<213> ORGANISM: Artificial Sequence
<220> FEATURE:
<223> OTHER INFORMATION: Synthetic

<400> SEQUENCE: 1651
aucgcuuuua aggcacgcuc                                               20

<210> SEQ ID NO 1652
<211> LENGTH: 20
<212> TYPE: RNA
<213> ORGANISM: Artificial Sequence
<220> FEATURE:
<223> OTHER INFORMATION: Synthetic

<400> SEQUENCE: 1652
uauacgacug aucgcuuuua                                               20
```